US008853492B2

(12) United States Patent
Sanz Molinero et al.

(10) Patent No.: US 8,853,492 B2
(45) **Date of Patent: *Oct. 7, 2014**

(54) PLANTS HAVING IMPROVED GROWTH CHARACTERISTICS AND A METHOD FOR MAKING THE SAME

(75) Inventors: Ana Isabel Sanz Molinero, Gentbrugge (BE); Christophe Reuzeau, Tocane (FR); Yves Hatzfeld, Lille (FR); Veronique Boudolf, Oosterzele (BE); Lieven de Veylder, Drongen (BE); Dirk Inze, Moorsel-Aalst (BE); Vladimir Mironov, Ghent (BE)

(73) Assignee: CropDesign N.V., Zwijnaarde (BE)

( * ) Notice: Subject to any disclaimer, the term of this patent is extended or adjusted under 35 U.S.C. 154(b) by 1705 days.

This patent is subject to a terminal disclaimer.

(21) Appl. No.: 11/799,083

(22) Filed: Apr. 30, 2007

(65) Prior Publication Data

US 2008/0127365 A1 May 29, 2008

Related U.S. Application Data

(63) Continuation-in-part of application No. PCT/EP2006/068190, filed on Nov. 7, 2006.

(60) Provisional application No. 60/736,194, filed on Nov. 14, 2005, provisional application No. 60/739,686, filed on Nov. 23, 2005, provisional application No. 60/742,287, filed on Dec. 5, 2005.

(30) Foreign Application Priority Data

| | | |
|---|---|---|
| Nov. 7, 2005 | (EP) | 05110413 |
| Nov. 7, 2005 | (EP) | 05110429 |
| Nov. 17, 2005 | (EP) | 05110900 |
| Nov. 24, 2005 | (EP) | 05111260 |

(51) Int. Cl.

| | |
|---|---|
| ***A01H 5/00*** | (2006.01) |
| ***A01H 1/00*** | (2006.01) |
| ***C12N 15/09*** | (2006.01) |
| ***C12N 15/82*** | (2006.01) |
| ***C07K 14/415*** | (2006.01) |
| ***C12N 9/12*** | (2006.01) |

(52) U.S. Cl.

CPC .......... *C07K 14/415* (2013.01); *C12N 15/8261* (2013.01); *C12N 15/8273* (2013.01); *C12N 9/1205* (2013.01); *C12N 15/8271* (2013.01)

USPC ........... 800/290; 800/278; 800/298; 800/320; 800/317; 435/69.1; 435/468

(58) Field of Classification Search

USPC .................. 800/278, 298, 295, 290; 435/468

See application file for complete search history.

(56) References Cited

U.S. PATENT DOCUMENTS

| | | | | |
|---|---|---|---|---|
| 5,981,729 | A | 11/1999 | Chun et al. | |
| 6,696,623 | B1 | 2/2004 | Doerner et al. | |
| 7,235,710 | B2 * | 6/2007 | Hatzfeld et al. | 800/278 |
| 2005/0044585 | A1 | 2/2005 | Good et al. | |
| 2007/0022495 | A1 | 1/2007 | Reuber et al. | |
| 2007/0186308 | A1 | 8/2007 | Reuber et al. | |
| 2007/0192889 | A1 * | 8/2007 | La Rosa et al. | 800/278 |
| 2007/0234439 | A1 | 10/2007 | Chan et al. | |
| 2010/0251423 | A1 | 9/2010 | Sanz Molinero | |

FOREIGN PATENT DOCUMENTS

| | | | |
|---|---|---|---|
| EP | 1586652 | A1 | 10/2005 |
| WO | WO-03/007699 | A2 | 1/2003 |
| WO | WO-03/014327 | A2 | 2/2003 |
| WO | WO-03/100054 | A1 | 12/2003 |
| WO | WO-2004/065596 | A2 | 8/2004 |
| WO | WO-2004/0099365 | A2 | 11/2004 |
| WO | WO-2007/051866 | A2 | 5/2007 |

OTHER PUBLICATIONS

Li et al (1994, Cereal Chem. 71(1):87-90).*
Aoyama et al (1995, The Plant Cell 7:1773-1785).*
"*Arabidopsis thaliana* cDNA clone:RAFL06-11-C05, 3'-end", EMBL Database, Accession No. AV785059, Mar. 19, 2002.
"*Arabidopsis thaliana* clone 11036 mRNA, complete sequence", EMBL Database, Accession No. AY084518, Jun. 14, 2002.
"Hypothetical protein", UniProt Database, Accession No. Q8W481, Mar. 1, 2002.

(Continued)

*Primary Examiner* — Medina A Ibrahim
(74) *Attorney, Agent, or Firm* — Drinker Biddle & Reath LLP

(57) ABSTRACT

The present invention relates generally to the field of molecular biology and concerns a method for improving plant growth characteristics relative to corresponding wild type plants. More specifically, the present invention concerns a method for improving plant growth characteristics comprising modulating expression in a plant of a nucleic acid encoding a class I homeodomain leucine zipper (HDZip) hox5 polypeptide or a homologue thereof; or comprising modulating expression in a plant of a nucleic acid encoding a nitrate transporter protein (NRT) or a homologue thereof; or comprising modulating expression in a plant of a nucleic acid encoding a polypeptide denoted Yield Enhancing Protein 16 (YEP16); or comprising modulating expression in a plant of a Group I glycogen synthase kinase (Group I shaggy-like kinase) or a homologue thereof. The present invention also concerns plants having modulated expression of a nucleic acid encoding a class I HDZip hox5 polypeptide or a homologue thereof; or having modulated expression of a nucleic acid encoding a NRT protein or a homologue thereof; or having modulated expression of a nucleic acid encoding a polypeptide denoted YEP16; or having modulated expression of a Group I shaggy-like kinase or a homologue thereof, which plants have improved growth characteristics relative to corresponding wild type plants. The invention also provides constructs useful in the methods of the invention.

69 Claims, 94 Drawing Sheets

(56) References Cited

OTHER PUBLICATIONS

"*Oryza sativa* Nrt2 mRNA for high affinity nitrate transporter, complete cds", EMBL Database, Accession No. AB008519, Sep. 23, 1998.
Mori, M. et al., "Analysis of Nitrate Uptake Ability in Transgenic Rice Plants Over-Expressing High Affinity Nitrate Transporter", Plant Cell Physiol., vol. 46, Suppl., (2005), pp. S150.
Fraisier, V., et al., "Constitutive Expression of a Putative High-Affinity Nitrate Transporter in *Nicotiana plumbaginifolia*: Evidence for Post-Transcriptional Regulation by a Reduced Nitrogen Source", The Plant Journal, vol. 23, No. 4, (2000), pp. 489-496.
Forde, B.G., "Nitrate Transporters in Plants: Structure, Function and Regulation", Biochimica et Biophysica Acta, vol. 1465, (2000), pp. 219-235.
Orsel, M., et al., "Disruption of the Nitrate Transporter Genes *AtNRT2.1* and *AtNRT2.2* Restricts Growth at Low External Nitrate Concentration", Planta, vol. 219, (2004), pp. 714-721.
Tong, Y, et al., "A Two-Component High-Affinity Nitrate Uptake System in Barley", The Plant Journal, vol. 41, (2005), pp. 442-450.
Crawford, N.M., et al., "Molecular and Physiological Aspects of Nitrate Uptake in Plants", Trends in Plant Science, vol. 3, No. 10, (1998), pp. 389-395.
Deng, X., et al., "Characterization of Five Novel Dehydration-responsive Homeodomain Leucine Zipper Genes from the Resurrection Plant *Craterostigma plantagineum*", Plant Molecular Biology, vol. 49, (2002), pp. 601-610.
Meijer, A.H., et al., "HD-Zip Proteins of Families I and II From Rice: Interactions and Functional Properties", Mol. Gen. Genet, vol. 263, (2000), pp. 12-21.
"Homeodomain leucine zipper protein (Os08g0416000 protein)", UniProt Database, Accession No. Q6ZA74, Jul. 5, 2004.
Henriksson, E., et al., "Homeodomain Leucine Zipper Class I Genes in Arabidopsis. Expression Patterns and Phylogenetic Relationships", Plant Physiology, vol. 139, (2005), pp. 509-518.
Hanson, J. et al., "Sugar-dependent Alterations in Cotyledon and Leaf Development in Transgenic Plants Expressing the HDZhdip Gene *ATHB13*", Plant Molecular Biology, vol. 45, (2001), pp. 247-262.
"*Oryza sativa* homeodomain leucine zipper protein (Oshox5) mRNA, complete cds", EMBL Database, Accession No. AF145729, Jun. 9, 1999.
Sreenivasulu, N., et al., "Deciphering the Regulatory Mechanisms of Abiotic Stress Tolerance in Plants by Genomic Approaches", Gene, vol. 388, (2007), pp. 1-13.
De Pater et al., "The Promoter of the Rice Gene *GOS2* is Active in Various Different Monocot Tissues and Binds Rice Nuclear Factor ASF-1", The Plant Journal, 1992, vol. 2, No. 6, pp. 837-844.
Tittonell et al., "Estimating Yields of Tropical Maize Genotypes from Non-Destructive, on-farm Plant Morphological Measurements", Agriculture Ecosystems & Environment, 2005, vol. 105, pp. 213-220.
Chan et al., "Homeoboxes in Plant Development", Biochimica et Biophysica Acta, 1998, vol. 1442, pp. 1-19.
Palena et al., "Positively Charged Residues at the N-terminal Arm of the Homeodomain are Required for Efficient DNA Binding by Homeodomain-leucine Zipper Proteins", J. Mol. Biol., 2001, vol. 308, pp. 39-47.
Lazar et al., "Transforming Growth Factor $\alpha$: Mutation of Aspartic Acid 47 and Leucine 48 Results in Different Biological Activities", Molecular and Cellular Biology, 1988, vol. 8, No. 3, pp. 1247-1252.
"Homeobox-leucine zipper protein HAT7 [*Arabidopsis thaliana*]", Genbank Database, Accession No. AED92122, Jun. 16, 2011.
International Preliminary Report on Patentability for PCT/EP2006/068190, issued May 7, 2008.

* cited by examiner

Class I homeodomain of HDZip

Helix 1 Helix 2 Helix 3

1 60

| | | |
|---|---|---|
| Zeama_hox5 | (SEQ ID NO 06) | APEKKRRLTAEQVQLLERSFEEENKLEPERKTELARRLGMAPRQVAVWFQNRRARWKTKQ |
| Glyma_HD157 | (SEQ ID NO 20) | QPGKKRRLTSEQVQFLERNFEVENKLEPERKVQLAKELGLQPRQVAIWFQNRRARFKTKQ |
| Lyces_VaHOX1 | (SEQ ID NO 28) | QAEKKRRLTDNQVQFLEKSFGEENKLEPERKVQLAKELGLQPRQIAIWFQNRRARWKTKQ |
| Dauca_CHB3 | (SEQ ID NO 18) | QPEKKRRLKADQIQFLEKSFETDNKLEPERKVQLAKELGLQPRQVAIWFQNRRARWKTKT |
| Medsa_hox16 | (SEQ ID NO 30) | QSEKKRRLSVDQVQFLEKSFEEDNKLEPERKTKLAKDLGLQPRQVAIWFQNRRARWKTKQ |
| Triae_hox16 | (SEQ ID NO 14) | LPEKKRRLTPEQVHLLERSFEEENKLEPERKTELARKLGLQPRQVAVWFQNRRARWKTKT |
| Goshi_hox5 | (SEQ ID NO 24) | LPEKKRRLTSEQVYLLEKSFEAENKLEPERKSQLAKKLGLQPRQVAVWFQNRRARWKTKQ |
| Sorbi_hox5 | (SEQ ID NO 12) | APEKKRRLTAEQVQLLERSFEEENKLEPERKTELARRLGMAPRQVAVWFQNRRARWKTKQ |
| Sacof_hox5 | (SEQ ID NO 10) | APEKKRRLTAEQVQLLERSFEEENKLEPERKTELARRLGMAPRQVAVWFQNRRARWKTKQ |
| Aqufo_hox5 | (SEQ ID NO 32) | LPEKKRRLTSEQVHLLEKSFETENKLEPDRKTQLAKKLGLQPRQVAVWFQNRRARWKTKQ |
| Orysa_hox5 | (SEQ ID NO 02) | APEKKRRLTAEQVQMLERSFEEENKLEPERKTELARRLGMAPRQVAVWFQNRRARWKTKQ |
| Zeama_hox16 | (SEQ ID NO 08) | LPEKKRRLTPEQVLLLERSFEEENKLEPERKTELARKLGLQPRQVAVWFQNRRARWKTKQ |
| Orysa_hox16 | (SEQ ID NO 04) | LPEKKRRLTPEQVHLLERSFEEENKLEPERKTELARKLGLQPRQVAVWFQNRRARWKTKQ |
| Lyces_hox5 | (SEQ ID NO 26) | SPEKKRRLTPEQVHLLEKSFETENKLEPERKTQLAXKLGLQPRQVAVWFQNRRARWKTKQ |
| Arath_ATHB1 | (SEQ ID NO 16) | LPEKKRRLTTEQVHLLEKSFETENKLEPERKTQLAKKLGLQPRQVAVWFQNRRARWKTKQ |
| Crapl_CPHB-5 | (SEQ ID NO 22) | LPEKKRRLTAEQVHLLEKSFEAENKLEPERKAELAKKLGLQPRQVAIWFQNRRARWKTKQ |
| Orysa_hox6 | (SEQ ID NO 39) | AADRKKRFSEEQIKSLESMFATQTKLEPRQKLQLARELGLQPRQVAIWFQNKRARWKSKQ |
| Orysa_hox4 | (SEQ ID NO 37) | GGEKKRRLSVEQVRALERSFEVENKLEPERKARLARDLGLQPRQVAVWFQNRRARWKTKQ |
| Consensus | | PEKKRRLTAEQV LLERSFEEENKLEPERKT LARKLGLQPRQVAVWFQNRRARWKTKQ |

| | | |
|---|---|---|
| Homeodomain invariant amino acids | $L_{16}$ | $W_{48}F_{49}N_{51}R_{53}$ |
| HDZip Class I preferred amino acids | $A_{46}$ | $W_{56}$ |

FIGURE 1

Class I leucine zipper of HDZip

```
Zeama_hox5   (SEQ ID NO 06)   TKQLETDYDRLKAAYDALAADHQGLLADNDNLRAQVISLTEK
Glyma_HD157  (SEQ ID NO 20)   TKQLEKDYGVLKASYDRLKSDYESLVQENDKLKAEVNSLESK
Lyces_VaHOX1 (SEQ ID NO 28)   TKQLEKDYDELRNRYDTLKSNYNNLLKEKEDLRTEVFRLTGK
Dauca_CHB3   (SEQ ID NO 18)   TKTLEKDYDVLQNSYNSLKADYDNLLAEKEKLKAEVLDLTDK
Medsa_hox16  (SEQ ID NO 30)   TKQLEKDYDSLNDGYESLKTEYDNLLKEKDRLQSEVASLTEK
Triae_hox16  (SEQ ID NO 14)   TKTLERDFDRLKASFDALRADHDALLQDNHRLRSQVVTLTEK
Goshi_hox5   (SEQ ID NO 24)   TKQLERDYDLLKSSFDSLQSNYDTILKENEKLKSEVASLTEK
Sorbi_hox5   (SEQ ID NO 12)   TKQLETDYDRLKAAYDALAADHQGLLADNDSLRAQVISLTDK
Sacof_hox5   (SEQ ID NO 10)   TKQLETDYDHLKAAYDALAADHQGLLADNDSLRAQVVSLTEK
Aqufo_hox5   (SEQ ID NO 32)   TKQLERDYDLLKASYDSLRSDYDDIVKENEKLKSEVVSLTGK
Orysa_hox5   (SEQ ID NO 02)   TKQLEHDFDRLKAAYDALAADHHALLSDNDRLRAQVISLTEK
Zeama_hox16  (SEQ ID NO 08)   TKQLERDFDRLKASFDALRADHDALLQDNNRLRSQVVSLTEK
Orysa_hox16  (SEQ ID NO 04)   TKQLERDFDRLKASFDALRADHDALLQDNHRLHSQVMSLTEK*
Lyces_hox5   (SEQ ID NO 26)   TKQLERDYDQLKSSYDSLLSDFDSVRKDNDKLKSEVVSLMEK
Arath_ATHB1  (SEQ ID NO 16)   TKQLERDYDLLKSTYDQLLSNYDSIVMDNDKLRSEVTSLTEK
Crapl_CPHB-5 (SEQ ID NO 22)   TKQLERDYDKLKSSYDSLLSTYDSIRQENDKLKAELLSLNEK
Orysa_hox6   (SEQ ID NO 39)   SKQLEREYSALRDDYDALLCSYESLKKEKLALIKQLEKLAEM
Orysa_hox4   (SEQ ID NO 37)   TKQLERDYAALRHSYDSLRLDHDALRRDKDALLAEIKELKAK

Consensus                     TKQLERDYD LKASYDALRADYDALL DNDKLRAEVVSLTEK
                              abcdefgabcdefgabcdefgabcdefgabcdefgabcdefg

                              heptad1heptad2heptad3heptad4heptad5heptad6
```

FIGURE 1 (continued)

| | | Trp tail<br>401 414 | SEQ ID NO |
|---|---|---|---|
| Zeama_hox5 | (263) | LANWTSMFWN---- | 6 |
| Aqufo_hox5 | (273) | TLGWWDWA------ | 32 |
| Arath_ATHB1 | (265) | SLAFWGWP------ | 16 |
| Orysa_hox5 | (340) | LGSWTAWFWS---- | 2 |
| Crapl_CPHB-5 | (278) | PFAWCIWS------ | 22 |
| Dauca_CHB3 | (312) | DHTFGFWGTEL--- | 18 |
| Glyma_HD157 | (337) | DQTFCFWPY----- | 20 |
| Goshi_Hox5 | (263) | ALGLWAWX------ | 24 |
| Lyces_hox5 | (279) | PIGWFWS------- | 26 |
| Lyces_VaHOX1 | (315) | DQGFGFWTY----- | 28 |
| Medtr_HOX16_1 | (316) | DQTFCFWPY----- | 47 |
| Orysa_hox16 | (336) | ISCWWMWN------ | 4 |
| Sacof_hox5 | (265) | LANWTSWFWN---- | 10 |
| Sorbi_hox5 | (266) | LANWTSWFWN---- | 12 |
| Triae_hox16 | (334) | IS-YWMWN------ | 14 |
| Zeama_hox16 | (324) | IS-WWMWN------ | 8 |
| Poptr_HOX16_1 | (306) | DHAFWSWSY----- | 41 |
| Poptr_HOX16_2 | (309) | DHAFWCWSY----- | 43 |
| Poptr_HOX16_3 | (294) | DQPFWSWIY----- | 45 |
| Phavu_hox16 | (319) | DQTFCFWPY----- | 49 |
| Lotco_HOX16 | (310) | DHALWSWSY----- | 51 |
| Medtr_HOX unknown | (273) | ---FWPWLEQQHFN | 184 |
| Picgl_hox unknown | (299) | ILWDYNWSSGL--- | 186 |
| Orysa_hox4 | (270) | AEPTEHWN------ | 37 |
| Medtr_HOX unknown2 | (289) | QAPTLQWYCPDQWS | 185 |
| Orysa_hox6 | (240) | STPWWEFESE---- | 39 |
| Consensus | (401) | W | |

FIGURE 2 (continued)

SEQ ID NO: 1 Oryza sativa Orysa_hox5 cDNA sequence XM_482406.1
ATGGATCCCGGCCGCGTCGTGTTCGACTCCGGCGTGGCGCGGCGGGCGTGCCCCGGCGGCGC
GCAGATGCTTCTCTTCGGCGGCGGCGGCAGCGCCAACAGCGGCGGCTTCTTCCGAGGCGTGC
CGGCGGCGGTGCTGGGGATGGATGAATCGCGGTCGTCGTCGTCGGCGGCGGGGGCGGGGGCG
AAGCGGCCGTTCTTCACGACGCACGAGGAGCTCCTGGAGGAGGAGTACTACGACGAGCAGGC
GCCGGAGAAGAAGCGGCGGCTGACGGCGGAGCAGGTGCAGATGCTGGAGCGGAGCTTCGAGG
AGGAGAACAAGCTGGAGCCGGAGCGGAAGACGGAGCTCGCCCGCCGCCTCGGCATGGCCCCC
CGGCAGGTCGCCGTCTGGTTCCAGAACCGCCGCGCCCGCTGGAAGACCAAGCAGCTCGAGCA
CGACTTCGACCGCCTCAAGGCCGCCTACGACGCCCTCGCCGCCGACCACCATGCCCTCCTCT
CCGACAACGACCGCCTCCGCGCGCAGGTAATCTCATTAACCGAGAAGCTGCAAGACAAGGAG
ACGTCGCCGTCGTCGGCGACCATCACCACCGCGGCGCAGGAGGTCGACCAGCCGGACGAACA
CACGGAGGCCGCGTCAACCACCGGCTTCGCCACCGTCGACGGCGCATTGGCGGCGCCACCGC
CCGGCCACCAGCAGCCGCCGCATAAAGATGATCTTGTGAGCAGCGGCGGCACCAACGACGAC
GGCGATGGCGGCGCGGCCGTGGTGGTCTTCGACGTCACCGAGGGCGCCAACGACCGCCTCAG
CTGCGAGTCGGCGTACTTCGCCGACGCCGCGGAGGCGTACGAGCGCGACTGCGCCGGGCACT
ACGCCCTCTCGTCGGAGGAGGAGGACGGCGGCGCGGTCAGCGACGAGGGCTGCAGCTTCGAC
CTCCCCGACGCCGCCGCCGCCGCCGCCGCCATGTTCGGCGCCGCCGGAGTTGTGCACCACGA
CGCCGCGGACGACGAGGAGGCGCAGCTCGGCAGCTGGACCGCCTGGTTCTGGAGCTGA

SEQ ID NO: 2 Oryza sativa Orysa_hox5 translated amino acid sequence
MDPGRVVFDSGVARRACPGGAQMLLFGGGGSANSGGFFRGVPAAVLGMDESRSSSSAAGAGA
KRPFFTTHEELLEEEYYDEQAPEKKRRLTAEQVQMLERSFEEENKLEPERKTELARRLGMAP
RQVAVWFQNRRARWKTKQLEHDFDRLKAAYDALAADHHALLSDNDRLRAQVISLTEKLQDKE
TSPSSATITTAAQEVDQPDEHTEAASTTGFATVDGALAAPPPGHQQPPHKDDLVSSGGTNDD
GDGGAAVVVFDVTEGANDRLSCESAYFADAAEAYERDCAGHYALSSEEEDGGAVSDEGCSFD
LPDAAAAAAAMFGAAGVVHHDAADDEEAQLGSWTAWFWS

SEQ ID NO : 3 Oryza sativa Orysa_hox16 cDNA sequence XM_467603.1
ATGGAGTCCGGCCGGCTCATCTTCAGCACGGCGGGCTCCGGCGCCGGGCAGATGCTCTTCTT
GGACTGCGGCGCTGGCGGCGGCGGCGTCGGCGGCGGGGCCATGTTCCATCGAGGGGCGAGAC
CGGTGCTCGGCATGGAGGAAGGAGGGCGCGGCGTCAAGCGGCCCTTCTTCACCACCCCCGAC
GAGCTCCTCGAAGAGGAGTACTACGACGAGCAGCTCCCGGAGAAGAAGCGGCGCCTCACGCC
GGAGCAGGTGCATCTGCTGGAGAGGAGCTTCGAGGAGGAGAACAAGCTGGAGCCGGAGCGGA
AGACGGAGCTGGCGCGGAAGCTAGGGCTGCAGCCGCGGCAGGTCGCCGTGTGGTTCCAGAAC
CGCCGCGCGCGCTGGAAGACCAAGCAGCTCGAGCGCGACTTCGACCGCCTCAAGGCGTCGTT
CGACGCCCTCCGCGCCGACCACGACGCCCTCCTCCAGGACAACCACCGCCTCCACTCTCAGG
TCATGTCGTTGACCGAGAAGCTGCAAGAGAAGGAGACGACGACCGAGGGCAGCGCCGGCGCG
GCCGTTGACGTCCCGGGCTTGCCTGCGGCGGCCGACGTGAAGGTCGCCGTCCCGGACGCCGA
GGAACCGGCGCTGGAGGAGGCGGCGGCGGCGTTCGAGGAGCAGCAGGAGCAGCAGGTGAAGG
CCGAGGACAGGCTGAGCACGGGCAGCGGCGGGAGCGCGGTGGTGGACACGGACGCGCAACTG
GTGGTCGGGTGCGGCCGGCAAGCATCTCGCCGCCGTGGACAGCAGCGTGGAGTCGTACTTCC
CGGGCGGCGACGAGTACCACGACTGCGTGATGGGCCCCATGGACCACGCCGCGGGGGGCATC
CAGTCGGAGGAGGACGACGGCGCCGGCAGCGACGAGGGCTGCAGCTACTACGCCGACGACGC
CGGCGTCCTCTTCGCCGACCACGGCCACCACCACCACCACCAACACGCGGACGACGACGAGG
AGGACGGCCAGCAGATCAGCTGCTGGTGGATGTGGAACTAGATTTCTCGCGCGCGCGCGTCG
TCGTGCATTCAATTCTCGTGTTAAAAAAATCGTTCTCTTTTTCATTTTTCCGCTTCTTTGTC
TGTAATGTTGAGTTTCGATCGGCTATGAGAAGGAAGGAGGTGTATGCATGTGCATGGTATGG
TAGGGTAACACATCGGTGA

FIGURE 4 (continued)

SEQ ID NO: 4 Oryza sativa Orysa_hox16 translated amino acid sequence
MESGRLIFSTAGSGAGQMLFLDCGAGGGGVGGGAMFHRGARPVLGMEEGGRGVKRPFFTTPD
ELLEEEYYDEQLPEKKRRLTPEQVHLLERSFEEENKLEPERKTELARKLGLQPRQVAVWFQN
RRARWKTKQLERDFDRLKASFDALRADHDALLQDNHRLHSQVMSLTEKLQEKETTTEGSAGA
AVDVPGLPAAADVKVAVPDAEEPALEEAAAAFEEQQEQQVKAEDRLSTGSGGSAVVDTDAQL
VVGCGRQHLAAVDSSVESYFPGGDEYHDCVMGPMDHAAGGIQSEEDDGAGSDEGCSYYADDA
GVLFADHGHHHHHQHADDDEEDGQQISCWWMWN

SEQ ID NO: 5 Zea mays Zeama_hox5 cDNA sequence contig from essentially CO458693 & DV024016
ATGGATCCGAGCGCGGTCAGTTTCGACTCTGGCGGCGCGCGGCGGGGCGGCGGCGCGCAGAT
GCTGCTCTTCGGCGGCGGAGGCAGCGCCAACAGCAACGGCTTCTTCCGAGGTGTTCCGATGG
CGGTCCTGGGCATGGACGACGCGACGCGCGTGGGCAAGCGGCCCTTCTTCACGACACACGAG
GAGCTCCTAGAGGAGGAGTACTACGACGAGCAGGCGCCGGAGAAGAAGCGCCGACTGACGGC
GGAGCAGGTGCAGCTGCTGGAGCGGAGCTTCGAAGAAGAGAACAAGCTGGAGCCGGAGCGCA
AGACCGAGCTGGCTCGCCGCCTGGGGATGGCGCCCCGCCAGGTAGCTGTTTGGTTCCAGAAC
CGCCGCGCGCGCTGGAAGACCAAGCAACTCGAGACCGACTATGACCGCCTCAAGGCTGCTTA
CGACGCACTCGCCGCCGACCACCAGGGCCTCCTGGCCGACAACGATAACCTCCGGGCACAGG
TGATCTCCCTGACGGAGAAGCTGCAAGGCAAGGAGACATCCCCGTCGGCAACCACTGCTGCC
CAAGAGGTCGACCAGCCAGACGAACACACCGCTGTGTCAGGCACGGAAGAACTGCTGGCGCA
GCAGCTCAAGGACAACCTCCACAGCAGCGGCGACTGCACTGGCCATGGCACCCTCTCTTCGG
AAGAAGACGACGGTGGCGTGGTCAGTGACGAGGGCTGCAGCTTCGCTCTCCCGGATGCCATG
TTCGCTGCCGGGTTCACCCACCATGGCGCCGAGGAGGTGCAGCTGGCCAACTGGACATCCAT
GTTCTGGAACTGA

SEQ ID NO : 6 Zea mays Zeama_hox5 translated amino acid sequence
MDPSAVSFDSGGARRGGGAQMLLFGGGGSANSNGFFRGVPMAVLGMDDATRVGKRPFFTTHE
ELLEEEYYDEQAPEKKRRLTAEQVQLLERSFEEENKLEPERKTELARRLGMAPRQVAVWFQN
RRARWKTKQLETDYDRLKAAYDALAADHQGLLADNDNLRAQVISLTEKLQGKETSPSATTAA
QEVDQPDEHTAVSGTEELLAQQLKDNLHSSGDCTGHGTLSSEEDDGGVVSDEGCSFALPDAM
FAAGFTHHGAEEVQLANWTSMFWN

SEQ ID NO: 7 Zea mays Zeama_hox16 cDNA sequence AY105265
ATGGAGTCTGGACGGCTCATCTTCAACGCGCCGGGCTCTGGCGCCGGGCAGATGCTCTTCCT
CGACTGCGGCGCAGGCGGCGGTCCCGGCGGCGGCTTGTTCCATCGAGGCGGGAGACCGATGC
TTGGCCTTGAAGAAGGGCGCGGCGTAAAACGGCCCTTCTTCACCTCGCCCGACGAGCTCCTC
GAGGAAGAGTACTACGACGAGCAGCTGCCGGAGAAGAAGCGCCGCCTCACCCCAGAGCAGGT
GCTTCTGCTGGAGAGGAGCTTCGAGGAGGAGAACAAGCTGGAGCCGGAGCGCAAGACGGAGC
TGGCGCGCAAGCTGGGCCTGCAGCCTCGCCAGGTGGCCGTCTGGTTCCAGAACCGCCGCGCC
CGGTGGAAGACCAAGCAGCTCGAGCGCGACTTCGACCGCCTCAAGGCCTCCTTCGACGCTCT
CCGAGCGGACCACGACGCCCTCCTCCAGGACAACAACCGCCTCCGCTCACAGGTTGTGTCGT
TGACCGAGAAGCTGCAAGAGAAGGAGGATGCGACGGAGGGCGGCGCCACCGCTGACACCGCC
GCGCCGGCGGTGGACGTCGAGGCTTCCCTGGCCGACGACGTCGAGGAGCCAGCAGAGCCTGC
GGCGACGTTCGAGGTGCTGCAGGAGGTGAAGTCCGAGGACAGGCTGAGCACCGGCAGCGGCG
GGAGCGCGGTGGTGGACGCGGACGCGCTGCTGTACGGCAGGTTCGCCGCGGCAGTTGATAGC
AGCGTGGAGTCGTACTTCCCCGGCGGCGAGGACCACTACCACGACTGCGGGACGATGGGCCC FIGURE 4 (continued)

CGTGAATCATGGCGCCGGAGGAGGCATCCAGTCGGACGACGACGGCGCCGGCAGCGACGAGG
GGTGCAGCTACTACGCCGACGAAGCCGCCGCCGCCGCCGCCGCGTTCTTCGCCGGACACGCC
ACCCACCACCACGCGGACGAGGACGAGGACGCCGGCCAGATCAGCTGGTGGATGTGGAACTA
G

SEQ ID NO: 8 Zea mays Zeama_hox16 translated amino acid sequence
MESGRLIFNAPGSGAGQMLFLDCGAGGGPGGGLFHRGGRPMLGLEEGRGVKRPFFTSPDELL
EEEYYDEQLPEKKRRLTPEQVLLLERSFEEENKLEPERKTELARKLGLQPRQVAVWFQNRRA
RWKTKQLERDFDRLKASFDALRADHDALLQDNNRLRSQVVSLTEKLQEKEDATEGGATADTA
APAVDVEASLADDVEEPAEPAATFEVLQEVKSEDRLSTGSGGSAVVDADALLYGRFAAAVDS
SVESYFPGGEDHYHDCGTMGPVNHGAGGGIQSDDDGAGSDEGCSYYADEAAAAAAAFFAGHA
THHHADEDEDAGQISWWMWN

SEQ ID NO: 9 Saccharum officinarum Sacof_hox5 cDNA sequence contig from essentially CA088615, CA115362 & CA142506
ATGGATCCGAGCGCGGTCAGTTTCAACTCCGGCGGCGCGCGGCGGGGCGGCGGCGGCACGCA
GATGCTGCTCTTCGGCGGCGGAGGCAGCGCCAACAGCAACGGCTTCTTCCGAGGTGTTCCGA
TGGCGGTCCTGGGCATGGACGACGCGACGCGCGTGGGCAAGCGGCCCTTCTTCACCACACAC
GAGGAGCTCCTGGAGGAGGAGTACTACGACGAGCAGGCGCCCGAGAAGAAGCGCCGTCTGAC
GGCGGAGCAGGTGCAGCTGCTGGAGCGGAGCTTCGAGGAAGAGAACAAGCTGGAGCCCGAGC
GCAAGACCGAGCTGGCTCGCCGCCTCGGGATGGCGCCCCGCCAGGTGGCCGTCTGGTTCCAG
AACCGCCGCGCGCGCTGGAAGACCAAGCAGCTCGAGACCGACTATGACCACCTCAAGGCTGC
CTACGACGCGCTCGCCGCCGACCACCAGGGCCTCCTGGCCGACAACGATAGCCTCCGGGCAC
AGGTGGTCTCCCTAACAGAGAAGCTGCAAGGCAAGGAGACATCCCCGTCGGCCACCACTGCT
GCCCAAGAGGTCGACCAGCCAGACGAACACACCGCGGCGTCAGGCACTGAGAAACTGCTGGC
GCAGCAGCTCAAGGACGACCTCCACAGCAGCGGCGACTGCACTGGCCATGGTGCCCTCTCCT
CAGAGGAAGAAGATGGTGGTGTGGTCAGTGACGAGGGCAGCTTTGATCTCCCGGATGCCATG
TTTGCTGCCGGGGTCACCCACCATGGCGCCGACGCCGAGGAGGCACAGCTGGCCAACTGGAC
ATCCTGGTTCTGGAACTGA

SEQ ID NO: 10 Saccharum officinarum Sacof_hox5 translated amino acid sequence
MDPSAVSFNSGGARRGGGGTQMLLFGGGGSANSNGFFRGVPMAVLGMDDATRVGKRPFFTTH
EELLEEEYYDEQAPEKKRRLTAEQVQLLERSFEEENKLEPERKTELARRLGMAPRQVAVWFQ
NRRARWKTKQLETDYDHLKAAYDALAADHQGLLADNDSLRAQVVSLTEKLQGKETSPSATTA
AQEVDQPDEHTAASGTEKLLAQQLKDDLHSSGDCTGHGALSSEEEDGGVVSDEGSFDLPDAM
FAAGVTHHGADAEEAQLANWTSWFWN

SEQ ID NO: 11 Sorghum bicolor Sorbi_hox5 BE363386,CD432381
ATGGATCCGAGCGCGGTCAGTTTCGACTCCGGCGGCGCGCGGCGGGGCGGCGGCGGCGGCGG
CGCGCAGATGCTGCTCTTCGGCGGCGGAGGCAGCGCCAACAGCAACGGCTTCTTCCGAGGTG
TTCCGATGGCGGTCCTGGGCATGGACGACGCGACGCGCGTGGGCAAGCGGCCTTTCTTCACC
ACGCACGAGGAGCTCCTGGAGGAGGAGTACTACGACGAGCAGGCGCCCGAGAAGAAGCGCCG
TCTGACGGCGGAGCAGGTGCAGCTGCTGGAGCGGAGCTTCGAGGAAGAGAACAAGCTGGAGC
CGGAGCGCAAGACCGAGCTGGCTCGCCGCCTCGGGATGGCGCCTCGCCAGGTGGCCGTCTGG
TTCCAGAACCGCCGCGCGCGCTGGAAGACTAAGCAGCTCGAGACCGACTATGACCGCCTCAA
GGCTGCCTACGACGCGCTCGCCGCCGACCACCAGGGCCTCCTGGCCGACAACGATAGCCTCC FIGURE 4 (continued)

GGGCACAGGTGATCTCCCTAACGGATAAGCTGCAACGCAAGGAGACATCCCCGTCGGCGACC
ACTGCTGCCCAAGAGGTCGACCAGCCAGACGAACACACCGCTGCGTCAGGCACTGAGAAACT
GCTGGTGCAGCAGCTCAAGGACGACCTCCACAGCAGCGGCGACTTCACTGGCCATGGTGCCC
TCTCTTCAGAGGAAGAGGATGGTGGTGTGGTCAGCGACGAGGGCTGCAGCTTTGATCTCCCG
GATGCCATGTTCGCTGCCGGGGTCACCCACCATGGCGCCGAGGAGGCGCAGCTGGCCAACTG
GACATCCTGGTTCTGGAACTGA

SEQ ID NO: 12 Sorghum bicolor Sorbi_hox5 translated amino acid sequence

MDPSAVSFDSGGARRGGGGGGAQMLLFGGGGSANSNGFFRGVPMAVLGMDDATRVGKRPFFT
THEELLEEEYYDEQAPEKKRRLTAEQVQLLERSFEEENKLEPERKTELARRLGMAPRQVAVW
FQNRRARWKTKQLETDYDRLKAAYDALAADHQGLLADNDSLRAQVISLTDKLQRKETSPSAT
TAAQEVDQPDEHTAASGTEKLLVQQLKDDLHSSGDFTGHGALSSEEEDGGVVSDEGCSFDLP
DAMFAAGVTHHGAEEAQLANWTSWFWN

SEQ ID NO: 13 Triticum aestivum Triae_hox16 DR735359,DR741379, CD916488

ATGGAGCCCGGCCGGCTCATCTTCAACACGTCGGGCTCCGGCAACGGACAGATGCTCTTCAT
GGACTGCGGCGCGGGCGGCATCGCCGGCGCGGCCGGCATGTTCCATCGAGGGGTGAGACCGG
TCCTCGGCGGCATGGAAGAAGGGCGCGGCGTGAAGCGGCCCTTCTTCACCTCGCCGGATGAC
ATGCTCGAGGAGGAGTACTACGACGAGCAGCTCCCGGAGAAGAAGCGGCGCCTCACCCCGGA
GCAGGTCCACCTGCTGGAGAGGAGCTTCGAGGAGGAGAACAAGCTGGAGCCGGAGAGGAAGA
CGGAGCTGGCCCGCAAGCTCGGGCTGCAGCCACGCCAGGTGGCCGTCTGGTTCCAGAACCGC
CGCGCCCGGTGGAAGACAAAGACGCTGGAGCGCGACTTCGACCGCCTCAAGGCGTCCTTCGA
CGCCCTCCGGGCCGACCACGACGCCCTCCTCCAGGACAACCACCGGCTCCGGTCACAGGTGG
TAACGTTGACCGAGAAGATGCAAGATAAGGAGGCGCCGGAAGGCAGCTTCGGTGCAGCCGCC
GACGCCTCGGAGCCGGAGCAGGCGGCGGCGGAGGCGAAGGCTTCCTTGGCCGACGCCGAGGA
GCAGGCCGCGGCAGCGGAGGCGTTCGAGGTGGTGCAGCAGCAGCTGCACGTGAAGGACGAGG
AGAGGCTGAGCCCGGGGAGCGGCGGGAGCGCGGTGCTGGACGCGAGGGACGCGCTGCTCGGG
AGCGGATGCGGCCTCGCCGGCGTGGTGGACAGCAGCGTGGACTCGTACTGCTTCCCGGGGGG
CGCCGGCGGCGACGAGTACCACGAGTGCGTGGTGGGCCCCGTGGCGGGCGGCATCCAGTCGG
AGGAGGACGACGGCGCGGGCAGCGACGAGGGCTGCAGCTACTACCCCGACGACGCCGCCGTC
TTCTTCGCCGCCGCGCAAGGGCACGGCCACCATCGCACGGACGACGACGATCAGCAGGACGA
CGGCCAGATCAGCTACTGGATGTGGAACTAG

SEQ ID NO: 14 Triticum aestivum Triae_hox16 translated amino acid sequence

MEPGRLIFNTSGSGNGQMLFMDCGAGGIAGAAGMFHRGVRPVLGGMEEGRGVKRPFFTSPDD
MLEEEYYDEQLPEKKRRLTPEQVHLLERSFEEENKLEPERKTELARKLGLQPRQVAVWFQNR
RARWKTKTLERDFDRLKASFDALRADHDALLQDNHRLRSQVVTLTEKMQDKEAPEGSFGAAA
DASEPEQAAAEAKASLADAEEQAAAAEAFEVVQQQLHVKDEERLSPGSGGSAVLDARDALLG
SGCGLAGVVDSSVDSYCFPGGAGGDEYHECVVGPVAGGIQSEEDDGAGSDEGCSYYPDDAAV
FFAAAQGHGHHRTDDDDQQDDGQISYWMWN

FIGURE 4 (continued)

SEQ ID NO: 15 Arabidopsis thaliana Arath_ATHB1 cDNA sequence X58821

ATGGAATCCAATTCGTTTTTCTTCGATCCATCTGCTTCACACGGCAACAGCATGTTCTTCCT
TGGGAATCTCAATCCCGTCGTCCAAGGAGGAGGAGCAAGATCGATGATGAACATGGAGGAAA
CTTCGAAGCGAAGGCCCTTCTTTAGCTCCCCTGAGGATCTCTACGACGATGACTTTTACGAC
GACCAGTTGCCTGAAAAGAAGCGTCGCCTCACTACCGAACAAGTGCATCTGCTGGAGAAAAG
CTTCGAGACAGAGAACAAGCTAGAGCCTGAACGCAAGACTCAGCTTGCCAAGAAGCTTGGTC
TACAGCCAAGGCAAGTGGCTGTCTGGTTTCAGAATCGCCGAGCTCGTTGGAAAACAAAACAG
CTTGAGAGAGACTACGATCTTCTCAAGTCCACTTACGACCAACTTCTTTCTAACTACGACTC
CATCGTCATGGACAACGATAAGCTCAGATCCGAGGTTACTTCCCTGACCGAAAAGCTTCAGG
GCAAACAAGAGACAGCTAATGAACCACCTGGTCAAGTGCCCGAACCAAACCAACTTGATCCG
GTTTACATTAATGCGGCAGCAATCAAAACCGAGGACCGGTTAAGTTCAGGGAGCGTTGGGAG
CGCGGTACTAGACGACGACGCACCTCAACTACTAGACAGCTGTGACTCTTACTTCCCAAGCA
TCGTACCCATCCAAGACAACAGCAACGCCAGTGATCATGACAATGACCGGAGCTGTTTCGCC
GACGTCTTTGTGCCCACCACTTCACCGTCGCACGATCATCACGGTGAATCATTGGCTTTCTG
GGGATGGCCTTAG

SEQ ID NO: 16 Arabidopsis thaliana Arath_ATHB1 translated amino acid sequence

MESNSFFFDPSASHGNSMFFLGNLNPVVQGGGARSMMNMEETSKRRPFFSSPEDLYDDDFYD
DQLPEKKRRLTTEQVHLLEKSFETENKLEPERKTQLAKKLGLQPRQVAVWFQNRRARWKTKQ
LERDYDLLKSTYDQLLSNYDSIVMDNDKLRSEVTSLTEKLQGKQETANEPPGQVPEPNQLDP
VYINAAAIKTEDRLSSGSVGSAVLDDDAPQLLDSCDSYFPSIVPIQDNSNASDHDNDRSCFA
DVFVPTTSPSHDHHGESLAFWGWP

SEQ ID NO: 17 Daucus carota Dauca_CHB3 cDNA sequence D26575

ATGGCGGGTCGGAGGGTGTTCTATGGGGAGGGAGCCAATACGACGTCGGCTAGCCTGTTGTT
TCATAGTCAAAGACCTGAGCCTTTCTTTCTTTCTGCACCTTCTCCTTCTCTAATTGGTTCAA
AATCCATGGTTAGCTTTCAAGATGCTAAGCGAAAAAATCCCTACGATGGGTTCTTTATGCGG
TCATATGATGAAGAAGAAATTGGGGATGAAGAATATGATGAATACTTTCAGCAGCCTGAGAA
GAAGAGGAGGCTCAAGGCTGATCAAATCCAGTTTCTTGAGAAAAGTTTTGAGACTGATAACA
AGCTTGAGCCTGAAAGAAAAGTTCAGCTTGCAAAAGAACTCGGCTTGCAGCCAAGACAGGTT
GCGATATGGTTTCAGAACCGTCGAGCACGGTGGAAGACCAAAACACTAGAAAAAGATTATGA
TGTATTGCAAAATAGCTACAACAGCCTCAAGGCTGACTATGACAATCTACTTGCCGAGAAAG
AAAAACTTAAAGCCGAGGTTCTCGACCTGACAGACAAGCTACTTCTCAAAGAAGATAAGGGG
AGCAAGACAGTAGTTTTTGATAAGCAAAAGGTGTCTGCAGCATTCCAACAAGAACGTGTTAG
TAATGACATATCTGTGGGTGAAGTACTCAGTAACTCAGTTATGGACTGCAAGCAAGAAGATC
ATAACTCTGTGAAAAGTGATGCAGTTGATTCTGACAGTCCACACTACAGTGATGAAGTCTAC
TCCAGTTTTATGGAGCCAGTGGATCGCTCTTATGTTTTTGAACCTGCTCAGTCGGATATATC
TCAAGATGAAGAAGATGACATGGGGAACAACTTATTTCTCCCATCATATCATGTTTTCTCAA
AGACTGAAGACGGTAGTTACTCCGACCAGCCTTCGAACTCTTCGTACTTTGGCTTCCCAGTT
GAAGATCATACGTTTGGCTTTTGGGGTACTGAATTATAA

FIGURE 4 (continued)

SEQ ID NO: 18 Daucus carota Dauca_CHB3 translated amino acid sequence
MAGRRVFYGEGANTTSASLLFHSQRPEPFFLSAPSPSLIGSKSMVSFQDAKRKNPYDGFFMR
SYDEEEIGDEEYDEYFQQPEKKRRLKADQIQFLEKSFETDNKLEPERKVQLAKELGLQPRQV
AIWFQNRRARWKTKTLEKDYDVLQNSYNSLKADYDNLLAEKEKLKAEVLDLTDKLLLKEDKG
SKTVVFDKQKVSAAFQQERVSNDISVGEVLSNSVMDCKQEDHNSVKSDAVDSDSPHYSDEVY
SSFMEPVDRSYVFEPAQSDISQDEEDDMGNNLFLPSYHVFSKTEDGSYSDQPSNSSYFGFPV
EDHTFGFWGTEL

SEQ ID NO: 19 Glycine max Glyma_HD157 cDNA sequence AF184278
ATGGCGAGTGGCAAGCTTTATGCGGGTTCAAACATGTCACTTCTCCTCCAAAACGAAAGGCT
CCCTTGCTCCTCTGAAGTCCTTGAGTCTCTTTGGGCTCAGACCTCTAACCCTGCTTCCTTCC
AAGGTTCAAAACCCGTGGTTGATTTTGAGAATGTAAGTGGGAGCAGGATGACGGATAGGCCT
TTCTTTCAAGCGTTGGAGAAGGAAGAGAACTGTGATGAGGATTACGAGGGGTGTTTCCACCA
ACCGGGGAAGAAAAGGAGGCTCACAAGCGAACAAGTTCAGTTCCTTGAAAGGAACTTTGAGG
TAGAGAACAAGCTTGAACCCGAAAGGAAAGTCCAACTTGCAAAAGAGCTTGGCTTGCAGCCA
AGGCAAGTTGCTATATGGTTCCAAAACCGAAGGGCAAGGTTCAAGACCAAGCAGCTAGAAAA
AGACTATGGCGTGTTGAAAGCTAGTTATGACAGACTCAAAAGTGACTATGAAAGTCTTGTTC
AAGAGAATGACAAGTTAAAAGCAGAGGTGAATTCTCTGGAGAGCAAATTGATTCTTAGAGAT
AAAGAGAAGGAGGAGAATTCGGATGACAAGTCATCTCCTGATGATGCTGTCAATTCTTCTTC
ACCCCACAACAACAAGGAGCCTATGGATTTATTAATTATTTCAAAAAATGCAACAACAACAA
CAACATCTGAAAATGGGACCAAAGTGTTGTCACCACTCCCACTCCCTATTATGGTAACATGC
TGCAAGCAAGAAGATGCCAACTCAGCCAAAAGTGATGTCCTTGATTCGGATAGCCCACATTG
CACTTCATTCGTGGAGCCTGCTGATTCCTCTCATGCCTTTGAACCAGAAGACCACTCAGAAG
ACTTCTCCCAAGATGAAGAGGATAACCTTAGTGAAAACCTTTTGATGACCTTCCCTTCTTCT
TGTTGCTTACCTAAGGTTGAAGAACACTGCTATGACGGCCCTCCTGAAAACTCTTGTAATTT
TGGCTTCCAGGTTGAGGATCAAACCTTCTGTTTCTGGCCCTATTGA

SEQ ID NO: 20 Glycine max Glyma_HD157 translated amino acid sequence
MASGKLYAGSNMSLLLQNERLPCSSEVLESLWAQTSNPASFQGSKPVVDFENVSGSRMTDRP
FFQALEKEENCDEDYEGCFHQPGKKRRLTSEQVQFLERNFEVENKLEPERKVQLAKELGLQP
RQVAIWFQNRRARFKTKQLEKDYGVLKASYDRLKSDYESLVQENDKLKAEVNSLESKLILRD
KEKEENSDDKSSPDDAVNSSSPHNNKEPMDLLIISKNATTTTSENGTKVLSPLPLPIMVTC
CKQEDANSAKSDVLDSDSPHCTSFVEPADSSHAFEPEDHSEDFSQDEEDNLSENLLMTFPSS
CCLPKVEEHCYDGPPENSCNFGFQVEDQTFCFWPY

SEQ ID NO: 21 Craterostigma plantagineum CPHB-5 AF443621
ATGAACTCTGCTCGGATTTTCTTCGACCCATCTTCCCACGGCAACATGCTGCAGTTTCTTGG
GAACGCCGGCGGCGATTCATCCGTTTTCCGAGGAACAAGATCGTCGTCGGTGCTGAACATGG
AGGAGAGCTCGTTAAAACGACAGATTTTCAGCGGCGGCGGCGGCGATGAATTCTACGACGAG
GAATACTACGACGAGCAGTTGTTGCCTGAGAAGAAGCGCCGACTCACCGCCGAGCAGGTTCA
CTTGCTTGAGAAGAGCTTCGAGGCTGAGAACAAGCTTGAGCCTGAGCGAAAGGCTGAGCTGG
CGAAGAAGCTCGGATTGCAGCCGAGGCAAGTCGCCATTTGGTTCCAAAACCGCCGAGCACGG
TGGAAGACTAAGCAGTTAGAGAGGGACTACGACAAGCTTAAGTCTTCCTATGATTCTCTTCT
CTCAACCTACGACTCTATTCGCCAGGAAAACGACAAGCTCAAAGCCGAGCTCCTTTCCCTGA
ACGAGAAATTGCAACCCAAAGACGACGACGACCCATCGGCCGAAATAGGTCGAAATCTCAGT

FIGURE 4 (continued)

TCATCGTCGCCGCCTGTCGACGCGGCTGAGCCGCCGTGCCTGAAGCTGACGGTGAAGGTGGA
GGACCGCCTGAGCACGGGGAGCAACGGCAGCGCAGTAATGGACGGCGACGGACCTCAGCAGC
TCCTCGACGACAGCGGCGACTCGTACTTCGAGAACGACGAGGAATACGACTGCGCCGCCGCA
AGTTTGGCTGCTGCGAAGGAGGACGACGGCAGCGATGAGGGCGGGTGTTACTTCACCGAGGC
TCTCGCGGCGGAGGAGGAGGAGGCGCCGTTTGCTTGGTGTATTTGGTCTTAA

SEQ ID NO: 22 Craterostigma plantagineum CPHB-5 translated amino acid sequence
MNSARIFFDPSSHGNMLQFLGNAGGDSSVFRGTRSSSVLNMEESSLKRQIFSGGGGDEFYDE
EYYDEQLLPEKKRRLTAEQVHLLEKSFEAENKLEPERKAELAKKLGLQPRQVAIWFQNRRAR
WKTKQLERDYDKLKSSYDSLLSTYDSIRQENDKLKAELLSLNEKLQPKDDDDPSAEIGRNLS
SSSPPVDAAEPPCLKLTVKVEDRLSTGSNGSAVMDGDGPQQLLDDSGDSYFENDEEYDCAAA
SLAAAKEDDGSDEGGCYFTEALAAEEEEAPFAWCIWS

SEQ ID NO: 23 Gossypium hirsutum Goshi_hox5 cDNA sequence DT465649, CD486134
ATGGAGTCTGGCCGTCTTTTTTTCAATCCCTCCACTACCCACCGCAACATGTTGCTTCTCGG
GAACACTGAACCCATCTTTCGAGGGGCAAGAACAATGGTTAGCATGGAGGAAAACCCAAAGA
AGCGACTGTTCTTCAGCTCGCCGGAGGATTTGTACGACGAAGAGTACTACGACGAGCAGTTG
CCCGAGAAAAAGCGTCGCCTTACGTCGGAGCAGGTGTATCTGCTAGAGAAGAGCTTTGAGGC
AGAGAACAAGCTGGAGCCGGAGAGGAAGAGCCAGTTGGCCAAGAAGTTAGGACTGCAACCAA
GGCAGGTGGCGGTATGGTTCCAGAACCGCCGTGCAAGGTGGAAGACAAAGCAGCTTGAAAGG
GACTATGACCTCCTCAAATCTTCCTTTGATTCCCTTCAGTCCAATTATGACACTATTCTCAA
AGAAAATGAGAAGCTCAAATCTGAGGTAGCTTCCTTGACTGAAAAACTACAAGCCAAAGATG
TGGCAACAGAAGCAATAGCAGGTGAAAAGGATGAAGGGTTAGCAGCTGAGATGGCCTCCGCC
CTCCAATTCAGTATGAAGGTGGAGGACCGTCTTAGTAGCGGCAGTGTCGGAAGCGCGGTGGT
GGATGAGGATGCCCCACAGCTGGTGGACAGCGGCAATTCCTACTTTCCAAGCGATGAATACT
CCAGAGGCATTGGCCCTTTCGATGGGGTTCAGTCGGAAGATGAGGATGGCAGTGATAATTGC
GGGAGTTACTTCTCCGATGTGTTCGCAACCACAGAGCAGGGAGCATTAGGATTGTGGGCCTG
GNTCTAA

SEQ ID NO: 24 Gossypium hirsutum Goshi_hox5 translated amino acid sequence
MESGRLFFNPSTTHRNMLLLGNTEPIFRGARTMVSMEENPKKRLFFSSPEDLYDEEYYDEQL
PEKKRRLTSEQVYLLEKSFEAENKLEPERKSQLAKKLGLQPRQVAVWFQNRRARWKTKQLER
DYDLLKSSFDSLQSNYDTILKENEKLKSEVASLTEKLQAKDVATEAIAGEKDEGLAAEMASA
LQFSMKVEDRLSSGSVGSAVVDEDAPQLVDSGNSYFPSDEYSRGIGPFDGVQSEDEDGSDNC
GSYFSDVFATTEQGALGLWAWX

SEQ ID NO: 25 Lycopersicon esculentum Lyces_hox5 cDNA sequence BT014213.1
ATGGGATCTGGGCATATATTTTTCGACCCGTCGTCGTGTCACGGCAACATGCTGTTCCTTGG
GAGCGGAGATCCTGTTTTCCGAGGACCAAGATCGACGATGATGAAGATGGAGGACTCCTCGA
AGAGGCGACCCTTCTTTAGCTCGCCGGAGGATCTATATGACGAGGAATACTACGACGAGCAG
TCACCGGAGAAGAAGCGCCGTCTCACTCCTGAGCAGGTGCACTTGTTGGAGAAGAGCTTTGA
GACAGAAAACAAGCTGGAGCCCGAGCGCAAAACCCAGCTGGCCTANAAGCTGGGGCTGCAGC

FIGURE 4 (continued)

CCAGACAGGTGGCTGTATGGTTCCAAAACCGCCGTGCCCGGTGGAAGACCAAGCAGCTCGAG
AGGGATTATGATCAGCTCAAATCCTCTTATGACTCCCTTCTCTCTGATTTTGACTCCGTTCG
CAAAGATAACGATAAGCTCAAATCTGAGGTTGTTTCATTGATGGAAAAGTTACAGGGGAAAG
TGGTTGGAGGAGCAGGGGGAAATGAAAAATCTGACATCTTGGAGGTGGATGCTATGACGATC
CTTCAAGTGAAGGTGAAGGCTGGGGACCGGTTGAGCAGTGGCAGTGGTGGGAGCGCGGTGGT
AGATGAGCATAGTTCACAGCTGGTGGACAGTGGGGACTCATATTTTCACACTGATCATGAGG
AGTATCCAGGGCCTGGAGGATGCAATGTTCCTCCACCCATGGATGGTTTACAATCGGAGGAA
GATGATGGTAGTGATGATCATGGCAGTTGCCATGGCTACTTCTCTAACGTCTTTGTGGCAGA
AGAGCAGCACCATGAACAAGGAGAAGAGCCTATTGGATGGTTCTGGTCTTAA

SEQ ID NO: 26 Lycopersicon esculentum Lyces_hox5 translated amino acid sequence
MGSGHIFFDPSSCHGNMLFLGSGDPVFRGPRSTMMKMEDSSKRRPFFSSPEDLYDEEYYDEQ
SPEKKRRLTPEQVHLLEKSFETENKLEPERKTQLAXKLGLQPRQVAVWFQNRRARWKTKQLE
RDYDQLKSSYDSLLSDFDSVRKDNDKLKSEVVSLMEKLQGKVVGGAGGNEKSDILEVDAMTI
LQVKVKAGDRLSSGSGGSAVVDEHSSQLVDSGDSYFHTDHEEYPGPGGCNVPPPMDGLQSEE
DDGSDDHGSCHGYFSNVFVAEEQHHEQGEEPIGWFWS

SEQ ID NO: 27 Lycopersicon esculentum VaHOX1 cDNA sequence X94947
ATGGCTCCAGGGATTCTCTATGGTGGTTCTTCTAATTTCGATGGCGTTTTTACTCAAAAACA
GAGAGACGTGTTTTCTTCATCTACTGCACCGAAAGGGCATCTTGGTTCCCTTTTTGCCCCTG
CCTCTTCTTCTTCTAATTTCTTGGGATCCAGTTCTATGGTGAGTTTTCGCGGTGTTAATGGA
GGGAAGAGATCATTCTTTGATTCGTTCGATCAGGATGACAATGAAGCTGATGAATTGGGGGA
ATATCTTCATCAAGCGGAGAAGAAGAGGCGACTTACTGACAACCAAGTTCAGTTTCTTGAGA
AGAGTTTTGGGGAAGAGAACAAACTTGAACCAGAAAGAAAAGTTCAGCTTGCTAAAGAACTT
GGTCTGCAGCCTCGCCAAATTGCAATTTGGTTTCAGAATCGTCGTGCGCGATGGAAGACTAA
GCAGCTCGAGAAAGATTATGATGAATTGAGGAATAGATACGATACTCTGAAATCAAATTACA
ATAATCTTCTCAAGGAAAAAGAAGATCTTCGAACTGAAGTTTTCCGTCTCACCGGTAAGCTG
TTTATCAAAGAGAAAGGAAATGGGCAATTGGATTTGCGCGATGAACACAAACACTCCAATGC
ATTGGCAAAAGAAACCGTGGTTGATCCAATGTCCAATGTACCAGCTCTGGTTGTTAAGCACC
AGCAGGAAGATTTAAGCTCTGCTAAGAGTGATGTTTTCGACTCAGAAAGCCCACGTTACACC
AGTAGAATGCATTCCTCAGTCGTAGATCAGGATGATTCTGCTCGCGCATTTGAAACTGATCA
GTCGGATTCATCTCAGGATGATGATGAAAACTTCAGCAAGAATATGCTTTCTACTGCCAACC
TACTTGGCAAAGACGCGGATGATGATTATCCCGCGACATCATCAAATTTGAGTTACTTTGGA
TTTCCAGTTGAAGACCAAGGTTTTGGTTTCTGGACTTATTAA

SEQ ID NO: 28 Lycopersicon esculentum VaHOX1 translated amino acid sequence
MAPGILYGGSSNFDGVFTQKQRDVFSSSTAPKGHLGSLFAPASSSSNFLGSSSMVSFRGVNG
GKRSFFDSFDQDDNEADELGEYLHQAEKKRRLTDNQVQFLEKSFGEENKLEPERKVQLAKEL
GLQPRQIAIWFQNRRARWKTKQLEKDYDELRNRYDTLKSNYNNLLKEKEDLRTEVFRLTGKL
FIKEKGNGQLDLRDEHKHSNALAKETVVDPMSNVPALVVKHQQEDLSSAKSDVFDSESPRYT
SRMHSSVVDQDDSARAFETDQSDSSQDDDENFSKNMLSTANLLGKDADDDYPATSSNLSYFG
FPVEDQGFGFWTY

FIGURE 4 (continued)

SEQ ID NO: 29 Medicago sativa Medsa_hox16 cDNA sequence CB892061, CA858059

ATGGCGGGTGGGAGAGTTTTTTCAAATGGTCCTGCAAATATTTCAAATATAAATATGAATAT
TTTGCTTCAGAATCAACAACAAACTCCTCGTGGAAACTCTTCTCAACAACCTCTTGATTCTC
TTTTCCTTTCTTCTTCTGCTTCTTTCTTTGGTTCAAGATCTATGGTGAGTTTTGAAGATGTT
CAAGGAAGGAAAAGGCGCAACAGGTCTTTCTTTGGAGGATTTGATCTTGACGAAAACGGAGA
GGATGAGATGGATGAGTACTTTCATCAATCCGAGAAGAAACGGCGTCTCTCAGTGGATCAAG
TTCAGTTTCTTGAGAAAAGCTTTGAGGAGGACAACAAACTTGAACCAGAGAGGAAAAACCAAG
CTAGCTAAAGACCTTGGTTTGCAGCCACGGCAAGTTGCTATTTGGTTTCAAAACCGTCGTGC
AAGGTGGAAGACTAAACAGCTTGAGAAGGATTATGATTCTCTTAATGATGGTTATGAGTCTC
TTAAGACAGAGTATGACAACCTTCTCAAAGAGAAAGATAGGTTACAATCTGAGGTGGCAAGC
CTAACTGAAAAGGTACTTGAAAGAGAGAAACAAGAGGGAAAATTCAAACAAGGTGAAAGTGA
AACAAAGGAATTCTTGAAGGAACCAACAATTAATAAGCCTTTGGTTGATTCAGTTTCTGAGG
GTGAAGGATCCAAATTGTCAATTGTTGAGGCTTCTAATAATAATAATAATAATAACAAACTT
GAAGATATTAGTTCAGCAAGGAGTGACATATTGGATTGTGAAAGTCCACGCTACACTGATGG
AGTGTTAGAGACATGTGATTCTTCCTATGTATTTGAACCTGAATATCAATCGGACCTATCAC
AAGATGAAGAAGATCACAATTTATTGCCTCCTTACATCTTTACAAAACTTGAAGATGTGAAT
TACTCCGACCCGCCACATAATTCAACAAGTTATGGATTTCAAGAGGAAGATCATCATCAAGC
TCTTTGGCCTTGGTCTTATTAG

SEQ ID NO: 30 Medicago sativa Medsa_hox16 translated amino acid sequence

MAGGRVFSNGPANISNINMNILLQNQQQTPRGNSSQQPLDSLFLSSSASFFGSRSMVSFEDV
QGRKRRNRSFFGGFDLDENGEDEMDEYFHQSEKKRRLSVDQVQFLEKSFEEDNKLEPERKTK
LAKDLGLQPRQVAIWFQNRRARWKTKQLEKDYDSLNDGYESLKTEYDNLLKEKDRLQSEVAS
LTEKVLEREKQEGKFKQGESETKEFLKEPTINKPLVDSVSEGEGSKLSIVEASNNNNNNNKL
EDISSARSDILDCESPRYTDGVLETCDSSYVFEPEYQSDLSQDEEDHNLLPPYIFTKLEDVN
YSDPPHNSTSYGFQEEDHHQALWPWSY

SEQ ID NO: 31 Aquilegia formosa x Aquilegia pubescens Aqufo_hox5 cDNA sequence DT758247

ATGGATTCAACAACAAGCCGTCTTTTCTTTGATGGTTCCTGCCATGGGAACATGTTGCTTTT
AGGGAGTGGAGATCCCGTTCTTCGAGGTTCAAGATCATTCATTAATATGGAAGATTCTTTGA
AAAGACGTCCTTTTTATAGTTCAACAGATGAACTAATTGAAGAGGAGTTTTATGATGAACAG
CTACCTGAAAAGAAACGTCGTCTTACTTCTGAGCAGGTTCATCTATTGGAGAAGAGCTTTGA
GACAGAGAACAAGCTGGAACCAGATCGTAAGACCCAGCTTGCTAAGAAGCTTGGGTTGCAAC
CGAGACAAGTTGCAGTTTGGTTTCAGAATAGACGAGCTCGTTGGAAGACTAAGCAACTAGAG
AGAGATTATGATCTTCTTAAAGCTTCTTATGATTCCCTTCGTTCTGATTACGATGACATTGT
TAAAGAGAATGAGAAGCTCAAATCTGAGGTGGTTTCCTTAACTGGGAAGTTGCAGGTCAAGG
AGGGAGCTGGGATGGAGTTAAATCAGATATCTGACCCACCACTCTCCACTGAAGAAAATGTT
GATGTAACTACGATGCAATTTAATGTTAAGGTTGAGGATCGCTTGAGCTCTGGCAGTGGGGT
AAGTGCTGTGGTTGATGAGGAATGTCGACAGCTTGTTGACAGTGTTGATTCCTATTTCCCTG
GCGATGACTATGGTCAATGCATAGGCCCAGTAGATGGAGTCCAGTCAGAAGAAGATGACATT
AGTGACGACAGCCGGAGCTATTTCTCAGATGTCTTTCCAGCTGCACCAGAGCAGAACCACCA
GGAGAGTGAGACATTGGGTTGGTGGGACTGGGCTTAA

FIGURE 4 (continued)

SEQ ID NO: 32 Aquilegia formosa x Aquilegia pubescens Aqufo_hox5 translated amino acid sequence
MDSTTSRLFFDGSCHGNMLLLGSGDPVLRGSRSFINMEDSLKRRPFYSSTDELIEEEFYDEQ
LPEKKRRLTSEQVHLLEKSFETENKLEPDRKTQLAKKLGLQPRQVAVWFQNRRARWKTKQLE
RDYDLLKASYDSLRSDYDDIVKENEKLKSEVVSLTGKLQVKEGAGMELNQISDPPLSTEENV
DVTTMQFNVKVEDRLSSGSGVSAVVDEECRQLVDSVDSYFPGDDYGQCIGPVDGVQSEEDDI
SDDSRSYFSDVFPAAPEQNHQESETLGWWDWA

SEQ ID NO: 33 Oryza sativa GOS2 promoter
AATCCGAAAAGTTTCTGCACCGTTTTCACCCCCTAACTAACAATATAGGGAACGTGTGCTAA
ATATAAAATGAGACCTTATATATGTAGCGCTGATAACTAGAACTATGCAAGAAAAACTCATC
CACCTACTTTAGTGGCAATCGGGCTAAATAAAAAAGAGTCGCTACACTAGTTTCGTTTTCCT
TAGTAATTAAGTGGGAAAATGAAATCATTATTGCTTAGAATATACGTTCACATCTCTGTCAT
GAAGTTAAATTATTCGAGGTAGCCATAATTGTCATCAAACTCTTCTTGAATAAAAAAATCTT
TCTAGCTGAACTCAATGGGTAAAGAGAGAGATTTTTTTTAAAAAAATAGAATGAAGATATTC
TGAACGTATTGGCAAAGATTTAAACATATAATTATATAATTTTATAGTTTGTGCATTCGTCA
TATCGCACATCATTAAGGACATGTCTTACTCCATCCCAATTTTTATTTAGTAATTAAAGACA
ATTGACTTATTTTTATTATTTATCTTTTTTCGATTAGATGCAAGGTACTTACGCACACACTT
TGTGCTCATGTGCATGTGTGAGTGCACCTCCTCAATACACGTTCAACTAGCAACACATCTCT
AATATCACTCGCCTATTTAATACATTTAGGTAGCAATATCTGAATTCAAGCACTCCACCATC
ACCAGACCACTTTTAATAATATCTAAAATACAAAAAATAATTTTACAGAATAGCATGAAAAG
TATGAAACGAACTATTTAGGTTTTTCACATACAAAAAAAAAAAGAATTTTGCTCGTGCGCGA
GCGCCAATCTCCCATATTGGGCACACAGGCAACAACAGAGTGGCTGCCCACAGAACAACCCA
CAAAAAACGATGATCTAACGGAGGACAGCAAGTCCGCAACAACCTTTTAACAGCAGGCTTTG
CGGCCAGGAGAGAGGAGGAGAGGCAAAGAAAACCAAGCATCCTCCTCCTCCCATCTATAAAT
TCCTCCCCCCTTTTCCCCTCTCTATATAGGAGGCATCCAAGCCAAGAAGAGGGAGAGCACCA
AGGACACGCGACTAGCAGAAGCCGAGCGACCGCCTTCTTCGATCCATATCTTCCGGTCGAGT
TCTTGGTCGATCTCTTCCCTCCTCCACCTCCTCCTCACAGGGTATGTGCCCTTCGGTTGTTC
TTGGATTTATTGTTCTAGGTTGTGTAGTACGGGCGTTGATGTTAGGAAAGGGGATCTGTATC
TGTGATGATTCCTGTTCTTGGATTTGGGATAGAGGGGTTCTTGATGTTGCATGTTATCGGTT
CGGTTTGATTAGTAGTATGGTTTTCAATCGTCTGGAGAGCTCTATGGAAATGAAATGGTTTA
GGGTACGGAATCTTGCGATTTTGTGAGTACCTTTTGTTTGAGGTAAAATCAGAGCACCGGTG
ATTTTGCTTGGTGTAATAAAAGTACGGTTGTTTGGTCCTCGATTCTGGTAGTGATGCTTCTC
GATTTGACGAAGCTATCCTTTGTTTATTCCCTATTGAACAAAAATAATCCAACTTTGAAGAC
GGTCCCGTTGATGAGATTGAATGATTGATTCTTAAGCCTGTCCAAAATTTCGCAGCTGGCTT
GTTTAGATACAGTAGTCCCCATCACGAAATTCATGGAAACAGTTATAATCCTCAGGAACAGG
GGATTCCCTGTTCTTCCGATTTGCTTTAGTCCCAGAATTTTTTTTCCCAAATATCTTAAAAA
GTCACTTTCTGGTTCAGTTCAATGAATTGATTGCTACAAATAATGCTTTTATAGCGTTATCC
TAGCTGTAGTTCAGTTAATAGGTAATACCCCTATAGTTTAGTCAGGAGAAGAACTTATCCGA
TTTCTGATCTCCATTTTTAATTATATGAAATGAACTGTAGCATAAGCAGTATTCATTTGGAT
TATTTTTTTATTAGCTCTCACCCCTTCATTATTCTGAGCTGAAAGTCTGGCATGAACTGTC
CTCAATTTTGTTTTCAAATTCACATCGATTATCTATGCATTATCCTCTTGTATCTACCTGTA
GAAGTTTCTTTTTGGTTATTCCTTGACTGCTTGATTACAGAAAGAAATTTATGAAGCTGTAA
TCGGGATAGTTATACTGCTTGTTCTTATGATTCATTTCCTTTGTGCAGTTCTTGGTGTAGCT
TGCCACTTTCACCAGCAAAGTTC

FIGURE 4 (continued)

SEQ ID NO: 34 primer prm6000
GGGGACAAGTTTGTACAAAAAAGCAGGCTTAAACAATGGATCCCGGCCG

SEQ ID NO: 35 primer prm6001
GGGGACCACTTTGTACAAGAAAGCTGGGTGATCAGCTCCAGAACCAGG

SEQ ID NO : 36 Oryza sativa Orysa_hox4 cDNA sequence AF145728
ATGAAGCGACCCGGCGGTGCCGGCGGCGGCGGAGGCAGCCCATCGCTCGTCACGATGGCTAA
TTCTAGTGATGATGGATATGGAGGGGTTGGGATGGAGGCGGAGGGGGACGTGGAGGAGGAGA
TGATGGCGTGCGGCGGCGGCGGGGAGAAGAAGCGGCGGCTGAGCGTGGAGCAGGTTCGCGCG
CTGGAGCGGAGCTTCGAGGTGGAGAACAAGCTTGAGCCTGAGCGGAAGGCGCGGCTGGCGCG
CGACCTCGGCCTGCAGCCGCGCCAGGTCGCCGTCTGGTTCCAGAACCGCCGCGCGCGGTGGA
AGACCAAGCAGCTCGAGCGCGACTACGCCGCGCTCCGCCATTCCTACGACTCCCTGCGCCTC
GATCACGACGCGCTCCGCCGCGACAAGGACGCCCTCCTCGCCGAGATCAAGGAGCTGAAGGC
GAAGCTCGGGGACGAGGAGGCGGCGGCGAGCTTCACGTCGGTGAAGGAGGAGCCGGCGGCCT
CCGACGGGCCACCGGCGGCGGGATTTGGGTCGTCCGACAGCGACTCAAGCGCGGTGCTGAAC
GACGTGGACGCGGCCGGCGCCGCGCCCGCGGCGACGGACGCGCTGGCTCCGGAGGCGTGCAC
GTTTCTCGGTGCGCCGCCCGCCGCGGGCGCGGGCGCGGGCGCAGCGGCGGCGGCGAGCCACG
AGGAGGTGTTCTTCCACGGCAATTTCCTCAAGGTGGAGGAGGACGAGACGGGGTTCCTCGAC
GACGACGAGCCGTGCGGCGGGTTCTTCGCCGACGATCAGCCCCCGCCGCTCTCGTCGTGGTG
GGCCGAACCCACGGAGCACTGGAACTGA

SEQ ID NO : 37 Oryza sativa Orysa_hox4 translated amino acid sequence
MKRPGGAGGGGGSPSLVTMANSSDDGYGGVGMEAEGDVEEEMMACGGGGEKKRRLSVEQVRA
LERSFEVENKLEPERKARLARDLGLQPRQVAVWFQNRRARWKTKQLERDYAALRHSYDSLRL
DHDALRRDKDALLAEIKELKAKLGDEEAAASFTSVKEEPAASDGPPAAGFGSSDSDSSAVLN
DVDAAGAAPAATDALAPEACTFLGAPPAAGAGAGAAAAASHEEVFFHGNFLKVEEDETGFLD
DDEPCGGFFADDQPPPLSSWWAEPTEHWN

SEQ ID NO : 38 Oryza sativa Orysa_hox6 cDNA sequence AK103160
ATGGATGGGGAGGAGGACAGCGAGTGGATGATGATGGACGTTGGAGGGAAGGGCGGGAAGGG
CGGCGGCGGCGGCGGCGCGGCGGACAGGAAGAAGCGGTTCAGCGAGGAGCAGATCAAGTCGC
TGGAGTCCATGTTCGCGACGCAGACCAAGCTGGAGCCGAGGCAGAAGCTGCAGCTCGCCAGG
GAGCTCGGCCTGCAGCCTCGCCAGGTCGCCATCTGGTTCCAGAACAAGCGCGCGCGGTGGAA
GTCCAAGCAGCTCGAGCGCGAGTACTCCGCCCTCCGCGACGACTACGACGCCCTCCTCTGCA
GCTACGAGTCCCTCAAGAAGGAGAAGCTCGCCCTCATCAAGCAGCTGGAGAAGCTGGCGGAG
ATGCTGCAGGAGCCACGGGGGAAGTACGGCGATAATGCCGGGGACGACGCGCGGTCGGGCGG
CGTCGCCGGCATGAAGAAGGAGGAGTTCGTCGGCGCGGGCGGCGCCGCCACGCTCTACTCGT
CGGCCGAGGGTGGCGGGACGACGACGACGACGACGGCCAAGTTGATGCCCCACTTCGGCAGC
GACGACGTCGACGCGGGGCTCTTCCTCCGGCCGTCGTCGCAGCATCATCCGCCGCCGCCGCA
CGCCGGTGCCGGCTTCACGTCCTCCGAGCCGGCCGCCGACCACCAGTCCTTCAACTTCCACT
CGAGCTGGCCGTCGTCCACGGAGCAGACCTGCAGCAGCACGCCATGGTGGGAATTCGAGAGC
GAGTGA

FIGURE 4 (continued)

SEQ ID NO : 39 Oryza sativa Orysa_hox6 translated amino acid sequence
MDGEEDSEWMMMDVGGKGGKGGGGGGAADRKKRFSEEQIKSLESMFATQTKLEPRQKLQLAR
ELGLQPRQVAIWFQNKRARWKSKQLEREYSALRDDYDALLCSYESLKKEKLALIKQLEKLAE
MLQEPRGKYGDNAGDDARSGGVAGMKKEEFVGAGGAATLYSSAEGGGTTTTTAKLMPHFGS
DDVDAGLFLRPSSQHHPPPPHAGAGFTSSEPAADHQSFNFHSSWPSSTEQTCSSTPWWEFES
E

SEQ ID NO: 40 Populus tremuloides Poptr_HOX16_1 cDNA sequence
ATGGCGGGTGGTACCGGTGGTTCTAATTCCAATTTGTCTGTTTTGCTTCAAAGCCAAAGAGG
CCCTTGTGCTGCTTCACAACCTCTTGAATCTTTTTTCCTTTCTGGCTCTTCTCCTTCTTTTC
TTGGTTCAAGATCCATGATGAGTTTTGAAGATGTTCATCAAGCAAACGGATCAACCAGGCCT
TTTTTCCGCTCGTTTGATCACGAAGACAATGGAGACGATGATCTGGATGAATATTTTCATCA
ACCTGAAAAGAAGAGGAGACTTACTGTTGATCAAGTTCAGTTTCTTGAAAAGAGTTTTGAGC
TTGAGAACAAGCTTGAACCTGAAAGGAAAATCCAGCTTGCAAAGGATCTTGGCCTTCAGCCG
CGTCAGGTTGCTATATGGTTTCAAAACCGCCGAGCAAGATGGAAGACTAAACAGCTGGAAAA
GGATTATGACGTTTTGCAATCTAGCTACAATAGCCTTAAGGCTGACTATGACAACCTCCTCA
AGGAGAAGGAGAAACTAAAAGCTGAGGTTAATCTTCTCACCGACAAGTTGCTCCTCAAAGAG
AAAGAGAAGGGAATCTCAGAATTGTCTGATAAAGATGCATTATCGCAAGAGCCACCTAAAAG
GGCTATAGCTGATTCAGCTTCCGAGGGTGAAGTGTCGAAAATCTCAACAGTGGCCTGTAAGC
AGGAAGATATCAGCTCAGCCAAAAGCGACATATTTGATTCAGACAGCCCACATTACGCTGAT
GGGGTGCATTCCTCACTCTTAGAGGCAGGAGATTCTTCATATGTTTTCGAACCCGATCAATC
AGATTTGTCACAAGATGAAGAAGATAACTTTAGCAAGAGCTTATTGCCTCCATACGTCTTTC
CGAAGCTTGAAGATGACGATTACTCTGACCCGCCTGCAAGTTTTGAAGATCATGCCTTTTGG
TCCTGGTCATACTAA

SEQ ID NO: 41 Populus tremuloides Poptr_HOX16_1 translated amino acid sequence
MAGGTGGSNSNLSVLLQSQRGPCAASQPLESFFLSGSSPSFLGSRSMMSFEDVHQANGSTRP
FFRSFDHEDNGDDDLDEYFHQPEKKRRLTVDQVQFLEKSFELENKLEPERKIQLAKDLGLQP
RQVAIWFQNRRARWKTKQLEKDYDVLQSSYNSLKADYDNLLKEKEKLKAEVNLLTDKLLLKE
KEKGISELSDKDALSQEPPKRAIADSASEGEVSKISTVACKQEDISSAKSDIFDSDSPHYAD
GVHSSLLEAGDSSYVFEPDQSDLSQDEEDNFSKSLLPPYVFPKLEDDDYSDPPASFEDHAFW
SWSY

SEQ ID NO: 42 Populus tremuloides Poptr_HOX16_2 cDNA sequence
ATGGCGGCTTGTGGTGGTGGTGGTGGTGGTTCTAATCCCAATTTGTCTGTTTTAGTTCAAAG
CCAAAGAGGCCCTTGTGCTGCTTCTCAACCTCTTGAAGCTTTTTTCCTTTCTGGCTCTTCTC
CTTCTTTTCTTGGTTCAAGATCCATGATGAGTTTTGCAGATGTTCACCAAGCAAATGGATCA
ACTAGACCGTTTTTCCGCCCATATGATCACGAAGACAACGGCGACGATGATTTGGATGAATA
TTTTCATCAACCTGAAAAGAAGAGGAGACTTACTGTTGATCAAGTTCAGTTTCTTGAAAGAA
GTTTTGAGGTTGAGAACAAGCTTGAACCCGAAAGGAAAATCCAGCTGGCGAAGGATCTTGGC
TTGCAGCCTCGGCAGGTTGCCATATGGTTTCAAAACCGCCGGGCAAGATGGAAGACGAAACA
GCTTGAAAAAGATTATGAGGTTCTGCAATCTAGCTACAATGGCCTTAAGGCTGACTACGACA
ACCTCTTCAAGGAGAAGGAGAAACTAAAAGCTGAGGTTAATCTTCTCACCAACGAGTTGCTC
CTTAAAGAGAAAGAGAAAGGAAGCTCAGAATTGTCTGATAAAGATGCATTATCTCAAGAGCC
ACCCAAAAAGGCAATAGCCGATTCAGCTTCAGAGGGTGAAGTGTCGAAAACTTCAACCGTGG FIGURE 4 (continued)

CCTGCCAGCAGGAAGATATTAGCTCAGCCAAAAGTGATATGTTTGATTCAGACAGCCCACAT
TTTGCGGATGGGGTACATTCCTCACTCTTAGAGGCAGGTGATTCTTCACATGTCTTCGAGCC
CGACCAATCGGATTTATCACAAGATGAAGAAGATAACTTGAGCAAGAGTCTTTTGCCTCCGT
ACGTCTTTCCAAAGCTTGAAGATGGTGATTACTCTGACCCGCCAGCAAGTTTTGAAGATCAT
GCCTTTTGGTGCTGGTCATACTAA

SEQ ID NO: 43 Populus tremuloides Poptr_HOX16_2 translated amino acid sequence
MAACGGGGGGSNPNLSVLVQSQRGPCAASQPLEAFFLSGSSPSFLGSRSMMSFADVHQANGS
TRPFFRPYDHEDNGDDDLDEYFHQPEKKRRLTVDQVQFLERSFEVENKLEPERKIQLAKDLG
LQPRQVAIWFQNRRARWKTKQLEKDYEVLQSSYNGLKADYDNLFKEKEKLKAEVNLLTNELL
LKEKEKGSSELSDKDALSQEPPKKAIADSASEGEVSKTSTVACQQEDISSAKSDMFDSDSPH
FADGVHSSLLEAGDSSHVFEPDQSDLSQDEEDNLSKSLLPPYVFPKLEDGDYSDPPASFEDH
AFWCWSY

SEQ ID NO: 44 Populus tremuloides Poptr_HOX16_3 cDNA sequence
ATGGCGGGTGATAAAGACTGTGGCAGTTCTAAAATGACCATTTTTCTTCGAAACGGCAGGCT
CCCTCCTTGTGAATCTCTCTGTATTCTCACCTCTTTTAGCACTCTTCATGGTGCAAAATCTA
TGGTTAATTTTAGGAATGATGGAGGAGACACTGTAGACATGTCTTTTTTCCAACCACATGTC
AAAGAAGAAAGTAGCGATGAGGATTATGATGCGCACCTTAAGCCATCTGAAAAGAAAAGGCG
GCTTACAGCTGCTCAAGTCCAGTTTCTTGAGAAGAGCTTTGAGGCGGAGAATAAGCTTGAAC
CAGAGAGGAAGATGCAGCTTGCTAAAGAACTCGGCTTGCAGCCTCGCCAGGTTGCAATATGG
TTTCAAAACCGTAGAGCTCGGTTCAAGAACAAGCAGCTGGAAAGGGACTACGACTCCTTGAG
AATCAGCTTTGACAAACTCAAGGCTGATTATGACAAACTCCTCCTCGAGAAGCAGAATTTGA
AAAACGAGCTTCTTTCACTGAAAGAAAAATTGCTTAGCAGAGAGGAAAGTATGGAAAGTTCA
GAACCATTTGATGTCATCCATTCACCGGATGCAGAACTTGAGCCTATTCCTGATACAGTGTC
TGAAAATGTTTCCGCCATTGTGCCAATGGTGACACCCAAACAAGAAGAAAGTTCAGCTAAAA
ATGATGTTTTCAACTCAGACAGCCCACGTTCATTTTTGGAGCCCCGTGATTGTTATCGTGTT
TTCGAGTCAGACCAACCAGATTTTTCCCAAGTTGAAGAAGATAATCTCACCAGGAGCTTTCT
ACCCCCTCCGTACTTTCCAAAACTCTACCGAGAGCCACCTGCAAGTTCACGTAATTTTGAAT
TCTCAGCGGAAGATCAGCCCTTTTGGTCCTGGATTTACTGA

SEQ ID NO 45 Populus tremuloides Poptr_HOX16_3 translated amino acid sequence
MAGDKDCGSSKMTIFLRNGRLPPCESLCILTSFSTLHGAKSMVNFRNDGGDTVDMSFFQPHV
KEESSDEDYDAHLKPSEKKRRLTAAQVQFLEKSFEAENKLEPERKMQLAKELGLQPRQVAIW
FQNRRARFKNKQLERDYDSLRISFDKLKADYDKLLLEKQNLKNELLSLKEKLLSREESMESS
EPFDVIHSPDAELEPIPDTVSENVSAIVPMVTPKQEESSAKNDVFNSDSPRSFLEPRDCYRV
FESDQPDFSQVEEDNLTRSFLPPPYFPKLYREPPASSRNFEFSAEDQPFWSWIY

SEQ ID NO 46 Medicago truncatula Medr_HOX16_1 cDNA sequence
ATGGCAGGTGGCAAGCTTTTTGGTGGTTCTAATATGTCACTTTTGCTTCAAAATGAAAGACT
CCCTTGTACTTCTGAAGTCCTTGAATCTCTTTGGGTTCACACCCCTGCTTCTTTTCAAGGTT
CAAATTCAGTGGTTAATTTTGAGAATGGTGGTGGTAGCAACAGAGTGGTAACAGATAGACCC
TTCTTTCAACAACTTGAGAAAGAAGAGAATTGTGGTGATGAAGATTATGAAGCATGCTACCA
TCAACAAGGAAAGAAAAGGAGGCTTTCAAGTGAACAAGTTCAATTTCTTGAAAAGAGTTTTG
AGGTAGAAAACAAGCTTGAACCTGATAGGAAAGTTCAACTTGCAAAAGAGCTTGGTTTGCAA FIGURE 4 (continued)

CCAAGACAAGTTGCTATATGGTTTCAAAACAGAAGGGCAAGGTTCAAAACTAAACAGCTTGA
AAAAGATTATGGCACATTGAAAGCTAGCTTTGATAGTCTCAAAGATGATTATGATAATCTTC
TTCAAGAGAATGACAAGTTAAAAGAAGAGGTGAATTCTCTCAAGAACAAATTGATCCCAAGA
GATAAAGAAAAAGTGAATTCAGAAGACAAATCATCACCAGAAGCAATCAATTCACCTCATAA
CAACATAGATCCAATGGATATAATTTCAATTACAAATTCAGAAAATGGGTCCAAAATGTCAC
TCCCTAATATGGTACTAAAATGTAAGCAAGAAGATGCCAATTCAGCTAAAAGTGATGTGCTT
GATTCTGATAGCCCACATTGCAATGATGGGAACAATCTTTCTTCTTTCATAGAGCCTACAGA
TTCAGATTTCTCACAAGATGAAGAGGATAATGATAACTTGAGTCATAATCTTTTGACTCTTC
CTTGCTTACCAAAAGTTGAAGATGTTTGCTATGATGACCCACATGAAAATTCTTGTAATTTT
GGGTTCCCTGTTGAAGATCAAACCTTTTGTTTCTGGCCTTATTGA

SEQ ID NO 47 Medicago truncatula Medtr_HOX16_1 translated amino acid sequence

MAGGKLFGGSNMSLLLQNERLPCTSEVLESLWVHTPASFQGSNSVVNFENGGGSNRVVTDRP
FFQQLEKEENCGDEDYEACYHQQGKKRRLSSEQVQFLEKSFEVENKLEPDRKVQLAKELGLQ
PRQVAIWFQNRRARFKTKQLEKDYGTLKASFDSLKDDYDNLLQENDKLKEEVNSLKNKLIPR
DKEKVNSEDKSSPEAINSPHNNIDPMDIISITNSENGSKMSLPNMVLKCKQEDANSAKSDVL
DSDSPHCNDGNNLSSFIEPTDSDFSQDEEDNDNLSHNLLTLPCLPKVEDVCYDDPHENSCNF
GFPVEDQTFCFWPY

SEQ ID NO 48 Phaseolus vulgaris Phavu_HOX16 cDNA sequence

ATGGCGGGTGGCAAGCTTCATCCTGGTTCAAACATGTCACTTCTCCTCCAAAACGACAGGCT
CCCTTGCTCCTCTGAAGTCCTTGAGTCTCTTTGGGCTCACACCTCTAACGCTGCTTCCTTCC
AAGGTTCAAAATCTATGGTTGATTTTGAGAATGTTAGTGGGGGCAGGGTGACGGATAGGCCC
TTTTTTCAAGCGTTGGAGAAGGAAGATAACTGTGATGATGATTATGAGGGTTGCTTCCATCA
ACCGGGTAAGAAAAGGAGGCTCACAAGCGAACAAGTTCAGTTCCTTGAAAGGAACTTTGAGG
TCGAGAACAAGCTTGAACCTGAAAGGAAGGTCCAACTTGCAAAGGAGCTTGGCTTGCAGCCA
AGGCAAGTGGCTATATGGTTCCAAAACCGAAGGGCAAGGTTCAAGACCAAGCAGCTAGAAAA
AGATTATGGCACATTGAAAGCTAGCTATGACAGACTCAAAGGTGACTATGAAAGTCTTCTTC
AAGAGAATGACAAGTTAAAAGCAGAGGTGAATTCTCTGGAGAGCAAATTGATTCTTAGAGAT
AAAGAGAAGGAGAATTCGGACGACAAGTCATCTCCTGATGCTGTCAATTCACCCCACAAAGA
GCCTATGGATTTAATTTCAAATTCAACATCTGAAAATGGGACCAAAGTGTCACTCCCTATTA
TGGTAACATGCAAGCAAGAAGATGCCAATTCAGCCAAAAGTGATGTGCTTGATTCGGACAGC
CCACATTGCACTGATGGGAACCATCCCTCTTCATTCGTGGAGCCTGCTGATTCCTCCCATGC
TTTTGAACCAGACCACTCCGACTTCTCCCAAGATGAAGAGGATAATCTTAGTGAAAGCCTTT
TGACCCTCCCTTGCTTACCAAAGGTTGAAGAAGCCTGCTATGATGACCCTCCTGAAAACCCT
TGTAATTTTGGCTTCCATGTCGAGGATCAAACCTTCTGTTTCTGGCCCTATTGA

SEQ ID NO 49 Phaseolus vulgaris Phavu_HOX16 translated amino acid sequence

MAGGKLHPGSNMSLLLQNDRLPCSSEVLESLWAHTSNAASFQGSKSMVDFENVSGGRVTDRP
FFQALEKEDNCDDDYEGCFHQPGKKRRLTSEQVQFLERNFEVENKLEPERKVQLAKELGLQP
RQVAIWFQNRRARFKTKQLEKDYGTLKASYDRLKGDYESLLQENDKLKAEVNSLESKLILRD
KEKENSDDKSSPDAVNSPHKEPMDLISNSTSENGTKVSLPIMVTCKQEDANSAKSDVLDSDS
PHCTDGNHPSSFVEPADSSHAFEPDHSDFSQDEEDNLSESLLTLPCLPKVEEACYDDPPENP
CNFGFHVEDQTFCFWPY

FIGURE 4 (continued)

SEQ ID NO 50 Lotus corniculatus Lotco_Hox16 cDNA sequence

ATGGCGGGAGGGAGGGTCTTTAGCGGCGGTTCTGCTGCTCCTGCAAATGTTTCCGATACCAG
TCTTTTGCTTCAGAATCAACCTCCTGATTCTTCTCTCTTCCTCTCTACCTCTGCTTCTTTTC
TCGGTTCAAGATCCATGGTGAGCTTCGCAGATAATAAATTAGGGCAAACGCGGTCGTTCTTC
TCCGCGTTTGACCTCGATGAGAACGGCGATGAGGTCATGGACGAGTACTTTCACCAATCGGA
GAAGAAGCGCCGTCTCTCTGTTGACCAAGTTCAGTTTCTGGAGAAGAGCTTCGAGGTGGATA
ACAAGCTCGAACCTGACAGGAAAACCAAGATTGCCAAGGACCTTGGTTTGCAGCCACGCCAA
GTCGCAATCTGGTTCCAGAACCGCCGTGCACGGTGGAAGACGAAACAGCTTGAGAAGGATTA
TGATTCTCTGCATAGTAGCTTTGAGAGTCTCAAATCCAACTATGATAATCTTCTCAAGGAGA
AAGACATGTTAAAAGCTGAGGTGGCAAGTCTCACTGAGAAGGTGCTTGCAAGAGAGAATTTG
AAACAAGTTGAAAGTGAAACAAAGGGATTGGTTGAACCACCCCAAAGGCCTTTACTTGATTC
AGTTTCAGAGGGTGAAGAATCTAAAGTCTCTGTTGGGGCTTGTAAACATGAGGATATCAGTT
CAGCCAGGAGTGAGAGTTTGGATTCTGATAGCCCACGTTACAGGGATGGATATGGAGTTAAC
TCAGCAGTGCTAGAGACATGTGATTCTTCTTATGTGGTTGAACCTGATCAATCGGATATGTC
ACAGGATGAGGAAGACAACCTGACCAAGACCCTGTTGCCTCCATACATGTTTTCCAAACTTG
GAGATATGGATTACTCCGACCCGCCTGAAAGTTCATGTAATTTCGGATTTCCGGAGGAAGAT
CATGCCCTTTGGTCATGGTCTTACTGA

SEQ ID NO 51 Lotus corniculatus Lotco_Hox16 translated amino acid sequence

MAGGRVFSGGSAAPANVSDTSLLLQNQPPDSSLFLSTSASFLGSRSMVSFADNKLGQTRSFF
SAFDLDENGDEVMDEYFHQSEKKRRLSVDQVQFLEKSFEVDNKLEPDRKTKIAKDLGLQPRQ
VAIWFQNRRARWKTKQLEKDYDSLHSSFESLKSNYDNLLKEKDMLKAEVASLTEKVLARENL
KQVESETKGLVEPPQRPLLDSVSEGEESKVSVGACKHEDISSARSESLDSDSPRYRDGYGVN
SAVLETCDSSYVVEPDQSDMSQDEEDNLTKTLLPPYMFSKLGDMDYSDPPESSCNFGFPEED
HALWSWSY

FIGURE 4 (continued)

MDSSTVGAPGSSLHGVTGREPAFAFSTEVGGEDAAAASKFDLPVDSEHKAKTIRLLSFANPH
MRTFHLSWISFFSCFVSTFAAAPLVPIIRDNLNLTKADIGNAGVASVSGSIFSRLAMGAICD
MLGPRYGCAFLIMLAAPTVFCMSLIDSAAGYIAVRFLIGFSLATFVSCQYWMSTMFNSKIIG
LVNGLAAGWGNMGGGATQLIMPLVYDVIRKCGATPFTAWRLAYFVPGTLHVVMGVLVLTLGQ
DLPDGNLRSLQKKGDVNRDSFSRVLWYAVTNYRTWIFVLLYGYSMGVELTTDNVIAEYFYDR
FDLDLRVAGIIAASFGMANIVARPTGGLLSDLGARYFGMRARLWNIWILQTAGGAFCLLLGR
ASTLPTSVVCMVLFSFCAQAACGAIFGVIPFVSRRSLGIISGMTGAGGNFGAGLTQLLFFTS
SRYSTGTGLEYMGIMIMACTLPVVLVHFPQWGSMFLPPNAGAEEEHYYGSEWSEQEKSKGLH
GASLKFAENSRSERGRRNVINAAAAAATPPNNSPEHA (SEQ ID NO: 53)

FIGURE 5

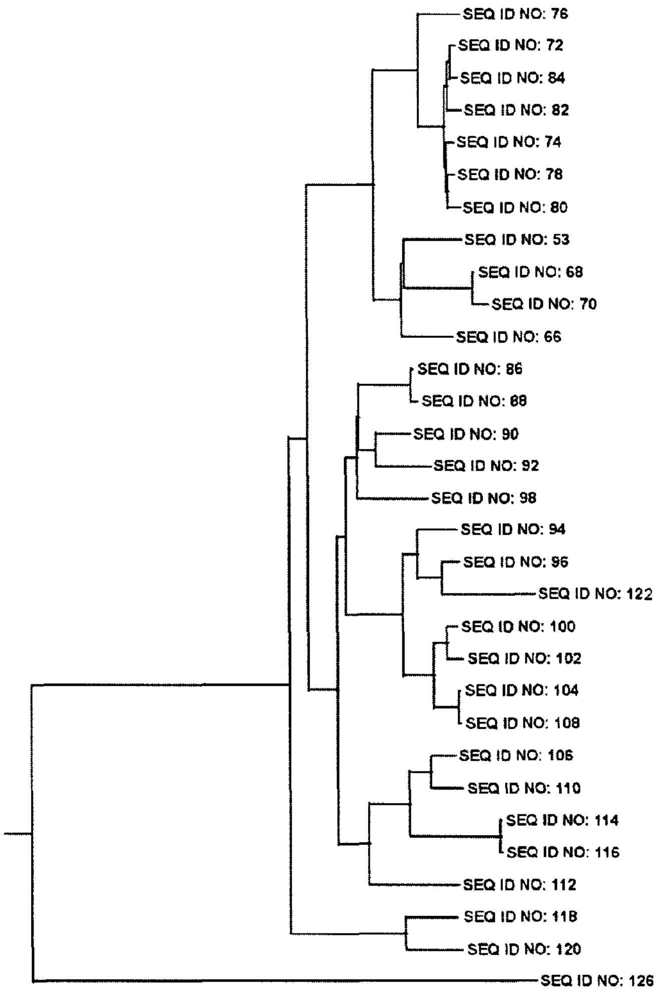

FIGURE 6 A

```
CLUSTAL W (1.83) multiple sequence alignment

SEQID68          -----MAAVGAPGSSLHGVTGREPAFAFSTEHEE-AASNG------GKFDLPVDSEHKAK
SEQID70          -----MAAVGAPGSSLHGVTGREPAFAFSTEHEE-AASNG------GKFDLPVDSEHKAK
SEQID66          ------MEVGAPGSSLHGVTGREPAFAFSTSAVP-DDDAA------SKFDLPVDSEHKAK
SEQID53          ---MDSSTVGAPGSSLHGVTGREPAFAFSTEVGGEDAAAA------SKFDLPVDSEHKAK
SEQID78          ---------------------------MEVEASAHGDTAA------SKFTLPVDSEHKAK
SEQID80          ---------------------------MEVESSAHGDAAA------SKFTLPVDSEHKAK
SEQID74          ---------------------------MEVQAGSHADAAA------SKFTLPVDSEHKAK
SEQID72          ---------------------------MEVEAGAHGDTAA------SKFTLPVDSEHKAK
SEQID84          ---------------------------MEVEAGAHGDTAA------SKFTLPVDSEHKAK
SEQID82          ---------------------------MEVEAGAHGDAAA------SKFTLPVDSEHKAK
SEQID76          -------------------------MEVESSSHGAGDEAA------SKFSLPVDSEHKAK
SEQID86          ----MAEVEGEPGSSMHGVTGREQTFAFSVASPIVP------TDPTAKFDLPVDSEHKAK
SEQID88          ----MAEVEGEPGSSMHGVTGREQTFAFSVASPIVP------TDPTAKFDLPVDSEHKAK
SEQID90          ----MAEIEGSPGSSMHGVTGREQTFVASVASPIVP------TDTTAKFALPVDSEHKAK
SEQID92          ----MVEIEGSPGTSMHGVTGREQTFISSVSSPMVP------TDTTAKFDLPVDSQHKAK
SEQID98          ----MADVEGSPGSSMHGVTGREQSFAFSVASPTVP------TDTTAKFALPVDSEHKAK
SEQID96          ----MGDIEGSPGSSMHGVTGREPVLAFSVASLIVP------TDTSANFKVPVDSEHKAK
SEQID122         ----MGDMEGSPGSSMHGVTGREPSLAFSVASRID---------TSAEFHVPVDSEHKAK
SEQID94          ----MVDIEGSPGSSMHGVTGREPVLAFSVASPMVQ------TDTTAHFKVPVDSEHKAK
SEQID100         ----MGDIEGEPGSSMHGVTGREPVLAFSVASPMVP------TDTTAKFSVPVDTEHKAK
SEQID102         ----MADIEGEPGSSMHGVTGREPVLAFSVASPMVP------TDTTAKFSVPVDTEHKAK
SEQID104         ----MADVEGSPGSSMHGVTGREPVLAFSVASPMVP------TDTSAKFSVPVDTEHKAK
SEQID108         ----MTDVEGSPGSSMHGVTGREPVLAFSVASPMVP------TDTSAKFSVPVDTEHKAK
SEQID106         ----MGDSTGEPGSSMHGVTGREQSFAFSVQSPIVH------TDKTAKFDLPVDTEHKAT
SEQID110         ----MGDSTGEPGSSMHGVTGREQTFAFSVASPIVP------TDKTAKFDLPVDSEHKAT
SEQID114         -----MGSTDEPGSSMHGVTGREQSYAFSVDG-SEP------TNTKKKYNLPVDAEDKAT
SEQID116         -----MGSTDEPRSSMHGVTGREQSYAFSVDG-SEP------TNTKKKYNLPVDAEDKAT
SEQID112         ----MADGFGEPGSSMHGVTGREQSYAFSVESPAVP------SDSSAKFSLPVDTEHKAK
SEQID118         MTHNHSNEEGSIGTSLHGVTAREQVFSFSVDASS---QTVQSDDPTAKFALPVDSEHRAK
SEQID120         MAHNHSNEDGSIGTSLHGVTAREQVFSFSVQEDVPSSQAVRTNDPTAKFALPVDSEHRAK
                                             .                  .: :***::.:*.

SEQID68          SVRLFSVANPHMRTFHLSWISFFTCFVSTFAAAPLVPIIRDNLNLTKADIGNAGVASVSG
SEQID70          SVRLFSVANPHMRTFHLSWISFFTCFVSTFAAAPLVPIIRDNLNLTKADIGNAGVASVSG
SEQID66          SIRLFSFANPHMRTFHLSWISFFTCFVSTFAAAPLVPIIRDNLNLTKADIGNAGVASVSG
SEQID53          TIRLLSFANPHMRTFHLSWISFFSCFVSTFAAAPLVPIIRDNLNLTKADIGNAGVASVSG
SEQID78          SFRLFSFANPHMRTFHLSWISFFTCFVSTFAAAPLVPIIRDNLNLAKADIGNAGVASVSG
SEQID80          SFRLFSFANPHMRTFHLSWISFFTCFVSTFAAAPLVPIIRDNLNLAKADIGNAGVASVSG
SEQID74          SFRLFSFANPHMRTFHLSWISFFTCFVSTFAAAPLVPIIRDNLNLAKADIGNAGVASVSG
SEQID72          SFRLFSFANPHMRTFHLSWISFFTCFISTFAAAPLVPIIRDNLNLAKADIGNAGVASVSG
SEQID84          SFRLFSFANPHMRTFHLSWISFFTCFVSTFAAAPLVPIIRDNLNLAKADIGNAGVASVSG
SEQID82          SFRLFSFANPHMRTFHLSWISFFTCFVSTFAAAPLVPIIRDNLNLAKADIGNAGVASVSG
SEQID76          SIRLFSFANPHMRTFHLSWISFFTCFVSTFAAAPLVPIIRDNLNLAKADIGNAGVASVSG
SEQID86          VFKIFSLANPHMRTFHLSWISFFTCFVSTFAAAPLVPIIRDNLNLTKQDIGNAGVASVSG
SEQID88          VFKIFSLANPHMRTFHLSWISFFTCFVSTFAAAPLVPIIRDNLNLTKQDIGNAGVASVSG
SEQID90          VFKLFSLANPHMRTFHLSWISFFTCFVSTFAAAPLVPIIRDNLNLTKSDIGNAGVASVSG
SEQID92          VFKLFSLANPHMTTFHLSWISFFTCFVSTFAAAPLVPIIRDNLNLTKSDIGNAGVASVSG
SEQID98          VFKIFSFANPHMRTFHLSWISFFTCFVSTFAAAPLVPIIRDNLNLTKSDIGNAGVASVSG
SEQID96          VFKFYSFSKPHGLTFQLSWISFCTCFVSTFAAAPLVPIIRDNLNLTKMDVGNAGVASVSG
SEQID122         VFKFKSFSPPHGLQFQLTWISFPTCFVSTFAARPLVVIIRDNLNPTKMDVGNAGVASVTG
SEQID94          VFKFYSFSKPHGLTFQLSWISFFTCFVSTFAAAPLVPIIRDNLNLTKMDVGNAGVASVSG
SEQID100         IFKFYSFSKPHGLTFQLSWISFFTCFVSTFAAAPLVPIIRDNLNLTKMDVGNAGVASVSG
SEQID102         VFKFYSFSKPHGLTFQLSWISFFTCFVSTFAAAPLVPLIRDNLNLTKMDVGNAGVASVSG
SEQID104         QFKFYSFSKPHGLTFQLSWISFFTCFVSTFAAAPLVPIIRDNLNLTKMDVGNAGVASVSG
SEQID108         QFKFYSFSKPHGLTFQLSWISFFTCFVSTFAAAPLVPIIRDNLNLTKMDVGNAGVASVSG
SEQID106         VFKLFSFAKPHMRTFHLSWISFSTCFVSTFAAAPLVPIIRENLNLTKQDIGNAGVASVSG
SEQID110         VFKLFSFAKPHMRTFHLSWISFSTCFVSTFAAAPLVPIIRENLNLTKQDIGNAGVASVSG
SEQID114         VFKLFSFAKPHMRTFHLSWISFSTCFVSTFAAAPLIPIIRENLNLTKHDIGNAGVASVSG
SEQID116         VFKLFSFAKPHMRTFHLSWISFSTCFVSTFAAAPLIPIIRENLNLTKHDIGNAGVASVSG
SEQID112         VFKLLSFEAPHMRTFHLAWISFFTCFISTFAAAPLVPIIRDNLNLTRQDVGNAGVASVSG
SEQID118         VFNPLSFAKPHMRAFHLGWLSFFTCFISTFAAAPLVPIIRDNLDLTKTDIGNAGVASVSG
SEQID120         VFKPLSFAKPHMRAFHLGWISFFTCFISTFAAAPLVPVIRDNLDLTKTDIGNAGVASVSG
                  ..  *.  **   *:* *:** :**:***** **: :**:**: :: *:********:*
```

FIGURE 6 B

```
SEQID68     SIFSRLTMGAVCDLLGPRYGCAFLIMLSAPTVFCMSLIDDAAGYITVRFLIGFSLATFVS
SEQID70     SIFSRLTMGAVCDLLGPRYGCAFLIMLSAPTVFCMSLIDDAAGYITVRFLIGFSLATFVS
SEQID66     SIFSRLAMGAICDLLGPRYGCAFLIMLTAPTVFCMSLIDDAAGYIVVRFLIGFSLATFVS
SEQID53     SIFSRLAMGAICDMLGPRYGCAFLIMLAAPTVFCMSLIDSAAGYIAVRFLIGFSLATFVS
SEQID78     SIFSRLAMGAICDLLGPRYGCAFLVMLSAPTVFCMAAIDDASGYIAVRFLIGFSLATFVS
SEQID80     SIFSRLAMGAVCDLLGPRYGCAFLVMLSAPTVFCMAVIDDASGYIAVRFLIGFSLAAFVS
SEQID74     SIFSRLAMGAICDLLGPRYGCAFLVMLSAPTVFCMAVIDDASGYIAVRFLIGFSLATFVS
SEQID72     SIFSRLAMGAICDLLGPRYGCAFLVMLSAPTVFCMAVIDDASGYIAVRFLIGFSLATFVS
SEQID84     SIFSRLAMGAICDLLGPRYGCAFLVMLSAPTVFCMAVIDDASGYIAVRFLIGFSLATFVS
SEQID82     SIFSRLAMGAICDLLGPRYGCAFLVMLSAPTVFCMAVIDDASGYIAVRFLIGFSLATFVS
SEQID76     SIFSRLAMGAICDLLGPRYGCAFLVMLAAPTVFCMSLIDDAAGYITVRFLIGFSLATFVS
SEQID86     SIFSRLVMGAVCDLLGPRYGCAFLIMLSAPTVFCMSFVSDAGGYLAVRFMIGFSLATFVS
SEQID88     SIFSRLVMGAVCDLLGPRYGCAFLIMLSAPTVFCMSFVSDAGGYLAVRFMIGFSLATFVS
SEQID90     SIFSRLAMGAVCDMLGPRYGCAFLIMLSAPTVFCMSFVKDAAGYIAVRFLIGFSLATFVS
SEQID92     SIFSRLTMGVICDLLGPRYGCAFLIMLSAPTVFCMSFVNDAAGYIVVRFMIGFSLATFVS
SEQID98     SIFSRLVMGAVCDLLGPRYGCAFLIMLSAPTVFCMSFVDSAGGYLAVRFMIGFSLATFVS
SEQID96     SILSRLAMGAICDMLGPRYGCAFLIMLSAPTVLCMSFVSSAGGYVAVRFMIGFSLATFVS
SEQID122    SILSRGAMGAICDMLGPRYGCAFLIMLSAPKVLCMSFVSSAGGYVAVRFMIGFSLATFVS
SEQID94     SILSRLAMGAICDMLGPRYGCAFLIMLSAPTVFCMSFVSSAGGYVAVRFMIGFSLATFVS
SEQID100    SILSRLVMGAVCDMLGPRYGCAFLIMLSAPTVFCMSFVSSAGGYVAVRFMIGFSLATFVS
SEQID102    SILSRLVMGAVCDMLGPRYGCAFLIMLSAPTVFCMSFVSSAGGYVAVRFMIGFSLATFVS
SEQID104    SILSRLTMGAVCDLLGPRYGCAFLIMLSAPTVFCMSFVSSAGGYVAVRFMIGFSLATFVS
SEQID108    SILSRLTMGAVCDLLGPRYGCAFLIMLSAPTVFCMSFVSSAGGYVAVRFMIGFSLATFVS
SEQID106    SIFSRLVMGAVCDLLGPRYGCAFLVMLSAPTVFSMSFVSDAAGFITVRFMIGFCLATFVS
SEQID110    SIFSRLVMGAVCDLLGPRYGCAFLVMLSAPTVFSMSFVSGAAGFITVRFMIGFCLATFVS
SEQID114    SIFSRLVMGAVCDLLGPRYGCAFLVMLSAPTVFSMSFVSDAAGFITVRFMIGFCLATFVS
SEQID116    SIFSRLVMGAVCDLLGPRYGCAFLVMLSAPTVFSMSFVSDAAGFITVRFMIGFCLATFVS
SEQID112    SIFSRLVMGAVCDLLGPRYGCAFLVMLSAPTVFSMSFVGGAGGYITVRFMIGFCLATFVS
SEQID118    AIFSRLAMGAVCDLLGARYGTAFSLMLTAPTVFSMSFVGGPSGYLGVRFMIGFCLATFVS
SEQID120    AIFSRLAMGAVCDLLGARYGTAFSLMLTAPAVFSMSFVADAGSYLAVRFMIGFCLATFVS
            :*:** .**.:**:**.*** ** :**:** *:.*: : ....:: ***:***.**:***

SEQID68     CQYWMSTMFSSKIIGTVNGLAAGWGNMGGGATQLIMPLVYDVIRKCGATPFTAWRLAYFV
SEQID70     CQYWMSTMFSSKIIGTVNGLAAGWGTMGRRRHAAHMPLVYDVIRKCGATPFTAWRLAYFV
SEQID66     CQYWMSTMFNSKIIGTVNGLAAGWGNMGGGATQLPMPLVYDVIRKCGATPFTAWRIAYFV
SEQID53     CQYWMSTMFNSKIIGLVNGLAAGWGNMGGGATQLIMPLVYDVIRKCGATPFTAWRLAYFV
SEQID78     CQYWMSTMFNSKIIGTVNGLAAGWGNMGGGATQLIMPLVFHAIQKCGATPFVAWRIAYFV
SEQID80     CQYWMSTMFNSKIIGTVNGLAAGWGNMGGGATQLIMPLVFHAIQKCGATPFVAWRIAYFV
SEQID74     CQYWMSTMFNSKIIGTVNGLAAGWGNMGGGATQLIMPLVFHAIQKCGATPFVAWRIAYFV
SEQID72     CQYWMSTMFNSKIIGTVNGLAAGWGNMGGGATQLIMPLVFHAIQKCGATPFVAWRIAYFV
SEQID84     CQYWMSTMFNSKIIGTVNGLAAGWGNMGGGATQLIMPLVFHAIQKCGATPFVAWRIAYFV
SEQID82     CQYWMSTMFNSKIIGTVNGLAAGWGNMGGGATQLIMPLVFHAIQKCGATPFVAWRIAYFV
SEQID76     CQYWMSTMFNSKIIGTVNGLAAGWGNMGGGATQLIMPLVFHAIQKCGATPFVAWRIAYFV
SEQID86     CQYWMSTMFNSKIIGLVNGTAAGWGNMGGGATQLLMPLVFDIIGRVGATPFTAWRIAFFI
SEQID88     CQYWMSTMFNSKIIGLVNGTAAGWGNMGGGATQLLMPLVFDIIGRVGATPFTAWRIAFFI
SEQID90     CQYWMSTMFNSKIIGLANGTAAGWGNMGGGATQLIMPLVYELIRRAGATPFTAWRIAFFV
SEQID92     CQYWMSTMFNSKIIGLVNGTAAGWGNMGGGATQLIMPIVYELIRRAGSTGFTAWRIAFFI
SEQID98     CQYWMSTMFNSKIIGLVNGTAAGWGNMGGGATQLVMPLVYELIKRAGSTSFSAWRIAFFV
SEQID96     CQYWMSTMFNSQIIGLVNGTAAGWGNMGGGATQLIMPLLYDIIRRAGATPFTAWRIAFFI
SEQID122    CRYWMSTSMHSDIIGLVNGTAAGWGNMTGGATQLIMPLLYDIIREAGATPFTAWRIALFI
SEQID94     CQYWMSTMFNSQIIGLVNGTAAGWGNMGGGATQLIMPILYDIIRRAGATPFTAWRIAFFI
SEQID100    CQYWMSTMFNSQIIGLVNGTAAGWGNMGGGATQLIMPIVYDIIRRAGATPFTAWRIAFFI
SEQID102    CQYWMSTMFNSQIIGLVNGTAAGWGNMGGGATQLIMPILYDIIRKAGATPFTAWRIAFFI
SEQID104    CQYWMSTMFNSKIIGLVNGTAAGWGNMGGGATQLIMPLLYDIIRRAGATPFTAWRIAFFI
SEQID108    CQYWMSTMFNSKIIGLVNGTAAGWGNMGGGATQLIMPLLYDIIRRAGAIPFTAWRIAFFI
SEQID106    CQYWMSTMFNSQIIGLVNGTAAGWGNMGGGITQLLMPIVYEIIRRCGSTAFTAWRIAFFV
SEQID110    CQYGMSTMFNSQIIGLVNGTAAGWGNMGGGITQLLMPVVYEIIRRCGATAFTAWRLAFFV
SEQID114    CQYWMSTMFNSQIIGLVNGTAAGWGNMGGGITQLLMPIVYEIIRRCGSTAFTAWRIAFFV
SEQID116    CQYWMSTMFNSQIIGLVNGTAAGWGNMGGGITQLLMPIVYEIIRRCGSTAFTAWRIAFFV
SEQID112    CQYWMSTMFNGQIIGLVNGTAAGWGNMGGGVTQLLMPMVYEIIRRLGSTSFTAWRMAFFV
SEQID118    CQYWTSVMFNGKIIGLVNGCAGGWGDMGGGVTQLLMPMVFHVIKLAGATPFMAWRIAFFV
SEQID120    CQYWTSVMFTGKIIGLVNGCAGGWGDMGGGVTQLLMPMVFHVIKLTGATPFTAWRFAFFI
            *:*  *. : ..*** .** *.*** *        **:::. *   *:  * ***:* *:
```

FIGURE 6 B (continued)

```
SEQID68     PGLMHVVMGVLVLTLGQDLPDG---NLRSLQKKGNVNKDSFSKVMWYAVINYRTWIFVLL
SEQID70     PGLMHVVMGVLVLTLGQDLPDG---NLRSLQKKGNVNKDSFSKVMWYAVINYRTWIFVLL
SEQID66     PGLMHVVMGILVLTLGQDLPDG---NLRSLQKKGDANKDKFSKVLWYAVTNYRTWIFVLL
SEQID53     PGTLHVVMGVLVLTLGQDLPDG---NLRSLQKKGDVNRDSFSRVLWYAVTNYRTWIFVLL
SEQID78     PGMMHIVMGLLVLTMGQDLPDG---NLASLQKKGDMAKDKFSKVLWGAVTNYRTWIFVLL
SEQID80     PGMMHIVMGLLVLTMGQDLPDG---NLASLQKKGDMAKDKFSKVLWGAVTNYRTWIFVLL
SEQID74     PGMMHIVMGLLVLTMGQDLPDG---NLASLQKKGDMAKDKFSKVLWGAVTNYRTWIFVLL
SEQID72     PGMMHIVMGLLVLTMGQDLPDG---NLASLQKKGDMAKDKFSKVLWGAVTNYRTWIFVLL
SEQID84     PGMMHIVMGLLVLTMGQDLPDG---NLASLQKRGDMAKDKFSKVLWGAVTNYRTWIFVLL
SEQID82     PGMMHIVMGLLVLTMGQDLPDG---NLASLQKKGDMAKDKFSKVLWGAVTNYRTWIFVLL
SEQID76     PGMMHVVMGLLVLTMGQDLPDG---NLASLQKKGEMAKDKFSKVVWGAVTNYRTWIFVLL
SEQID86     PGWLHVIMGIMVLTLGQDLPDG---NLAALQKKGDVAKDQFSKVLWHAVTNYRTWIFVLL
SEQID88     PGWLHVIMGIMVLTLGQDLPDG---NLAALQKKGDVAKDQFSKVLWHAITNYRTWIFVLL
SEQID90     PGFMHVIMGILVLTLGQDLPDG---NLGALRKKGDVAKDKFSKVLWYAITNYRTWIFALL
SEQID92     PGFMHVFMGILVLTLGQDLPDG---NLSALQKKGDVAKDKFSKVLWYAITNYRTWIFALL
SEQID98     PGWLHVIMGILVLNLGQDLPDG---NLGALKKKGDVAKDKFSKVLWYAVTNYRTWIFVLL
SEQID96     PGWLHVIMGILVLTLGQDLPDG---NLASLQKKGDVSKDKFSKILWYAATNYRTWILVLL
SEQID122    PGWLHVISGILVLTLGQDLPDGNAQNEASLRKKGRVHKDKFSKILRYAATNYRTWILVLL
SEQID94     PGWLHVIMGILVLTLGQDLPDG---NLASLQKKGDVSKDKFSKILWYAATNYRTWIFVLL
SEQID100    PGWLHIVMGILVLTLGQDLPDG---NRGDLQKKGDVSKDKFSNILWYAATNYRTWIFVLL
SEQID102    PGWLHVVMGILVLTLGQDLPDG---NRGDLQKKGGVSKDKFTNILWYAATNYRTWIFVLL
SEQID104    PGWLHVVMGILVLTLGQDLPDG---NRGTLQKTGTVAKDKFGNILWYAATNYRTWIFVLL
SEQID108    PGWLHVVMGILVLTLGQDLPDG---NRGTLQKTGTVAKDKFGNILWYAATNYRTWIFVLL
SEQID106    PGWLHIIMGILVLNLGQDLPDG---NRATLEKAGEVAKDKFGKILWYAVTNYRTWIFVLL
SEQID110    PGWLHIIMGVLVLNLGQDLPDG---NRSALEKKGEVAKDKFGKIMWYAVTNYRTWIFVLL
SEQID114    PGWLHIIMGILVLTLGQDLPGG---NRAAMEKAGEVAKDKFGKILWYAVTNYRTWIFVLL
SEQID116    PGWLHIIMGILVLTLGQDLPGG---NRAAMEKAGEVAKDKFGKILWYAVTNYRTWIFVLL
SEQID112    PGWMHIIMGILVLTLGQDLPDG---NRSTLEKKGAVTKDKFSKVLWYAITNYRTWVFVLL
SEQID118    PGFLQVVMGILVLSLGQDLPDG---NLSTLQKSGQVSKDKFSKVFWFAVKNYRTWILFVL
SEQID120    PGILQIVMGILVLTLGQDLPDG---NLSTLQKSGQVSKDKFSKVFWFAVKNYRTWILFML
            ** :::. *::**.:*****.*    *    :.* *    :*.* .:.  *  *****:: :*

SEQID68     YGYCMGVELTTDNVIAEYMYDRFDLDLRVAGTIAACFGMANIVARPMGGIMSDMGARYWG
SEQID70     YGYCMGVELTTDNVIAEYMYDRFDLDLRVAGTIAACFGMANIVARPMGGIMSDMGARYWG
SEQID66     YGYCMGVELTTDNVIAEYYYDHFDLDLRVAGIIAACFGMANIVARPLGGILSDIGARYWG
SEQID53     YGYSMGVELTTDNVIAEYFYDRFDLDLRVAGIIAASFGMANIVARPTGGLLSDLGARYFG
SEQID78     YGYCMGVELTTDNVIAEYYYDHFHLDLRAAGTIAACFGMANIVARPMGGYLSDLGARYFG
SEQID80     YGYCMGVELTTDNVIAEYYYDHFHLHLRAAGTIAACFGMANIVARPMGGYLSDLGARYFG
SEQID74     YGYCMGVELTTDNVIAEYYYDHFHLDLRAAGTIAACFGMANIVARPMGGYLSDLGARYFG
SEQID72     YGYCMGVELTTDNVIAEYYFDHFHLDLRAAGTIAACFGMANIVARPTGGYLSDLGARYFG
SEQID84     YGYCMGVELTTDNVIAEYYFDHFHLDLRAAGTIAACFGMANIVARPMGGYLSDLGARYFG
SEQID82     YGYCMGVELTTGNVIAEYYFDHFHLNLRAAGTIAACFGMANIVARPMGGYLSDLGARYFG
SEQID76     YGYCMGVELTTDNVIAEYYFDHFHLDLRTSGTIAACFGMANIVARPAGGYLSDLGARYFG
SEQID86     YGYSMGVELSTDNVIAEYFYDRFNLKLHTAGIIAATFGMANLVARPFGGFASDRAARYFG
SEQID88     YGYSMGVELSIDNVIAEYFYDRFNLKLHTAGIIAAAFGMANIVARPFGGFASDRAARYFG
SEQID90     YGYSMGVELTTDNVIAEYFYDRFNLKLHTAGIIAASFGMANLVARPFGGYASDVAARLFG
SEQID92     YGYSMGVELTTDNVIAEYFYDRFNLKLHTVGIIAASFGMANLVARPFGGYVSDVAARLFG
SEQID98     YGYSMGVELSTDNVIAEYFYNRFDLKLHTAGVIAATFGMANLVARPFGGYFSDVAARYFG
SEQID96     YGYSMGVELTTDNVIAEYFFDRFDLKLHTAGIIAATFGMANLLARPFGGWSSDVAAKHFG
SEQID122    YGYSMGVELTTDNVIAEYFFDRFDLKLHTPGIIAATFGMANLLARPFGGWSSDVAAKHFG
SEQID94     YGYSMGVELTTDNVIAEYFFDRFDLKLHTAGIIAATFGMANLLARPFGGWSSDIAAKHFG
SEQID100    YGYSMGVELSTDNVIAEYFFDRFDLKLHTAGIIAATFGMANLLARPFGGFSSDYAAKRFG
SEQID102     YGYSMGVELSTDNVIAEYFFDRFDLKLHTAGIIAATFGMANLLARPFGGFSSDFAAKRFG
SEQID104    YGYSMGVELSTDNVIAEYFFDRFDLKLSTAGIIAATFGMANLLARPFGGFSSDYAAKKFG
SEQID108    YGYSMGVELSTDNVIAEYFFDRFDLKLSTAGIIAATFGMANLLARPFGGFSSDYAAKKFG
SEQID106    YGYSMGVELSTDNVIAEYFFDRFHLKLHTAGLIAACFGMANFFARPAGGYASDFAAKYFG
SEQID110    YGYSMGVELSTDNVIAEYFFDRFHLKLHTAGIIAACFGMANFFARPAGGYASDLAAKYFG
SEQID114    YGYSMGVELSTDNVIAEYFFDRFHLKLHTAGIIAACFGMANFFARPAGGWASDIAAKRFG
SEQID116    YGYSMGVELSTDNVIAEYFFDRFHLKLHTAGIIAACFGMANFFARPAGGWASDIAAKRFG
SEQID112    YGYSMGIELTTDNVIAEYFFDRFHLKLHTAGIIASFGMANFFARPIGGWASDIAARRFG
SEQID118    YGSSMGIELTINNVISGYFYDRFNLKLQTAGIVAASFGMANFIARPFGGYASDVAARVFG
SEQID120    YGFSMGVELTINNVISGYFYDRFNLTLHTAGIIAASFGMANFFARPFGGYASDVAARLFG
            ** .**:**: .***: * :::*.* * . * :** *****:.*** **  ** .*: :*
```

FIGURE 6 B (continued)

```
SEQID68     MRARLWNIWILQTAGGAFCLWLGRASTLP---VSVVAMVLFSFCAQAACGAIFGVIPFVS
SEQID70     MRARLWNIWILQTAGGAFCLWLGRASTLP---VSVVAMVLFSFCAQAACGAIFGVIPFVS
SEQID66     MRARLWNIWILQTAGGAFCLWLGRASTLP---ASITAMVLFSFCAQAACGAIFGVTPFVT
SEQID53     MRARLWNIWILQTAGGAFCLLLGRASTLP---TSVVCMVLFSFCAQAACGAIFGVIPFVS
SEQID78     MRARLWNIWILQTAGGAFCIWLGRASALP---ASVTAMVLFSICAQAACGAVFGVAPFVS
SEQID80     MRARLWNIWILQTAGGAFCIWLGRASALP---ASVTAMVLFSICAQAACGAVFGVAPFVS
SEQID74     MRARLWNIWILQTAGGAFCIWLGRASALP---ASVTAMVLFSICAQAACGAVFGVAPFVS
SEQID72     MRARLWNIWILQTAGGAFCIWLGRASALP---ASVTAMVLFSICAQAACGAIFGVAPFVS
SEQID84     MRA-LWNIWILQTAGGAFCIWLGRASALP---ASVTAMVLFSICAQAACGAIFGVAPFVS
SEQID82     MRARLWNIWILQTAGGAFCIWLGRASALP---ASVTAMVLFSICAQAACGAIFGVEPFVS
SEQID76     MRARLWNIWILQTAGGAFCLWLGRAKALP---ESITAMVLFSICAQAACGAVFGVIPFVS
SEQID86     MRGRLWTLWILQTLGGVFCIWLGRANSLP---IAVFAMILFSVGAQAACGATFGVIPFIS
SEQID88     MRGRLWTLWILQTLGGVFCIWLGRANSLP---IAVFAMILFSVGAQAACGATFGVIPFIS
SEQID90     MRGRLWTLWILQTLGGVFCIWLGRANSLP---IAVLAMILFSIGAQAACGATFGIIPFIS
SEQID92     MRGRLWTLWILQTLGGVFCIWLGRANSLP---IAVLAMILFSVGAQAACGATFGIIPFIS
SEQID98     MRGRLWVLWILQTLGGVFCTWLGRANSLP---LAVTAMILFSIGAQAACGATFGIIPFIS
SEQID96     MRGRLWNSWILQTLGGVFCLLLGRATT---LPLAITWMIIFSIGAQAACGVTFGIIPFIS
SEQID122    MRGRHWNSWDLQTLGGVFCLLLVRATTSPIDALAITWMIIFSIGAQAATGVTFGIIPFIS
SEQID94     MRGRLWNLWILQTLGGVFCFLLGKANTLP---MAIAWMIIFSLGAQAACGATFGIIPFIS
SEQID100    MRGRLWVLWILQTLGGVFCVLLGRSNPLP---IAVTFMILFSIGAQAACGATFGIIPFIS
SEQID102    MRGRLWVLWILQTLGGVFCVLLGRSNSLP---IAVTFMILFSVGAQAACGATFGIIPFIS
SEQID104    MRGRLWVLWILQTLGGVFCVLLGRSNSLP---LAVTFMILFSIGAQAACGATFGIIPFIS
SEQID108    MRGRLWVLWILQTLGGVFCVLLGRSNSLP---LAVTFMILFSIGAQAACGATFGIIPFIS
SEQID106    MRGRLWTLWIIQTAGGLFCVWLGRANTLVT---AVVAMVLFSMGAQAACGATFAIVPFVS
SEQID110    MRGRLWALWIIQTAGGVFCVWLGRANTLVT---AVVAMVLFSLGAQAACGATFAIVPFVS
SEQID114    MRGRLWTLWIIQTSGGLFCVWLGRANTLVT---AVVSMVLFSLGAQAACGATFAIVPFVS
SEQID116    MRGRLWTLWIIQTSGGLFCVWLGRANTLVT---AVVSMVLFSLGAQAACGATFAIVPFVS
SEQID112    MRGRLWTLWIIQTLGGFFCLWLGRATTLPT---AVVFMILFSLGAQAACGATFAIIPFIS
SEQID118    MRGRLWTLWIFQTVGGALFCIWLGRASSLP---IAILAMMLFSIGTQAACGALFGVAPFVS
SEQID120    MRGRLWILWILQTVGGALFCIWLGRASSLP---IAILAMMLFSMGTQAACGALFGVAPFVS
            **.  *  * :** *. **  * ::..      ::  *::**. :*** *. *.: **::

SEQID68     RRSLGIISGMTGAGGNFGAGLTQLLFFTSSTYSTGRGLEYMGIMIMACTLPVVFVHFPQW
SEQID70     RRSLGIISGMTGAGGNFGAGLTQLLFFTSSTYSTGRGLEYMGIMIMACTLPVVFVHFPQW
SEQID66     RRSLGIMSGMTGAGGNFGAGLTQLLFFTSSKYSTGMGLEYMGIMIMACTLPVVFVHFPQW
SEQID53     RRSLGIISGMTGAGGNFGAGLTQLLFFTSSRYSTGTGLEYMGIMIMACTLPVVLVHFPQW
SEQID78     RRSLGIISGLTGAGGNVGAGLTQLLFFTSSQYSTGRGLEYMGIMIMACTLPVALVHFPQW
SEQID80     RRSLGIISGLTGAGGNVGAGLTQLLFFTSSQYSTGRGLEYMGIMIMACTLPITLVHFPQW
SEQID74     RRSLGIISGLTGAGGNVGAGLTQLLFFTSSQYSTGRGLEYMGIMIMACTLPVALVHFPQW
SEQID72     RRSLGIISGLTGAGGNVGAGLTQLLFFTSSQYSTGRGLEYMGIMIMACTLPVALVHFPQW
SEQID84     RRSLGIISGLTGAGGNVGAGLTQLLFFTSSQYSTGRGLEYMGIMIMACTLPVALVHFPQW
SEQID82     RRSLGIISGLTGAGGNVGAGLTQLLFFTSSQYSTGRGLEYMGIMIMACTLPVALVHFPQW
SEQID76     RRSLGIISGLSGAGGNFGAGLTQLLFFTSSKYGTGRGLEYMGIMIMACTLPVALVHFPQW
SEQID86     RRSLGIISGLTGAGGNFGSGLTQLVFFSSSAFSTATGLSLMGVMIVCCTLPVTLVHFPQW
SEQID88     RRSLGIISGLTGAGGNFGSGLTQLVFFSSAAFSTATGLSLMGVMIVCCTLPVTLVHFPQW
SEQID90     RRSLGIISGLTGAGGNFGSGLTQLVFFSTSKFSTATGLSLMGVMIVACTLPVSVVHFPQW
SEQID92     KRSLGIISGLTGAGGNFGSGLTQLVFFSTSRFSTGAGLSWMGVMIVGCTLPVTLVHFPQW
SEQID98     RRSLGIISGLTGAGGNFGSGLTQLVFFSSSSLSTAAGLSWMGVMICGCTLPVTLVYFPQW
SEQID96     RRSLGIISGMTGAGGNFGSGLTQLLFFTSTKYSTGTGLTYMGMMIIACTLPVMLVRFPQW
SEQID122    RRYLGIISQMTGANGNFGSGQTQPLEFDSTKYNTGLGLTYMGMMIIACTLPPMLVWFWQD
SEQID94     RRSLGIISGMTGAGGNFGSGLTQLLFFTTTKWSTETGLSYMGIMIIACTLPVSLVHFPQW
SEQID100    RRSLGIISGMTGAGGNFGSGLTQLLFFTSSKYSTATGLTYMGLMIIGCTLPVTFCHFPQW
SEQID102    RRSLGIISGMTGAGGNFGSGLTQLLFFTSSKYSTATGLTYMGMMIIGCTLPVTLCHFPQW
SEQID104    RRSLGIISGMTGAGGNFGSGLTQLLFFTSSKYSTATGLTYMGFMIIGCTLPVTFCHFPQW
SEQID108    RRSLGIISGMTGAGGNFGSGLTQLLFFTSSKYSTATGLTYMGFMIIGCTLPVTFCHFPQW
SEQID106    RRALGIISGLTGAGGNFGSGLTQLLFFSTSHFTTEQGLTWMGVMIVACTLPVTLVHFPQW
SEQID110    RRALGIISGLTGAGGNFGSGLTQLIFFSTSRFTTEQGLTWMGVMIVACTLPVTLIHFPQW
SEQID114    RRALGIISGLTGAGGNFGSGLTQLVFFSTSRFTTEEGLTWMGVMIVACTLPVTLIHFPQW
SEQID116    RRALGIISGLTGAGGNFGSGLTQLVFFSTSRFTTEEGLTWMGVMIVACTLPVTLIHFPQW
SEQID112    RRSLGIISGLTGAGGNFGSGLTQLVFFSTSTFSTEQGLTWMGVMIMACTLPVTLVHFPQW
SEQID118    RRSLGLISGLTGAGGNFGSGLTQLLFFSSARFSTAEGLSLMGVMAVLCTLPVAFIHFPQW
SEQID120    RRSLGLISGLTGAGGNFGSGVTQLLFFSSSRFSTAEGLSLMGVMAVVCSLPVAFIHFPQW
            :* **::* ::**.**.*:* ** : * ::   *  **  **.*   *:**  .  * *
```

FIGURE 6 B (continued)

```
SEQID68     GSMFFPPSATADEE----GYYASEWNDDEKSKGLHSASLKFAENSRSERGKRNVIQADAA
SEQID70     GSMFFPPSATADEE----GYYASEWNDDEKSKGLHSASLKFAENSRSERGKRNVIQADAA
SEQID66     GSMLLPPSAGAVEE----HYYSSEWSEEEKSKGLHSSSLKFSENCRSERGNRNVILAAPN
SEQID53     GSMFLPPNAGAEEE----HYYGSEWSEQEKSKGLHGASLKFAENSRSERGRRNVINAAAA
SEQID78     GSMFFPASADATEE----EYYASEWSEEEKGKGLHITGQKFAENSRSERGRRNVILATSA
SEQID80     GSMFFPASADATEE----EYYASEWSEEEKGKGLHIAGQKFAENSRSERGRRNVILATSA
SEQID74     GSMFFPASADATEE----EYYASEWSEEEKNKGLHIAGQKFAENSRSERGRRNVILATSA
SEQID72     GSMFFPASADATEE----EYYASEWSEEEKAKGLHIAGQKFAENSRSERGRRNVILATSA
SEQID84     GSMFFPASADATEE----EYYASEWSEEEKGKGLHIAGQKFAENSRSERGRRNVIFATSA
SEQID82     GSMFLAASADATEE----EYYASEWSEEEKSKGLHIAGQKFAENSRSERGRRNVILATSA
SEQID76     GSMLLPPNANATEE----EFYAAEWSEEEKKKGLHIPGQKFAENSRSERGRRNVILATAA
SEQID86     GSMFLPPSKDVVKS-TEEFYYGAEWNEEEKQKGLHQQSLRFAENSRSERGR-RVASAPTP
SEQID88     GSMFLPPSKDVVKS-TEEFYYGAEWNEEEKQKGLHQQSLRFAENSRSERGR-RVASAPTP
SEQID90     GSMFLPPSKDVSKS-TEEFYYTSEWNEEEKQKGLHQQSLKFAENSRSERGK-RVASAPTP
SEQID92     GSMFLPPSKDINKS-SEEHYYTAEWDEEERKKGLHSQSLKFAENSRSERGK-RVSSAPTP
SEQID98     GGMFFPPSKDVVKS-TEESYYASEWDEDEKQRGMHQKSLKFAENSRSERGK-RIASAPTP
SEQID96     GSMFLPPSKDPIKG-TEEHYFGSEYTEDEKQKGMHQNSIKFAENSRTERGKKRVGSAPTP
SEQID122    GSMFLPPSKDPIKGTEPEHYFGSEYTEDEKVKGMHQNSIKFAENSRTEFGKKRVGSAPTP
SEQID94     GSMFLPPTKDPVKS-TEEHYFTSEYTEAEKQKGMHQNSIKFAENCRSERGK-RVGSALTP
SEQID100    GSMFFPPTKDPVKG-SEEHYYAAEYTEAERQKGMHQNSLKFAENCRSERGK-RVGSAPTP
SEQID102    GSMFFPPTKDPVKG-SEEHYYAAEYTEAERQKGMHQNSLKFAENCRSERGK-RVGSAPTP
SEQID104    GSMFLPPTKDPVKG-TEEHYYTSEYTEAERQKGMHQNSLKFAENCRSERGK-RVGSAPTP
SEQID108    GSMFLPPTKDPVKG-TEEHYYTSEYTEAERQKGMHQNSLKFAENCRSERGK-RVGSAPTP
SEQID106    GSMFLPPSTD-PVKGTEAHYYGSEWNEQEKQKNMHQGSLRFAENAKSEGGR-RVRSAATP
SEQID110    GSMFLPPSTD-PVKGPKEHYYASEWNEQEKEKNMHQGSLRFAKNAKSEGGR-RVRSAATP
SEQID114    GSMFFPPSND-SVDAT-EHYYVGEYSKEEQQIGMHLKSKLFADGAKTEGGS-SVHKGNAT
SEQID116    GSMFFPPSND-SVDAT-EHYYVGEYSKEEQQIGMHLKSKLFADGAKTEGGS-SVHKGNAT
SEQID112    GSMFLPSTED-EVKSTEEYYYMKEWTETEKRKGMHEGSLKFAVNSRSERGR-RVASAPSP
SEQID118    GSMFLRPSTDGERS-QEEYYYGSEWTENEKQQGLHEGSIKFAENSRSERGRKVALANIPT
SEQID120    GSMFLRPSQDGEKS-KEEHYYGAEWTEEEKSLGLHEGSIKFAENSRSERGRKAMLADIPT
            *.*:: ..           ::  *: . *:  .:*  .  *: ..::* *

SEQID68     ATPEHV------
SEQID70     ATPEHV------
SEQID66     STPEHV------
SEQID53     AATPPNNSPEHA
SEQID78     TPPNNTPQHV--
SEQID80     TPPNNTPQHV--
SEQID74     TPPNNTPQHV--
SEQID72     TPPNNTPQHV--
SEQID84     TPPNNTPQQV--
SEQID82     TPPNNTPLHV--
SEQID76     TPPNNTPQHA--
SEQID86     PNTTPSHV----
SEQID88     PNTTPSHV----
SEQID90     PNATPTHV----
SEQID92     PNTTPTHV----
SEQID98     PSTTPNR-----
SEQID96     PNVTPNRV----
SEQID122    PNVYPNRV----
SEQID94     PNVTPNRV----
SEQID100    PNLTPNRV----
SEQID102    PNLTPNRV----
SEQID104    PNLTPNRV----
SEQID108    PNLTPNRV----
SEQID106    PENTPNNV----
SEQID110    PENTPNNV----
SEQID114    NNA---------
SEQID116    NNA---------
SEQID112    PPEHV-------
SEQID118    PENGTPSHV---
SEQID120    PETGSPAHV---
```

FIGURE 6 B (continued)

SEQ ID NO: 52, OsNRT coding sequence

ATGGACTCGTCGACGGTGGGCGCTCCGGGGAGCTCGCTGCACGGCGTGACGGGGCGCGAGCC
GGCGTTCGCGTTCTCGACGGAGGTGGGCGGCGAGGACGCGGCGGCGGCGAGCAAGTTCGACT
TGCCGGTGGACTCGGAGCACAAGGCGAAGACGATCAGGTTGCTGTCGTTCGCGAACCCGCAT
ATGAGGACGTTCCACCTATCATGGATCTCCTTCTTCTCCTGCTTCGTCTCCACCTTCGCCGC
CGCCCCTCTCGTCCCCATCATCCGCGACAACCTCAACCTCACCAAGGCCGACATCGGCAACG
CCGGCGTCGCCTCCGTCTCCGGCTCCATCTTCTCCAGGCTCGCCATGGGCGCCATCTGCGAC
ATGCTCGGCCCGCGCTACGGCTGCGCCTTCCTCATCATGCTCGCCGCGCCCACCGTCTTCTG
CATGTCGCTCATCGACTCCGCCGCGGGGTACATCGCCGTGCGCTTCCTCATCGGCTTCTCCC
TCGCCACCTTCGTGTCATGCCAGTACTGGATGAGCACCATGTTCAACAGCAAGATCATCGGC
CTCGTCAACGGCCTCGCCGCCGGGTGGGGAAACATGGGCGGCGGCGCGACGCAGCTCATCAT
GCCGCTCGTCTACGACGTGATCCGCAAGTGCGGCGCGACGCCGTTCACGGCGTGGAGGCTGG
CCTACTTCGTGCCGGGGACGCTGCACGTGGTGATGGGCGTGCTGGTGCTGACGCTGGGGCAG
GACCTCCCCGACGGCAACCTGCGCAGCCTGCAGAAGAAGGGTGACGTCAACAGGGACAGCTT
CTCCAGGGTGCTCTGGTACGCCGTCACCAACTACCGCACCTGGATCTTCGTCCTCCTCTACG
GCTACTCCATGGGCGTCGAGCTCACCACCGACAACGTCATCGCCGAGTACTTCTACGATCGC
TTCGACCTCGACCTCCGCGTCGCCGGCATCATCGCCGCATCCTTCGGCATGGCCAACATCGT
CGCGCGCCCCACCGGCGGCCTCCTCTCGGACCTCGGCGCGCGCTACTTCGGCATGCGCGCCC
GCCTCTGGAACATTTGGATCCTCCAGACCGCCGGCGGCGCGTTCTGCCTCCTGCTCGGCCGC
GCATCCACCCTCCCCACCTCCGTCGTCTGCATGGTCCTCTTCTCCTTCTGCGCGCAGGCCGC
CTGCGGCGCCATCTTCGGCGTCATCCCCTTCGTCTCCCGCCGCTCGCTCGGCATCATCTCCG
GCATGACCGGCGCCGGCGGCAACTTCGGCGCCGGGCTCACGCAGCTGCTCTTCTTCACGTCG
TCGAGGTACTCCACGGGCACGGGGCTGGAGTACATGGGCATCATGATCATGGCGTGCACGCT
GCCGGTGGTGCTCGTCCATTTCCCGCAGTGGGGCTCCATGTTCCTCCCGCCCAACGCCGGCG
CCGAGGAGGAGCACTACTACGGCTCCGAGTGGAGCGAACAGGAGAAGAGCAAGGGCCTCCAC
GGTGCAAGTCTCAAGTTCGCCGAGAACTCCCGCTCCGAGCGTGGCCGCCGCAACGTCATCAA
CGCCGCCGCCGCCGCCGCCACGCCGCCCAACAACTCGCCGGAGCACGCCTAA

SEQ ID NO: 53, OsNRT deduced protein sequence

MDSSTVGAPGSSLHGVTGREPAFAFSTEVGGEDAAAASKFDLPVDSEHKAKTIRLLSFANPH
MRTFHLSWISFFSCFVSTFAAAPLVPIIRDNLNLTKADIGNAGVASVSGSIFSRLAMGAICD
MLGPRYGCAFLIMLAAPTVFCMSLIDSAAGYIAVRFLIGFSLATFVSCQYWMSTMFNSKIIG
LVNGLAAGWGNMGGGATQLIMPLVYDVIRKCGATPFTAWRLAYFVPGTLHVVMGVLVLTLGQ
DLPDGNLRSLQKKGDVNRDSFSRVLWYAVTNYRTWIFVLLYGYSMGVELTTDNVIAEYFYDR
FDLDLRVAGIIAASFGMANIVARPTGGLLSDLGARYFGMRARLWNIWILQTAGGAFCLLLGR
ASTLPTSVVCMVLFSFCAQAACGAIFGVIPFVSRRSLGIISGMTGAGGNFGAGLTQLLFFTS
SRYSTGTGLEYMGIMIMACTLPVVLVHFPQWGSMFLPPNAGAEEEHYYGSEWSEQEKSKGLH
GASLKFAENSRSERGRRNVINAAAAAATPPNNSPEHA

SEQ ID NO: 54, prm07061, start codon in bold, AttB1 site in italics

*GGGGACAAGTTTGTACAAAAAAGCAGGCTTAAACA*ATGGACTCGTCGACGGTG

Figure 8

SEQ ID NO: 55, prm07062, reverse, complementary, stop codon in bold, AttB2 site in italic

*GGGGACCACTTTGTACAAGAAAGCTGGGT*CTCGGTCGCAGAATTGTTTAC

**SEQ ID NO: 56, *NRT* expression cassette with the promoter-gene combination, promoter sequence in italics, start and stop codon of the *NRT* ORF in bold and underlined**

*AATCCGAAAAGTTTCTGCACCGTTTTCACCCCCTAACTAACAATATAGGGAACGTGTGCTAA*
*ATATAAAATGAGACCTTATATATGTAGCGCTGATAACTAGAACTATGCAAGAAAAACTCATC*
*CACCTACTTTAGTGGCAATCGGGCTAAATAAAAAAGAGTCGCTACACTAGTTTCGTTTTCCT*
*TAGTAATTAAGTGGGAAAATGAAATCATTATTGCTTAGAATATACGTTCACATCTCTGTCAT*
*GAAGTTAAATTATTCGAGGTAGCCATAATTGTCATCAAACTCTTCTTGAATAAAAAAATCTT*
*TCTAGCTGAACTCAATGGGTAAAGAGAGAGATTTTTTTAAAAAAATAGAATGAAGATATTC*
*TGAACGTATTGGCAAAGATTTAAACATATAATTATATAATTTTATAGTTTGTGCATTCGTCA*
*TATCGCACATCATTAAGGACATGTCTTACTCCATCCCAATTTTTATTTAGTAATTAAAGACA*
*ATTGACTTATTTTTATTATTTATCTTTTTTCGATTAGATGCAAGGTACTTACGCACACACTT*
*TGTGCTCATGTGCATGTGTGAGTGCACCTCCTCAATACACGTTCAACTAGCAACACATCTCT*
*AATATCACTCGCCTATTTAATACATTTAGGTAGCAATATCTGAATTCAAGCACTCCACCATC*
*ACCAGACCACTTTTAATAATATCTAAAATACAAAAAATAATTTTACAGAATAGCATGAAAAG*
*TATGAAACGAACTATTTAGGTTTTTCACATACAAAAAAAAAAAGAATTTTGCTCGTGCGCGA*
*GCGCCAATCTCCCATATTGGGCACACAGGCAACAACAGAGTGGCTGCCCACAGAACAACCCA*
*CAAAAAACGATGATCTAACGGAGGACAGCAAGTCCGCAACAACCTTTTAACAGCAGGCTTTG*
*CGGCCAGGAGAGAGGAGGAGAGGCAAAGAAAACCAAGCATCCTCCTCCTCCCATCTATAAAT*
*TCCTCCCCCCTTTTCCCCTCTCTATATAGGAGGCATCCAAGCCAAGAAGAGGGAGAGCACCA*
*AGGACACGCGACTAGCAGAAGCCGAGCGACCGCCTTCTTCGATCCATATCTTCCGGTCGAGT*
*TCTTGGTCGATCTCTTCCCTCCTCCACCTCCTCCTCACAGGGTATGTGCCCTTCGGTTGTTC*
*TTGGATTTATTGTTCTAGGTTGTGTAGTACGGGCGTTGATGTTAGGAAAGGGGATCTGTATC*
*TGTGATGATTCCTGTTCTTGGATTTGGGATAGAGGGGTTCTTGATGTTGCATGTTATCGGTT*
*CGGTTTGATTAGTAGTATGGTTTTCAATCGTCTGGAGAGCTCTATGGAAATGAAATGGTTTA*
*GGGTACGGAATCTTGCGATTTTGTGAGTACCTTTTGTTTGAGGTAAAATCAGAGCACCGGTG*
*ATTTTGCTTGGTGTAATAAAAGTACGGTTGTTTGGTCCTCGATTCTGGTAGTGATGCTTCTC*
*GATTTGACGAAGCTATCCTTTGTTTATTCCCTATTGAACAAAAATAATCCAACTTTGAAGAC*
*GGTCCCGTTGATGAGATTGAATGATTGATTCTTAAGCCTGTCCAAAATTTCGCAGCTGGCTT*
*GTTTAGATACAGTAGTCCCCATCACGAAATTCATGGAAACAGTTATAATCCTCAGGAACAGG*
*GGATTCCCTGTTCTTCCGATTTGCTTTAGTCCCAGAATTTTTTTTCCCAAATATCTTAAAAA*
*GTCACTTTCTGGTTCAGTTCAATGAATTGATTGCTACAAATAATGCTTTTATAGCGTTATCC*
*TAGCTGTAGTTCAGTTAATAGGTAATACCCCTATAGTTTAGTCAGGAGAAGAACTTATCCGA*
*TTTCTGATCTCCATTTTTAATTATATGAAATGAACTGTAGCATAAGCAGTATTCATTTGGAT*
*TATTTTTTTTATTAGCTCTCACCCCTTCATTATTCTGAGCTGAAAGTCTGGCATGAACTGTC*
*CTCAATTTTGTTTTCAAATTCACATCGATTATCTATGCATTATCCTCTTGTATCTACCTGTA*
*GAAGTTTCTTTTTGGTTATTCCTTGACTGCTTGATTACAGAAAGAAATTTATGAAGCTGTAA*
*TCGGGATAGTTATACTGCTTGTTCTTATGATTCATTTCCTTTGTGCAGTTCTTGGTGTAGCT*
*TGCCACTTTCACCAGCAAAGTTC*ATTTAAATCAACTAGGGATATCACAAGTTTGTACAAAAA
AGCAGGCTTAAACAATGGACTCGTCGACGGTGGGCGCTCCGGGGAGCTCGCTGCACGGCGTG

Figure 8 (continued)

ACGGGGCGCGAGCCGGCGTTCGCGTTCTCGACGGAGGTGGGCGGCGAGGACGCGGCGGCGGC
GAGCAAGTTCGACTTGCCGGTGGACTCGGAGCACAAGGCGAAGACGATCAGGTTGCTGTCGT
TCGCGAACCCGCATATGAGGACGTTCCACCTATCATGGATCTCCTTCTTCTCCTGCTTCGTC
TCCACCTTCGCCGCCGCCCCTCTCGTCCCCATCATCCGCGACAACCTCAACCTCACCAAGGC
CGACATCGGCAACGCCGGCGTCGCCTCCGTCTCCGGCTCCATCTTCTCCAGGCTCGCCATGG
GCGCCATCTGCGACATGCTCGGCCCGCGCTACGGCTGCGCCTTCCTCATCATGCTCGCCGCG
CCCACCGTCTTCTGCATGTCGCTCATCGACTCCGCCGCGGGGTACATCGCCGTGCGCTTCCT
CATCGGCTTCTCCCTCGCCACCTTCGTGTCATGCCAGTACTGGATGAGCACCATGTTCAACA
GCAAGATCATCGGCCTCGTCAACGGCCTCGCCGCCGGGTGGGGAAACATGGGCGGCGGCGCG
ACGCAGCTCATCATGCCGCTCGTCTACGACGTGATCCGCAAGTGCGGCGCGACGCCGTTCAC
GGCGTGGAGGCTGGCCTACTTCGTGCCGGGGACGCTGCACGTGGTGATGGGCGTGCTGGTGC
TGACGCTGGGGCAGGACCTCCCCGACGGCAACCTGCGCAGCCTGCAGAAGAAGGGTGACGTC
AACAGGGACAGCTTCTCCAGGGTGCTCTGGTACGCCGTCACCAACTACCGCACCTGGATCTT
CGTCCTCCTCTACGGCTACTCCATGGGCGTCGAGCTCACCACCGACAACGTCATCGCCGAGT
ACTTCTACGATCGCTTCGACCTCGACCTCCGCGTCGCCGGCATCATCGCCGCATCCTTCGGC
ATGGCCAACATCGTCGCGCGCCCCACCGGCGGCCTCCTCTCGGACCTCGGCGCGCGCTACTT
CGGCATGCGCGCCCGCCTCTGGAACATTTGGATCCTCCAGACCGCCGGCGGCGCGTTCTGCC
TCCTGCTCGGCCGCGCATCCACCCTCCCCACCTCCGTCGTCTGCATGGTCCTCTTCTCCTTC
TGCGCGCAGGCCGCCTGCGGCGCCATCTTCGGCGTCATCCCCTTCGTCTCCCGCCGCTCGCT
CGGCATCATCTCCGGCATGACCGGCGCCGGCGGCAACTTCGGCGCCGGGCTCACGCAGCTGC
TCTTCTTCACGTCGTCGAGGTACTCCACGGGCACGGGGCTGGAGTACATGGGCATCATGATC
ATGGCGTGCACGCTGCCGGTGGTGCTCGTCCATTTCCCGCAGTGGGGCTCCATGTTCCTCCC
GCCCAACGCCGGCGCCGAGGAGGAGCACTACTACGGCTCCGAGTGGAGCGAACAGGAGAAGA
GCAAGGGCCTCCACGGTGCAAGTCTCAAGTTCGCCGAGAACTCCCGCTCCGAGCGTGGCCGC
CGCAACGTCATCAACGCCGCCGCCGCCGCCGCCACGCCGCCCAACAACTCGCCGGAGCACGC
C<u>TAA</u>

SEQ ID NO: 57, signature sequence 1

(N/S)(Y/P)(T/G/S/A)W(I/V/L)(F/L/T)(V/A/F/L)(L/V/M/I)(L/T/I/A/N
)YG(Y/F)(S/C/T)(M/F/Y)G(V/I)EL(T/S)(T/I/V)(D/G/N)N(V/I/N)(I/V)
(A/S/H/V)(E/Q/G)Y

SEQ ID NO: 58, signature sequence 2

LG(P/A)RYG(C/T)AF(L/S)

SEQ ID NO: 59, signature sequence 3

STFAA(A/R)PL(V/I)(P/V)(I/L/V)IR(D/E)NL(N/D)(L/P)

SEQ ID NO: 60, signature sequence 4

VRF(L/M)IGF(S/C)LA

Figure 8 (continued)

SEQ ID NO: 61, signature sequence 5

FVSC(Q/R)YW(M/T)S(T/V)(M/S)(F/M)

SEQ ID NO: 62, signature sequence 6

K(A/Q/S/M/H/T)D(I/V)GNAGVASV(S/T)G(S/A)I(F/L)SR(L/G)

SEQ ID NO: 63, signature sequence 7

NG(L/T/C)A(A/G)GWG

SEQ ID NO: 64, signature sequence 8

G(A/S)G(L/V/Q)TQ(L/P)(L/V/I)(F/E)F(T/S/D)(S/T)(S/A/T).

SEQ ID NO: 65, Phragmites australis NRT2 mRNA for putative high affinity nitrate transporter, complete cds (AB096061)

ACAACAGCTCAGATCAAGCACCTGCATTTGCATAAGAGCTAGCAAGCAAGCAAGTCCAAGAA
AGAAGCTAGCTAGCTTGTATCAGATCAAGACTCGAGAGGCCAGCTATGGAGGTTGGCGCGCC
GGGGAGCTCGCTGCACGGCGTCACGGGGCGCGAGCCGGCGTTCGCCTTCTCGACGTCTGCGG
TGCCCGACGACGATGCAGCGAGCAAGTTCGACCTGCCGGTGGACTCGGAGCACAAGGCCAAG
AGCATCCGGCTCTTCTCCTTCGCCAACCCGCACATGCGCACCTTCCATCTCTCGTGGATCTC
CTTCTTCACCTGCTTCGTCTCCACCTTCGCCGCCGCGCCGCTCGTCCCCATCATCCGCGACA
ACCTCAACCTCACCAAGGCCGACATCGGCAACGCCGGCGTGGCCTCCGTCTCGGGATCCATC
TTCTCCCGTCTCGCCATGGGCGCCATCTGCGACCTCCTCGGCCCGCGCTACGGCTGCGCCTT
CCTCATCATGCTCACGGCGCCCACCGTCTTCTGCATGTCCCTCATCGACGACGCAGCCGGCT
ACATCGTCGTCAGGTTCTTGATCGGCTTCTCTCTGGCCACGTTCGTGTCGTGCCAGTACTGG
ATGAGCACCATGTTCAATAGCAAGATCATCGGGACGGTGAACGGGCTGGCGGCTGGGTGGGG
GAACATGGGCGGCGGCGCCACGCAGCTCCCCATGCCGCTCGTCTACGACGTCATCCGCAAGT
GCGGCGCGACGCCCTTCACGGCGTGGCGCATCGCCTACTTCGTGCCGGGGCTAATGCACGTG
GTGATGGGCATCCTGGTGCTCACGCTGGGGCAGGACCTCCCCGACGGCAACCTGAGGAGCCT
CCAGAAGAAGGGCGACGCCAACAAGGACAAGTTCTCCAAGGTGCTCTGGTACGCCGTCACCA
ACTATCGCACCTGGATCTTCGTGCTGCTCTACGGCTACTGCATGGGCGTGGAGCTGACCACC
GACAACGTCATCGCCGAGTACTACTACGACCACTTCGACCTAGACCTCCGCGTCGCCGGCAT
CATCGCCGCTTGCTTCGGAATGGCCAACATCGTGGCACGGCCCTTGGGCGGCATCCTCTCCG
ACATCGGCGCGCGCTACTGGGGCATGCGCGCGCGCCTCTGGAACATCTGGATCCTCCAGACT
GCTGGCGGCGCCTTCTGCCTCTGGCTCGGCCGCGCCAGCACGCTTCCTGCCTCCATTACCGC
CATGGTGCTCTTCTCCTTCTGCGCCCAGGCCGCCTGCGGCGCCATTTTCGGCGTCACCCCTT
TCGTCACCCGCCGCTCCCTCGGCATCATGTCCGGGATGACGGGGGCTGGCGGCAACTTCGGC
GCGGGGCTCACGCAGCTGCTCTTCTTCACCTCGTCCAAGTACTCCACGGGCATGGGGCTGGA
GTACATGGGCATCATGATCATGGCGTGCACGCTGCCCGTGGTGTTCGTGCACTTCCCGCAAT
GGGGATCCATGCTCCTCCCGCCCAGCGCCGGCGCCGTCGAGGAGCACTACTACAGCTCGGAG

Figure 8 (continued)

TGGAGTGAGGAGGAGAAGAGCAAGGGGCTCCACAGCTCCAGCCTCAAGTTTTCAGAGAACTG
CCGTTCAGAGCGCGGCAACCGCAACGTCATCCTCGCGGCACCAAACAGCACGCCCGAGCACG
TATAAGACGCACGTATATGTCCGCATTCGTACCCCTGTGCGCGTATACGCATACGCCAGCGG
TTTGTTTAATAAGGTGCGCATATATATATATGTAACTAGCTATAATGCGTATCACCGTTATG
CGCACGCACACGAAATATATATAATTCGATGTTGACGCATATACAAAAAAAAAAAAAAAA

SEQ ID NO: 66, Phragmites australis putative high affinity nitrate transporter (BAC76606)

MEVGAPGSSLHGVTGREPAFAFSTSAVPDDDAASKFDLPVDSEHKAKSIRLFSFANPHMRTF
HLSWISFFTCFVSTFAAAPLVPIIRDNLNLTKADIGNAGVASVSGSIFSRLAMGAICDLLGP
RYGCAFLIMLTAPTVFCMSLIDDAAGYIVVRFLIGFSLATFVSCQYWMSTMFNSKIIGTVNG
LAAGWGNMGGGATQLPMPLVYDVIRKCGATPFTAWRIAYFVPGLMHVVMGILVLTLGQDLPD
GNLRSLQKKGDANKDKFSKVLWYAVTNYRTWIFVLLYGYCMGVELTTDNVIAEYYYDHFDLD
LRVAGIIAACFGMANIVARPLGGILSDIGARYWGMRARLWNIWILQTAGGAFCLWLGRASTL
PASITAMVLFSFCAQAACGAIFGVTPFVTRRSLGIMSGMTGAGGNFGAGLTQLLFFTSSKYS
TGMGLEYMGIMIMACTLPVVFVHFPQWGSMLLPPSAGAVEEHYYSSEWSEEEKSKGLHSSSL
KFSENCRSERGNRNVILAAPNSTPEHV

SEQ ID NO: 67, Zea mays putative high affinity nitrate transporter (nrt2.2) mRNA, complete cds (AY559405)

CCAAGGGAAAGGGATACATCACCTGCTGCTCTAGCTCTGCTATAGCGCTAGCAGCAATATAA
TGGCGGCCGTCGGCGCTCCGGGGAGCTCTCTGCACGGAGTCACGGGGCGCGAGCCGGCGTTC
GCATTCTCCACGGAGCACGAGGAGGCGGCGAGCAATGGCGGCAAGTTCGACCTGCCGGTGGA
CTCGGAGCACAAGGCGAAGAGCGTCCGGCTCTTCTCCGTGGCGAACCCGCACATGCGCACCT
TCCACCTCTCCTGGATCTCCTTCTTCACCTGCTTCGTGTCCACCTTCGCCGCCGCGCCGCTG
GTCCCCATCATCCGCGACAACCTCAACCTCACCAAGGCCGACATCGGCAACGCGGGCGTGGC
CTCCGTGTCGGGCTCCATCTTCTCCCGCCTCACCATGGGCGCCGTCTGCGACCTGCTGGGCC
CGCGCTACGGCTGCGCCTTCCTCATCATGCTGTCCGCGCCCACCGTGTTCTGCATGTCGCTC
ATCGACGACGCCGCGGGCTACATCACCGTCAGGTTCCTCATCGGCTTCTCCCTCGCCACCTT
CGTCTCCTGCCAGTACTGGATGAGCACCATGTTCAGCAGCAAGATCATCGGCACCGTCAACG
GGCTCGCCGCCGGATGGGGCAACATGGGAGGCGGCGCCACGCAGCTCATCATGCCGCTCGTC
TACGACGTCATCCGCAAGTGCGGCGCCACGCCCTTCACGGCGTGGCGCCTCGCCTACTTCGT
GCCGGGCCTCATGCACGTCGTCATGGGCGTCCTGGTGCTCACGCTGGGGCAGGACCTCCCCG
ACGGCAACCTCAGGTCGCTGCAGAAGAAGGGCAACGTCAACAAGGACAGCTTCTCCAAGGTC
ATGTGGTACGCCGTCATCAACTACCGCACCTGGATCTTCGTCCTCCTCTACGGCTACTGCAT
GGGCGTCGAGCTCACCACCGACAACGTCATCGCCGAGTACATGTACGACCGCTTCGACCTCG
ACCTCCGCGTCGCCGGGACCATCGCCGCCTGCTTCGGCATGGCCAACATCGTCGCGCGCCCC
ATGGGCGGCATCATGTCCGACATGGGCGCGCGCTACTGGGGCATGCGCGCTCGCCTCTGGAA
CATCTGGATCCTCCAGACCGCCGGCGGCGCCTTCTGCCTCTGGCTGGGACGCGCCAGCACCC
TCCCCGTCTCCGTCGTCGCCATGGTGCTCTTCTCCTTCTGCGCGCAGGCGGCCTGCGGCGCC
ATCTTCGGGGTCATCCCCTTCGTCTCCCGCCGCTCCCTCGGCATCATCTCCGGCATGACGGG
CGCCGGCGGCAACTTCGGCGCGGGGCTCACGCAGCTGCTCTTCTTCACCTCCTCAACCTACT
CCACGGGCAGGGGGCTAGAGTACATGGGCATCATGATCATGGCGTGCACGCTACCTGTGGTG

Figure 8 (continued)

TTCGTGCACTTCCCGCAGTGGGGGTCCATGTTCTTCCCGCCCAGCGCCACCGCCGACGAGGA
GGGCTACTACGCCTCCGAGTGGAACGACGACGAGAAGAGCAAGGGACTCCATAGCGCCAGCC
TCAAGTTTGCCGAGAACAGCCGCTCAGAGCGCGGCAAGCGAAACGTCATCCAGGCCGATGCC
GCCGCCACGCCGGAGCATGTCTAAGTCTACTACTAATAAGATGGATCGATCCATCATCCATG
TTCACCTGCTACCTACC

SEQ ID NO: 68, Zea mays putative high affinity nitrate transporter (AAT66252)

MAAVGAPGSSLHGVTGREPAFAFSTEHEEAASNGGKFDLPVDSEHKAKSVRLFSVANPHMRT
FHLSWISFFTCFVSTFAAAPLVPIIRDNLNLTKADIGNAGVASVSGSIFSRLTMGAVCDLLG
PRYGCAFLIMLSAPTVFCMSLIDDAAGYITVRFLIGFSLATFVSCQYWMSTMFSSKIIGTVN
GLAAGWGNMGGGATQLIMPLVYDVIRKCGATPFTAWRLAYFVPGLMHVVMGVLVLTLGQDLP
DGNLRSLQKKGNVNKDSFSKVMWYAVINYRTWIFVLLYGYCMGVELTTDNVIAEYMYDRFDL
DLRVAGTIAACFGMANIVARPMGGIMSDMGARYWGMRARLWNIWILQTAGGAFCLWLGRAST
LPVSVVAMVLFSFCAQAACGAIFGVIPFVSRRSLGIISGMTGAGGNFGAGLTQLLFFTSSTY
STGRGLEYMGIMIMACTLPVVFVHFPQWGSMFFPPSATADEEGYYASEWNDDEKSKGLHSAS
LKFAENSRSERGKRNVIQADAAATPEHV

SEQ ID NO: 69, Zea mays putative high affinity nitrate transporter (nrt2.1) mRNA, complete cds (AY129953)

ACGCGGGGAAGCACAAGCAACCAGCCAGCTAGTTTCCAAGGGATCACCTGCTCTCTAGCACT
AGCAGCAATGGCGGCCGTCGGCGCTCCGGGCAGCTCTCTGCACGGAGTCACGGGGCGCGAGC
CGGCGTTCGCCTTCTCCACGGAGCACGAGGAGGCGGCGAGCAATGGTGGCAAGTTCGACCTG
CCGGTGGACTCAGAGCACAAGGCGAAGAGCGTCCGTCTCTTCTCCGTGGCGAACCCACACAT
GCGCACCTTCCACCTCTCCTGGATCTCCTTCTTCACCTGCTTCGTGTCCACCTTCGCCGCCG
CGCCGCTGGTCCCCATCATCCGCGACAACCTCAACCTCACCAAGGCCGACATCGGCAACGCG
GGCGTGGCCTCGGTGTCGGGCTCCATCTTCTCCCGCCTCACCATGGGCGCCGTCTGCGACCT
GCTGGGCCCGCGCTACGGCTGCGCCTTCCTCATCATGCTGTCCGCGCCCACCGTGTTCTGCA
TGTCGCTCATCGACGACGCCGCGGGCTACATCACCGTCAGGTTCCTCATCGGCTTCTCCCTC
GCCACCTTCGTCTCCTGCCAGTACTGGATGAGCACCATGTTCAGCAGCAAGATCATCGGCAC
CGTCAACGGGCTCGCCGCCGGATGGGGCACAATGGGAAGGCGGCGCCACGCAGCTCATATGC
CGCTCGTCTACGACGTCATCCGCAAGTGCGGCGCCACGCCATTCACGGCCTGGCGCCTCGCC
TACTTCGTGCCGGGCCTCATGCACGTCGTCATGGGCGTCCTGGTGCTCACGCTGGGGCAGGA
CCTCCCCGACGGCAACCTCAGGTCGCTGCAGAAGAAGGGCAACGTCAACAAGGACAGCTTCT
CCAAGGTCATGTGGTACGCCGTCATCAACTACCGTACCTGGATCTTTGTCCTCCTCTACGGC
TACTGCATGGGCGTCGAGCTCACCACCGACAACGTCATCGCCGAGTACATGTACGACCGCTT
CGACCTCGACCTCCGCGTCGCTGGGACCATCGCCGCCTGCTTCGGCATGGCCAACATCGTCG
CACGCCCCATGGGCGGCATCATGTCCGACATGGGCGCGCGCTACTGGGGCATGCGCGCTCGC
CTCTGGAACATCTGGATCCTCCAGACCGCCGGCGGCGCCTTCTGCCTCTGGCTGGGGCGCGC
CAGCACCCTCCCCGTCTCCGTCGTCGCCATGGTGCTCTTCTCCTTCTGCGCGCAGGCGGCAT
GCGGCGCCATCTTCGGGGTTATCCCCTTTGTCTCCCGCCGCTCCCTCGGCATCATCTCCGGC
ATGACGGGCGCCGGCGGCAACTTCGGCGCCGGGCTCACGCAGCTGCTCTTCTTTACCTCCTC
GACCTACTCCACGGGCAGGGGGCTGGAGTACATGGGCATCATGATCATGGCGTGCACGCTGC

Figure 8 (continued)

CCGTGGTGTTCGTGCACTTCCCTCAGTGGGGGTCCATGTTCTTTCCGCCCAGCGCCACCGCC
GACGAGGAGGGCTACTACGCCTCCGAGTGGAACGACGACGAGAAGAGCAAGGGACTCCATAG
CGCCAGCCTCAAGTTCGCCGAGAACAGCCGCTCAGAGCGCGGCAAGCGAAACGTCATCCAGG
CCGACGCCGCCGCCACGCCGGAGCATGTCTAAGTCTACTACTAAGATGGATCGATCGACGAT
CACCTATACCTCTTTGTATGTACGAATATGCCTTGTTATTACTGCGCGCGCGCATATACAAT
ACACGTGTGCTCCGTTGACATGAGTTAGAAAAAAAAAAAAAAAAAAAAAAAAA

SEQ ID NO: 70, Zea mays putative high affinity nitrate transporter (AAN05088)

MAAVGAPGSSLHGVTGREPAFAFSTEHEEAASNGGKFDLPVDSEHKAKSVRLFSVANPHMRT
FHLSWISFFTCFVSTFAAAPLVPIIRDNLNLTKADIGNAGVASVSGSIFSRLTMGAVCDLLG
PRYGCAFLIMLSAPTVFCMSLIDDAAGYITVRFLIGFSLATFVSCQYWMSTMFSSKIIGTVN
GLAAGWGTMGRRRHAAHMPLVYDVIRKCGATPFTAWRLAYFVPGLMHVVMGVLVLTLGQDLP
DGNLRSLQKKGNVNKDSFSKVMWYAVINYRTWIFVLLYGYCMGVELTTDNVIAEYMYDRFDL
DLRVAGTIAACFGMANIVARPMGGIMSDMGARYWGMRARLWNIWILQTAGGAFCLWLGRAST
LPVSVVAMVLFSFCAQAACGAIFGVIPFVSRRSLGIISGMTGAGGNFGAGLTQLLFFTSSTY
STGRGLEYMGIMIMACTLPVVFVHFPQWGSMFFPPSATADEEGYYASEWNDDEKSKGLHSAS
LKFAENSRSERGKRNVIQADAAATPEHV

SEQ ID NO: 71, Hordeum vulgare high affinity nitrate transporter homolog BCH1 mRNA, complete cds (HVU34198)

GAATTCGCGGCCGCTCCCTTACTACATTGCAAGCCAAGCTCAAGAGCAGCAGCAACAGCCAC
CATTAGCTGCTTCTAGTTGTTGGCAAAGATGGAGGTCGAGGCGGGCGCCCATGGCGACACTG
CCGCGAGCAAGTTCACGCTGCCGGTAGACTCCGAGCACAAGGCCAAGTCCTTCAGGCTCTTC
TCCTTCGCCAACCCGCACATGCGCACCTTCCATCTCTCGTGGATCTCCTTCTTCACTTGCTT
CATCTCCACCTTCGCCGCAGCGCCCCTTGTCCCCATCATTCGTGATAACCTCAACCTTGCCA
AGGCCGACATCGGCAATGCCGGTGTGGCATCCGTTTCTGGGTCCATCTTCTCCAGGCTTGCC
ATGGGTGCCATCTGCGATCTCCTCGGGCCGCGGTATGGATGTGCATTCCTCGTCATGCTCTC
GGCACCGACCGTTTTCTGCATGGCCGTTATCGATGATGCCTCAGGGTACATCGCCGTCCGCT
TTCTCATTGGCTTCTCGCTTGCTACGTTCGTGTCATGCCAATATTGGATGAGCACCATGTTT
AATAGCAAGATCATCGGCACAGTCAACGGCCTCGCTGCTGGATGGGGCAACATGGGTGGTGG
CGCCACGCAGCTCATCATGCCGCTCGTCTTCCATGCAATCCAGAAGTGTGGTGCCACGCCCT
TCGTAGCGTGGCGTATTGCCTACTTCGTGCCCGGAATGATGCACATCGTGATGGGCTTGTTG
GTACTCACCATGGGGCAAGATCTCCCTGATGGGAACCTCGCAAGTCTCCAGAAGAAGGGAGA
CATGGCCAAGGACAAGTTCTCCAAGGTCCTTTGGGGCGCCGTTACCAACTACCGAACATGGA
TCTTTGTCCTCCTCTATGGCTACTGCATGGGTGTCGAGCTCACCACCGACAATGTCATTGCC
GAGTACTACTTCGACCACTTCCACCTAGACCTCCGTGCCGCCGGTACCATCGCTGCCTGCTT
CGGCATGGCCAACATCGTCGCACGTCCTACGGGTGGCTACCTCTCTGACCTTGGCGCCCGCT
ATTTCGGCATGCGTGCTCGCCTCTGGAATATCTGGATCCTCCAAACCGCTGGTGGCGCTTTC
TGCATCTGGCTCGGTCGTGCATCGGCCCTCCCTGCCTCGGTGACCGCCATGGTCCTCTTCTC
CATCTGCGCCCAGGCTGCGTGTGGTGCTATCTTTGGTGTCGCACCCTTCGTCTCCAGGCGTT
CCCTTGGCATCATTTCCGGGTTGACCGGTGCTGGTGGAAACGTGGGCGCAGGGCTCACACAG
CTTCTCTTCTTCACGTCATCGCAATACTCCACTGGTAGGGGTCTCGAGTACATGGGCATCAT
GATCATGGCATGCACGCTGCCCGTCGCTCTTGTGCACTTCCCACAATGGGGATCCATGTTCT

Figure 8 (continued)

TCCCTGCCAGCGCCGACGCCACGGAGGAGGAGTACTACGCCTCGGAGTGGTCCGAAGAGGAG
AAAGCCAAGGGTCTCCATATCGCCGGCCAAAAATTTGCTGAGAATTCCCGCTCGGAGCGCGG
TAGGCGCAACGTCATCCTTGCCACGTCCGCCACACCACCCAACAATACGCCCCAGCACGTAT
GAGACTGGATTGTTTTTCATACCTATGTACAAGTACTGAACTACAGTGCACGTTCGTATATA
TATACGCCTGCAACATCGGCTGTAATAAGGCGTATGAATTTACATTTGTAGTGTAGGCCTGT
GTAATGCGTTTCTTACGCACGAAATGTTTGGTCTGTGCATGCACGCATGCGAGGGTACCTGT
GCTCTGAATTTACAACAGCTTTGAGGCGGCCGCGAATTC

SEQ ID NO: 72, Hordeum vulgare high affinity nitrate transporter homolog BCH1 (AAC49531)

MEVEAGAHGDTAASKFTLPVDSEHKAKSFRLFSFANPHMRTFHLSWISFFTCFISTFAAAPL
VPIIRDNLNLAKADIGNAGVASVSGSIFSRLAMGAICDLLGPRYGCAFLVMLSAPTVFCMAV
IDDASGYIAVRFLIGFSLATFVSCQYWMSTMFNSKIIGTVNGLAAGWGNMGGGATQLIMPLV
FHAIQKCGATPFVAWRIAYFVPGMMHIVMGLLVLTMGQDLPDGNLASLQKKGDMAKDKFSKV
LWGAVTNYRTWIFVLLYGYCMGVELTTDNVIAEYYFDHFHLDLRAAGTIAACFGMANIVARP
TGGYLSDLGARYFGMRARLWNIWILQTAGGAFCIWLGRASALPASVTAMVLFSICAQAACGA
IFGVAPFVSRRSLGIISGLTGAGGNVGAGLTQLLFFTSSQYSTGRGLEYMGIMIMACTLPVA
LVHFPQWGSMFFPASADATEEEYYASEWSEEEKAKGLHIAGQKFAENSRSERGRRNVILATS
ATPPNNTPQHV

SEQ ID NO: 73, Triticum aestivum high affinity nitrate transporter mRNA, complete cds (AF332214)

TAGTTTTGAGTGCAACTAGGCTAGCTCAAGAAAGATGGAGGTGCAGGCCGGCTCTCATGCCG
ACGCCGCGGCGAGCAAGTTCACGCTGCCGGTGGACTCCGAGCACAAGGCCAAGTCCTTCAGG
CTCTTCTCCTTCGCCAACCCCCACATGCGCACCTTTCACCTCTCGTGGATCTCCTTCTTCAC
CTGCTTCGTCTCCACCTTTGCTGCGGCGCCCCTCGTGCCCATCATCCGCGACAACCTCAACC
TTGCCAAGGCTGACATCGGCAATGCCGGTGTCGCGTCCGTGTCTGGGTCCATCTTCTCCAGG
CTGGCCATGGGCGCTATCTGTGACTTGCTTGGCCCACGGTATGGTTGTGCCTTCCTCGTCAT
GCTCTCGGCACCGACCGTCTTCTGCATGGCCGTCATCGATGATGCCTCAGGGTACATCGCCG
TCCGGTTCCTCATTGGCTTCTCCCTCGCCACCTTCGTGTCATGCCAATACTGGATGAGCACC
ATGTTCAATAGCAAGATCATTGGCACGGTCAATGGCTTGGCTGCAGGCTGGGGCAACATGGG
TGGCGGCGCCACGCAGCTCATCATGCCGCTTGTCTTCCACGCAATCCAGAAGTGTGGCGCCA
CGCCCTTCGTGGCATGGCGTATTGCCTACTTCGTGCCGGGAATGATGCACATCGTGATGGGC
TTGCTGGTCCTCACCATGGGGCAAGATCTCCCTGACGGGAACCTTGCGAGCCTCCARAAGAA
GGGAGACATGGCCAAGGACAAGTTCTCCAAGGTCCTTTGGGGCGCYGTCACCAACTACCGGA
CATGGATCTTCGTCCTCCTCTACGGCTACTGCATGGGYGTCGAGCTCACCACSGACAATGTC
ATCGCCGAGTACTACTACGACCACTTCCACCTAGACCTCCGCGCYGCWGGCACCATTGCYGC
TTGYTTYGGCATGGCAAACATYGTCGCGCGTCCTATGGGKGGCTACCTCTCYGACCTTGGTG
CCCGCTACTTTGGCATGCGTGCTCGCCTTTGGAACATCTGGATCCTMCAAACYGCCGGTGGC
GCTTTCTGCATCTGGCTCGGTCGTGCGTCAGCCCTCCCTGCCTCAGTGACTGCCATGGTTCT
CTTCTCCATCTGCGCCCAAGCCGCGTGTGGTGCTGTATTTGGCGTCGCACCCTTCGTTTCTA
GACGTTCCCTTGGCATCATCTCNGGGCTGACCGGTGCTGGTGGAAACGTGGGTGCRGGGCTC
ACGCAGCTTCTCTTCTTTACTTCATCACAATACTCCACYGGAAGGGGTCTCGAGTACATGGG

Figure 8 (continued)

CATCATGATCATGGCATGCACGCTGCCTGTCGCTCTTGTGCACTTCCCACAGTGGGGCTCGA
TGTTCTTCCCGGCCAGCGCCGACGCCACAGAGGAGGAATACTATGCCTCTGAGTGGTCGGAG
GAGGAGAAGAACAAGGGTCTCCATATTGCTGGCCAAAAGTTTGCCGAGAACTCACGATCGGA
GCGTGGAAGGCGCAACGTCATCCTTGCCACGTCCGCCACGCCACCCAACAATACGCCCCAGC
ACGTATAAGACCGGATTGTTTTTCATATACTATGTACAAGTACTGAACATCGGCTGTAATAA
GGTGTACGCATTTATATTTCCAGTGTAGACTTGTGTAATGCGTTTCTTACGCACGAAATGTT
TTGGTGTGTGCATGCACGCATGCGAGGTACCTGTGGTCTGAATTTACAGCAACTTTGAGACT
AAAAAAAAAAAAAA

SEQ ID NO: 74, Triticum aestivum high affinity nitrate transporter (AAK19519)

MEVQAGSHADAAASKFTLPVDSEHKAKSFRLFSFANPHMRTFHLSWISFFTCFVSTFAAAPL
VPIIRDNLNLAKADIGNAGVASVSGSIFSRLAMGAICDLLGPRYGCAFLVMLSAPTVFCMAV
IDDASGYIAVRFLIGFSLATFVSCQYWMSTMFNSKIIGTVNGLAAGWGNMGGGATQLIMPLV
FHAIQKCGATPFVAWRIAYFVPGMMHIVMGLLVLTMGQDLPDGNLASLQKKGDMAKDKFSKV
LWGAVTNYRTWIFVLLYGYCMGVELTTDNVIAEYYYDHFHLDLRAAGTIAACFGMANIVARP
MGGYLSDLGARYFGMRARLWNIWILQTAGGAFCIWLGRASALPASVTAMVLFSICAQAACGA
VFGVAPFVSRRSLGIISGLTGAGGNVGAGLTQLLFFTSSQYSTGRGLEYMGIMIMACTLPVA
LVHFPQWGSMFFPASADATEEEYYASEWSEEEKNKGLHIAGQKFAENSRSERGRRNVILATS
ATPPNNTPQHV

SEQ ID NO: 75, Hordeum vulgare high affinity nitrate transporter homolog BCH2 mRNA, complete cds (U34290)

TTACAAGCTCCATCTGAGAGCAGCAGCAACCACCATTAGAGACACACTTAGTTGCCAGTGCG
ACTAAGCTAGCTAGCTCGAGGAAGATGGAGGTGGAGTCGAGCTCGCATGGCGCCGGCGACGA
GGCTGCGAGCAAGTTCTCGCTGCCCGTGGACTCGGAGCACAAGGCCAAGTCCATCAGGCTCT
TCTCCTTCGCCAACCCCCACATGCGCACCTTCCACCTCTCCTGGATCTCCTTCTTCACCTGC
TTCGTCTCCACCTTCGCTGCCGCGCCCCTCGTCCCTATCATCCGCGACAACCTAAACCTCGC
CAAGGCCGACATCGGCAACGCCGGTGTGGCGTCCGTGTCCGGGTCTATCTTCTCGAGGCTCG
CCATGGGGGCCATCTGCGATCTCCTTGGCCCTCGATATGGATGCGCCTTCCTCGTCATGCTC
GCAGCACCCACCGTCTTCTGCATGTCCCTCATCGATGATGCGGCGGGCTACATCACGGTCCG
CTTCCTCATCGGCTTCTCCCTCGCGACGTTTGTGTCGTGCCAGTATTGGATGAGCACCATGT
TCAACAGCAAGATCATCGGCACCGTCAACGGCCTGGCGGCCGGCTGGGGCAACATGGGTGGT
GGTGCCACCCAGCTCATTATGCCACTCGTCTTCCACGCCATCCAGAAGTGTGGTGCCACGCC
CTTCGTCGCATGGCGCATCGCCTACTTCGTGCCAGGAATGATGCACGTGGTGATGGGCTTGC
TCGTGCTCACCATGGGACAGGATCTCCCCGATGGTAACCTTGCAAGCCTCCAGAAGAAGGGG
GAGATGGCCAAGGACAAGTTCTCCAAGGTTGTGTGGGGTGCTGTTACAAACTACCGTACATG
GATCTTCGTTCTTCTTTACGGATACTGCATGGGTGTTGAGCTCACCACCGACAACGTCATCG
CCGAGTACTACTTCGACCACTTTCACCTTGACCTTCGAACATCCGGCACCATTGCCGCCTGT
TTTGGCATGGCCAACATCGTTGCTCGGCCTGCGGGTGGCTACCTCTCCGACCTCGGTGCCCG
CTACTTCGGCATGCGTGCCCGCCTCTGGAACATCTGGATCCTCCAGACCGCTGGTGGCGCAT
TCTGCCTCTGGCTCGGCCGTGCAAAAGCCCTCCCCGAATCCATCACTGCCATGGTCCTCTTC
TCCATCTGCGCTCAGGCAGCATGTGGTGCAGTCTTTGGTGTCATCCCCTTCGTCTCCCGCCG
CTCCCTCGGCATCATTTCGGGCTTGAGTGGAGCCGGTGGGAACTTTGGCGCCGGGCTGACAC

Figure 8 (continued)

AATTGCTCTTCTTCACTTCGTCGAAGTATGGCACCGGCAGGGGGCTTGAGTACATGGGTATC
ATGATCATGGCCTGCACGCTCCCTGTGGCGCTTGTGCACTTCCCACAGTGGGGTTCCATGCT
CTTGCCGCCAAACGCCAACGCCACCGAGGAGGAGTTCTATGCCGCCGAATGGAGCGAGGAGG
AGAAGAAGAAGGGTCTCCATATCCCTGGCCAAAAGTTTGCCGAGAATTCCCGCTCGGAGCGT
GGCAGGCGCAACGTCATCCTTGCCACAGCCGCCACACCCCCCAACAACACTCCCCAACACGC
ATAAGACTCGAGCTTTTCTTTACCTGTGTACACGTACAGTGCGCGTATTATACACACATCGA
TCGTGTATATACGCCTGGAATCCGCAAGCAGTATGTTTTTTGAAAAAAAAAAAGCGGCCGCG
AATTC

SEQ ID NO: 76, Hordeum vulgare high affinity nitrate transporter homolog BCH2 (AAC49532)

MEVESSSHGAGDEAASKFSLPVDSEHKAKSIRLFSFANPHMRTFHLSWISFFTCFVSTFAAA
PLVPIIRDNLNLAKADIGNAGVASVSGSIFSRLAMGAICDLLGPRYGCAFLVMLAAPTVFCM
SLIDDAAGYITVRFLIGFSLATFVSCQYWMSTMFNSKIIGTVNGLAAGWGNMGGGATQLIMP
LVFHAIQKCGATPFVAWRIAYFVPGMMHVVMGLLVLTMGQDLPDGNLASLQKKGEMAKDKFS
KVVWGAVTNYRTWIFVLLYGYCMGVELTTDNVIAEYYFDHFHLDLRTSGTIAACFGMANIVA
RPAGGYLSDLGARYFGMRARLWNIWILQTAGGAFCLWLGRAKALPESITAMVLFSICAQAAC
GAVFGVIPFVSRRSLGIISGLSGAGGNFGAGLTQLLFFTSSKYGTGRGLEYMGIMIMACTLP
VALVHFPQWGSMLLPPNANATEEEFYAAEWSEEEKKKGLHIPGQKFAENSRSERGRRNVILA
TAATPPNNTPQHA

SEQ ID NO: 77, Triticum aestivum high affinity nitrate transporter TaNRT2 mRNA, complete cds (AF288688)

AAGCTAGCACCAAGCCTCCAAGGAGCAAGAAGAGAAGAAGCCTTGCTCGATCAAGCAAGGTC
GAAATGGAGGTGGAGGCCAGCGCCCATGGCGACACGGCGGCGAGCAAGTTCACGCTGCCCGT
GGACTCCGAGCACAAGGCCAAGTCCTTCAGACTCTTCTCCTTCGCCAACCCCCACATGCGTA
CCTTCCACCTCTCCTGGATATCCTTCTTCACCTGCTTCGTCTCCACCTTCGCGGCGGCACCG
TTGGTGCCCATCATCCGTGACAACCTCAACCTCGCTAAGGCCGACATAGGGAATGCCGGTGT
GGCATCTGTGTCTGGGTCCATCTTCTCCAGGCTTGCCATGGGTGCCATCTGCGACCTTTTAG
GGCCGCGGTATGGCTGCGCCTTCCTCGTCATGCTCTCAGCACCCACTGTGTTTTGCATGGCT
GCTATCGACGATGCGTCAGGCTACATCGCCGTACGCTTCCTCATTGGCTTCTCCCTCGCCAC
CTTCGTGTCATGCCAATATTGGATGAGCACCATGTTCAACAGTAAGATCATTGGCACGGTGA
ATGGCCTCGCGGCCGGCTGGGGCAACATGGGCGGTGGTGCCACACAACTCATCATGCCGCTT
GTTTTCCATGCCATCCAAAAGTGTGGTGCCACACCCTTCGTGGCATGGCGTATTGCCTATTT
CGTGCCGGGAATGATGCACATCGTCATGGGGTTGCTTGTGCTCACTATGGGCCAAGATCTCC
CCGACGGCAACCTTGCGAGTCTCCAGAAGAAGGGGGACATGGCCAAGGACAAATTCTCGAAG
GTCCTTTGGGGTGCGGTCACCAACTACCGGACATGGATATTCGTCCTCCTCTACGGCTACTG
CATGGGTGTCGAGCTCACCACCGACAACGTCATCGCCGAGTACTACTACGACCACTTCCACC
TTGACCTTCGCGCCGCTGGCACCATTGCCGCTTGCTTCGGCATGGCCAACATCGTCGCGCGT
CCTATGGGTGGCTATCTCTCTGACCTTGGTGCCCGCTACTTCGGCATGCGTGCTCGGCTCTG
GAACATCTGGATCCTCCAGACCGCTGGTGGCGCTTTCTGCATCTGGCTCGGTCGTGCATCGG
CCCTTCCTGCCTCAGTCACGGCCATGGTCCTCTTTTCCATTTGTGCACAAGCTGCTTGTGGT
GCTGTATTTGGCGTCGCACCCTTCGTTTCCAGGCGTTCCCTTGGCATCATCTCCGGGCTGAC

Figure 8 (continued)

CGGCGCTGGTGGCAATGTTGGCGCAGGGCTAACGCAACTTCTTTTCTTCACATCGTCGCAAT
ACTCCACCGGGAGGGGTCTCGAGTACATGGGCATCATGATCATGGCATGCACATTACCCGTC
GCTCTGGTGCACTTCCCCCAATGGGGCTCCATGTTCTTCCCGGCTAGCGCTGATGCCACGGA
AGAGGAATACTATGCTTCTGAGTGGTCGGAGGAGGAGAAGGGCAAGGGTCTCCATATTACAG
GCCAAAAGTTCGCAGAGAACTCCCGCTCAGAGCGCGGCAGGCGCAACGTCATCCTTGCCACA
TCCGCCACGCCACCCAACAACACACCCCAGCACGTATAAGGCCCTTATTTTTATGTCACCTA
AGAATTTTACTGTTCATCACGTATATATACAAACCGTATATCTACGTCTGCAGCCCCAGCGT
AATAAGTTGTATGGGGATTTATGTTTCTACTAGTAAACTTAAGGAAACGCTGCTTTTGCGTT
CCTGCTCTGTACGCATGAAATGTAATATCAATTTGAGTCCGAAATTACTACAAAAAAAAA

SEQ ID NO: 78, Triticum aestivum high affinity nitrate transporter (AAG01172)

MEVEASAHGDTAASKFTLPVDSEHKAKSFRLFSFANPHMRTFHLSWISFFTCFVSTFAAAPL
VPIIRDNLNLAKADIGNAGVASVSGSIFSRLAMGAICDLLGPRYGCAFLVMLSAPTVFCMAA
IDDASGYIAVRFLIGFSLATFVSCQYWMSTMFNSKIIGTVNGLAAGWGNMGGGATQLIMPLV
FHAIQKCGATPFVAWRIAYFVPGMMHIVMGLLVLTMGQDLPDGNLASLQKKGDMAKDKFSKV
LWGAVTNYRTWIFVLLYGYCMGVELTTDNVIAEYYYDHFHLDLRAAGTIAACFGMANIVARP
MGGYLSDLGARYFGMRARLWNIWILQTAGGAFCIWLGRASALPASVTAMVLFSICAQAACGA
VFGVAPFVSRRSLGIISGLTGAGGNVGAGLTQLLFFTSSQYSTGRGLEYMGIMIMACTLPVA
LVHFPQWGSMFFPASADATEEEYYASEWSEEEKGKGLHITGQKFAENSRSERGRRNVILATS
ATPPNNTPQHV

SEQ ID NO: 79, Triticum aestivum high-affinity nitrate transporter (NRT2.3) mRNA, complete cds (AY053452)

GCAGTATAATCAAGCAAGCTAGCTGCAAGCCGAGGAGCCTAGCTCGATCAAGCAAGGTCGAA
ATGGAGGTGGAGTCTAGCGCCCATGGCGACGCCGCGGCGAGCAAGTTCACGCTGCCTGTGGA
CTCCGAGCACAAGGCCAAGTCCTTCAGGCTCTTCTCCTTCGCCAACCCCCACATGCGCACCT
TCCACCTCTCCTGGATATCCTTCTTCACCTGCTTTGTCTCCACCTTCGCCGCCGCGCCGTTG
GTGCCCATCATCCGTGACAACCTCAACCTCGCCAAGGCCGACATAGGGAATGCCGGTGTGGC
ATCTGTGTCAGGGTCCATCTTCTCCAGGCTTGCCATGGGCGCCGTCTGCGACCTTTTGGGGC
CGCGGTATGGCTGTGCCTTCCTCGTCATGCTCTCAGCGCCAACGGTCTTCTGCATGGCCGTC
ATCGATGACGCCTCGGGGTACATCGCTGTACGCTTCCTCATTGGCTTCTCCCTCGCCGCCTT
TGTGTCCTGCCAATACTGGATGAGCACCATGTTCAACAGTAAGATCATTGGCACGGTGAATG
GCCTCGCGGCCGGCTGGGGCAACATGGGGGGCGGTGCCACACAACTCATTATGCCACTTGTT
TTCCATGCCATCCAAAAGTGCGGTGCCACACCCTTCGTGGCATGGCGTATCGCCTACTTCGT
GCCGGGAATGATGCACATCGTCATGGGGTTGCTTGTCCTCACAATGGGCCAAGATCTCCCCG
ACGGCAACCTTGCGAGCCTCCAGAAGAAGGGAGACATGGCCAAGGACAAGTTCTCCAAGGTC
CTTTGGGGCGCCGTCACCAACTACCGGACATGGATCTTCGTCCTCCTCTACGGCTACTGCAT
GGGTGTCGAGCTCACCACTGACAACGTCATCGCCGAGTACTACTACGACCATTTCCACCTAC
ACCTTCGCGCTGCAGGCACCATCGCCGCCTGCTTTGGCATGGCCAATATCGTCGCACGTCCT
ATGGGAGGTTACCTCTCTGACCTTGGCGCTCGCTACTTTGGTATGCGTGCTCGCCTATGGAA
CATCTGGATCCTCCAGACCGCCGGCGGCGCTTTCTGCATCTGGCTCGGTCGTGCATCGGCCC
TCCCCGCCTCAGTGACTGCCATGGTTCTCTTCTCCATCTGCGCCCAAGCTGCATGTGGCGCT
GTCTTTGGTGTTGCACCATTCGTTTCCAGGCGTTCCCTTGGCATCATCTCTGGGTTAACCGG

Figure 8 (continued)

CGCTGGTGGCAATGTGGGCGCGGGGCTCACACAACTTCTCTTCTTCACTTCGTCGCAATACT
CCACCGGGAGGGGTCTCGAGTACATGGGCATCATGATCATGGCATGCACATTACCTATCACT
CTGGTGCACTTCCCACAATGGGGCTCCATGTTCTTCCCGGCCAGTGCTGATGCTACGGAGGA
GGAGTACTACGCTTCCGAGTGGTCAGAGGAGGAGAAGGGCAAGGGTCTCCATATCGCAGGCC
AGAAGTTTGCAGAGAACTCCCGCTCGGAGCGTGGTAGGCGCAATGTTATCCTCGCCACATCC
GCCACGCCGCCCAACAATACACCCCAGCATGTATAAGGCCCTTGTTTTCTGTCACCTATGAA
TTGTACGGTTCGTCACGTACATATACAAACCGTATATCTACGTCGGCAGCCCCAGCGTAATA
AGTTGTATGGGGATTTATCTTTCTACTAGTAAACTTAAGGAAACGCTGGTTTTGCGTTCCTG
CTCTGTAC

SEQ ID NO: 80, Triticum aestivum high-affinity nitrate transporter (AAL11016)

MEVESSAHGDAAASKFTLPVDSEHKAKSFRLFSFANPHMRTFHLSWISFFTCFVSTFAAAPL
VPIIRDNLNLAKADIGNAGVASVSGSIFSRLAMGAVCDLLGPRYGCAFLVMLSAPTVFCMAV
IDDASGYIAVRFLIGFSLAAFVSCQYWMSTMFNSKIIGTVNGLAAGWGNMGGGATQLIMPLV
FHAIQKCGATPFVAWRIAYFVPGMMHIVMGLLVLTMGQDLPDGNLASLQKKGDMAKDKFSKV
LWGAVTNYRTWIFVLLYGYCMGVELTTDNVIAEYYYDHFHLHLRAAGTIAACFGMANIVARP
MGGYLSDLGARYFGMRARLWNIWILQTAGGAFCIWLGRASALPASVTAMVLFSICAQAACGA
VFGVAPFVSRRSLGIISGLTGAGGNVGAGLTQLLFFTSSQYSTGRGLEYMGIMIMACTLPIT
LVHFPQWGSMFFPASADATEEEYYASEWSEEEKGKGLHIAGQKFAENSRSERGRRNVILATS
ATPPNNTPQHV

SEQ ID NO: 81, Hordeum vulgare putative high affinity nitrate transporter (BCH4) mRNA, complete cds (AF091116)

CACCACTGCAAGCATATTTAGGCTTAGTTAGCTCCAAGGAGCAAAGCTAAAAAGAACCTAGC
TAGGCTAGCTCGATCCAGCTAGCTCAGTAGATATGGAGGTGGAGGCCGGAGCTCATGGCGAT
GCGGCGGCGAGCAAGTTCACGCTGCCCGTGGACTCCGAGCACAAGGCCAAGTCCTTCAGGCT
CTTCTCCTTCGCCAACCCGCACATGCGCACCTTCCACCTCTCGTGGATCTCCTTCTTCACCT
GCTTCGTCTCCACCTTTGCCGCTGCTCCGTTGGTGCCCATCATCCGCGACAACCTCAACCTC
GCCAAGGCCGACATCGGCAATGCCGGTGTGGCGTCCGTGTCCGGCTCCATCTTCTCGAGGCT
CGCCATGGGCGCCATTTGTGACCTGCTTGGCCCGCGGTACGGTTGTGCCTTTCTCGTCATGC
TATCGGCGCCAACCGTCTTCTGCATGGCCGTCATCGACGACGCGTCGGGATACATCGCAGTC
CGCTTCCTCATCGGCTTCTCCCTCGCAACCTTCGTGTCATGCCAGTACTGGATGAGCACAAT
GTTCAACAGTAAAATCATCGGCACGGTTAATGGCCTCGCAGCCGGGTGGGGCAACATGGGTG
GCGGGGCCACACAGCTCATCATGCCCCTCGTCTTCCATGCCATCCAAAAGTGTGGTGCCACA
CCCTTTGTGGCATGGCGTATCGCCTACTTCGTGCCGGGGATGATGCACATCGTGATGGGCCT
ACTCGTGCTCACCATGGGACAAGACCTCCCTGATGGGAACCTCGCAAGCCTGCAGAAGAAGG
GAGACATGGCCAAGGACAAGTTCTCCAAGGTCCTTTGGGGCGCCGTTACCAACTACCGGACA
TGGATCTTTGTCCTCCTCTATGGCTACTGCATGGGTGTCGAGCTCACCACTGGCAATGTCAT
TGCCGAGTACTACTTCGATCACTTCCACCTAAACCTCCGTGCCGCCGGTACCATCGCCGCTT
GCTTCGGCATGGCCAACATCGTCGCACGTCCTATGGGCGGCTACCTCTCCGACCTTGGTGCT
CGCTACTTCGGTATGCGTGCTCGCCTTTGGAACATCTGGATCCTTCAGACAGCTGGCGGCGC
CTTTTGCATCTGGCTTGGGCGCGCCTCGGCCCTCCCCGCCTCAGTGACTGCCATGGTCCTCT
TCTCCATCTGCGCCCAGGCTGCGTGTGGTGCTATCTTTGGTGTCGAACCCTTCGTCTCCAGG

CGTTCCCTTGGCATCATTTCCGGGTTGACCGGTGCTGGTGGAAACGTGGGCGCAGGGCTCAC
ACAGCTTCTCTTCTTCACTTCGTCGCAATACTCCACTGGCAGGGGTCTTGAGTACATGGGCA
TCATGATCATGGCATGCACCTTACCCGTCGCTCTCGTTCACTTCCCTCAGTGGGGCTCTATG
TTCTTGGCTGCCAGTGCCGACGCCACGGAGGAGGAGTACTACGCCTCAGAGTGGTCAGAGGA
GGAGAAGAGCAAGGGTCTCCATATCGCAGGACAAAAGTTTGCTGAGAACTCCCGCTCGGAAC
GCGGCAGGCGCAACGTCATCCTTGCCACATCCGCCACACCACCCAACAACACGCCCCTACAC
GTATAAGTTTCAAATTTTGTGTTACACAAGAAATGTACATCTTGCTGAGTATATATACACAT
CGTATATTTTAGTAAAAAAAAAAAAAAAAA

SEQ ID NO: 82, Hordeum vulgare putative high affinity nitrate transporter (AAD28364)

MEVEAGAHGDAAASKFTLPVDSEHKAKSFRLFSFANPHMRTFHLSWISFFTCFVSTFAAAPL
VPIIRDNLNLAKADIGNAGVASVSGSIFSRLAMGAICDLLGPRYGCAFLVMLSAPTVFCMAV
IDDASGYIAVRFLIGFSLATFVSCQYWMSTMFNSKIIGTVNGLAAGWGNMGGGATQLIMPLV
FHAIQKCGATPFVAWRIAYFVPGMMHIVMGLLVLTMGQDLPDGNLASLQKKGDMAKDKFSKV
LWGAVTNYRTWIFVLLYGYCMGVELTTGNVIAEYYFDHFHLNLRAAGTIAACFGMANIVARP
MGGYLSDLGARYFGMRARLWNIWILQTAGGAFCIWLGRASALPASVTAMVLFSICAQAACGA
IFGVEPFVSRRSLGIISGLTGAGGNVGAGLTQLLFFTSSQYSTGRGLEYMGIMIMACTLPVA
LVHFPQWGSMFLAASADATEEEYYASEWSEEEKSKGLHIAGQKFAENSRSERGRRNVILATS
ATPPNNTPLHV

SEQ ID NO: 83, Hordeum vulgare putative high affinity nitrate transporter (BCH3) mRNA, complete cds (AF091115)

TCTCAGTTGCCACTGCAGCTGATCAAGCAAGCTAGCTCCAAACCTCCAAGGAGGAAGCAGAG
AAGGAGACTAGCTCGATCAAGCAAGGTCCAAATGGAGGTGGAGGCTGGTGCCCATGGCGACA
CGGCGGCGAGCAAGTTCACGTTGCCCGTGGACTCCGAGCACAAGGCCAAGTCCTTCAGGCTC
TTCTCCTTCGCCAACCCACACATGCGCACCTTTCACCTATCGTGGATATCCTTCTTCACATG
CTTCGTCTCCACCTTTGCCGCGGCGCCCCTGGTGCCCATCATCCGCGACAACCTGAACCTCG
CCAAGGCCGACATAGGGAATGCCGGTGTGGCATCTGTGTCTGGGTCTATCTTCTCGAGGCTT
GCCATGGGCGCCATCTGCGACCTTTTGGGGCCGCGGTATGGGTGTGCCTTCCTCGTCATGCT
CTCAGCGCCAACCGTCTTCTGCATGGCCGTCATCGATGACGCCTCAGGGTACATCGCCGTAC
GCTTCCTCATCGGCTTCTCCCTTGCCACCTTTGTGTCGTGCCAATACTGGATGAGCACCATG
TTCAACAGTAAAATCATCGGCACGGTCAATGGCCTCGCGGCCGGCTGGGGCAACATGGGCGG
TGGTGCCACACAACTCATCATGCCGCTTGTTTTCCACGCCATCCAAAAATGTGGTGCCACAC
CATTTGTGGCATGGCGTATTGCCTACTTCGTGCCCGGAATGATGCACATCGTGATGGGCTTG
CTGGTACTCACCATGGGGCAAGATCTCCCTGATGGGAACCTCGCGAGCCTCCAGAAGAGAGG
AGACATGGCCAAGGACAAGTTCTCCAAGGTCCTTTGGGGCGCCGTCACCAACTACCGGACAT
GGATCTTTGTCCTCCTATATGGCTACTGCATGGGTGTCGAACTCACCACTGACAATGTCATT
GCCGAGTACTACTTCGACCACTTCCACCTAGACCTTCGCGCCGCTGGTACCATCGCCGCCTG
CTTCGGTATGGCCAACATAGTCGCACGTCCTATGGGCGGCTACCTCTCTGACCTTGGCGCCC
GCTATTTCGGCATGCGTGCCCTTTGGAACATCTGGATCCTCCAAACCGCTGGTGGCGCTTTC
TGCATCTGGCTCGGTCGTGCATCGGCCCTCCCTGCCTCGGTGACCGCCATGGTCCTCTTCTC
CATCTGTGCCCAGGCTGCCTGTGGTGCTATCTTTGGTGTCGCACCCTTCGTCTCCAGGCGTT
CCCTTGGCATCATTTCCGGGTTGACCGGTGCCGGTGGAAACGTGGGCGCAGGACTCACACAA

Figure 8 (continued)

CTTCTATTCTTCACCTCATCGCAATACTCCACTGGTAGGGGTCTCGAGTACATGGGCATCAT
GATCATGGCATGCACGCTGCCCGTCGCTCTTGTGCACTTTCCGCAATGGGGATCCATGTTCT
TCCCGGCCAGCGCTGATGCCACTGAGGAGGAGTACTATGCTTCCGAGTGGTCGGAGGAGGAG
AAGGGCAAGGGTCTCCATATCGCAGGCCAAAAGTTCGCCGAGAACTCCCGCTCGGAGCGCGG
CAGGCGCAACGTCATCTTTGCCACATCCGCCACGCCGCCCAACAACACACCCCAGCAGGTAT
AAGGCATTTTTTTTTGTTACCTATGAATTTTACAGCTCATGGCGTATATATACAAACAGTAT
ATTTACGTTTGCAGCCCCAGCGTAATAAGTTGTATGGGGGTTTATCTTTTTACTATGGTAAA
CCTAAGGACATGTATTGTCAAATTGAGTCCGAAATTAATACATGAACAGTGTTGATGTTTGT
GTATGCTTGAAAAAAAAAAAAAAAAAA

SEQ ID NO: 84, Hordeum vulgare putative high affinity nitrate transporter (AAD28363)

MEVEAGAHGDTAASKFTLPVDSEHKAKSFRLFSFANPHMRTFHLSWISFFTCFVSTFAAAPL
VPIIRDNLNLAKADIGNAGVASVSGSIFSRLAMGAICDLLGPRYGCAFLVMLSAPTVFCMAV
IDDASGYIAVRFLIGFSLATFVSCQYWMSTMFNSKIIGTVNGLAAGWGNMGGGATQLIMPLV
FHAIQKCGATPFVAWRIAYFVPGMMHIVMGLLVLTMGQDLPDGNLASLQKRGDMAKDKFSKV
LWGAVTNYRTWIFVLLYGYCMGVELTTDNVIAEYYFDHFHLDLRAAGTIAACFGMANIVARP
MGGYLSDLGARYFGMRALWNIWILQTAGGAFCIWLGRASALPASVTAMVLFSICAQAACGAI
FGVAPFVSRRSLGIISGLTGAGGNVGAGLTQLLFFTSSQYSTGRGLEYMGIMIMACTLPVAL
VHFPQWGSMFFPASADATEEEYYASEWSEEEKGKGLHIAGQKFAENSRSERGRRNVIFATSA
TPPNNTPQQV

SEQ ID NO: 85, Prunus persica PpNRT2;1 mRNA for high-affinity nitrate transporter, complete cds (AB097402)

CATTTAGTCTAAGTAGTTTCTAAATTCGAAACTTGAGTGCTGAAACTCGAGATTCAAAATCC
AAACTCCAAACCCCAAATTCAAAACCCCAAAAACATGGCCGAAGTCGAAGGTGAACCCGGAA
GCTCCATGCATGGAGTGACAGGCAGAGAGCAAACCTTTGCGTTCTCGGTAGCTTCCCCCATC
GTCCCAACAGACCCAACAGCCAAATTTGACCTACCAGTTGATTCAGAGCACAAGGCCAAAGT
TTTCAAAATCTTCTCTTTGGCCAACCCTCACATGAGAACTTTCCACTTGTCTTGGATCTCTT
TCTTCACTTGCTTTGTCTCAACTTTTGCAGCGGCCCCACTTGTCCCTATAATCCGAGACAAC
CTCAACCTCACAAAGCAAGACATTGGAAATGCTGGGGTTGCCTCTGTCTCAGGCAGCATATT
CTCAAGACTTGTAATGGGTGCAGTGTGTGATTTGCTAGGGCCACGATATGGGTGTGCCTTTC
TCATAATGCTCAGCGCACCCACTGTGTTTTGCATGTCATTTGTATCTGATGCTGGGGGCTAC
TTGGCAGTGAGATTCATGATTGGTTTTTCGCTTGCTACATTCGTGTCATGCCAGTATTGGAT
GAGTACCATGTTTAACAGTAAGATTATTGGGCTGGTTAATGGGACAGCTGCTGGGTGGGGAA
ACATGGGTGGTGGGGCCACCCAGCTCTTGATGCCATTGGTGTTTGATATAATTGGAAGAGTT
GGTGCAACTCCTTTCACTGCTTGGAGAATTGCCTTTTTCATTCCTGGCTGGCTTCATGTCAT
TATGGGAATAATGGTCTTGACCCTTGGCCAAGACTTGCCTGATGGGAATCTTGCTGCCCTGC
AAAAGAAGGGTGATGTTGCCAAAGATCAATTCTCCAAGGTATTGTGGCATGCTGTAACAAAT
TACAGGACATGGATCTTTGTCCTTCTCTATGGCTACTCCATGGGTGTTGAATTGTCCACTGA
TAATGTCATTGCTGAATACTTCTATGACAGGTTCAATCTCAAGCTTCACACAGCTGGAATCA
TTGCTGCAACATTTGGCATGGCCAACCTAGTAGCCCGTCCCTTTGGAGGATTTGCGTCTGAT
CGAGCAGCCAGGTACTTTGGCATGAGGGGCAGGCTATGGACTCTTTGGATCCTCCAAACACT
AGGAGGAGTCTTCTGCATCTGGCTCGGCCGAGCAAACTCACTCCCCATTGCGGTCTTTGCCA

Figure 8 (continued)

TGATCCTCTTCTCTGTAGGAGCCCAAGCTGCATGCGGAGCCACCTTTGGCGTCATCCCCTTC
ATCTCCCGGCGATCCCTCGGCATCATATCGGGCCTCACTGGAGCGGGTGGGAACTTCGGGTC
CGGGCTGACCCAACTAGTGTTCTTCTCAAGCTCAGCATTCTCAACTGCGACAGGGTTGTCTC
TGATGGGGGTAATGATCGTGTGCTGCACACTTCCAGTGACTTTGGTGCACTTCCCTCAGTGG
GGGAGCATGTTCCTTCCGCCTTCAAAAGATGTCGTGAAATCGACGGAAGAGTTTTACTATGG
AGCTGAGTGGAATGAGGAGGAGAAGCAGAAGGGGCTACACCAGCAGAGTTTGAGGTTTGCAG
AGAATAGTAGGTCTGAGCGTGGTAGGCGTGTTGCCTCAGCTCCAACCCCACCCAACACCACA
CCTTCCCATGTTTAGGTTATGTTATGATCTCATGAGAATTGTTTCTTTGAAATGCTTTGCAA
ACTCCTCATGCGCCCAATTATTCTCCTTAAGTTGACCGAGAAGCTTACTTCTCTCTTGGGGA
AATTTTTTCTTTATTATTATCAGTTTTTTCCCAAGCATATAAGTGAACTGATGATTATTTTT
ATTTCAGAAAAAAAAAAAAAAAAAA

SEQ ID NO: 86, Prunus persica high-affinity nitrate transporter (BAD02939)

MAEVEGEPGSSMHGVTGREQTFAFSVASPIVPTDPTAKFDLPVDSEHKAKVFKIFSLANPHM
RTFHLSWISFFTCFVSTFAAAPLVPIIRDNLNLTKQDIGNAGVASVSGSIFSRLVMGAVCDL
LGPRYGCAFLIMLSAPTVFCMSFVSDAGGYLAVRFMIGFSLATFVSCQYWMSTMFNSKIIGL
VNGTAAGWGNMGGGATQLLMPLVFDIIGRVGATPFTAWRIAFFIPGWLHVIMGIMVLTLGQD
LPDGNLAALQKKGDVAKDQFSKVLWHAVTNYRTWIFVLLYGYSMGVELSTDNVIAEYFYDRF
NLKLHTAGIIAATFGMANLVARPFGGFASDRAARYFGMRGRLWTLWILQTLGGVFCIWLGRA
NSLPIAVFAMILFSVGAQAACGATFGVIPFISRRSLGIISGLTGAGGNFGSGLTQLVFFSSS
AFSTATGLSLMGVMIVCCTLPVTLVHFPQWGSMFLPPSKDVVKSTEEFYYGAEWNEEEKQKG
LHQQSLRFAENSRSERGRRVASAPTPPNTTPSHV

SEQ ID NO: 87, Prunus persica PpNRT2;2 mRNA for high-affinity nitrate transporter, complete cds (AB097676)

GCTTCATTTAGTCTAAGTAGTTTCTAAATTCGAAACTCGAGTTTTGAAACTCGAGATTCAAA
ATCCAAACTCCAAACCCCAAATAATGGCCGAAGTCGAAGGTGAACCCGGAAGCTCCATGCAT
GGAGTGACAGGCAGAGAGCAAACCTTTGCGTTCTCAGTAGCTTCCCCCATCGTCCCAACAGA
CCCAACAGCTAAATTTGACCTACCTGTTGATTCAGAGCACAAGGCCAAAGTTTTCAAAATCT
TCTCTTTGGCCAACCCGCACATGAGAACCTTCCACTTGTCTTGGATCTCCTTCTTCACTTGC
TTTGTCTCAACTTTTGCAGCGGCCCCACTTGTCCCTATAATCCGAGACAACCTCAACCTCAC
AAAGCAAGACATTGGAAATGCTGGGGTTGCCTCTGTCTCAGGCAGCATATTCTCAAGACTTG
TAATGGGTGCAGTGTGTGATTTGCTAGGGCCACGATATGGGTGTGCCTTTCTCATAATGCTC
AGCGCACCCACTGTGTTTTGCATGTCATTTGTATCTGATGCTGGGGGCTACTTGGCAGTGAG
ATTCATGATTGGTTTTTCGCTTGCTACATTCGTGTCATGCCAGTATTGGATGAGTACCATGT
TTAACAGTAAGATTATTGGGCTGGTTAATGGGACAGCTGCTGGGTGGGGAAACATGGGTGGT
GGGGCCACCCAGCTCTTGATGCCATTGGTGTTTGATATAATTGGAAGAGTTGGTGCAACTCC
TTTCACTGCTTGGAGAATTGCCTTTTTCATCCCTGGCTGGCTTCATGTCATTATGGGAATAA
TGGTCTTGACCCTTGGCCAAGACTTGCCTGATGGAAATCTTGCTGCCCTGCAAAAGAAGGGT
GATGTTGCCAAAGATCAATTCTCCAAGGTATTGTGGCATGCTATAACAAACTACAGGACATG
GATCTTTGTCCTTCTCTATGGCTACTCCATGGGTGTTGAATTGTCCATTGATAATGTCATTG
CTGAATACTTCTATGACAGGTTCAATCTCAAGCTTCACACAGCTGGAATCATTGCTGCAGCA

Figure 8 (continued)

TTTGGCATGGCCAACATAGTGGCCCGTCCCTTTGGAGGATTTGCGTCTGATCGAGCAGCCAG
GTACTTTGGCATGAGGGGCAGGCTATGGACTCTTTGGATCCTCCAAACACTAGGAGGAGTCT
TTTGCATCTGGCTCGGCCGAGCAAACTCACTCCCCATTGCGGTCTTTGCCATGATCCTCTTC
TCTGTAGGAGCCCAAGCTGCATGCGGAGCCACCTTTGGCGTCATCCCCTTCATCTCCCGGCG
ATCCCTCGGCATCATATCGGGCCTCACTGGAGCGGGTGGGAACTTCGGATCCGGGCTGACCC
AACTAGTGTTCTTCTCAAGCGCAGCATTCTCAACTGCGACAGGGTTGTCTCTGATGGGGGTA
ATGATCGTGTGCTGCACACTTCCAGTGACTTTGGTGCACTTCCCTCAGTGGGGGAGCATGTT
CCTTCCGCCTTCAAAAGATGTCGTGAAATCAACGGAAGAGTTTTACTATGGAGCTGAGTGGA
ATGAGGAGGAGAAGCAGAAGGGGCTACACCAGCAGAGTTTGAGGTTTGCAGAGAATAGTAGG
TCTGAGCGTGGTAGGCGTGTTGCCTCAGCTCCAACCCCACCCAACACCACACCTTCCCATGT
TTAGTCAAACAAGGGAAAAAGGTCAACATGCACCAAGGTGCATATGTGGTGTGGAACAAACC
AATAATCAGAGAAGTGCTATTTTGTATCATCTCAATCAATCATATGTGTACTGTATTTCTAT
TAGAAATACAAGAGATGATCAGTTGAGTTGATACAAGTAGTTTTATTTGTAATGAAAATAGA
GTTGCCATATAGCGTGTGCCTCTATATATGTATCTTGTACACAAATGTTTTTACTTTCAAGG
TTTAAACTTATGATAATTTTCAAAAAAAAAAAAAAAAAAA

SEQ ID NO: 88, Prunus persica high-affinity nitrate transporter (BAD04063)

MAEVEGEPGSSMHGVTGREQTFAFSVASPIVPTDPTAKFDLPVDSEHKAKVFKIFSLANPHM
RTFHLSWISFFTCFVSTFAAAPLVPIIRDNLNLTKQDIGNAGVASVSGSIFSRLVMGAVCDL
LGPRYGCAFLIMLSAPTVFCMSFVSDAGGYLAVRFMIGFSLATFVSCQYWMSTMFNSKIIGL
VNGTAAGWGNMGGGATQLLMPLVFDIIGRVGATPFTAWRIAFFIPGWLHVIMGIMVLTLGQD
LPDGNLAALQKKGDVAKDQFSKVLWHAITNYRTWIFVLLYGYSMGVELSIDNVIAEYFYDRF
NLKLHTAGIIAAAFGMANIVARPFGGFASDRAARYFGMRGRLWTLWILQTLGGVFCIWLGRA
NSLPIAVFAMILFSVGAQAACGATFGVIPFISRRSLGIISGLTGAGGNFGSGLTQLVFFSSA
AFSTATGLSLMGVMIVCCTLPVTLVHFPQWGSMFLPPSKDVVKSTEEFYYGAEWNEEEKQKG
LHQQSLRFAENSRSERGRRVASAPTPPNTTPSHV

SEQ ID NO: 89, Glycine max putative high affinity nitrate transporter (NRT2) mRNA, complete cds (AF047718)

TCACACTTTCTTCCTTAATTTTCTAGCTCTTGCTACGTACTTGAATTCAATTAGTTATTAAT
GGCTGAGATTGAGGGTTCTCCCGGAAGCTCCATGCATGGAGTAACAGGAAGAGAACAAACAT
TTGTAGCCTCAGTTGCTTCTCCAATTGTCCCTACAGACACCACAGCCAAATTTGCTCTCCCA
GTGGATTCAGAACACAAGGCCAAGGTTTTCAAACTCTTCTCCCTGGCCAATCCCCACATGAG
AACCTTCCACCTTTCTTGGATCTCCTTCTTCACCTGCTTCGTCTCGACATTCGCAGCAGCAC
CTCTTGTGCCCATCATCCGCGACAACCTTAACCTCACCAAAAGCGACATTGGAAACGCCGGG
GTTGCTTCTGTCTCCGGAAGCATCTTCTCAAGGCTCGCAATGGGTGCAGTCTGTGACATGTT
GGGTCCACGCTATGGCTGCGCCTTCCTCATCATGCTTTCGGCCCCTACGGTGTTCTGCATGT
CCTTTGTGAAAGATGCTGCGGGGTACATAGCGGTTCGGTTCTTGATTGGGTTCTCGTTGGCG
ACGTTTGTGTCGTGCCAGTACTGGATGAGCACGATGTTCAACAGTAAGATTATAGGGCTTGC
GAATGGGACTGCTGCGGGGTGGGGGAACATGGGTGGTGGAGCCACTCAGCTCATAATGCCTT
TGGTGTATGAGCTTATCAGAAGAGCTGGGGCTACTCCCTTCACTGCTTGGAGGATTGCCTTC
TTTGTTCCGGGTTTCATGCATGTCATCATGGGGATTCTTGTCCTCACTCTAGGCCAGGACTT

Figure 8 (continued)

GCCTGATGGAAACCTCGGGGCCTTGCGGAAGAAGGGTGATGTAGCTAAAGACAAGTTTTCCA
AGGTGCTATGGTATGCCATAACAAATTACAGGACATGGATTTTTGCTCTCCTCTATGGGTAC
TCCATGGGAGTTGAATTAACAACTGACAATGTCATTGCTGAGTATTTCTATGACAGATTTAA
TCTCAAGCTACACACTGCTGGAATCATTGCTGCTTCATTTGGAATGGCAAACTTAGTTGCTC
GACCTTTTGGTGGATATGCTTCAGATGTTGCAGCCAGGCTGTTTGGCATGAGGGGAAGACTC
TGGACCCTTTGGATCCTCCAAACCTTAGGAGGGGTTTTCTGTATTTGGCTTGGCCGTGCCAA
TTCTCTTCCTATTGCTGTATTGGCCATGATCCTGTTCTCTATAGGAGCTCAAGCTGCATGTG
GTGCAACTTTTGGCATCATTCCTTTCATCTCAAGAAGGTCTTTGGGGATCATATCAGGTCTA
ACTGGTGCAGGTGGAAACTTTGGGTCTGGCCTCACCCAATTGGTCTTCTTTTCAACCTCCAA
ATTCTCTACTGCCACAGGTCTCTCCTTGATGGGTGTAATGATAGTGGCTTGCACTCTACCAG
TGAGTGTTGTTCACTTCCCACAGTGGGGTAGCATGTTTCTACCACCCTCAAAAGATGTCAGC
AAATCCACTGAAGAATTCTATTACACCTCTGAATGGAATGAGGAAGAGAAGCAGAAGGGTTT
GCACCAGCAAAGTCTCAAATTTGCTGAGAATAGCCGATCTGAGAGAGGAAAGCGAGTGGCTT
CAGCACCAACACCTCCAAATGCAACTCCCACTCATGTCTAGCCATAGCACTTCAATCAAAGA
AGATCATGAAACATAATTACTGAGCAGTATTGGGAATGAAGAACCATGAGTTGAAGAATTTT
CTAATAAGAAATCTTGTAACATGTAGACATAGAATGTTCTGGTTCTGGTTTGCGTGTGGTGT
AAGAGTTGTCTACTTGTGGTAAGTCATAAGTATCATAATCAGTATGTCAATGCAGATCTTGA
TGCTGAGTATCAATAGTATCAAAAAAAAAA

SEQ ID NO: 90, Glycine max putative high affinity nitrate transporter; GmNRT2 (AAC09320)

MAEIEGSPGSSMHGVTGREQTFVASVASPIVPTDTTAKFALPVDSEHKAKVFKLFSLANPHM
RTFHLSWISFFTCFVSTFAAAPLVPIIRDNLNLTKSDIGNAGVASVSGSIFSRLAMGAVCDM
LGPRYGCAFLIMLSAPTVFCMSFVKDAAGYIAVRFLIGFSLATFVSCQYWMSTMFNSKIIGL
ANGTAAGWGNMGGGATQLIMPLVYELIRRAGATPFTAWRIAFFVPGFMHVIMGILVLTLGQD
LPDGNLGALRKKGDVAKDKFSKVLWYAITNYRTWIFALLYGYSMGVELTTDNVIAEYFYDRF
NLKLHTAGIIAASFGMANLVARPFGGYASDVAARLFGMRGRLWTLWILQTLGGVFCIWLGRA
NSLPIAVLAMILFSIGAQAACGATFGIIPFISRRSLGIISGLTGAGGNFGSGLTQLVFFSTS
KFSTATGLSLMGVMIVACTLPVSVVHFPQWGSMFLPPSKDVSKSTEEFYYTSEWNEEEKQKG
LHQQSLKFAENSRSERGKRVASAPTPPNATPTHV

SEQ ID NO: 91, Lotus japonicus mRNA for membrane transporter (nrt2 gene) (AJ292342)

GCACAAGTTTTTCTCTGTTGCATGTTCTGTTTCTGAATTACTTTAATTACTTCACACAACAA
CATTCAACAATGGTTGAAATTGAAGGATCTCCAGGAACCTCCATGCATGGAGTAACAGGGAG
GGAACAAACCTTCATATCCTCAGTTTCTTCCCCAATGGTCCCAACAGACACCACAGCCAAAT
TCGATTTACCAGTTGATTCACAGCACAAAGCCAAAGTTTTCAAACTGTTCTCATTAGCTAAT
CCTCACATGACAACCTTCCACTTATCATGGATTTCCTTCTTCACCTGCTTTGTCTCTACCTT
TGCAGCAGCTCCTCTTGTCCCCATCATCCGAGACAACCTCAATCTCACCAAAAGCGACATTG
GCAACGCCGGTGTCGCGTCTGTCTCCGGCAGCATTTTCTCCAGGCTCACCATGGGTGTAATT
TGTGACCTCTTAGGCCCACGTTACGGGTGTGCCTTCCTGATCATGCTGTCTGCACCAACTGT
GTTCTGCATGTCGTTTGTGAATGATGCTGCAGGCTACATTGTGGTTCGGTTCATGATCGGGT
TCTCATTGGCCACGTTTGTTTCGTGCCAGTACTGGATGAGTACCATGTTTAACAGTAAGATT
ATTGGGCTTGTTAATGGAACTGCAGCTGGTTGGGGTAACATGGGTGGTGGAGCCACTCAGCT

Figure 8 (continued)

CATCATGCCTATTGTCTATGAATTGATCAGGAGAGCGGGGTCCACTGGGTTCACTGCTTGGA
GGATTGCCTTCTTCATCCCTGGTTTCATGCATGTTTTCATGGGGATCCTTGTCTTAACCCTT
GGCCAAGACTTGCCTGATGGCAACCTCAGTGCCCTCCAGAAGAAGGGTGATGTTGCTAAAGA
CAAATTCTCCAAGGTGTTATGGTATGCCATAACAAATTACAGGACATGGATCTTTGCACTTC
TCTATGGATACTCTATGGGAGTCGAATTAACCACTGACAATGTCATTGCTGAGTATTTTTAT
GACAGATTTAATCTGAAGTTGCACACAGTTGGAATCATTGCTGCTTCTTTTGGAATGGCAAA
TCTTGTTGCTCGCCCCTTTGGCGGATATGTATCTGATGTTGCAGCCCGGTTGTTTGGTATGA
GAGGAAGACTGTGGACTCTGTGGATCCTCCAAACACTTGGAGGAGTGTTCTGTATATGGCTT
GGGCGTGCGAATTCACTTCCAATTGCGGTGTTGGCGATGATCCTTTTCTCAGTTGGAGCTCA
AGCTGCTTGTGGTGCAACATTTGGAATCATTCCTTTCATCTCAAAAAGGTCTTTGGGGATCA
TTTCAGGTCTAACTGGTGCAGGTGGCAACTTTGGTTCTGGATTGACACAGTTGGTATTCTTT
TCTACTTCAAGATTCTCCACAGGTGCAGGATTGTCATGGATGGGTGTGATGATTGTTGGTTG
CACTCTTCCGGTGACTCTTGTTCACTTCCCACAGTGGGGTAGCATGTTCCTTCCTCCTTCAA
AAGACATCAACAAGTCCAGTGAGGAACACTATTACACTGCTGAATGGGATGAGGAAGAGAGG
AAGAAGGGGTTGCACTCTCAAAGTCTTAAGTTTGCAGAGAATAGTCGCTCTGAGAGAGGAAA
ACGTGTTTCCTCTGCTCCAACTCCTCCAAACACAACCCCTACCCATGTCTAAGATGGATGGA
TGATCACCACAGTGGAAAGCTAATGAGGAAAAGAGTATATGGATCCCTTGATTGAATAATTT
ATCCTTAAGCCTTTAAAGATACTTTGGCATCCAGAAATTTGGTGTTTGCCCTTCAAATTCTA
CTTGTTATAGAAATTTGGTGTGATTTTCTATAAGGGACTTTGGTGTCTGTGGGAGTGTGGGT
CTATCAGTTAATTATACAAACAGGTGGTGTACAAAAATAATATATTGAGTTTTTTAATTTTG
GTGTGATATATATTAATGAATGTTACTCAAAAAAAAAAAAAAAAAAAAAACTCGAGGGGGGGC
CCGGTA

SEQ ID NO: 92, Membrane transporter - Lotus japonicus (Q9ARC5)

MVEIEGSPGTSMHGVTGREQTFISSVSSPMVPTDTTAKFDLPVDSQHKAKVFKLFSLANPHM
TTFHLSWISFFTCFVSTFAAAPLVPIIRDNLNLTKSDIGNAGVASVSGSIFSRLTMGVICDL
LGPRYGCAFLIMLSAPTVFCMSFVNDAAGYIVVRFMIGFSLATFVSCQYWMSTMFNSKIIGL
VNGTAAGWGNMGGGATQLIMPIVYELIRRAGSTGFTAWRIAFFIPGFMHVFMGILVLTLGQD
LPDGNLSALQKKGDVAKDKFSKVLWYAITNYRTWIFALLYGYSMGVELTTDNVIAEYFYDRF
NLKLHTVGIIAASFGMANLVARPFGGYVSDVAARLFGMRGRLWTLWILQTLGGVFCIWLGRA
NSLPIAVLAMILFSVGAQAACGATFGIIPFISKRSLGIISGLTGAGGNFGSGLTQLVFFSTS
RFSTGAGLSWMGVMIVGCTLPVTLVHFPQWGSMFLPPSKDINKSSEEHYYTAEWDEEERKKG
LHSQSLKFAENSRSERGKRVSSAPTPPNTTPTHV

SEQ ID NO: 93, Nicotiana tabacum mRNA for high affinity nitrate transporter protein (nrt2.2 gene) (AJ557584)

TTAAAGAAGAAATTAAAAATGGTTGATATTGAAGGATCACCAGGTAGTTCTATGCATGGAGT
TACAGGTAGAGAACCAGTTCTTGCTTTCTCTGTTGCATCTCCAATGGTACAAACTGATACCA
CTGCACATTTTAAAGTTCCGGTCGATTCTGAACACAAGGCCAAGGTTTTCAAATTCTACTCA
TTTTCAAAACCTCACGGTCTAACTTTTCAACTTTCTTGGATTTCTTTCTTTACTTGTTTTGT
TTCTACTTTTGCTGCTGCCCCTTTAGTTCCTATTATTAGAGACAACCTTAACTTGACCAAAA
TGGACGTTGGTAATGCTGGGGTTGCCTCTGTTTCCGGAAGTATTCTATCTAGGCTTGCAATG
GGTGCGATTTGTGACATGTTGGGACCAAGATATGGATGCGCGTTTCTTATCATGTTATCAGC
TCCGACTGTTTTTTGCATGTCTTTCGTGTCTTCGGCTGGTGGCTACGTTGCTGTGAGATTCA

Figure 8 (continued)

TGATTGGATTCTCACTCGCGACGTTTGTGTCGTGTCAATATTGGATGAGTACGATGTTTAAT
AGTCAGATTATTGGACTTGTTAATGGAACAGCAGCAGGATGGGGAAATATGGGGGGTGGAGC
TACTCAGCTTATTATGCCTATTCTCTATGATATTATTAGAAGAGCAGGAGCCACCCCTTTTA
CTGCTTGGAGAATTGCTTTCTTTATTCCTGGTTGGCTTCATGTTATTATGGGAATTTTAGTG
TTAACTCTTGGCCAAGATTTGCCTGATGGTAACCTTGCTTCCCTACAGAAGAAAGGCGATGT
TTCTAAAGATAAGTTCTCTAAGATATTGTGGTATGCTGCAACAAATTACAGGACATGGATCT
TTGTCCTGCTCTATGGTTACTCCATGGGAGTTGAATTGACTACAGATAATGTGATTGCTGAG
TACTTCTTTGATAGATTTGATCTAAAGCTTCACACGGCTGGAATCATTGCTGCCACATTTGG
TATGGCTAATCTCTTAGCTCGACCTTTTGGAGGATGGTCATCAGATATTGCAGCCAAACATT
TTGGAATGAGAGGCAGATTATGGAACTTATGGATTTTACAAACACTTGGTGGTGTTTTCTGT
TTCTTACTTGGAAAAGCAAACACACTTCCTATGGCTATAGCTTGGATGATCATATTCTCCTT
AGGTGCTCAAGCAGCATGTGGAGCTACATTTGGTATTATTCCTTTCATTTCGCGTCGATCGT
TAGGTATAATCTCAGGTATGACAGGAGCTGGAGGAAATTTTGGTTCTGGATTGACACAACTC
TTGTTTTTCACAACTACAAAATGGTCAACAGAAACAGGATTGAGTTATATGGGGATTATGAT
TATAGCTTGTACACTTCCTGTATCTTTGGTTCATTTCCCACAATGGGGAAGTATGTTTTTGC
CTCCAACTAAAGATCCTGTTAAGAGTACTGAAGAGCATTACTTCACGTCTGAGTACACTGAG
GCTGAGAAGCAAAAGGGTATGCACCAAAACAGCATCAAGTTTGCTGAAAACTGTCGGTCGGA
GCGTGGTAAGCGTGTGGGTTCAGCTCTTACTCCGCCTAATGTAACGCCAAACCGTGTCTGAG
CTTGAGTCTCACGGATCAGTACGGAGAAATAGTGATTTTGAAAAGCTTACTTGCTTAATTGG
TGTTTGTATCAACACAATAAACGTGTGATATGTGTCTTTTAATGAGCTTTATATTACCCAAG
TGTGAGTAGTTAATTTGTATTATCACTTTGTGTTGTGAGACTGATCTTAATATTAAAACAGT
TGATTTGGTGTAAACTTTCATTAAAAAAAAAAAAAAAAAA

SEQ ID NO: 94, Nicotiana tabacum high affinity nitrate transporter protein (CAD89799)

MVDIEGSPGSSMHGVTGREPVLAFSVASPMVQTDTTAHFKVPVDSEHKAKVFKFYSFSKPHG
LTFQLSWISFFTCFVSTFAAAPLVPIIRDNLNLTKMDVGNAGVASVSGSILSRLAMGAICDM
LGPRYGCAFLIMLSAPTVFCMSFVSSAGGYVAVRFMIGFSLATFVSCQYWMSTMFNSQIIGL
VNGTAAGWGNMGGGATQLIMPILYDIIRRAGATPFTAWRIAFFIPGWLHVIMGILVLTLGQD
LPDGNLASLQKKGDVSKDKFSKILWYAATNYRTWIFVLLYGYSMGVELTTDNVIAEYFFDRF
DLKLHTAGIIAATFGMANLLARPFGGWSSDIAAKHFGMRGRLWNLWILQTLGGVFCFLLGKA
NTLPMAIAWMIIFSLGAQAACGATFGIIPFISRRSLGIISGMTGAGGNFGSGLTQLLFFTTT
KWSTETGLSYMGIMIIACTLPVSLVHFPQWGSMFLPPTKDPVKSTEEHYFTSEYTEAEKQKG
MHQNSIKFAENCRSERGKRVGSALTPPNVTPNRV

SEQ ID NO: 95, Lycopersicon esculentum putative high-affinity nitrate transporter (NRT2;3) mRNA, complete cds (AY038800)

GCCTAAAATGGGTGATATTGAAGGATCACCAGGAAGTTCAATGCATGGTGTTACTGGTAGAG
AGCCAGTTCTTGCATTTTCAGTTGCTTCACTAATTGTACCAACTGATACATCAGCCAATTTC
AAAGTCCCTGTTGATTCTGAACATAAAGCTAAAGTTTTTAAATTTTATTCGTTTTCGAAACC
TCATGGACTAACGTTTCAACTCTCATGGATTTCATTTTGTACTTGTTTCGTATCGACTTTTG
CTGCAGCCCCTTTAGTCCCTATTATTAGGGACAATCTTAATCTAACTAAAATGGATGTTGGT
AATGCTGGAGTTGCCTCTGTTTCGGGTAGTATCTTGTCTAGGCTAGCTATGGGCGCGATTTG
TGACATGTTAGGTCCTAGATATGGTTGCGCGTTCCTTATAATGTTATCAGCCCCAACTGTTT

Figure 8 (continued)

TATGTATGTCTTTTGTGTCATCGGCTGGAGGGTACGTTGCTGTGAGGTTTATGATTGGGTTT
TCACTAGCAACGTTTGTGTCATGTCAGTATTGGATGAGTACGATGTTTAATAGTCAAATCAT
TGGACTTGTGAATGGTACAGCTGCTGGATGGGGTAATATGGGTGGTGGTGCTACTCAACTTA
TTATGCCTTTGCTCTACGATATAATACGTAGAGCAGGGGCAACCCCGTTCACTGCTTGGAGA
ATCGCATTTTTTATTCCTGGATGGCTTCATGTTATTATGGGAATTTTAGTTTTAACTCTTGG
ACAAGATTTACCTGATGGTAACCTCGCTTCTTTACAGAAGAAAGGCGATGTTTCTAAAGATA
AATTCTCAAAGATATTATGGTATGCTGCAACAAATTACAGAACATGGATCCTTGTTCTGCTC
TATGGATACTCAATGGGAGTTGAATTAACTACAGATAACGTGATTGCTGAGTATTTCTTCGA
TAGATTTGATTTGAAGCTTCATACGGCTGGAATCATCGCTGCAACATTTGGCATGGCTAACT
TATTAGCGCGACCATTTGGAGGATGGTCATCAGATGTTGCAGCTAAACATTTCGGGATGAGA
GGCAGATTATGGAATTCATGGATTTTACAAACACTTGGTGGTGTGTTCTGTTTACTACTTGG
AAGGGCTACTACACTTCCTCTGGCTATTACTTGGATGATCATATTCTCAATAGGTGCACAAG
CAGCATGTGGTGTAACGTTTGGAATTATTCCCTTTATTTCGCGAAGATCATTAGGTATAATA
TCAGGTATGACAGGAGCTGGAGGCAATTTTGGTTCCGGATTGACACAACTACTGTTTTTCAC
GAGTACAAAGTACTCGACAGGAACAGGACTAACGTATATGGGGATGATGATCATCGCGTGTA
CACTTCCAGTAATGTTAGTTCGTTTTCCACAGTGGGGTAGTATGTTTTTGCCTCCATCTAAA
GATCCTATTAAGGGTACTGAAGAACATTATTTGGTTCTGAGTATACTGAGGATGAGAAACA
AAAGGGAATGCACCAGAACAGCATCAAGTTCGCGGAAAACAGCAGGACAGAGCGTGGGAAGA
AGCGCGTTGGTTCAGCACCTACTCCGCCTAATGTAACACCAAATCGCGTCTGATGGGGAAAA
AAATTAAAATACTTACTTCGCAGTTCATGCTCGT

SEQ ID NO: 96, Lycopersicon esculentum putative high-affinity nitrate transporter (AAK72402)

MGDIEGSPGSSMHGVTGREPVLAFSVASLIVPTDTSANFKVPVDSEHKAKVFKFYSFSKPHG
LTFQLSWISFCTCFVSTFAAAPLVPIIRDNLNLTKMDVGNAGVASVSGSILSRLAMGAICDM
LGPRYGCAFLIMLSAPTVLCMSFVSSAGGYVAVRFMIGFSLATFVSCQYWMSTMFNSQIIGL
VNGTAAGWGNMGGGATQLIMPLLYDIIRRAGATPFTAWRIAFFIPGWLHVIMGILVLTLGQD
LPDGNLASLQKKGDVSKDKFSKILWYAATNYRTWILVLLYGYSMGVELTTDNVIAEYFFDRF
DLKLHTAGIIAATFGMANLLARPFGGWSSDVAAKHFGMRGRLWNSWILQTLGGVFCLLLGRA
TTLPLAITWMIIFSIGAQAACGVTFGIIPFISRRSLGIISGMTGAGGNFGSGLTQLLFFTST
KYSTGTGLTYMGMMIIACTLPVMLVRFPQWGSMFLPPSKDPIKGTEEHYFGSEYTEDEKQKG
MHQNSIKFAENSRTERGKKRVGSAPTPPNVTPNRV

SEQ ID NO: 97, Populus tremula x Populus tremuloides mRNA for nitrate transporter (tNit2.1 gene) (AJ646890)

CTTCCCTAGTCTGAAACTCCTATCACAATCCGGTTTGGAAGAGAATAGAGGAAGGGAATGGC
TGACGTTGAGGGTTCCCCGGGTAGTTCCATGCATGGAGTGACAGGCAGAGAACAAAGCTTTG
CCTTTTCGGTTGCCTCTCCTACAGTCCCGACGGATACAACAGCAAAATTTGCCTTGCCAGTT
GATTCTGAGCACAAGGCCAAAGTGTTCAAGATTTTCTCTTTTGCTAACCCTCATATGAGAAC
ATTTCACCTTTCTTGGATATCATTCTTCACTTGTTTTGTCTCCACTTTTGCTGCAGCACCCC
TTGTTCCTATCATTCGGGACAACCTCAATTTAACCAAAAGTGACATCGGTAATGCTGGTGTT
GCTTCTGTCTCTGGAAGCATCTTCTCTAGGCTTGTAATGGGTGCAGTTTGTGACCTCTTGGG
GCCGCGATATGGGTGTGCGTTTCTGATCATGCTCTCAGCCCCAACTGTGTTTTGCATGTCGT
TTGTGGACTCAGCTGGAGGATACCTAGCAGTCCGTTTCATGATTGGATTCTCTCTTGCAACG

Figure 8 (continued)

TTCGTGTCATGCCAGTACTGGATGAGCACAATGTTTAACAGCAAGATTATCGGACTCGTCAA
TGGAACCGCAGCCGGTTGGGGCAATATGGGTGGAGGTGCAACTCAGCTCGTAATGCCCTTGG
TCTACGAGCTCATTAAGCGAGCTGGTTCAACTTCATTCAGTGCTTGGAGGATAGCATTTTTT
GTCCCAGGATGGCTTCATGTTATCATGGGAATCTTGGTCTTGAATCTAGGCCAAGACTTGCC
TGATGGGAATCTCGGTGCCCTAAAGAAGAAGGGTGATGTTGCTAAAGATAAGTTCTCCAAGG
TACTCTGGTATGCTGTTACAAACTATAGGACCTGGATCTTTGTCCTTCTCTATGGCTACTCC
ATGGGAGTTGAATTATCCACCGACAATGTTATCGCCGAGTACTTCTATAACAGGTTCGATCT
AAAGCTTCACACAGCAGGTGTCATTGCTGCTACCTTTGGTATGGCTAACCTTGTAGCTCGTC
CCTTTGGTGGATATTTTTCTGATGTAGCAGCAAGGTACTTCGGGATGAGAGGCAGGTTATGG
GTGCTCTGGATTTTACAGACACTTGGAGGAGTTTTCTGTACTTGGCTCGGTCGAGCTAATTC
ACTTCCCCTTGCTGTCACCGCTATGATTCTCTTCTCTATTGGAGCGCAAGCCGCATGTGGAG
CAACTTTTGGTATCATTCCCTTTATTTCTCGACGATCATTGGGCATCATATCCGGCCTAACT
GGTGCAGGTGGAAATTTTGGGTCCGGATTGACACAACTAGTATTCTTTTCGAGCTCAAGTTT
GTCCACAGCTGCAGGTCTATCCTGGATGGGTGTCATGATTTGCGGCTGCACTCTCCCTGTGA
CATTGGTTTACTTCCCACAATGGGGCGGCATGTTCTTTCCGCCTTCTAAAGACGTAGTGAAG
TCAACAGAAGAATCCTATTATGCATCAGAGTGGGATGAGGACGAGAAGCAAAGGGGCATGCA
CCAGAAAAGCCTCAAGTTTGCGGAGAACAGCCGATCTGAACGTGGCAAGCGCATTGCCTCTG
CACCAACACCACCAAGTACCACACCAAACCGTGTGTAGATCAAAGCGTTGGCCATGCTTCTA
TAGTGC

SEQ ID NO: 98, Populus tremula x Populus tremuloides nitrate transporter (CAG26716)

MADVEGSPGSSMHGVTGREQSFAFSVASPTVPTDTTAKFALPVDSEHKAKVFKIFSFANPHM
RTFHLSWISFFTCFVSTFAAAPLVPIIRDNLNLTKSDIGNAGVASVSGSIFSRLVMGAVCDL
LGPRYGCAFLIMLSAPTVFCMSFVDSAGGYLAVRFMIGFSLATFVSCQYWMSTMFNSKIIGL
VNGTAAGWGNMGGGATQLVMPLVYELIKRAGSTSFSAWRIAFFVPGWLHVIMGILVLNLGQD
LPDGNLGALKKKGDVAKDKFSKVLWYAVTNYRTWIFVLLYGYSMGVELSTDNVIAEYFYNRF
DLKLHTAGVIAATFGMANLVARPFGGYFSDVAARYFGMRGRLWVLWILQTLGGVFCTWLGRA
NSLPLAVTAMILFSIGAQAACGATFGIIPFISRRSLGIISGLTGAGGNFGSGLTQLVFFSSS
SLSTAAGLSWMGVMICGCTLPVTLVYFPQWGGMFFPPSKDVVKSTEESYYASEWDEDEKQRG
MHQKSLKFAENSRSERGKRIASAPTPPSTTPNR

SEQ ID NO: 99, Nicotiana tabacum mRNA for high affinity nitrate transporter protein (nrt2.1 gene) (AJ557583)

TTAAAAAAAAAATGGGTGATATTGAGGGCGAACCAGGGAGTTCCATGCATGGAGTCACTGGT
AGAGAGCCAGTTCTTGCTTTCTCAGTGGCTTCTCCGATGGTGCCAACTGATACCACTGCAAA
ATTTTCAGTACCAGTTGATACTGAACACAAAGCCAAGATTTTTAAGTTCTATTCATTTTCAA
AGCCACATGGTCTTACTTTCCAGCTCTCCTGGATTTCTTTCTTCACTTGTTTTGTTTCAACT
TTTGCCGCTGCCCCTTTAGTTCCTATCATTAGGGACAACCTTAATTTAACCAAAATGGATGT
TGGTAATGCCGGAGTTGCTTCCGTTTCCGGAAGTATTTTATCTAGGCTTGTTATGGGTGCAG
TTTGTGATATGTTAGGGCCAAGATATGGCTGTGCATTTCTGATTATGTTGTCAGCCCCAACT
GTATTTTGCATGTCATTTGTGTCGTCGGCTGGAGGATATGTTGCTGTCCGGTTCATGATCGG
ATTCTCGCTAGCAACATTTGTGTCGTGCCAATATTGGATGAGTACTATGTTTAATAGTCAGA
TTATAGGACTTGTCAATGGGACAGCTGCAGGATGGGGAAATATGGGTGGTGGTGCGACTCAA

Figure 8 (continued)

CTTATTATGCCAATTGTGTATGATATAATAAGAAGAGCAGGAGCAACTCCATTCACTGCTTG
GAGAATTGCATTTTTCATTCCTGGCTGGCTTCATATTGTGATGGGTATTTTGGTGTTGACTC
TTGGCCAAGATTTGCCTGATGGGAACCGTGGTGATTTACAGAAGAAGGGTGATGTTTCTAAA
GATAAATTCTCCAACATATTGTGGTACGCTGCAACAAACTACAGGACGTGGATCTTTGTTCT
TCTCTACGGATACTCTATGGGAGTTGAACTGTCTACAGACAACGTAATTGCGGAGTACTTCT
TCGACAGATTTGATCTAAAGCTTCACACAGCGGGAATTATTGCAGCGACCTTTGGTATGGCT
AATTTATTAGCTCGTCCATTCGGAGGATTTTCTTCAGATTACGCAGCCAAAAGATTCGGCAT
GAGAGGCAGACTTTGGGTCCTTTGGATATTACAAACACTGGGAGGAGTATTCTGCGTCCTGT
TGGGCCGTTCAAATCCTCTGCCCATAGCCGTCACATTCATGATCCTTTTCTCTATTGGTGCT
CAAGCTGCATGTGGTGCAACATTCGGTATTATTCCATTCATTTCTCGCCGATCCTTAGGTAT
AATCTCAGGAATGACTGGGGCTGGAGGAAATTTCGGTTCTGGATTGACACAACTGTTGTTCT
TCACGAGCTCAAAATACTCGACAGCAACAGGGCTAACTTACATGGGACTAATGATCATAGGA
TGCACTCTTCCAGTGACTTTCTGTCATTTCCCACAATGGGGAAGTATGTTTTTCCCACCAAC
GAAAGACCCTGTTAAGGGAAGTGAGGAACATTATTATGCCGCAGAGTATACCGAAGCTGAGA
GGCAGAAAGGTATGCACCAAAACAGCTTGAAGTTCGCCGAGAACTGCCGATCGGAGCGTGGC
AAGCGCGTGGGATCGGCACCTACTCCTCCAAATTTAACGCCTAATCGTGTCTGAGATCCCG

SEQ ID NO: 100, Nicotiana tabacum high affinity nitrate transporter protein (CAD89798)

MGDIEGEPGSSMHGVTGREPVLAFSVASPMVPTDTTAKFSVPVDTEHKAKIFKFYSFSKPHG
LTFQLSWISFFTCFVSTFAAAPLVPIIRDNLNLTKMDVGNAGVASVSGSILSRLVMGAVCDM
LGPRYGCAFLIMLSAPTVFCMSFVSSAGGYVAVRFMIGFSLATFVSCQYWMSTMFNSQIIGL
VNGTAAGWGNMGGGATQLIMPIVYDIIRRAGATPFTAWRIAFFIPGWLHIVMGILVLTLGQD
LPDGNRGDLQKKGDVSKDKFSNILWYAATNYRTWIFVLLYGYSMGVELSTDNVIAEYFFDRF
DLKLHTAGIIAATFGMANLLARPFGGFSSDYAAKRFGMRGRLWVLWILQTLGGVFCVLLGRS
NPLPIAVTFMILFSIGAQAACGATFGIIPFISRRSLGIISGMTGAGGNFGSGLTQLLFFTSS
KYSTATGLTYMGLMIIGCTLPVTFCHFPQWGSMFFPPTKDPVKGSEEHYYAAEYTEAERQKG
MHQNSLKFAENCRSERGKRVGSAPTPPNLTPNRV

SEQ ID NO: 101, N.plumbaginifolia mRNA for nitrate transporter Nrt2;1Np (Y08210)

TTCACTTTCAACATTTAATCAATCTTAGTGCTATCAGTTTATTTTCCTTAAGAAAAAAAATG
GCTGATATTGAGGGAGAACCAGGGAGTTCTATGCATGGAGTCACTGGTAGAGAGCCAGTTCT
TGCTTTCTCAGTGGCTTCTCCAATGGTGCCAACTGATACCACTGCTAAATTTTCAGTACCAG
TTGATACTGAACACAAAGCCAAGGTTTTTAAATTTTATTCATTTTCAAAGCCTCATGGACTT
ACTTTCCAGCTCTCCTGGATTTCTTTCTTCACTTGTTTTGTATCAACTTTTGCTGCTGCTCC
TTTAGTTCCTCTCATTAGGGACAACCTTAATTTAACCAAAATGGATGTTGGTAATGCCGGAG
TTGCTTCCGTTTCTGGAAGTATTTTATCTAGGCTTGTTATGGGTGCAGTTTGTGATATGTTA
GGGCCAAGATACGGCTGTGCATTTCTGATTATGTTGTCAGCCCCAACTGTATTTTGTATGTC
GTTCGTGTCGTCGGCTGGAGGATATGTTGCTGTCCGGTTCATGATCGGATTCTCGCTCGCAA
CATTTGTGTCGTGCCAATATTGGATGAGTACTATGTTTAATAGTCAGATTATAGGACTTGTC
AATGGAACAGCTGCTGGGTGGGGAAATATGGGTGGTGGTGCGACTCAACTTATTATGCCAAT
TCTGTATGATATAATAAGAAAAGCAGGAGCAACTCCATTCACTGCTTGGAGAATTGCATTTT
TCATTCCTGGCTGGCTTCATGTTGTAATGGGTATTTTGGTGTTGACTCTTGGTCAAGATTTG

Figure 8 (continued)

CCTGATGGAAACCGTGGTGATTTACAGAAGAAGGGTGGTGTTTCTAAAGATAAATTCACCAA
CATATTGTGGTACGCTGCAACAAACTACAGGACGTGGATCTTTGTCCTTCTCTACGGATACT
CTATGGGAGTTGAACTGTCTACCGACAACGTAATTGCAGAGTACTTCTTCGACAGATTTGAT
CTAAAGCTTCACACAGCGGGAATCATCGCAGCCACATTTGGTATGGCAAATTTATTAGCTCG
TCCATTCGGAGGGTTTTCTTCAGATTTCGCAGCCAAAAGATTCGGCATGAGGGGTAGACTTT
GGGTCCTTTGGATATTACAAACACTTGGAGGAGTATTCTGTGTCCTGTTGGGCCGTTCAAAT
TCTCTGCCCATAGCTGTCACATTCATGATCCTTTTCTCAGTTGGTGCTCAAGCTGCATGTGG
TGCAACATTCGGTATTATTCCCTTCATATCTCGTCGATCATTAGGTATAATCTCGGGAATGA
CTGGAGCTGGAGGCAATTTCGGTTCTGGATTGACACAACTGCTGTTTTTCACAAGCTCAAAA
TACTCGACAGCAACAGGGCTAACTTATATGGGGATGATGATCATTGGATGCACTCTTCCTGT
GACACTATGTCATTTCCCACAATGGGGAAGCATGTTTTTCCCACCAACAAAAGATCCAGTTA
AGGGAAGTGAGGAACATTATTATGCCGCAGAGTATACAGAAGCTGAGAGGCAGAAAGGTATG
CATCAAAACAGCTTGAAATTCGCCGAGAACTGTCGATCGGAGCGTGGCAAGCGCGTGGGATC
GGCACCTACTCCTCCAAATTTAACGCCTAACCGTGTCTGAGTTTCTCAGATTTGATAATTTT
CTCTAAGGGGATGGATCATTGTCAATCTCTGATTGGATGAAGATTCAATGAGCTGAGTCTCA
ATAAGCATATTATTTTTAAAGAATGTATCTTTATTTTTCTTGTCCTTTCTTCTTCTTCTTCT
TCTTTTTCTTGGAATCTACTTATAAGTTTTATGTTTTTTTTTTTAAATGAAGTATATATATG
ACGCATTGTGTATCTTTCCTCTTGCTTTTTACATCTGAATATTCGTATGAGCCAATGGGTTG
TTGTAGAATCAAAAGTAATATTAATAAAACTTTTGACTTCCAAAAAAAAAAAAAAAAAAAAA
AAAAAAAA

SEQ ID NO: 102, Nicotiana plumbaginifolia nitrate transporter (CAA69387)

MADIEGEPGSSMHGVTGREPVLAFSVASPMVPTDTTAKFSVPVDTEHKAKVFKFYSFSKPHG
LTFQLSWISFFTCFVSTFAAAPLVPLIRDNLNLTKMDVGNAGVASVSGSILSRLVMGAVCDM
LGPRYGCAFLIMLSAPTVFCMSFVSSAGGYVAVRFMIGFSLATFVSCQYWMSTMFNSQIIGL
VNGTAAGWGNMGGGATQLIMPILYDIIRKAGATPFTAWRIAFFIPGWLHVVMGILVLTLGQD
LPDGNRGDLQKKGGVSKDKFTNILWYAATNYRTWIFVLLYGYSMGVELSTDNVIAEYFFDRF
DLKLHTAGIIAATFGMANLLARPFGGFSSDFAAKRFGMRGRLWVLWILQTLGGVFCVLLGRS
NSLPIAVTFMILFSVGAQAACGATFGIIPFISRRSLGIISGMTGAGGNFGSGLTQLLFFTSS
KYSTATGLTYMGMMIIGCTLPVTLCHFPQWGSMFFPPTKDPVKGSEEHYYAAEYTEAERQKG
MHQNSLKFAENCRSERGKRVGSAPTPPNLTPNRV

SEQ ID NO: 103, Lycopersicon esculentum putative high-affinity nitrate transporter (NRT2;1) mRNA, complete cds (AF092655)

TATTCTCAATACATTTCAAATCAATCATTTATAAAATTAACCAGTTATTTCCTCAATTGAAG
AAATGGCTGATGTAGAAGGATCACCGGGGAGTTCTATGCATGGAGTCACCGGAAGAGAACCT
GTTCTCGCTTTCTCCGTGGCTTCTCCAATGGTGCCTACGGATACCTCCGCCAAATTTTCAGT
ACCGGTGGACACTGAACACAAGGCTAAACAATTTAAGTTTTATTCGTTTTCGAAGCCTCATG
GACTTACGTTCCAGCTCTCCTGGATCTCCTTTTTCACTTGTTTCGTTTCGACTTTTGCTGCT
GCACCTTTAGTTCCTATTATTAGGGACAATCTTAATTTGACAAAAATGGATGTTGGTAACGC
TGGGGTTGCTTCCGTATCCGGAAGTATTTTATCTAGGCTTACGATGGGTGCGGTTTGTGATT
TGTTGGGTCCAAGGTATGGGTGCGCTTTTCTTATCATGTTGTCAGCGCCAACTGTTTTTTGT
ATGTCTTTTGTTTCATCCGCTGGTGGCTACGTAGCTGTCCGGTTCATGATTGGGTTTTCGCT

Figure 8 (continued)

CGCAACGTTTGTGTCTTGTCAATATTGGATGAGTACTATGTTTAATAGTAAGATCATAGGGC
TAGTGAACGGAACGGCTGCTGGATGGGGTAATATGGGTGGAGGTGCAACTCAACTCATTATG
CCACTTTTGTATGATATAATTCGAAGGGCGGGTGCAACTCCGTTCACTGCTTGGAGAATTGC
ATTTTTTATTCCTGGATGGCTTCATGTGGTGATGGGTATTTTAGTGTTGACTCTTGGCCAAG
ATTTACCCGACGGAAATCGTGGCACTTTACAGAAGACGGGTACTGTTGCTAAAGATAAATTC
GGTAACATATTGTGGTATGCTGCAACAAACTACAGGACATGGATCTTTGTTCTTCTCTATGG
ATACTCTATGGGAGTTGAACTGTCAACAGACAACGTCATTGCTGAGTACTTCTTCGACAGAT
TTGATCTAAAGCTTAGCACAGCGGGGATCATTGCTGCCACATTTGGTATGGCTAACCTTTTG
GCTCGACCATTTGGAGGATTTTCTTCTGATTACGCAGCAAAGAAATTCGGTATGAGAGGGAG
ACTTTGGGTTTTGTGGATTTTACAAACACTTGGAGGAGTATTTTGTGTTCTTTTGGGTCGTT
CGAATTCTCTACCACTTGCGGTAACCTTTATGATCCTTTTCTCAATCGGAGCTCAAGCTGCT
TGTGGTGCAACTTTTGGTATTATTCCATTCATTTCTCGACGATCGTTAGGAATTATAAGCGG
AATGACAGGGGCAGGTGGAAATTTTGGTTCTGGATTGACTCAATTGTTGTTTTTCACGAGCT
CAAAGTACTCGACAGCGACAGGGTTAACTTACATGGGATTCATGATCATAGGATGCACTCTT
CCTGTTACATTTTGTCATTTCCCACAATGGGGAAGCATGTTTTTGCCACCAACAAAAGATCC
AGTCAAGGGAACGGAAGAACATTATTATACTTCAGAGTACACAGAGGCCGAGAGGCAAAAAG
GGATGCACCAAAACAGCTTGAAATTCGCTGAAAATTGCCGATCAGAGCGTGGTAAGCGTGTT
GGTTCCGCACCAACCCCACCAAATTTGACACCAAATCGTGTTTGATGATCTTTATGAGGAAT
GGATAGTCTTGAATCTGTGATTTAAATTTAAGGTTCAATGTGCTGAGTCGTCTCAATAAGCA
AAATCTATCTTGATTTTTCTTCTTTGTTTTTTTTTTATAATGATATTGCTTGTTGATCTTTC
CAGACAAATACCTTGAATCCACGAAGGTGTATGCTTTTTTTTTAATGAAGTATATATAATAT
ATTACTCATTGTGTATGTTTTCTATTGCTTTTTTCAAAAGAATATTCTATGGCCAATGGTGG
TTGTGTTTTACTCTGTAGATTCAAAAGTGTATTATAATAAAACTCTTGACTTGTAAGAAGGG
GACTGATCATTTATTCCAGTTGATTTATAGAAAGTTCGTGAAAAAAAAAAAAAAAAAAAAAA
AAAAAAAAAAAAAA

SEQ ID NO: 104, Lycopersicon esculentum putative high-affinity nitrate transporter (AAF00053)

MADVEGSPGSSMHGVTGREPVLAFSVASPMVPTDTSAKFSVPVDTEHKAKQFKFYSFSKPHG
LTFQLSWISFFTCFVSTFAAAPLVPIIRDNLNLTKMDVGNAGVASVSGSILSRLTMGAVCDL
LGPRYGCAFLIMLSAPTVFCMSFVSSAGGYVAVRFMIGFSLATFVSCQYWMSTMFNSKIIGL
VNGTAAGWGNMGGGATQLIMPLLYDIIRRAGATPFTAWRIAFFIPGWLHVVMGILVLTLGQD
LPDGNRGTLQKTGTVAKDKFGNILWYAATNYRTWIFVLLYGYSMGVELSTDNVIAEYFFDRF
DLKLSTAGIIAATFGMANLLARPFGGFSSDYAAKKFGMRGRLWVLWILQTLGGVFCVLLGRS
NSLPLAVTFMILFSIGAQAACGATFGIIPFISRRSLGIISGMTGAGGNFGSGLTQLLFFTSS
KYSTATGLTYMGFMIIGCTLPVTFCHFPQWGSMFLPPTKDPVKGTEEHYYTSEYTEAERQKG
MHQNSLKFAENCRSERGKRVGSAPTPPNLTPNRV

SEQ ID NO: 105, Arabidopsis thaliana trans-membrane nitrate transporter protein AtNRT2:1 mRNA, complete cds (AF093754)

AGTGTGAGTAATTTAGCTTGAATCAAATCTCAAACTTGCAAAGAAACTTGAAATATTTTATA
ACAATGGGTGATTCTACTGGTGAGCCGGGGAGCTCCATGCATGGAGTCACCGGTAGAGAACA
AAGCTTTGCATTCTCGGTGCAATCACCAATTGTGCATACCGACAAGACGGCCAAGTTCGACC
TTCCGGTGGACACAGAGCATAAGGCAACGGTTTTCAAGCTCTTCTCCTTCGCCAAACCTCAC

Figure 8 (continued)

ATGAGAACGTTCCATCTCTCGTGGATCTCTTTCTCCACATGTTTTGTCTCGACTTTCGCAGC
TGCACCACTTGTCCCTATCATCCGGGAGAATCTCAACCTCACCAAACAAGACATTGGAAACG
CCGGAGTTGCCTCTGTCTCTGGGAGTATCTTCTCTAGGCTCGTGATGGGAGCCGTGTGTGAT
CTTTTGGGTCCCCGTTACGGTTGTGCCTTCCTTGTGATGTTGTCTGCCCCAACGGTGTTCTC
CATGAGCTTCGTGAGTGACGCAGCAGGCTTCATAACGGTGAGGTTCATGATTGGTTTTTGCC
TGGCGACGTTTGTGTCTTGTCAATACTGGATGAGCACTATGTTCAACAGTCAGATCATTGGT
CTGGTGAATGGGACAGCAGCCGGATGGGGAAACATGGGTGGCGGCATAACGCAGTTGCTCAT
GCCCATTGTGTATGAAATCATTAGGCGCTGCGGTTCCACAGCCTTCACGGCCTGGAGGATCG
CCTTCTTTGTACCCGGTTGGTTGCACATCATCATGGGAATCTTGGTGCTCAATCTAGGTCAA
GATCTGCCAGATGGAAATCGAGCTACCTTGGAGAAAGCGGGAGAAGTTGCCAAAGACAAATT
CGGAAAGATTCTGTGGTATGCCGTTACAAACTACAGGACTTGGATCTTCGTTCTTCTCTACG
GATACTCCATGGGAGTTGAGTTGAGCACTGATAATGTTATCGCCGAGTACTTCTTTGACAGG
TTTCACTTGAAGCTCCACACAGCAGGGCTCATAGCAGCATGTTTCGGAATGGCCAATTTCTT
TGCTCGTCCAGCAGGAGGCTACGCATCTGACTTTGCAGCCAAGTACTTCGGGATGAGAGGGA
GGTTGTGGACGTTGTGGATCATACAGACGGCTGGTGGCCTCTTCTGTGTGTGGCTCGGCCGC
GCCAACACCCTTGTAACTGCCGTTGTGGCTATGGTGCTCTTCTCTATGGGGGCACAAGCTGC
TTGCGGAGCCACCTTTGCAATTGTGCCCTTTGTCTCCCGGCGAGCTCTAGGCATCATCTCGG
GTTTAACCGGGGCTGGAGGGAACTTTGGATCAGGGCTCACACAACTCCTCTTCTTCTCGACC
TCACACTTCACAACTGAACAAGGGCTAACGTGGATGGGAGTGATGATAGTCGCTTGCACGTT
ACCTGTGACCTTAGTTCACTTTCCTCAATGGGGAAGCATGTTCTTGCCTCCTTCCACAGATC
CAGTGAAAGGTACAGAGGCTCATTATTATGGTTCTGAGTGGAATGAGCAGGAGAAGCAGAAG
AACATGCATCAAGGAAGCCTCCGGTTTGCCGAGAACGCCAAGTCAGAGGGTGGACGCCGCGT
CCGCTCTGCTGCTACGCCGCCTGAGAACACACCCAACAATGTTTGATCATACATTCCACCCA
CGGTGGAATGGTGAAGGATGATCGCATATAAGAATATGTCACACAGTGAAAAAAAAAAATGC
AAATGTTATCAATGCTTGCATAACATTACTATCTATCTTTCATTTACTAAACAAACCTTTTG
CTTTTTGCCTTGAAATCTTTTTATTATATATCAAAATATATCTCTATGTCTTGAGGTTTGAT
TATTTTGCATATATCATTAATGATTTGATAATATTGGAACTG

SEQ ID NO: 106, Arabidopsis thaliana trans-membrane nitrate transporter protein AtNRT2:1 (AAC64170)

MGDSTGEPGSSMHGVTGREQSFAFSVQSPIVHTDKTAKFDLPVDTEHKATVFKLFSFAKPHM
RTFHLSWISFSTCFVSTFAAAPLVPIIRENLNLTKQDIGNAGVASVSGSIFSRLVMGAVCDL
LGPRYGCAFLVMLSAPTVFSMSFVSDAAGFITVRFMIGFCLATFVSCQYWMSTMFNSQIIGL
VNGTAAGWGNMGGGITQLLMPIVYEIIRRCGSTAFTAWRIAFFVPGWLHIIMGILVLNLGQD
LPDGNRATLEKAGEVAKDKFGKILWYAVTNYRTWIFVLLYGYSMGVELSTDNVIAEYFFDRF
HLKLHTAGLIAACFGMANFFARPAGGYASDFAAKYFGMRGRLWTLWIIQTAGGLFCVWLGRA
NTLVTAVVAMVLFSMGAQAACGATFAIVPFVSRRALGIISGLTGAGGNFGSGLTQLLFFSTS
HFTTEQGLTWMGVMIVACTLPVTLVHFPQWGSMFLPPSTDPVKGTEAHYYGSEWNEQEKQKN
MHQGSLRFAENAKSEGGRRVRSAATPPENTPNNV

SEQ ID NO: 107, Lycopersicon esculentum putative high-affinity nitrate transporter (NRT2;2) mRNA, complete cds (AF092654)

TTTCAAATCAATCATTTATAAAATTAACCAGTTATTTCCTCAATTGAAGAAATGACTGATGT
AGAAGGATCACCGGGGAGTTCTATGCATGGAGTCACCGGAAGAGAACCTGTTCTCGCTTTCT

Figure 8 (continued)

CCGTGGCTTCTCCAATGGTGCCTACGGATACCTCCGCCAAGTTTTCAGTACCGGTGGATACT
GAACACAAGGCTAAACAATTTAAGTTTTATTCGTTTTCGAAGCCTCATGGACTTACGTTCCA
GCTCTCCTGGATCTCCTTTTTCACTTGTTTCGTTTCGACTTTTGCTGCTGCACCTTTAGTTC
CTATTATTAGGGACAATCTTAATTTGACAAAAATGGATGTCGGTAACGCTGGGGTTGCTTCC
GTATCCGGAAGTATTTTATCTAGGCTTACGATGGGTGCGGTTTGTGATTTGTTGGGTCCAAG
GTATGGGTGCGCTTTTCTTATCATGTTGTCGGCCCCAACTGTTTTTTGTATGTCCTTTGTTT
CATCCGCTGGTGGCTACGTAGCCGTCCGGTTCATGATTGGGTTTTCCCTCGCAACGTTTGTG
TCGTGTCAATATTGGATGAGTACTATGTTTAATAGTAAGATCATAGGGCTAGTGAACGGAAC
GGCTGCTGGATGGGGTAATATGGGTGGAGGTGCAACTCAACTCATTATGCCACTTTTGTATG
ATATAATTCGGAGGGCGGGTGCAATTCCGTTCACTGCTTGGAGAATTGCATTTTTTATTCCT
GGATGGCTTCATGTGGTGATGGGTATTTTAGTGTTGACTCTTGGCCAAGATTTACCCGACGG
AAATCGTGGCACTTTACAGAAGACGGGTACTGTTGCTAAAGATAAATTCGGTAACATATTGT
GGTATGCTGCAACAAACTACAGGACATGGATCTTTGTTCTTCTCTATGGATACTCTATGGGA
GTTGAACTGTCAACAGACAACGTCATTGCTGAGTACTTCTTCGACAGATTTGATCTAAAGCT
TAGCACAGCGGGGATCATTGCTGCCACATTTGGTATGGCTAACCTTTTGGCTCGACCATTTG
GAGGATTTTCTTCTGATTACGCAGCAAAGAAATTCGGTATGAGAGGGAGACTTTGGGTTTTG
TGGATTTTACAAACACTTGGAGGAGTATTTTGTGTTCTTTTGGGTCGTTCGAATTCTCTACC
ACTTGCTGTAACCTTTATGATCCTTTTCTCAATCGGAGCTCAAGCTGCTTGTGGTGCAACTT
TTGGTATTATTCCATTCATTTCTCGACGATCGTTAGGAATTATAAGCGGAATGACAGGGGCA
GGTGGAAATTTTGGTTCTGGATTGACTCAATTGTTGTTTTTCACGAGCTCAAAGTACTCGAC
AGCGACAGGGTTAACTTACATGGGATTCATGATCATAGGATGCACTCTTCCTGTTACATTTT
GTCATTTCCCACAATGGGGAAGCATGTTTCTCCCACCAACAAAAGATCCAGTCAAGGGAACG
GAAGAACATTATTATACTTCAGAGTACACAGAGGCAGAGAGGCAAAAAGGGATGCACCAAAA
CAGCTTGAAATTCGCTGAAAATTGCCGATCGGAGCGTGGTAAGCGCGTTGGTTCCGCACCCA
CTCCACCAAATTTGACACCAAACCGTGTCTGATCGGATTGATGATCGTCAATCTTTAGTTCA
ATGAGCTGAGTTGTTTCAATAAGCAAAATAAGTCCTGATTTTTTTTTCTTCTTTCTTTTTTG
TTTTTTTCTTAAATGATGTTGCTTGTCAATACGCTGGAATCTACTAAGGTGTATGTGGTTTT
AAATTTACGTATATATAATATATATATATATATATATTACACATTTTAATGTTAAAAAAAAA
AAAAAAAAAA

SEQ ID NO: 108, Lycopersicon esculentum putative high-affinity nitrate transporter (AAF00054)

MTDVEGSPGSSMHGVTGREPVLAFSVASPMVPTDTSAKFSVPVDTEHKAKQFKFYSFSKPHG
LTFQLSWISFFTCFVSTFAAAPLVPIIRDNLNLTKMDVGNAGVASVSGSILSRLTMGAVCDL
LGPRYGCAFLIMLSAPTVFCMSFVSSAGGYVAVRFMIGFSLATFVSCQYWMSTMFNSKIIGL
VNGTAAGWGNMGGGATQLIMPLLYDIIRRAGAIPFTAWRIAFFIPGWLHVVMGILVLTLGQD
LPDGNRGTLQKTGTVAKDKFGNILWYAATNYRTWIFVLLYGYSMGVELSTDNVIAEYFFDRF
DLKLSTAGIIAATFGMANLLARPFGGFSSDYAAKKFGMRGRLWVLWILQTLGGVFCVLLGRS
NSLPLAVTFMILFSIGAQAACGATFGIIPFISRRSLGIISGMTGAGGNFGSGLTQLLFFTSS
KYSTATGLTYMGFMIIGCTLPVTFCHFPQWGSMFLPPTKDPVKGTEEHYYTSEYTEAERQKG
MHQNSLKFAENCRSERGKRVGSAPTPPNLTPNRV

Figure 8 (continued)

SEQ ID NO: 109, Brassica napus mRNA for high-affinity nitrate transporter (nrt2 gene)( AJ293028)

CACATTCTTGTGAAAGAACTTAAACATTTTGCATCAATGGGTGATTCTACTGGCGAGCCGGG
AAGCTCCATGCATGGAGTGACCGGTAGAGAACAAACATTTGCTTTCTCGGTGGCTTCACCGA
TTGTCCCAACCGACAAGACAGCAAAGTTCGACCTGCCGGTGGACTCGGAGCATAAGGCAACG
GTTTTCAAGCTCTTCTCCTTCGCCAAACCTCACATGCGAACGTTCCATCTCTCGTGGATCTC
TTTCTCCACGTGTTTTGTCTCGACGTTTGCGGCTGCACCACTTGTCCCCATCATCCGAGAGA
ATCTCAACCTCACGAAACAAGACATCGGTAACGCAGGAGTTGCGTCCGTCTCGGGGAGTATC
TTCTCTAGGCTGGTGATGGGAGCAGTGTGTGATCTTCTCGGTCCACGTTACGGCTGTGCCTT
CCTTGTTATGCTTTCCGCACCAACGGTGTTCTCAATGAGCTTCGTGAGTGGAGCCGCAGGAT
TCATAACGGTGAGGTTCATGATTGGGTTCTGTCTAGCAACGTTTGTGTCTTGTCAATATGGA
ATGAGTACTATGTTCAATAGTCAGATCATCGGTCTGGTGAACGGTACAGCCGCCGGGTGGGG
AAACATGGGTGGTGGCATAACGCAGTTGCTCATGCCGGTTGTCTATGAGATCATAAGGCGCT
GTGGTGCAACAGCGTTCACGGCCTGGAGGCTTGCCTTCTTCGTCCCTGGTTGGTTGCACATC
ATCATGGGAGTCTTGGTGCTCAATCTAGGTCAAGATTTGCCAGATGGTAACCGAAGTGCCTT
GGAGAAAAAGGGAGAAGTTGCCAAAGACAAATTCGGAAAGATTATGTGGTACGCCGTCACAA
ACTACAGGACTTGGATCTTTGTTCTTCTCTATGGATACTCCATGGGAGTTGAGCTGAGCACT
GACAATGTTATCGCCGAATACTTCTTTGACAGGTTCCACTTGAAGCTTCACACAGCTGGAAT
CATAGCAGCATGTTTCGGAATGGCCAACTTCTTTGCTCGTCCAGCAGGAGGCTATGCATCTG
ACCTTGCAGCCAAATACTTCGGGATGAGAGGGAGGTTATGGGCGTTGTGGATCATTCAGACA
GCAGGTGGTGTCTTCTGCGTGTGGCTCGGCCGTGCCAACACCCTCGTTACTGCCGTTGTAGC
TATGGTCCTCTTCTCTTTAGGAGCACAAGCCGCTTGTGGAGCCACCTTCGCAATCGTTCCCT
TTGTTTCTCGGCGAGCCCTTGGTATCATCTCAGGTTTAACCGGTGCTGGAGGAAACTTTGGG
TCAGGGCTCACACAGCTCATCTTCTTCTCGACCTCAAGGTTCACAACCGAACAAGGGCTAAC
ATGGATGGGAGTGATGATAGTTGCCTGCACGTTGCCTGTGACTTTAATCCACTTCCCTCAGT
GGGGAAGCATGTTCTTGCCTCCTTCTACCGATCCAGTCAAAGGTCCGAAGGAGCACTATTAT
GCTTCAGAGTGGAATGAGCAGGAGAAGGAGAAGAACATGCATCAGGGAAGCCTCAGGTTTGC
TAAGAACGCCAAGTCTGAGGGCGGCCGCCGTGTCCGTTCTGCTGCTACCCCGCCTGAGAACA
CACCAAACAATGTTTGATCATACCAGCCACAAGGAAAGTGTGAAGGATGGTCGCAGATAAGA
ATTTATATGTCCCACAGTGAAAACAAATGCGTATGTTATCAATGCTTGCTGGACGTTATTTG
TTGTGTATCTTTCTTTTTTTCACTGAAGAAACATTTGTTTTGTTTACGGCTTCAAGAAATAT
TTTTCTAATCAAAATGTCTACCTCTTGCGACATT

SEQ ID NO: 110, Brassica napus high-affinity nitrate transporter (CAC05338)

MGDSTGEPGSSMHGVTGREQTFAFSVASPIVPTDKTAKFDLPVDSEHKATVFKLFSFAKPHM
RTFHLSWISFSTCFVSTFAAAPLVPIIRENLNLTKQDIGNAGVASVSGSIFSRLVMGAVCDL
LGPRYGCAFLVMLSAPTVFSMSFVSGAAGFITVRFMIGFCLATFVSCQYGMSTMFNSQIIGL
VNGTAAGWGNMGGGITQLLMPVVYEIIRRCGATAFTAWRLAFFVPGWLHIIMGVLVLNLGQD
LPDGNRSALEKKGEVAKDKFGKIMWYAVTNYRTWIFVLLYGYSMGVELSTDNVIAEYFFDRF
HLKLHTAGIIAACFGMANFFARPAGGYASDLAAKYFGMRGRLWALWIIQTAGGVFCVWLGRA
NTLVTAVVAMVLFSLGAQAACGATFAIVPFVSRRALGIISGLTGAGGNFGSGLTQLIFFSTS
RFTTEQGLTWMGVMIVACTLPVTLIHFPQWGSMFLPPSTDPVKGPKEHYYASEWNEQEKEKN
MHQGSLRFAKNAKSEGGRRVRSAATPPENTPNNV

Figure 8 (continued)

SEQ ID NO: 111, Arabidopsis thaliana putative high-affinity nitrate transporter (At5g60770) mRNA, complete cds (DQ056732)

ATGGCCGATGGTTTTGGTGAACCGGGAAGCTCAATGCATGGAGTCACCGGCAGAGAACAAAG
CTATGCATTCTCTGTCGAGTCTCCGGCAGTTCCTTCCGACTCATCAGCAAAATTTTCTCTCC
CCGTGGACACCGAACACAAAGCCAAAGTCTTCAAACTCTTATCCTTTGAAGCTCCACATATG
AGAACTTTCCATCTTGCTTGGATCTCATTCTTCACTTGCTTCATTTCCACTTTCGCTGCTGC
TCCTCTTGTCCCCATCATTAGAGATAACCTTAATCTCACAAGACAAGATGTCGGAAATGCTG
GTGTTGCTTCTGTCTCTGGCAGTATCTTCTCTAGGCTTGTTATGGGAGCAGTTTGTGATCTC
CTTGGGCCACGTTATGGCTGTGCTTTCCTCGTCATGCTCTCTGCTCCAACCGTCTTCTCCAT
GTCTTTCGTTGGTGGTGCCGGAGGGTACATAACGGTGAGGTTCATGATCGGGTTCTGCCTGG
CGACTTTCGTGTCATGCCAGTATTGGATGAGCACAATGTTCAATGGTCAGATCATAGGTCTA
GTGAACGGGACAGCGGCAGGGTGGGGGAACATGGGCGGTGGGGTCACTCAGTTGCTCATGCC
AATGGTCTATGAGATCATCCGACGGTTAGGGTCCACGTCCTTCACCGCATGGAGGATGGCTT
TCTTCGTCCCCGGGTGGATGCACATCATCATGGGGATCTTGGTCTTGACTCTAGGGCAAGAC
CTCCCTGATGGTAATAGAAGCACACTCGAGAAGAAAGGTGCAGTTACTAAAGACAAGTTCTC
AAAGGTTTTATGGTACGCGATCACGAACTATAGGACATGGGTTTTCGTGCTGCTATATGGAT
ACTCCATGGGAGTAGAGCTCACAACCGATAACGTCATCGCTGAGTACTTTTTCGACAGGTTC
CATCTTAAGCTTCATACCGCCGGTATAATCGCGGCAAGCTTTGGTATGGCAAACTTCTTTGC
CCGTCCTATTGGTGGTTGGGCCTCAGATATTGCGGCTAGACGCTTCGGCATGAGAGGCCGTC
TCTGGACCCTATGGATCATCCAAACCTTAGGCGGTTTCTTCTGCCTATGGCTAGGCCGAGCC
ACCACGCTCCCGACCGCGGTTGTCTTCATGATCCTCTTCTCTCTCGGCGCTCAAGCCGCTTG
TGGAGCTACCTTTGCTATCATACCTTTCATCTCACGCCGCTCCTTAGGGATCATCTCTGGTC
TTACTGGAGCTGGTGGAAACTTCGGCTCTGGTTTGACCCAACTCGTATTCTTCTCGACCTCA
ACGTTCTCCACGGAACAAGGGCTGACATGGATGGGGGTGATGATTATGGCGTGTACATTACC
CGTCACTTTAGTGCACTTCCCGCAATGGGGAAGCATGTTTTTGCCTTCCACGGAAGATGAAG
TGAAGTCTACGGAGGAGTATTATTACATGAAAGAGTGGACAGAGACCGAGAAGCGAAAGGGT
ATGCATGAAGGGAGTTTGAAGTTCGCCGTGAATAGTAGATCGGAGCGTGGACGGCGCGTGGC
TTCTGCACCGTCTCCTCCGCCGGAACACGTTTAA

SEQ ID NO: 112, Arabidopsis thaliana putative high-affinity nitrate transporter (AAY78876)

MADGFGEPGSSMHGVTGREQSYAFSVESPAVPSDSSAKFSLPVDTEHKAKVFKLLSFEAPHM
RTFHLAWISFFTCFISTFAAAPLVPIIRDNLNLTRQDVGNAGVASVSGSIFSRLVMGAVCDL
LGPRYGCAFLVMLSAPTVFSMSFVGGAGGYITVRFMIGFCLATFVSCQYWMSTMFNGQIIGL
VNGTAAGWGNMGGGVTQLLMPMVYEIIRRLGSTSFTAWRMAFFVPGWMHIIMGILVLTLGQD
LPDGNRSTLEKKGAVTKDKFSKVLWYAITNYRTWVFVLLYGYSMGVELTTDNVIAEYFFDRF
HLKLHTAGIIAASFGMANFFARPIGGWASDIAARRFGMRGRLWTLWIIQTLGGFFCLWLGRA
TTLPTAVVFMILFSLGAQAACGATFAIIPFISRRSLGIISGLTGAGGNFGSGLTQLVFFSTS
TFSTEQGLTWMGVMIMACTLPVTLVHFPQWGSMFLPSTEDEVKSTEEYYYMKEWTETEKRKG
MHEGSLKFAVNSRSERGRRVASAPSPPPEHV

Figure 8 (continued)

SEQ ID NO: 113, Arabidopsis thaliana high-affinity nitrate transporter (ACH2) (At1g08100) mRNA, complete cds (NM_100685)

AAACTTGAATTTTCTCAAAGGAACTTGATACGTTTAAAATACATGGGTTCTACTGATGAGCC
CGGAAGTTCCATGCATGGAGTTACCGGTAGAGAACAGAGCTATGCTTTCTCGGTAGATGGTA
GTGAGCCGACCAACACAAAGAAAAAGTACAATCTGCCGGTGGACGCGGAGGATAAGGCAACG
GTTTTCAAGCTCTTCTCCTTCGCCAAACCTCACATGAGAACGTTCCACCTCTCGTGGATCTC
TTTCTCCACATGTTTTGTTTCGACGTTCGCAGCTGCACCACTTATCCCGATCATCAGGGAGA
ATCTTAACCTCACCAAACATGACATTGGAAACGCTGGAGTTGCCTCCGTCTCGGGGAGTATC
TTCTCTAGGCTCGTGATGGGAGCCGTGTGTGATCTTTTGGGTCCTCGTTACGGTTGTGCCTT
CCTTGTGATGTTGTCTGCCCCAACGGTGTTCTCCATGAGCTTCGTGAGTGACGCAGCAGGCT
TCATAACGGTGAGGTTCATGATTGGTTTTTGCCTGGCGACGTTTGTGTCTTGTCAATACTGG
ATGAGCACTATGTTCAACAGTCAGATCATCGGTCTGGTGAACGGGACAGCAGCCGGATGGGG
AAACATGGGTGGCGGCATAACGCAGTTGCTCATGCCCATTGTGTATGAAATCATTAGGCGCT
GCGGATCAACAGCGTTCACGGCCTGGAGGATCGCCTTCTTTGTCCCCGGTTGGTTGCACATC
ATCATGGGAATCTTGGTGCTCACGCTAGGTCAAGATCTGCCAGGTGGAAACAGAGCTGCCAT
GGAGAAAGCGGGAGAAGTTGCCAAAGACAAATTCGGAAAGATTCTATGGTACGCCGTTACAA
ATTACAGGACTTGGATTTTCGTTCTTCTGTATGGATATTCCATGGGAGTTGAGTTAAGCACA
GACAATGTTATCGCCGAGTACTTCTTTGATAGGTTTCACTTGAAGCTTCACACAGCGGGGAT
TATAGCAGCATGTTTCGGAATGGCCAATTTCTTTGCTCGTCCAGCAGGAGGCTGGGCATCTG
ACATTGCAGCCAAGCGCTTCGGAATGCGAGGGAGGTTGTGGACTTTGTGGATCATTCAGACG
TCCGGTGGTCTCTTTTGTGTGTGGCTCGGACGTGCCAACACCCTCGTCACTGCCGTTGTATC
TATGGTCCTCTTCTCTTTAGGAGCACAAGCCGCTTGCGGAGCCACCTTTGCTATCGTGCCCT
TTGTCTCCCGGCGAGCTCTAGGCATTATCTCGGGTTTAACCGGGGCTGGAGGGAACTTTGGG
TCAGGACTCACACAGCTCGTCTTTTTCTCGACTTCGCGCTTCACAACTGAAGAAGGGCTAAC
GTGGATGGGAGTGATGATAGTTGCTTGCACGTTGCCTGTTACCTTAATCCACTTTCCTCAGT
GGGGAAGCATGTTCTTCCCTCCTTCCAACGATTCGGTCGACGCTACGGAGCACTATTATGTT
GGCGAATATAGTAAGGAGGAGCAGCAGATTGGCATGCATTTAAAAAGCAAACTGTTTGCTGA
TGGAGCCAAGACCGAGGGAGGCAGCAGCGTCCACAAAGGGAACGCAACCAACAATGCTTGAT
CATGTGTCATTGATATCAAGAAATTAATAATTTCACTTATGTGAAATGGACATAAACTGTTG
GAAAATAAAGAACCATTTCTTTCATCATTTGCTTT

SEQ ID NO: 114, Arabidopsis thaliana high-affinity nitrate transporter (ACH2) (NP_172289)

MGSTDEPGSSMHGVTGREQSYAFSVDGSEPTNTKKKYNLPVDAEDKATVFKLFSFAKPHMRT
FHLSWISFSTCFVSTFAAAPLIPIIRENLNLTKHDIGNAGVASVSGSIFSRLVMGAVCDLLG
PRYGCAFLVMLSAPTVFSMSFVSDAAGFITVRFMIGFCLATFVSCQYWMSTMFNSQIIGLVN
GTAAGWGNMGGGITQLLMPIVYEIIRRCGSTAFTAWRIAFFVPGWLHIIMGILVLTLGQDLP
GGNRAAMEKAGEVAKDKFGKILWYAVTNYRTWIFVLLYGYSMGVELSTDNVIAEYFFDRFHL
KLHTAGIIAACFGMANFFARPAGGWASDIAAKRFGMRGRLWTLWIIQTSGGLFCVWLGRANT
LVTAVVSMVLFSLGAQAACGATFAIVPFVSRRALGIISGLTGAGGNFGSGLTQLVFFSTSRF
TTEEGLTWMGVMIVACTLPVTLIHFPQWGSMFFPPSNDSVDATEHYYVGEYSKEEQQIGMHL
KSKLFADGAKTEGGSSVHKGNATNNA

Figure 8 (continued)

SEQ ID NO: 115, Arabidopsis thaliana high-affinity nitrate transporter ACH2 variant mRNA, complete cds (AF019749)

AAACTTGAATTTTCTCAAAGGAACTTGATACGTTTAAAATACATGGGTTCTACTGATGAGCC
CAGAAGTTCCATGCATGGAGTTACCGGTAGAGAACAGAGCTATGCTTTCTCGGTAGATGGTA
GTGAGCCGACCAACACAAAGAAAAAGTACAATCTGCCGGTGGACGCGGAGGATAAGGCAACG
GTTTTCAAGCTCTTCTCCTTCGCCAAACCTCACATGAGAACGTTCCACCTCTCGTGGATCTC
TTTCTCCACATGTTTTGTTTCGACGTTCGCAGCTGCACCACTTATCCCGATCATCAGGGAGA
ATCTTAACCTCACCAAACATGACATTGGAAACGCTGGAGTTGCCTCCGTCTCGGGGAGTATC
TTCTCTAGGCTCGTGATGGGAGCCGTGTGTGATCTTTTGGGTCCTCGTTACGGTTGTGCCTT
CCTTGTGATGTTGTCTGCCCCAACGGTGTTCTCCATGAGCTTCGTGAGTGACGCAGCAGGCT
TCATAACGGTGAGGTTCATGATTGGTTTTTGCCTGGCGACGTTTGTGTCTTGTCAATACTGG
ATGAGCACTATGTTCAACAGTCAGATCATCGGTCTGGTGAACGGGACAGCAGCCGGATGGGG
AAACATGGGTGGCGGCATAACGCAGTTGCTCATGCCCATTGTGTATGAAATCATTAGGCGCT
GCGGATCAACAGCGTTCACGGCCTGGAGGATCGCCTTCTTTGTCCCCGGTTGGTTGCACATC
ATCATGGGAATCTTGGTGCTCACGCTAGGTCAAGATCTGCCAGGTGGAAACAGAGCTGCCAT
GGAGAAAGCGGGAGAAGTTGCCAAAGACAAATTCGGAAAGATTCTATGGTACGCCGTTACAA
ATTACAGGACTTGGATTTTCGTTCTTCTGTATGGATATTCCATGGGAGTTGAGTTAAGCACA
GACAATGTTATCGCCGAGTACTTCTTTGACAGGTTTCACTTGAAGCTTCACACAGCGGGGAT
TATAGCAGCATGTTTCGGAATGGCCAATTTCTTTGCTCGTCCAGCAGGAGGCTGGGCATCTG
ACATTGCAGCCAAGCGCTTCGGAATGCGAGGGAGGTTGTGGACTTTGTGGATCATTCAGACG
TCCGGTGGTCTCTTTTGTGTGTGGCTCGGACGTGCCAACACCCTCGTCACTGCCGTTGTATC
TATGGTCCTCTTCTCTTTAGGAGCACAAGCCGCTTGCGGAGCCACCTTTGCTATCGTGCCCT
TTGTCTCCCGGCGAGCTCTAGGCATTATCTCGGGTTTAACCGGGGCTGGAGGGAACTTTGGG
TCAGGACTCACACAGCTCGTCTTTTTCTCGACTTCGCGCTTCACAACTGAAGAAGGGCTAAC
GTGGATGGGAGTGATGATAGTTGCTTGCACGTTGCCTGTTACCTTAATCCACTTTCCTCAGT
GGGGAAGCATGTTCTTCCCTCCTTCCAACGATTCGGTCGACGCTACGGAGCACTATTATGTT
GGCGAATATAGTAAGGAGGAGCAGCAGATTGGCATGCATTTAAAAAGCAAACTGTTTGCTGA
TGGAGCCAAGACCGAGGGAGGCAGCAGCGTCCACAAAGGGAACGCAACCAACAATGCTTGAT
CATGTGTCATTGATATCAAGAAATTAATAATTTCACTTATGTGAAATGGACATAAACTGTTG
GAAAATAAAGAACCATTTCTTTCATCATTTGCTTT

SEQ ID NO: 116, Arabidopsis thaliana high-affinity nitrate transporter ACH2 variant (AAC35884)

MGSTDEPRSSMHGVTGREQSYAFSVDGSEPTNTKKKYNLPVDAEDKATVFKLFSFAKPHMRT
FHLSWISFSTCFVSTFAAAPLIPIIRENLNLTKHDIGNAGVASVSGSIFSRLVMGAVCDLLG
PRYGCAFLVMLSAPTVFSMSFVSDAAGFITVRFMIGFCLATFVSCQYWMSTMFNSQIIGLVN
GTAAGWGNMGGGITQLLMPIVYEIIRRCGSTAFTAWRIAFFVPGWLHIIMGILVLTLGQDLP
GGNRAAMEKAGEVAKDKFGKILWYAVTNYRTWIFVLLYGYSMGVELSTDNVIAEYFFDRFHL
KLHTAGIIAACFGMANFFARPAGGWASDIAAKRFGMRGRLWTLWIIQTSGGLFCVWLGRANT
LVTAVVSMVLFSLGAQAACGATFAIVPFVSRRALGIISGLTGAGGNFGSGLTQLVFFSTSRF
TTEEGLTWMGVMIVACTLPVTLIHFPQWGSMFFPPSNDSVDATEHYYVGEYSKEEQQIGMHL
KSKLFADGAKTEGGSSVHKGNATNNA

Figure 8 (continued)

SEQ ID NO: 117, Arabidopsis thaliana high-affinity nitrate transporter, putative (At5g60780) mRNA, complete cds (NM_125471)

ATGACTCACAACCATTCTAATGAAGAAGGCTCCATTGGAACCTCCTTGCATGGAGTTACAGC
AAGAGAACAAGTCTTCTCTTTCTCCGTCGATGCTTCGTCTCAAACAGTCCAATCAGACGATC
CAACAGCTAAATTCGCCCTTCCGGTTGATTCCGAACATCGAGCCAAAGTGTTCAACCCACTC
TCTTTTGCTAAACCTCACATGAGAGCCTTCCACTTAGGATGGCTCTCATTCTTCACATGCTT
CATCTCCACCTTCGCGGCAGCACCATTAGTCCCCATCATCCGCGACAACCTCGACCTCACTA
AAACCGACATTGGAAACGCCGGAGTCGCATCCGTCTCTGGTGCCATTTTCTCAAGGTTAGCC
ATGGGAGCGGTTTGTGATCTCCTCGGTGCACGATATGGGACTGCCTTCTCCCTCATGCTAAC
CGCCCCAACCGTCTTCTCAATGTCGTTTGTGGGTGGCCCTAGCGGATACTTAGGCGTCCGGT
TCATGATCGGATTCTGTCTCGCCACGTTTGTATCATGCCAGTATTGGACCAGCGTTATGTTC
AACGGTAAGATCATAGGACTAGTGAACGGCTGTGCAGGCGGGTGGGGTGATATGGGCGGTGG
AGTGACTCAACTCCTAATGCCGATGGTCTTCCACGTCATCAAACTTGCCGGAGCCACTCCGT
TCATGGCCTGGCGGATAGCTTTCTTCGTTCCCGGATTTCTTCAAGTTGTTATGGGCATTCTC
GTCCTCAGTCTCGGCCAAGATCTCCCTGACGGTAACCTAAGTACCCTTCAGAAGAGTGGTCA
AGTCTCTAAAGACAAATTCTCCAAGGTTTTCTGGTTTGCTGTGAAGAACTACAGAACATGGA
TTTTATTCGTTCTTTATGGATCTTCCATGGGAATTGAATTAACTATCAACAACGTTATCTCC
GGATATTTTTACGACAGGTTTAACCTTAAGCTTCAAACAGCTGGTATAGTAGCAGCCAGCTT
TGGAATGGCTAACTTCATCGCCCGTCCCTTCGGTGGTTACGCTTCTGATGTAGCGGCTCGGG
TTTTTGGCATGAGAGGCCGGTTATGGACCTTATGGATCTTTCAAACCGTAGGAGCTCTTTTC
TGTATCTGGCTAGGTCGAGCTAGTTCACTTCCCATAGCAATCCTAGCAATGATGCTCTTCTC
AATCGGTACACAAGCAGCTTGCGGAGCCCTCTTCGGAGTTGCACCTTTTGTCTCGCGCCGCT
CTCTAGGGCTCATATCGGGACTAACCGGCGCAGGAGGAAACTTCGGGTCCGGTTTGACTCAA
CTGCTTTTCTTCTCATCAGCGAGGTTTAGTACAGCTGAGGGACTCTCATTGATGGGCGTTAT
GGCGGTTTTGTGCACACTCCCAGTTGCGTTTATACATTTTCCGCAATGGGGAAGCATGTTTT
TAAGACCGTCGACCGATGGAGAAAGATCACAGGAGGAATATTATTACGGTTCTGAGTGGACG
GAGAATGAGAAACAACAAGGATTGCACGAAGGAAGCATCAAATTTGCAGAGAATAGTAGGTC
AGAGAGAGGCCGGAAAGTAGCTTTGGCTAACATTCCAACGCCGGAGAACGGAACTCCAAGTC
ATGTTTGA

SEQ ID NO: 118, Arabidopsis thaliana high-affinity nitrate transporter, putative (NP_200886)

MTHNHSNEEGSIGTSLHGVTAREQVFSFSVDASSQTVQSDDPTAKFALPVDSEHRAKVFNPL
SFAKPHMRAFHLGWLSFFTCFISTFAAAPLVPIIRDNLDLTKTDIGNAGVASVSGAIFSRLA
MGAVCDLLGARYGTAFSLMLTAPTVFSMSFVGGPSGYLGVRFMIGFCLATFVSCQYWTSVMF
NGKIIGLVNGCAGGWGDMGGGVTQLLMPMVFHVIKLAGATPFMAWRIAFFVPGFLQVVMGIL
VLSLGQDLPDGNLSTLQKSGQVSKDKFSKVFWFAVKNYRTWILFVLYGSSMGIELTINNVIS
GYFYDRFNLKLQTAGIVAASFGMANFIARPFGGYASDVAARVFGMRGRLWTLWIFQTVGALF
CIWLGRASSLPIAILAMMLFSIGTQAACGALFGVAPFVSRRSLGLISGLTGAGGNFGSGLTQ
LLFFSSARFSTAEGLSLMGVMAVLCTLPVAFIHFPQWGSMFLRPSTDGERSQEEYYYGSEWT
ENEKQQGLHEGSIKFAENSRSERGRKVALANIPTPENGTPSHV

Figure 8 (continued)

SEQ ID NO: 119, Arabidopsis thaliana At3g45060 gene, complete cds (BT015382)

ATGGCTCACAACCATTCTAATGAAGACGGCTCTATTGGAACCTCCTTGCATGGAGTCACGGC
AAGGGAGCAAGTCTTCTCCTTCTCCGTCCAAGAAGATGTCCCTTCATCTCAAGCCGTCCGAA
CAAACGATCCAACGGCTAAGTTTGCCCTACCAGTGGACTCCGAACATAGGGCAAAAGTGTTC
AAACCACTATCATTCGCTAAACCACATATGAGAGCCTTCCACTTAGGATGGATCTCTTTCTT
CACTTGCTTCATCTCCACCTTCGCAGCCGCACCTCTAGTCCCCGTCATTCGCGACAATCTCG
ACCTGACCAAAACCGACATCGGAAATGCTGGAGTTGCATCAGTTTCCGGCGCCATTTTCTCG
AGACTCGCTATGGGTGCTGTATGTGACCTTCTAGGGGCACGTTATGGAACCGCCTTCTCACT
TATGCTTACAGCTCCAGCAGTTTTCTCCATGTCGTTCGTAGCTGACGCGGGAAGCTACTTAG
CCGTAAGGTTCATGATCGGTTTTTGCTTAGCAACGTTCGTATCATGTCAGTACTGGACGAGT
GTTATGTTCACTGGAAAGATTATCGGACTCGTTAACGGATGTGCTGGAGGGTGGGGAGATAT
GGGAGGAGGAGTGACTCAGCTACTAATGCCAATGGTCTTCCACGTCATCAAACTCACCGGAG
CCACTCCCTTCACGGCTTGGAGGTTCGCCTTCTTCATCCCCGGCATTCTTCAGATAGTTATG
GGTATTCTCGTTCTCACTCTCGGCCAAGATCTTCCCGATGGTAACCTCAGTACTCTCCAAAA
GAGTGGTCAAGTTTCTAAAGACAAATTCTCCAAGGTCTTTTGGTTCGCTGTGAAAAACTATA
GAACATGGATCTTATTCATGCTCTATGGATTTTCTATGGGAGTTGAATTAACGATCAACAAC
GTTATATCTGGATACTTCTACGATAGGTTTAACCTTACGCTTCACACAGCTGGTATTATAGC
AGCCAGCTTTGGTATGGCAAACTTCTTTGCCCGTCCTTTTGGTGGCTACGCTTCAGATGTAG
CTGCACGGCTCTTCGGTATGAGGGGACGGTTATGGATCTTGTGGATCTTACAAACTGTTGGA
GCTCTCTTTTGCATCTGGCTTGGTCGTGCTAGTTCACTACCTATAGCTATCTTAGCCATGAT
GCTTTTTTCCATGGGCACACAAGCTGCTTGTGGAGCTCTCTTTGGTGTTGCTCCTTTTGTTT
CCCGCCGTTCTCTTGGACTTATCTCGGGATTAACTGGTGCTGGTGGAAATTTTGGGTCGGGA
GTTACTCAACTTCTTTTCTTCTCTTCCTCGAGGTTTAGTACGGCGGAAGGACTATCGTTGAT
GGGCGTTATGGCTGTTGTGTGCTCTCTTCCGGTTGCGTTTATACATTTTCCGCAGTGGGGAA
GCATGTTCTTGAGGCCATCACAAGATGGAGAGAAATCAAAGGAAGAGCATTACTATGGAGCG
GAATGGACAGAGGAAGAGAAGAGCTTAGGACTACACGAAGGAAGCATTAAATTTGCTGAAAA
CAGCCGGTCAGAGAGAGGCCGCAAGGCGATGTTGGCTGATATTCCAACGCCGGAAACCGGAT
CTCCGGCTCATGTCTAG

SEQ ID NO: 120, Arabidopsis thaliana At3g45060 (AAU05505)

MAHNHSNEDGSIGTSLHGVTAREQVFSFSVQEDVPSSQAVRTNDPTAKFALPVDSEHRAKVF
KPLSFAKPHMRAFHLGWISFFTCFISTFAAAPLVPVIRDNLDLTKTDIGNAGVASVSGAIFS
RLAMGAVCDLLGARYGTAFSLMLTAPAVFSMSFVADAGSYLAVRFMIGFCLATFVSCQYWTS
VMFTGKIIGLVNGCAGGWGDMGGGVTQLLMPMVFHVIKLTGATPFTAWRFAFFIPGILQIVM
GILVLTLGQDLPDGNLSTLQKSGQVSKDKFSKVFWFAVKNYRTWILFMLYGFSMGVELTINN
VISGYFYDRFNLTLHTAGIIAASFGMANFFARPFGGYASDVAARLFGMRGRLWILWILQTVG
ALFCIWLGRASSLPIAILAMMLFSMGTQAACGALFGVAPFVSRRSLGLISGLTGAGGNFGSG
VTQLLFFSSSRFSTAEGLSLMGVMAVVCSLPVAFIHFPQWGSMFLRPSQDGEKSKEEHYYGA
EWTEEEKSLGLHEGSIKFAENSRSERGRKAMLADIPTPETGSPAHV

Figure 8 (continued)

SEQ ID NO: 121, Daucus carota high-affinity nitrate transporter mRNA, partial cds (AY081213)

ATGGGTGACATGGAAGGTTCCCCGGGTTCCTCCATGCACGGTGTTACCGGTCGTGAACCGTC
CCTGGCTTTCTCCGTTGCTTCCCGTATCGACACCTCCGCTGAATTCCACGTTCCGGTTGACT
CCGAACACAAAGCTAAAGTTTTCAAATTCAAATCCTTCTCCCCGCCGCACGGTCTGCAGTTC
CAGCTGACCTGGATCTCCTTCCCGACCTGCTTCGTTTCCACCTTCGCTGCTCGTCCGCTGGT
TGTTATCATCCGTGACAACCTGAACCCGACCAAAATGGACGTTGGTAACGCTGGTGTTGCTT
CCGTTACCGGTTCCATCCTGTCCCGTGGTGCTATGGGTGCTATCTGCGACATGCTGGGTCCG
CGTTACGGTTGCGCTTTCCTGATCATGCTGTCCGCTCCGAAAGTTCTGTGCATGTCCTTCGT
TTCCTCCGCTGGTGGTTACGTTGCTGTTCGTTTCATGATCGGTTTCTCCCTGGCTACCTTCG
TTTCCTGCCGTTACTGGATGTCCACCTCCATGCACTCCGACATCATCGGTCTGGTTAACGGT
ACCGCTGCTGGTTGGGGTAACATGACCGGTGGTGCTACCCAGCTGATCATGCCGCTGCTGTA
CGACATCATCCGTGAAGCTGGTGCTACCCCGTTCACCGCTTGGCGTATCGCTCTGTTCATCC
CGGGTTGGCTGCACGTTATCTCCGGTATCCTGGTTCTGACCCTGGGTCAGGACCTGCCGGAC
GGTAACGCTCAGAACGAAGCTTCCCTGCGTAAAAAAGGTCGTGTTCACAAAGACAAATTCTC
CAAAATCCTGCGTTACGCTGCTACCAACTACCGTACCTGGATCCTGGTTCTGCTGTACGGTT
ACTCCATGGGTGTTGAACTGACCACCGACAACGTTATCGCTGAATACTTCTTCGACCGTTTC
GACCTGAAACTGCACACCCCGGGTATCATCGCTGCTACCTTCGGTATGGCTAACCTGCTGGC
TCGTCCGTTCGGTGGTTGGTCCTCCGACGTTGCTGCTAAACACTTCGGTATGCGTGGTCGTC
ACTGGAACTCCTGGGACCTGCAGACCCTGGGTGGTGTTTTCTGCCTGCTGCTGGTTCGTGCT
ACCACCTCCCCGATCGACGCTCTGGCTATCACCTGGATGATCATCTTCTCCATCGGTGCTCA
GGCTGCTACCGGTGTTACCTTCGGTATCATCCCGTTCATCTCCCGTCGTTACCTGGGTATCA
TCTCCCAGATGACCGGTGCTAACGGTAACTTCGGTTCCGGTCAGACCCAGCCGCTGGAATTC
GACTCCACCAAATACAACACCGGTCTGGGTCTGACCTACATGGGTATGATGATCATCGCTTG
CACCCTGCCGCCGATGCTGGTTTGGTTCTGGCAGGACGGTTCCATGTTCCTGCCGCCGTCCA
AAGACCCGATCAAAGGTACCGAACCGGAACACTACTTCGGTTCCGAATACACCGAAGACGAA
AAAGTTAAAGGTATGCACCAGAACTCCATCAAATTCGCTGAAAACTCCCGTACCGAATTCGG
TAAAAAACGTGTTGGTTCCGCTCCGACCCCGCCGAACGTTTACCCCAACCGTGTT

SEQ ID NO: 122, Daucus carota high-affinity nitrate transporter (AAL99362)

MGDMEGSPGSSMHGVTGREPSLAFSVASRIDTSAEFHVPVDSEHKAKVFKFKSFSPPHGLQF
QLTWISFPTCFVSTFAARPLVVIIRDNLNPTKMDVGNAGVASVTGSILSRGAMGAICDMLGP
RYGCAFLIMLSAPKVLCMSFVSSAGGYVAVRFMIGFSLATFVSCRYWMSTSMHSDIIGLVNG
TAAGWGNMTGGATQLIMPLLYDIIREAGATPFTAWRIALFIPGWLHVISGILVLTLGQDLPD
GNAQNEASLRKKGRVHKDKFSKILRYAATNYRTWILVLLYGYSMGVELTTDNVIAEYFFDRF
DLKLHTPGIIAATFGMANLLARPFGGWSSDVAAKHFGMRGRHWNSWDLQTLGGVFCLLLVRA
TTSPIDALAITWMIIFSIGAQAATGVTFGIIPFISRRYLGIISQMTGANGNFGSGQTQPLEF
DSTKYNTGLGLTYMGMMIIACTLPPMLVWFWQDGSMFLPPSKDPIKGTEPEHYFGSEYTEDE
KVKGMHQNSIKFAENSRTEFGKKRVGSAPTPPNVYPNRV

Figure 8 (continued)

SEQ ID NO: 123, Zea mays partial mRNA for high affinity nitrate transporter (nrt2-1 gene) (AJ344451)

CAGCAAGATCATCGGCACCGTCAACGGGCTCGCCGCCGGATGGGGCAACATGGGAGGCGGCG
CCACGCAGCTCATCATGCCGCTCGTCTACGACGTCATCCGCAAGTGCGGCGCCACGCCATTC
ACGGCCTGGCGCCTCGCCTACTTCGTGCCGGGCCTCATGCACGTCGTCATGGGCGTCCTGGT
GCTCACGCTGGGGCAGGACCTCCCCGACGGCAACCTCAGGTCGCTGCAGAAGAAGGGCAACG
TCAACAAGGACAGCTTCTCCAAGGTCATGTGGTACGCCGTCATCAACTACCGTACCTGGATC
TTCGTCCTCCTCTACGGCTACTGCATGGGCGTCGAGCTCACCACCGACAACGTCATCGCCGA
GTACATGTACGACCGCTTCGACCTCGACCTCCGCGTCGCCGGGACCATCGCCGCCTGCTTCG
GCATGGCCAACATCGTCGCACGCCCTATGGGCGGCATCATGTCGGACATGGGCGCGCGCTAC
TGGGGCATGCGCGCTCGCCTCTGGAACATCTGGATCCTCCAGACCGCCGGCGGCGCCTTCTG
CCTCTGGCTGGGACGCGCCAGCACCCTCCCCGTCTCCGTCGTCGCCATGGTGCTCTTCTCCT
TCTGCGCGCAGGCGGCCTGCGGCGCCATCTTCGGGGTCATCCCCTTCGTCTCCCGCCGCTCC
CTCGGCATCATCTCCGGCATGACGGGCGCCGGCGGCAACTTCGGCGCCGGGCTCACGCAGCT
GCTCTTCTTTACCTCCTCGACCTACTCCACGGGCAGGGGGCTGGAGTACATGGGCATCATGA
TCATGGCGTGCACGCTGCCGGTGGTGTTCGTGCACTTCCCGCAGTGGGGGTCCATGTTCTTC
CCGCCCAGCGCCACCGCCGACGAGGAGGGCTACTACGCCTCCGAGTGGAACGACGACGAGAA
GAGCAAGGGACTCCATAGCGCTAGCCTCAAGTTCGCCGAGAACAGCCGCTCAGAGCGCGGCA
AGCGCAACGTCATCCAGGCCGACGCCGCCGCCACGCCGGAGCATGTCTAAGTTCACTACTAA
GATGGATCGATCGACGATCACCTATACCTCTTTGTATGTACGAATATGCCTTGTTATTACTG
TGCGCGCGCATATACAATACACGTGTGCTCCGTTGACATGAGTTATATAGCACTAAAAACTT
CTTTTGAAAAAAAAAAAAAAAA

SEQ ID NO: 124, Zea mays high affinity nitrate transporter (CAC87729)

SKIIGTVNGLAAGWGNMGGGATQLIMPLVYDVIRKCGATPFTAWRLAYFVPGLMHVVMGVLV
LTLGQDLPDGNLRSLQKKGNVNKDSFSKVMWYAVINYRTWIFVLLYGYCMGVELTTDNVIAE
YMYDRFDLDLRVAGTIAACFGMANIVARPMGGIMSDMGARYWGMRARLWNIWILQTAGGAFC
LWLGRASTLPVSVVAMVLFSFCAQAACGAIFGVIPFVSRRSLGIISGMTGAGGNFGAGLTQL
LFFTSSTYSTGRGLEYMGIMIMACTLPVVFVHFPQWGSMFFPPSATADEEGYYASEWNDDEK
SKGLHSASLKFAENSRSERGKRNVIQADAAATPEHV

SEQ ID NO: 125, Oryza sativa nitrate transporter (NRT1) mRNA, complete cds (AF140606)

GGTGGAGGAGAGTGAGGACGGCCCACGCGGACGAGCAGAGAGTGGCGGGCTCAGTGTCGGGC
TCGCCGGAGTCCGCGCAATCCGGCCGTTCATGCTTCATTCTCTCGGACATTAACCTGGTTTA
CTTGTAAGAAAGTAGAGCCATGGACTCCTCATACCAGCATGACAAGCCTCTGCTGGATGAAG
AGAACTCCTCGCAAGTGACCCTTGAATATACAGGTGATGGATCTGTTTGCATCCGTGGGCAT
CCTGCTTTAAGGAAACATACAGGGAACTGGAAGGGTTCCTCATTAGCCATCGTTTTTTCATT
CTGCTCTTATCTGGCCTTTACTTCAATTGTAAAAAACCTAGTCAGTTATCTCACAAAAGTTC
TACATGAAACAAACGTGGCCGCTGCAAGAGATGTTGCAACTTGGTCAGGAACAAGTTATCTT
GCACCTCTGGTTGGAGCCTTCTTAGCTGATTCATATCTGGGGAAGTACTGTACAATTCTGAT
CTTCTGCACGATCTTCATTATCGGATTGATGATGTTGCTTCTGTCAGCAGCAGTTCCATTAA
TCTCTACTGGTCCTCACTCATGGATCATATGGACAGATCCAGTCTCTTCTCAGAACATCATA

Figure 8 (continued)

TTCTTTGTCGGTTTGTACATGGTTGCTTTAGGGTATGGTGCACAGTGCCCCTGCATATCATC
ATTTGGTGCTGATCAATTTGATGACACTGATGAAAATGAGAGAACAAAAAAGAGTTCTTTTT
TCAATTGGACCTATTTCGTAGCCAATGCGGGCTCATTGATCTCGGGGACTGTTATTGTGTGG
GTGCAAGATCACAAAGGTTGGATCTGGGGTTTTACCATTTCTGCACTATTTGTGTATTTAGG
TTTTGGTACTTTTATCTTTGGCTCCTCTATGTATGATTTCAGAAACCTGGAGGAAGCCCCTC
TTGCGAGAATATGCCAGGTTGTTGTTGCTGCTATTCACAAACGCGATAAAGATTTGCCATGT
GATTCCTCAGTTCTTTATGAGTTTCTGGGGCAGAGTTCAGCAATCGAAGGCAGCCGAAAATT
GGAGCATACAACTGGACTTAAGTTCTTTGATAGAGCTGCAATGGTGACACCATCTGATTTTG
AATCTGATGGCCTACTAAACACATGGAAGATTTGCACAGTCACTCAAGTGGAGGAACTGAAG
ATTTTGATCAGGATGTTCCCCGTTTGGGCAACGATGATATTATTTGCTGCAGTTCTGGACAA
CATGTTTTCGACATTCATAGAACAGGGGATGGTGATGGAGAAACACATCGGCTCTTTCGAAA
TACCTGCGGCGTCCTTCCAATCCATTGATGTCATTGCTGTCCTTATACTAGTTCCAGTCTAT
GAAAGAGTCCTTGTTCCAGTGTTCAGAAAATTCACTGGCAGAGCAAATGGCATTACTCCACT
GCAGCGAATGGGGATCGGCCTGTTCTTTTCCATGCTCTCCATGGTATCAGCAGCATTGGTGG
AGAGTAATCGGTTGCGGATTGCGCAGGATGAAGGTTTGGTGCACAGGAAGGTGGCTGTTCCA
ATGAGCATCCTGTGGCAGGGACCCCAGTACTTCCTGATAGGCGTGGGAGAGGTGTTCTCAAA
CATTGGGTTAACTGAATTTTTCTACCAGGAATCACCGGACGCCATGAGAAGCTTATGTCTCG
CATTCTCACTTGCTAACGTTTCGGCAGGAAGTTACCTCAGCTCGTTTATCGTTTCTCTTGTG
CCAGTGTTCACAGCCAGAGAAGGCAGTCCTGGATGGATACCTGATAACTTGAACGAAGGGCA
TTTGGATCGGTTCTTCTGGATGATGGCTGGCTTGTGTTTCTTGAATATGCTGGCCTTTGTGT
TCTGTGCCATGAGGTACAAATGTAAGAAGGCTTCCTGAACCTTGTTAACATTAGCAATATAA
TGGTGGTGGAAAAGGACAATTGTGTTGCAAAAAAAAAAAAAAA

SEQ ID NO: 126, Oryza sativa nitrate transporter (NRT1) (AAF07875)

MDSSYQHDKPLLDEENSSQVTLEYTGDGSVCIRGHPALRKHTGNWKGSSLAIVFSFCSYLAF
TSIVKNLVSYLTKVLHETNVAAARDVATWSGTSYLAPLVGAFLADSYLGKYCTILIFCTIFI
IGLMMLLLSAAVPLISTGPHSWIIWTDPVSSQNIIFFVGLYMVALGYGAQCPCISSFGADQF
DDTDENERTKKSSFFNWTYFVANAGSLISGTVIVWVQDHKGWIWGFTISALFVYLGFGTFIF
GSSMYDFRNLEEAPLARICQVVVAAIHKRDKDLPCDSSVLYEFLGQSSAIEGSRKLEHTTGL
KFFDRAAMVTPSDFESDGLLNTWKICTVTQVEELKILIRMFPVWATMILFAAVLDNMFSTFI
EQGMVMEKHIGSFEIPAASFQSIDVIAVLILVPVYERVLVPVFRKFTGRANGITPLQRMGIG
LFFSMLSMVSAALVESNRLRIAQDEGLVHRKVAVPMSILWQGPQYFLIGVGEVFSNIGLTEF
FYQESPDAMRSLCLAFSLANVSAGSYLSSFIVSLVPVFTAREGSPGWIPDNLNEGHLDRFFW
MMAGLCFLNMLAFVFCAMRYKCKKAS

Figure 8 (continued)

SEQ ID NO 127: Arabidopsis thaliana
TCATACTCACAGAACAGAAACCCTAATTTCCTCAAAGCAATCTCGTTTCATCTTCCGCAAAC
GAAACCCTCGAGAGTTGTTACTCCTCCTCCTCCTCTGGTGCATGATAAAGCGGCCTCAGGGT
TTGCTGCGGCGCTCGTTAGCGTTTGTCAATCGAAGAATTGTCTTGGTCGGACTCAAGAAGAT
GTCAGAAGATTGATGGAGTTTCTTGTGGGAGAAGAAAAGAAGAGGAACAAGGTCTTAGTCAA
TGATGTTGTTGAGAGAGGTAAATTTGGTAAACACTTCAAGGGCTTGGTCAAGATGTTGATTG
CAAGAGGTAAATCTGGGATTCTGGTGGATGTTTTAATGGAATTTGAGAGAATCTGTAATGAA
TTGGTCTCAAAAAAACTTGTCTGGGTTTCTTGA

SEQ ID NO 128: Arabidopsis thaliana
ASYSQNRNPNFLKAISFHLPQTKPSRVVTPPPPLVHDKAASGFAAALVSVCQSKNCLGRTQE
DVRRLMEFLVGEEKKRNKVLVNDVVERGKFGKHFKGLVKMLIARGKSGILVDVLMEFERICN
ELVSKKLVWVS

SEQ ID NO 129: Arabidopsis thaliana
ATGGATACTCTCTCAGCATCCGTTTCATCCTTGAACCTCCCTTCTCTTCCTCCACCACCGCA
GCCACCGTTGAGATCCATCTCCAGCCGCTTTAAATCCACCGTAAACGCCACCACTTCTGCTT
CATCTACCAATCTTTCAAAACCAACATCGTCTTCACCTTCTTCAGCATCATACTCACAGAAC
AGAAACCCTAATTTCCTCAAAGCAATCTCGTTTCATCTTCCGCAAACGAAACCCTCGAGAGT
TGTTACTCCTCCTCCTCCTCTGGTGCATGATAAAGCGGCCTCAGGGTTTGCTGCGGCGCTCG
TTAGCGTTTGTCAATCGAAGAATTGTCTTGGTCGGACTCAAGAAGATGTCAGAAGATTGATG
GAGTTTCTTGTGGGAGAAGAAAAGAAGAGGAACAAGGTCTTAGTCAATGATGTTGTTGAGAG
AGGTAAATTTGGTAAACACTTCAAGGGCTTGGTCAAGATGTTGATTGCAAGAGGTAAATCTG
GGATTCTGGTGGATGTTTTAATGGAATTTGAGAGAATCTGTAATGAATTGGTCTCAAAAAAA
CTTGTCTGGGTTTCTTGA

SEQ ID NO 130: Arabidopsis thaliana
MDTLSASVSSLNLPSLPPPPQPPLRSISSRFKSTVNATTSASSTNLSKPTSSSPSSASYSQN
RNPNFLKAISFHLPQTKPSRVVTPPPPLVHDKAASGFAAALVSVCQSKNCLGRTQEDVRRLM
EFLVGEEKKRNKVLVNDVVERGKFGKHFKGLVKMLIARGKSGILVDVLMEFERICNELVSKK
LVWVS

SEQ ID NO 131: Arabidopsis thaliana
MDTLSASVSSLNLPSLPPPPQPPLRSISSRFKSTVNATTSASSTNLSKPTSSSPSSS

SEQ ID NO 132: Chlamydomonas
MAMAMRSTFAARVGAKPAVRGARPASRMSCMA

SEQ ID NO 133: Chlamydomonas
MQVTMKSSAVSGQRVGGARVATRSVRRAQLQV

FIGURE 10

SEQ ID NO 134: Arabidopsis thaliana
MASLMLSLGSTSLLPREINKDKLKLGTSASNPFLKAKSFSRVTMTVAVKPSR

SEQ ID NO 135: Arabidopsis thaliana
MATQFSASVSLQTSCLATTRISFQKPALISNHGKTNLSFNLRRSIPSRRLSVSC

SEQ ID NO 136: Arabidopsis thaliana
MASIAASASISLQARPRQLAIAASQVKSFSNGRRSSLSFNLRQLPTRLTVSCAAKPETVDKV
CAVVRKQL

SEQ ID NO 137: Arabidopsis thaliana
MASIATSASTSLQARPRQLVIGAKQVKSFSYGSRSNLSFNLRQLPTRLTVYCAAKPETVDKV
CAVVRKQLSLKE

SEQ ID NO 138: Arabidopsis thaliana
MASSAAAIVSGSPFRSSPLIHNHHASRYAPGSISVVSLPRQVSRRGLSVKS

SEQ ID NO 139: Brassica napus
MATANALSSPSVLCSSRQGKLSGGSQQKGQRVSYRKANRRFSLRANVKEIAFDQSSRAALQA
GIDKLADAVGLTLGPRGRNVVLDEFGSPKVVNDGVTIA

SEQ ID NO 140: Hordeum vulgare
MAPTVMASSATSVAPFQGLKSTAGLPVSRRSNASSASVSNGGRIRCMQVWPIEGIKKFETLS
YLPPLSTEALLKQVDYLIRSKWVPCLEFSKVGFIFREH

SEQ ID NO 141: Medicago truncatula
MTTIFRLASSSSPSLRHDATPHNFHIRKTSISNTFSFSSKNSLSFKRILTSGGSRRFIVAAS
PPTEDAVVATEPLTKQDLIDYLASGCKTKDKWRIGTEH

SEQ ID NO 142: Spinacia oleracea
METSMACCSRSIVLPRVSPQHSSALVPSSINLKSLKSSSLFGESLRMTTKSSVRVNKAKNSS
LVTKCELGDSLEEFLAKATTDKGLIRLMMCMGEALRTI

SEQ ID NO 143: Oryza sativa
GGTCAGCCAATACATTGATCCGTTGCCAATCATGCAAAGTATTTTGGCTGTGGCCGAGTGCC
GGAATTGATAATTGTGTTCTGACTAAATTAAATGACCAGAAGTCGCTATCTTCCAATGTATC
CGAAACCTGGATTAAACAATCCTGTTCTGTTCTCTAGCCCCTCCTGCATGGCCGGATTGTTT
TTTTGACATGTTTTCTTGACTGAGGCCTGTTTGTTCTAAACTTTTTCTTCAAACTTTTAACT
TTTTCATCACATCAGAACTTTTCTACACATATAAACTTTTAACTTTTCCGTCACATCGTTCC
AATTTCAATCAAACTTTCAATTTTGGCGTGAACTAAACACACCCTGAGTCTTTTATTGCTCC
TCCGTACGGGTTGGCTGGTTGAGAATAGGTATTTTCAGAGAGAAAATCTAGATATTGGGAGG
AACTTGGCATGAATGGCCACTATATTTAGAGCAATTCTACGGTCCTTGAGGAGGTACCATGA

FIGURE 10 (continued)

CATCAAACAAGAGTTCACCAAACCGCCCATGCGGCCATGCTGTCACGCAACGCACCGCATTG
CCTGATGGCCGCTCGATGCATGCATGCTTCCCCGTGCACATATCCGACAGACGCGCCGTGTC
AGCGAGCTCCTCGACCGACCTGTGTAGCCCATGCAAGCATCCACCCCCGCCACGTACACCCC
GGTACCAAAATTTTAGTGTAAATTTTAGTATCTCATTATAACTAGGTATTATGAGGTACCAA
ATTTACAATAGAAAAAATAGTACTTCATGGTACTTTCTTAAGTACCGTAAAATTGCTCCTAT
ATTTAAGGGGATGTTTATATCTATCCATATCCATAATTTGATTTTGATAAGAAAAAATGTGA
GCACACCAAGCATGTCCATGACCTTGCACTCTTGGCTCACTCGTCAACTGTGAAGAACCTCA
AAAATGCTCAATATAGCTACAGGTGCCTGAAAAAATAACTTTAAAGTTTTGAACATCGATTT
CACTAAACAACAATTATTATCTCCCTCTGAAAGATGATAGTTTAGAACTCTAGAATCATTGT
CGGCGGAGAAAGTAAATTATTTTCCCCAAATTTCCAGCTATGAAAAAACCCTCACCAAACAC
CTCCTCCTCCCTACGTGTCACCGCTCTCTCCACCTATATATGCCCACCTGGCCCCTCTCCTC
CCATCTCCACTTCACCCGATCGCTTCTTCTTCTTCTTCGTTGCATTCATCTTGCTAGC

SEQ ID NO 144: Artificial sequence prm00735

GGGGACAAGTTTGTACAAAAAAGCAGGCTTCACAATGGATACTCTCTCAGCATCC

SEQ ID NO 145: Artificial sequence prm00736

GGGGACCACTTTGTACAAGAAAGCTGGGTTGTATCATCAAGAAACCCAGA

FIGURE 10 (continued)

| Stimulus | NaCl | Wounding | Flower development | BR |
|---|---|---|---|---|
| Regulator | ? | ? | ? | BRI1 |
| GSK | AtGSK1 | WIG | AtSK11/AtSK12 | BIN2 |
| Substrate | ? | ? | ? | BES1/BZR1 |
| Response | NaCl stress-responsive genes | ? | Gynoecium patterning / Perianth primordia | BR response |
| Experimental evidence | Enhanced salt tolerance by overexpression | Induction of protein kinase activity | Reduction of transcript levels by antisense | Analysis of brassinosteroid mutants |

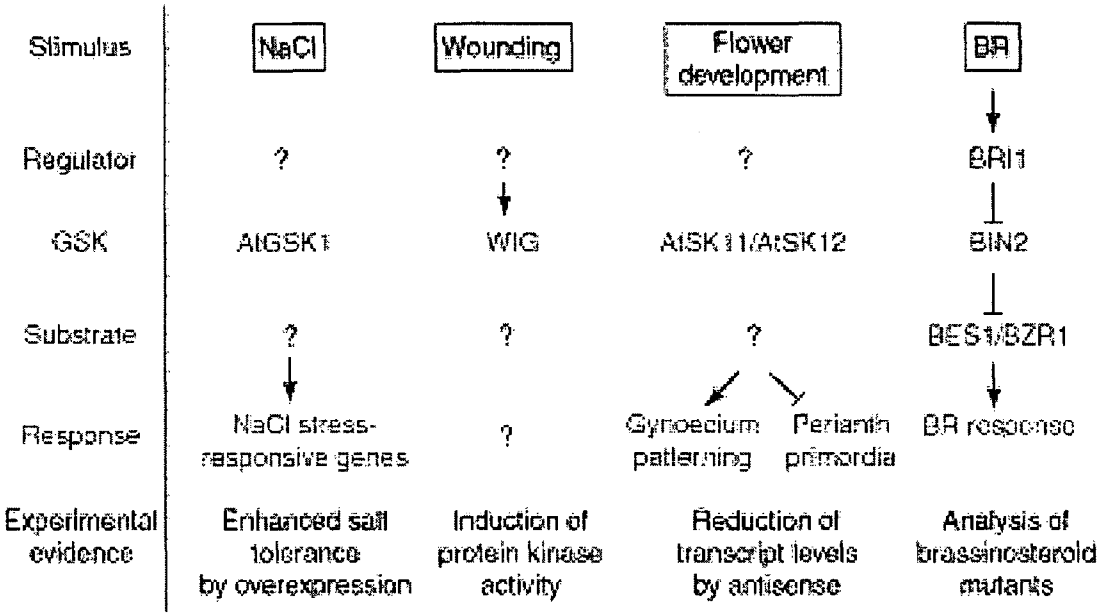

FIGURE 12

```
AY108486        -MASVGVAR-SSLGFQNGTSSSSDPDRLPNELGSMSIRDD---KDVEDI-VVNGNGAEPG 54
AK058276        -MASVGVVR-SSLGFQNETSTSGDADRLPNEMSNMSIRDDN--KDIDDI-VVNGNGTEPG 55
AAM77397.1      -------------------------------MGNMSIRDD---RDPEDI-VVNGNGTEPG 25
BAB40983.1      -MGSVGVAP-SGLKNSSSTS--MGAEKLPDQMHDLKIRDD---KEVEAT-IINGKGTETG 52
AY103545        -MASAGVAP-SGYKNSSSTS--IGAEKLQDHMNELKIRDD---KEVEAT-IINGKGTETG 52
AT5g14640       -MASVGTLPASSMATKQSNAS-ICAEKLPEGINEMKIKDD---KEMEAA-VVDGNGTETG 54
CAA58594.1      -MAS-GIMP--SAGGKHRTDA-MLVDKLPEEINEMKIRDDKAEKEMEAA-VVDGNGTEKG 54
AT5g26750       -MASVGIAPNPGARDSTG------VDKLPEEMNDMKIRDD---KEMEAT-VVDGNGTETG 49
CAA48538.1      -MASVGIAPNPGARDSTG------VDKLPEEMNDMKIRDD---KEMEAT-VVDGNGTETG 49
At3g05840       -MASVGIEPSAAVRESTGN--VTDADRLPEEMKDMKIQDD---KEMEAT-IVNGNVTETG 53
CAA73247.1      -MASVGIEPSAAVRESTGN--VTDADRLPEEMKDMKIQDD---KEMEAT-IVNGNVTETG 53
CAA48474.1      -MASVGVAPTSGFREVLGDGEIGVDDILPEEMSDMKIRDD---REMEAT-VVDGNGTETG 55
CAA54803.1      -MTSVGLAPVSGLRESSSHS--VGVDRLPEEMNDMRIRDD---KEIEAA-IVDGNGTETG 53
CAA48472.1      MMASGGVAPASGFIDKNASS--VGVEKLPEEMNDMKIRDD---KEMEAATIVDGNGTETG 55
CAA48473.1      -MATAGVAPASGIVDVNASSA-IAVDKLPDEILGMRIKDD---KEMEAH-VVDGNSTEAG 54
AK099599        -MTSVGLVDSSSGFPETSTSG--ATDRLTDDISEMSIRDK----EVEAV-VVSGNSMDIG 52
                                               :  : *:*.    : :   ::.*:  : *

AY108486        HIIVTSIDGRNGQAKQTISYMAERVVGHGSFGTVFQAKCLETGETVAIKKVLQDKRYKNR 114
AK058276        HVIVTSIDGRNGQAKQTISYMAERVVGHGSFGTVFQAKCLETGETVAIKKVLQDKRYKNR 115
AAM77397.1      HIIVTSIEGRNGQAKQTISYMAERVVGNGSFGTVFQAKCLETGETVAIKKVLQDKRYKNR 85
BAB40983.1      HIIVTTTGGRNGQPKQTVSYMAERIVGQGSFGIVFQAKCLETGETVAIKKVLQDKRYKNR 112
AY103545        HIIVTTTGGKNGQPKQTVSYMAERIVGQGSFGIVFQAKCLETGETVAIKKVLQDKRYKNR 112
AT5g14640       HIIVTTIGGKNGQPKQTISYMAERIVGQGSFGIVFQAKCLETGETVAIKKVLQDKRYKNR 114
CAA58594.1      HIIVTTIGGKNGEPKQTISYMAERVVGQGSFGIVFQAKCLETGETVAIKKVLQDKRYKNR 114
AT5g26750       HIIVTTIGGRNGQPKQTISYMAERVVGHGSFGVVFQAKCLETGETVAIKKVLQDRRYKNR 109
CAA48538.1      HIIVTTIGGRNGQPKQTISYMAERVVGHGSFGVVFQAKCLETGETVAIKKVLQDRRYKNR 109
At3g05840       HIIVTTIGGRNGQPKQTISYMAERVVGHGSFGVVFQAKCLETGETVAIKKVLQDRRYKNR 113
CAA73247.1      HIIVTTIGGRNGQPKQTISYMAERVVGHGSFGVVFQAKCLETGETVAIKKVLQDRRYKNR 113
CAA48474.1      HIIVTTIGGRNGQPKQTISYMAERVVGHGSFGVVFQAKCLETGETVAIKKVLQDKRYKNR 115
CAA54803.1      HIIVTTIGGRHGQPKQTISYMAERIVGQGSFGVVFQAKCLETGETVAIKKVLQDKRYKNR 113
CAA48472.1      HIIVTTIGGKNGQPKQTISYMAERVVGHGSFGVVFQAKCLETGETVAIKKVLQDKRYKNR 115
CAA48473.1      HVIVTTIGGKNGQPKQTISYMAERAVGQGSFGVVFQAKCLETGETVAIKKVLQDKRYKNR 114
AK099599        HTIVTTVGGRNGQPKQTISYIAERAVGRGSFGVVFQAKCLETGERVAVKKVLQDARYKNR 112
                * ***:  *::*:.***:**:*** **.**** *********** **:****** *****

AY108486        ELQTMRVLDHPNVVALKHCFFSKTEKEELYLNLVLEYVPETAHRVIKHYNKMNQRMPLIY 174
AK058276        ELQTMRVLDHPNVVSLKHCFFSKTEKEELYLNLVLEYVPETAHRVIKHYNKMNQRMPLIY 175
AAM77397.1      ELQTMRVLDHPNVVALKHCFFSKTEKEELYLNLVLEYVPETAHRVIKHYNKMNQRMPLIY 145
BAB40983.1      ELQTMRLLDHPNVVALKHCFFSTTEKDELYLNLVLEYVPETVHRVVKHYNKMNQRMPLIY 172
AY103545        ELQTMRLLDHPNVVALKHCFFSTTEKDELYLNLVLEYVPETVHRVVKHHNKMHQRMPLIY 172
AT5g14640       ELQTMRLLDHPNVVSLKHCFFSTTEKDELYLNLVLEYVPETVYRVSKHYSRANQRMPIIY 174
CAA58594.1      ELQTIRLLDHPNVVALRHCFFSTTEKDELYLNLVLEYVPETVYRVLRHYSKANQQMPMIY 174
AT5g26750       ELQTMRLLDHPNVVSLKHCFFSTTEKDELYLNLVLEYVPETVHRVIKHYNKLNQRMPLIY 169
CAA48538.1      ELQTMRLLDHPNVVSLKHCFFSTTEKDELYLNLVLEYVPETVHRVIKHYNKLNQRMPLIY 169
At3g05840       ELQTMRLLDHPNVVSLKHCFFSTTEKDELYLNLVLEYVPETVHRVIKHYNKLNQRMPLVY 173
CAA73247.1      ELQTMRLLDHPNVVSLKHCFFSTTEKDELYLNLVLEYVPETVHRVIKHYNKLNQRMPLVY 173
CAA48474.1      ELQTMRLLDHPNVVSLKHCFFSTTEKDELYLNLVLEYVPETVHRVIKHYSKLNQRMPMIY 175
CAA54803.1      ELQTMRLLDHPNVVCLKHCFFSTTEKDEVYLNLVLEYVPETVHRVIKHYNKLNQRMPLIL 173
CAA48472.1      ELQTMRLLDHPNVVSLKHCFFSTTEKDELYLNLVLEYVPETVSRVIRHYNKMNQRMPMIY 175
CAA48473.1      ELQTMRLLDHPNVVTLKHCFFSTTEKDELYLNLVLEFVPETVHRVIRHYSKMNQRMPLIY 174
AK099599        ELQTMQVLDHPNVACLKHYFCSTTAKEELYLNLVLEYVPETVHRVIRHYNKMSQRMPLIY 172
                ****:::******. *:* * *.* *:*:*******:****. ** :*:.:  *:**::
```

FIGURE 14

```
AY108486        AKLYMYQICRALAYIHNSIGVCHRDIKPQNLLVNPHTHQLKLCDFGSAKVLVKGEPNISY 234
AK058276        AKLYMYQICRALAYIHNTIGVCHRDIKPQNLLVNPHTHQLKLCDFGSAKVLVKGEPNISY 235
AAM77397.1      AKLYMYQICRSLAYIHNSIGVCHRDIKPQNLLVNPHTHQLKLCDFGSAKVLVKGEPNISY 205
BAB40983.1      VKLYMYQICRALAYIHNSIGVCHRDIKPQNLLVNPHTHQLKLCDFGSAKVLVKGEPNISY 232
AY103545        VKLYMYQICRALAYIHGTIGVCHRDIKPQNLLVNPHTHQLKICDFGSAKVLVKGEPNISY 232
AT5g14640       VKLYTYQICRALAYIHGGVGVCHRDIKPQNLLVNPHTHQVKLCDFGSAKVLVKGEPNISY 234
CAA58594.1      VKLYTYQIFRALAYIHG-IGVCHRDIKPQNLLVNPHTHQLKLCDFGSAKVLVKGEPNISY 233
AT5g26750       VKLYTYQIFRALSYIHRCIGVCHRDIKPQNLLVNPHTHQVKLCDFGSAKVLVKGEPNISY 229
CAA48538.1      VKLYTYQIFRALSYIHRCIGVCHRDIKPQNLLVNPHTHQVKLCDFGSAKVLVKGEPNISY 229
At3g05840       VKLYTYQIFRSLSYIHRCIGVCHRDIKPQNLLVNPHTHQVKLCDFGSAKVLVKGEPNISY 233
CAA73247.1      VKLYTYQIFRSLSYIHRCIGVCHRDIKPQNLLVNPHTHQVKLCDFGSAKVLVKGEPNISY 233
CAA48474.1      VKLYTYQIFRALSYIHRCIGVCHRDIKPQNLLVNPHTHQVKLCDFGSAKVLVKGEPNISY 235
CAA54803.1      VKLYTYQIFRALSYIHHTIGVCHRDIKPQNLLVNPHTHQVKLCDFGSAKVLVKGEPNISY 233
CAA48472.1      VKLYSYQICRALAYIHNSIGVCHRDIKPQNLLVNPHTHQLKICDFGSAKVLVKGEPNISY 235
CAA48473.1      VKLYSYQICRSLAYIHNCVGVSHRDIKPQNLLVNPHTHQLKLCDFGSAKVLVKGEPNISY 234
AK099599        VKLYMYQICRALAYIHNCVGVCHRDIKPQNILVNPHNHQLKLCDFGSAKVLVKGEPNISY 232
                .*** *** *:*:***  :**.********:*****.**:*:******************

AY108486        ICSRYYRAPELIFGATEYTTAIDVWSAGCVLAELLLGQPLFPGESGVDQLVEIIKVLGTP 294
AK058276        ICSRYYRAPELIFGATEYTTAIDVWSAGCVLAELLLGQPLFPGDSGVDQLVEIIKVLGTP 295
AAM77397.1      ICSRYYRAPELIFGATEYTTAIDVWSAGCVLAELLLGQPIFPGDSGVDQLVEIIKVLGTP 265
BAB40983.1      ICSRYYRAPELIFGATEYTTAIDIWSAGCVLAELMLGQPLFPGESGVDQLVEIIKVLGTP 292
AY103545        ICSRYYRAPELIFGATEYTTAIDIWSAGCVLAELMLGQPLFPGESGVDQLVEIIKVLGTP 292
AT5g14640       ICSRYYRAPELIFGATEYTTTIDIWSAGCVLAELLLGQPLFPGESGVDQLVEIIKVLGTP 294
CAA58594.1      ICSRYYRAPELIFGATEYTFAIDIWSVGCVLAELLLGQPLFPGESGVDQLVEIIKVLGTP 293
AT5g26750       ICSRYYRAPELIFGATEYTTAIDVWSAGCVLAELLLGQPLFPGESGVDQLVEIIKVLGTP 289
CAA48538.1      ICSRYYRAPELIFGATEYTTAIDVWSAGCVLAELLLGQPLFPGESGVDQLVHIIKVLGTP 289
At3g05840       ICSRYYRAPELIFGATEYTTAIDVWSAGCVLAELLLGQPLFPGESGVDQLVEIIKVLGTP 293
CAA73247.1      ICSRYYRAPELIFGATEYTTAIDVWSAGCVLAELLLGQPLFPGESGVDQLVEIIKVLGTP 293
CAA48474.1      ICSRYYRAPELIFGATEYTTAIDVWSVGCVLAELLLGQPLFPGERGVDQLVEIIKVLGTP 295
CAA54803.1      ICSRYYRAPELIFGATEYTTAIDIWSAGCVLAELLLGQPLFPGESGVDQLVEIIKVLGTP 293
CAA48472.1      ICSRYYRAPELIFGATEYTTAIDIWSAGCVLGELLLGQPLFPGESGVDQLVEIIKVLGTP 295
CAA48473.1      ICSRYYRAPELIFGATEYTSAIDIWSAGCVLGELLLGQPLFPGASGVDQLVEIIKVLGTP 294
AK099599        ICSRYYRAPALIFGATEYTTAIDVWSAGCVLAELLLGQPVFPGDSGVDQLVEIIKVLGTP 292
                ********* ********* :**:**.****.**:****:***  ******.********

AY108486        TREEIKCMNPNYTEFKFPQIKAHPWHKIFHKRMPAEAVDLVSRLLQYSPKLRSTALEALV 354
AK058276        TREEIKCMNPNYTEFKFPQIKAHPWHKIFHKRMPAEAVDLVSRLLQYSPYLRSTASEALI 355
AAM77397.1      TREEIKCMNPNYTEFKFPQIKAHPWHKIFHKRMPAEAVDLVSRLLQYSPSLRSTALEALI 325
BAB40983.1      TREEIKCMNPNYTEFKFPQIKAHPWHKVFHKRLPPEAVDLVSRLLQYSPNLRCTAVEALV 352
AY103545        TREEIKCMNPNYTEFKFPQIKAHPWHKVFHKRMPPEAVDLVSRLLQYSPNLRCTAMEALV 352
AT5g14640       TREEIKCMNPNYTEFKFPQIKAHPWHKIFHKRTPPEAVDLVSRLLQYSPNLRSTAMEAIV 354
CAA58594.1      TREEIKSMNPNYTEFKFPQIKAHPWHKIFHKRMPPEAVDLVSRLLQYSPNLRSTALEACT 353
AT5g26750       TREEIKCMNPNYTEFKFPQIKAHPWHKIFHKRMPPEAVDLVSRLLQYSPNLRSAALDTLV 349
CAA48538.1      TREEIKCMNPNYTEFKFPQIKAHPWHKIFHKRMPPEAVDLVSRLLQYSPNLRSAALDTLV 349
At3g05840       TREEIKCMNPNYTEFKFPQIKAHPWHKIFHKRMPPEAVDLVSRLLQYSPNLRCAALDSLV 353
CAA73247.1      TREEIKCMNPNYTEFKFPQIKAHPWHKIFHKRMPPEAVDLVSRLLQYSPNLRCAALDSLV 353
CAA48474.1      TREEIKCMNPNYTEFKFPQIKAHPWHKIFHKRMPAEAVDLVSRLLQYSPNLRCQALDCLT 355
CAA54803.1      TREEIKCMNPNYNEFKFPQIKAHPWHKIFHKRMPPEAVDLVSRLLQYSPNLRCTALEAVT 353
CAA48472.1      TREEIKCMNPNYTEFKFPQIKAHPWHKIFHKRMPPEAVDLVSRLLQYSPNLRSTALEALV 355
CAA48473.1      TREEIKCMNPNYTEFKFPQIKAHPWHKIFRKRMPPEAVDLVSRLLQYSPNLRSTALEALV 354
AK099599        TREEIKHMNPNYTEFKFPQIKAHPWHKIFHKRMPSEAVDLVSRLLQYSPHLRCSALEVLI 352
                ****** *****.**************:*:** *.************** **. * :
```

FIGURE 14 (continued)

```
                                                                                         SEQ
                                                                                        ID NO

AY108486      HPFFDELRDPNTRLPNGRFLPPLFNFKPHELKNVPADFMVKLVPEHARKQCAFVGW- 410    165
AK058276      HPFFDELRDPNTRLPNGRFLPPLFNFKPHELKGMPMEFLVKLIPEHARKQCAFVGW- 411    149
AAM77397.1    HPFFDELRDPNTRLPNGRFLPPLFNFKPHELKGVPMDILVKLIPEHARKNCAFVGW- 381    175
BAB40983.1    HPFFDELRDPNARLPNGRFLPPLFNFKPHELKGIPSDIMAKLIPEHVKKQCSYAGV- 408    147
AY103545      HPFFDELRDPNTRLPNGRFLPPLFNFKPHELKGVPSDIVAKLVPEHAKKQCSYVGL- 408    163
AT5g14640     HPFFDELRDPNTRLPNGRALPPLFNFKPQELKGASLELLSKLIPDHARKQCSFLAL- 410    159
CAA58594.1    HTFFDELRDPKTRLPNGRPLPPLFNFRPQELKGASADLLNKLIPEHAKKQCTFLGV- 409    177
AT5g26750     HPFFDELRDPNARLPNGRFLPPLFNFKPHELKGVPLEMVAKLVPEHARKQCPWLGL- 405    153
CAA48538.1    HPFFDELRDPNARLPNGRFLPPAFHFKPHELKGVPLEMVAKLVPEHARKQCPWLGL- 405    157
At3g05840     HPFFDELRDPNARLPNGRFLPPLFNFKPHELKGVPVEMVAKLVPEHARKQCPWLSL- 409    155
CAA73247.1    HPFFDELRDPNARLPNGRFLPPLFNFKPHELKGVPVEMVAKLVPEHARKQCPWLSL- 409    160
CAA48474.1    HPFFDELRDPNARLPTGRFLPPLFNFKPHELKGVPVETLMKLVPEHARKQCPFLGL- 411    169
CAA54803.1    HAFFDELRDPNTRLPNGRVLPPLFNFKAHELKGVSAENLLKLVPEHARKQCPSLGL- 409    173
CAA48472.1    HPFYDDVRDPNTRLPNGRFLPPLFNFKVNELKGVPAEMLVKLVPPHARKQCALFGSS 412    167
CAA48473.1    HPFFDELRDPNTRLPNGRHLPPLFNFKANELKGVPAEMLVKLVPSHARKQCSLFASS 411    171
AK099599      HPFFDELRDPNARLPNGRTLPPLFNFKPRELKGASMEFLVKLVPQHAKKQCAFLGL- 408    151
              *.*:*::***::***.** *** *:*: .***. . : : **:* *.:*:*.  .
```

FIGURE 14 (continued)

**SEQ ID NO 146 - *Oryza sativa* DNA sequence**

CAAAAGCAAGAGGAGGAGGCCGCGGCTAGCGAGCGAGCGAGAGAGAGGGGAGAAGAAGAGGT
GGGACAGCCGGGAGATCCATCCCTGTGGAGAGGAGGGAGGGAGGAAGGAGGCGTTGGAGGAG
GAGAGGTTGACCGATAGATCCATTGCGGAGTTGAGTGTTGATGCAAAGCTGATTCGCCATCG
TTTAGCTTTTTATAAGAGATGGGTTCAGTAGGGGTTGCGCCGTCTGGGTTAAAGAACAGCAG
TAGCACCAGCATGGGTGCTGAGAAGTTGCCTGATCAGATGCATGATCTGAAGATAAGGGACG
ATAAGGAAGTTGAAGCGACTATTATTAACGGCAAGGGAACAGAAACCGGCCACATAATTGTC
ACAACTACTGGTGGCAGAAATGGTCAGCCGAAACAGACAGTTAGCTACATGGCTGAGCGTAT
TGTAGGGCAAGGTTCATTTGGGATTGTCTTCCAGGCAAAATGTCTGGAGACAGGTGAGACAG
TTGCTATCAAGAAGGTTCTTCAGGATAAGCGCTACAAGAACCGTGAGCTTCAGACCATGCGC
CTTCTTGACCACCCAAATGTTGTAGCTCTGAAGCACTGTTTCTTCTCTACAACTGAGAAGGA
TGAACTGTATCTAAACTTGGTTCTTGAGTATGTGCCTGAAACTGTTCATCGTGTTGTGAAGC
ATTACAACAAGATGAACCAGCGTATGCCACTTATCTATGTGAAGCTGTATATGTACCAGATT
TGTAGGGCATTAGCTTACATCCATAATAGCATCGGAGTTTGCCACAGAGATATCAAGCCACA
GAATCTTCTGGTAAACCCACATACCCATCAACTCAAGCTATGTGACTTTGGGAGTGCAAAAG
TTCTGGTCAAGGGAGAACCGAACATATCGTACATTTGCTCCCGATACTATAGGGCTCCGGAG
CTCATATTTGGTGCCACCGAATACACTACAGCTATTGACATCTGGTCTGCTGGATGTGTTCT
TGCTGAACTTATGTTAGGGCAGCCTCTGTTTCCTGGTGAAAGTGGTGTAGACCAACTTGTGG
AAATCATCAAGGTCCTTGGAACACCTACAAGGGAGGAAATTAAATGCATGAATCCAAACTAT
ACCGAGTTCAAGTTTCCACAGATTAAAGCACACCCATGGCACAAGGTATTCCATAAAAGGTT
GCCTCCAGAAGCTGTTGATCTTGTCTCTAGGCTGCTCCAGTACTCACCCAACCTAAGATGCA
CTGCTGTGGAAGCACTTGTTCACCCATTCTTTGATGAGCTTCGAGACCCTAATGCTCGCCTT
CCGAATGGCCGCTTTTTGCCTCCTCTCTTCAACTTCAAGCCTCATGAACTGAAAGGAATCCC
ATCAGATATTATGGCGAAATTGATCCCAGAACATGTGAAGAAGCAATGCTCCTATGCAGGAG
TATGAGACAGCTTCCGCACGACCCCCCTGGAAATTTCCATGACAAGTGCCCATTTCCTCCCC
CCTGGACGACGATGGATCGTCAGCATATGCGTGCATGATGGTTGGTGAGGATGTGAAGTTAC
GTTGTTGTTGTGTGACCACCTAGAGCTTGAACAGAAGGAAAA

**SEQ ID NO 147 - *Oryza sativa* - protein sequence**

MGSVGVAPSGLKNSSSTSMGAEKLPDQMHDLKIRDDKEVEATIINGKGTETGHIIVTTTGGR
NGQPKQTVSYMAERIVGQGSFGIVFQAKCLETGETVAIKKVLQDKRYKNRELQTMRLLDHPN
VVALKHCFFSTTEKDELYLNLVLEYVPETVHRVVKHYNKMNQRMPLIYVKLYMYQICRALAY
IHNSIGVCHRDIKPQNLLVNPHTHQLKLCDFGSAKVLVKGEPNISYICSRYYRAPELIFGAT
EYTTAIDIWSAGCVLAELMLGQPLFPGESGVDQLVEIIKVLGTPTREEIKCMNPNYTEFKFP
QIKAHPWHKVFHKRLPPEAVDLVSRLLQYSPNLRCTAVEALVHPFFDELRDPNARLPNGRFL
PPLFNFKPHELKGIPSDIMAKLIPEHVKKQCSYAGV

FIGURE 16

**SEQ ID NO 148 - *Oryza sativa* - AK058276 DNA sequence**

CTCTCCGAATCCTCCCCCGCATTCCGCGCCGGAGCTGAGGAGGGACAGCGAGCCAGCGAGGG
AGGTGGGGCAATCCAGCGAGCGCCAGATCGTGCCGCCAGCCCCGCTCCGTCCTCTCTCCGGC
GACCCTCCGCCCCGCCTGATCCCGTGGTGGATCAACTACAACTCATCTTTAGGAAAGCCTCT
TGAACATTAGCCTTGTGTGCCTTTCAACAGTATGGCCTCGGTAGGTGTGGTGCGTTCTTCCT
TGGGGTTTCAGAACGAAACAAGTACAAGTGGCGATGCCGACCGACTTCCGAATGAGATGAGC
AATATGAGTATAAGGGATGATAATAAGGACATTGACGACATAGTTGTCAATGGCAATGGGAC
AGAACCTGGTCATGTTATTGTGACAAGCATTGATGGAAGAAATGGACAGGCTAAACAGACCA
TTAGCTACATGGCCGAGCGTGTCGTAGGTCATGGATCCTTTGGAACTGTTTTCCAGGCCAAG
TGCCTGGAAACCGGTGAGACTGTGGCTATAAAGAAGGTTCTTCAAGACAAGAGATATAAGAA
CCGTGAGCTGCAAACAATGCGAGTTCTTGACCACCCAAATGTGGTGTCACTAAAGCATTGTT
TTTTCTCAAAGACTGAGAAGGAGGAGCTTTACCTCAATTTGGTGCTTGAGTATGTGCCAGAG
ACTGCTCACCGTGTAATTAAACATTACAACAAGATGAACCAACGCATGCCATTGATATATGC
AAAACTATACATGTATCAGATATGCAGAGCTTTGGCGTACATTCACAACACCATTGGCGTGT
GTCACAGGGATATCAAGCCACAAAATCTTCTGGTGAACCCACATACTCATCAGCTGAAATTA
TGTGACTTCGGCAGCGCGAAAGTCTTGGTAAAAGGAGAACCAAATATTTCTTACATCTGTTC
AAGGTACTACAGAGCTCCAGAGCTCATATTTGGTGCTACTGAATACACAACAGCGATTGATG
TTTGGTCTGCCGGTTGTGTGCTTGCTGAACTCCTCCTGGGGCAGCCTCTATTCCCTGGCGAC
AGTGGCGTTGATCAGCTTGTTGAAATCATCAAGGTTCTGGGTACCCCTACACGAGAGGAGAT
TAAGTGCATGAACCCAAATTACACCGAGTTTAAATTTCCGCAAATCAAAGCTCACCCATGGC
ACAAGATCTTCCATAAAAGAATGCCTGCTGAAGCAGTCGATCTCGTCTCCAGGCTTTTGCAG
TATTCACCATACCTCCGGTCCACTGCTTCGGAAGCATTGATCCATCCCTTCTTCGATGAACT
CCGTGATCCAAACACCCGCTTACCGAACGGCCGTTTCCTTCCTCCTCTCTTCAACTTCAAGC
CCCATGAACTGAAGGGTATGCCAATGGAATTCCTGGTGAAGCTTATCCCCGAACATGCTCGA
AAGCAATGCGCGTTTGTAGGATGGTGATTTCTGAGGTCAGCATGAAAACTAGTTCAGAATTT
CTTCACCGTCCTCCATTAGAAAGCAGAGATGAACCCTGTGTGCAGCCATTTGGGAAAGCTGG
TGCATATGGAAGTGGAACTACATTTTTTTGTCCGAGATTCTGACGCCGCGTATTCTTTTCCC
CCCTCCCACTTTGCTGCTGCCGGTGTAACCAAAAAATCATCCACGGTTCTGTAAAGTTGATG
AAGAAGAGTGTAAAATCAGGTTGAAAACTGAATTCGATCGGTTTGTCAAGATTGTAGCAACA
TGCAAGGAAGGATGTTGCACACTTTGTATGGCAATGTTCGTTCGGTCCAAATATTTGGACAT
GG

**SEQ ID NO 149 - *Oryza sativa* - AK058276 protein sequence**

MASVGVVRSSLGFQNETSTSGDADRLPNEMSNMSIRDDNKDIDDIVVNGNGTEPGHVIVTSI
DGRNGQAKQTISYMAERVVGHGSFGTVFQAKCLETGETVAIKKVLQDKRYKNRELQTMRVLD
HPNVVSLKHCFFSKTEKEELYLNLVLEYVPETAHRVIKHYNKMNQRMPLIYAKLYMYQICRA
LAYIHNTIGVCHRDIKPQNLLVNPHTHQLKLCDFGSAKVLVKGEPNISYICSRYYRAPELIF
GATEYTTAIDVWSAGCVLAELLLGQPLFPGDSGVDQLVEIIKVLGTPTREEIKCMNPNYTEF
KFPQIKAHPWHKIFHKRMPAEAVDLVSRLLQYSPYLRSTASEALIHPFFDELRDPNTRLPNG
RFLPPLFNFKPHELKGMPMEFLVKLIPEHARKQCAFVGW

FIGURE 16 (continued)

**SEQ ID NO 150 - *Oryza sativa* - AK099599 DNA sequence**

TTGGGGCGGAGAGACGGGAGAGAGAGGAGAGGAGTCGAACTAGGGTTAGTGAGGTGAAGGGG
GGCGATTTTGCTCATCGCCCTCCGCCTAGATCGAATCCGAATCCCGCCTCCTCCTCCTCCTC
CTCCTCCCCCCGCGCCGATCTTGCCCCGCTCCCTCGCCGCAGCTGCGGGCTTGCCCTAGCCC
GCCGCATCGCCGACGTACTACGCCCGCTCGGCTCCAGGCTCCAGATCCGGCCTCCAGGGCGT
GCCCGCTGCTGGACGGCGCTCTCCCGCGTCCGTGGCTACCTCCTCCTCCGGGTTTGCGTTGC
CGTCGCCGAAGCGATCCGTTGGTGGATTGTGTGTAGCTCTGTAACAAAGGATCTTGGTCCAT
AGGAGTGAACCAGAAGGTACAAAACTTCTTGGCTATTATGACATCGGTGGGTCTAGTAGATT
CTTCATCAGGTTTCCCGGAAACGAGTACTAGTGGAGCCACTGATCGTCTGACAGATGATATC
AGCGAGATGAGCATAAGAGATAAGGAAGTTGAAGCTGTAGTGGTCAGTGGCAATAGTATGGA
CATAGGTCACACTATTGTGACAACTGTTGGTGGAAGAAATGGGCAGCCAAAGCAGACAATTA
GTTACATCGCAGAGCGTGCTGTTGGGCGTGGTTCATTTGGAGTTGTCTTCCAGGCTAAGTGT
CTAGAAACTGGTGAGAGAGTTGCTGTAAAGAAAGTTCTTCAAGATGCGAGATACAAGAACCG
GGAGCTGCAAACGATGCAAGTTCTCGATCACCCAAATGTTGCATGCTTGAAGCATTACTTTT
GCTCGACTACTGCGAAGGAGGAGCTATACCTCAACTTGGTTCTTGAATATGTGCCAGAAACT
GTTCATCGTGTTATTAGACATTACAATAAGATGAGCCAACGCATGCCATTGATTTATGTTAA
ACTTTATATGTACCAGATTTGTAGGGCTTTGGCATACATTCATAACTGTGTGGGAGTATGCC
ACAGAGATATAAAGCCACAGAATATATTGGTGAATCCACATAATCATCAGTTGAAATTGTGT
GACTTTGGCAGTGCAAAAGTCCTGGTGAAAGGGGAACCAAATATTTCATATATCTGTTCTAG
ATACTACAGAGCCCCAGCACTCATATTTGGGGCTACAGAGTACACGACAGCTATTGATGTGT
GGTCTGCTGGCTGTGTTCTTGCTGAACTACTTCTAGGGCAGCCTGTTTTTCCTGGTGACAGT
GGCGTCGACCAACTTGTTGAAATTATCAAGGTACTGGGTACTCCAACAAGGGAAGAAATCAA
ACATATGAATCCGAACTACACTGAGTTTAAGTTCCCCCAAATCAAAGCTCACCCATGGCACA
AGATCTTTCATAAAAGAATGCCATCTGAAGCTGTAGATCTTGTGTCTCGGCTTCTGCAGTAC
TCACCACACCTCCGGTGCAGTGCATTGGAGGTGTTAATTCATCCATTCTTCGATGAACTACG
AGATCCAAATGCTCGCTTACCAAATGGCCGTACTCTTCCCCCACTATTCAATTTCAAGCCTC
GTGAGCTGAAAGGAGCATCAATGGAATTTCTTGTGAAGTTGGTTCCACAGCATGCTAAGAAG
CAATGTGCCTTCTTAGGATTATGAGCAGACAGTTCATACACTAATCGGGTATTACGTTGGTC
TACTTGGTTCCGTAGAACAGCATGGCCTGCAGTATTATTGAATGGGCCCTAATTTTGTTCTA
CGTGCACCCTGCTTGGGCATGCCTTCTACCATCATATTCTGTAAAGCAGATGAAGACATGGA
GTGAGTGGTTATTGATTGGGGCTTGTATATTGGTCTGCCCTTGACTTGAGAACTTTATTCAC
TCTGCTGTATCAAGCAAGAAAGAACACGTATGTATGCTTGAGCCATATTTCATTCCAGAGCC
TCTATCAGGTTTCACCGACCATCAGATTTAAGTCTTCCAGTTTGTAGGGCTAAGCCAAAAAA
GTTCTATGTGTGAAGAGTTGGAGACATCTGTTTGGTTACAAGCTATTTGATTGTATTTGATC
ATTCTTTTGTATTAACACTCTGATAAACTTACATGAGTTAATTCTATTGTTATGTGATATAG
TTGTGTGCCACTTTTAAACACCTAAACAACTCTGTTCAATGTTGAAATGTTTGGCATGTATC
AACATATCACCTCATTATTTCGAGGTTGATTTTGTACACCTGATATCTGTTAGCTTGAATGC
TTGATTACAAGCAAATGATTAAATATTTT

FIGURE 16 (continued)

**SEQ ID NO 151 - *Oryza sativa* - AK099599 protein sequence**

MTSVGLVDSSSGFPETSTSGATDRLTDDISEMSIRDKEVEAVVVSGNSMDIGHTIVTTVGGR
NGQPKQTISYIAERAVGRGSFGVVFQAKCLETGERVAVKKVLQDARYKNRELQTMQVLDHPN
VACLKHYFCSTTAKEELYLNLVLEYVPETVHRVIRHYNKMSQRMPLIYVKLYMYQICRALAY
IHNCVGVCHRDIKPQNILVNPHNHQLKLCDFGSAKVLVKGEPNISYICSRYYRAPALIFGAT
EYTTAIDVWSAGCVLAELLLGQPVFPGDSGVDQLVEIIKVLGTPTREEIKHMNPNYTEFKFP
QIKAHPWHKIFHKRMPSEAVDLVSRLLQYSPHLRCSALEVLIHPFFDELRDPNARLPNGRTL
PPLFNFKPRELKGASMEFLVKLVPQHAKKQCAFLGL

**SEQ ID NO 152 - *Arabidopsis thaliana* - AF428327 - SHAGGY alpha**

ACAAAATAATATAAAGTAAAAATATTTCATAATTCGTCTCTCACCGGAAAAATAAATAAAGT
TAGAGAGAGAGATTCATAATCATCAAACCCACAAATCCTTTTTTTTTTTTTTGTTAAAACC
CACAAATCCTTACTCGTACGGATCTCTCTCTCTTTAATATCCTAATTCTTCTCTTCATCGAT
CTGAGATTTTTACGTTTTCATCGGCTTGAAAGTTTGAAGAGTTTTGTAGCCTGAAAAATGGC
GTCAGTGGGTATAGCTCCTAATCCTGGAGCAAGAGACTCTACTGGTGTTGATAAATTGCCTG
AAGAAATGAATGACATGAAAATTCGTGACGATAAAGAAATGGAAGCGACAGTGGTAGATGGA
AATGGAACAGAGACTGGACATATCATTGTGACTACTATTGGTGGTAGAAATGGCCAACCAAA
ACAGACAATTAGCTACATGGCTGAGCGTGTTGTTGGTCACGGATCTTTTGGTGTTGTGTTCC
AAGCGAAATGTCTTGAGACAGGAGAAACTGTTGCGATAAAGAAAGTTTTACAAGATAGGAGG
TACAAGAACCGTGAGCTTCAAACCATGAGGCTACTTGACCATCCTAATGTTGTGTCTCTGAA
ACATTGTTTCTTCTCAACCACTGAAAAAGATGAGCTTTACCTCAATCTTGTTCTTGAGTACG
TTCCAGAAACTGTTCATCGTGTTATCAAACACTACAACAAACTGAATCAGAGAATGCCTCTT
ATATACGTCAAACTTTACACTTATCAGATTTTTAGAGCCTTATCTTACATTCACCGATGCAT
TGGTGTGTGTCATCGTGACATAAAACCTCAAAACTTGTTGGTAAATCCGCACACTCATCAAG
TAAAGCTATGTGATTTTGGAAGTGCAAAAGTATTGGTAAAAGGAGAACCAAACATTTCCTAC
ATCTGCTCGAGGTATTACAGAGCACCTGAACTTATTTTTGGAGCAACCGAGTATACGACAGC
CATTGATGTCTGGTCTGCAGGATGTGTTCTAGCTGAACTATTGCTTGGACAGCCCTTGTTCC
CTGGTGAGAGCGGTGTTGATCAACTTGTAGAGATTATCAAGGTCTTGGGAACGCCTACTAGA
GAAGAAATCAAGTGCATGAACCCAAACTACACGGAATTCAAATTCCCTCAGATTAAAGCTCA
TCCATGGCACAAGATTTTCCACAAACGCATGCCTCCAGAAGCTGTTGATTTGGTCTCAAGAC
TTCTTCAATACTCTCCTAATCTACGAAGTGCCGCTCTCGACACATTAGTCCACCCATTCTTT
GATGAGTTAAGAGACCCAAACGCACGTCTACCTAATGGACGTTTCCTTCCACCGCTTTTCAA
CTTCAAGCCTCACGAGCTGAAAGGTGTACCATTGGAGATGGTAGCTAAGTTAGTACCTGAGC
ATGCAAGGAAGCAGTGTCCTTGGCTCGGTTTGTGATTTCCTCTTAATGTAGCATGAACACAA
CAAACACTTCTTATAAATTACCTCTCTATGTATCAATATGTCACAAACTGATATGCACCCTT
TGTTTGTTGTATGAGTAGAGAAAAAAAGAGTTATTACTATGGTTGGTTGGTTCATAATGTAA
AAGCCCACCAAGATTTTTATC

FIGURE 16 (continued)

**SEQ ID NO 153 - *Arabidopsis thaliana* - At5g26750 - SHAGGY alpha**

MASVGIAPNPGARDSTGVDKLPEEMNDMKIRDDKEMEATVVDGNGTETGHIIVTTIGGRNGQ
PKQTISYMAERVVGHGSFGVVFQAKCLETGETVAIKKVLQDRRYKNRELQTMRLLDHPNVVS
LKHCFFSTTEKDELYLNLVLEYVPETVHRVIKHYNKLNQRMPLIYVKLYTYQIFRALSYIHR
CIGVCHRDIKPQNLLVNPHTHQVKLCDFGSAKVLVKGEPNISYICSRYYRAPELIFGATEYT
TAIDVWSAGCVLAELLLGQPLFPGESGVDQLVEIIKVLGTPTREEIKCMNPNYTEFKFPQIK
AHPWHKIFHKRMPPEAVDLVSRLLQYSPNLRSAALDTLVHPFFDELRDPNARLPNGRFLPPL
FNFKPHELKGVPLEMVAKLVPEHARKQCPWLGL

**SEQ ID NO 154 - *Arabidopsis thaliana* - NM_180189 - ASK-gamma**

CAGACCAACAACAAAAAGGAGATAAAGAGAAGAGGATTCATCATCATCAATCAATCCTTCAT
TTTATGGATCTACTCATATCTTGATTCTTCCTTCTATCTCTCCCTTTTCTTCCATCTCTTTT
TCTCTGGGTTTCCCCGATTTGAAGAGCGTGACAAAGGAAGAATCTTTTATTAAAACAAATTC
TTCTGTTTTAATCTTGGGATGGCCTCGGTGGGCATAGAGCCTAGTGCCGCGGTTAGAGAATC
TACTGGAAACGTTACTGATGCTGATAGATTACCCGAGGAGATGAAGGACATGAAAATTCAAG
ATGATAAAGAAATGGAAGCTACGATTGTTAATGGCAATGTGACTGAGACTGGCCATATAATA
GTAACTACTATAGGAGGAAGAAATGGCCAGCCAAAACAGACAATCAGTTACATGGCGGAGCG
AGTTGTTGGACATGGCTCCTTTGGTGTTGTGTTTCAGGCCAAATGTTTAGAAACAGGAGAAA
CTGTTGCTATAAAGAAAGTTCTACAAGATCGGAGGTACAAGAATCGTGAGCTTCAAACAATG
AGGCTACTTGACCATCCAAATGTTGTGTCTTTGAAACATTGTTTCTTCTCTACAACCGAAAA
AGATGAGCTTTATCTCAACTTGGTTCTGGAATACGTTCCGGAAACTGTGCACCGCGTCATCA
AACACTACAACAAACTTAACCAACGAATGCCTCTCGTTTACGTCAAACTTTACACTTATCAG
ATTTTTAGGTCCTTATCCTACATTCACCGATGTATCGGCGTATGTCATCGAGACATCAAACC
TCAAAACTTGTTGGTAAATCCACACACTCATCAAGTGAAACTATGCGATTTTGGAAGTGCGA
AAGTATTGGTTAAAGGAGAGCCAAACATTTCATACATTTGCTCGAGGTATTACAGAGCACCT
GAGCTCATTTTTGGAGCCACCGAGTATACTACAGCCATTGATGTCTGGTCTGCAGGATGTGT
TCTCGCCGAGCTTCTTCTCGGGCAGCCATTGTTCCCGGGTGAGAGCGGTGTTGATCAACTTG
TAGAGATTATAAAGGTTTTGGGAACACCAACAAGGGAAGAAATCAAATGCATGAACCCGAAT
TACACAGAGTTCAAATTTCCTCAGATTAAAGCTCATCCATGGCATAAGATTTTCCACAAGAG
AATGCCTCCAGAAGCTGTTGATTTGGTCTCAAGGCTTCTTCAATACTCTCCCAATCTCCGTT
GTGCTGCTCTTGATTCATTGGTCCACCCATTCTTTGACGAGCTAAGAGATCCGAATGCGCGA
TTACCCAACGGACGTTTCCTTCCACCGCTCTTTAACTTTAAGCCTCATGAACTTAAAGGTGT
GCCTGTGGAGATGGTGGCGAAGTTAGTTCCAGAACATGCGAGGAAGCAATGTCCGTGGCTCA
GTTTGTGATTTGTTCTCACCTGCAAACACGAAAACTAGAGCAAAGCAGTCGAGATATTCATC
TCTTCTCTTCTCTCTCCTTCTCTGTATTAATATTATTATAATGATCATATCTCAATCTGATG
ATTTAGTAACCCTTTGTTTGTTGTATGAGTAGAGAAAGAGTGAATCATTTGTGGGGGTTATG
ATATTGTATAAGCCAACAAAGATTATTTTTAAAGAGAGTTTCGTGTTTTCTGTCTC

FIGURE 16 (continued)

**SEQ ID NO 155 - *Arabidopsis thaliana* - At3g05840 - ASK-gamma**

MASVGIEPSAAVRESTGNVTDADRLPEEMKDMKIQDDKEMEATIVNGNVTETGHIIVTTIGG
RNGQPKQTISYMAERVVGHGSFGVVFQAKCLETGETVAIKKVLQDRRYKNRELQTMRLLDHP
NVVSLKHCFFSTTEKDELYLNLVLEYVPETVHRVIKHYNKLNQRMPLVYVKLYTYQIFRSLS
YIHRCIGVCHRDIKPQNLLVNPHTHQVKLCDFGSAKVLVKGEPNISYICSRYYRAPELIFGA
TEYTTAIDVWSAGCVLAELLLGQPLFPGESGVDQLVEIIKVLGTPTREEIKCMNPNYTEFKF
PQIKAHPWHKIFHKRMPPEAVDLVSRLLQYSPNLRCAALDSLVHPFFDELRDPNARLPNGRF
LPPLFNFKPHELKGVPVEMVAKLVPEHARKQCPWLSL

**SEQ ID NO 156 - *Arabidopsis thaliana* - X68525 - ASK-alpha**

CTCAGATCGATGAAGAGAAGAATTAGGATTTTTACGTTTTCATCGGCTTGAAAGTTTGAAGA
GTTTTGTAGCCTGAAAAATGGCGTCAGTGGGTATAGCTCCTAATCCTGGAGCAAGAGACTCT
ACTGGTGTTGATAAATTGCCTGAAGAAATGAATGACATGAAAATTCGTGACGATAAAGAAAT
GGAAGCGACAGTGGTAGATGGAAATGGAACAGAGACTGGACATATCATTGTGACTACTATTG
GTGGTAGAAATGGCCAACCAAAACAGACAATTAGCTACATGGCTGAGCGTGTTGTTGGTCAC
GGATCTTTTGGTGTTGTGTTCCAAGCGAAATGTCTTGAGACAGGAGAAACTGTTGCGATAAA
GAAAGTTTTACAAGATAGGAGGTACAAGAACCGTGAGCTTCAAACCATGAGGCTACTTGACC
ATCCTAATGTTGTGTCTCTGAAACATTGTTTCTTCTCAACCACTGAAAAAGATGAGCTTTAC
CTCAATCTTGTTCTTGAGTACGTTCCAGAAACTGTTCATCGTGTTATCAAACACTACAACAA
ACTGAATCAGAGAATGCCTCTTATATACGTCAAACTTTACACTTATCAGATTTTTAGAGCCT
TATCTTACATTCACCGATGCATTGGTGTGTGTCATCGTGACATAAAACCTCAAAACTTGTTG
GTAAATCCGCACACTCATCAAGTAAAGCTATGTGATTTTGGAAGTGCAAAAGTATTGGTAAA
AGGAGAACCAAACATTTCCTACATCTGCTCGAGGTATTACAGAGCACCTGAACTTATTTTTG
GAGCAACCGAGTATACGACAGCCATTGATGTCTGGTCTGCAGGATGTGTTCTAGCTGAACTA
TTGCTTGGACAGCCCTTGTTCCCTGGTGAGAGCGGTGTTGATCAACTTGTACACATTATCAA
GGTCTTGGGAACGCCTACTAGAGAAGAAATCAAGTGCATGAACCCAAACTACACGGAATTCA
AATTCCCTCAGATTAAAGCTCATCCATGGCACAAGATTTTCCACAAACGCATGCCTCCAGAA
GCTGTTGATTTGGTCTCAAGACTTCTTCAATACTCTCCTAATCTACGAAGTGCCGCTCTCGA
CACATTAGTCCACCCATTCTTTGATGAGTTAAGAGACCCAAACGCACGTCTACCTAATGGAC
GTTTCCTTCCACCGGCTTTTCACTTCAAGCCTCACGAGCTGAAAGGTGTACCATTGGAGATG
GTAGCTAAGTTAGTACCTGAGCATGCAAGGAAGCAGTGTCCTTGGCTCGGTTTGTGATTTCC
TCTTAATGTAGCATGAACACAACAAACACTTCTTATAAATTACCTCTCTATGTATCAATATG
TCACAAACTGATATGCACCCTTTGTTTGTTGTATGAGTAGAGAAAAAAAGAGTTATTACTAT
GGTTGGTTGGTTCATAATGTAAAAGCCCACCAAGATTTTTTATCTAGATAAAGAGTTTGCTA
AAAAAAAA

FIGURE 16 (continued)

**SEQ ID NO 157 - *Arabidopsis thaliana* - CAA48538 - ASK-alpha**

MASVGIAPNPGARDSTGVDKLPEEMNDMKIRDDKEMEATVVDGNGTETGHIIVTTIGGRNGQ
PKQTISYMAERVVGHGSFGVVFQAKCLETGETVAIKKVLQDRRYKNRELQTMRLLDHPNVVS
LKHCFFSTTEKDELYLNLVLEYVPETVHRVIKHYNKLNQRMPLIYVKLYTYQIFRALSYIHR
CIGVCHRDIKPQNLLVNPHTHQVKLCDFGSAKVLVKGEPNISYICSRYYRAPELIFGATEYT
TAIDVWSAGCVLAELLLGQPLFPGESGVDQLVHIIKVLGTPTREEIKCMNPNYTEFKFPQIK
AHPWHKIFHKRMPPEAVDLVSRLLQYSPNLRSAALDTLVHPFFDELRDPNARLPNGRFLPPA
FHFKPHELKGVPLEMVAKLVPEHARKQCPWLGL

**SEQ ID NO 158 - *Arabidopsis thaliana* - NM_121468 - protein kinase family protein**

ATTGGGGTCCGCTCTCTCTCTCTCTCTGCCATCAGAAGAAAAAACCAAACACCGAGACAAAA
CACATCACGAAGAAGAGAGAGATTTGCCATTTTCGGCAAGGAAGTGTTTTATTCTAGGGCTT
CTCTAGTTGCTGCGTAGACAAGATGGTGGAGTGAAATTGCGGCGGTGACTTTTCAGATTGAC
AAATTGAATTAAAGATCTTGAATACATATGGCTTCTGTGGGAACATTACCAGCTTCTTCTAT
GGCTACAAAACAAAGCAATGCTTCTATATGCGCTGAAAAATTACCTGAAGGGATTAATGAGA
TGAAGATAAAAGATGATAAGGAAATGGAAGCAGCTGTGGTTGATGGGAATGGAACTGAAACA
GGTCACATTATTGTTACAACTATTGGTGGTAAAAATGGTCAGCCTAAACAGACCATAAGTTA
TATGGCAGAGCGCATCGTTGGACAAGGTTCTTTTGGAATCGTTTTTCAGGCCAAGTGTTTAG
AAACGGGGGAAACTGTTGCAATCAAGAAAGTTTTGCAAGACAAGAGATACAAGAATCGGGAG
CTGCAGACAATGCGTCTTCTTGATCACCCTAATGTTGTATCCCTCAAGCATTGTTTTTTCTC
AACGACTGAAAAAGATGAGCTCTATCTCAATCTGGTCCTTGAATACGTTCCTGAGACTGTCT
ATCGCGTCTCAAAGCACTATAGTCGGGCAAACCAGAGGATGCCCATTATATATGTTAAACTC
TATACTTATCAGATTTGCAGAGCTTTGGCTTATATTCATGGTGGAGTAGGAGTCTGCCACAG
AGACATAAAACCACAGAATCTTCTGGTTAATCCTCATACGCATCAGGTCAAACTATGCGATT
TTGGTAGCGCAAAAGTTCTGGTTAAAGGCGAGCCAAACATCTCATACATCTGCTCCCGTTAC
TATCGAGCACCTGAACTTATATTTGGAGCTACAGAATATACAACAACAATTGACATATGGTC
TGCAGGCTGTGTTCTTGCTGAATTGCTTCTGGGACAGCCTCTATTTCCAGGTGAGAGTGGAG
TTGACCAGCTAGTTGAGATAATAAAGGTTCTTGGAACACCAACACGGGAGGAAATCAAATGC
ATGAATCCAAACTACACAGAATTCAAATTCCCGCAAATAAAGGCTCATCCTTGGCACAAAAT
ATTCCATAAGCGTACACCTCCAGAAGCTGTAGACCTTGTCTCAAGACTTCTCCAGTATTCTC
CAAACCTCAGATCAACCGCTATGGAGGCGATAGTTCACCCGTTCTTCGATGAGCTACGTGAT
CCCAATACACGTCTTCCTAATGGTCGTGCCTTGCCTCCTCTCTTCAACTTTAAACCTCAAGA
GCTAAAAGGAGCAAGTTTAGAGTTGTTGTCCAAGCTTATACCTGACCACGCCCGAAAACAAT
GTTCCTTCCTCGCTCTCTAAATCTCTTCCTCTCTCTCTATATATATGTGTGTGTGTGTGTAT
GTACACATGCATATAATATGCTTATCGTTTCTAAGTAATGGAGATAGCTTCTCAGGATTATC
ATTAGCTTTCATCTTTCATGTATCTTTGTTGTTTATTGTCTTATCACAACCTTTGTACTTTA
TTACATACAATGATTAGTGTAATGTATGTGACGGTCTTTGACTCGCCGGTCGCTACAGTTAT
GTTGGATACTAAATTATAAAATAAACTTCTCGCTCGTC

FIGURE 16 (continued)

**SEQ ID NO 159 - *Arabidopsis thaliana* - At5g14640 - protein kinase family protein**

MASVGTLPASSMATKQSNASICAEKLPEGINEMKIKDDKEMEAAVVDGNGTETGHIIVTTIG
GKNGQPKQTISYMAERIVGQGSFGIVFQAKCLETGETVAIKKVLQDKRYKNRELQTMRLLDH
PNVVSLKHCFFSTTEKDELYLNLVLEYVPETVYRVSKHYSRANQRMPIIYVKLYTYQICRAL
AYIHGGVGVCHRDIKPQNLLVNPHTHQVKLCDFGSAKVLVKGEPNISYICSRYYRAPELIFG
ATEYTTTIDIWSAGCVLAELLLGQPLFPGESGVDQLVEIIKVLGTPTREEIKCMNPNYTEFK
FPQIKAHPWHKIFHKRTPPEAVDLVSRLLQYSPNLRSTAMEAIVHPFFDELRDPNTRLPNGR
ALPPLFNFKPQELKGASLELLSKLIPDHARKQCSFLAL

**SEQ ID NO 160 - *Arabidopsis thaliana* - Y12710 - shaggy-like kinase gamma**

ATGGCCTCGGTGGGCATAGAGCCTAGTGCCGCGGTTAGAGAATCTACTGGAAACGTTACTGA
TGCTGATAGATTACCCGAGGAGATGAAGGACATGAAAATTCAAGATGATAAAGAAATGGAAG
CTACGATTGTTAATGGCAATGTGACTGAGACTGGCCATATAATAGTAACTACTATAGGAGGA
AGAAATGGCCAGCCAAAACAGACAATCAGTTACATGGCGGAGCGAGTTGTTGGACATGGCTC
CTTTGGTGTTGTGTTTCAGGCCAAATGTTTAGAAACAGGAGAAACTGTTGCTATAAAGAAAG
TTCTACAAGATCGGAGGTACAAGAATCGTGAGCTTCAAACAATGAGGCTACTTGACCATCCA
AATGTTGTGTCTTTGAAACATTGTTTCTTCTCTACAACCGAAAAAGATGAGCTTTATCTCAA
CTTGGTTCTGGAATACGTTCCGGAAACTGTGCACCGCGTCATCAAACACTACAACAAACTTA
ACCAACGAATGCCTCTCGTTTACGTCAAACTTTACACTTATCAGATTTTTAGGTCCTTATCC
TACATTCACCGATGTATCGGCGTATGTCATCGAGACATCAAACCTCAAAACTTGTTGGTAAA
TCCACACACTCATCAAGTGAAACTATGCGATTTTGGAAGTGCGAAAGTATTGGTTAAAGGAG
AGCCAAACATTTCATACATTTGCTCGAGGTATTACAGAGCACCTGAGCTCATTTTTGGAGCC
ACCGAGTATACTACAGCCATTGATGTCTGGTCTGCAGGATGTGTTCTCGCCGAGCTTCTTCT
CGGGCAGCCATTGTTCCCGGGTGAGAGCGGTGTTGATCAACTTGTAGAGATTATAAAGGTTT
TGGGAACACCAACAAGGGAAGAAATCAAATGCATGAACCCGAATTACACAGAGTTCAAATTT
CCTCAGATTAAAGCTCATCCATGGCATAAGATTTTCCACAAGAGAATGCCTCCAGAAGCTGT
TGATTTGGTCTCAAGGCTTCTTCAATACTCTCCCAATCTCCGTTGTGCTGCTCTTGATTCAT
TGGTCCACCCATTCTTTGACGAGCTAAGAGATCCGAATGCGCGATTACCCAACGGACGTTTC
CTTCCACCGCTCTTTAACTTTAAGCCTCATGAACTTAAAGGTGTGCCTGTGGAGATGGTGGC
GAAGTTAGTTCCAGAACATGCGAGGAAGCAATGTCCGTGGCTCAGTTTATGA

**SEQ ID NO 161 - *Arabidopsis thaliana* - CAA73247 - shaggy-like kinase gamma**

MASVGIEPSAAVRESTGNVTDADRLPEEMKDMKIQDDKEMEATIVNGNVTETGHIIVTTIGG
RNGQPKQTISYMAERVVGHGSFGVVFQAKCLETGETVAIKKVLQDRRYKNRELQTMRLLDHP
NVVSLKHCFFSTTEKDELYLNLVLEYVPETVHRVIKHYNKLNQRMPLVYVKLYTYQIFRSLS
YIHRCIGVCHRDIKPQNLLVNPHTHQVKLCDFGSAKVLVKGEPNISYICSRYYRAPELIFGA
TEYTTAIDVWSAGCVLAELLLGQPLFPGESGVDQLVEIIKVLGTPTREEIKCMNPNYTEFKF
PQIKAHPWHKIFHKRMPPEAVDLVSRLLQYSPNLRCAALDSLVHPFFDELRDPNARLPNGRF
LPPLFNFKPHELKGVPVEMVAKLVPEHARKQCPWLSL

FIGURE 16 (continued)

**SEQ ID NO 162 - *Zea mays* - AY103545 - DNA sequence**

TTGACTGCAGGCCTCGGCACGGTAGGCACAAATCATTTGGCCGCTGCGTCGCGTTGGGAGC
AGTATTCTACTGTGCCTGCGTCCCGACAAGCGAAAAGAAGAGACGGGGGAGGGTGGGAGAAC
GGATACCGAAAGGGGTAGGAGAGTGAGCAGCCAGAGAACAGGGAGGTAGAGAGGAGGAGGAG
GTAGAAGGCGAAAGAAGGGGAACCAAATCTTGGACGGGAACACATAGATTTCTTTGGTGGAG
GAAGGAGGAGGGCAACAAGAGGAGGTTACAGGTAGCCCAATAGATCTACTGCTGTTGAGGGA
GTTGATGCAAAGCTGAGTTGCTGCGCGTTGGCTTTCTTTAGAGATGGCTTCAGCTGGTGTTG
CCCCTTCTGGGTACAAGAACAGCAGCAGCACCAGCATTGGTGCCGAAAAGTTGCAAGATCAC
ATGAACGAGCTAAAGATTAGAGATGATAAGGAAGTTGAAGCAACCATAATTAATGGGAAAGG
GACTGAAACTGGGCACATAATTGTCACCACTACTGGTGGCAAGAATGGTCAACCAAAACAGA
CAGTGAGCTACATGGCTGAGCGCATTGTAGGTCAAGGTTCTTTTGGGATCGTCTTCCAGGCC
AAGTGTTTGGAAACGGGTGAGACTGTTGCCATAAAGAAGGTTCTTCAAGACAAGCGTTACAA
GAACCGCGAACTGCAGACCATGCGCCTTCTTGACCACCCTAATGTTGTTGCTTTGAAGCATT
GCTTCTTTTCAACTACTGAGAAGGATGAGCTTTATCTGAACTTGGTCCTTGAGTATGTTCCG
GAGACAGTTCATCGAGTTGTGAAACATCACAACAAGATGCACCAACGCATGCCACTTATTTA
TGTGAAGCTTTATATGTACCAGATATGTAGAGCATTGGCTTACATTCATGGTACTATCGGTG
TCTGCCACAGAGATATTAAGCCACAAAATCTTCTGGTGAACCCACACACCCACCAGCTTAAA
ATATGTGACTTTGGTAGTGCAAAAGTTCTGGTCAAGGGGGAACCAAACATATCATACATCTG
CTCGCGATACTATAGGGCTCCAGAGCTCATATTTGGTGCCACTGAGTATACCACAGCGATTG
ACATTTGGTCTGCTGGATGTGTTCTTGCTGAGCTTATGCTAGGGCAGCCTTTGTTTCCGGGT
GAAAGTGGTGTGGACCAACTTGTTGAAATCATCAAGGTCCTCGGTACGCCAACAAGGGAAGA
AATTAAATGCATGAACCCAAATTACACAGAGTTTAAGTTCCCACAAATCAAAGCACACCCAT
GGCACAAGGTATTCCACAAAAGGATGCCGCCAGAAGCTGTTGATCTGGTCTCTCGGCTACTC
CAGTACTCCCCAAATCTGAGATGCACTGCTATGGAGGCACTTGTTCACCCATTCTTTGATGA
GCTTCGAGATCCTAATACTCGCCTTCCAAATGGTCGCTTTTTGCCACCACTATTCAATTTCA
AGCCTCACGAACTTAAAGGAGTCCCATCAGACATTGTTGCGAAATTGGTTCCAGAACATGCG
AAGAAGCAATGCTCTTATGTTGGATTGTGAAATGACCGCGCCTTGGGACTGGAACCTGAGGT
CGCAATCGTGCATTTCCCCTGGGATGTTGGATGATCTTGAGGCATGCGAGCCTGTTGTTGAA
GATGCAAGGTTACGTACTTGTACGACAATGTGACCTGTGTAGCTGAGTAGTCTATGTCGCAG
TGACATGTAACGGCACCCCCCTTCCTACTAACTGACGCTTACTCGAGATTGCCATAGTTGAT
CTTGTAATTTGTTATAGAGCAGTATGAATGTATTTATGGTAGCTTGAATCTATGTATGGATT
CACTTCGTTTTTCCATGTTTCCTTGTCTCCAGACCCAGATTGCTACCGTATTGTTTCAGAAT
TCCTAGCTACCTGTTGCCTAAAAAAAAAAAAAAAAAAACCTCGTGC

**SEQ ID NO 163 - *Zea mays* - AY103545 - protein sequence**

MASAGVAPSGYKNSSSTSIGAEKLQDHMNELKIRDDKEVEATIINGKGTETGHIIVTTTGGK
NGQPKQTVSYMAERIVGQGSFGIVFQAKCLETGETVAIKKVLQDKRYKNRELQTMRLLDHPN
VVALKHCFFSTTEKDELYLNLVLEYVPETVHRVVKHHNKMHQRMPLIYVKLYMYQICRALAY
IHGTIGVCHRDIKPQNLLVNPHTHQLKICDFGSAKVLVKGEPNISYICSRYYRAPELIFGAT
EYTTAIDIWSAGCVLAELMLGQPLFPGESGVDQLVEIIKVLGTPTREEIKCMNPNYTEFKFP
QIKAHPWHKVFHKRMPPEAVDLVSRLLQYSPNLRCTAMEALVHPFFDELRDPNTRLPNGRFL
PPLFNFKPHELKGVPSDIVAKLVPEHAKKQCSYVGL

FIGURE 16 (continued)

**SEQ ID NO 164 - *Zea mays* - AY108486 - DNA sequence**

GCACGAGCCGCGCCGGAGTTGGAGGAGGGAGAGGGGACAAGCTTTCCGGCGCCGACGCCGAC
GCGGACCCGGCGCCGACACGATCCGGTGGATCAAGTGCATCACACCTTTAGGGAGGCCCCTT
GGACAGCAGTTTGTGCTGCAAATTCTATATAGCTCTGTCGCAGCATGGCCTCGGTGGGCGTG
GCACGCTCTTCTTTGGGATTTCAGAATGGCACAAGTTCTAGCAGTGACCCAGATCGTCTTCC
CAACGAGTTGGGCAGTATGAGCATAAGGGACGACAAGGACGTTGAAGATATTGTAGTCAATG
GCAATGGGGCGGAGCCTGGTCATATCATAGTGACCAGCATTGATGGGAGAAATGGGCAGGCA
AAGCAGACCATTAGTTACATGGCTGAGCGGGTGGTAGGTCATGGGTCCTTCGGAACCGTTTT
CCAGGCCAAGTGTCTTGAAACTGGTGAGACCGTAGCTATAAAAAAGGTTCTTCAAGACAAGA
GATACAAGAATCGTGAGCTGCAAACCATGCGAGTGCTTGACCACCCAAATGTGGTGGCTCTA
AAGCACTGTTTCTTCTCAAAGACTGAGAAAGAGGAGCTTTACCTCAATTTGGTGCTTGAGTA
TGTACCGGAGACTGCTCATCGTGTCATCAAACATTACAACAAGATGAACCAGCGCATGCCTT
TGATTTATGCAAAACTGTATATGTATCAGATTTGTAGAGCCTTGGCATACATTCACAACAGC
ATTGGAGTGTGCCACAGGGACATTAAGCCGCAAAATCTCCTGGTTAATCCTCATACCCATCA
GCTAAAATTGTGTGACTTTGGCAGCGCGAAAGTTCTGGTAAAAGGCGAACCAAACATTTCTT
ACATCTGTTCTAGGTACTACAGAGCTCCAGAGCTCATATTTGGTGCTACTGAATACACAACA
GCCATTGATGTTTGGTCTGCTGGCTGTGTGCTCGCTGAGCTGCTTCTAGGACAGCCTCTGTT
CCCTGGAGAAAGCGGTGTTGATCAGCTTGTTGAAATCATCAAGGTTCTGGGCACACCCACAC
GTGAAGAAATTAAGTGCATGAATCCAAATTATACCGAGTTTAAATTCCCGCAAATCAAAGCT
CACCCATGGCATAAGATATTCCATAAAAGGATGCCTGCTGAAGCGGTAGATCTCGTGTCCAG
GCTTCTGCAGTACTCACCAAAACTTCGGTCGACTGCTTTGGAAGCATTGGTCCATCCGTTCT
TTGATGAACTTCGGGATCCAAACACCCGCTTACCGAATGGTCGTTTTCTTCCGCCTCTCTTC
AATTTTAAGCCCCATGAGCTGAAGAACGTGCCGGCGGATTTCATGGTGAAATTGGTCCCTGA
GCATGCACGGAAGCAATGTGCCTTCGTAGGGTGGTGATCTCTGGATAAGAGGATGACGACTC
GATGATTAGCTGAGGACCAAGTTAATGTCTGTTAGAAACTGCCGGAGATCGACATTGCCAGA
TGTGGTGTGGTATAAGATAGGCAATATGTGTGATTATTTTTTGTTCGAGGTTATCACCCCCC
TTGCCCCAGAAAAGATGAGAAGATGTCGATGTAACAAGCCCTCTGCGCTTCTGTAAGTAGAT
GAGTGTTGCTGCATGCCCCCTGGGTACATGTATCGGTTTGAGCAGAATTCTGTTTGCCTGAA
TCGTGCCATCACCACGCAGGGATCCATCCCTTGTGTGACGATGTTCAGCCCAAAAAAAAAAA
AAAAAAAAAAAAAAAA

**SEQ ID NO 165 - *Zea mays* - AY108486 - DNA sequence**

MASVGVARSSLGFQNGTSSSSDPDRLPNELGSMSIRDDKDVEDIVVNGNGAEPGHIIVTSID
GRNGQAKQTISYMAERVVGHGSFGTVFQAKCLETGETVAIKKVLQDKRYKNRELQTMRVLDH
PNVVALKHCFFSKTEKEELYLNLVLEYVPETAHRVIKHYNKMNQRMPLIYAKLYMYQICRAL
AYIHNSIGVCHRDIKPQNLLVNPHTHQLKLCDFGSAKVLVKGEPNISYICSRYYRAPELIFG
ATEYTTAIDVWSAGCVLAELLLGQPLFPGESGVDQLVEIIKVLGTPTREEIKCMNPNYTEFK
FPQIKAHPWHKIFHKRMPAEAVDLVSRLLQYSPKLRSTALEALVHPFFDELRDPNTRLPNGR
FLPPLFNFKPHELKNVPADFMVKLVPEHARKQCAFVGW

FIGURE 16 (continued)

**SEQ ID NO 166 - *Medicago sativa* - X68409 - AMMSK3A**

TTTTTTTTTTTTTTTTTTTTCAAAATATTTCCATTTGTCTCTTCTTTCTTCTTTCCTAAT
TCCGAATCCCACGGATTTCACTTCCATTCAAAGTCATAGCTAGATCCAATCCATTCCATTCC
TCTGTTTGAGTTGAAGAGTTGATTTGGGGGTTGGATGTTCAGTTTTGAAGCTGTGTATGATC
TGAAAGGAAATAATTAAGTAAAGTGTTTTGCACTTTTTTTAAGAAGATATGATGGCATCAGG
TGGTGTTGCACCTGCTTCTGGATTTATAGATAAGAATGCAAGTTCAGTTGGTGTTGAAAAGT
TGCCTGAGGAGATGAATGACATGAAAATTAGGGATGATAAGGAAATGGAAGCCGCTACCATT
GTAGATGGAAATGGGACCGAAACCGGACATATAATTGTCACAACCATTGGTGGTAAAAATGG
CCAGCCAAAGCAGACAATAAGTTACATGGCCGAGCGTGTTGTTGGACATGGATCTTTTGGTG
TAGTTTTTCAGGCAAAGTGTTTGGAGACTGGAGAAACTGTGGCTATAAAGAAGGTTCTTCAA
GATAAGAGGTACAAGAACCGGGAATTGCAAACTATGCGCCTTCTGGACCACCCTAATGTTGT
ATCTTTGAAGCACTGCTTCTTCTCAACGACTGAAAAGGACGAGCTTTATCTTAACCTGGTGC
TTGAATATGTTCCTGAGACTGTCAGCCGTGTGATTAGACACTACAACAAAATGAATCAAAGA
ATGCCTATGATATATGTCAAACTTTATTCTTACCAGATTTGCAGGGCACTTGCTTATATTCA
CAACAGTATTGGAGTATGTCACAGGGATATTAAACCTCAAAATTTACTGGTCAATCCTCACA
CCCACCAACTGAAGATATGCGACTTTGGAAGTGCTAAAGTCTTGGTAAAAGGTGAACCAAAC
ATATCTTACATCTGTTCTAGGTACTATAGAGCTCCTGAGCTTATATTCGGTGCAACTGAGTA
CACCACAGCCATTGACATCTGGTCAGCTGGTTGCGTACTTGGTGAACTTTTGCTTGGCCAGC
CACTGTTTCCTGGTGAGAGTGGAGTAGACCAACTTGTGGAAATTATCAAGGTTTTAGGCACC
CCAACAAGGGAAGAAATCAAGTGCATGAATCCTAATTATACAGAGTTTAAATTTCCTCAAAT
CAAAGCTCATCCATGGCATAAGATTTTTCACAAGAGAATGCCTCCTGAAGCTGTGGATCTTG
TCTCAAGACTATTGCAATACTCTCCAAATCTTCGAAGCACAGCTTTGGAGGCTTTGGTTCAT
CCATTCTATGATGACGTGCGCGATCCAAACACTCGGTTGCCAAATGGGCGTTTCCTTCCACC
ATTATTTAACTTCAAAGTCAATGAGCTCAAGGGAGTACCTGCAGAGATGCTGGTGAAACTGG
TTCCACCTCATGCAAGAAAGCAATGTGCCTTGTTCGGGTCATCATGAAGCAGCCTTGTGTAG
TTATTAAGTACTTTCTTCTACCTATGTAAAGGTGTATCTAGTCAAATTTCAAGTGGTTAAAT
AGGTTATTTCTATTTTCTTTCTGTTTGATTTGTTCTCACCCAACCTACCATCCAATTTATTA
TTATTTTTCTTCCTCGATGTAGAAGAAAGCTGTGCTGTTTAAGAAGCAACTTCAGCTTGATT
ATTACTTTGTAGGATCTGATGTGTTCACTCACCTTAACATGAACCATTGTTTATTGAAGTGA
TAGACTTGATCACAACCTCACTGAACTAGTAGGAGATGTTTCAAATCTTGAAAAAAAAAAAA
AA

**SEQ ID NO 167 - *Medicago sativa* - CAA48472 - AMMSK3A**

MMASGGVAPASGFIDKNASSVGVEKLPEEMNDMKIRDDKEMEAATIVDGNGTETGHIIVTTI
GGKNGQPKQTISYMAERVVGHGSFGVVFQAKCLETGETVAIKKVLQDKRYKNRELQTMRLLD
HPNVVSLKHCFFSTTEKDELYLNLVLEYVPETVSRVIRHYNKMNQRMPMIYVKLYSYQICRA
LAYIHNSIGVCHRDIKPQNLLVNPHTHQLKICDFGSAKVLVKGEPNISYICSRYYRAPELIF
GATEYTTAIDIWSAGCVLGELLLGQPLFPGESGVDQLVEIIKVLGTPTREEIKCMNPNYTEF
KFPQIKAHPWHKIFHKRMPPEAVDLVSRLLQYSPNLRSTALEALVHPFYDDVRDPNTRLPNG
RFLPPLFNFKVNELKGVPAEMLVKLVPPHARKQCALFGSS

FIGURE 16 (continued)

**SEQ ID NO 168 - *Medicago sativa* - X68411 - AMMSK1A**

GAGCACATGCTTTGGTTTCGTTTCGTTGGTGGATGAGTGGTTAAAATTGAAAGGGTTTCAGT
GGCAATGGCGTCGGTTGGTGTTGCACCAACTTCAGGTTTTAGAGAAGTCCTTGGTGATGGTG
AAATTGGTGTTGATGATATATTGCCAGAGGAAATGAGTGATATGAAAATTAGGGATGATAGA
GAAATGGAAGCCACCGTTGTTGACGGCAATGGAACGGAGACAGGACATATCATTGTCACTAC
TATTGGTGGTAGAAATGGTCAGCCAAAGCAGACTATAAGCTATATGGCAGAGCGTGTTGTAG
GACATGGATCATTTGGAGTTGTCTTCCAGGCTAAGTGCTTGGAAACTGGTGAAACCGTGGCT
ATCAAAAAGGTTCTTCAAGACAAGAGGTACAAGAACCGGGAATTGCAAACAATGCGACTGCT
TGATCACCCGAATGTCGTCTCTTTAAAGCATTGTTTCTTTTCAACCACCGAAAAGGATGAAC
TATACCTGAATTTGGTACTTGAGTATGTTCCTGAAACAGTTCATCGCGTGATTAAGCATTAC
AGCAAGTTGAACCAAAGGATGCCAATGATTTATGTGAAGCTCTATACATACCAGATCTTTAG
AGCATTATCTTATATTCATCGTTGCATTGGAGTCTGTCATCGGGATATCAAGCCCCAAAATC
TATTGGTCAATCCACACACCCACCAGGTTAAATTATGCGACTTTGGAAGTGCGAAAGTCTTG
GTTAAAGGCGAACCAAATATATCGTATATATGTTCTAGATACTACAGAGCACCCGAGCTTAT
TTTTGGAGCAACTGAATATACTACTGCTATTGATGTATGGTCTGTTGGTTGTGTTTTGGCTG
AGCTGCTGCTTGGACAGCCATTGTTCCCAGGTGAGAGAGGAGTTGATCAGCTTGTTGAGATC
ATCAAGGTTCTGGGAACTCCGACAAGAGAAGAAATTAAATGCATGAATCCTAATTATACCGA
ATTTAAATTCCCTCAAATCAAAGCACATCCATGGCACAAGATCTTCCATAAGCGCATGCCTG
CAGAAGCTGTTGATTTGGTATCAAGATTATTACAATACTCCCCAAACCTGCGGTGCCAAGCT
TTAGATTGCTTGACCCATCCTTTCTTCGATGAGCTTCGTGACCCAAATGCTCGCTTGCCAAC
TGGCCGTTTCCTCCCACCACTGTTTAACTTCAAACCTCACGAACTGAAAGGAGTTCCAGTCG
AGACCTTGATGAAACTGGTTCCAGAGCATGCGAGGAAGCAATGCCCGTTTCTTGGCTTGTAA
TATGTCGTAAAATGTAACAAAACTGCAAGTGTTGTTTCCATATGAACGTTCTATTTGATGAT
ATGATATTTATTAGTATCTTTGTTGTATTCGGTTGCCTGTGATAGAAAATTTAGAGATATAT
GCTACCCAATATTACCCAAACCCTTATATGGGTATTCAGAATACCCTTTTCCTGTATCACAG
CAGATTGTAACATGCAATAGAAGACAAGTGTCTACAATTATCTAAATGTTGTATCAGTATTT
GTACTTGTATTTGTATTTGTGGAGATAATGACGGATTATTGCGTAAAAAAAAAAAAAAAAAA
A

**SEQ ID NO 169 - *Medicago sativa* - CAA48474 - AMMSK1A**

MASVGVAPTSGFREVLGDGEIGVDDILPEEMSDMKIRDDREMEATVVDGNGTETGHIIVTTI
GGRNGQPKQTISYMAERVVGHGSFGVVFQAKCLETGETVAIKKVLQDKRYKNRELQTMRLLD
HPNVVSLKHCFFSTTEKDELYLNLVLEYVPETVHRVIKHYSKLNQRMPMIYVKLYTYQIFRA
LSYIHRCIGVCHRDIKPQNLLVNPHTHQVKLCDFGSAKVLVKGEPNISYICSRYYRAPELIF
GATEYTTAIDVWSVGCVLAELLLGQPLFPGERGVDQLVEIIKVLGTPTREEIKCMNPNYTEF
KFPQIKAHPWHKIFHKRMPAEAVDLVSRLLQYSPNLRCQALDCLTHPFFDELRDPNARLPTG
RFLPPLFNFKPHELKGVPVETLMKLVPEHARKQCPFLGL

FIGURE 16 (continued)

**SEQ ID NO 170 - *Medicago sativa* - X68410 - AMMSK2A**

GTTCAATTGAAGCTGCAAAAAAAAAAAAAAATCTTGATCTACTTTGGTTGTGATAATGGCAAC
AGCGGGTGTAGCACCTGCTTCTGGAATAGTAGATGTAAATGCAAGTTCAGCTATTGCTGTTG
ATAAGTTACCTGATGAGATTCTTGGCATGAGAATTAAGGATGATAAGGAAATGGAAGCACAT
GTGGTAGATGGAAATAGTACTGAAGCAGGACATGTAATTGTCACTACCATTGGTGGTAAAAA
TGGCCAGCCAAAGCAGACAATAAGCTACATGGCTGAGCGTGCTGTTGGACAGGGATCATTTG
GTGTAGTTTTCCAGGCTAAGTGCTTGGAGACAGGTGAAACTGTGGCTATAAAAAAGGTTCTT
CAAGACAAGAGGTATAAGAACCGGGAATTGCAAACAATGCGCCTTCTGGACCACCCCAATGT
TGTAACTTTGAAGCATTGTTTCTTTTCAACAACTGAAAAAGACGAGCTCTATCTTAACTTGG
TACTTGAGTTTGTTCCTGAGACTGTCCATCGTGTGATCAGACACTACAGCAAAATGAATCAG
AGGATGCCATTGATATACGTAAAACTTTATTCTTACCAGATATGTAGATCACTAGCTTATAT
TCATAACTGTGTTGGAGTGTCTCATAGGGACATAAAACCTCAAAATTTACTGGTCAATCCTC
ACACCCATCAGCTGAAGCTGTGTGACTTTGGGAGTGCAAAAGTCTTGGTCAAGGGTGAACCA
AACATATCTTACATCTGTTCGAGGTATTATAGAGCTCCTGAGCTTATATTTGGTGCAACTGA
ATACACCTCAGCCATTGACATTTGGTCAGCTGGCTGTGTGCTTGGCGAACTATTGCTTGGCC
AGCCTCTCTTTCCCGGTGCGAGTGGAGTAGACCAGCTCGTTGAAATTATCAAGGTTTTAGGT
ACCCCAACAAGGGAAGAAATAAAGTGTATGAATCCTAATTACACTGAGTTCAAATTCCCACA
AATCAAAGCTCATCCATGGCACAAGATCTTTCGCAAGCGTATGCCACCGGAAGCTGTGGATC
TCGTCTCAAGACTACTTCAATACTCTCCAAATCTTCGAAGCACAGCTTTGGAGGCTCTGGTT
CATCCCTTCTTTGATGAATTGCGTGATCCAAATACCCGCTTACCAAATGGGCGACATCTTCC
TCCTTTATTTAACTTCAAAGCCAACGAGCTTAAGGGAGTGCCTGCTGAAATGCTGGTGAAGT
TGGTTCCGTCTCACGCAAGAAAGCAGTGTTCTTTGTTTGCGTCGTCATAGACTTAGAATGCT
GTCTTGTGTAAATATTATGGACTCCCTGTTTGTAGAATTGTATGTAGCCTGTTTCATGTTGT
TAATAGTCTCTCTTTTGTTATTTGTTCCATTAATTTGTTTCTACCAAAGAAAACCACCTCAG
TTTATTATAAGTTTCAAGTTGATCTCTCTTCACGATTTAATTGTTCTCCTGATCTTCAATTA
TTAACAGATTGTATTAACTATTAACTATTAACTAGAACAATTGTTTATTCTAGCG

**SEQ ID NO 171 - *Medicago sativa* - CAA48473 - AMMSK2A**

MATAGVAPASGIVDVNASSAIAVDKLPDEILGMRIKDDKEMEAHVVDGNSTEAGHVIVTTIG
GKNGQPKQTISYMAERAVGQGSFGVVFQAKCLETGETVAIKKVLQDKRYKNRELQTMRLLDH
PNVVTLKHCFFSTTEKDELYLNLVLEFVPETVHRVIRHYSKMNQRMPLIYVKLYSYQICRSL
AYIHNCVGVSHRDIKPQNLLVNPHTHQLKLCDFGSAKVLVKGEPNISYICSRYYRAPELIFG
ATEYTSAIDIWSAGCVLGELLLGQPLFPGASGVDQLVEIIKVLGTPTREEIKCMNPNYTEFK
FPQIKAHPWHKIFRKRMPPEAVDLVSRLLQYSPNLRSTALEALVHPFFDELRDPNTRLPNGR
HLPPLFNFKANELKGVPAEMLVKLVPSHARKQCSLFASS

FIGURE 16 (continued)

**SEQ ID NO 172 - *Nicotiana tabacum* - X77763 - NtK-1**

TCTCTCTCATCTTCCCTGCGATTCTCTCTCTCAATTTCAGGTTTTCTCTGTTTCTGTGCGAG
CCTCTAATGATCGGTGTATTCTCAATATCCTGAAGATTTTCTGATTTCATCGGTGAATGACT
TTTTGAGGTGATAATAGTTCGCAAAATTTCAGGAAATGACTTCAGTAGGCTTAGCACCTGTA
TCCGGTTTGAGAGAATCCAGTAGCCATAGTGTTGGTGTAGATAGGCTGCCTGAGGAGATGAA
TGACATGAGAATCAGGGATGATAAGGAAATCGAAGCAGCTATTGTGGATGGTAATGGGACTG
AGACAGGCCATATAATAGTGACAACTATTGGTGGTAGACATGGTCAGCCAAAACAGACTATC
AGTTATATGGCTGAACGTATTGTTGGACAAGGATCATTTGGAGTGGTTTTCCAGGCAAAATG
CTTAGAGACTGGTGAAACTGTTGCTATTAAAAAGGTTCTTCAAGACAAGAGATATAAGAACA
GGGAGCTGCAGACCATGCGTCTTCTTGATCACCCAAATGTTGTGTGCCTGAAGCACTGCTTC
TTTTCAACAACTGAGAAGGATGAAGTATATCTTAATTTGGTTCTTGAATACGTCCCTGAAAC
TGTCCATCGTGTTATTAAACACTACAATAAGTTGAATCAAAGGATGCCATTGATACTAGTGA
AGCTTTATACATATCAGATTTTCAGGGCATTGTCTTACATCCATCACACAATTGGAGTGTGC
CACAGGGACATAAAGCCTCAGAATCTTTTGGTGAATCCACATACTCACCAGGTTAAATTGTG
TGACTTTGGAAGTGCTAAAGTTCTGGTTAAAGGAGAACCAAATATTTCTTACATCTGCTCTA
GGTATTATAGAGCGCCTGAACTTATATTTGGAGCAACAGAGTACACTACCGCTATTGACATC
TGGTCTGCTGGCTGTGTTCTAGCCGAGCTACTTCTTGGGCAGCCTTTGTTTCCGGGTGAAAG
TGGAGTTGATCAGCTTGTTGAGATTATTAAGGTCTTGGGTACTCCTACCAGGGAAGAAATTA
AATGCATGAATCCAAATTATAACGAGTTCAAATTCCCCCAAATTAAAGCTCATCCGTGGCAC
AAGATATTTCACAAGCGCATGCCTCCAGAAGCTGTTGATCTGGTTTCAAGACTACTGCAGTA
CTCACCTAACTTGCGTTGCACTGCTTTAGAGGCAGTGACCCATGCCTTCTTCGATGAGCTTC
GTGATCCTAATACACGCCTCCCAAATGGCCGCGTCCTTCCCCCCTTGTTTAACTTTAAGGCC
CATGAGTTAAAGGGTGTGTCTGCAGAGAATCTATTGAAGTTGGTTCCGGAGCATGCCAGGAA
ACAGTGCCCGTCCCTTGGTTTATGAGTTCCCACTGTACGGTAGATATAATTTAAGTGTAAGC
TATGTTATTTCTCTGTATCCATTTTTCCCCCTTTGCTCCCCACATGTACCAGTTGTCTCTTT
GTATTATTATCCTAGTTTGTAAAAGCAGAGGTAGGATGTGGTCTTTAACATTCCTTACCTCC
AACACTTTCCTTTCACCCTGTTCCTTTTATGTCCTACTGTTGTAACTTTTATGTGGTTAAGG
GTGGACTGCTTTCTATATGAACTATTATTTTATGATGAAATTTCAAAGTGATTTTTAGTGAA
AAAAAAAAAAAAAAAAAAAAAAAAAAAAAAAAAAAAAAAAAAAAAAAAA

**SEQ ID NO 173 - *Nicotiana tabacum* - CAA54803 - NtK-1**

MTSVGLAPVSGLRESSSHSVGVDRLPEEMNDMRIRDDKEIEAAIVDGNGTETGHIIVTTIGG
RHGQPKQTISYMAERIVGQGSFGVVFQAKCLETGETVAIKKVLQDKRYKNRELQTMRLLDHP
NVVCLKHCFFSTTEKDEVYLNLVLEYVPETVHRVIKHYNKLNQRMPLILVKLYTYQIFRALS
YIHHTIGVCHRDIKPQNLLVNPHTHQVKLCDFGSAKVLVKGEPNISYICSRYYRAPELIFGA
TEYTTAIDIWSAGCVLAELLLGQPLFPGESGVDQLVEIIKVLGTPTREEIKCMNPNYNEFKF
PQIKAHPWHKIFHKRMPPEAVDLVSRLLQYSPNLRCTALEAVTHAFFDELRDPNTRLPNGRV
LPPLFNFKAHELKGVSAENLLKLVPEHARKQCPSLGL

FIGURE 16 (continued)

**SEQ ID NO 174 - *Triticum aestivum* - AF525086 - GSK-like kinase**

GTTGGTGTGGTGCGTCCTTCCTCGCGCTTTCAGAACGACACGAGTACTAGTGGTGATGCCGA
CCGACTTCCGAACGAGATGGGCAATATGAGCATAAGGGATGACAGGGACCCTGAGGATATAG
TAGTCAACGGCAATGGGACGGAACCAGGCCATATTATAGTCACAAGCATTGAGGGAAGAAAT
GGGCAAGCAAAACAGACCATTAGCTACATGGCTGAGCGTGTGGTTGGTAATGGGTCATTTGG
AACTGTTTTCCAGGCTAAGTGTCTTGAAACTGGCGAGACGGTGGCTATAAAGAAGGTTCTTC
AAGACAAGAGATATAAGAACCGTGAGCTGCAAACGATGCGAGTTCTTGACCACCCAAATGTT
GTGGCTTTAAAGCATTGTTTTTCTCAAAGACTGAGAAAGAGGAGCTTTACCTCAACCTGGT
GCTTGAGTATGTGCCGGAGACTGCTCATCGTGTCATTAAGCATTATAACAAGATGAACCAAC
GCATGCCATTGATATATGCAAAACTGTACATGTATCAGATATGTAGATCTTTGGCATACATT
CACAACAGCATTGGAGTATGCCACAGAGACATCAAGCCTCAAAATCTTCTGGTGAATCCACA
TACGCACCAATTGAAATTATGTGACTTCGGAAGTGCGAAAGTGTTGGTAAAAGGAGAACCAA
ATATTTCCTATATCTGTTCAAGGTACTATAGAGCCCCAGAGCTCATATTTGGTGCTACTGAA
TACACAACGGCAATTGACGTTTGGTCTGCTGGCTGTGTTCTTGCTGAACTCCTTCTAGGACA
GCCTATATTCCCTGGCGACAGTGGTGTTGATCAGCTTGTTGAAATCATCAAGGTTTTAGGTA
CCCCTACAAGAGAAGAAATTAAGTGCATGAATCCAAATTATACGGAGTTTAAATTCCCACAA
ATCAAAGCTCACCCATGGCACAAGATCTTCCATAAAAGAATGCCTGCTGAAGCAGTAGATCT
TGTCTCCAGACTCTTGCAATATTCACCAAGCCTGCGTTCAACTGCTTTGGAAGCATTAATTC
ATCCATTCTTCGATGAACTCCGGGACCCAAACACCCGTTTGCCGAACGGCCGTTTTCTTCCT
CCCCTCTTTAACTTTAAGCCCCATGAGTTGAAGGGTGTGCCGATGGACATCCTGGTGAAGCT
CATCCCTGAACATGCTCGGAAGAACTGTGCCTTTGTAGGATGGTGATCCGCCAGACGGCTGC
TTGAAGTTTAGTTCAGAACAAATCCAGTTGTTGTCTACTAGAAACCCCAGGAGTTTGAGATT
GTCTGCAGCCACACGGGATATAGGCGATGACACATGTGATTATTATTCCTTTTCTCGTCCGA
GACCTCGATGCCATGTATTCTTTCCCCCTACTGCCGATGTAACAAACCACCCATGATACTGT
AAGTAGATGAGAAGTGTTTCGACCGTTTTCCCCTGAGCTCATGTGCTATGCAATGAAGGATG
CACCCTATGTACCGCCAATATTTGGTCCAGTATTTGTTCATGGATCGAGGCCCCCAAAAAAA
AAAAAAAAAAAAAAAAAAAAAA

**SEQ ID NO 175 - *Triticum aestivum* - AAM77397 - GSK-like kinase**

MGNMSIRDDRDPEDIVVNGNGTEPGHIIVTSIEGRNGQAKQTISYMAERVVGNGSFGTVFQA
KCLETGETVAIKKVLQDKRYKNRELQTMRVLDHPNVVALKHCFFSKTEKEELYLNLVLEYVP
ETAHRVIKHYNKMNQRMPLIYAKLYMYQICRSLAYIHNSIGVCHRDIKPQNLLVNPHTHQLK
LCDFGSAKVLVKGEPNISYICSRYYRAPELIFGATEYTTAIDVWSAGCVLAELLLGQPIFPG
DSGVDQLVEIIKVLGTPTREEIKCMNPNYTEFKFPQIKAHPWHKIFHKRMPAEAVDLVSRLL
QYSPSLRSTALEALIHPFFDELRDPNTRLPNGRFLPPLFNFKPHELKGVPMDILVKLIPEHA
RKNCAFVGW

FIGURE 16 (continued)

**SEQ ID NO 176 - *Petunia hybrida* - X83619 - SHAGGY kinase 4**

TCTCTCAGGTTTAGGGTTTCGTATTGTCCGATCGCTATACTTTGAAGCTCTTTCCGATCACT
GTTTTGTGTTTTTGTAAAATGTGAGCTGTTCTTTAGCTACAGGTTTGAAGCTGTTAATCTGT
CATTTGAGTTGTGCCCATTACTCAGTAGTATAAGTAAGTTTATTTTTGTTGCTGATATGGCG
TCTGGTATAATGCCTTCGGCTGGTGGAAAACATCGAACTGATGCCATGCTTGTTGACAAACT
TCCCGAAGAAATAAATGAAATGAAGATCAGAGATGATAAAGCAGAAAAGGAAATGGAAGCAG
CTGTAGTGGATGGAAATGGAACTGAAAAAGGCCACATCATCGTGACAACTATTGGGGGCAAA
AATGGTGAGCCTAAGCAGACCATTAGTTACATGGCCGAGCGTGTTGTTGGACAGGGTTCGTT
TGGAATAGTGTTCCAGGCCAAATGCCTTGAAACTGGAGAAACTGTTGCAATAAAAAAGGTTT
TACAGGATAAGAGATACAAGAATCGGGAATTGCAAACAATACGCCTTCTAGATCATCCTAAT
GTTGTTGCACTGAGGCACTGCTTCTTTTCAACCACAGAAAAGGATGAGCTTTATCTGAATTT
GGTCCTTGAATATGTACCAGAGACTGTCTACCGTGTCTTGAGACATTACAGCAAAGCAAACC
AACAGATGCCTATGATTTATGTCAAGCTCTACACATATCAGATTTTCAGAGCTTTGGCCTAC
ATACACGGCATAGGAGTCTGCCACAGGGACATCAAGCCTCAGAATCTACTGGTCAACCCCCA
CACCCACCAGCTTAAGCTCTGCGACTTTGGGAGTGCAAAAGTTCTGGTCAAAGGCGAACCAA
ATATTTCATATATTTGTTCTCGTTACTATCGTGCACCCGAACTTATATTCGGAGCAACTGAA
TACACTTTTGCAATTGACATTTGGTCTGTGGGTTGCGTCCTTGCCGAACTGCTTCTGGGGCA
GCCCCTCTTTCCTGGTGAGAGTGGAGTTGATCAGCTTGTTGAAATAATCAAGGTTCTTGGAA
CACCAACTCGGGAGGAAATCAAGAGTATGAATCCAAATTACACTGAGTTCAAATTCCCACAA
ATCAAAGCTCACCCTTGGCACAAAATTTTTCATAAGCGGATGCCTCCAGAAGCTGTGGACCT
TGTGTCAAGGCTTCTCCAATATTCTCCAAATTTGAGGTCCACTGCGTTGGAGGCTTGCACTC
ACACTTTCTTTGATGAACTCCGTGATCCTAAGACTCGCCTCCCTAATGGTCGGCCATTGCCA
CCTCTTTTCAACTTCAGGCCTCAAGAGCTGAAAGGAGCGTCGGCAGACCTCTTAAACAAGCT
GATACCAGAACATGCTAAGAAGCAGTGTACCTTTCTTGGTGTCTAGGTTTATGAATGTTGTG
TATCTATTGTATACTTGAAATATTTTGCAACCACTGGTTAATTCTCTACTTTGGCTAAACCT
GTTTGACATGTCTTCCTTTCCATGAAAACTTATAACTGAAACCACATTGTGTAAGTTGTTCC
TAGTAGTGCAAATGCTATTTACTTGAACTTG

**SEQ ID NO 177 - *Petunia hybrida* - CAA58594 - SHAGGY kinase 4**

MASGIMPSAGGKHRTDAMLVDKLPEEINEMKIRDDKAEKEMEAAVVDGNGTEKGHIIVTTIG
GKNGEPKQTISYMAERVVGQGSFGIVFQAKCLETGETVAIKKVLQDKRYKNRELQTIRLLDH
PNVVALRHCFFSTTEKDELYLNLVLEYVPETVYRVLRHYSKANQQMPMIYVKLYTYQIFRAL
AYIHGIGVCHRDIKPQNLLVNPHTHQLKLCDFGSAKVLVKGEPNISYICSRYYRAPELIFGA
TEYTFAIDIWSVGCVLAELLLGQPLFPGESGVDQLVEIIKVLGTPTREEIKSMNPNYTEFKF
PQIKAHPWHKIFHKRMPPEAVDLVSRLLQYSPNLRSTALEACTHTFFDELRDPKTRLPNGRP
LPPLFNFRPQELKGASADLLNKLIPEHAKKQCTFLGV

FIGURE 16 (continued)

**SEQ ID NO 178 - *Oryza sativa* - GOS2 promoter** aatccgaaaagtttctgcaccgttttcacccccctaactaacaatatagggaacgtgtgctaa
atataaaatgagaccttatatatgtagcgctgataactagaactatgcaagaaaaactcatc
cacctactttagtggcaatcgggctaaataaaaaagagtcgctacactagtttcgttttcct
tagtaattaagtgggaaaatgaaatcattattgcttagaatatacgttcacatctctgtcat
gaagttaaattattcgaggtagccataattgtcatcaaactcttcttgaataaaaaaatctt
tctagctgaactcaatgggtaaagagagagatttttttaaaaaaatagaatgaagatattc
tgaacgtattggcaaagatttaaacatataattatataatttatagtttgtgcattcgtca
tatcgcacatcattaaggacatgtcttactccatcccaatttttatttagtaattaaagaca
attgacttattttattatttatctttttcgattagatgcaaggtacttacgcacacactt
tgtgctcatgtgcatgtgtgagtgcacctcctcaatacacgttcaactagcaacacatctct
aatatcactcgcctatttaatacatttaggtagcaatatctgaattcaagcactccaccatc
accagaccacttttaataatatctaaaatacaaaaaataattttacagaatagcatgaaaag
tatgaaacgaactatttaggtttttcacatacaaaaaaaaaaagaattttgctcgtgcgcga
gcgccaatctcccatattgggcacacaggcaacaacagagtggctgcccacagaacaaccca
caaaaaacgatgatctaacggaggacagcaagtccgcaacaacctttaacagcaggctttg
cggccaggagagagaggaggagaggcaaagaaaaccaagcatcctcctcctcccatctataaat
tcctcccccctttcccctctctatataggaggcatccaagccaagaagagggagagcacca
aggacacgcgactagcagaagccgagcgaccgccttcttcgatccatatcttccggtcgagt
tcttggtcgatctcttccctcctccacctcctcctcacagggtatgtgcccttcggttgttc
ttggatttattgttctaggttgtgtagtacgggcgttgatgttaggaaaggggatctgtatc
tgtgatgattcctgttcttggatttgggatagaggggttcttgatgttgcatgttatcggtt
cggtttgattagtagtatggttttcaatcgtctggagagctctatggaaatgaaatggttta
gggtacggaatcttgcgattttgtgagtacctttttgtttgaggtaaaatcagagcaccggtg
attttgcttggtgtaataaaagtacggttgtttggtcctcgattctggtagtgatgcttctc
gatttgacgaagctatcctttgtttattccctattgaacaaaaataatccaactttgaagac
ggtcccgttgatgagattgaatgattgattcttaagcctgtccaaaatttcgcagctggctt
gtttagatacagtagtccccatcacgaaattcatggaaacagttataatcctcaggaacagg
ggattccctgttcttccgatttgctttagtcccagaatttttttcccaaatatcttaaaaa
gtcactttctggttcagttcaatgaattgattgctacaaataatgcttttatagcgttatcc
tagctgtagttcagttaataggtaataccccctatagtttagtcaggagaagaacttatccga
tttctgatctccattttttaattatatgaaatgaactgtagcataagcagtattcatttggat
tattttttttattagctctcaccccttcattattctgagctgaaagtctggcatgaactgtc
ctcaattttgttttcaaattcacatcgattatctatgcattatcctcttgtatctacctgta
gaagtttcttttggttattccttgactgcttgattacagaaagaaatttatgaagctgtaa
tcgggatagttatactgcttgttcttatgattcatttcctttgtgcagttcttggtgtagct
tgccactttcaccagcaaagttc

SEQ ID NO 179 - sense primer: prm5797 ggggacaagtttgtacaaaaaagcaggcttaaacaatgggttcagtaggggttg

SEQ ID NO 180 - antisense primer: prm5798 ggggaccactttgtacaagaaagctgggtgaagctgtctcatactcctgc

FIGURE 16 (continued)

**SEQ ID NO 181 - *Oryza sativa* - beta-expansin promoter**

```
aaaaccaccgagggacctgatctgcaccggttttgatagttgagggacccgttgtgtctggt
tttccgatcgagggacgaaaatcggattcggtgtaaagttaagggacctcagatgaacttat
tccggagcatgattgggaagggaggacataaggcccatgtcgcatgtgtttggacggtccag
atctccagatcactcagcaggatcggccgcgttcgcgtagcacccgcggtttgattcggctt
cccgcaaggcggcggccggtggccgtgccgccgtagcttccgccggaagcgagcacgccgcc
gccgccgacccggctctgcgtttgcaccgccttgcacgcgatacatcgggatagatagctac
tactctctccgtttcacaatgtaaatcattctactattttccacattcatattgatgttaat
gaatatagacatatatatctatttagattcattaacatcaatatgaatgtaggaaatgctag
aatgacttacattgtgaattgtgaaatggacgaagtacctacgatggatggatgcaggatca
tgaaagaattaatgcaagatcgtatctgccgcatgcaaaatcttactaattgcgctgcatat
atgcatgacagcctgcatgcgggcgtgtaagcgtgttcatccattaggaagtaaccttgtca
ttacttataccagtactacatactatatagtattgatttcatgagcaaatctacaaaactgg
aaagcaataaggaatacgggactggaaaagactcaacattaatcaccaaatatttcgccttc
tccagcagaatatatatctctccatcttgatcactgtacacactgacagtgtacgcataaac
gcagcagccagcttaactgtcgtctcaccgtcgcacactggccttccatctcaggctagctt
tctcagccacccatcgtacatgtcaactcggcgcgcgcacaggcacaaattacgtacaaaac
gcatgaccaaatcaaaaccaccggagaagaatcgctcccgcgcgcggcggcggcgcgcacgt
acgaatgcacgcacgcacgcccaaccccacgacacgatcgcgcgcgacgccggcgacaccgg
ccatccacccgcgccctcacctcgccgactataaatacgtaggcatctgcttgatcttgtca
tccatctcaccaccaaaaaaaaggaaaaaaaaacaaaacacaccaagccaaataaaagcga
caa
```

FIGURE 16 (continued)

PLANTS HAVING IMPROVED GROWTH CHARACTERISTICS AND A METHOD FOR MAKING THE SAME

RELATED APPLICATIONS

This application is a continuation-in-part of International Application PCT/EP2006/068190 filed Nov. 7, 2006, which claims benefit of European Application EP 05110413.1 filed Nov. 7, 2005, European Application EP 05110429.7 filed Nov. 7, 2005, European Application EP 05110900.7 filed Nov. 17, 2005, European Application EP 05111260.5 filed Nov. 24, 2005, U.S. Provisional Application 60/736,194 filed Nov. 14, 2005, U.S. Provisional Application 60/739,686 filed Nov. 23, 2005, and U.S. Provisional Application 60/742,287 filed Dec. 5, 2005. The disclosure of each of the above-mentioned applications is incorporated herein by reference in its entirety.

SUBMISSION ON COMPACT DISC

The contents of the following submission on compact disc-sis incorporated herein by reference in its entirety: two copies of the Sequence Listing (COPY 1 and COPY 2) and a computer readable form copy of the Sequence Listing (CRF COPY), all on compact disc, each containing: file name: Sequence Listing-14546-00016; date recorded: Apr. 30, 2007; size: 453 KB.

FIELD OF THE INVENTION

The present invention relates generally to the field of molecular biology and concerns a method for improving plant growth characteristics relative to corresponding wild type plants or other control plants. More specifically, the present invention concerns a method for improving plant growth characteristics comprising modulating expression in a plant of a nucleic acid encoding a class I homeodomain leucine zipper (HDZip) hox5 polypeptide or a homologue thereof; or comprising modulating expression in a plant of a nucleic acid encoding a nitrate transporter protein (NRT) or a homologue thereof; or comprising modulating expression in a plant of a nucleic acid encoding a polypeptide denoted Yield Enhancing Protein 16 (hereinafter referred to as YEP16) or a homologue thereof; or comprising modulating expression in a plant of a nucleic acid encoding a Group I glycogen synthase kinase (Group I shaggy-like kinase) or a homologue thereof. The present invention also concerns plants having modulated expression of a nucleic acid encoding a class I HDZip hox5 polypeptide or a homologue thereof; or having modulated expression of a nucleic acid encoding an NRT polypeptide or a homologue thereof; or having modulated expression of a nucleic acid encoding a YEP16; or having modulated expression of a nucleic acid encoding a Group I shaggy-like kinase) or a homologue thereof, which plants have improved growth characteristics relative to corresponding wild type or other control plants. The invention also provides constructs useful in the methods of the invention.

BACKGROUND OF THE INVENTION

The ever-increasing world population and the dwindling supply of arable land available for agriculture fuels research towards increasing the efficiency of agriculture. Conventional means for crop and horticultural improvements utilise selective breeding techniques to identify plants having desirable characteristics. However, such selective breeding techniques have several drawbacks, namely that these techniques are typically labour intensive and result in plants that often contain heterogeneous genetic components that may not always result in the desirable trait being passed on from parent plants. Advances in molecular biology have allowed mankind to modify the germplasm of animals and plants. Genetic engineering of plants entails the isolation and manipulation of genetic material (typically in the form of DNA or RNA) and the subsequent introduction of that genetic material into a plant. Such technology has the capacity to deliver crops or plants having various improved economic, agronomic or horticultural traits.

A trait of particular economic interest is yield. Yield is normally defined as the measurable produce of economic value from a crop. This may be defined in terms of quantity and/or quality. Yield is directly dependent on several factors, for example, the number and size of the organs, plant architecture (for example, the number of branches), seed production leaf scenescence and more. Root development, nutrient uptake and stress tolerance and early vigour may also be important factors in determining yield. Optimizing one of the abovementioned factors may therefore contribute to increasing crop yield.

Seed yield is a particularly important trait, since the seeds of many plants are important for human and animal nutrition. Crops such as, corn, rice, wheat, canola and soybean account for over half the total human caloric intake, whether through direct consumption of the seeds themselves or through consumption of meat products raised on processed seeds. They are also a source of sugars, oils and many kinds of metabolites used in industrial processes. Seeds contain an embryo (the source of new shoots and roots) and an endosperm (the source of nutrients for embryo growth during germination and during early growth of seedlings). The development of a seed involves many genes, and requires the transfer of metabolites from the roots, leaves and stems into the growing seed. The endosperm, in particular, assimilates the metabolic precursors of carbohydrates, oils and proteins and synthesizes them into storage macromolecules to fill out the grain.

Plant biomass is yield for forage crops like alfalfa, silage corn and hay. In particular root biomass is yield for crops such as potato, manioc or sugarbeet. Many proxies for yield have been used in grain crops. Chief amongst these are estimates of plant size. Plant size can be measured in many ways depending on species and developmental stage, but include total plant dry weight, above-ground dry weight, above-ground fresh weight, leaf area, stem volume, plant height, rosette diameter, leaf length, root length, root mass, tiller number and leaf number. Many species maintain a conservative ratio between the size of different parts of the plant at a given developmental stage. These allometric relationships are used to extrapolate from one of these measures of size to another (e.g. Tittonell et al. (2005) Agric Ecosys & Environ 105: 213). Plant size at an early developmental stage will typically correlate with plant size later in development. A larger plant with a greater leaf area can typically absorb more light and carbon dioxide than a smaller plant and therefore will likely gain a greater weight during the same period (Fasoula & Tollenaar (2005) Maydica 50: 39). This is in addition to the potential continuation of the micro-environmental or genetic advantage that the plant had to achieve the larger size initially. There is a strong genetic component to plant size and growth rate (e.g. ter Steege et al. (2005) Plant Physiology 139:1078), and so for a range of diverse genotypes plant size under one environmental condition is likely to correlate with size under another (Hittalmani et al. (2003) Theoretical Applied Genetics 107:679). In this way a standard environment is used as a proxy for the diverse and dynamic environments encountered at different locations and times by crops in the field.

Harvest index, the ratio of seed yield to aboveground dry weight, is relatively stable under many environmental conditions and so a robust correlation between plant size and grain yield can often be obtained (e.g. Rebetzke et al. (2002) Crop Science 42:739). These processes are intrinsically linked because the majority of grain biomass is dependent on current or stored photosynthetic productivity by the leaves and stem of the plant (Gardener et al. (1985) Physiology of Crop Plants. Iowa State University Press, pp 68-73). Therefore, selecting for plant size, even at early stages of development, has been used as an indicator for future potential yield (e.g. Tittonell et al. (2005) Agric Ecosys & Environ 105: 213). When testing for the impact of genetic differences on stress tolerance, the ability to standardize soil properties, temperature, water and nutrient availability and light intensity is an intrinsic advantage of greenhouse or plant growth chamber environments compared to the field. However, artificial limitations on yield due to poor pollination due to the absence of wind or insects, or insufficient space for mature root or canopy growth, can restrict the use of these controlled environments for testing yield differences. Therefore, measurements of plant size in early development, under standardized conditions in a growth chamber or greenhouse, are standard practices to provide indication of potential genetic yield advantages.

Another trait of importance is that of improved abiotic stress tolerance. Abiotic stress is a primary cause of crop loss worldwide, reducing average yields for most major crop plants by more than 50% (Wang et al. (2003) Planta 218: 1-14). Abiotic stresses may be caused by drought, salinity, extremes of temperature, chemical toxicity, excess or lack of nutrients (macroelements and/or microelements), radiation and oxidative stress. The ability to increase plant tolerance to abiotic stress would be of great economic advantage to farmers worldwide and would allow for the cultivation of crops during adverse conditions and in territories where cultivation of crops may not otherwise be possible.

The ability to increase plant yield would have many applications in areas such as agriculture, including in the production of ornamental plants, arboriculture, horticulture and forestry. Increasing yield may also find use in the production of algae for use in bioreactors (for the biotechnological production of substances such as pharmaceuticals, antibodies or vaccines, or for the bioconversion of organic waste) and other such areas.

Homeodomain Leucine Zipper (HDZiP) Proteins

Homeodomain leucine zipper (HDZip) proteins constitute a family of transcription factors characterized by the presence of a DNA-binding domain (HD) and an adjacent leucine zipper (Zip) motif. The homeodomain usually consists of 60 conserved amino acid residues that form a helix1-loop-helix2-turn-helix3 that binds DNA. This DNA binding site is usually pseudopalindromic. The leucine zipper, adjacent to the C-terminal end of the homeodomain, consists of several heptad repeats (at least four) in which usually a leucine (occasionally a valine or an isoleucine) appears every seventh amino acid. The leucine zipper is important for protein dimerisation. This dimerisation is a prerequisite for DNA binding (Sessa et al. (1993) EMBO J 12(9): 3507-3517), and may proceed between two identical HDZip proteins (homodimer) or between two different HDZip proteins (heterodimer).

Homeodomain genes are present in all eucaryotes, and constitute a gene family of at least 89 members in *Arabidopsis thaliana*. The leucine zipper is also found by itself in eukaryotes other than plants. However, the presence of both a homeodomain and a leucine zipper is plant-specific (found in at least 47 out of the 89 proteins in *Arabidopsis*), and has been encountered in moss in addition to vascular plants (Sakakibara et al. (2001) Mol Biol Evol 18(4): 491-502). The leucine zipper is then located at the C-terminal end of the homeodomain, these two features overlapping by three amino acids.

The *Arabidopsis* HDZip genes have been classified into four different classes, HDZip I to IV, based on sequence similarity criteria (Sessa et al. (1994) *In* Plant Molec Biol, pp 412-426). Like the HD-Zip proteins from the three other classes, class I HDZip proteins are quite divergent in their primary amino structure outside of the homeodomain and the leucine zipper. Within both the homeodomain and the leucine zipper, class I HDZip proteins are further characterized by two specific features:

1) in the homeodomain, in addition to the invariant amino acids $Leu_{16}Trp_{48}Phe_{4}9Asn_{51}Arg_{53}$, position 46 is occupied by an Ala (A) and position 56 by a Try (W) (or occasionally by a Phe (F)) (Sessa et al. (1997) J Mol Biol 274(3):303-309; see FIG. 1), referred to as a class I homeodomain, and
2) the leucine zipper comprises six heptads, except for the fern *Ceratopteris richardii* which presents seven heptads (within each heptad, positions are named a, b, c, d, e, f and 9, the conserved leucine being at position d; Sakakibara et al. (2001) Mol Biol Evol 18(4): 491-502; see FIG. 2). HDZip II, III and IV present a leucine zipper with five heptads only.

Concerning their DNA binding properties, class I HDZip proteins preferably bind to 5 bp half-sites that overlap at a central position, CAA(A/T)ATTG (Sessa et al. (1993) EMBO J 12(9): 3507-3517).

Different HDZip proteins have been shown to either activate or repress transcription. In *Arabidopsis*, the class I HDZip ATHB1, -5, -6, and -16 were shown to act as transcriptional activators in transient expression assays on *Arabidopsis* leaves using a reporter gene (luciferase; Henriksson et al. (2005) Plant Phys 139: 509-518). Two rice class I HDZip proteins, Oshox4 and Oshox5, acted as activators in transient expression assays on rice cell suspension cultures using another reporter gene (glucuronidase; Meijer et al. (2000) Mol Gen Genet 263:12-21). In contrast, two rice class II HDZip proteins, Oshox1 and Oshox3, acted as transcriptional repressors in the same experiments (Meijer et al. (1997) Plant J 11: 263-276; Meijer et al. (2000) supra).

Several class I HDZip proteins have been shown to be involved in light response and in abscisic acid (ABA)/water deficit related response (Hjellström et al., (2003) Plant Cell Environ 26: 1127-1136). Transgenic *Arabidopsis* overexpressing class I HDZip ATHB1, -3, -13, -20, and -23 suggest that these genes are involved in the regulation of cotyledon and leaf development (Aoyama et al. (1995) Plant Cell 7: 1773-1785; Hanson (2000) *In* Comprehensive summaries of Uppsala Dissertations from the Faculty of Science and Technology, Uppsala). The ATHB3, -13, -20, and -23 genes are similar and form a distinct subclass within the class I HDZip. Since these genes cause similar alterations in cotyledon shape when expressed constitutively, they are referred to as the pointed cotyledon (POC) HDZip genes. Hanson concludes that class I HDZip proteins that are closely related phylogenetically are also functionally related, in most cases.

Nitrate Transporter Proteins (NRT)

Plants lead a sessile life and have to rely on resources in the soil for their nutrition. Nitrogen in soil is mainly present as ammonium or nitrate. Nitrate uptake by the plants may occur via three $NO_3^-$ uptake systems: a low affinity transport system that is active when the $NO_3^-$ concentration is more than 1 mM, a constitutive and an inducible high affinity transport system, both for $NO_3^-$ concentrations between 1 μM and 1 mM. The three uptake systems are regulated in a complex way. Once taken up, nitrate is transported into the vacuole or reduced to nitrite, which on its turn is further metabolised in the chloroplast. Nitrate may also be secreted again in the apoplasm or into the xylem for transport to the shoot. Proteins for uptake of nitrate in root cells (NRT, NitRate Transporter proteins) belong to the so-called Major Facilitator Superfamily, which encompasses proteins involved in transport of small solutes and which are generally 450 to 600 amino acids in length with 12 transmembrane domains. NRT proteins fall into two families, NRT1 and NRT2 (Crawford & Glass, Trends Plant Sci. 3, 389-395, 1998) and are encoded by a multigene family. NRT proteins are highly conserved in their sequence, for example, NRT2 proteins from mosses share 60% sequence identity with NRT2 protein from dicotyledonous plants, within the group of dicotyledonous plants the sequence identity among NRT2 proteins is around 81%, which may amount up to 89% for monocotyledonous NRT2 proteins. The NRT2 family of proteins in *Arabidopsis* was extensively studied by Orsel et al. (Plant Physiol. 129, 886-896, 2002). The family comprises 7 members, distributed over three chromosomes. The protein structure is conserved and five of the seven NRT2 proteins are preferentially expressed in the roots of young plants. Structurally, NRT2 proteins comprise a MFS_1 domain that spans about 90% of the protein and a C-terminal transmembrane domain. The MFS_1 domain itself is predicted to comprise 10 or 11 transmembrane domains.

NRT2 proteins are proposed to be mainly involved in the high affinity transport system. In higher plants, this high affinity uptake system is postulated to be controlled by a two-protein complex, consisting of NRT2 and NAR, a protein with an unclear function (Zhou et al. FEBS Letters 466, 225-227; Tong et al. Plant J. 41, 442-450, 2005). Overexpression of NRT2 increased the capacity of the high affinity uptake system (Fraisier et al. Plant J. 23, 489-496). NRT2 possibly also functions as a nitrate sensor (Little et al., Proc. Natl. Acad. Sci. USA 102, 13693-13698, 2005).

Mori et al. studied transgenic rice plants overexpressing the rice NRT2 gene and showed that nitrate starved seedlings had a better $NO_3^-$ uptake compared to wild type plants. Good et al. (US 20050044585) discloses transgenic plants with elevated levels of nitrogen utilisation proteins, and in particular aminotransferases, under control of a root specific promoter that may or may not be stress inducible. These plants showed improved nitrogen uptake efficiency, but no effects on seed yield were reported. In addition, this document also discloses that overexpression of nitrate transporter proteins in plants did not result in advantageous growth properties for these plants. Furthermore, NRT proteins have not been studied yet in normal growth conditions or for a complete plant life cycle.

Yield Enhancing Protein 16 (YEP16)

A YEP16 polypeptide shares some similarity with the N-terminal domain of the delta subunit of the F1F0-ATP synthase ATPase delta domain (see InterPro IPR000711 for details of the delta subunit).

Shaggy-Like Kinases

Plant shaggy-like kinases are encoded by a multigene family. The *Arabidopsis* genome has been found to contain ten shaggy-like kinase-encoding genes which fall into four distinct subfamilies. The protein sequences of distinct family members are highly conserved throughout the kinase domain, however the N- and C-terminal regions differ considerably indicating that the various plant shaggy-like kinases are involved in diverse biological processes, such as hormone signalling, development and stress responses. Based on protein sequence homology, the plant shaggy-like kinases can be classed into four groups (1-IV), with each of the four groups being involved in different processes (see FIG. 13). In addition to the full-length cDNA sequences available for *Arabidopsis thaliana* shaggy-like kinases, full-length cDNA sequences are also available in public databases for shaggy-like kinases from *Brassica napus, Medicago sativa, Nicotiana tabacum, Oryza sativa* and *Petunia hybrida* and *Zea mays*, among others. AtGSK1, a gene encoding a group II *Arabidopsis* shaggy-like kinase, has been reported to complement the salt sensitive phenotype of yeast calcineurin mutants. In seedlings, the production of the same shaggy-like kinase has been shown to be induced by NaCl and abscisic acid. Overproduction of the AtGSK1 gene has been reported to induce salt-stress-responsive genes and anthocyanin accumulation and to alter intracellular cation levels, which result in improved salt and drought tolerance.

Given that shaggy-like kinases from different groups are known to be involved in diverse biological processes, it was surprising to find shaggy-like kinases from two different groups to be involved in the same biological process, i.e. in stress responses. It was unexpected to find that a shaggy-like kinase from a group other than Group II was able to confer increased tolerance in plants to abiotic stress.

DETAILED DESCRIPTION OF THE INVENTION

It has now been found that modulating expression in a plant of a nucleic acid encoding a class I HDZip hox5 polypeptide or a homologue thereof; or modulating expression in a plant of a nucleic acid encoding a nitrate transporter protein (NRT) or a homologue thereof; or modulating expression in a plant of a nucleic acid encoding a YEP16 polypeptide; or modulating expression in a plant of a Group I shaggy-like kinase or a homologue thereof gives plants having improved growth characteristics relative to corresponding wild type plants or other control plants.

The present invention therefore provides a method for improving plant growth characteristics comprising modulating expression in a plant of a nucleic acid encoding a class I HDZip hox5 polypeptide or a homologue thereof; or comprising modulating expression in a plant of a nucleic acid encoding an NRT or a homologue thereof; or comprising modulating expression in a plant of a nucleic acid encoding a YEP16 polypeptide; or comprising modulating expression in a plant of a Group I shaggy-like kinase or a homologue thereof.

The choice of suitable control plants is a routine part of an experimental setup and may include corresponding wild type plants or corresponding plants without the gene of interest. The control plant is typically of the same plant species or even of the same variety as the plant to be assessed. The control plant may also be a nullizygote of the plant to be assessed. A "control plant" as used herein refers not only to whole plants, but also to plant parts, including seeds and seed parts.

Advantageously, performance of the methods according to the present invention results in plants having improved growth characteristics, particularly one or more of increased yield, improved growth, improved biomass, improved architecture, improved cell division and improved tolerance to abiotic stress relative to corresponding wild type or other control plants.

The term "increased yield" as defined herein is taken to mean an increase in any one or more of the following, each relative to corresponding wild type or other control plants: (i) increased biomass (weight) of one or more parts of a plant, particularly aboveground (harvestable) parts, or increased root biomass, increased root volume, increased root number, increased root diameter or increased root length (of thick or thin roots), or increased biomass of any other harvestable part; (ii) increased total seed yield, which includes an increase in seed biomass (seed weight) and which may be an increase in the seed weight per plant or on an individual seed basis and/or per hectare or acre; (iii) increased number of flowers (florets) per panicle, which is expressed as a ratio of number of filled seeds over number of primary panicles; (iv) increased seed fill rate (expressed in percentage terms as the proportion of the number of filled seeds over the number of florets); (v) increased number of (filled) seeds; (vi) increased seed size, which may also influence the composition of seeds; (vii) increased seed volume, which may also influence the composition of seeds (including oil, protein and carbohydrate total content and composition); (viii) increased (individual or average) seed area; (ix) increased (individual or average) seed length; (x) increased (individual or average) seed width; (xi) increased (individual or average) seed perimeter; (xii) increased harvest index (HI), which is expressed as a ratio of the yield of harvestable parts, such as seeds, over the total biomass; and (xiii) increased thousand kernel weight (TKW), which is extrapolated from the number of filled seeds counted and their total weight. An increased TKW may result from an increased seed size and/or seed weight. An increased TKW may result from an increase in embryo size and/or endosperm size.

Taking corn as an example, a yield increase may be manifested as one or more of the following: increase in the number of plants established per hectare or acre, an increase in the number of ears per plant, an increase in the number of rows, number of kernels per row, kernel weight, thousand kernel weight, ear length/diameter, increase in the seed filling rate (which is the number of filled seeds divided by the total number of seeds and multiplied by 100), among others. Taking rice as an example, a yield increase may manifest itself as an increase in one or more of the following: number of plants per hectare or acre, number of panicles per plant, number of spikelets per panicle, number of flowers (florets) per panicle (which is expressed as a ratio of the number of filled seeds over the number of primary panicles), increase in the seed filling rate (which is the number of filled seeds divided by the total number of seeds and multiplied by 100), increase in thousand kernel weight, among others.

Since the transgenic plants according to the present invention have increased yield, it is likely that these plants exhibit an increased growth rate (during at least part of their life cycle), relative to the growth rate of control plants at a corresponding stage in their life cycle. The increased growth rate may be specific to one or more parts of a plant (including seeds), or may be throughout substantially the whole plant. Plants having an increased growth rate may have a shorter life cycle. The life cycle of a plant may be taken to mean the time needed to grow from a dry mature seed up to the stage where the plant has produced dry mature seeds, similar to the starting material. This life cycle may be influenced by factors such as early vigour, growth rate, greenness index, flowering time and speed of seed maturation. The increase in growth rate may take place at one or more stages in the life cycle of a plant or during substantially the whole plant life cycle. Increased growth rate during the early stages in the life cycle of a plant may reflect enhanced vigour. The increase in growth rate may alter the harvest cycle of a plant allowing plants to be sown later and/or harvested sooner than would otherwise be possible (a similar effect may be obtained with earlier flowering time). If the growth rate is sufficiently increased, it may allow for the further sowing of seeds of the same plant species (for example sowing and harvesting of rice plants followed by sowing and harvesting of further rice plants all within one conventional growing period). Similarly, if the growth rate is sufficiently increased, it may allow for the further sowing of seeds of different plants species (for example the sowing and harvesting of rice plants followed by, for example, the sowing and optional harvesting of soybean, potato or any other suitable plant). Harvesting additional times from the same rootstock in the case of some crop plants may also be possible. Altering the harvest cycle of a plant may lead to an increase in annual biomass production per acre (due to an increase in the number of times (say in a year) that any particular plant may be grown and harvested). An increase in growth rate may also allow for the cultivation of transgenic plants in a wider geographical area than their wild-type counterparts, since the territorial limitations for growing a crop are often determined by adverse environmental conditions either at the time of planting (early season) or at the time of harvesting (late season). Such adverse conditions may be avoided if the harvest cycle is shortened. The growth rate may be determined by deriving various parameters from growth curves, such parameters may be: T-Mid (the time taken for plants to reach 50% of their maximal size) and T-90 (time taken for plants to reach 90% of their maximal size), amongst others.

Performance of the methods of the invention gives plants having an increased growth rate. Therefore, according to the present invention, there is provided a method for increasing the growth rate of plants relative to corresponding wild type or other control plants, which method comprises modulating expression in a plant of a nucleic acid encoding a class I HDZip hox5 polypeptide or a homologue thereof; or comprising modulating expression in a plant of a nucleic acid encoding an NRT or a homologue thereof; or comprising modulating expression in a plant of a nucleic acid encoding a YEP16 polypeptide; or comprising modulating expression in a plant of a Group I shaggy-like kinase or a homologue thereof.

An improvement of plant growth characteristics (particularly increased yield) occurs whether the plant is under non-stress conditions or whether the plant is exposed to various stresses compared to corresponding wild type plants or other control plants grown under comparable conditions. Plants typically respond to exposure to stress by growing more slowly. In conditions of severe stress, the plant may even stop growing altogether. Mild stress on the other hand is defined herein as being any stress to which a plant is exposed which does not result in the plant ceasing to grow altogether without the capacity to resume growth. Mild stress in the sense of the invention leads to a reduction in the growth of the stressed plants of less than 40%, 35% or 30%, preferably less than 25%, 20% or 15%, more preferably less than 14%, 13%, 12%, 11% or 10% or less in comparison to the control plant under non-stress conditions. Due to advances in agricultural practices (irrigation, fertilization, pesticide treatments) severe stresses are not often encountered in cultivated crop plants. As a consequence, the compromised growth induced by mild stress is often an undesirable feature for agriculture. Mild stresses (as used herein) are the everyday biotic and/or abiotic (environmental) stresses to which a plant is exposed. Abiotic stresses may be due to drought or excess water, anaerobic stress, salt stress, chemical toxicity, oxidative stress, reduced or excess nutrient availability stress, and hot, cold or freezing temperatures. The abiotic stress may be an osmotic stress caused by a water stress (particularly due to drought), salt stress, oxidative stress or an ionic stress. Biotic stresses are typically those stresses caused by pathogens, such as bacteria, viruses, nematodes, fungi and insects.

Performance of the methods of the invention gives plants having improved growth characteristics when grown under non-stress conditions or under mild stress conditions, relative to corresponding wild type or other control plants grown under comparable conditions. Therefore, according to the present invention, there is provided a method for improving growth characteristics of plants when grown under non-stress conditions or under mild stress conditions relative to corresponding wild type or other control plants grown under comparable conditions, which method comprises modulating expression in a plant of a nucleic acid encoding a class I HDZip hox5 polypeptide or a homologue thereof; or comprising modulating expression in a plant of a nucleic acid encoding an NRT or a homologue thereof; or comprising modulating expression in a plant of a nucleic acid encoding a YEP16 polypeptide; or comprising modulating expression in a plant of a Group I shaggy-like kinase or a homologue thereof.

The term "non-stress" conditions as used herein are preferably those environmental conditions that do not significantly go beyond the everyday climatic and other abiotic conditions that plants may encounter most preferably those conditions that allow optimal growth of plants. Persons skilled in the art are aware of normal soil conditions and climatic conditions for a given location.

Performance of the methods according to the present invention results in plants having improved tolerance to abiotic stress. As reported in Wang et al. (Planta (2003) 218: 1-14), abiotic stress leads to a series of morphological, physiological, biochemical and molecular changes that adversely affect plant growth and productivity. Drought, salinity, extreme temperatures and oxidative stress are known to be interconnected and may induce growth and cellular damage through similar mechanisms. For example, drought and/or salinisation are manifested primarily as osmotic stress, resulting in the disruption of homeostasis and ion distribution in the cell. Oxidative stress, which frequently accompanies high or low temperature, salinity or drought stress may cause denaturation of functional and structural proteins. Availability of one or more nutrients that need to be assimilated by the plants is rate limiting for their growth and development. Productivity of plants ordinarily is limited by three primary nutrients, phosphorous, potassium and nitrogen, the latter being the major nutritional element required for plant growth. Reduced nutrient availability (particularly, reduced nitrogen availability) has a major impact on protein accumulation and amino acid composition, and thus on plant growth. As a consequence, these diverse environmental stresses often activate similar cell signaling pathways and cellular responses, such as the production of stress proteins, reduced production of the other non-stress proteins, up-regulation of anti-oxidants, accumulation of compatible solutes and growth arrest.

Since diverse environmental stresses activate similar pathways, the exemplification of the present invention with plants grow under drought stress conditions, salt stress conditions and reduced nutrient availability conditions (insofar as the invention concerns the use of class I HDZip hox5 polypeptides and their encoding nucleic acids) should not be seen as a limitation to drought stress or salt stress or reduced nutrient availability stress, but more as a screen to indicate the involvement of class I HDZip hox5 polypeptides or a homologues thereof in abiotic stresses in general.

Because of the "cross talk" reported in the literature between different abiotic stresses, it would be apparent that a Group I shaggy-like kinase (as defined herein) would, along with its usefulness in conferring salt-tolerance in plants, also find use in protecting the plant against various other abiotic stresses.

Furthermore, Rabbani et al. (2003, Plant Physiol 133: 1755-1767) report that similar molecular mechanisms of stress tolerance and responses exist between dicots and monocots. The methods of the invention are therefore advantageously applicable to any plant.

The term "abiotic stress" as defined herein is taken to mean any one or more of: water stress (due to drought or excess water), anaerobic stress, salt stress, temperature stress (due to hot, cold or freezing temperatures), chemical toxicity stress, oxidative stress, excess or reduced nutrient availability. According to one aspect of the invention, the abiotic stress is an osmotic stress (selected from water stress, salt stress, oxidative stress, ionic stress) or a reduced nutrient availability stress. Preferably, the water stress is drought stress. The term salt stress is not restricted to common salt (NaCl), but may be any one or more of: NaCl, KCl, LiCl, $MgCl_2$, $CaCl_2$, amongst others. Preferably, the reduced nutrient availability is reduced nitrogen availability.

Improved tolerance to abiotic stress is manifested by plants with improved growth characteristics, in particular with increased yield, in abiotic stress conditions relative to corresponding wild type or other control plants grown under comparable conditions. Particularly insofar as the invention concerns the use of class I HDZip hox5 polypeptides and their encoding nucleic acids, such increased yield may include one or more of the following: increased total number of seeds, increased number of filled seeds, increased total seed yield, increased number of flowers per panicle, increased seed fill rate, increased HI, increased TKW, increased root length or increased root diameter, each relative to corresponding wild type plants.

According to the present invention, there is provided a method for improving abiotic stress tolerance in plants relative to corresponding wild type or other control plants grown under comparable conditions, which method comprises modulating expression in a plant of a nucleic acid encoding a class I HDZip hox5 polypeptide or a homologue thereof. According to one aspect of the invention, the abiotic stress is an osmotic stress (selected from one or more of the following: water stress, salt stress, oxidative stress and ionic stress) or a reduced nutrient availability stress. Preferably, the water stress is drought stress. Preferably, the reduced nutrient availability is reduced nitrogen availability.

The present invention also provides a method for improving abiotic stress tolerance in plants relative to corresponding wild type or other control plants grown under comparable conditions, comprising increasing activity in a plant of a Group I shaggy-like kinase or a homologue thereof, which Group I shaggy-like kinase has: (i) at least 77% sequence identity to the amino acid sequence represented by SEQ ID NO: 147; and (ii) motif I: R/HN/N/Q E/G LK G/N (SEQ ID NO: 182) and motif II: K Q/N CXXX G/A/S (SEQ ID NO: 183), where X may be any amino acid.

The present invention also provides a method for improving plant growth characteristics (particularly increasing yield) in plants grown under non-stress conditions or under mild drought conditions relative to corresponding wild type or other control plants grown under comparable conditions, which method comprises modulating expression (preferably increasing expression) in a plant of a nucleic acid encoding a NRT polypeptide or a homologue thereof. In a preferred embodiment of the invention, the increase in yield and/or growth rate occurs according to the methods of the present invention under non-stress conditions.

Particularly insofar as the invention concerns the use of class I HDZip hox5 polypeptides and their encoding nucleic acids, performance of the methods of the invention gives an increased greenness index relative to corresponding wild type plants or other control plants. The greenness index is calculated from the digital images of plants. For each pixel belonging to the plant object on the image, the ratio of the green value versus the red value (in the RGB model for encoding color) is calculated. The greenness index as defined herein is expressed as the percentage of pixels for which the green-to-red ratio exceeds a given threshold. An increased greenness index may indicate reduced or delayed senescence which in turn allows prolongation of the photosynthetic activity of a plant, which in turn leads to various beneficial effects well known in the art.

Therefore, according to the present invention, there is provided a method for increasing greenness index in plants, which method comprises modulating expression in a plant of a nucleic acid sequence encoding a class I HDZip hox5 polypeptide or a homologue thereof. Preferably, the greenness index is increased in abiotic stress growth conditions, preferably in osmotic stress growth conditions and/or reduced nutrient availability conditions.

Preferably, where the method of the invention comprises modulating expression in a plant of a nucleic acid encoding a class I HDZip hox5 polypeptide or a homologue thereof, the increased yield includes one or more of the following: increased total number of seeds, increased number of filled seeds, increased total seed yield, increased number of flowers per panicle, increased seed fill rate, increased HI, increased TKW, increased root length or increased root diameter, each relative to corresponding wild type or other control plants.

According to a preferred feature of the present invention, there is provided a method for increasing plant yield relative to corresponding wild type or other control plants, which method comprises modulating expression in a plant of a nucleic acid encoding a class I HDZip hox5 polypeptide or a homologue thereof.

Preferably, where the method of the invention comprises modulating expression in a plant of a nucleic acid encoding an NRT or a homologue thereof, the resultant plants have increased yield and more particularly, increased biomass and/or increased seed yield. Preferably, the increased seed yield comprises an increase in one or more of number of (filled) seeds, total seed weight, seed size, thousand kernel weight and harvest index, each relative to corresponding wild type or other control plants.

According to another preferred feature of the present invention, there is provided a method for increasing plant yield, which method comprises modulating expression (preferably increasing activity and/or expression) in a plant of a nucleic acid encoding an NRT polypeptide or a homologue thereof.

Preferably, where the method of the invention comprises modulating expression in a plant of a nucleic acid encoding a YEP16 polypeptide, the increased or improved yield is improved seed yield relative to the seed yield of corresponding wild type plants.

Therefore, according to another preferred feature of the present invention, there is provided a method for increasing seed yield in a plant relative to corresponding wild type or other control plants, comprising modulating expression in a plant of a nucleic acid encoding a YEP16 polypeptide or a homologue thereof.

Preferably, where the method of the invention comprises modulating expression in a plant of a nucleic acid encoding a Group I shaggy-like kinase or a homologue thereof, the improved growth characteristic is improved tolerance to abiotic stress.

According to the another preferred feature of the present invention, there is provided a method for improving abiotic stress tolerance in plants, comprising modulating expression (preferably increasing activity and/or expression) in a plant of a Group I shaggy-like kinase or a homologue thereof, which Group I shaggy-like kinase has: (i) at least 77% sequence identity to the amino acid sequence represented by SEQ ID NO: 147; and (ii) motif I: R/HN/N/Q E/G LK G/N (SEQ ID NO: 182) and motif II: K Q/N CXXX G/A/S (SEQ ID NO: 183), where X may be any amino acid.

The methods of the invention are therefore advantageously applicable to any plant.

The term "plant" as used herein encompasses whole plants, ancestors and progeny of the plants and plant parts, including seeds, shoots, stems, leaves, roots (including tubers), flowers, and tissues and organs, wherein each of the aforementioned comprise the gene/nucleic acid of interest. The term "plant" also encompasses plant cells, suspension cultures, callus tissue, embryos, meristematic regions, gametophytes, sporophytes, pollen and microspores, again wherein each of the aforementioned comprises the gene/nucleic acid of interest.

Plants that are particularly useful in the methods of the invention include all plants which belong to the superfamily Viridiplantae, in particular monocotyledonous and dicotyledonous plants including fodder or forage legumes, ornamental plants, food crops, trees or shrubs selected from the list comprising *Acacia* spp., *Acer* spp., *Actinidia* spp., *Aesculus* spp., *Agathis australis, Albizia amara, Alsophila tricolor, Andropogon* spp., *Arachis spp, Areca catechu, Astelia fragrans, Astragalus cicer, Baikiaea pluriuga, Betula* spp., *Brassica* spp., *Bruguiera gymnorrhiza, Burkea africana, Butea frondosa, Cadaba farinosa, Calliandra spp, Camellia sinensis, Canna indica, Capsicum* spp., *Cassia* spp., *Centroema pubescens, Chaenomeles* spp., *Cinnamomum cassia, Coffea arabica, Colophospermum mopane, Coronillia varia, Cotoneaster serotina, Crataegus* spp., *Cucumis* spp., *Cupressus* spp., *Cyathea dealbata, Cydonia oblonga, Cryptomeria japonica, Cymbopogon* spp., *Cynthea dealbata, Cydonia oblonga, Dalbergia monetaria, Davallia divaricata, Desmodium* spp., *Dicksonia squarosa, Diheteropogon amplectens, Dioclea spp, Dolichos* spp., *Dorycnium rectum, Echinochloa pyramidalis, Ehrartia* spp., *Eleusine coracana, Eragrestis* spp., *Erythrina* spp., *Eucalyptus* spp., *Euclea schimperi, Eulalia villosa, Fagopyrum* spp., *Feijoa sellowiana, Fragaria* spp., *Flemingia spp, Freycinetia banksii, Geranium thunbergii, Ginkgo biloba, Glycine javanica, Gliricidia spp, Gossypium hirsutum, Grevillea* spp., *Guibourtia coleosperma, Hedysarum* spp., *Hemarthia altissima, Heteropogon contortus, Hordeum vulgare, Hyparrhenia rufa, Hypericum erectum, Hyperthelia dissoluta, Indigo incarnata, Iris* spp., *Leptarrhena pyrolifolia, Lespediza* spp., *Lettuca* spp., *Leucaena leucocephala, Loudetia simplex, Lotonus bainesii, Lotus* spp., *Macrotyloma axillare, Malus* spp., *Manihot esculenta, Medicago sativa, Metasequoia glyptostroboides, Musa sapientum, Nicotianum* spp., *Onobrychis* spp., *Ornithopus* spp., *Oryza* spp., *Peltophorum africanum, Pennisetum* spp., *Persea gratissima, Petunia* spp., *Phaseolus* spp., *Phoenix canariensis, Phormium cookianum, Photinia* spp., *Picea glauca, Pinus* spp., *Pisum sativum, Podocarpus totara, Pogonarthria fleckii, Pogonarthria squarrosa, Populus* spp., *Prosopis cineraria, Pseudotsuga menziesii, Pterolobium stellatum, Pyrus communis, Quercus* spp., *Rhaphiolepsis umbellata, Rhopalo-*

*stylis sapida, Rhus natalensis, Ribes grossularia, Ribes* spp., *Robinia pseudoacacia, Rosa* spp., *Rubus* spp., *Salix* spp., *Schyzachyrium sanguineum, Sciadopitys verticillata, Sequoia sempervirens, Sequoiadendron giganteum, Sorghum bicolor, Spinacia* spp., *Sporobolus fimbriatus, Stiburus alopecuroides, Stylosanthos humilis, Tadehagi spp, Taxodium distichum, Themeda triandra, Trifolium* spp., *Triticum* spp., *Tsuga heterophylla, Vaccinium* spp., *Vicia* spp., *Vitis vinifera, Watsonia pyramidata, Zantedeschia aethiopica, Zea mays*, amaranth, artichoke, asparagus, broccoli, Brussels sprouts, cabbage, canola, carrot, cauliflower, celery, collard greens, flax, kale, lentil, oilseed rape, okra, onion, potato, rice, soybean, strawberry, sugar beet, sugar cane, sunflower, tomato, squash, tea and algae, amongst others.

According to a preferred embodiment of the present invention, the plant is a crop plant such as soybean, sunflower, canola, alfalfa, rapeseed, cotton, tomato, potato or tobacco. Further preferably, the plant is a monocotyledonous plant, such as sugarcane. More preferably the plant is a cereal, such as rice, maize, wheat, barley, triticale, millet, rye, sorghum or oats.

Class I HDZip Hox5 Polypeptides and Homologues Thereof, and Class I HDZip Hox5 Nucleic Acids/Genes Useful in the Methods of the Invention The term "class I HDZip hox5 polypeptide or homologue thereof" as defined herein refers to a polypeptide comprising from N-terminal to C-terminal: (i) an acidic box; and (ii) a class I homeodomain; and (iii) a leucine zipper with more than 5 heptads.

Additionally, the class I HDZip hox5 polypeptide or a homologue thereof may comprise any one or both of the following: (a) a Trp tail; and (b) the RPFF amino acid motif, where R is Arg, P Pro and F Phe. Within this motif, are allowed one or more conservative change(s) at any position, and/or one or two non-conservative change(s) at any position. The motif of (b) precedes the acidic box, when examining the protein from N-terminal to C-terminal.

An example of a class I HDZip hox5 polypeptide as defined hereinabove comprising from N-terminal to C-terminal: (i) an acidic box; and (ii) a class I homeodomain; and (iii) a leucine zipper with more than 5 heptads; and additionally comprising: (a) a Trp tail; and (b) the RPFF amino acid motif, where R is Arg, P is Pro and F is Phe, is represented as in SEQ ID NO: 2. Further such examples are given in Table A of Example 1 herein.

A class I HDZip hox5 polypeptide or homologue thereof is encoded by a class I HDZip hox5 nucleic acid/gene. Therefore the term "class I HDZip hox5 nucleic acid/gene" as defined herein is any nucleic acid/gene encoding a class I HDZip hox5 polypeptide or a homologue thereof as defined hereinabove.

Class I HDZip hox5 polypeptides or homologues thereof may readily be identified using routine techniques well known in the art, such as by sequence alignment. Methods for the alignment of sequences for comparison are well known in the art, such methods include GAP, BESTFIT, BLAST, FASTA and TFASTA. GAP uses the algorithm of Needleman and Wunsch ((1970) J Mol Biol 48: 443-453) to find the alignment of two complete sequences that maximizes the number of matches and minimizes the number of gaps. The BLAST algorithm (Altschul et al. (1990) J Mol Biol 215: 403-10) calculates percent sequence identity and performs a statistical analysis of the similarity between the two sequences. The software for performing BLAST analysis is publicly available through the National Centre for Biotechnology Information. Homologues of class I HDZip hox5 comprising a class I homeodomain and a leucine zipper with more than 5 heptads may readily be identified using, for example, the ClustalW multiple sequence alignment algorithm (version 1.83) available at clustalw.genome.jp/sit-bin/nph-ClustalW, with the default pairwise alignment parameters, and a scoring method in percentage. Minor manual editing may be performed to optimise alignment between conserved motifs, as would be apparent to a person skilled in the art (see Example 2 and FIG. 2 herein).

The various structural domains in a class I HDZip hox5 protein, such as the homeodomain and the leucine zipper, may be identified using specialised databases e.g. SMART (Schultz et al. (1998) Proc. Natl. Acad. Sci. USA 95, 5857-5864; Letunic et al., (2002) Nucl Acids Res 30, 242-244; hosted by EMBL at Heidleberg), InterPro (Mulder et al., (2003) Nucl Acids Res. 31, 315-318), Prosite (Bucher and Bairoch (1994), A generalized profile syntax for biomolecular sequences motifs and its function in automatic sequence interpretation. (In) ISMB-94; Proceedings 2nd International Conference on Intelligent Systems for Molecular Biology. Altman R., Brutlag D., Karp P., Lathrop R., Searls D., Eds., pp 53-61, AAAIPress, Menlo Park; Hulo et al., Nucl. Acids. Res. 32:D134-D137, (2004)) or Pfam (Bateman et al., Nucl Acids Res 30(1):276-280 (2002)). Leucine zipper prediction and heptad identification may be done using specialised software such as 2ZIP, which combines a standard coiled coil prediction algorithm with an approximate search for the characteristic leucine repeat (Bornberg-Bauer et al. (1998) Computational Approaches to Identify Leucine Zippers, Nucl Acids Res, 26(11): 2740-2746). Results of domain Identification comprised in class I HDZip hox5 polypeptide sequences are presented in Example 4 of this application.

Furthermore, the presence of an acidic box may also readily be identified. Primary amino acid composition (in %) to determine if a polypeptide domain is rich in specific amino acids may be calculated using software programs from the ExPASy server, in particular the ProtParam tool (Gasteiger E et al. (2003) ExPASy: the proteomics server for in-depth protein knowledge and analysis. Nucleic Acids Res 31:3784-3788). The composition of the protein of interest may then be compared to the average amino acid composition (in %) in the Swiss-Prot Protein Sequence data bank. Within this databank, the average Asp (D) and Glu (E) content are of 5.3% and of 6.6% respectively, the combined average being of 11.9%. As an example, the acidic box of SEQ ID NO: 2 contains 9.1% of D and 54.5% of E, the combined average being of 63.6% (see Example 4 herein). As defined herein, an acidic rich box has a combined Asp (D) and Glu (E) content (in % terms) above that found in the average amino acid composition (in % terms) of the proteins in the Swiss-Prot Protein Sequence database. An acidic box may be part of a transcription activation domain. Eukaryotic transcription activation domains have been classified according to their amino acid content, and major categories include acidic, glutamine-rich and proline-rich activation domains (Rutherford et al. (2005) Plant J. 43(5):769-88, and references therein).

A selected number of proteins amongst the class I HDZip hox5 polypeptides or homologues thereof further comprise the RPFF amino acid motif, where R is Arg, P Pro and F Phe. Within this motif, are allowed one or more conservative change(s) at any position, and/or one or two non-conservative change(s) at any position. This motif precedes the acidic box, when examining the protein from N-terminal to C-terminal (see FIG. 2). The presence of the RPFF may be identified using methods for the alignment of sequences for comparison as described hereinabove. In some instances, the default parameters may be adjusted to modify the stringency of the search. For example using BLAST, the statistical significance threshold (called "expect" value) for reporting matches against database sequences may be increased to show less stringent matches. This way, short nearly exact matches may be identified.

A selected number of proteins amongst the class I HDZip hox5 polypeptides or homologues thereof may further comprise a Trp tail. A Trp tail as defined herein is the last 10 amino acids of the C-terminal of the protein comprising at least one Trp residue (see FIG. 2).

Examples of class I HDZip hox5 polypeptides or homologues thereof (encoded by polynucleotide sequence accession number in parenthesis) are given in Table A of Example 1.

It is to be understood that sequences falling under the definition of "class I HDZip hox5 polypeptide or homologue thereof" are not to be limited to the sequences given in Table A, but that any polypeptide comprising from N-terminal to C-terminal: (i) an acidic box; and (ii) a class I homeodomain; and (iii) a leucine zipper with more than 5 heptads, may be suitable for use in performance of the methods of the invention.

Class I HDZip hox5 polypeptides or homologues thereof have DNA binding activity, preferably to 5 bp half-sites that overlap at a central position, CAA(A/T)ATTG, as detected in yeast one-hybrid assays (Meijer et al. (2000) Mol Gen Genet 263:12-21). In transient assays on rice cell suspensions, co-bombardement of a class I HDZip hox5 polypeptide with the GUS reporter gene resulted in an increase number of stained spots, which were also more intense in color (Meijer et al, supra). This assay is useful to demonstrate the activator function of class I HDZip hox5 polypeptides or homologues.

NRT Polypeptides and Homologues Thereof and their Encoding Nucleic Acids Useful in the Methods of the Invention The term "NRT or homologue thereof" as defined herein refers to a polypeptide comprising (i) an MFS_1 domain (Pfam accession PF07690, InterPro accession IPR011701) followed by (ii) a transmembrane domain. An example is given in FIG. 6. Preferably, the NRT protein or homologue thereof has NRT activity such as high affinity nitrate transport, and does not comprise a PTR2 domain (Pfam accession PF00854, InterPro accession IPR000109).

Preferably, the NRT protein or homologue thereof comprises a signature sequence 1 (SEQ ID NO: 57):

(N/S)(Y/P)(T/G/S/A)W(I/V/L)(F/L/T)(V/A/F/L)(L/V/M/I)(L/T/I/A/N)YG(Y/F)(S/C/T)(M/F/Y)G(V/I)E L(T/S)(T/V)(D/G/N)N(V/I/N)(I/V)(A/S/H/V)(E/Q/G)Y.

Further preferably, the NRT protein or homologue thereof comprises one or more of: signature sequence 2 (SEQ ID NO: 58):

LG(P/A)RYG(C/T)AF(L/S);

signature sequence 3 (SEQ ID NO: 59):

STFAA(A/R)PL(V/I)(P/V)(I/L/V)IR(D/E)NL(N/D)(L/P);

signature sequence 4 (SEQ ID NO: 60):

VRF(L/M)IGF(S/C)LA;

signature sequence 5 (SEQ ID NO: 61):

FVSC(Q/R)YW(M/T)S(TN)(M/S)(F/M).

More preferably, the NRT protein or homologue thereof comprises one or more of:

signature sequence 6 (SEQ ID NO: 62):

K(A/Q/S/M/H/T)D(IN)GNAGVASV(S/T)G(S/A)I(F/L)SR(L/G);

signature sequence 7 (SEQ ID NO: 63):

NG(L/T/C)A(A/G)GWG;

signature sequence 8 (SE ID NO: 64):

G(A/S)G(L/V/Q)TQ(L/P)(L/V/I)(F/E)F(T/S/D)(S/T)(S/A/T).

Most preferably, the NRT protein is as represented in SEQ ID NO: 53.

Transmembrane domains are about 15 to 30 amino acids long and are usually composed of hydrophobic residues that form an alpha helix. They are usually predicted on the basis of hydrophobicity (for example Klein et al., Biochim. Biophys. Acta 815, 468, 1985; or Sonnhammer et al., In J. Glasgow, T. Littlejohn, F. Major, R. Lathrop, D. Sankoff, and C. Sensen, editors, Proceedings of the Sixth International Conference on Intelligent Systems for Molecular Biology, pages 175-182, Menlo Park, Calif., 1998. AAAI Press.).

Alternatively, the homologue of an NRT protein has in increasing order of preference 50%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, or 99% overall sequence identity to the amino acid represented by SEQ ID NO: 53. The overall sequence identity is determined using a global alignment algorithm, such as the Needleman Wunsch algorithm in the program GAP (GCG Wisconsin Package, Accelrys), preferably with default parameters.

The various structural domains in an NRT protein may be identified using specialised databases e.g. SMART (Schultz et al. (1998) Proc. Natl. Acad. Sci. USA 95, 5857-5864; Letunic et al. (2002) Nucleic Acids Res 30, 242-244; at smart.embl-heidelberg.de/), InterPro (Mulder et al., (2003) Nucl. Acids. Res. 31, 315-318; at ebi.ac.uk/interpro/), Prosite (Bucher and Bairoch (1994), A generalized profile syntax for biomolecular sequences motifs and its function in automatic sequence interpretation. (In) ISMB-94; Proceedings 2nd International Conference on Intelligent Systems for Molecular Biology. Altman R., Brutlag D., Karp P., Lathrop R., Searls D., Eds., pp 53-61, AAAIPress, Menlo Park; Hulo et al., Nucl. Acids. Res. 32:D134-D137, (2004), at expasy.org/prosite/) or Pfam (Bateman et al., Nucleic Acids Research 30(1):276-280 (2002), at sanger.ac.uk/Software/Pfam/).

Methods for the search and identification of NRT homologues would be well within the realm of persons skilled in the art. Such methods comprise comparison of the sequences represented by SEQ ID NO: 1 or 2, in a computer readable format, with sequences that are available in public databases such as MIPS (at mips.gsf.de/), GenBank (at ncbi.nlm.nih.gov/Genbank/index.html) or EMBL Nucleotide Sequence Database (at ebi.ac.uk/embl/index.html), using algorithms well known in the art for the alignment or comparison of sequences, such as GAP (Needleman and Wunsch, J. Mol. Biol. 48; 443-453 (1970)), BESTFIT (using the local homology algorithm of Smith and Waterman (Advances in Applied Mathematics 2; 482-489 (1981))), BLAST (Altschul, S. F., Gish, W., Miller, W., Myers, E. W. & Lipman, D. J., J. Mol. Biol. 215:403-410 (1990)), FASTA and TFASTA (W. R. Pearson and D. J. Lipman Proc. Natl. Acad. Sci. USA 85:2444-2448 (1988)). The software for performing BLAST analysis is publicly available through the National Centre for Biotechnology Information (NCBI).

Examples of proteins falling under the definition of "NRT polypeptide or a homologue thereof" include rice proteins and proteins from other species such as *Zea mays, Phragmites australis, Hordeum vulgare, Triticum aestivum, Brassica napus, Lycopersicon esculentum, Nicotiana tabacum, Daucus carota, Populus tremulus, Lotus japonica, Prunus persica, Glycine max* and *Arabidopsis thaliana*, among others. A non-limiting list of examples of NRT proteins is given in Table J of Example 15 herein.

It is however envisaged that NRT proteins from other plant taxa, such as mosses or ferns, may equally be useful in the methods of the present invention. For example, the moss *Physcomitrella patens* possesses at least 5 NRT proteins (GenBank accession numbers BAD00097, BAD00098, BAD00099, BAD00100, BAD00101).

It is to be understood that the term "NRT polypeptide or a homologue thereof" is not to be limited to the sequence represented by SEQ ID NO: 53 or to the sequences given in Table J, but that any polypeptide meeting the criteria of comprising a functional MFS_1 domain, and one or more of the conserved signature sequences of SEQ ID NO: 57 to 64, and a transmembrane domain located C-terminally of the MFS_1 domain as defined above; or having at least 50% sequence identity to the sequence of SEQ ID NO: 53, may be suitable for use in the methods of the invention.

To determine the transporter activity of NRT, the nitrate uptake assay as described by Tong et al. (*Plant J.* 41, 442-450, 2005). Briefly, the NRT protein of interest is expressed in *Xenopus* oocytes, and the uptake of $^{15}$N-enriched nitrate is measured. If required, a nar2 gene may be co-expressed to increase nitrate transport.

Alternatively, the activity of an NRT protein or homologue thereof may be assayed by expressing the NRT protein or homologue thereof under control of a GOS2 promoter in the *Oryza sativa* cultivar Nipponbare, which results in plants with increased aboveground biomass and/or increased seed yield compared to corresponding wild type plants. This increase in seed yield may be measured in several ways, for example as an increase of total seed weight, number of filled seeds or total number of seeds, as an increase of harvest index or as an increase of flowers per panicle.

An NRT protein or homologue thereof is encoded by an NRT nucleic acid/gene. Therefore the term "NRT nucleic acid/gene" as defined herein is any nucleic acid/gene encoding an NRT protein or a homologue thereof as defined above.

YEP16 Polypeptides and Homologues and Their Encoding Nucleic Acids Useful in the Methods of the Invention The term "YEP16 polypeptide" refers to the sequence of SEQ ID NO: 128. A homologue of a YEP16 polypeptide refers to any amino acid sequence sharing, in increasing order of preference, at least 30%, 35%, 40%, 45%, 50%, 55%, 60%, 65%, 70%, 75%, 80%, 85%, 90%, 95% sequence identity to the amino acid sequence of SEQ ID NO: 128. Reference herein to "a nucleic acid encoding a YEP16 polypeptide or a homologue thereof" therefore refers to any nucleic acid sequence encoding a YEP16 polypeptide as defined hereinabove or any nucleic acid encoding a homologue of a YEP16 polypeptide as defined hereinabove.

Group I Shaggy-Like Kinases and Homologues Thereof and their Encoding Nucleic Acids Useful in the Methods of the Invention The term "Group I shaggy-like kinase or homologue thereof" as defined herein refers to a polypeptide having: (i) at least 77% sequence identity to the amino acid sequence represented by SEQ ID NO: 147; and (ii) motif I: R/HN/N/Q E/G LK G/N (SEQ ID NO: 182) and motif II: K Q/N CXXX G/A/S (SEQ ID NO: 183), where X may be any amino acid. A polypeptide meeting the aforementioned requirements allows a Group I shaggy-like kinase to be distinguished from those of other groups.

A "Group I shaggy-like kinase or a homologue thereof" falling within the above definition may readily be identified using routine techniques well known to persons skilled in the art. For example, a polypeptide having at least 77% identity to the amino acid represented by SEQ ID NO: 147 may readily be established by sequence alignment. Methods for the alignment of sequences for comparison are well known in the art, such methods include GAP, BESTFIT, BLAST, FASTA and TFASTA. GAP uses the algorithm of Needleman and Wunsch (J. Mol. Biol. 48: 443-453, 1970) to find the alignment of two complete sequences that maximises the number of matches and minimises the number of gaps. The BLAST algorithm calculates percent sequence identity and performs a statistical analysis of the similarity between the two sequences. The software for performing BLAST analysis is publicly available through the National Centre for Biotechnology Information. A shaggy-like kinase or a homologue thereof having at least 77% identity to the amino acid represented by SEQ ID NO: 147 may readily be identified by aligning a query amino acid sequence with known Group I shaggy-like kinase sequences (see for example the alignment shown in FIG. 14) using, for example, the VNTI AlignX multiple alignment program, based on a modified clustal W algorithm (InforMax, Bethesda, Md., at informaxinc.com), with default settings for gap opening penalty of 10 and a gap extension of 0.05.

A person skilled in the art will also readily be able to identify sequences having motif I: R/H/V/N/Q E/G LK G/N (SEQ ID NO: 182) and motif II: K Q/N CXXX G/A/S (SEQ ID NO: 183), where X may be any amino acid. This may be achieved by making an alignment and searching for homologous regions.

Table 1 below shows motif I: R/H/V/N/Q E/G LK G/N (SEQ ID NO: 182) and motif II: K Q/N CXXX G/A/S (SEQ ID NO: 183; where X may be any amino acid) as found in the sequence of SEQ ID NO: 147 and the corresponding motifs in homologous sequences. The overall percentage identity shown in Table 1 is when comparing SEQ ID NO: 147 with the accession numbers shown in the Table (full-length sequence to full-length sequence).

TABLE 1

Conserved motifs found in Group I shaggy-like kinases and in homologues thereof

| Accession number: Group I shaggy-like kinase | Gene name | Motif 1 SEQ ID NO: 182 | Motif 2 SEQ ID NO: 183 | % overall identity with SEQ ID NO: 147 (EMBOSS) |
|---|---|---|---|---|
| BAB40983.1 (SEQ ID NO: 147) | Rice OSK gamma | HELKG | KQCSYAG | — |
| AY103545 | Corn | HELKG | KQCSYVG | 94.4% |
| AY108486 | Corn | HELKN | KQCAFVG | 84.4% |
| AAM77397.1 | Triticum | HELKG | KNCAFVG | 80.9% |
| CAA48538.1, At5g26750 | Ara ASK Alpha | HELKG | KQCPWLG | 85.6% |

TABLE 1-continued

Conserved motifs found in Group I shaggy-like kinases and in homologues thereof

| | Gene name | Motif 1 SEQ ID NO: 182 | Motif 2 SEQ ID NO: 183 | % overall identity with SEQ ID NO: 147 (EMBOSS) |
|---|---|---|---|---|
| CAA48474.1 | Medicago MSK-1 | HELKG | KQCPFLG | 83.5% |
| CAA04265 | Ara Ask alpha | HGLKG | KQCPWLG | 84.6% |
| CAA54803.1 | Tobacco NtK1 | HELKG | KQCPSLG | 85.3% |
| CAA48472.1 | Medicago MSK3 | NELKG | KQCALFG | 85.0% |
| CAA48473.1 | Medicago MSK2 | VELKG | KQCSLFA | 82.0% |
| CAA58594.1 | Petunia Shaggy 4 | QELKG | KQCTFLG | 81.5% |
| At5g14640 | Ara ASK epsilon | QELKG | KQCSFLA | 83.9% |
| At3g05840 | Ara ASK gamma | HELKG | KQCPWLS | 84.6% |
| CAA04265 | Rice shaggy alpha | HGLKG | KQCPWLG | 84.6% |
| AK058276 | Rice shaggy | HELKG | KQCAFVG | 83.2% |
| AK099599 | Rice Shaggy | RELKG | KQCAFLG | 78.5% |
| Other shaggy-like groups | | | | |
| At4g18710 | Ara Ask eta | No | No | 70.0% |
| At2g30980 | Ara Ask dzeta | No | No | 72.9% |
| At4g00720 | Ara Ask theta | No | No | 64.1% |
| At1g57870 | Ara Ask delta | No | No | 73.4% |
| At1g09840 | Ara Ask kappa | No | No | 72.4% |
| At1g06390 | Ara Ask iota | No | No | 71.6% |
| At3g61160 | Ara Ask beta | No | No | 61.3% |

Examples of polypeptides falling under the definition of a "shaggy-like kinase or a homologue thereof" include the following sequences: SEQ ID NO: 147, a gamma shaggy-like kinase from rice (NCBI Accession number AB059621); SEQ ID NO: 149 (NCBI Accession number AK058276) a shaggy-like kinase from rice; SEQ ID NO: 151 (NCBI Accession number AK099599) a shaggy like kinase from rice; SEQ ID NO: 153, an alpha shaggy-like kinase from *Arabidopsis thaliana* (NCBI Accession number At5g26750); SEQ ID NO: 155, a gamma shaggy-like kinase from *Arabidopsis thaliana* (NCBI Accession number At3g05840); SEQ ID NO: 157, an alpha shaggy-like kinase from *Arabidopsis thaliana* (NCBI Accession number CAA48538.1); SEQ ID NO: 159, an epsilon shaggy-like kinase from *Arabidopsis thaliana* (NCBI Accession number At5g14640); SEQ ID NO: 161, a gamma shaggy-like kinase from *Arabidopsis thaliana* (NCBI Accession number CAA73247.1); SEQ ID NO: 163 from maize (NCBI Accession number AY103545); SEQ ID NO: 165 from maize (NCBI Accession number AY108486.1); SEQ ID NO: 167 from *Medicago* (NCBI Accession number CAA48472.1); SEQ ID NO: 169 from *Medicago* (NCBI Accession number CAA48474.1); SEQ ID NO: 171 from *Medicago* (NCBI Accession number CAA48473.1); SEQ ID NO: 173 from tobacco (NCBI Accession number CAA54803.1); SEQ ID NO: 175 a protein prediction of a shaggy-like kinase from *Triticum aestivum* (NCBI Accession number AMM77397.1); SEQ ID NO: 177 from *Petunia hybrida* (NCBI Accession number CAA58594.1).

The "term shaggy-like kinase or a homologue thereof" is not to be limited to the sequences represented by the SEQ ID NOs mentioned in the aforementioned paragraph, but that any polypeptide meeting the criteria of having: (i) at least 77% sequence identity to the amino acid sequence represented by SEQ ID NO: 147; and (ii) motif I: R/HN/N/Q E/G LK G/N (SEQ ID NO: 182) and motif II: K Q/N CXXX G/A/S (SEQ ID NO: 183), where X may be any amino acid, would be suitable for use in the methods of the invention.

Shaggy-like kinases, as the name suggests, have kinase activity. An assay for glycogen synthase kinase-3 (GSK-3), the animal homologue, is reported in The Biochemical Journal, Vol. 303 (Pt3), Nov. 1, 1994, pp 701-704 (Stambolic and Woodgett).

Sequences useful in the methods of the invention are not limited to the aforementioned class I homeodomain leucine zipper (HDZip) hox5 nucleic acids and polypeptides (listed in Table A of Example 1); or to the aforementioned NRT polypeptides and their encoding nucleic acids; or to the aforementioned YEP16 polypeptides and their encoding nucleic acids; or to the aforementioned Group I shaggy-like kinases and their encoding polypeptides. The methods according to the present invention may also be performed using variants of nucleic acids encoding class I homeodomain leucine zipper (HDZip) hox5 polypeptides or homologues thereof; or using variants of nucleic acids encoding NRT polypeptides or homologues thereof; or using variants of nucleic acids encoding YEP16 polypeptides and homologues thereof; or using variants of nucleic acids encoding Group I shaggy-like kinases and homologues thereof Examples of such variants include portions, hybridizing sequences, allelic variants, splice variants and variants obtained by gene shuffling.

A portion may be prepared, for example, by making one or more deletions to a nucleic acid. The portions may be used in isolated form or they may be fused to other coding (or non coding) sequences in order to, for example, produce a protein that combines several activities. When fused to other coding sequences, the resulting polypeptide produced upon translation may be bigger than that predicted for the portion.

Where the sequence useful in the methods of the invention is a class I HDZip hox5, the portion encodes a polypeptide comprising from N-terminal to C-terminal: (i) an acidic box; and (ii) a class I homeodomain; and (iii) a leucine zipper with more than 5 heptads. Preferably, the portion is a portion of one of the nucleic acids given in Table A. Most preferably the portion is a portion of a nucleic acid as represented by SEQ ID NO: 1.

Where the sequence useful in the methods of the invention is a nucleic acid encoding an NRT, the portion refers to a piece of DNA encoding a polypeptide comprising a MFS_1 domain and a transmembrane domain located C-terminally of the MFS_1 domain. Preferably, the portion comprises one or more of the signature sequences defined above. Preferably, the portion is a portion of one of the nucleic acids given in Table J. Most preferably the portion of a nucleic acid is as represented by SEQ ID NO: 52.

Where the sequence useful in the methods of the invention is a YEP16-encoding nucleic acid, the portion refers to a piece of DNA encoding a YEP16 polypeptide or a homologue thereof having, in increasing order of preference, at least 100, 125, 150, 175, 200, 225, 250, 275, 300, 325, 350, 375, 400, 425, 450, 475, 500, 525, 550, 575 consecutive nucleotides of the nucleic acid sequence represented by SEQ ID NO: 127 or SEQ ID NO: 129, or wherein a portion has in increasing order of preference, at least 100, 125, 150, 175, 200, 225, 250, 275, 300, 325, 350, 375, 400, 425, 450, 475, 500, 525, 550, 575 consecutive nucleotides of a nucleic acid sequence encoding a YEP16 polypeptide or a homologue thereof. Preferably, the portion is a portion of a nucleic acid as represented by SEQ ID NO: 127 or SEQ ID NO: 129.

Where the sequence useful in the methods of the invention in a Group I shaggy-like kinase, the portion refers to a shaggy-like kinase-encoding piece of DNA of at least 1,200 nucleotides in length, and which portion encodes a polypeptide having: (i) at least 77% sequence identity to the amino acid sequence represented by SEQ ID NO: 147; and (ii) having motif I: R/H/V/N/Q E/G LK G/N (SEQ ID NO: 182) and motif II: K Q/N CXXX G/A/S (SEQ ID NO: 183), where X may be any amino acid. Preferably, the portion is a portion of a nucleic acid as represented by any one of SEQ ID NO: 146, SEQ ID NO: 148, SEQ ID NO: 150, SEQ ID NO: 152, SEQ ID NO: 154, SEQ ID NO: 156, SEQ ID NO: 158, SEQ ID NO: 160, SEQ ID NO: 162, SEQ ID NO: 164, SEQ ID NO: 166, SEQ ID NO: 168, SEQ ID NO: 170, SEQ ID NO: 0.172, SEQ ID NO: 174 and SEQ ID NO: 176.

The invention therefore provides a method for improving plant growth characteristics comprising modulating expression in a plant of a portion of a nucleic acid encoding a class I homeodomain leucine zipper (HDZip) hox5 polypeptide or a homologue thereof; or comprising modulating expression in a plant of a portion of a nucleic acid encoding an NRT polypeptide or a homologue thereof; or comprising modulating expression in a plant of a portion of a nucleic acid encoding a YEP16 polypeptide or homologue thereof; or comprising modulating expression in a plant of a portion of a nucleic acid encoding a Group I shaggy-like kinase or a homologue thereof.

Another nucleic acid variant is a nucleic acid capable of hybridising under reduced stringency conditions, preferably under stringent conditions, with a nucleic acid encoding a class I HDZip hox5 nucleic acid/gene or homologue thereof; or with a nucleic acid encoding an NRT polypeptide or homologue thereof; or with a nucleic acid encoding a YEP16 polypeptide or homologue thereof; or with a nucleic acid encoding a Group I shaggy-like kinase or homologue thereof.

The term "hybridisation" as defined herein is a process wherein substantially homologous complementary nucleotide sequences anneal to each other. The hybridisation process can occur entirely in solution, i.e. both complementary nucleic acids are in solution. The hybridisation process can also occur with one of the complementary nucleic acids immobilised to a matrix such as magnetic beads, Sepharose beads or any other resin. The hybridisation process can furthermore occur with one of the complementary nucleic acids immobilised to a solid support such as a nitro-cellulose or nylon membrane or immobilised by e.g. photolithography to, for example, a siliceous glass support (the latter known as nucleic acid arrays or microarrays or as nucleic acid chips). In order to allow hybridisation to occur, the nucleic acid molecules are generally thermally or chemically denatured to melt a double strand into two single strands and/or to remove hairpins or other secondary structures from single stranded nucleic acids. The stringency of hybridisation is influenced by conditions such as temperature, salt concentration, ionic strength and hybridisation buffer composition.

"Stringent hybridisation conditions" and "stringent hybridisation wash conditions" in the context of nucleic acid hybridisation experiments such as Southern and Northern hybridisations are sequence dependent and are different under different environmental parameters. The skilled artisan is aware of various parameters which may be altered during hybridisation and washing and which will either maintain or change the stringency conditions.

The $T_m$ is the temperature under defined ionic strength and pH, at which 50% of the target sequence hybridises to a perfectly matched probe. The $T_m$ is dependent upon the solution conditions and the base composition and length of the probe. For example, longer sequences hybridise specifically at higher temperatures. The maximum rate of hybridisation is obtained from about 16° C. up to 32° C. below $T_m$. The presence of monovalent cations in the hybridisation solution reduce the electrostatic repulsion between the two nucleic acid strands thereby promoting hybrid formation; this effect is visible for sodium concentrations of up to 0.4M. Formamide reduces the melting temperature of DNA-DNA and DNA-RNA duplexes with 0.6 to 0.7° C. for each percent formamide, and addition of 50% formamide allows hybridisaton to be performed at 30 to 45° C., though the rate of hybridisation will be lowered. Base pair mismatches reduce the hybridisation rate and the thermal stability of the duplexes. On average and for large probes, the $T_m$ decreases about 1° C. per % base mismatch. The $T_m$ may be calculated using the following equations, depending on the types of hybrids:

1. DNA-DNA hybrids (Meinkoth and Wahl, Anal. Biochem., 138: 267-284, 1984):

$$T_m=81.5° \text{ C.}+16.6\times\log[Na^+]^a+0.41\times\%[G/C^b]-500\times[L^c]^{-1}-0.61\times\% \text{ formamide}$$

2. DNA-RNA or RNA-RNA hybrids:

$$T_m=79.8+18.5(\log_{10}[Na^+]^a)+0.58(\% G/C^b)+11.8(\% G/C^b)^2-820/L^c$$

3. oligo-DNA or oligo-RNA$^d$ hybrids:

For <20 nucleotides: $T_m=2(l_n)$

For 20-35 nucleotides: $T_m=22+1.46(l_n)$ $^a$ or for other monovalent cation, but only accurate in the 0.01-0.4 M range.

$^b$ only accurate for % GC in the 30% to 75% range.

$^c$L=length of duplex in base pairs.

$^d$Oligo, oligonucleotide; $l_n$, effective length of primer=2×(no. of G/C)+(no. of A/T).

Note: for each 1% formamide, the $T_m$ is reduced by about 0.6 to 0.7° C., while the presence of 6 M urea reduces the $T_m$ by about 30° C.

Specificity of hybridisation is typically the function of post-hybridisation washes. To remove background resulting from non-specific hybridisation, samples are washed with dilute salt solutions. Critical factors of such washes include the ionic strength and temperature of the final wash solution: the lower the salt concentration and the higher the wash temperature, the higher the stringency of the wash. Wash conditions are typically performed at or below hybridisation stringency. Generally, suitable stringent conditions for nucleic acid hybridisation assays or gene amplification detection procedures are as set forth above. Conditions of greater or less stringency may also be selected. Generally, low stringency conditions are selected to be about 50° C. lower than the thermal melting point ($T_m$) for the specific sequence at a defined ionic strength and pH. Medium stringency conditions are when the temperature is 20° C. below $T_m$, and high stringency conditions are when the temperature is 10° C. below $T_m$. For example, stringent conditions are those that are at least as stringent as, for example, conditions A-L; and reduced stringency conditions are at least as stringent as, for example, conditions M-R. Non-specific binding may be controlled using any one of a number of known techniques such as, for example, blocking the membrane with protein containing solutions, additions of heterologous RNA, DNA, and SDS to the hybridisation buffer, and treatment with RNase. Examples of hybridisation and wash conditions are listed in Table 2 below.

TABLE 2

Examples of hybridisation and wash conditions

| Stringency Condition | Polynucleotide Hybrid± | Hybrid Length (bp)‡ | Hybridisation Temperature and Buffer† | Wash Temperature and Buffer† |
|---|---|---|---|---|
| A | DNA:DNA | > or equal to 50 | 65° C. 1xSSC; or 42° C., 1xSSC and 50% formamide | 65° C.; 0.3xSSC |
| B | DNA:DNA | <50 | Tb*; 1xSSC | Tb*; 1xSSC |
| C | DNA:RNA | > or equal to 50 | 67° C. 1xSSC; or 45° C., 1xSSC and 50% formamide | 67° C.; 0.3xSSC |
| D | DNA:RNA | <50 | Td*; 1xSSC | Td*; 1xSSC |
| E | RNA:RNA | > or equal to 50 | 70° C. 1xSSC; or 50° C., 1xSSC and 50% formamide | 70° C.; 0.3xSSC |
| F | RNA:RNA | <50 | Tf*; 1xSSC | Tf*; 1xSSC |
| G | DNA:DNA | > or equal to 50 | 65° C. 4xSSC; or 45° C., 4xSSC and 50% formamide | 65° C.; 1xSSC |
| H | DNA:DNA | <50 | Th*; 4 xSSC | Th*; 4xSSC |
| I | DNA:RNA | > or equal to 50 | 67° C. 4xSSC; or 45° C., 4xSSC and 50% formamide | 67° C.; 1xSSC |
| J | DNA:RNA | <50 | Tj*; 4 xSSC | Tj*; 4 xSSC |
| K | RNA:RNA | > or equal to 50 | 70° C. 4xSSC; or 40° C., 6xSSC and 50% formamide | 67° C.; 1xSSC |
| L | RNA:RNA | <50 | Tl*; 2 xSSC | Tl*; 2xSSC |
| M | DNA:DNA | > or equal to 50 | 50° C. 4xSSC; or 40° C., 6xSSC and 50% formamide | 50° C.; 2xSSC |
| N | DNA:DNA | <50 | Tn*; 6 xSSC | Tn*; 6xSSC |
| O | DNA:RNA | > or equal to 50 | 55° C. 4xSSC; or 42° C., 6xSSC and 50% formamide | 55° C.; 2xSSC |
| P | DNA:RNA | <50 | Tp*; 6 xSSC | Tp*; 6xSSC |
| Q | RNA:RNA | > or equal to 50 | 60° C. 4xSSC; or 45° C., 6xSSC and 50% formamide | 60° C.; 2xSSC |
| R | RNA:RNA | <50 | Tr*; 4 xSSC | Tr*; 4xSSC |

‡The "hybrid length" is the anticipated length for the hybridising nucleic acid. When nucleic acids of known sequence are hybridised, the hybrid length may be determined by aligning the sequences and identifying the conserved regions described herein.

†SSPE (1xSSPE is 0.15M NaCl, 10 mM $NaH_2PO_4$, and 1.25 mM EDTA, pH7.4) may be substituted for SSC (1xSSC is 0.15M NaCl and 15 mM sodium citrate) in the hybridisation and wash buffers; washes are performed for 15 minutes after hybridisation is complete. The hybridisations and washes may additionally include 5 × Denhardt's reagent, 0.5-1.0% SDS, 100 μg/ml denatured, fragmented salmon sperm DNA, 0.5% sodium pyrophosphate, and up to 50% formamide.

*Tb-Tr: The hybridisation temperature for hybrids anticipated to be less than 50 base pairs in length should be 5-10° C. less than the melting temperature $T_m$ of the hybrids; the $T_m$ is determined according to the above-mentioned equations.

±The present invention also encompasses the substitution of any one, or more DNA or RNA hybrid partners with either a PNA, or a modified nucleic acid.

For the purposes of defining the level of stringency, reference can be made to Sambrook et al., (2001) Molecular Cloning: a laboratory manual, 3rd Edition Cold Spring Harbor Laboratory Press, CSH, New York or to Current Protocols in Molecular Biology, John Wiley & Sons, N.Y. (1989).

Where the sequence useful in the methods of the invention is a class I HDZip hox5, the hybridizing sequence encodes a polypeptide comprising from N-terminal to C-terminal: (i) an acidic box; and (ii) a class I homeodomain; and (iii) a leucine zipper with more than 5 heptads. Preferably, the hybridising sequence is capable of hybridizing under reduced stringency conditions, preferably under stringent conditions, with one of the nucleic acids given in Table A or a portion thereof as defined herein. Most preferably the portion is a portion of a nucleic acid as represented by SEQ ID NO: 1.

Where the sequence useful in the methods of the invention is a nucleic acid encoding an NRT polypeptide or homologue thereof, the hybridising sequence is a nucleic acid/gene capable of hybridising under reduced stringency conditions, preferably under stringent conditions, with an NRT nucleic acid/gene encodes a polypeptide comprising an MFS_1 domain and a transmembrane domain located C-terminally of the MFS_1 domain, and preferably also one or more of the signature sequences defined above. Preferably, the hybridising sequence is one that is capable of hybridising to a nucleic acid given in Table J of Example 15 or to a portion of any of the nucleic acids given in Table J, a portion being as defined above. Most preferably the hybridising sequence is capable of hybridising to SEQ ID NO: 52.

Where the sequence useful in the methods of the invention is a nucleic acid encoding a YEP16 polypeptide or homologue thereof, the hybridising sequence is a nucleic acid sequence capable of hybridising under reduced stringency conditions, preferably under stringent conditions, with a nucleic acid sequence encoding a YEP16 polypeptide or a homologue thereof. Preferably, the hybridizing sequence is capable of hybridizing under reduced stringency conditions to a nucleic acid as represented by SEQ ID NO: 127 or SEQ ID NO: 129.

Where the nucleic acid useful in the methods of the invention is a nucleic acid encoding a Group I shaggy-like kinase, the hybridising sequence is a nucleic acid capable of hybridising under reduced stringency conditions, preferably under stringent conditions, with a Group I shaggy-like kinase-encoding nucleic acid/gene as hereinbefore defined, which hybridising sequence encodes a polypeptide having: (i) at least 77% sequence identity to the amino acid sequence represented by SEQ ID NO: 147; and (ii) motif I: R/H/V/N/Q E/G LK G/N (SEQ ID NO: 182) and motif II: K Q/N CXXX G/A/S (SEQ ID NO: 183), where X may be any amino acid. The hybridising sequence is at least 1,200 nucleotides in length. Preferably, the hybridising sequence is capable of hybridising to a nucleic acid as represented by any one of SEQ ID NO: 146, SEQ ID NO: 148, SEQ ID NO: 150, SEQ ID NO: 152, SEQ ID NO: 154, SEQ ID NO: 156, SEQ ID NO: 158, SEQ ID NO: 160, SEQ ID NO: 162, SEQ ID NO: 164, SEQ ID NO: 166, SEQ ID NO: 168, SEQ ID NO: 170, SEQ ID NO: 172, SEQ ID NO: 174 and SEQ ID NO: 176.

The invention therefore provides a method for improving plant growth characteristics comprising modulating expression in a plant of a nucleic acid capable of hybridising under reduced stringency, preferably under stringent conditions to a nucleic acid encoding a class I homeodomain leucine zipper (HDZip) hox5 polypeptide or a homologue thereof; or comprising modulating expression in a plant of a nucleic acid capable of hybridising under reduced stringency, preferably under stringent conditions to a nucleic acid encoding an NRT polypeptide or a homologue thereof; or comprising modulating expression in a plant of a nucleic acid capable of hybridising under reduced stringency, preferably under stringent conditions to a nucleic acid encoding a YEP16 polypeptide or homologue thereof; or comprising modulating expression in a plant of a nucleic acid capable of hybridising under reduced stringency, preferably under stringent conditions to a nucleic acid encoding a Group I shaggy-like kinase or a homologue thereof.

The nucleic acids or variant thereof may be derived from any natural or artificial source. The nucleic acid/gene or variant thereof may be isolated from a microbial source, such as yeast or fungi, or from a plant, algae or animal (including human) source. This nucleic acid may be modified from its native form in composition and/or genomic environment through deliberate human manipulation. The nucleic acid is preferably of plant origin, whether from the same plant species (for example to the one in which it is to be introduced) or whether from a different plant species. The nucleic acid may be isolated from a monocotyledonous species, preferably from the family Poaceae, further preferably from *Oryza* genus, most preferably from *Oryza sativa*. The nucleic acid may be isolated from a dicotyledonous species, preferably from the family Brassicaceae, further preferably from *Arabidopsis thaliana*.

The expression of a nucleic acid may be modulated by introducing a genetic modification (preferably in the locus of the gene in question). The locus of a gene as defined herein is taken to mean a genomic region, which includes the gene of interest and 10 kb up- or down stream of the coding region.

The genetic modification may be introduced, for example, by any one (or more) of the following methods: T-DNA activation, TILLING, site-directed mutagenesis, directed evolution and homologous recombination or by introducing and expressing in a plant a nucleic acid encoding a class I HDZip hox5 polypeptide or a homologue thereof; or by introducing and expressing in a plant a nucleic acid encoding an NRT or a homologue thereof; or by introducing and expressing in a plant a nucleic acid encoding a YEP16 or homologue thereof; or by introducing and expressing in a plant a nucleic acid encoding a Group I shaggy-like kinase or a homologue thereof. Following introduction of the genetic modification, there follows a step of selecting for modulated expression of the nucleic acid, which modulation in expression gives plants having improved growth characteristics, particularly increased yield.

T-DNA activation tagging (Hayashi et al. Science (1992) 1350-1353) involves insertion of T-DNA, usually containing a promoter (may also be a translation enhancer or an intron), in the genomic region of the gene of interest or 10 kb up- or downstream of the coding region of a gene in a configuration such that the promoter directs expression of the targeted gene. Typically, regulation of expression of the targeted gene by its natural promoter is disrupted and the gene falls under the control of the newly introduced promoter. The promoter is typically embedded in a T-DNA. This T-DNA is randomly inserted into the plant genome, for example, through *Agrobacterium* infection and leads to overexpression of genes near the inserted T-DNA. The resulting transgenic plants show dominant phenotypes due to overexpression of genes close to the introduced promoter. The promoter to be introduced may be any promoter capable of directing expression of a gene in the desired organism, in this case a plant. For example, constitutive, tissue-preferred, cell type-preferred and inducible promoters are all suitable for use in T-DNA activation.

A genetic modification may also be introduced in the locus of the gene in question using the technique of TILLING (Targeted Induced Local Lesions In Genomes). This is a mutagenesis technology useful to generate and/or identify and isolate mutagenised variants. TILLING also allows selection of plants carrying such mutant variants. These mutant variants may even exhibit higher activity than that exhibited by the gene in its natural form. TILLING combines high-density mutagenesis with high-throughput screening methods. The steps typically followed in TILLING are: (a) EMS mutagenesis (Redei G P and Koncz C (1992) In Methods in *Arabidopsis* Research, Koncz C, Chua N H, Schell J, eds. Singapore, World Scientific Publishing Co, pp. 16-82; Feldmann et al., (1994) In Meyerowitz E M, Somerville C R, eds, *Arabidopsis*. Cold Spring Harbor Laboratory Press, Cold Spring Harbor, N.Y., pp 137-172; Lightner J and Caspar T (1998) In J Martinez-Zapater, J Salinas, eds, Methods on Molecular Biology, Vol. 82. Humana Press, Totowa, N.J., pp 91-104); (b) DNA preparation and pooling of individuals; (c) PCR amplification of a region of interest; (d) denaturation and annealing to allow formation of heteroduplexes; (e) DHPLC, where the presence of a heteroduplex in a pool is detected as an extra peak in the chromatogram; (f identification of the mutant individual; and (g) sequencing of the mutant PCR product. Methods for TILLING are well known in the art (McCallum et al., (2000) Nat Biotechnol 18: 455-457; reviewed by Stemple (2004) Nat Rev Genet 5(2): 145-50).

Site-directed mutagenesis may be used to generate variant nucleic acids. Several methods are available to achieve site-directed mutagenesis, the most common being PCR based methods (Current Protocols in Molecular Biology, Wiley Eds at 4ulr.com/products/currentprotocols/index.html).

Directed evolution or gene shuffling may also be used to generate nucleic acid variants. This consists of iterations of DNA shuffling followed by appropriate screening and/or selection to generate variants having a modified biological activity (Castle et al., (2004) Science 304(5674): 1151-4; U.S. Pat. Nos. 5,811,238 and 6,395,547).

T-DNA activation, TILLING, site-directed mutagenesis and directed evolution are examples of technologies that enable the generation of novel alleles and variants.

Homologous recombination allows introduction in a genome of a selected nucleic acid at a defined selected position. Homologous recombination is a standard technology used routinely in biological sciences for lower organisms such as yeast or the moss *Physcomitrella*. Methods for performing homologous recombination in plants have been described not only for model plants (Offringa et al. (1990) EMBO J 9(10): 3077-84) but also for crop plants, for example rice (Terada et al. (2002) Nat Biotech 20(10): 1030-4; Iida and Terada (2004) Curr Opin Biotech 15(2): 132-8). The nucleic acid to be targeted need not be targeted to the locus of the gene in question, but may be introduced in, for example, regions of high expression. The nucleic acid to be targeted may be an improved allele used to replace the endogenous gene or may be introduced in addition to the endogenous gene.

A preferred method for introducing a genetic modification is to introduce and express in a plant a nucleic acid encoding a class I HDZip hox5 polypeptide or a homologue thereof; or to introduce and express in a plant a nucleic acid encoding an NRT or a homologue thereof; or to introduce and express in a plant a nucleic acid encoding a YEP16 or homologue thereof; or to introduce and express in a plant a nucleic acid encoding a Group I shaggy-like kinase or a homologue thereof. The nucleic acid to be introduced into a plant may be a full-length nucleic acid or may be a portion or a hybridising sequence as hereinbefore defined.

Where the sequence useful in the methods of the invention is a YEP16 polypeptide or homologue thereof, targeting to a plastid is preferred; methods for such targeting of proteins to plastids are well known in the art, as is the use of transit peptides for such targeting. Table 3 below shows examples of transit peptides suitable for targeting any YEP16 polypeptide or homologue thereof to a plastid, preferably to a chloroplast. Preferred is the use of the transit peptide native to the YEP16 polypeptide sequence of SEQ ID NO: 128, which native transit peptide is shown in SEQ ID NO: 131. SEQ ID NO: 130 represents the YEP16 polypeptide together with its native transit peptide for targeting to the chloroplast (SEQ ID NO: 129 represents the nucleic acid sequence encoding the amino acid sequence of SEQ ID NO: 130). Most preferred is the use of the native transit peptide as shown in SEQ ID NO: 131 to target a YEP16 polypeptide as represented by SEQ ID NO: 128, although any transit peptide may be used with any YEP16 polypeptide or homologue thereof.

TABLE 3

Examples of transit peptide sequences useful in targeting amino acids to plastids.

| NCBI Accession Number/SEQ ID NO | Source Organism | Protein Function | Transit Peptide Sequence |
|---|---|---|---|
| SEQ ID NO: 131 | | | MDTLSASVSSLNLPSLPPPPQPPLRSI SSRFKSTVNATTSASSTNLSKPTSSSP SSS |
| SEQ ID NO: 132-P07839 | *Chlamydomonas* | Ferredoxin | MAMAMRSTFAARVGAKPAVRGARPA SRMSCMA |
| SEQ ID NO: 133-AR23425 | *Chlamydomonas* | Rubisco activase | MQVTMKSSAVSGQRVGGARVATRSV RRAQLQV |
| SEQ ID NO: 134-AA56932 | *Arabidopsis thaliana* | asp Amino transferase | MASLMLSLGSTSLLPREINKDKLKLGT SASNPFLKAKSFSRVTMTVAVKPSR |
| SEQ ID NO: 135-CAA31991 | *Arabidopsis thaliana* | Acyl carrier protein1 | MATQFSASVSLQTSCLATTRISFQKPA LISNHGKTNLSFNLRRSIPSRRLSVSC |
| SEQ ID NO: 136-CAB63798 | *Arabidopsis thaliana* | Acyl carrier protein2 | MASIAASASISLQARPRQLAIAASQVK SFSNGRRSSLSFNLRQLPTRLTVSCA AKPETVDKVCAVVRKQL |
| SEQ ID NO: 137-CAB63799 | *Arabidopsis thaliana* | Acyl carrier protein3 | MASIATSASTSLQARPRQLVIGAKQVK SFSYGSRSNLSFNLRQLPTRLTVYCA AKPETVDKVCAVVRKQLSLKE |
| SEQ ID NO: 138-NP_199191 | *Arabidopsis thaliana* | ATP sulfurylase | MASSAAAIVSGSPFRSSPLIHNHHASR YAPGSISVVSLPRQVSRRGLSVKS |
| SEQ ID NO: 139-CAA81736 | *Brassica napus* | RuBisCO subunit binding-protein alpha subunit | MATANALSSPSVLCSSRQGKLSGGS QQKGQRVSYRKANRRFSLRANVKEIA FDQSSRAALQAGIDKLADAVGLTLGP RGRNVVLDEFGSPKVVNDGVTIA |
| SEQ ID NO: 140-AAA87039 | *Hordeum vulgare* | ribulose-1,5-bisphosphate carboxylase small subunit | MAPTVMASSATSVAPFQGLKSTAGLP VSRRSNASSASVSNGGRIRCMQVWPI EGIKKFETLSYLPPLSTEALLKQVDYLI RSKWVPCLEFSKVGFIFREH |
| SEQ ID NO: 141-AAC82334 | *Medicago truncatula* | Gamma-glutamylcysteine synthetase | MTTIFRLASSSSPSLRHDATPHNFHIR KTSISNTFSFSSKNSLSFKRILTSGGS RRFIVAASPPTEDAVVATEPLTKQDLI DYLASGCKTKDKWRIGTEH |

TABLE 3-continued

| Examples of transit peptide sequences useful in targeting amino acids to plastids. | | | |
|---|---|---|---|
| NCBI Accession Number/SEQ ID NO | Source Organism | Protein Function | Transit Peptide Sequence |
| SEQ ID NO: 142-AAB81104 | *Spinacia oleracea* | Sedoheptulose-1,7-bisphosphatase | METSMACCSRSIVLPRVSPQHSSALV PSSINLKSLKSSSLFGESLRMTTKSSV RVNKAKNSSLVTKCELGDSLEEFLAK ATTDKGLIRLMMCMGEALRTI |

"Homologues" of a protein encompass peptides, oligopeptides, polypeptides, proteins and enzymes having amino acid substitutions, deletions and/or insertions relative to the unmodified protein in question and having similar biological and functional activity as the unmodified protein from which they are derived. To produce such homologues, amino acids of the protein may be replaced by other amino acids having similar properties (such as similar hydrophobicity, hydrophilicity, antigenicity, propensity to form or break α-helical structures or β-sheet structures). Conservative substitution tables are well known in the art (see for example Creighton (1984) Proteins. W.H. Freeman and Company and Table 4 below). The homologues useful in the methods according to the invention are preferably polypeptides have in increasing order of preference at least 30%, 40%, 50%, 60%, 70%, 80%, 85%, 90%, 95%, 96%, 97%, 98% or 99% or more sequence identity or similarity (functional identity) to the sequences mentioned herein as being useful in the methods of the invention, for example the sequences given in Table A and J herein.

Also encompassed by the term "homologues" are two special forms of homology, which include orthologous sequences and paralogous sequences, which encompass evolutionary concepts used to describe ancestral relationships of genes. The term "paralogous" relates to gene-duplications within the genome of a species leading to paralogous genes. The term "orthologous" relates to homologous genes in different organisms due to speciation.

Orthologues in, for example, monocot plant species may easily be found by performing a so-called reciprocal blast search. Taking the example of finding an orthologue or paralogue of a class I HDZip hox5 nucleic acid or class I HDZip hox5 polypeptide, this may be done by a first blast involving blasting the sequence in question (for example, SEQ ID NO: 1 or SEQ ID NO: 2) against any sequence database, such as the publicly available NCBI database which may be found at: ncbi.nlm.nih.gov. BLASTN or TBLASTX may be used when starting from nucleotide sequence, or BLASTP or TBLASTN when starting from the protein, with standard default values. The BLAST results may be filtered. The full-length sequences of either the filtered results or the non-filtered results are then BLASTed back (second BLAST) against the sequences of the organism from which the sequence in question is derived. The results of the first and second BLASTs are then compared. When the results of the second BLAST give as hits with the highest similarity a class I HDZip hox5 nucleic acid or class I HDZip hox5 polypeptide, then a paralogue has been found, if it originates from the same organism as for the sequence used in the first BLAST. In case it originates from an organism other than that of the sequence used in the first BLAST, then an orthologue has been found. In the case of large families, ClustalW may be used, followed by a neighbour joining tree, to help visualize the clustering. Preferably, such class I HDZip hox5 polypeptides have in increasing order of preference at least 30%, 40%, 50%, 60%, 70%, 80%, 85%, 90%, 95%, 96%, 97%, 98% or 99% or more sequence identity or similarity (functional identity) to an unmodified class I HDZip hox5 polypeptide (preferably SEQ ID NO: 2; see Example 3 herein). Percentage identity between class I HDZip hox5 homologues outside of the homeodomain and the leucine zipper is reputedly low (see Example 3 herein). Examples of orthologs and paralogs of a class I HDZip hox5 polypeptide as represented by SEQ ID NO: 2 may be found in Table A of Example 1 herein.

The same procedure may also be used to find orthologues and paralogues of nucleic acids encoding an NRT and NRT polypeptides; and for finding orthologues and paralogues of YEP16-encoding nucleic acids and YEP16 polypetides; and for finding orthologues and paralogues of nucleic acids encoding Group I shaggy-like kinases and Group I shaggy-like kinase polypeptides.

A homologue may be in the form of a "substitutional variant" of a protein, i.e. where at least one residue in an amino acid sequence has been removed and a different residue inserted in its place. Amino acid substitutions are typically of single residues, but may be clustered depending upon functional constraints placed upon the polypeptide; insertions will usually be of the order of about 1 to 10 amino acid residues. Preferably, amino acid substitutions comprise conservative amino acid substitutions. Conservative substitution tables are readily available in the art. The table below gives examples of conserved amino acid substitutions.

TABLE 4

Examples of conserved amino acid substitutions

| Residue | Conservative Substitutions | Residue | Conservative Substitutions |
|---|---|---|---|
| Ala | Ser | Leu | Ile; Val |
| Arg | Lys | Lys | Arg; Gln |
| Asn | Gln; His | Met | Leu; Ile |
| Asp | Glu | Phe | Met; Leu; Tyr |
| Gln | Asn | Ser | Thr; Gly |
| Cys | Ser | Thr | Ser; Val |
| Glu | Asp | Trp | Tyr |
| Gly | Pro | Tyr | Trp; Phe |
| His | Asn; Gln | Val | Ile; Leu |
| Ile | Leu, Val | | |

A homologue may also be in the form of an "insertional variant" of a protein, i.e. where one or more amino acid residues are introduced into a predetermined site in a protein. Insertions may comprise N-terminal and/or C-terminal fusions as well as intra-sequence insertions of single or multiple amino acids. Generally, insertions within the amino acid sequence will be smaller than N- or C-terminal fusions, of the order of about 1 to 10 residues. Examples of N- or C-terminal fusion proteins or peptides include the binding domain or activation domain of a transcriptional activator as used in the yeast two-hybrid system, phage coat proteins, (histidine)-6-tag, glutathione S-transferase-tag, protein A, maltose-binding protein, dihydrofolate reductase, Tag-100 epitope, c-myc epitope, FLAG®-epitope, IacZ, CMP (calmodulin-binding peptide), HA epitope, protein C epitope and VSV epitope.

Homologues in the form of "deletion variants" of a protein are characterised by the removal of one or more amino acids from a protein.

Amino acid variants of a protein may readily be made using peptide synthetic techniques well known in the art, such as solid phase peptide synthesis and the like, or by recombinant DNA manipulations. Methods for the manipulation of DNA sequences to produce substitution, insertion or deletion variants of a protein are well known in the art. For example, techniques for making substitution mutations at predetermined sites in DNA are well known to those skilled in the art and include M13 mutagenesis, T7-Gen in vitro mutagenesis (USB, Cleveland, Ohio), QuickChange Site Directed mutagenesis (Stratagene, San Diego, Calif.), PCR-mediated site-directed mutagenesis or other site-directed mutagenesis protocols.

The class I HDZip hox5 polypeptide or homologue thereof; the nucleic acid encoding a nitrate transporter protein (NRT) or a homologue thereof; the nucleic acid encoding a YEP16 polypeptide; and the nucleic acid encoding a Group I shaggy-like kinase or a homologue thereof may be a derivative. "Derivatives" include peptides, oligopeptides, polypeptides which may, compared to the amino acid sequence of the naturally-occurring form of the protein, such as the protein of interest, comprise substitutions of amino acids with non-naturally occurring amino acid residues, or additions of non-naturally occurring amino acid residues. "Derivatives" of a protein also encompass peptides, oligopeptides, polypeptides which comprise naturally occurring altered (glycosylated, acylated, prenylated, phosphorylated, myristoylated, sulphated etc.) or non-naturally altered amino acid residues compared to the amino acid sequence of a naturally-occurring form of the polypeptide. A derivative may also comprise one or more non-amino acid substituents or additions compared to the amino acid sequence from which it is derived, for example a reporter molecule or other ligand, covalently or non-covalently bound to the amino acid sequence, such as a reporter molecule which is bound to facilitate its detection, and non-naturally occurring amino acid residues relative to the amino acid sequence of a naturally-occurring protein.

The class I HDZip hox5 polypeptide or homologue thereof may be encoded by an alternative splice variant; the NRT polypeptide or homologue thereof may be encoded by an alternative splice variant; the YEP16 polypeptide or homologue thereof may be encoded by an alternative splice variant; and the Group I shaggy-like kinase or a homologue thereof may be encoded by an alternative splice variant.

Where the sequence useful in the methods of the invention is a nucleic acid encoding a class I HDZip hox5 polypeptide or homologue thereof, the splice variant encodes a polypeptide comprising from N-terminal to C-terminal: (i) an acidic box; and (ii) a class I homeodomain; and (iii) a leucine zipper with more than 5 heptads. Additionally, the class I HDZip hox5 polypeptide or a homologue thereof may comprise one or both of the following: (a) a Trp tail; and (b) the RPFF amino acid motif, where R is Arg, P Pro and F Phe. Within this motif, are allowed one or more conservative change(s) at any position, and/or one or two non-conservative change(s) at any position. The motif of (b) precedes the acidic box, when examining the protein from N-terminal to C-terminal. Further preferred are splice variants of nucleic acid sequences given in Table A of Example 1 herein. Most preferred is a splice variant of a nucleic acid sequence as represented by SEQ ID NO: 1.

Where the sequence useful in the methods of the invention is an NRT polypeptide or homologue thereof or nucleic acid encoding the same, the splice variant encodes a polypeptide comprising the MFS_1 domain and a transmembrane domain located C-terminally of the MFS_1 domain, and preferably also one or more of the conserved signature sequences of SEQ ID NO: 57 to SEQ ID NO: 64 as defined above. Further preferred are splice variants of any of the nucleic acids given in Table J. Most preferred is a splice variant of the nucleic acid of SEQ ID NO: 52.

Where the sequence useful in the methods of the invention is a YEP16-encoding nucleic acid, the splice variant is of a nucleic acid sequence represented by SEQ ID NO: 127 or SEQ ID NO: 129.

Where the sequence useful in the methods of the invention is a nucleic acid encoding a Group I shaggy-like kinase or homologue thereof, the alternative splice variants are splice variants of the nucleic acid represented by any one of SEQ ID NO: 146, SEQ ID NO: 148, SEQ ID NO: 150, SEQ ID NO: 152, SEQ ID NO: 154, SEQ ID NO: 156, SEQ ID NO: 158, SEQ ID NO: 160, SEQ ID NO: 162, SEQ ID NO: 164, SEQ ID NO: 166, SEQ ID NO: 168, SEQ ID NO: 170, SEQ ID NO: 172, SEQ ID NO: 174 and SEQ ID NO: 176. Further preferred are splice variants encoding a polypeptide having: (i) at least 77% sequence identity to the amino acid sequence represented by SEQ ID NO: 147; and (ii) motif I: R/H/V/N/Q E/G LK G/N (SEQ ID NO: 182) and motif II: K Q/N CXXX G/A/S (SEQ ID NO: 183), where X may be any amino acid.

The present invention therefore provides a method for improving plant growth characteristics comprising modulating expression in a plant of an alternative splice variant of a nucleic acid encoding a class I homeodomain leucine zipper (HDZip) hox5 polypeptide or a homologue thereof; or comprising modulating expression in a plant of an alternative splice variant of a nucleic acid encoding an NRT polypeptide or a homologue thereof; or comprising modulating expression in a plant of an alternative splice variant of a nucleic acid encoding a YEP16 polypeptide or homologue thereof; or comprising modulating expression in a plant of an alternative splice variant of a nucleic acid encoding an Group I glycogen synthase kinase (Group I shaggy-like kinase) or a homologue thereof.

The term "alternative splice variant" as used herein encompasses variants of a nucleic acid sequence in which selected introns and/or exons have been excised, replaced or added, or in which introns have been shortened or lengthened. Such variants will be ones in which the biological activity of the protein is retained, which may be achieved by selectively retaining functional segments of the protein. Such splice variants may be found in nature or may be manmade. Methods for making such splice variants are well known in the art.

The homologue may also be encoded by an allelic variant of a nucleic acid encoding a class I HDZip hox5 polypeptide or a homologue thereof; or encoded by an allelic variant of a nucleic acid encoding a nitrate transporter protein (NRT) or a homologue thereof; or encoded by an allelic variant of a nucleic acid encoding a YEP16 polypeptide; or encoded by an allelic variant of a nucleic acid encoding a Group I shaggy-like kinase or a homologue thereof.

Where the sequence useful in the methods of the invention is a nucleic acid encoding a class I HDZip hox5 polypeptide or homologue thereof, the allelic variant encodes a polypeptide comprising from N-terminal to C-terminal: (i) an acidic box; and (ii) a class I homeodomain; and (iii) a leucine zipper with more than 5 heptads. Additionally, the class I HDZip hox5 polypeptide or a homologue thereof may comprise one or both of the following: (a) a Trp tail; and (b) the RPFF amino acid motif, where R is Arg, P Pro and F Phe. Within this motif, are allowed one or more conservative change(s) at any position, and/or one or two non-conservative change(s) at any position. The motif of (b) precedes the acidic box, when examining the protein from N-terminal to C-terminal. Further preferred are allelic variants of nucleic acid sequences given in Table A in Example 1. Most preferred is an allelic variant of a nucleic acid sequence as represented by SEQ ID NO: 1.

Where the sequence useful in the methods of the invention is an NRT polypeptide or homologue thereof or nucleic acid encoding the same, the allelic variant encodes a polypeptide comprising the MFS_1 domain and a transmembrane domain located C-terminally of the MFS_1 domain, and preferably also one or more of the conserved signature sequences of SEQ ID NO: 57 to SEQ ID NO: 64 as defined above. Further preferred are allelic variants of any of the nucleic acids given in Table J. Most preferred is an allelic variant of the nucleic acid of SEQ ID NO: 52.

Where the sequence useful in the methods of the invention is a YEP16-encoding nucleic acid, the allelic variant is of a nucleic acid sequence represented by SEQ ID NO: 127 or SEQ ID NO: 129.

Where the sequence useful in the methods of the invention is a nucleic acid encoding a Group I shaggy-like kinase or homologue thereof, the allelic variants are allelic variants of the nucleic acid represented by any one of SEQ ID NO: 146, SEQ ID NO: 148, SEQ ID NO: 150, SEQ ID NO: 152, SEQ ID NO: 154, SEQ ID NO: 156, SEQ ID NO: 158, SEQ ID NO: 160, SEQ ID NO: 162, SEQ ID NO: 164, SEQ ID NO: 166, SEQ ID NO: 168, SEQ ID NO: 170, SEQ ID NO: 172, SEQ ID NO: 174 and SEQ ID NO: 176. Further preferred are allelic variants encoding a polypeptide having: (i) at least 77% sequence identity to the amino acid sequence represented by SEQ ID NO: 147; and (ii) motif I: R/H/V/N/Q E/G LK G/N (SEQ ID NO: 182) and motif II: K Q/N CXXX G/A/S (SEQ ID NO: 183), where X may be any amino acid.

The present invention therefore provides a method for improving plant growth characteristics comprising modulating expression in a plant of an allelic variant of a nucleic acid encoding a class I homeodomain leucine zipper (HDZip) hox5 polypeptide or a homologue thereof; or comprising modulating expression in a plant of an allelic variant of a nucleic acid encoding an NRT polypeptide or a homologue thereof; or comprising modulating expression in a plant of an allelic variant of a nucleic acid encoding a YEP16 polypeptide or homologue thereof; or comprising modulating expression in a plant of an allelic variant of a nucleic acid encoding an Group I glycogen synthase kinase (Group I shaggy-like kinase) or a homologue thereof.

Allelic variants exist in nature, and encompassed within the methods of the present invention is the use of these natural alleles. Allelic variants encompass Single Nucleotide Polymorphisms (SNPs), as well as Small Insertion/Deletion Polymorphisms (INDELs). The size of INDELs is usually less than 100 bp. SNPs and INDELs form the largest set of sequence variants in naturally occurring polymorphic strains of most organisms.

According to the present invention, modulated expression of the nucleic acid or variant thereof is envisaged. Methods for modulating expression of genes or gene products are well documented in the art and include, for example, overexpression driven by appropriate promoters, the use of transcription enhancers or translation enhancers. Isolated nucleic acids which serve as promoter or enhancer elements may be introduced in an appropriate position (typically upstream) of a non-heterologous form of a polynucleotide so as to upregulate expression of the nucleic acid or variant thereof. For example, endogenous promoters may be altered in vivo by mutation, deletion, and/or substitution (see, Kmiec, U.S. Pat. No. 5,565,350; Zarling et al., PCT/US93/03868), or isolated promoters may be introduced into a plant cell in the proper orientation and distance from a gene of the present invention so as to control the expression of the gene.

Methods for reducing the expression of genes or gene products are well documented in the art.

If polypeptide expression is desired, it is generally desirable to include a polyadenylation region at the 3'-end of a polynucleotide coding region. The polyadenylation region can be derived from the natural gene, from a variety of other plant genes, or from T-DNA. The 3' end sequence to be added may be derived from, for example, the nopaline synthase or octopine synthase genes, or alternatively from another plant gene, or from any other eukaryotic gene.

An intron sequence may also be added to the 5' untranslated region or the coding sequence of the partial coding sequence to increase the amount of the mature message that accumulates in the cytosol. Inclusion of a spliceable intron in the transcription unit in both plant and animal expression constructs has been shown to increase gene expression at both the mRNA and protein levels up to 1000-fold (Buchman and Berg (1988) Mol. Cell. biol. 8: 4395-4405; Callis et al., (1987) Genes Dev 1:1183-1200). Such intron enhancement of gene expression is typically greatest when placed near the 5' end of the transcription unit. Use of the maize introns Adh1-S intron 1, 2, and 6, the Bronze-1 intron are known in the art. See generally, The Maize Handbook, Chapter 116, Freeling and Walbot, Eds., Springer, N.Y. (1994).

The invention also provides genetic constructs and vectors to facilitate introduction and/or expression of the nucleotide sequences useful in the methods according to the invention.

Therefore, there is provided a gene construct comprising:

(i) A class I HDZip hox5 nucleic acid or variant thereof; or an NRT-encoding nucleic acid or variant thereof; or a YEP16-encoding nucleic acid or variant thereof; or a Group I shaggy-like kinase-encoding nucleic acid or variant thereof;

(ii) One or more control sequences capable of driving expression of the nucleic acid sequence of (i); and optionally (iii) A transcription termination sequence.

Constructs useful in the methods according to the present invention may be constructed using recombinant DNA technology well known to persons skilled in the art. The gene constructs may be inserted into vectors, which may be commercially available, suitable for transforming into plants and suitable for expression of the gene of interest in the transformed cells. The invention therefore provides use of a gene construct as defined hereinabove in the methods of the invention.

Plants are transformed with a vector comprising the sequence of interest. The sequence of interest is operably linked to one or more control sequences (at least to a promoter). The terms "regulatory element", "control sequence" and "promoter" are all used interchangeably herein and are to be taken in a broad context to refer to regulatory nucleic acid sequences capable of effecting expression of the sequences to which they are ligated. Encompassed by the aforementioned terms are transcriptional regulatory sequences derived from a classical eukaryotic genomic gene (including the TATA box which is required for accurate transcription initiation, with or without a CCAAT box sequence) and additional regulatory elements (i.e. upstream activating sequences, enhancers and silencers) which alter gene expression in response to developmental and/or external stimuli, or in a tissue-specific manner. Also included within the term is a transcriptional regulatory sequence of a classical prokaryotic gene, in which case it may include a −35 box sequence and/or −10 box transcriptional regulatory sequences. The term "regulatory element" also encompasses a synthetic fusion molecule or derivative that confers, activates or enhances expression of a nucleic acid molecule in a cell, tissue or organ. The term "operably linked" as used herein refers to a functional linkage between the promoter sequence and the gene of interest, such that the promoter sequence is able to initiate transcription of the gene of interest.

Advantageously, any type of promoter may be used to drive expression of the nucleic acid sequence. The promoter may be an inducible promoter, i.e. having induced or increased transcription initiation in response to a developmental, chemical, environmental or physical stimulus. An example of an inducible promoter being a stress-inducible promoter, i.e. a promoter activated when a plant is exposed to various stress conditions. Additionally or alternatively, the promoter may be a tissue-preferred promoter, i.e. one that is capable of preferentially initiating transcription in certain tissues, such as the leaves, roots, seed tissue etc. Promoters able to initiate transcription in certain tissues only are referred to herein as "tissue-specific".

Preferably, the class I HDZip hox5 nucleic acid or variant thereof; the NRT-encoding nucleic acid or variant thereof; the Group I shaggy-like kinase-encoding nucleic acid or variant thereof is operably linked to a constitutive promoter. A constitutive promoter is transcriptionally active during most but not necessarily all phases of growth and development and is substantially ubiquitously expressed. The constitutive promoter is preferably a GOS2 promoter, more preferably the constitutive promoter is a rice GOS2 promoter, further preferably the constitutive promoter is represented by a nucleic acid sequence substantially similar to SEQ ID NO: 33 or SEQ ID NO: 178, most preferably the constitutive promoter is as represented by SEQ ID NO: 33 or SEQ ID NO: 178. It should be clear that the applicability of the present invention is not restricted to the class I HDZip hox5 nucleic acid or variant thereof; the NRT-encoding nucleic acid or variant thereof; or Group I shaggy-like kinase-encoding nucleic acid or variant thereof when driven by a GOS2 promoter. Examples of other constitutive promoters which may also be used perform the methods of the invention are shown in Table 5 below.

TABLE 5

Examples of constitutive promoters

| Gene Source | Reference |
|---|---|
| Actin | McElroy et al, Plant Cell, 2: 163-171, 1990 |
| CAMV 35S | Odell et al, Nature, 313: 810-812, 1985 |
| CaMV 19S | Nilsson et al., Physiol. Plant. 100: 456-462, 1997 |
| GOS2 | de Pater et al, Plant J Nov; 2(6): 837-44, 1992, WO 2004/065596 |
| Ubiquitin | Christensen et al, Plant Mol. Biol. 18: 675-689, 1992 |
| Rice cyclophilin | Buchholz et al, Plant Mol Biol. 25(5): 837-43, 1994 |
| Maize H3 histone | Lepetit et al, Mol. Gen. Genet. 231: 276-285, 1992 |
| Alfalfa H3 histone | Wu et al. Plant Mol. Biol. 11: 641-649, 1988 |
| Actin 2 | An et al, Plant J. 10(1); 107-121, 1996 |
| 34S FMV | Sanger et al., Plant. Mol. Biol., 14, 1990: 433-443 |
| Rubisco small subunit | U.S. Pat. No. 4,962,028 |
| OCS | Leisner (1988) Proc Natl Acad Sci USA 85(5): 2553 |
| SAD1 | Jain et al., Crop Science, 39 (6), 1999: 1696 |
| SAD2 | Jain et al., Crop Science, 39 (6), 1999: 1696 |
| Nos | Shaw et al. (1984) Nucleic Acids Res. 12(20): 7831-7846 |
| V-ATPase | WO 01/14572 |
| Super promoter | WO 95/14098 |
| G-box proteins | WO 94/12015 |

Preferably, the nucleic acid sequence encoding a YEP16 polypeptide or homologue thereof is operably linked to a seed-specific promoter. A seed-specific promoter is one that is transcriptionally active predominantly in seed tissue. A seed-specific promoter may also have some residual activity in other parts. Preferably, the seed-specific promoter is an endosperm-specific and/or an aleurone-specific promoter meaning that the promoter is transcriptionally active predominantly in endosperm tissue and/or in the aleurone layers of a seed, although there may be some residual activity or leaky expression elsewhere. Preferably, the promoter is an oleosin promoter, such as from rice (SEQ ID NO: 143). It should be clear that the applicability of the present invention is not restricted to a YEP16-encoding nucleic acid represented by SEQ ID NO: 127 or SEQ ID NO: 129, nor is the applicability of the invention restricted to expression of a YEP16-encoding nucleic acid when driven by an oleosin promoter. Examples of other seed-specific promoters which may also be used to drive expression of a nucleic acid encoding a YEP16 polypeptide or homologue thereof are shown in Table 6 below.

TABLE 6

Examples of seed-specific promoters

| Gene source | Expression pattern | Reference |
|---|---|---|
| seed-specific genes | seed | Simon, et al., *Plant Mol. Biol.* 5: 191, 1985; Scofield, et al., *J. Biol. Chem.* 262: 12202, 1987.; Baszczynski, et al., *Plant Mol. Biol.* 14: 633, 1990. |
| Brazil Nut albumin | seed | Pearson, et al., Plant Mol. Biol. 18: 235-245, 1992. |
| Legumin | seed | Ellis, et al., Plant Mol. Biol. 10: 203-214, 1988. |
| Glutelin (rice) | seed | Takaiwa, et al., Mol. Gen. Genet. 208: 15-22, 1986; Takaiwa, et al., FEBS Letts. 221: 43-47, 1987. |
| Zein | seed | Matzke et al Plant Mol Biol, 14(3): 323-32 1990 |
| napA | seed | Stalberg, et al, *Planta* 199: 515-519, 1996. |

TABLE 6-continued

| Examples of seed-specific promoters | | |
|---|---|---|
| Gene source | Expression pattern | Reference |
| wheat LMW and HMW glutenin-1 | endosperm | Mol Gen Genet 216: 81-90, 1989; NAR 17: 461-2, 1989 |
| wheat SPA | seed | Albani et al, Plant Cell, 9: 171-184, 1997 |
| wheat α, β, γ-gliadins | endosperm | EMBO 3: 1409-15, 1984 |
| barley ltr1 promoter | endosperm | |
| barley B1, C, D, hordein | endosperm | Theor Appl Gen 98: 1253-62, 1999; Plant J 4: 343-55, 1993; Mol Gen Genet 250: 750-60, 1996 |
| barley DOF | endosperm | Mena et al, The Plant Journal, 116(1): 53-62, 1998 |
| blz2 | endosperm | EP99106056.7 |
| synthetic promoter | endosperm | Vicente-Carbajosa et al., *Plant J.* 13: 629-640, 1998. |
| rice prolamin NRP33 | endosperm | Wu et al, Plant Cell Physiology 39(8) 885-889, 1998 |
| rice α-globulin Glb-1 | endosperm | Wu et al, Plant Cell Physiology 39(8) 885-889, 1998 |
| rice OSH1 | embryo | Sato et al, Proc. Natl. Acad. Sci. USA, 93: 8117-8122, 1996 |
| rice □-globulin REB/OHP-1 | endosperm | Nakase et al. Plant Mol. Biol. 33: 513-522, 1997 |
| rice ADP-glucose PP | endosperm | Trans Res 6: 157-68, 1997 |
| maize ESR gene family | endosperm | Plant J 12: 235-46, 1997 |
| Sorgum □-kafirin | endosperm | PMB 32: 1029-35, 1996 |
| KNOX | embryo | Postma-Haarsma et al, Plant Mol. Biol. 39: 257-71, 1999 |
| rice oleosin | embryo and aleuron | Wu et at, J. Biochem., 123: 386, 1998 |
| sunflower oleosin | seed (embryo and dry seed) | Cummins, et al., Plant Mol. Biol. 19: 873-876, 1992 |
| putative rice 40S ribosomal protein | weak in endosperm | |
| rice alpha-globulin | strong in endosperm | |
| rice alanine aminotransferase | weak in endosperm | |
| trypsin inhibitor ITR1 (barley) | weak in endosperm | |
| rice WSI18 | embryo + stress | |
| rice RAB21 | embryo + stress | |
| rice oleosin 18 kd | aleurone + embryo | |

For the identification of functionally equivalent promoters, the promoter strength and/or expression pattern of a candidate promoter may be analysed for example by operably linking the promoter to a reporter gene and assay the expression level and pattern of the reporter gene in various tissues of the plant. Suitable well-known reporter genes include for example beta-glucuronidase or beta galactosidase. The promoter activity is assayed by measuring the enzymatic activity of the beta-glucuronidase or beta-galactosidase. The promoter strength and/or expression pattern may then be compared to that of a reference promoter (such as the one used in the methods of the present invention). Alternatively, promoter strength may be assayed by quantifying mRNA levels or by comparing mRNA levels of the nucleic acid used in the methods of the present invention, with mRNA levels of housekeeping genes such as 18S rRNA, using methods known in the art, such as Northern blotting with densitometric analysis of autoradiograms, quantitative real-time PCR or RT-PCR (Heid et al., 1996 Genome Methods 6: 986-994). Generally by "weak promoter" is intended a promoter that drives expression of a coding sequence at a low level. By "low level" is intended at levels of about 1/10,000 transcripts to about 1/100,000 transcripts, to about 1/500,0000 transcripts per cell. Conversely, a "strong promoter" drives expression of a coding sequence at high level, or at about 1/10 transcripts to about 1/100 transcripts to about 1/1,000 transcripts per cell.

Optionally, one or more terminator sequences may also be used in the construct introduced into a plant. The term "terminator" encompasses a control sequence which is a DNA sequence at the end of a transcriptional unit which signals 3' processing and polyadenylation of a primary transcript and termination of transcription. Additional regulatory elements may include transcriptional as well as translational enhancers. Those skilled in the art will be aware of terminator and enhancer sequences that may be suitable for use in performing the invention. Such sequences would be known or may readily be obtained by a person skilled in the art.

The genetic constructs of the invention may further include an origin of replication sequence that is required for maintenance and/or replication in a specific cell type. One example is when a genetic construct is required to be maintained in a bacterial cell as an episomal genetic element (e.g. plasmid or cosmid molecule). Preferred origins of replication include, but are not limited to, the f1-ori and colE1.

The genetic construct may optionally comprise a selectable marker gene. As used herein, the term "selectable marker gene" includes any gene that confers a phenotype on a cell in which it is expressed to facilitate the identification and/or selection of cells that are transfected or transformed with a nucleic acid construct of the invention.

For the detection of the successful transfer of the nucleic acid sequences as used in the methods of the invention and/or selection of transgenic plants comprising these nucleic acids, it is advantageous to use marker genes (or reporter genes). Therefore, the genetic construct may optionally comprise a selectable marker gene. As used herein, the term "selectable marker", "selectable marker gene" or "reporter gene" includes any gene that confers a phenotype on a cell in which it is expressed to facilitate the identification and/or selection of cells that are transfected or transformed with a nucleic acid construct of the invention. These marker genes enable the identification of a successful transfer of the nucleic acid molecules via a series of different principles. Suitable markers may be selected from markers that confer antibiotic or herbicide resistance, that introduce a new metabolic trait or that allow visual selection. Examples of selectable marker genes include genes conferring resistance to antibiotics (such as nptII that phosphorylates neomycin and kanamycin, or hpt, phosphorylating hygromycin, or genes conferring resistance to, for example, bleomycin, streptomycin, tetracyclin, chloramphenicol, ampicillin, gentamycin, geneticin (G418), spectinomycin or blasticidin), to herbicides (for example bar which provides resistance to Basta; aroA or gox providing resistance against glyphosate, or the genes conferring resistance to, for example, imidazolinone, phosphinothricin or sulfonylurea), or genes that provide a metabolic trait (such as manA that allows plants to use mannose as sole carbon source or xlose isomerase for the utilisation of xylose, or antinutritive markers such as the resistance to 2-deoxyglucose). Expression of visual marker genes results in the formation of colour (for example β-glucuronidase, GUS or β-galactosidase with its coloured substrates, for example X-Gal), luminescence (such as the luciferin/luciferase system) or fluorescence (Green Fluorescent Protein, GFP, and derivatives thereof). This list represents only a small number of possible markers. The skilled worker is familiar with such markers. Different markers are preferred, depending on the organism and the selection method.

It is known that upon stable or transient integration of nucleic acids into plant cells, only a minority of the cells takes up the foreign DNA and, if desired, integrates it into its genome, depending on the expression vector used and the transfection technique used. To identify and select these integrants, a gene coding for a selectable marker (such as the ones described above) is usually introduced into the host cells together with the gene of interest. These markers can for example be used in mutants in which these genes are not functional by, for example, deletion by conventional methods. Furthermore, nucleic acid molecules encoding a selectable marker can be introduced into a host cell on the same vector that comprises the sequence encoding the polypeptides of the invention or used in the methods of the invention, or else in a separate vector. Cells which have been stably transfected with the introduced nucleic acid can be identified for example by selection (for example, cells which have integrated the selectable marker survive whereas the other cells die).

Since the marker genes, particularly genes for resistance to antibiotics and herbicides, are no longer required or are undesired in the transgenic host cell once the nucleic acids have been introduced successfully, the process according to the invention for introducing the nucleic acids advantageously employs techniques which enable the removal or excision of these marker genes. One such a method is what is known as co-transformation. The co-transformation method employs two vectors simultaneously for the transformation, one vector bearing the nucleic acid according to the invention and a second bearing the marker gene(s). A large proportion of transformants receives or, in the case of plants, comprises (up to 40% or more of the transformants), both vectors. In case of transformation with *Agrobacteria*, the transformants usually receive only a part of the vector, i.e. the sequence flanked by the T-DNA, which usually represents the expression cassette. The marker genes can subsequently be removed from the transformed plant by performing crosses. In another method, marker genes integrated into a transposon are used for the transformation together with desired nucleic acid (known as the Ac/Ds technology). The transformants can be crossed with a transposase source or the transformants are transformed with a nucleic acid construct conferring expression of a transposase, transiently or stable. In some cases (approx. 10%), the transposon jumps out of the genome of the host cell once transformation has taken place successfully and is lost. In a further number of cases, the transposon jumps to a different location. In these cases, the marker gene must be eliminated by performing crosses. In microbiology, techniques were developed which make possible, or facilitate, the detection of such events. A further advantageous method relies on what is known as recombination systems; whose advantage is that elimination by crossing can be dispensed with. The best-known system of this type is what is known as the Cre/lox system. Cre1 is a recombinase that removes the sequences located between the loxP sequences. If the marker gene is integrated between the loxP sequences, it is removed once transformation has taken place successfully, by expression of the recombinase. Further recombination systems are the HIN/HIX, FLP/FRT and REP/STB system (Tribble et al., J. Biol. Chem., 275, 2000: 22255-22267; Velmurugan et al., J. Cell Biol., 149, 2000: 553-566). A site-specific integration into the plant genome of the nucleic acid sequences according to the invention is possible. Naturally, these methods can also be applied to microorganisms such as yeast, fungi or bacteria.

In a preferred embodiment, there is provided a gene construct comprising:

(i) A class I HDZip hox5 nucleic acid or variant thereof; or an NRT-encoding nucleic acid or variant thereof; or a Group I shaggy-like kinase-encoding nucleic acid or variant thereof;

(ii) A constitutive promoter capable of driving expression of the nucleic acid sequence of (i); and optionally (iii) A transcription termination sequence.

The constitutive promoter is preferably a GOS2 promoter, more preferably the constitutive promoter is the rice GOS2 promoter, further preferably the constitutive promoter is represented by a nucleic acid sequence substantially similar to SEQ ID NO: 33 or SEQ ID NO: 178, most preferably the constitutive promoter is as represented by SEQ ID NO: 33 or SEQ ID NO: 178. The invention further provides use of a construct as defined hereinabove in the methods of the invention.

In another preferred embodiment, there is provided a gene construct comprising:

(i) A YEP16-encoding nucleic acid or variant thereof;

(ii) A seed-specific promoter capable of driving expression of the nucleic acid sequence of (i); and optionally (iii) A transcription termination sequence.

The present invention also encompasses plants obtainable by the methods according to the present invention. The present invention therefore provides plants, plant parts (including plant cells) obtainable by the methods according to the present invention, which plants or parts (including cells) comprise a transgene class I HDZip hox5 nucleic acid or variant thereof; a transgene NRT-encoding nucleic acid or variant thereof; a transgene YEP16-encoding nucleic acid or variant thereof; or a transgene Group I shaggy-like kinase-encoding nucleic acid or variant thereof.

The invention also provides a method for the production of transgenic plants having improved growth characteristics, particularly increased yield, relative to corresponding wild type or other control plants, comprising introduction and expression in a plant of any of the nucleic acids described herein as being useful in the methods of the invention.

For the purposes of the invention, "transgenic", "transgene" or "recombinant" means with regard to, for example, a nucleic acid sequence, an expression cassette, gene construct or a vector comprising the nucleic acid sequence or an organism transformed with the nucleic acid sequences, expression cassettes or vectors according to the invention, all those constructions brought about by recombinant methods in which either a) the nucleic acid sequences encoding proteins useful in the methods of the invention, or
b) genetic control sequence(s) which is operably linked with the nucleic acid sequence according to the invention, for example a promoter, or
c) a) and b)

are not located in their natural genetic environment or have been modified by recombinant methods, it being possible for the modification to take the form of, for example, a substitution, addition, deletion, inversion or insertion of one or more nucleotide residues. The natural genetic environment is understood as meaning the natural genomic or chromosomal locus in the original plant or the presence in a genomic library. In the case of a genomic library, the natural genetic environment of the nucleic acid sequence is preferably retained, at least in part. The environment flanks the nucleic acid sequence at least on one side and has a sequence length of at least 50 bp, preferably at least 500 bp, especially preferably at least 1000 bp, most preferably at least 5000 bp. A naturally occurring expression cassette—for example the naturally occurring combination of the natural promoter of the nucleic acid sequences with the corresponding nucleic acid sequence encoding a polypeptide useful in the methods of the present invention, as defined above—becomes a transgenic expression cassette when this expression cassette is modified by non-natural, synthetic ("artificial") methods such as, for example, mutagenic treatment. Suitable methods are described, for example, in U.S. Pat. No. 5,565,350 or WO 00/15815.

More specifically, the present invention provides a method for the production of transgenic plants having improved growth characteristics (particularly increased yield) which method comprises:

(i) introducing and expressing in a plant, plant part or plant cell a class I HDZip hox5 nucleic acid or variant thereof; an NRT-encoding nucleic acid or variant thereof; a YEP16-encoding nucleic acid or variant thereof; a Group I shaggy-like kinase-encoding nucleic acid or variant thereof; and
(ii) cultivating the plant cell under conditions promoting plant growth and development.

The nucleic acid may be introduced directly into a plant cell or into the plant itself (including introduction into a tissue, organ or any other part of a plant). According to a preferred feature of the present invention, the nucleic acid is preferably introduced into a plant by transformation.

The term "transformation" as referred to herein encompasses the transfer of an exogenous polynucleotide into a host cell, irrespective of the method used for transfer. Plant tissue capable of subsequent clonal propagation, whether by organogenesis or embryogenesis, may be transformed with a genetic construct of the present invention and a whole plant regenerated therefrom. The particular tissue chosen will vary depending on the clonal propagation systems available for, and best suited to, the particular species being transformed. Exemplary tissue targets include leaf disks, pollen, embryos, cotyledons, hypocotyls, megagametophytes, callus tissue, existing meristematic tissue (e.g., apical meristem, axillary buds, and root meristems), and induced meristem tissue (e.g., cotyledon meristem and hypocotyl meristem). The polynucleotide may be transiently or stably introduced into a host cell and may be maintained non-integrated, for example, as a plasmid. Alternatively, it may be integrated into the host genome. The resulting transformed plant cell may then be used to regenerate a transformed plant in a manner known to persons skilled in the art.

Transformation of plant species is now a fairly routine technique. Advantageously, any of several transformation methods may be used to introduce the gene of interest into a suitable ancestor cell. Transformation methods include the use of liposomes, electroporation, chemicals that increase free DNA uptake, injection of the DNA directly into the plant, particle gun bombardment, transformation using viruses or pollen and microprojection. Methods may be selected from the calcium/polyethylene glycol method for protoplasts (Krens, F. A. et al. (1982) Nature 296, 72-74; Negrutiu I et al. (1987) Plant Mol Biol 8: 363-373); electroporation of protoplasts (Shillito R. D. et al. (1985) Bio/Technol 3, 1099-1102); microinjection into plant material (Crossway A et al. (1986) Mol. Gen. Genet 202: 179-185); DNA or RNA-coated particle bombardment (Klein T M et al. (1987) Nature 327: 70) infection with (non-integrative) viruses and the like. Transgenic rice plants are preferably produced via *Agrobacterium*-mediated transformation using any of the well known methods for rice transformation, such as described in any of the following: published European patent application EP 1198985 A1, Aldemita and Hodges (Planta 199: 612-617, 1996); Chan et al. (Plant Mol Biol 22 (3): 491-506, 1993), Hiei et al. (Plant J 6 (2): 271-282, 1994), which disclosures are incorporated by reference herein as if fully set forth. In the case of corn transformation, the preferred method is as described in either Ishida et al. (Nat. Biotechnol 14(6): 745-50, 1996) or Frame et al. (Plant Physiol 129(1): 13-22, 2002), which disclosures are incorporated by reference herein as if fully set forth.

Generally after transformation, plant cells or cell groupings are selected for the presence of one or more markers which are encoded by plant-expressible genes co-transferred with the gene of interest, following which the transformed material is regenerated into a whole plant.

Following DNA transfer and regeneration, putatively transformed plants may be evaluated, for instance using Southern analysis, for the presence of the gene of interest, copy number and/or genomic organisation. Alternatively or additionally, expression levels of the newly introduced DNA may be monitored using Northern and/or Western analysis, or quantitative PCR, all techniques being well known to persons having ordinary skill in the art.

The generated transformed plants may be propagated by a variety of means, such as by clonal propagation or classical breeding techniques. For example, a first generation (or T1) transformed plant may be selfed to give homozygous second generation (or T2) transformants, and the T2 plants further propagated through classical breeding techniques.

The generated transformed organisms may take a variety of forms. For example, they may be chimeras of transformed cells and non-transformed cells; clonal transformants (e.g., all cells transformed to contain the expression cassette);

grafts of transformed and untransformed tissues (e.g., in plants, a transformed rootstock grafted to an untransformed scion).

The present invention clearly extends to any plant cell or plant produced by any of the methods described herein, and to all plant parts and propagules thereof. The present invention extends further to encompass the progeny of a primary transformed or transfected cell, tissue, organ or whole plant that has been produced by any of the aforementioned methods, the only requirement being that progeny exhibit the same genotypic and/or phenotypic characteristic(s) as those produced by the parent in the methods according to the invention.

The invention also includes host cells comprising an isolated class I HDZip hox5 nucleic acid or variant thereof; host cells comprising an isolated NRT-encoding nucleic acid or variant thereof; host cells comprising an isolated YEP16-encoding nucleic acid or variant thereof; host cells comprising a Group I shaggy-like kinase-encoding nucleic acid or variant thereof. Preferred host cells are plant cells.

The invention also extends to harvestable parts of a plant such as, but not limited to seeds, leaves, fruits, flowers, stems, rhizomes, tubers and bulbs. The invention furthermore relates to products derived from a harvestable part of such a plant, such as dry pellets or powders, oil, fat and fatty acids, starch or proteins.

The present invention also encompasses use of class I HDZip hox5 nucleic acids and variants thereof and use of class I HDZip hox5 polypeptides and homologues thereof; use of NRT-encoding nucleic acids and variants thereof and use of NRT polypeptides and homologues thereof; use of YEP16-encoding nucleic acids and variants thereof and use of YEP16 polypetides and homologues thereof; use of Group I shaggy-like kinase-encoding nucleic acids and variants thereof and use of Group I shaggy-like kinase polypetides and homologues thereof. Such uses relate to improving any of the plant growth characteristics as defined hereinabove.

Class I HDZip hox5 nucleic acids or variants thereof, or class I HDZip hox5 polypeptides or homologues thereof; NRT-encoding nucleic acids and variants thereof, or NRT polypeptides and homologues thereof; YEP16-encoding nucleic acids and variants thereof or YEP16 polypetides and homologues thereof; Group I shaggy-like kinase-encoding nucleic acids and variants thereof, or Group I shaggy-like kinase polypetides and homologues thereof may find use in breeding programmes in which a DNA marker is identified which may be genetically linked to one of the aforementioned nucleic acids or variants. The nucleic acids or variants, or polypeptides or homologues thereof may be used to define a molecular marker. This DNA or protein marker may then be used in breeding programmes to select plants having improved growth characteristics (such as increased yield). The nucleic acids or variants are as defined hereinabove.

Allelic variants of a class I HDZip hox5 nucleic acid/gene; an NRT-encoding nucleic acid/gene; a YEP16-encoding nucleic acid/gene; a Group I shaggy-like kinase-encoding nucleic acid/gene may also find use in marker-assisted breeding programmes. Such breeding programmes sometimes require introduction of allelic variation by mutagenic treatment of the plants, using for example EMS mutagenesis; alternatively, the programme may start with a collection of allelic variants of so called "natural" origin caused unintentionally. Identification of allelic variants then takes place, for example, by PCR. This is followed by a step for selection of superior allelic variants of the sequence in question and which give improved growth characteristics, such as increased yield. Selection is typically carried out by monitoring growth performance of plants containing different allelic variants of the sequence in question, for example, different allelic variants of any of the nucleic acids/genes described herein as being useful in the methods of the invention. Growth performance may be monitored in a greenhouse or in the field. Further optional steps include crossing plants in which the superior allelic variant was identified with another plant. This could be used, for example, to make a combination of interesting phenotypic features.

The aforementioned nucleic acid and variants may also be used as probes for genetically and physically mapping the genes that they are a part of, and as markers for traits linked to those genes. Such information may be useful in plant breeding in order to develop lines with desired phenotypes. Such use of the nucleic acids or variants requires only a nucleic acid sequence of at least 15 nucleotides in length. The nucleic acids or variants may be used as restriction fragment length polymorphism (RFLP) markers. Southern blots (Sambrook J, Fritsch E F and Maniatis T (1989) Molecular Cloning, A Laboratory Manual) of restriction-digested plant genomic DNA may be probed with the nucleic acids or variants. The resulting banding patterns may then be subjected to genetic analyses using computer programs such as MapMaker (Lander et al. (1987) Genomics 1: 174-181) in order to construct a genetic map. In addition, the nucleic acids may be used to probe Southern blots containing restriction endonuclease-treated genomic DNAs of a set of individuals representing parent and progeny of a defined genetic cross. Segregation of the DNA polymorphisms is noted and used to calculate the position of the nucleic acid or variant in the genetic map previously obtained using this population (Botstein et al. (1980) Am. J. Hum. Genet. 32:314-331).

The production and use of plant gene-derived probes for use in genetic mapping is described in Bernatzky and Tanksley (1986) Plant Mol. Biol. Reporter 4: 37-41. Numerous publications describe genetic mapping of specific cDNA clones using the methodology outlined above or variations thereof. For example, F2 intercross populations, backcross populations, randomly mated populations, near isogenic lines, and other sets of individuals may be used for mapping. Such methodologies are well known to those skilled in the art.

The nucleic acid probes may also be used for physical mapping (i.e., placement of sequences on physical maps; see Hoheisel et al. In: Non-mammalian Genomic Analysis: A Practical Guide, Academic press 1996, pp. 319-346, and references cited therein).

In another embodiment, the nucleic acid probes may be used in direct fluorescence in situ hybridisation (FISH) mapping (Trask (1991) Trends Genet. 7:149-154). Although current methods of FISH mapping favor use of large clones (several kb to several hundred kb; see Laan et al. (1995) Genome Res. 5:13-20), improvements in sensitivity may allow performance of FISH mapping using shorter probes.

A variety of nucleic acid amplification-based methods for genetic and physical mapping may be carried out using the nucleic acids. Examples include allele-specific amplification (Kazazian (1989) J. Lab. Clin. Med 11:95-96), polymorphism of PCR-amplified fragments (CAPS; Sheffield et al. (1993) Genomics 16:325-332), allele-specific ligation (Landegren et al. (1988) Science 241:1077-1080), nucleotide extension reactions (Sokolov (1990) Nucleic Acid Res. 18:3671), Radiation Hybrid Mapping (Walter et al. (1997) Nat. Genet. 7:22-28) and Happy Mapping (Dear and Cook (1989) Nucleic Acid Res. 17:6795-6807). For these methods, the sequence of a nucleic acid is used to design and produce primer pairs for use in the amplification reaction or in primer extension reactions. The design of such primers is well known to those skilled in the art. In methods employing PCR-based genetic mapping, it may be necessary to identify DNA sequence differences between the parents of the mapping cross in the region corresponding to the instant nucleic acid sequence. This, however, is generally not necessary for mapping methods.

The methods according to the present invention result in plants having improved growth characteristics, as described hereinbefore. These improved growth characteristics may also be combined with other economically advantageous traits, such as further yield-enhancing traits, tolerance to other abiotic and biotic stresses, traits modifying various architectural features and/or biochemical and/or physiological features.

DESCRIPTION OF FIGURES

The present invention will now be described with reference to the following figures in which:

FIG. 1 shows a multiple alignment of class I HDZip homeodomains from different plant sources, using VNTI AlignX multiple alignment program, based on a modified ClustalW algorithm (InforMax, Bethesda, Md., at informaxinc.com), with default settings for gap opening penalty of 10 and a gap extension of 0.05). The homeodomain invariant amino acids $L_{16}$, $W_{48}$, $F_{49}$, $N_{51}$ and $R_{53}$ are boxed vertically. HDZip Class I preferred amino acids $A_{46}$ and $W_{56}$ are equally boxed vertically. The three helixes necessary for DNA binding are marked as black boxes above the alignment. The six heptads are separated by a vertical line. The seven positions within each heptad are named a, b, c, d, e, f and g. The Leu occupies the d position within each heptad, and is boxed vertically.

FIG. 4 details examples of class I homeodomain leucine zipper (HDZip) hox5 sequences useful in performing the methods according to the present invention. Several sequences result from public EST assemblies (see Table A), with lesser quality sequencing. As a consequence, a few nucleic acid substitutions may be expected. The start (ATG) and stop codons delimit the nucleic acid sequences.

FIG. 5 shows the typical domain structure of an NRT protein useful in the methods of the present invention, here exemplified with SEQ ID NO: 53. The protein of SEQ ID NO: 53 comprises an MFS_1 domain starting at S69 and ending with F432, indicated in bold. C-terminally of this MFS_1 domain, a putative transmembrane domain (T441 to P463, underlined) is present.

FIG. 6 (*a*) shows a phylogenetic tree, in which SEQ ID NO: 126 represents the rice NRT1 protein sequence, comprising a PTR2 domain, and (b) a multiple alignment of the of the sequences listed in Table J of Example 15. The asterisks in the multiple alignment indicate amino acids that are identical among the aligned sequences, the semicolons indicate conservative substitutions and the dots represent less conserved substitutions.

FIG. 8 details examples of NRT sequences useful (with the exception of SEQ ID NO: 125 and SEQ ID NO: 126) in performing the methods according to the present invention. The sequences SEQ ID NO: 123 and 124 are probably not full length sequences.

FIG. 10 shows YEP16 sequences useful in the methods of the invention.

FIG. 12 taken from TRENDS in plant Science Vol. 7, No. 10, October 2002 (Claudia Jonak and Heribert Hirt) shows possible shaggy-like kinase pathways in plants. AtGSK1 is a positive regulator of the high-salt response. WIG (wound-induced GSK) is implicated in wound signalling. AtSK11 and AtSK12 are involved in correct flower patterning. Genetic and biochemical analyses indicate that BIN2 (brassinosteroid-insensitive 1)-mediated brassinosteroid (BR) signalling, which controls nuclear accumulation of BES1 (BR11-EMS-suppressor 1) and BRZ1 (brassinazole-resistant 1).

FIG. 14 shows a CLUSTAL multiple alignment of plant Group I shaggy-like kinases. Motifs I and II are boxed.

Figure 2:
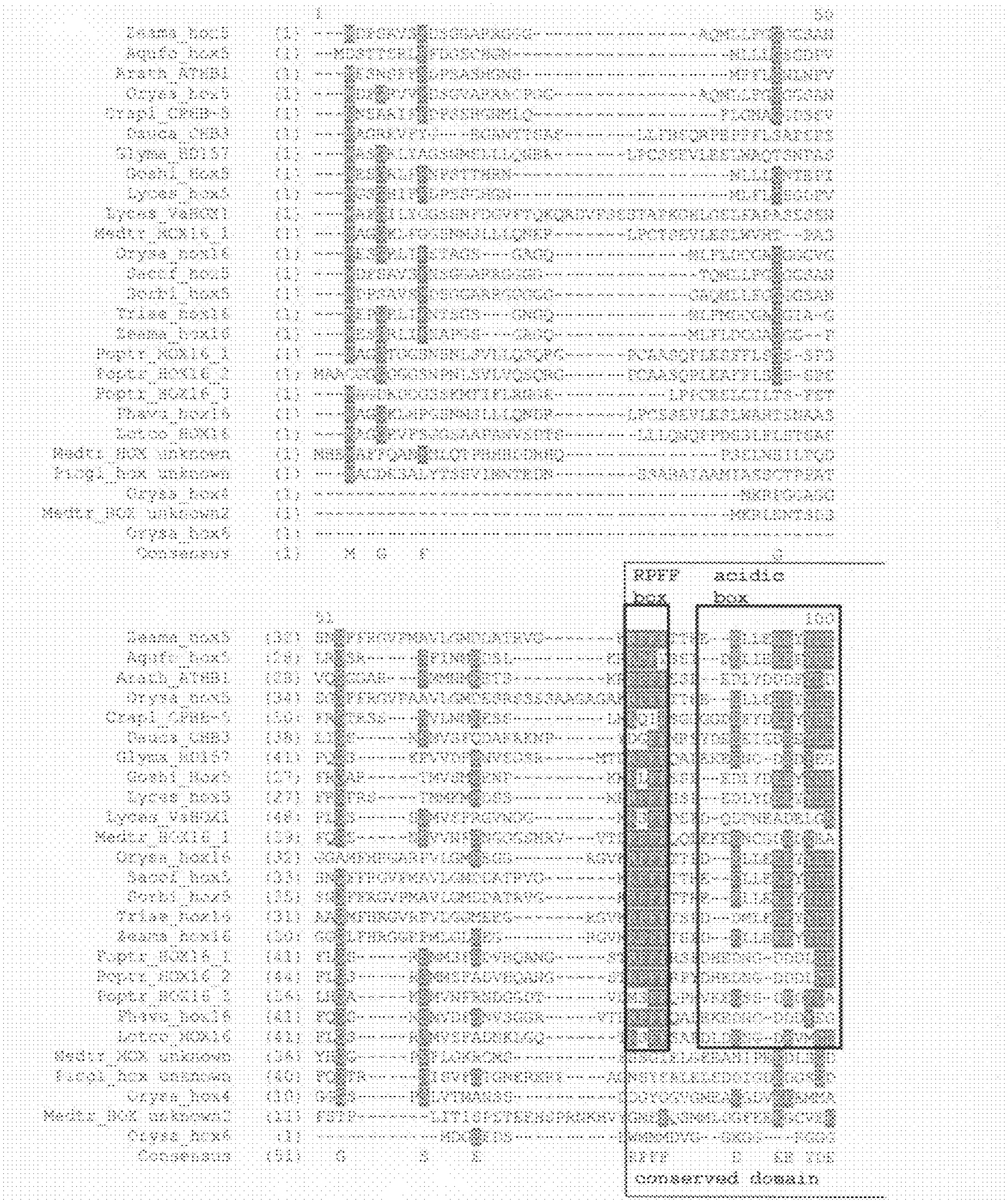
FIG. 2 shows a multiple alignment of several plant class I HDZip hox5 polypeptides, using VNTI AlignX multiple alignment program, based on a modified ClustalW algorithm (InforMax, Bethesda, Md., at informaxinc.com), with default settings for gap opening penalty of 10 and a gap extension of 0.05). The three main characterized domains, from N-terminal to C-terminal, are heavily boxed and identified as the acidic box, the class I homeodomain and the six heptad-leucine zipper. Additionally, the Trp tail and the RPFF amino acid motif are lightly boxed.
Figure 2:
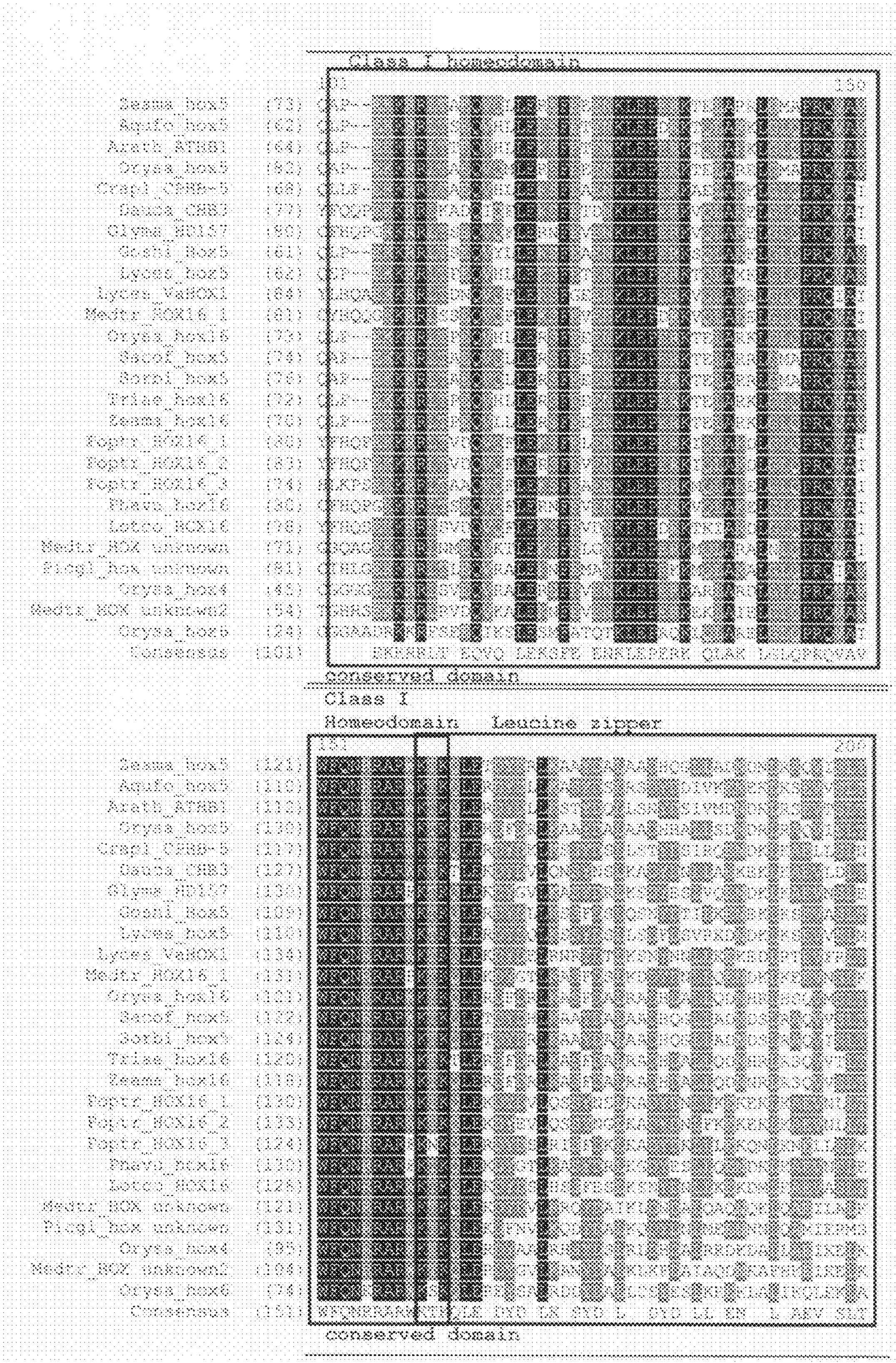
Figure 2:
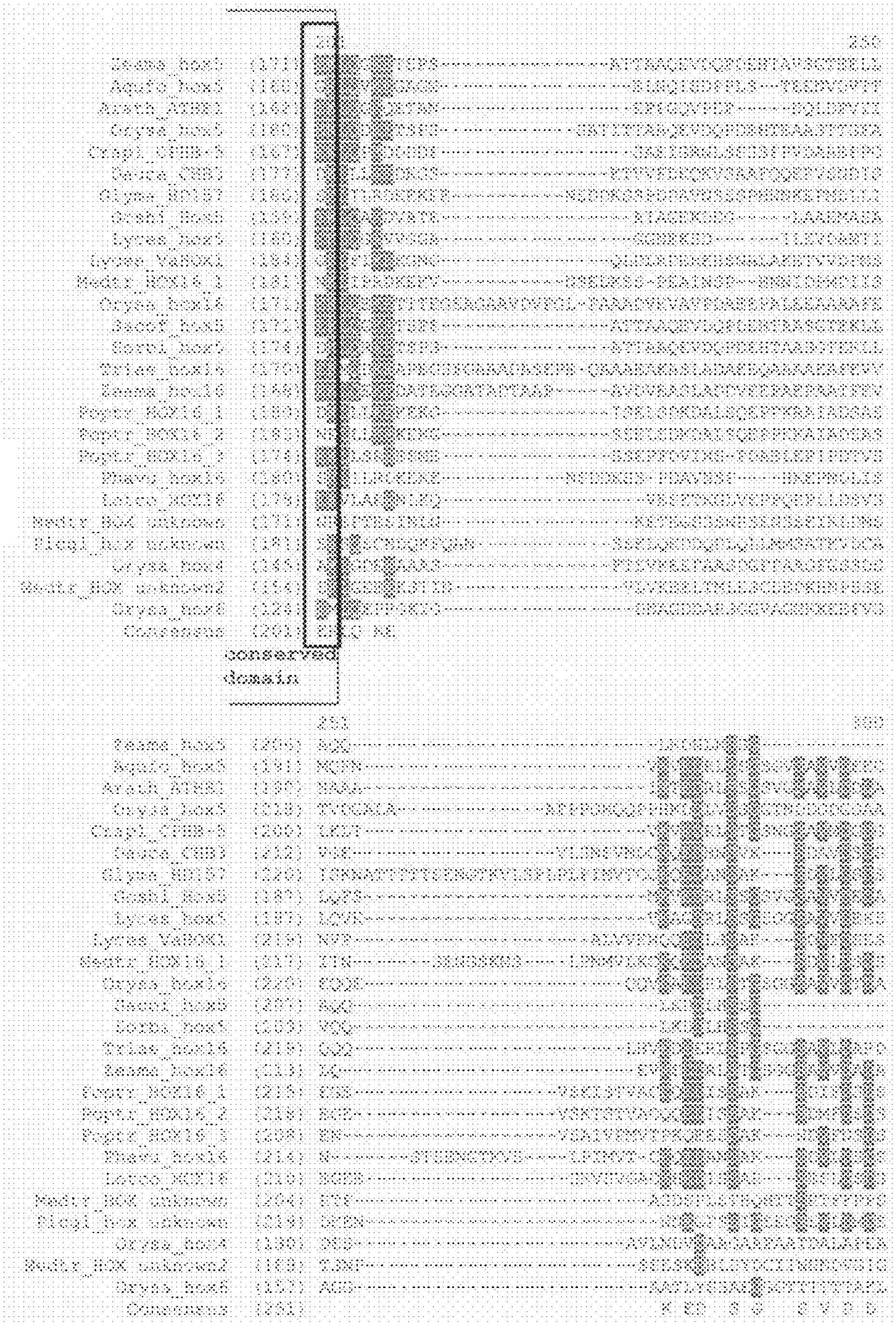
Figure 2:
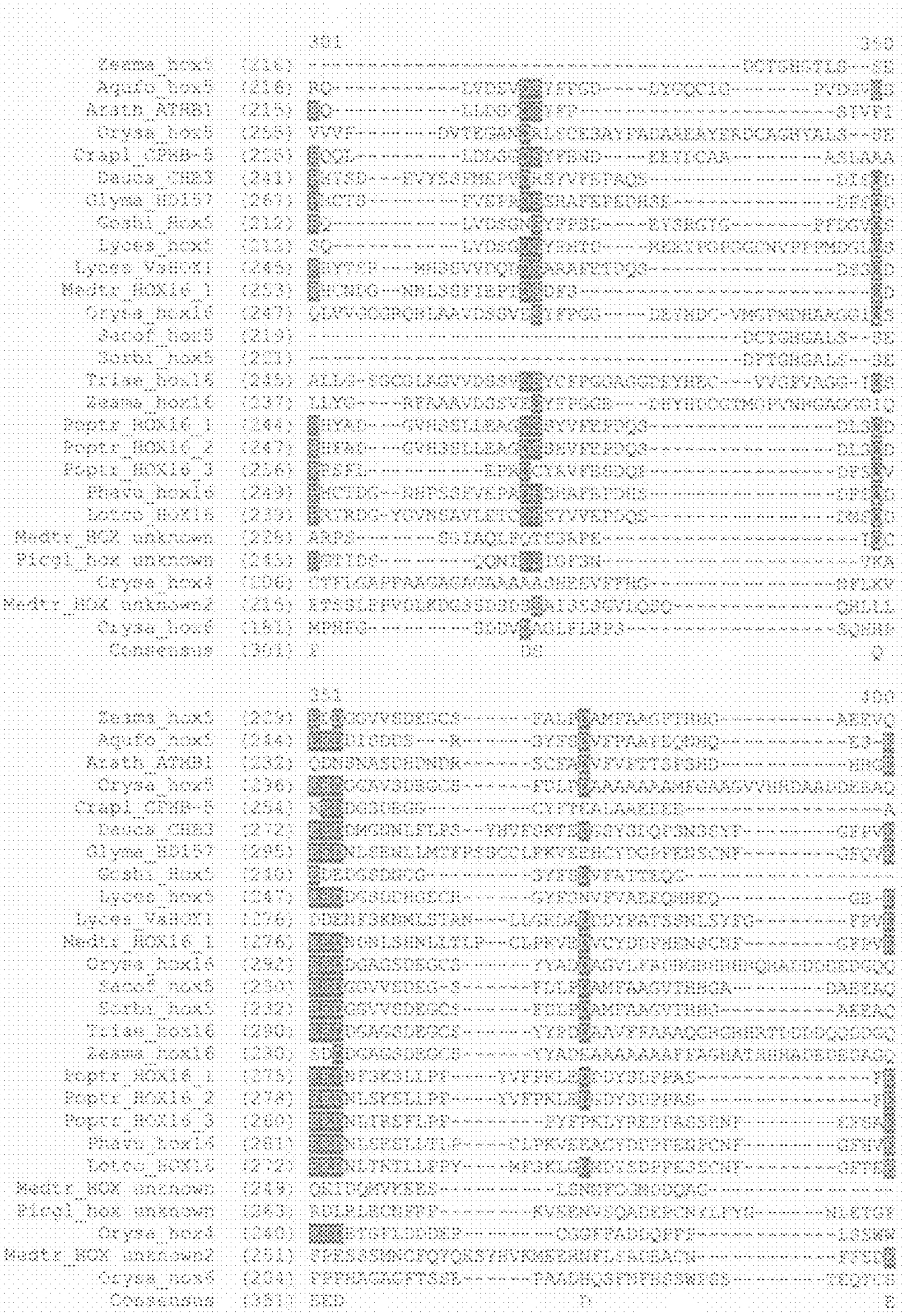

Unless otherwise defined, all technical and scientific terms used herein have the same meaning as commonly understood by one of ordinary skill in the art to which this invention belongs. Although methods and materials similar or equivalent to those described herein can be used in the practice or testing of the present invention, suitable methods and materials are described below. All publications, patent applications, patents, and other references mentioned herein are hereby incorporated by reference in their entirety. In the case of conflict, the present specification, including definitions, will control.

EXAMPLES

The present invention will now be described with reference to the following examples, which are by way of illustration alone and are not intended to completely define or to otherwise limit the scope of the invention.

Unless otherwise stated, recombinant DNA techniques were performed according to standard protocols described in (Sambrook (2001) Molecular Cloning: a laboratory manual, 3rd Edition Cold Spring Harbor Laboratory Press, CSH, New York) or in Volumes 1 and 2 of Ausubel et al. (1994), Current Protocols in Molecular Biology, Current Protocols. Standard materials and methods for plant molecular work are described in Plant Molecular Biology Labfase (1993) by R. D. D. Croy, published by BIOS Scientific Publications Ltd (UK) and Blackwell Scientific Publications (UK).

Examples Class I HDZip hox5 Polypeptides and Encoding Sequences

Example 1

Identification of Sequences Related to SEQ ID NO: 1 and SEQ ID NO: 2

Sequences (full length cDNA, ESTs or genomic) were identified amongst those maintained in the Entrez Nucleotides database at the National Center for Biotechnology Information (NCBI) using database sequence search tools, such as the Basic Local Alignment Tool (BLAST) (Altschul et al. (1990) J. Mol. Biol. 215:403-410; and Altschul et al. (1997) Nucleic Acids Res. 25:3389-3402). The program was used to find regions of local similarity between sequences by comparing nucleic acid or polypeptide sequences to sequence databases and by calculating the statistical significance of matches. For example, the polypeptide encoded by the nucleic acid of SEQ ID NO: 1 was used for the TBLASTN algorithm, with default settings and the filter to ignore low complexity sequences set off. The output of the analysis was viewed by pairwise comparison, and ranked according to the probability score (E-value), where the score reflects the probability that a particular alignment occurs by chance (the lower the E-value, the more significant the hit). In addition to E-values, comparisons were also scored by percentage identity. Percentage identity refers to the number of identical nucleotides (or amino acids) between the two compared nucleic acid (or polypeptide) sequences over a particular length. In some instances, the default parameters may be adjusted to modify the stringency of the search. For example the E-value may be increased to show less stringent matches. This way, short nearly exact matches may be identified.

Table A below provides a list of nucleic acid sequences (and polypeptide sequences encoded by these) related to the nucleic acid sequence of SEQ ID NO: 1.

TABLE A

Examples of sequences related to the nucleic acid sequence of SEQ ID NO: 1

| Name | NCBI nucleotide accession number | Nucleotide SEQ ID NO | Translated polypeptide SEQ ID NO | Source |
|---|---|---|---|---|
| Orysa_hox5 | XM_482406 | 1 | 2 | *Oryza sativa* |
| Orysa_hox16 | XM_467603 | 3 | 4 | *Oryza sativa* |
| Zeama_hox5* | CO458693<br>DV024016 | 5 | 6 | *Zea mays* |
| Zeama_hox16 | AY105265 | 7 | 8 | *Zea mays* |
| Sacof_hox5* | CA088615<br>CA115362<br>CA142506 | 9 | 10 | *Saccharum officinarum* |
| Sorbi_hox5* | BE363386<br>CD432381 | 11 | 12 | *Sorghum bicolor* |
| Triae_hox16* | DR735359<br>DR741379<br>CD916488 | 13 | 14 | *Triticum aestivum* |
| Arath_ATHB1 | X58821 | 15 | 16 | *Arabidopsis thaliana* |
| Dauca_CHB3** | D26575 | 17 | 18 | *Daucus carota* |
| Glyma_HD157** | AF184278 | 19 | 20 | *Glycine max* |
| Crapl_CPHB-5 | AF443621 | 21 | 22 | *Craterostigma plantagineum* |
| Goshi_hox5* | DT465649<br>CD486134 | 23 | 24 | *Gossypium hirsutum* |
| Lyces_hox5 | BT014213.1 | 25 | 26 | *Lycopersicon esculentum* |

TABLE A-continued

| Examples of sequences related to the nucleic acid sequence of SEQ ID NO: 1 | | | | |
|---|---|---|---|---|
| Name | NCBI nucleotide accession number | Nucleotide SEQ ID NO | Translated polypeptide SEQ ID NO | Source |
| Lyces_VaHOX1 | X94947 | 27 | 28 | *Lycopersicon esculentum* |
| Medsa_hox16* | CB892061 CA858059 | 29 | 30 | *Medicago sativa* |
| Aqufo_hox5 | DT758247 | 31 | 32 | *Aquilegia formosa* × *Aquilegia pubescens* |
| Poptr_hox16_1 | scaff_XV.439 | 40 | 41 | *Populus tremuloides* |
| Poptr_hox16_2 | scaff_XII.649 | 42 | 43 | *Populus tremuloides* |
| Poptr_hox16_3 | lcl\|scaff_VIII.1839 | 44 | 45 | *Populus tremuloides* |
| Medtr_hox16_1 | CR954197.2 | 46 | 47 | *Medicago truncatula* |
| Phavu_hox16 | AF402605 | 48 | 49 | *Phaseolus vulgaris* |
| Lotco_hox16 | AP006364 | 50 | 51 | *Lotus corniculatus* |

*Contig compiled from several EST accessions (main ones shown); EST sequencing quality being usually lower, a few nucleic acid substitutions may be expected.

**Sequences from *Daucus carota* and *Glycine max* have been corrected compared to their accession number.

Example 2

Alignment of Class I HDZip hox5 Polypeptide Sequences

AlignX from the Vector NTI (Invitrogen) based on the popular Clustal algorithm of progressive alignment (Thompson et al. (1997) Nucleic Acids Res 25:4876-4882; Chenna et al. (2003). Nucleic Acids Res 31:3497-3500) was used. A phylogenetic tree can be constructed using a neighbour-joining clustering algorithm. Default values are for the gap open penalty of 10, for the gap extension penalty of 0.1 and the selected weight matrix is Blosum 62 (if polypeptides are aligned).

The result of the multiple sequence alignment is shown in FIG. 2. The three main characterized domains, from N-terminal to C-terminal, are heavily boxed and identified as the acidic box, the class I homeodomain and the six heptad-leucine zipper. The "Conserved Domain" comprises these three domains. Additionally, the Trp tail and the RPFF amino acid motif are lightly boxed.

Example 3

Calculation of Global Percentage Identity Between Class I HDZip hox5 Polypeptides Sequences Global percentages of similarity and identity between full length class I HDZip hox5 polypeptide sequences were determined using the Matrix Global Alignment Tool (MatGAT) software (BMC Bioinformatics. 2003 4:29. MatGAT: an application that generates similarity/identity matrices using protein or DNA sequences. Campanella J J, Bitincka L, Smalley J; software hosted by Ledion Bitincka). MatGAT software generates similarity/identity matrices for DNA or protein sequences without needing pre-alignment of the data. The program performs a series of pair-wise alignments using the Myers and Miller global alignment algorithm (with a gap opening penalty of 12, and a gap extension penalty of 2), calculates similarity and identity using for example Blosum 62 (for polypeptides), and then places the results in a distance matrix. Sequence similarity is shown in the bottom half of the dividing line and sequence identity is shown in the top half of the diagonal dividing line.

Parameters used in the comparison were:

Scoring matrix: Blosum62

First Gap: 12

Extending gap: 2

Results of the software analysis are shown in Table B1 for the global similarity and identity over the full length of the polypeptide sequences (excluding the partial polypeptide sequences). Percentage identity is given above the diagonal and percentage similarity is given below the diagonal.

The percentage identity between the polypeptide sequences shown can be as low as 29% amino acid identity compared to SEQ ID NO: 2.

TABLE B 1

MatGAT results for global similarity and identity over the full length of the polypeptide sequences.

| | 1 | 2 | 3 | 4 | 5 | 6 | 7 | 8 | 9 | 10 | 11 | 12 | 13 | 14 | 15 | 16 | 17 | 18 | 19 | 20 | 21 | 22 |
|---|---|---|---|---|---|---|---|---|---|---|---|---|---|---|---|---|---|---|---|---|---|---|
| 1. Aqufo_Hox5 | ■ | 56 | 54 | 37 | 34 | 64 | 36 | 64 | 35 | 34 | 36 | 47 | 37 | 36 | 38 | 38 | 36 | 42 | 41 | 46 | 49 | 42 |
| 2. Arath_ATHB1 | 73 | ■ | 52 | 34 | 34 | 59 | 36 | 57 | 33 | 34 | 36 | 44 | 34 | 35 | 40 | 35 | 35 | 39 | 39 | 41 | 43 | 39 |
| 3. Crapl_CPHB-5 | 69 | 66 | ■ | 33 | 35 | 56 | 37 | 59 | 33 | 33 | 33 | 45 | 39 | 34 | 37 | 36 | 36 | 41 | 39 | 41 | 44 | 41 |
| 4. Dauca_CHB3 | 52 | 52 | 48 | ■ | 44 | 39 | 53 | 35 | 46 | 49 | 46 | 30 | 33 | 47 | 58 | 56 | 43 | 32 | 33 | 31 | 33 | 33 |
| 5. Glyma_HD157 | 50 | 47 | 48 | 58 | ■ | 33 | 44 | 32 | 43 | 43 | 72 | 33 | 31 | 84 | 48 | 48 | 47 | 32 | 31 | 31 | 31 | 32 |

TABLE B 1-continued

MatGAT results for global similarity and identity over the full length of the polypeptide sequences.

| | 1 | 2 | 3 | 4 | 5 | 6 | 7 | 8 | 9 | 10 | 11 | 12 | 13 | 14 | 15 | 16 | 17 | 18 | 19 | 20 | 21 | 22 |
|---|---|---|---|---|---|---|---|---|---|---|---|---|---|---|---|---|---|---|---|---|---|---|
| 6. Goshi_Hox5 | 79 | 74 | 71 | 53 | 49 | ■ | 38 | 64 | 36 | 36 | 37 | 46 | 38 | 35 | 39 | 36 | 35 | 40 | 39 | 46 | 49 | 40 |
| 7. Lotco_Hox16 | 51 | 53 | 51 | 66 | 62 | 53 | ■ | 35 | 45 | 66 | 50 | 29 | 31 | 49 | 62 | 59 | 49 | 30 | 31 | 30 | 32 | 31 |
| 8. Lyces_Hox5 | 75 | 70 | 72 | 51 | 45 | 75 | 50 | ■ | 34 | 34 | 36 | 46 | 38 | 34 | 37 | 36 | 33 | 41 | 41 | 45 | 47 | 41 |
| 9. Lyces_VaHOX1 | 49 | 48 | 47 | 63 | 58 | 48 | 62 | 47 | ■ | 45 | 44 | 31 | 32 | 47 | 53 | 49 | 44 | 33 | 33 | 32 | 33 | 33 |
| 10. Medtr_Hox16 | 48 | 48 | 50 | 65 | 64 | 49 | 78 | 48 | 63 | ■ | 46 | 30 | 30 | 45 | 59 | 55 | 42 | 31 | 30 | 31 | 31 | 30 |
| 11. Medtr_Hox16_1 | 52 | 49 | 50 | 61 | 81 | 49 | 67 | 49 | 61 | 64 | ■ | 33 | 28 | 77 | 51 | 48 | 50 | 32 | 31 | 29 | 29 | 32 |
| 12. Orysa_Hox16 | 62 | 59 | 58 | 50 | 50 | 60 | 47 | 58 | 45 | 50 | 51 | ■ | 49 | 34 | 32 | 31 | 30 | 46 | 45 | 73 | 76 | 45 |
| 13. Orysa_Hox5 | 53 | 47 | 52 | 48 | 48 | 52 | 48 | 50 | 44 | 45 | 46 | 59 | ■ | 32 | 32 | 32 | 30 | 66 | 66 | 49 | 50 | 65 |
| 14. Phavu_HOX16 | 51 | 51 | 48 | 64 | 89 | 49 | 65 | 47 | 63 | 65 | 88 | 49 | 48 | ■ | 56 | 55 | 51 | 34 | 32 | 31 | 32 | 33 |
| 15. Poptr_HOX16_1 | 54 | 54 | 52 | 71 | 66 | 52 | 75 | 50 | 66 | 73 | 69 | 48 | 49 | 71 | ■ | 92 | 48 | 35 | 35 | 32 | 34 | 34 |
| 16. Poptr_HOX16_2 | 51 | 49 | 51 | 70 | 66 | 50 | 73 | 49 | 65 | 70 | 66 | 47 | 46 | 71 | 96 | ■ | 47 | 34 | 33 | 32 | 32 | 34 |
| 17. Poptr_HOX16_3 | 52 | 51 | 47 | 59 | 59 | 52 | 63 | 45 | 59 | 59 | 62 | 44 | 44 | 65 | 63 | 63 | ■ | 34 | 33 | 30 | 31 | 33 |
| 18. Sacof_Hox5 | 62 | 58 | 57 | 47 | 44 | 60 | 48 | 57 | 44 | 45 | 46 | 56 | 69 | 46 | 48 | 47 | 47 | ■ | 95 | 46 | 46 | 94 |
| 19. Sorbi_Hox5 | 62 | 57 | 55 | 46 | 45 | 58 | 51 | 58 | 45 | 44 | 46 | 56 | 69 | 47 | 50 | 47 | 46 | 97 | ■ | 43 | 46 | 94 |
| 20. Triae_Hox16 | 62 | 54 | 56 | 48 | 48 | 59 | 47 | 58 | 47 | 49 | 47 | 82 | 61 | 48 | 52 | 51 | 46 | 56 | 55 | ■ | 72 | 45 |
| 21. Zeama_Hox16 | 63 | 58 | 59 | 51 | 49 | 62 | 51 | 60 | 49 | 50 | 47 | 81 | 62 | 51 | 49 | 48 | 46 | 56 | 57 | 81 | ■ | 45 |
| 22. Zeama_Hox5 | 62 | 58 | 56 | 46 | 44 | 59 | 49 | 57 | 45 | 45 | 45 | 55 | 68 | 46 | 50 | 46 | 48 | 96 | 96 | 57 | 56 | ■ |

The “Conserved Domain” of class I HDZip hox5 polypeptide sequences comprises from N-terminal to C-terminal, an acidic box, a class I homeodomain and the six heptad-leucine zipper (see FIG. 2), as defined hereinabove. When percentage identity analysis is performed on the conserved domains instead of on the full-length polypeptide sequences, an increase in percentage identity is observed, as shown in Table B 2. Lowest values are now above 50% amino acid identity compared to SEQ ID NO: 2.

TABLE B 2

MatGAT results for global similarity and identity over the “Conserved Domain” of the polypeptide sequences.

| | 1 | 2 | 3 | 4 | 5 | 6 | 7 | 8 | 9 | 10 | 11 | 12 | 13 | 14 | 15 | 16 | 17 | 18 | 19 | 20 |
|---|---|---|---|---|---|---|---|---|---|---|---|---|---|---|---|---|---|---|---|---|
| 1. Aqufo_hox5_CD | ■ | 81 | 74 | 66 | 82 | 62 | 82 | 62 | 61 | 75 | 66 | 61 | 67 | 63 | 60 | 68 | 67 | 73 | 76 | 67 |
| 2. Arath_ATHB1_CD | 93 | ■ | 74 | 59 | 82 | 61 | 85 | 61 | 61 | 71 | 66 | 63 | 65 | 62 | 59 | 67 | 66 | 71 | 71 | 67 |
| 3. Crapl_CPHB-5_CD | 85 | 85 | ■ | 61 | 78 | 62 | 77 | 57 | 60 | 69 | 63 | 62 | 62 | 58 | 65 | 65 | 64 | 66 | 68 | 65 |

TABLE B 2-continued

MatGAT results for global similarity and identity over the "Conserved Domain" of the polypeptide sequences.

| | 1 | 2 | 3 | 4 | 5 | 6 | 7 | 8 | 9 | 10 | 11 | 12 | 13 | 14 | 15 | 16 | 17 | 18 | 19 | 20 |
|---|---|---|---|---|---|---|---|---|---|---|---|---|---|---|---|---|---|---|---|---|
| 4. Dauca_CHB3_CD | 81 | 79 | 75 | | 64 | 70 | 62 | 66 | 69 | 57 | 57 | 64 | 80 | 75 | 66 | 58 | 59 | 57 | 57 | 58 |
| 5. Goshi_hox5_CD | 94 | 95 | 89 | 81 | | 66 | 83 | 63 | 63 | 74 | 66 | 63 | 68 | 63 | 64 | 67 | 66 | 73 | 75 | 67 |
| 6. Lotco_hox16_CD | 80 | 78 | 74 | 81 | 80 | | 62 | 67 | 85 | 54 | 52 | 62 | 77 | 73 | 64 | 53 | 52 | 54 | 54 | 53 |
| 7. Lyces_hox5_CD | 91 | 92 | 88 | 79 | 92 | 77 | | 57 | 61 | 75 | 68 | 63 | 66 | 62 | 60 | 71 | 69 | 75 | 76 | 70 |
| 8. Lyces_VaHOX1_CD | 77 | 75 | 71 | 79 | 76 | 84 | 74 | | 71 | 56 | 57 | 62 | 73 | 68 | 60 | 58 | 58 | 57 | 57 | 58 |
| 9. Medtr_hox16_CD | 77 | 75 | 74 | 81 | 77 | 93 | 75 | 84 | | 59 | 57 | 61 | 75 | 71 | 62 | 57 | 57 | 58 | 59 | 57 |
| 10. Orysa_hox16_CD | 93 | 92 | 85 | 77 | 92 | 79 | 92 | 74 | 75 | | 84 | 58 | 60 | 58 | 58 | 82 | 82 | 94 | 96 | 82 |
| 11. Orysa_hox5_CD | 90 | 87 | 83 | 78 | 88 | 77 | 88 | 71 | 74 | 91 | | 59 | 58 | 57 | 57 | 92 | 93 | 81 | 84 | 94 |
| 12. Phavu_hox16_CD | 79 | 79 | 75 | 80 | 79 | 81 | 76 | 75 | 80 | 76 | 75 | | 71 | 71 | 65 | 60 | 60 | 57 | 58 | 60 |
| 13. Poptr_hox16_1_CD | 81 | 80 | 75 | 88 | 82 | 90 | 79 | 84 | 87 | 79 | 80 | 86 | | 93 | 65 | 59 | 60 | 58 | 61 | 59 |
| 14. Poptr_hox16_2_CD | 79 | 77 | 74 | 85 | 79 | 87 | 76 | 82 | 84 | 75 | 75 | 85 | 98 | | 62 | 57 | 57 | 56 | 58 | 57 |
| 15. Poptr_hox16_3_CD | 74 | 75 | 73 | 80 | 75 | 76 | 71 | 76 | 77 | 73 | 71 | 78 | 77 | 77 | | 57 | 57 | 56 | 58 | 58 |
| 16. Sacof_hox5_CD | 89 | 86 | 80 | 77 | 87 | 77 | 86 | 71 | 73 | 88 | 96 | 74 | 79 | 75 | 72 | | 98 | 79 | 82 | 98 |
| 17. Sorbi_hox5_CD | 89 | 86 | 81 | 77 | 87 | 77 | 87 | 71 | 73 | 89 | 97 | 74 | 79 | 76 | 72 | 99 | | 78 | 82 | 98 |
| 18. Triae_hox16_CD | 93 | 92 | 85 | 79 | 92 | 80 | 92 | 74 | 75 | 98 | 91 | 77 | 80 | 77 | 73 | 88 | 89 | | 95 | 79 |
| 19. Zeama_hox16_CD | 93 | 92 | 86 | 78 | 92 | 81 | 92 | 75 | 77 | 98 | 92 | 79 | 80 | 76 | 74 | 90 | 91 | 98 | | 82 |
| 20. Zeama_hox5_CD | 89 | 86 | 81 | 77 | 87 | 77 | 87 | 71 | 73 | 89 | 97 | 74 | 79 | 75 | 72 | 99 | 100 | 89 | 91 | |

Example 4

Identification of Domains Comprised in Class I HDZip Hox5 Polypeptide Sequences The Integrated Resource of Protein Families, Domains and Sites (InterPro) database is an integrated interface for the commonly used signature databases for text- and sequence-based searches. The InterPro database combines these databases, which use different methodologies and varying degrees of biological information about well-characterized proteins to derive protein signatures. Collaborating databases include SWISS-PROT, PROSITE, TrEMBL, PRINTS, ProDom and Pfam, Smart and TIGRFAMs. Interpro is hosted at the European Bioinformatics Institute in the United Kingdom.

The results of the InterPro scan of the polypeptide sequence as represented by SEQ ID NO: 2 are presented in Table C.

TABLE C

InterPro scan results of the polypeptide sequence as represented by SEQ ID NO: 2

| | | | |
|---|---|---|---|
| InterPro | IPR000047 | Helix-turn-helix motif, lambda-like repressor | |
| | PRINTS | PR00031 | HTHREPRESSR |
| InterPro | IPR001356 | Homeobox | |
| | PRODOM | PD000010 | Homeobox |
| | PRINTS | PR00024 | HOMEOBOX |
| | PFAM | PF00046 | Homeobox |
| | SMART | SM00389 | HOX |
| | PROFILE | PS00027 | HOMEOBOX_1 |
| | PROFILE | PS50071 | HOMEOBOX_2 |

TABLE C-continued

| InterPro scan results of the polypeptide sequence as represented by SEQ ID NO: 2 | | | |
|---|---|---|---|
| InterPro | IPR003106 | Leucine zipper, homeobox-associated | |
| | PFAM | PF02183 | HALZ |
| InterPro | IPR009057 | Homeodomain-like | |
| | SUPERFAMILY | SSF46689 | Homeodomain_like |
| InterPro | IPR012287 | Homeodomain-related | |
| | GENE3D | G3DSA: 1.10.10.60 | Homeodomain-rel |

Primary amino acid composition (in %) to determine if a polypeptide domain is rich in specific amino acids (for example in an acidic box) may be calculated using software programs from the ExPASy server, in particular the ProtParam tool (Gasteiger E et al. (2003) ExPASy: the proteomics server for in-depth protein knowledge and analysis. Nucleic Acids Res 31:3784-3788). The composition of the polypeptide sequence of interest may then be compared to the average amino acid composition (in %) in the Swiss-Prot Protein Sequence data bank.

In the Table below (Table D), are compared the % Asp (D), % Glu (E) and their combined content in the acidic box of SEQ ID NO: 2 with the average in Swiss-Prot Protein Sequence databank.

TABLE D

| | % Asp (D) | % Glu (E) | % Asp (D) + % Glu (E) |
|---|---|---|---|
| Average in Swiss-Prot Protein Sequence databank | 5.3% | 6.6% | 11.9% |
| Acidic box of SEQ ID NO: 2 | 9.1% | 54.5% | 63.6% |

An acidic box may be part of a transcription activation domain. Eukaryotic transcription activation domains have been classified according to their amino acid content, and major categories include acidic, glutamine-rich and proline-rich activation domains (Rutherford et al. (2005) Plant J. 43(5):769-88, and references therein).

The Gene Ontology (GO) Consortium is an international collaboration among scientists at various biological databases, with an Editorial Office based at the European Bioinformatics Institute. The objective of GO is to provide controlled vocabularies for the description of the molecular function, biological process and cellular component of gene products. When performing an InterPro scan as described above, the GO database is also searched. The class I HDZip hox5 polypeptide sequences have as molecular function transcription factor and sequence-specific DNA binding activity, and localised in the nucleus of the plant cell (see Table below (Table E)).

TABLE E

| | Gene Ontology Entry |
|---|---|
| Homeodomain | Molecular Function: transcription factor activity (GO: 0003700)<br>Cellular Component: nucleus (GO: 0005634)<br>Molecular Function: sequence-specific DNA binding (GO: 0043565) |
| Leucine zipper, homeobox-associated | Molecular Function: DNA binding (GO: 0003677)<br>Cellular Component: nucleus (GO: 0005634) |

Example 5

Topology Prediction of Class I HDZip Hox5 Polypeptide Sequences

Leucine zipper prediction and heptad identification was carried out using specialised software such as 2ZIP, which combines a standard coiled coil prediction algorithm with an approximate search for the characteristic leucine repeat (Bornberg-Bauer et al. (1998) Nucleic Acids Res 26(11): 2740-2746; hosted at Max Planck Institut, Golm in Germany). A potential leucine zipper, a repeat of leucines or a coiled coil may be identified using this software.

The class I HDZip hox5 polypeptide sequences comprise a leucine zipper prediction, with at least 5, preferably 6 heptads. When the polypeptide of SEQ ID NO: 2 is submitted to this algorithm, a potential leucine zipper is between positions 143 and 178, as shown in the output below (numbers reflect amino acid position, C the coiled coil region, and L the leucine within the heptad):

```
1---------11--------21--------31--------41--------51--------
MDPGRVVFDSGVARRACPGGAQMLLFGGGGSANSGGFFRGVPAAVLGMDESRSSSSAAGA

61--------71--------81--------91--------101-------111-------
GAKRPFFTTHEELLEEEYYDEQAPEKKRRLTAEQVQMLERSFEEENKLEPERKTELARRL

121-------131-------141-------151-------161-------171-------
GMAPRQVAVWFQNRRARWKTKQLEHDFDRLKAAYDALAADRHALLSDNDRLRAQVISLTE
            CCCCCCCCCCCCCCCCCCCCCCCCCCCCCCCCCCCCCCCCCCCCCCCC

                      L------L------L------L------L------L
                      LZLZLZLZLZLZLZLZLZLZLZLZLZLZLZLZLZLZ

181-------191-------201-------211-------221-------231-------
KLQDKETSPSSATITTAAQEVDQPDEHTEAASTTGFATVDGALAAPPPGHQQPPHKDDLV
CCCCCCCC

241-------251-------261-------271-------281-------291-------
SSGGTNDDGDGGAAVVVFDVTEGANDRLSCESAYFADAAEAYERDCAGHYALSSEEEDGG

301-------311-------321-------331-------341------
AVSDEGCSFDLPDAAAAAAAMFGAAGVVHHDAADDEEAQLGSWTAWFWS
```

Example 6

Assay for Class I HDZip Hox5 Polypeptide Sequences

Class I HDZip hox5 polypeptides or homologues thereof have DNA binding activity, preferably to 5 bp half-sites that overlap at a central position, CAA(A/T)ATTG, as detected in yeast one-hybrid assays (Meijer et al. (2000) Mol Gen Genet. 263:12-21). In transient assays on rice cell suspensions, co-bombardement of a class I HDZip hox5 polypeptide with the GUS reporter gene reportedly resulted in an increased number of stained spots, which were also more intense in color (Meijer et al, supra). This assay is useful to demonstrate the activator function of class I HDZip hox5 polypeptides or homologues.

Example 7

Cloning of *Oryza sativa* class I HDZip Hox5 Nucleic Acid Sequence

The *Oryza sativa* class I HDZip hox5 nucleic acid sequence was amplified by PCR using as template an *Oryza sativa* seedling cDNA library (Invitrogen, Paisley, UK). After reverse transcription of RNA extracted from seedlings, the cDNAs were cloned into pCMV Sport 6.0. Average insert size of the bank was 1.6 kb and the original number of clones was of the order of $1.67\times10^7$ cfu. Original titer was determined to be $3.34\times10^6$ cfu/ml after first amplification of $6\times10^{10}$ cfu/ml. After plasmid extraction, 200 ng of template was used in a 50 μl PCR mix. Primers prm06000 (SEQ ID NO: 34; sense, start codon in bold, AttB1 site in italic: 5'-GGGGACAAGTTTG-TACAAAAAAGCAGGCTTAAACAATG-GATCCCGGCCG 3') and prm06001 (SEQ ID NO: 35; reverse, complementary, AttB2 site in italic: 5' GGGGAC-CACTTTGTACAAGAAAGCTGGGTGAT-CAGCTCCAGAACCAGG 3'), which include the AttB sites for Gateway recombination, were used for PCR amplification. PCR was performed using Hifi Taq DNA polymerase in standard conditions. A PCR fragment of 1116 bp (including attB sites; from start to stop 1050 bp) was amplified and purified also using standard methods. The first step of the Gateway procedure, the BP reaction, was then performed, during which the PCR fragment recombines in vivo with the pDONR201 plasmid to produce, according to the Gateway terminology, an "entry clone". Plasmid pDONR201 was purchased from Invitrogen, as part of the Gateway® technology.

Example 8

Vector Construction

The entry clone comprising the nucleic acid sequences was subsequently used in an LR reaction with a "destination" vector used for *Oryza sativa* transformation. This vector contained as functional elements within the T-DNA borders: a plant selectable marker; a screenable marker expression cassette; and a Gateway cassette intended for LR in vivo recombination with the sequence of interest already cloned in the entry clone. A rice GOS2 promoter (SEQ ID NO: 330R SEQ ID NO: 178) for constitutive expression was located upstream of this Gateway cassette.

Figure 3:
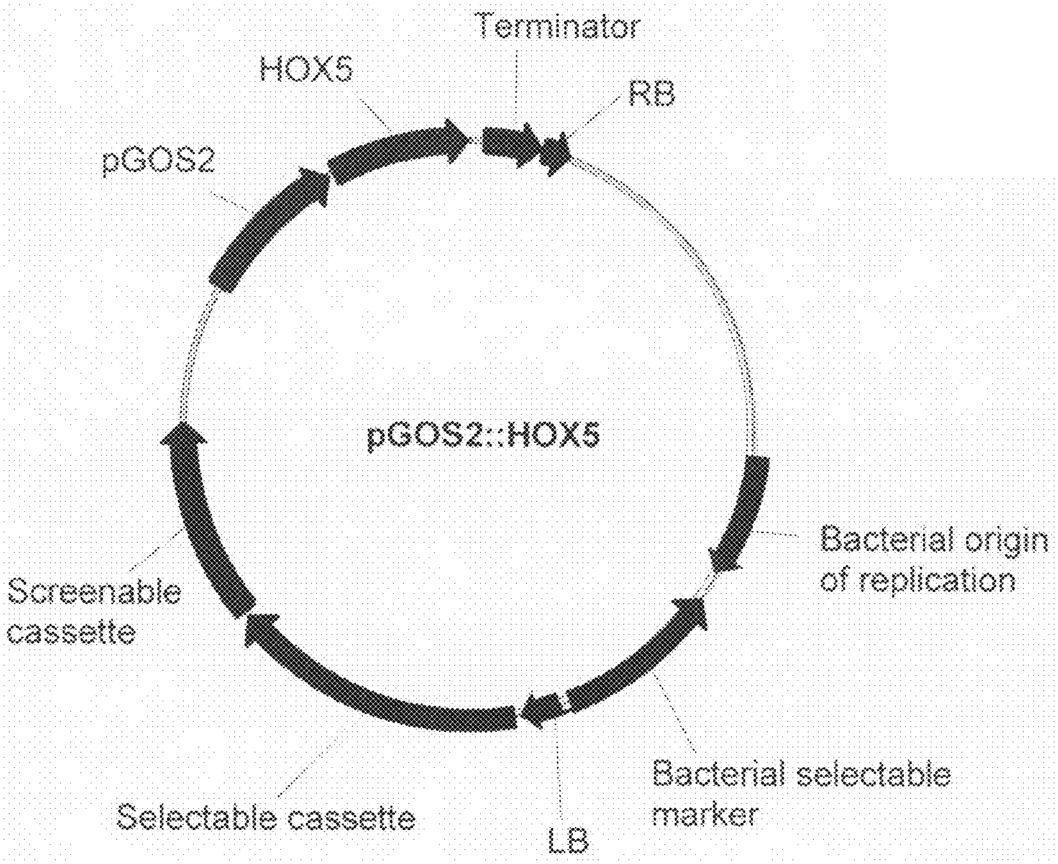
FIG. 3 shows a binary vector for expression in *Oryza sativa* of an *Oryza sativa* class I HDZip hox5 under the control of a GOS2 promoter.

After the LR recombination step, the resulting expression vector (FIG. 3) was transformed into *Agrobacterium* strain LBA4044 according to methods well known in the art.

Example 9

Plant Transformation

Rice Transformation

The *Agrobacterium* containing the expression vector was used to transform *Oryza sativa* plants. Mature dry seeds of the rice japonica cultivar Nipponbare were dehusked. Sterilization was carried out by incubating for one minute in 70% ethanol, followed by 30 minutes in 0.2% $HgCl_2$, followed by a 6 times 15 minutes wash with sterile distilled water. The sterile seeds were then germinated on a medium containing 2,4-D (callus induction medium). After incubation in the dark for four weeks, embryogenic, scutellum-derived calli were excised and propagated on the same medium. After two weeks, the calli were multiplied or propagated by subculture on the same medium for another 2 weeks. Embryogenic callus pieces were sub-cultured on fresh medium 3 days before co-cultivation (to boost cell division activity).

*Agrobacterium* strain LBA4404 containing the expression vector was used for cocultivation. *Agrobacterium* was inoculated on AB medium with the appropriate antibiotics and cultured for 3 days at 28° C. The bacteria were then collected and suspended in liquid co-cultivation medium to a density (OD600) of about 1. The suspension was then transferred to a Petri dish and the calli immersed in the suspension for 15 minutes. The callus tissues were then blotted dry on a filter paper and transferred to solidified, co-cultivation medium and incubated for 3 days in the dark at 25° C. Co-cultivated calli were grown on 2,4-D-containing medium for 4 weeks in the dark at 28° C. in the presence of a selection agent. During this period, rapidly growing resistant callus islands developed. After transfer of this material to a regeneration medium and incubation in the light, the embryogenic potential was released and shoots developed in the next four to five weeks. Shoots were excised from the calli and incubated for 2 to 3 weeks on an auxin-containing medium from which they were transferred to soil. Hardened shoots were grown under high humidity and short days in a greenhouse.

Approximately 35 independent T0 rice transformants were generated for one construct. The primary transformants were transferred from a tissue culture chamber to a greenhouse. After a quantitative PCR analysis to verify copy number of the T-DNA insert, only single copy transgenic plants that exhibit tolerance to the selection agent were kept for harvest of T1 seed. Seeds were then harvested three to five months after transplanting. The method yielded single locus transformants at a rate of over 50% (Aldemita and Hodgesl996, Chan et al. 1993, Hiei et al. 1994).

Example 10

Phenotypic Evaluation Procedure 10.1 Evaluation Setup

Approximately 35 independent T0 rice transformants were generated. The primary transformants were transferred from a tissue culture chamber to a greenhouse for growing and harvest of T1 seed. Seven events, of which the T1 progeny segregated 3:1 for presence/absence of the transgene, were retained. For each of these events, approximately 10 T1 seedlings containing the transgene (hetero- and homo-zygotes) and approximately 10 T1 seedlings lacking the transgene (nullizygotes) were selected by monitoring visual marker expression. The transgenic plants and the corresponding nullizygotes were grown side-by-side at random positions.

Greenhouse conditions were of shorts days (12 hours light), 28° C. in the light and 22° C. in the dark, and a relative humidity of 70%.

All T1 events were further evaluated in the T2 generation following the same evaluation procedure as for the T1 generation. From the stage of sowing until the stage of maturity the plants were passed several times through a digital imaging cabinet. At each time point, digital images (2048×1536 pixels, 16 million colours) were taken of each plant from at least 6 different angles.

Salt Stress Screen

Plants from 4 events (T2 seeds) were grown on a substrate made of coco fibers and argex (3 to 1 ratio). A normal nutrient solution was used during the first two weeks after transplanting the plantlets in the greenhouse. After the first two weeks, 25 mM of salt (NaCl) was added to the nutrient solution, until the plants were harvested.

Drought Screen

Plants from five events (T2 seeds) were grown in potting soil under normal conditions until they approached the heading stage. They were then transferred to a "dry" section where irrigation was withheld. Humidity probes were inserted in randomly chosen pots to monitor the soil water content (SWC). When SWC went below certain thresholds, the plants were automatically re-watered continuously until a normal level was reached again. The plants were then re-transferred again to normal conditions. The rest of the cultivation (plant maturation, seed harvest) was the same as for plants not grown under abiotic stress conditions. A confirmation round was performed consisting of repeating the screen with T2 seeds not harvested from plants of the first drought screen, but from plants grown under normal conditions.

Reduced Nutrient (Nitrogen) Availability Screen

Plants from six events (T2 seeds) were grown in potting soil under normal conditions except for the nutrient solution. The pots were watered from transplantation to maturation with a specific nutrient solution containing reduced N nitrogen (N) content, usually between 7 to 8 times less. The rest of the cultivation (plant maturation, seed harvest) was the same as for plants not grown under abiotic stress. Seed-related parameters were then measured 10.2 Statistical Analysis: F Test A two factor ANOVA (analysis of variants) was used as a statistical model for the overall evaluation of plant phenotypic characteristics. An F test was carried out on all the parameters measured of all the plants of all the events transformed with the gene of the present invention. The F test was carried out to check for an effect of the gene over all the transformation events and to verify for an overall effect of the gene, also known as a global gene effect. The threshold for significance for a true global gene effect was set at a 5% probability level for the F test. A significant F test value points to a gene effect, meaning that it is not only the mere presence or position of the gene that is causing the differences in phenotype.

10.3 Parameters Measured 10.3.1 Biomass-Related Parameter Measurement

From the stage of sowing until the stage of maturity the plants were passed several times through a digital imaging cabinet. At each time point digital images (2048×1536 pixels, 16 million colours) were taken of each plant from at least 6 different angles.

The plant aboveground area (or leafy biomass) was determined by counting the total number of pixels on the digital images from aboveground plant parts discriminated from the background. This value was averaged for the pictures taken on the same time point from the different angles and was converted to a physical surface value expressed in square mm by calibration. Experiments show that the aboveground plant area measured this way correlates with the biomass of plant parts above ground. The aboveground area is the time point at which the plant had reached its maximal leafy biomass. The early vigour is the plant (seedling) aboveground area three weeks post-germination.

An additional parameter was calculated from the digital images of plants: the greenness index. For each pixel belonging to the plant object on the image, the ratio of the green value versus the red value (in the RGB model for encoding color) is calculated. The greenness index is expressed as the percentage of pixels for which the green-to-red ratio exceeds a given threshold. Under normal growth conditions, under salt stress growth conditions, and under reduced nutrient availability growth conditions, the greenness index of plants was measured in the last imaging before flowering. In contrast, under drought stress growth conditions, the greenness index of plants was measured in the first imaging after drought.

To measure root-related parameters, plants were grown in specially designed pots with transparent bottoms to allow visualization of the roots. A digital camera recorded images through the bottom of the pot during plant growth. Root features such as total projected area (which can be correlated to total root volume), average diameter and length of roots above a certain thickness threshold (length of thick roots, or thick root length) were deduced from the picture using of appropriate software. Increase in root biomass is expressed as an increase in total root biomass (measured as maximum biomass of roots observed during the lifespan of a plant); or as an increase in the root/shoot index (measured as the ratio between root mass and shoot mass in the period of active growth of root and shoot).

10.3.2 Seed-Related Parameter Measurements

The mature primary panicles were harvested, counted, bagged, barcode-labelled and then dried for three days in an oven at 37° C. The panicles were then threshed and all the seeds were collected and counted. The filled husks were separated from the empty ones using an air-blowing device. The empty husks were discarded and the remaining fraction was counted again. The filled husks were weighed on an analytical balance. The number of filled seeds was determined by counting the number of filled husks that remained after the separation step. The total seed yield was measured by weighing all filled husks harvested from a plant. Total seed number per plant was measured by counting the number of husks harvested from a plant. Thousand Kernel Weight (TKW) is extrapolated from the number of filled seeds counted and their total weight. The Harvest Index (HI) in the present invention is defined as the ratio between the total seed yield and the above ground area ($mm^2$), multiplied by a factor 106. The total number of flowers per panicle as defined in the present invention is the ratio between the total number of seeds and the number of mature primary panicles. The seed fill rate as defined in the present invention is the proportion (expressed as a %) of the number of filled seeds over the total number of seeds (or florets).

Example 11

Results of Transgenic Rice Plants Expressing a Class I HDZip Hox5 Nucleic Acid Under Normal Growth Conditions The results of the evaluation of transgenic rice plants expressing the class I HDZip hox5 nucleic acid under normal growth conditions are presented in Table F. The percentage difference between the transgenics and the corresponding nullizygotes is shown.

TABLE F

Results of the evaluation of transgenic rice plants expressing a class I HDZip hox5 nucleic acid under normal growth conditions.

| Trait | % Difference in T1 | % Difference in T2 |
|---|---|---|
| Average root diameter | 2 | 1 |
| Length of thick roots | 9 | 17 |
| Total seed yield per plant | 17 | 19 |
| Number of filled seeds | 15 | 17 |
| Fill rate | 7 | 9 |
| Total number seeds | 6 | 9 |
| Number of flowers per panicle | 8 | 9 |
| TKW | 2 | 2 |
| Harvest index | 16 | 16 |
| Greenness index before flowering | 2 | 4 |

Example 12

Results of Transgenic Rice Plants Expressing the Nucleic Acid Sequence Useful in Performing the Methods of the Invention, Under Salt Stress Growth Conditions The results of the evaluation of transgenic rice plants expressing the nucleic acid encoding a class I HDZip hox5 polypeptide sequence under salt stress growth conditions are presented in Table G. The percentage difference between the transgenics and the corresponding nullizygotes is shown.

TABLE G

Results of the evaluation of transgenic rice plants expressing the class I HDZip hox5 nucleic acid under salt stress growth conditions.

| Trait | % Difference in T1 |
|---|---|
| Total seed yield per plant | 41 |
| Number of filled seeds | 40 |
| Fill rate | 30 |
| TKW | 1 |
| Harvest index | 36 |
| Greenness index before flowering | 7 |

Example 13

Results of Transgenic Rice Plants Expressing the Class I HDZip Hox5 Nucleic Acid Under Drought Stress Growth Conditions The results of the evaluation of transgenic rice plants expressing the nucleic acid sequence useful in performing the methods of the invention under drought stress growth conditions are presented in Table H. The percentage difference between the transgenics and the corresponding nullizygotes is shown.

TABLE H

Results of the evaluation of transgenic rice plants expressing the nucleic acid sequence useful in performing the methods of the invention, under drought stress growth conditions.

| Trait | % Difference in T1 | % Difference in T2 |
|---|---|---|
| Average root diameter | 2 | 1 |
| Length of thick roots | 9 | 14 |
| Total seed yield per plant | 18 | 31 |
| Number of filled seeds | 21 | 33 |
| Fill rate | 15 | 33 |
| Harvest index | 18 | 34 |
| Greenness index after drought | 2 | 3 |

Example 14

Results of Transgenic Rice Plants Expressing the Class I HDZip Hox5 Nucleic Acid Sequence, Under Reduced Nutrient Availability Growth Conditions The results of the evaluation of transgenic rice plants expressing the nucleic acid sequence useful in performing the methods of the invention under drought stress growth conditions are presented in Table I. The percentage difference between the transgenics and the corresponding nullizygotes is shown.

TABLE I

Results of the evaluation of transgenic rice plants expressing the nucleic acid sequence useful in performing the methods of the invention, under reduced nutrient availability growth conditions.

| Trait | % Difference in T1 |
|---|---|
| Total seed yield per plant | 20 |
| Number of filled seeds | 19 |
| Seed fill rate | 4 |
| Number of flowers per panicle | 9 |
| Harvest index | 12 |
| Greenness index before flowering | 11 |

Examples NRT Polypeptides and Encoding Nucleic Acids

Example 15

Identification of Sequences Related to SEQ ID NO: 52 and SEQ ID NO: 53

Sequences (full length cDNA, ESTs or genomic) related to SEQ ID NO: 52 and/or protein sequences related to SEQ ID NO: 53 were identified amongst those maintained in the Entrez Nucleotides database at the National Center for Biotechnology Information (NCBI) using database sequence search tools, such as the Basic Local Alignment Tool (BLAST) (Altschul et al., (1990) J. Mol. Biol. 215:403-410; and Altschul et al. (1997) Nucleic Acids Res. 25:3389-3402). The program is used to find regions of local similarity between sequences by comparing nucleic acid or polypeptide sequences to sequence databases and by calculating the statistical significance of matches. The polypeptide encoded by SEQ ID NO: 52 was used for the TBLASTN algorithm, with default settings and the filter to ignore low complexity sequences set off. The output of the analysis was viewed by pairwise comparison, and ranked according to the probability score (E-value), where the score reflects the probability that a particular alignment occurs by chance (the lower the E-value, the more significant the hit). In addition to E-values, comparisons were also scored by percentage identity. Percentage identity refers to the number of identical nucleotides (or amino acids) between the two compared nucleic acid (or polypeptide) sequences over a particular length. In some instances, the default parameters may be adjusted to modify the stringency of the search.

In addition to the publicly available nucleic acid sequences available at NCBI, proprietary sequence databases are also searched following the same procedure as described herein above.

Table J provides a list of nucleic acid and protein sequences related to the nucleic acid sequence as represented by SEQ ID NO: 52 and the protein sequence represented by SEQ ID NO: 53.

TABLE J

Nucleic acid sequences related to the nucleic acid sequence (SEQ ID NO: 52) useful in the methods of the present invention, and the corresponding deduced polypeptides.

| Species | GenBank accession | Protein SEQ ID NO: | Nucleic acid SEQ ID NO: |
|---|---|---|---|
| *Oryza sativa* | BAA33382 | 53 | 1 |
| *Phragmites australis* | BAC76606 | 66 | 65 |
| *Zea mays* | AAT66252 | 68 | 67 |
| *Zea mays* | AAN05088 | 70 | 69 |
| *Hordeum vulgare* | AAC49531 | 72 | 71 |
| *Triticum aestivum* | AAK19519 | 74 | 73 |
| *Hordeum vulgare* | AAC49532 | 76 | 75 |
| *Triticum aestivum* | AAG01172 | 78 | 77 |
| *Triticum aestivum* | AAL11016 | 80 | 79 |
| *Hordeum vulgare* | AAD28364 | 82 | 81 |
| *Hordeum vulgare* | AAD28363 | 84 | 83 |
| *Prunus persica* | BAD02939 | 86 | 85 |
| *Prunus persica* | BAD04063 | 88 | 87 |
| *Glycine max* | AAC09320 | 90 | 89 |
| *Lotus japonicus* | Q9ARC5 | 92 | 91 |
| *Nicotiana tabacum* | CAD89799 | 94 | 93 |
| *Lycopersicon esculentum* | AAK72402 | 96 | 95 |
| *Populus sp.* | CAG26716 | 98 | 97 |
| *Nicotiana tabacum* | CAD89798 | 100 | 99 |
| *Nicotiana plumbaginifolia* | CAA69387 | 102 | 101 |
| *Lycopersicon esculentum* | AAF00053 | 104 | 103 |
| *Arabidopsis thaliana* | AAC64170 | 106 | 105 |
| *Lycopersicon esculentum* | AAF00054 | 108 | 107 |
| *Brassica napus* | CAC05338 | 110 | 109 |
| *Arabidopsis thaliana* | AAY78876 | 112 | 111 |
| *Arabidopsis thaliana* | NP_172289 | 114 | 113 |
| *Arabidopsis thaliana* | AAC35884 | 116 | 115 |
| *Arabidopsis thaliana* | NP_200886 | 118 | 117 |
| *Arabidopsis thaliana* | AAU05505 | 120 | 119 |
| *Daucus carota* | AAL99362 | 122 | 121 |
| *Zea mays* | CAC87729 | 124 | 123 |

Example 16

Alignment of Relevant Polypeptide Sequences

AlignX from the Vector NTI (Invitrogen) is based on the popular Clustal algorithm of progressive alignment (Thompson et al. (1997) Nucleic Acids Res 25:4876-4882; Chenna et al. (2003). Nucleic Acids Res 31:3497-3500). A phylogenetic tree can be constructed using a neighbour-joining clustering algorithm. Default values are for the gap open penalty of 10, for the gap extension penalty of 0.1 and the selected weight matrix is Blosum 62 (if polypeptides are aligned).

The result of the multiple sequence alignment using polypeptides relevant in identifying the ones useful in performing the methods of the invention is shown in FIG. 6 of the present application. The multiple alignment shows the high sequence conservation among NRT proteins of the various species. Proteins comprising a PTR2 domain (exemplified by SEQ ID NO: 126) clearly do not fall within the group of NRT proteins as defined herein.

Example 17

Calculation of Global Percentage Identity Between NRT Polypeptide Sequences

Global percentages of similarity and identity between full length polypeptide sequences useful in performing the methods of the invention were determined using MatGAT (Matrix Global Alignment Tool) software (BMC Bioinformatics. 2003 4:29. MatGAT: an application that generates similarity/identity matrices using protein or DNA sequences. Campanella J J, Bitincka L, Smalley J; software hosted by Ledion Bitincka). MatGAT software generates similarity/identity matrices for DNA or protein sequences without needing pre-alignment of the data. The program performs a series of pair-wise alignments using the Myers and Miller global alignment algorithm (with a gap opening penalty of 12, and a gap extension penalty of 2), calculates similarity and identity using for example Blosum 62 (for polypeptides), and then places the results in a distance matrix. Sequence similarity is shown in the bottom half of the dividing line and sequence identity is shown in the top half of the diagonal dividing line.

Parameters used in the comparison were:

Scoring matrix: Blosum62

First Gap: 12

Extending gap: 2

Results of the software analysis are shown in Table K for the global similarity and identity over the full length of the polypeptide sequences (excluding the partial polypeptide sequences). Percentage identity is given above the diagonal and percentage similarity is given below the diagonal.

The percentage identity between the polypeptide sequences useful in performing the methods of the invention is usually above 60% amino acid identity compared to SEQ ID NO: 53 (although exceptions may occur); whereas proteins comprising a PTR2 domain (such as rice nitrate transporter represented by SEQ ID NO: 126, line 31 in the table below) shows only very limited sequence identity with the NRT proteins (17% or lower).

Example 18

Identification of Domains Comprised in Polypeptide Sequences Useful in Performing the Methods of the Invention The Integrated Resource of Protein Families, Domains and Sites (InterPro) database is an integrated interface for the commonly used signature databases for text- and sequence-based searches. The InterPro database combines these databases, which use different methodologies and varying degrees of biological information about well-characterized proteins to derive protein signatures. Collaborating databases include SWISS-PROT, PROSITE, TrEMBL, PRINTS, ProDom and Pfam, Smart and TIGRFAMs. Interpro is hosted at the European Bioinformatics Institute in the United Kingdom.

The results of the InterPro scan of the polypeptide sequence as represented by SEQ ID NO: 53 are presented in Table L.

TABLE L

InterPro scan results of the polypeptide sequence as represented by SEQ ID NO: 53

| Database | Accession number | Accession name |
|---|---|---|
| Pfam | PF07690 | MFS_1 |

TABLE K

MatGAT results for global similarity and identity over the full length of the polypeptide sequences.

| | 1 | 2 | 3 | 4 | 5 | 6 | 7 | 8 | 9 | 10 | 11 | 12 | 13 | 14 | 15 | 16 | 17 |
|---|---|---|---|---|---|---|---|---|---|---|---|---|---|---|---|---|---|
| 1. SEQID53 | | 87.4 | 87.2 | 85.7 | 79.9 | 79.9 | 80.7 | 80.1 | 79.7 | 79.9 | 79.4 | 75.4 | 75.0 | 75.7 | 73.7 | 73.7 | 73.9 |
| 2. SEQID66 | 91.9 | | 88.7 | 87.4 | 82.7 | 83.1 | 83.1 | 83.1 | 82.4 | 82.7 | 82.2 | 75.5 | 75.1 | 76.0 | 75.1 | 73.4 | 72.9 |
| 3. SEQID68 | 91.7 | 92.7 | | 98.5 | 80.9 | 81.1 | 80.7 | 81.3 | 81.1 | 80.5 | 80.7 | 75.1 | 74.8 | 75.9 | 73.6 | 70.8 | 71.2 |
| 4. SEQID70 | 90.2 | 91.4 | 98.5 | | 79.4 | 79.5 | 79.2 | 79.7 | 79.5 | 79.0 | 79.2 | 73.8 | 73.4 | 74.4 | 72.1 | 69.2 | 69.7 |
| 5. SEQID72 | 85.7 | 88.5 | 87.4 | 85.9 | | 98.2 | 91.9 | 98.4 | 97.4 | 98.0 | 98.6 | 73.2 | 72.8 | 73.5 | 71.3 | 68.3 | 68.7 |
| 6. SEQID74 | 85.7 | 88.9 | 87.8 | 86.3 | 99.2 | | 91.9 | 98.4 | 97.8 | 97.6 | 97.8 | 73.5 | 73.2 | 73.4 | 71.1 | 68.1 | 68.3 |
| 7. SEQID76 | 86.5 | 88.5 | 87.2 | 85.7 | 96.3 | 96.1 | | 92.3 | 91.6 | 91.6 | 91.4 | 72.8 | 72.4 | 72.8 | 71.1 | 68.7 | 68.5 |
| 8. SEQID78 | 85.6 | 88.5 | 87.2 | 85.7 | 99.0 | 98.8 | 96.3 | | 98.2 | 97.4 | 98.2 | 73.7 | 73.4 | 74.1 | 71.9 | 68.5 | 68.9 |
| 9. SEQID80 | 85.6 | 88.3 | 87.2 | 85.7 | 98.6 | 98.8 | 95.9 | 98.8 | | 97.0 | 97.2 | 73.7 | 73.4 | 73.9 | 71.3 | 67.9 | 68.3 |
| 10. SEQID82 | 85.4 | 88.3 | 86.8 | 85.3 | 98.6 | 98.8 | 95.9 | 98.0 | 98.2 | | 97.6 | 73.0 | 72.6 | 73.0 | 70.7 | 67.9 | 68.3 |
| 11. SEQID84 | 85.0 | 88.0 | 87.0 | 85.5 | 99.0 | 98.8 | 95.7 | 98.8 | 98.4 | 98.0 | | 72.8 | 72.4 | 73.2 | 70.9 | 68.1 | 68.5 |
| 12. SEQID86 | 85.6 | 84.5 | 84.7 | 83.2 | 83.0 | 83.0 | 83.4 | 83.2 | 83.0 | 82.6 | 82.5 | | 99.1 | 90.4 | 87.4 | 81.7 | 80.8 |
| 13. SEQID88 | 85.4 | 84.3 | 84.5 | 83.0 | 82.8 | 82.8 | 83.2 | 83.0 | 82.8 | 82.5 | 82.3 | 99.6 | | 90.0 | 87.0 | 81.1 | 80.2 |
| 14. SEQID90 | 86.1 | 85.3 | 85.3 | 83.8 | 83.8 | 83.0 | 84.2 | 84.0 | 83.6 | 83.0 | 83.2 | 95.8 | 95.7 | | 91.3 | 82.6 | 81.4 |
| 15. SEQID92 | 85.2 | 85.8 | 84.9 | 83.4 | 82.8 | 82.3 | 83.4 | 83.0 | 83.0 | 82.3 | 82.3 | 94.3 | 94.2 | 96.2 | | 80.6 | 78.5 |
| 16. SEQID94 | 84.8 | 84.0 | 82.1 | 88.6 | 81.3 | 88.6 | 81.5 | 81.5 | 81.1 | 80.6 | 81.1 | 91.9 | 91.3 | 91.7 | 90.9 | | 93.4 |
| 17. SEQID96 | 85.0 | 83.6 | 81.9 | 80.4 | 80.8 | 80.0 | 81.0 | 81.0 | 80.6 | 80.0 | 80.8 | 91.0 | 90.4 | 90.4 | 89.6 | 96.2 | |
| 18. SEQID98 | 85.0 | 84.1 | 84.5 | 83.0 | 82.6 | 81.9 | 83.4 | 82.8 | 82.6 | 81.7 | 82.4 | 94.5 | 94.2 | 94.0 | 93.2 | 91.3 | 90.2 |
| 19. SEQID100 | 82.6 | 82.3 | 80.9 | 79.4 | 80.0 | 80.0 | 79.2 | 79.8 | 79.6 | 79.2 | 79.8 | 91.3 | 90.9 | 90.6 | 89.4 | 95.5 | 94.4 |
| 20. SEQID102 | 82.9 | 82.1 | 80.9 | 79.4 | 80.2 | 80.2 | 79.4 | 80.0 | 79.8 | 79.4 | 80.0 | 91.7 | 91.3 | 90.9 | 89.6 | 95.7 | 94.4 |
| 21. SEQID104 | 82.7 | 82.3 | 80.6 | 79.1 | 79.4 | 78.7 | 79.4 | 79.6 | 79.4 | 78.7 | 79.2 | 90.4 | 90.0 | 90.4 | 89.2 | 95.3 | 93.8 |
| 22. SEQID106 | 83.7 | 82.8 | 82.1 | 80.8 | 80.4 | 80.0 | 81.5 | 80.6 | 80.4 | 79.8 | 79.8 | 90.6 | 90.4 | 88.5 | 88.5 | 87.5 | 86.6 |
| 23. SEQID108 | 82.6 | 82.1 | 80.2 | 78.7 | 79.2 | 78.5 | 79.2 | 79.4 | 79.2 | 78.5 | 79.1 | 90.0 | 89.6 | 90.0 | 89.1 | 95.1 | 93.6 |
| 24. SEQID110 | 83.7 | 83.2 | 82.1 | 80.8 | 80.8 | 80.8 | 81.7 | 80.9 | 80.8 | 80.2 | 80.2 | 90.6 | 90.4 | 89.1 | 89.1 | 88.1 | 87.2 |
| 25. SEQID112 | 83.7 | 82.7 | 82.5 | 81.2 | 80.6 | 80.6 | 80.6 | 81.0 | 80.8 | 80.3 | 80.3 | 90.4 | 90.2 | 89.2 | 88.3 | 87.9 | 86.8 |
| 26. SEQID114 | 81.8 | 81.8 | 82.1 | 80.7 | 79.5 | 79.3 | 80.8 | 79.7 | 79.5 | 78.7 | 79.1 | 86.6 | 86.4 | 85.7 | 85.5 | 84.2 | 83.1 |
| 27. SEQID116 | 81.6 | 81.6 | 81.9 | 80.5 | 79.5 | 79.5 | 80.8 | 79.7 | 79.5 | 78.7 | 79.1 | 86.4 | 86.2 | 85.5 | 85.3 | 84.0 | 82.9 |
| 28. SEQID118 | 79.0 | 77.6 | 76.3 | 75.0 | 75.7 | 75.7 | 76.1 | 75.9 | 75.5 | 75.3 | 75.1 | 83.3 | 83.5 | 84.6 | 82.9 | 82.4 | 81.6 |
| 29. SEQID120 | 78.6 | 77.5 | 76.9 | 75.6 | 75.1 | 74.7 | 74.9 | 75.1 | 74.7 | 74.7 | 74.4 | 83.0 | 83.2 | 83.4 | 81.2 | 81.5 | 81.2 |
| 30. SEQID122 | 79.1 | 77.0 | 75.1 | 73.6 | 73.5 | 73.1 | 73.8 | 74.0 | 73.6 | 73.1 | 73.5 | 82.8 | 82.2 | 82.4 | 82.1 | 87.3 | 90.3 |
| 31. SEQID126 | 28.8 | 29.5 | 26.4 | 26.2 | 30.3 | 28.6 | 33.4 | 29.5 | 28.6 | 28.8 | 29.1 | 28.8 | 28.6 | 28.1 | 30.5 | 29.8 | 29.6 |

| | 18 | 19 | 20 | 21 | 22 | 23 | 24 | 25 | 26 | 27 | 28 | 29 | 30 | 31 |
|---|---|---|---|---|---|---|---|---|---|---|---|---|---|---|
| 1. SEQID53 | 73.5 | 72.6 | 72.4 | 72.6 | 71.5 | 72.4 | 71.8 | 71.5 | 66.9 | 66.7 | 66.1 | 66.1 | 66.3 | 14.9 |
| 2. SEQID66 | 73.8 | 71.9 | 71.3 | 72.3 | 71.4 | 72.1 | 70.6 | 71.1 | 67.3 | 67.1 | 66.0 | 65.5 | 65.2 | 15.2 |
| 3. SEQID68 | 73.9 | 70.9 | 70.8 | 71.5 | 70.8 | 71.1 | 71.1 | 71.1 | 67.3 | 67.1 | 64.4 | 64.6 | 64.1 | 13.7 |
| 4. SEQID70 | 72.6 | 69.4 | 69.2 | 70.0 | 69.6 | 69.6 | 70.0 | 69.9 | 66.2 | 66.0 | 63.5 | 63.7 | 62.6 | 13.7 |
| 5. SEQID72 | 71.7 | 68.3 | 67.5 | 67.9 | 68.9 | 67.7 | 68.1 | 68.1 | 64.9 | 64.9 | 64.8 | 63.9 | 61.3 | 14.5 |
| 6. SEQID74 | 71.5 | 68.3 | 67.5 | 67.4 | 68.7 | 67.2 | 68.1 | 67.2 | 64.7 | 64.7 | 64.8 | 63.5 | 60.9 | 13.8 |
| 7. SEQID76 | 70.9 | 67.2 | 67.0 | 67.7 | 69.0 | 67.5 | 68.5 | 67.5 | 64.9 | 64.9 | 63.3 | 62.2 | 61.6 | 16.6 |
| 8. SEQID78 | 72.2 | 68.1 | 67.4 | 68.1 | 69.0 | 67.9 | 68.3 | 67.9 | 65.1 | 65.1 | 65.0 | 64.1 | 61.5 | 14.3 |
| 9. SEQID80 | 72.2 | 68.1 | 67.4 | 68.1 | 69.0 | 67.9 | 68.3 | 67.9 | 65.1 | 65.1 | 64.4 | 63.5 | 61.1 | 13.8 |
| 10. SEQID82 | 70.7 | 67.7 | 67.0 | 67.4 | 68.5 | 67.2 | 67.7 | 67.5 | 64.3 | 64.3 | 64.4 | 63.7 | 60.9 | 12.9 |
| 11. SEQID84 | 71.5 | 68.1 | 67.4 | 67.9 | 68.9 | 67.7 | 67.9 | 67.4 | 64.9 | 64.9 | 64.1 | 63.2 | 61.1 | 14.5 |
| 12. SEQID86 | 88.3 | 82.6 | 82.8 | 82.6 | 81.7 | 82.3 | 81.1 | 80.8 | 75.3 | 75.1 | 73.7 | 74.0 | 71.9 | 14.9 |
| 13. SEQID88 | 87.4 | 81.9 | 82.1 | 81.9 | 81.1 | 81.5 | 80.6 | 80.6 | 74.7 | 74.5 | 73.8 | 73.8 | 71.4 | 14.7 |
| 14. SEQID90 | 87.9 | 81.5 | 81.1 | 81.9 | 79.8 | 81.5 | 79.6 | 80.8 | 74.5 | 74.3 | 73.7 | 72.9 | 72.9 | 15.7 |
| 15. SEQID92 | 85.5 | 80.4 | 80.4 | 80.0 | 78.3 | 79.8 | 78.1 | 79.4 | 73.8 | 73.6 | 72.0 | 72.0 | 70.3 | 15.8 |
| 16. SEQID94 | 81.3 | 90.4 | 90.4 | 89.8 | 77.4 | 89.6 | 76.6 | 77.7 | 72.6 | 72.5 | 67.5 | 66.6 | 82.9 | 15.2 |
| 17. SEQID96 | 81.2 | 89.1 | 88.9 | 89.1 | 76.1 | 88.9 | 75.3 | 76.3 | 71.4 | 71.2 | 66.8 | 66.6 | 88.5 | 15.8 |
| 18. SEQID98 | | 82.8 | 82.6 | 83.4 | 80.2 | 83.0 | 79.6 | 80.0 | 74.9 | 74.7 | 71.4 | 70.1 | 72.7 | 14.8 |
| 19. SEQID100 | 91.7 | | 97.5 | 95.3 | 78.3 | 95.1 | 77.9 | 78.3 | 73.8 | 73.6 | 66.8 | 66.8 | 79.0 | 14.9 |
| 20. SEQID102 | 92.1 | 99.2 | | 95.1 | 77.9 | 94.7 | 77.4 | 77.9 | 73.2 | 73.0 | 66.4 | 66.6 | 79.2 | 14.6 |
| 21. SEQID104 | 90.6 | 97.5 | 97.7 | | 77.9 | 99.6 | 77.0 | 77.7 | 72.6 | 72.5 | 67.3 | 66.6 | 79.6 | 17.2 |
| 22. SEQID106 | 87.9 | 87.2 | 87.2 | 86.6 | | 77.7 | 94.7 | 82.8 | 87.0 | 86.8 | 68.5 | 68.1 | 68.4 | 14.9 |
| 23. SEQID108 | 90.2 | 97.4 | 97.4 | 99.6 | 86.4 | | 76.8 | 77.4 | 72.5 | 72.3 | 67.3 | 66.2 | 79.4 | 17.2 |
| 24. SEQID110 | 88.9 | 87.7 | 87.7 | 86.6 | 97.7 | 86.4 | | 82.1 | 85.5 | 85.3 | 67.9 | 67.5 | 67.5 | 15.5 |
| 25. SEQID112 | 89.0 | 87.5 | 88.1 | 86.8 | 90.6 | 86.4 | 90.4 | | 78.6 | 78.4 | 70.3 | 69.9 | 68.8 | 15.4 |
| 26. SEQID114 | 85.3 | 83.6 | 83.6 | 82.5 | 90.9 | 82.3 | 90.8 | 87.9 | | 99.8 | 64.4 | 63.7 | 63.8 | 13.8 |
| 27. SEQID116 | 85.1 | 83.4 | 83.4 | 82.3 | 90.8 | 82.1 | 90.6 | 87.7 | 99.8 | | 64.2 | 63.1 | 63.6 | 13.6 |
| 28. SEQID118 | 82.9 | 81.3 | 81.4 | 81.8 | 82.4 | 81.6 | 82.2 | 82.9 | 79.0 | 78.8 | | 89.3 | 59.2 | 16.0 |
| 29. SEQID120 | 81.7 | 80.4 | 80.6 | 80.8 | 81.2 | 80.6 | 80.8 | 82.1 | 78.4 | 77.7 | 93.9 | | 59.4 | 16.4 |
| 30. SEQID122 | 82.6 | 86.0 | 86.4 | 85.6 | 78.9 | 85.4 | 79.3 | 79.4 | 75.7 | 75.5 | 75.3 | 74.9 | | 15.6 |
| 31. SEQID126 | 29.6 | 28.8 | 28.6 | 32.4 | 27.9 | 32.4 | 28.8 | 30.7 | 31.8 | 31.8 | 32.0 | 31.8 | 31.0 | |

Example 19

Topology Prediction of the NRT Polypeptides (Subcellular Localization, Transmembrane . . . )

TargetP 1.1 predicts the subcellular location of eukaryotic proteins. The location assignment is based on the predicted presence of any of the N-terminal pre-sequences: chloroplast transit peptide (cTP), mitochondrial targeting peptide (mTP) or secretory pathway signal peptide (SP). Scores on which the final prediction is based are not really probabilities, and they do not necessarily add to one. However, the location with the highest score is the most likely according to TargetP, and the relationship between the scores (the reliability class) may be an indication of how certain the prediction is. The reliability class (RC) ranges from 1 to 5, where 1 indicates the strongest prediction. TargetP is maintained at the server of the Center for Biological Sequence Analysis, Technical University of Denmark.

For the sequences predicted to contain an N-terminal pre-sequence a potential cleavage site can also be predicted.

A number of parameters were selected, such as organism group (non-plant or plant), cutoff sets (none, predefined set of cutoffs, or user-specified set of cutoffs), and the calculation of prediction of cleavage sites (yes or no).

The results of TargetP 1.1 analysis of the polypeptide sequence as represented by SEQ ID NO: 53 are presented Table M. The "plant" organism group has been selected, no cutoffs defined, and the predicted length of the transit peptide requested. No subcellular localisation could be predicted.

TABLE M

| TargetP 1.1 analysis of the polypeptide sequence as represented by SEQ ID NO: 53 | |
|---|---|
| Length (AA) | 533 |
| Chloroplastic transit peptide | 0.116 |
| Mitochondrial transit peptide | 0.060 |
| Secretory pathway signal peptide | 0.008 |
| Other subcellular targeting | 0.874 |
| Predicted Location | — |
| Reliability class | 2 |
| Predicted transit peptide length | — |

Many other algorithms can be used to perform such analyses, including:

- ChloroP 1.1 hosted on the server of the Technical University of Denmark;
- Protein Prowler Subcellular Localisation Predictor version 1.2 hosted on the server of the Institute for Molecular Bioscience, University of Queensland, Brisbane, Australia;
- PENCE Proteome Analyst PA-GOSUB 2.5 hosted on the server of the University of Alberta, Edmonton, Alberta, Canada;

Using the TMHMM program (Center for Biological Sequence Analysis, Technical University of Denmark) the number of transmembrane helices was predicted to be 11, see Table N hereunder.

TABLE N

| Location | Region of amino acids involved |
|---|---|
| outside | 1 67 |
| TMhelix | 68 90 |
| inside | 91 129 |
| TMhelix | 130 152 |
| outside | 153 155 |
| TMhelix | 156 178 |
| inside | 179 184 |
| TMhelix | 185 207 |
| outside | 208 221 |
| TMhelix | 222 244 |
| inside | 245 272 |
| TMhelix | 273 295 |
| outside | 296 314 |
| TMhelix | 315 332 |
| inside | 333 352 |
| TMhelix | 353 375 |
| outside | 376 379 |
| TMhelix | 380 402 |
| inside | 403 408 |
| TMhelix | 409 431 |
| outside | 432 440 |
| TMhelix | 441 463 |
| inside | 464 533 |

The expected number of amino acids in transmembrane helices was predicted to be at least 242 (if more than 18, the protein is very likely a transmembrane protein). Furthermore, the presence of a secretion signal is not very likely, since there is no predicted transmembrane helix within the first 60 amino acids, nor a N-terminal signal sequence (Exp number, first 60 AAs: 0.00085).

Example 20

Assay for NRT

To determine the transporter activity of NRT, the nitrate uptake assay as described by Tong et al. (Plant J. 41, 442-450, 2005). Briefly, mRNA is prepared from constructs in which the ORF encoding the NRT protein of interest is preceded by 5'-UTR of *Xenopus* β-globin gene and followed by the 3'-UTR of the same gene. This mRNA is injected in *Xenopus* stage V and VI oocytes whereafter the NRT protein of interest is expressed. The oocytes are incubated in a solution with $^{15}NO_3^-$ during 3 to 12 hrs at 18° C. Next, the oocytes are washed and dried at 60° C. The uptake of $^{15}N$-enriched nitrate is measured by measuring the ratio $^{15}N/^{14}N$ with a mass spectrometer. Other suitable assays for measuring $NO_3$ uptake are known to persons skilled in the art, see for example Filleur et al ($15NO_3^-$ uptake in roots, FEBS Letters 489, 220-224, 2001), or Zhou et al (measurement of anion-elicited currents with the two-electrode voltage-clamp method, J. Biol. Chem. 275, 39894-39899, 2000). If required, a nar2 gene may be co-expressed to increase nitrate transport.

Alternatively, the activity of an NRT protein or homologue thereof may be assayed by expressing the NRT protein or homologue thereof under control of a GOS2 promoter in the *Oryza sativa* cultivar Nipponbare, which results in plants with increased aboveground biomass and/or increased seed yield compared to corresponding wild type plants. This increase in seed yield may be measured in several ways, for example as an increase of total seed weight, number of filled seeds or total number of seeds, as an increase of harvest index or as an increase of flowers per panicle.

Example 21

Cloning of Nucleic Acid Sequence as Represented by SEQ ID NO: 52

The *Oryza sativa* NRT gene was amplified by PCR using as template an *Oryza sativa* seedling cDNA library (Invitrogen, Paisley, UK). After-reverse transcription of RNA extracted from seedlings, the cDNAs were cloned into pCMV Sport 6.0. Average insert size of the bank was 1.5 kb and the original number of clones was of the order of $1.59\times10^7$ cfu. Original titer was determined to be $9.6\times10^5$ cfu/ml after first amplification of $6\times10^{11}$ cfu/ml. After plasmid extraction, 200 ng of template was used in a 50 µl PCR mix. Primers prm07061 (SEQ ID NO: 54; sense, start codon in bold, AttB1 site in italic: 5'-ggggacaagtttgtacaaaaaagcaggcttaaaca atggactcgtcgacggtg-3') and prm07062 (SEQ ID NO: 55 reverse, complementary, stop codon in bold, AttB2 site in italic: 5'-ggggaccactttgtacaagaaagctgggtctcggtcgcagaattgtttac-3'), which include the AttB sites for Gateway recombination, were used for PCR amplification. PCR was performed using Hifi Taq DNA polymerase in standard conditions. A PCR fragment of 1683 bp (including attB sites) was amplified and purified also using standard methods. The first step of the Gateway procedure, the BP reaction, was then performed, during which the PCR fragment recombines in vivo with the pDONR201 plasmid to produce, according to the Gateway terminology, an "entry clone". Plasmid pDONR201 was purchased from Invitrogen, as part of the Gateway® technology.

Example 22

Expression Vector Construction Using the Nucleic Acid Sequence as Represented by SEQ ID NO: 52

The entry clone was subsequently used in an LR reaction with a destination vector used for *Oryza sativa* transformation. This vector contains as functional elements within the T-DNA borders: a plant selectable marker; a screenable marker expression cassette; and a Gateway cassette intended for LR in vivo recombination with the sequence of interest already cloned in the entry clone. A rice GOS2 promoter (nucleotides 1 to 2188 of SEQ ID NO: 56, the promoter-gene combination) for constitutive expression was located upstream of this Gateway cassette.

Figure 7:
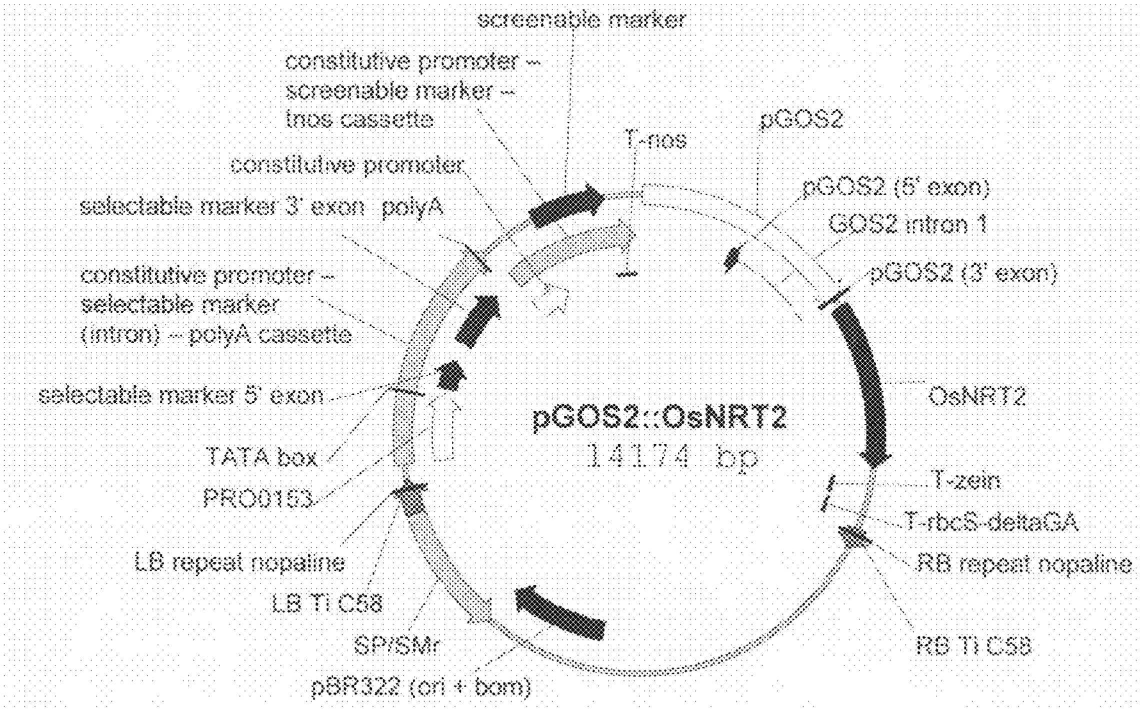
FIG. 7 shows the binary vector for increased expression in *Oryza sativa* of an rice NRT protein-encoding nucleic acid under the control of a GOS2 promoter.

After the LR recombination step, the resulting expression vector for NRT (FIG. 7) was transformed into *Agrobacterium* strain LBA4044 and subsequently to *Oryza sativa* plants.

Example 23

Plant Transformation

Rice Transformation

The *Agrobacterium* containing the expression vector was used to transform *Oryza sativa* plants. Mature dry seeds of the rice japonica cultivar Nipponbare were dehusked. Sterilization was carried out by incubating for one minute in 70% ethanol, followed by 30 minutes in 0.2% $HgCl_2$, followed by a 6 times 15 minutes wash with sterile distilled water. The sterile seeds were then germinated on a medium containing 2,4-D (callus induction medium). After incubation in the dark for four weeks, embryogenic, scutellum-derived calli were excised and propagated on the same medium. After two weeks, the calli were multiplied or propagated by subculture on the same medium for another 2 weeks. Embryogenic callus pieces were sub-cultured on fresh medium 3 days before co-cultivation (to boost cell division activity).

*Agrobacterium* strain LBA4404 containing the expression vector was used for cocultivation. *Agrobacterium* was inoculated on AB medium with the appropriate antibiotics and cultured for 3 days at 28° C. The bacteria were then collected and suspended in liquid co-cultivation medium to a density (OD600) of about 1. The suspension was then transferred to a Petri dish and the calli immersed in the suspension for 15 minutes. The callus tissues were then blotted dry on a filter paper and transferred to solidified, co-cultivation medium and incubated for 3 days in the dark at 25° C. Co-cultivated calli were grown on 2,4-D-containing medium for 4 weeks in the dark at 28° C. in the presence of a selection agent. During this period, rapidly growing resistant callus islands developed. After transfer of this material to a regeneration medium and incubation in the light, the embryogenic potential was released and shoots developed in the next four to five weeks. Shoots were excised from the calli and incubated for 2 to 3 weeks on an auxin-containing medium from which they were transferred to soil. Hardened shoots were grown under high humidity and short days in a greenhouse.

Approximately 35 independent T0 rice transformants were generated for one construct. The primary transformants were transferred from a tissue culture chamber to a greenhouse. After a quantitative PCR analysis to verify copy number of the T-DNA insert, only single copy transgenic plants that exhibit tolerance to the selection agent were kept for harvest of T1 seed. Seeds were then harvested three to five months after transplanting. The method yielded single locus transformants at a rate of over 50% (Aldemita and Hodgesl996, Chan et al., 1993, Hiei et al. 1994).

Example 24

Phenotypic Evaluation Procedure 23.1 Evaluation Setup

Approximately 35 independent T0 rice transformants were generated. The primary transformants were transferred from a tissue culture chamber to a greenhouse for growing and harvest of T1 seed. Five events, of which the T1 progeny segregated 3:1 for presence/absence of the transgene, were retained. For each of these events, approximately 10 T1 seedlings containing the transgene (hetero- and homo-zygotes) and approximately 10 T1 seedlings lacking the transgene (nullizygotes) were selected by monitoring visual marker expression. The transgenic plants and the corresponding nullizygotes were grown side-by-side at random positions under the following environmental settings: photoperiod=11.5 h, daylight intensity=30,000 lux or more, daytime temperature=28° C. or higher, night time temperature=22° C., relative humidity=60-70%.

Four T1 events were further evaluated in the T2 generation following the same evaluation procedure as for the T1 generation but with more individuals per event. From the stage of sowing until the stage of maturity the plants were passed several times through a digital imaging cabinet. At each time point digital images (2048×1536 pixels, 16 million colours) were taken of each plant from at least 6 different angles.

23.2 Statistical Analysis:

A two factor ANOVA (analysis of variants) was used as a statistical model for the overall evaluation of plant phenotypic characteristics. An F-test was carried out on all the parameters measured of all the plants of all the events transformed with the gene of the present invention. The F-test was carried out to check for an effect of the gene over all the transformation events and to verify for an overall effect of the gene, also known as a global gene effect. The threshold for significance for a true global gene effect was set at a 5% probability level for the F-test. A significant F-test value points to a gene effect, meaning that it is not only the mere presence or position of the gene that is causing the differences in phenotype.

To check for an effect of the genes within an event, i.e., for a line-specific effect, a t-test was performed within each event using data sets from the transgenic plants and the corresponding null plants. "Null plants" or "null segregants" or "nullizygotes" are the plants treated in the same way as the transgenic plant, but from which the transgene has segregated. Null plants can also be described as the homozygous negative transformed plants. The threshold for significance for the t-test is set at 10% probability level. The results for some events can be above or below this threshold. This is based on the hypothesis that a gene might only have an effect in certain positions in the genome, and that the occurrence of this position-dependent effect is not uncommon. This kind of gene effect is also named herein a "line effect of the gene". The p-value is obtained by comparing the t-value to the t-distribution or alternatively, by comparing the F-value to the F-distribution. The p-value then gives the probability that the null hypothesis (i.e., that there is no effect of the transgene) is correct.

Because two experiments with overlapping events had been carried out, a combined analysis was performed. This is useful to check consistency of the effects over the two experiments, and if this is the case, to accumulate evidence from both experiments in order to increase confidence in the conclusion. The method used was a mixed-model approach that takes into account the multilevel structure of the data (i.e. experiment-event-segregants). P-values are obtained by comparing likelihood ratio test to chi square distributions.

23.3 Parameters Measured

Biomass-Related Parameter Measurement

From the stage of sowing until the stage of maturity the plants were passed several times through a digital imaging cabinet. At each time point digital images (2048×1536 pixels, 16 million colours) were taken of each plant from at least 6 different angles.

The plant aboveground area (or leafy biomass) was determined by counting the total number of pixels on the digital images from aboveground plant parts discriminated from the background. This value was averaged for the pictures taken on the same time point from the different angles and was converted to a physical surface value expressed in square mm by calibration. Experiments show that the aboveground plant area measured this way correlates with the biomass of plant parts above ground. The aboveground area is the time point at which the plant had reached its maximal leafy biomass. The early vigour is the plant (seedling) aboveground area three weeks post-germination.

Seed-Related Parameter Measurements

The mature primary panicles were harvested, counted, bagged, barcode-labelled and then dried for three days in an oven at 37° C. The panicles were then threshed and all the seeds were collected and counted. The filled husks were separated from the empty ones using an air-blowing device. The empty husks were discarded and the remaining fraction was counted again. The filled husks were weighed on an analytical balance. The number of filled seeds was determined by counting the number of filled husks that remained after the separation step. The total seed yield was measured by weighing all filled husks harvested from a plant. Total seed number per plant was measured by counting the number of husks harvested from a plant. Thousand Kernel Weight (TKW) is extrapolated from the number of filled seeds counted and their total weight. The Harvest Index (HI) in the present invention is defined as the ratio between the total seed yield and the above ground area ($mm^2$), multiplied by a factor 106. The total number of flowers per panicle as defined in the present invention is the ratio between the total number of seeds and the number of mature primary panicles. The seed fill rate as defined in the present invention is the proportion (expressed as a %) of the number of filled seeds over the total number of seeds (or florets). The flowers-per-panicle is a parameter estimating the average number of florets per panicle on a plant, derived from the number of total seeds divided by the number of first panicles. The tallest panicle and all the panicles that overlapped with the tallest panicle when aligned vertically, were considered as first panicles and were counted manually.

Example 25

Results of the Phenotypic Evaluation of the Transgenic Plants

Upon analysis of the seeds as described above, the inventors found that plants transformed with the NRT gene construct had a higher seed yield, expressed as number of filled seeds (which may be at least in part the result of an increased fill rate), total weight of seeds and harvest index, compared to plants lacking the NRTtransgene.

The results obtained for plants in the T1 generation are summarised in Table O:

TABLE O

| | % difference | p-value |
|---|---|---|
| Nr filled seeds | +48 | 0.0000 |
| Total weight seeds | +54 | 0.0000 |
| Harvest Index | +38 | 0.0000 |
| Flowers/panicle | +14 | 0.0003 |
| Total nr seeds | +13 | 0.0287 |

These positive results seed yield were again obtained in the T2 generation. In Table P, data show the overall % increases for the number of filled seeds, total weight of seeds and harvest index, calculated from the data of the individual lines of the T2 generation, and the respective p-values. These T2 data were re-evaluated in a combined analysis with the results for the T1 generation, and the obtained p-values show that the observed effects were highly significant.

TABLE P

| | T2 generation | | Combined analysis |
|---|---|---|---|
| | % difference | p-value | p-value |
| Nr filled seeds | +100 | 0.0000 | 0.0000 |
| Total weight seeds | +104 | 0.0000 | 0.0000 |
| Harvest Index | +83 | 0.0000 | 0.0000 |
| Flowers/panicle | +18 | 0.0000 | 0.0000 |
| Total nr seeds | +20 | 0.0000 | 0.0000 |

In addition, the transgenic plants also showed an increase in biomass (areamax: +7% in the T1 generation and +4% in T2) which increase was significant (p-value of combined analysis: 0.0001).

Examples YEP16 Polypeptides and Encoding Nucleic Acids

Example 26

Gene Cloning of *Arabidopsis thaliana* YEP16-Encoding Nucleic Acid

The *Arabidopsis thaliana* YEP16-encoding gene was amplified by PCR using as template an *Oryza sativa* seedling cDNA library (Invitrogen, Paisley, UK). After reverse transcription of RNA extracted from seedlings, the cDNAs were cloned into pCMV Sport 6.0. Average insert size of the bank was 1.6 kb and the original number of clones was of the order of $1.67\times10^7$ cfu. Original titer was determined to be $3.34\times10^6$ cfu/ml after first amplification of $6\times10^{10}$ cfu/ml. After plasmid extraction, 200 ng of template was used in a 50 μl PCR mix. Primers prm00735 (SEQ ID NO: 144; sense, start codon in bold, AttB1 site in italic: 5'-ggggacaagtttgtacaaaaaagc aggcttcacaatggatactctctcagcatcc-3') and prm00736 (SEQ ID NO: 145; reverse, complementary, AttB2 site in italic: 5'-ggggaccacfftgtacaagaaagctgggttgtatcatcaagaaacccaga-3'), which include the AttB sites for Gateway recombination, were used for PCR amplification. PCR was performed using Hifi Taq DNA polymerase in standard conditions. A PCR fragment of 12173 bp (including attB sites; from start to stop 1050 bp) was amplified and purified also using standard methods. The first step of the Gateway procedure, the BP reaction, was then performed, during which the PCR fragment recombines in vivo with the pDONR201 plasmid to produce, according to the Gateway terminology, an "entry clone". Plasmid pDONR201 was purchased from Invitrogen, as part of the Gateway® technology.

Example 27

Vector Construction

The entry clone was subsequently used in an LR reaction with p00640, a destination vector used for *Oryza sativa* transformation. This vector contains as functional elements within the T-DNA borders: a plant selectable marker; a screenable marker expression cassette; and a Gateway cassette intended for LR in vivo recombination with the sequence of interest already cloned in the entry clone. A rice oleosin promoter (SEQ ID NO: 143) for seed-specific expression was located upstream of this Gateway cassette.

Figure 9:
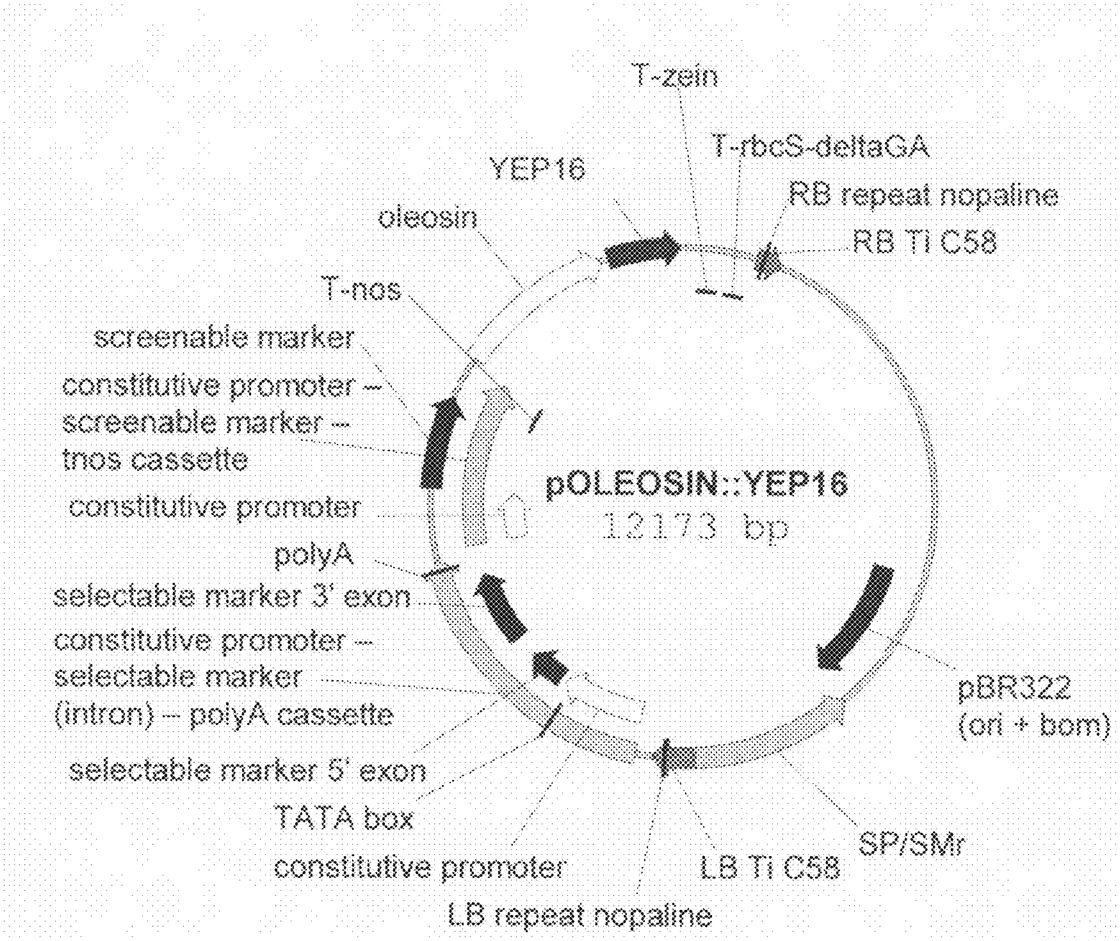
FIG. 9 shows a binary vector for expression in *Oryza sativa* of an *Arabidopsis thaliana* YEP16-encoding nucleic acid under the control of an oleosin promoter.
Figure 11:
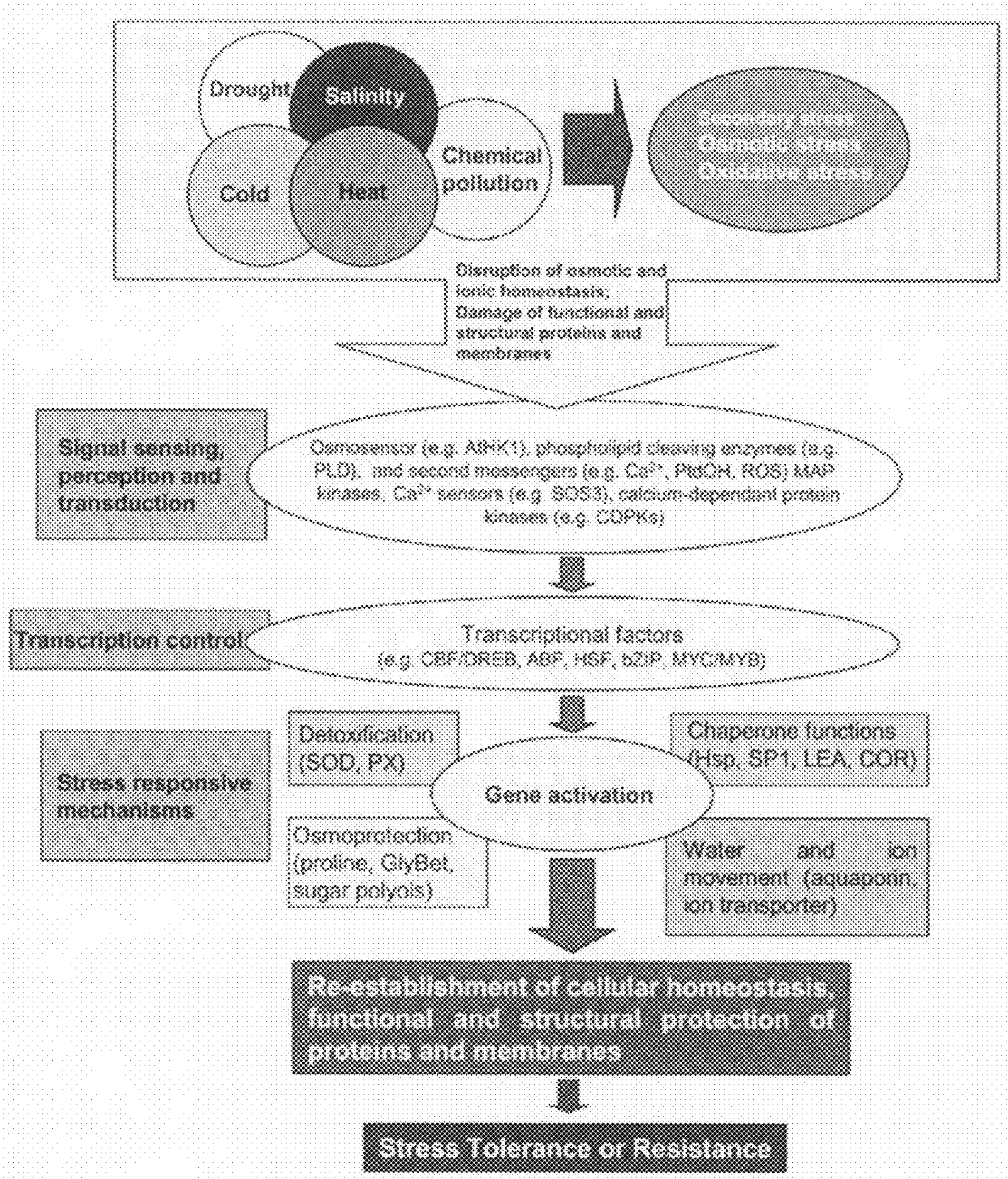
FIG. 11 taken from Planta (2003) 218: 1-14 (Wang et al.), shows plant response to abiotic stress. Primary stresses, such as drought, salinity, cold, heat and chemical pollution are often interconnected, and cause cellular damage and secondary stresses, such as osmotic and oxidative stress. The initial stress signals (e.g. osmotic and ionic effects, or temperature, membrane fluidity changes) trigger the downstream signalling process and transcription controls which activate stress-responsive mechanism to re-establish homeostasis and protect and repair damaged proteins and membranes. Inadequate response at one or several steps in the signalling and gene activation may ultimately result in irreversible changes of cellular homeostasis and in destruction of functional and structural proteins and membranes, leading to cell death.
Figure 13:
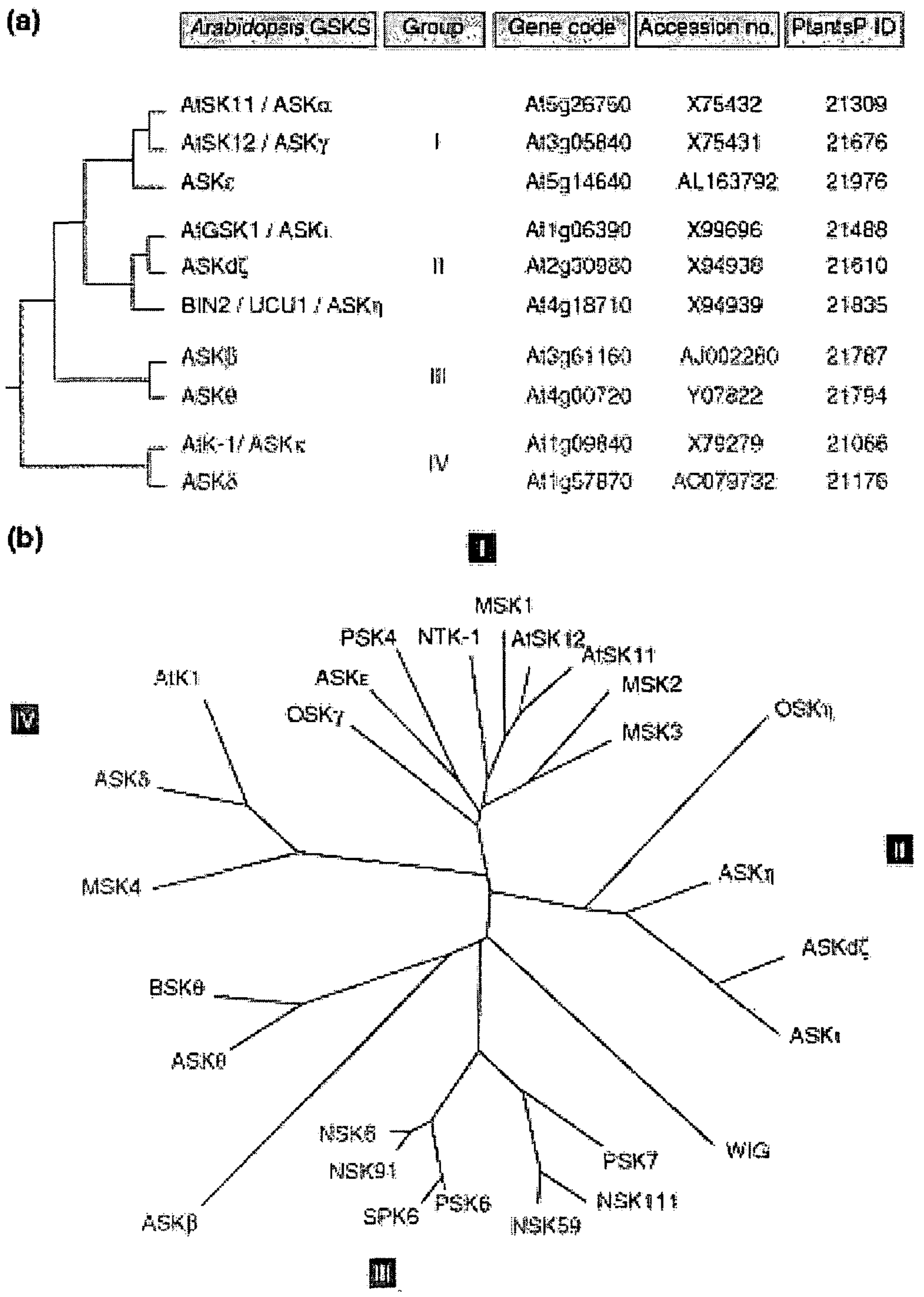
FIG. 13 taken from TRENDS in plant Science Vol. 7, No. 10, October 2002 (Claudia Jonak and Heribert Hirt) shows: (a) Phylogenetic analysis of the ten *Arabidopsis* glycogen synthase kinase 3/SHAGGY-like protein kinases (GSKs). The *Arabidopsis* GSKs can be classified into four subgroups. (b) Phylogenetic tree of full-length GSK cDNAs of different plant species obtained from various BLAST searches. *Brassica napus*, BSKθ (Y12674); *Medicago sativa*, MSK1 (X68411), MSK2 (X68410), MSK3 (X68409), MSK4 (AF432225), WIG (AJ295939); *Nicotiana tabacum*, NSK6 (Y08607), NSK59 (AJ002315), NSK91 (AJ224163), NSK111 (AJ002314), NTK-1 (X77763); *Oryza sativa*, OSKy (AB59612), OSKη (Y13437); *Petunia hybrida*, PSK4 (X83619), PSK6 (AJ224164), PSK7 (AJ224165), SPK6 (X83620). Alignments were performed with Clustal X by the neighbor-joining method using *Arabidopsis* MPK1 (Q39021) as an out-group; trees were designed by the TreeView program.

After the LR recombination step, the resulting expression vector (FIG. 9) was transformed into *Agrobacterium* strain LBA4044 and subsequently to *Oryza sativa* plants. Transformed rice plants were allowed to grow and were then examined for the parameters described in Example 28.

Example 28

Evaluation and Results of *Oryza sativa* YEP16-Encoding Nucleic Acid Under the Control of the Rice Oleosin Promoter in Normal Growth Conditions Approximately 15 to 20 independent T0 rice transformants were generated. The primary transformants were transferred from a tissue culture chamber to a greenhouse for growing and harvest of T1 seed. Seven events, of which the T1 progeny segregated 3:1 for presence/absence of the transgene, were retained. For each of these events, approximately 10 T1 seedlings containing the transgene (hetero- and homo-zygotes) and approximately 10 T1 seedlings lacking the transgene (nullizygotes) were selected by monitoring visual marker expression. 4 T1 events were further evaluated in the T2 generation following the same evaluation procedure as for the T1 generation but with more individuals per event.

27.1 Statistical Analysis: F-Test

A two factor ANOVA (analysis of variants) was used as a statistical model for the overall evaluation of plant phenotypic characteristics. An F-test was carried out on all the parameters measured of all the plants of all the events transformed with the gene of the present invention. The F-test was carried out to check for an effect of the gene over all the transformation events and for an overall effect of the gene, also known as a global gene effect. The threshold for significance for a true global gene effect was set at a 5% probability level for the F-test. A significant F-test value points to a gene effect, meaning that it is not only the presence or position of the gene that is causing the differences in phenotype.

Seed-Related Parameter Measurements

The mature primary panicles were harvested, counted, bagged, barcode-labelled and then dried for three days in an oven at 37° C. The panicles were then threshed and all the seeds were collected and counted. The filled husks were separated from the empty ones using an air-blowing device. The empty husks were discarded and the remaining fraction was counted again. The filled husks were weighed on an analytical balance. The number of filled seeds was determined by counting the number of filled husks that remained after the separation step. The total seed yield was measured by weighing all filled husks harvested from a plant. Total seed number per plant was measured by counting the number of husks harvested from a plant. Thousand kernel weight (TKW) was extrapolated from the number of filled seeds counted and their total weight. The harvest index (HI) in the present invention is defined as the ratio between the total seed yield and the above ground area ($mm^2$), multiplied by a factor $10^6$. The total number of flowers per panicle as defined in the present invention is the ratio between the total number of seeds and the number of mature primary panicles.

The number of filled seeds, the total seed yield (total weight of seeds), fill rate of seeds (which is the number of filled seeds divided by the total number of seeds and multiplied by 100) and the harvest index of transgenic plants transformed with a YEP16-encoding nucleic acid are shown in Table Q. These parameters were significantly increased in the T1 generation compared to corresponding control plants. Average increases in the same parameters were also observed in the T2 generation.

TABLE Q

Results of number of filled seeds, total seed weight, fill rate and harvest index in the T1 generation of transgenic plants transformed with a YEP16-encoding nucleic acid

| Phenotype | T1 evaluation: Number of events showing an increase | P value of F test |
|---|---|---|
| Total weight of seeds | All 3 lines showed an average increase of 22% | Significant |
| Number of filled seeds | All 3 lines showed an average increase of 22% | Significant |
| Fill rate of seeds | All 3 lines showed an average increase of 15% | Significant |
| Harvest Index | All 3 lines showed an average increase of 18% | Significant |

Examples: Group I Shaggy-Like Kinase and Encoding Nucleic Acids

Example 29

Gene Cloning

The *Oryza sativa* Group I shaggy-like kinase-encoding gene was amplified by PCR using as a template an *Arabidopsis thaliana* seedling cDNA library (Invitrogen, Paisley, UK). After reverse transcription of RNA extracted from seedlings, the cDNAs were cloned into pCMV Sport 6.0. Average insert size of the bank was 1.5 kb and the original number of clones was of the order of $1.59\times10^7$ cfu. Original titer was determined to be $9.6\times10^5$ cfu/ml after first amplification of $6\times10^{11}$ cfu/ml. After plasmid extraction, 200 ng of template was used in a 50 μl PCR mix. Primers prm5797 (SEQ ID NO: 179; sense, start codon in bold, AttB1 site in italic: 5'-ggggacaagtttgtacaaaaaagcaggcttaaacaatgggttcagtaggggttg-3') and prm5798 (SEQ ID NO: 180; reverse, complementary, stop codon in bold, AttB2 site in italic: 5'-ggggaccactttgtacaagaaagctgggtgaagctgtctcatactcctgc-3'), which include the AttB sites for Gateway recombination, were used for PCR amplification. PCR was performed using Hifi Taq DNA polymerase in standard conditions. A PCR fragment of 1328 bp was amplified and purified also using standard methods. The first step of the Gateway procedure, the BP reaction, was then performed, during which the PCR fragment recombines in vivo with the pDONR201 plasmid to produce, according to the Gateway terminology, an "entry clone". Plasmid pDONR201 was purchased from Invitrogen, as part of the Gateway® technology.

Example 30

Vector Construction

The entry clone was subsequently used in an LR reaction with a destination vector used for *Oryza sativa* transformation. This vector contains as functional elements within the T-DNA borders: a plant selectable marker; a screenable marker expression cassette; and a Gateway cassette intended for LR in vivo recombination with the sequence of interest already cloned in the entry clone. A GOS2 promoter from rice, for constitutive expression, was upstream of this Gateway cassette (De Pater et al., Plant J. 1992 November; 2(6): 837-44).

Figure 15:
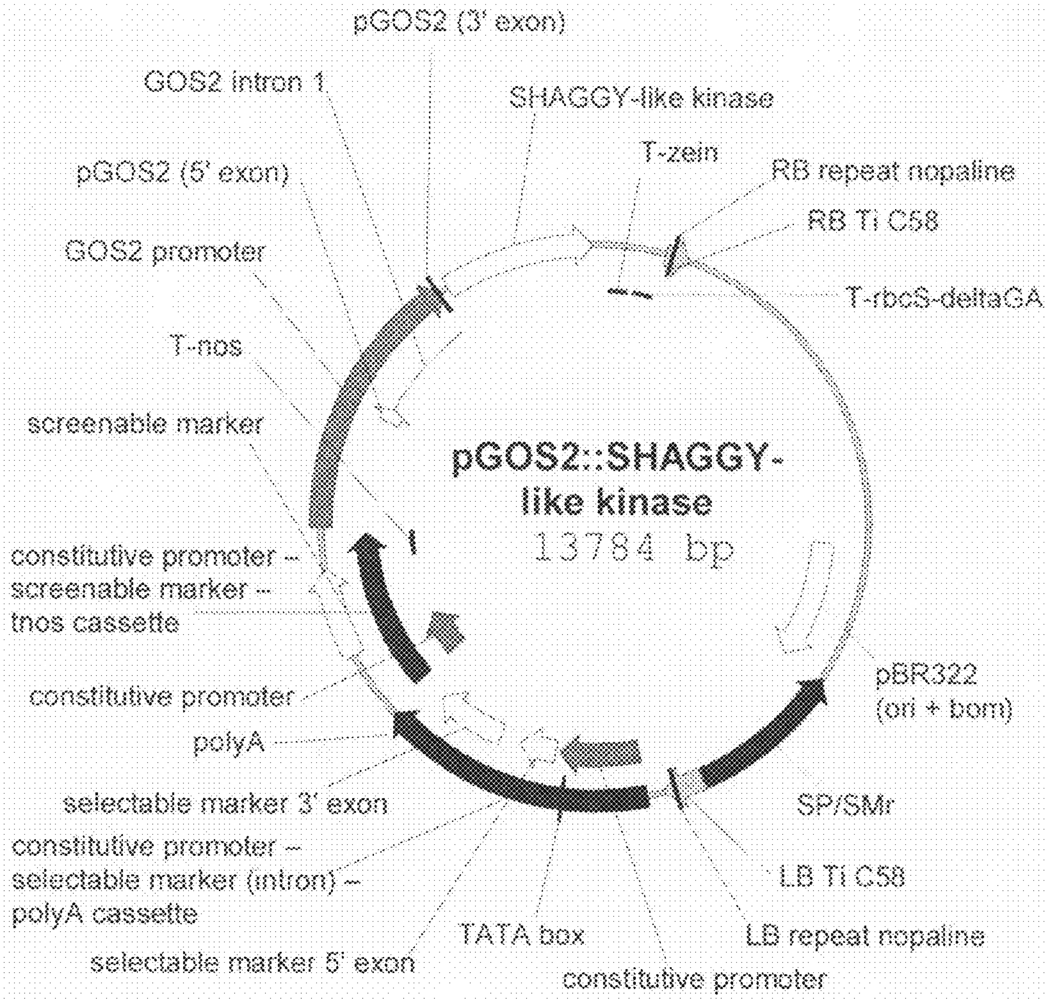
FIG. 15 shows a binary vector for expression in *Oryza sativa* of a Group I shaggy-like kinase from *Oryza sativa* under the control of a GOS2 promoter FIG. 16 details examples of Group I shaggy-like kinase sequences useful in performing the methods according to the present invention.

After the LR recombination step, the resulting expression vector (FIG. 15) was transformed into *Agrobacterium* strain LBA4044 and subsequently to *Oryza sativa* plants as described in Example 31.

Example 31

Rice Transformation

Mature dry seeds of a rice japonica cultivar were dehusked. Sterilization was carried out by incubating for one minute in 70% ethanol, followed by 30 minutes in 0.2% $HgCl_2$, followed by a 6×15 minute wash with sterile distilled water. The sterile seeds were then germinated on a medium containing 2,4-D (callus induction medium). After incubation in the dark for four weeks, embryogenic, scutellum-derived calli were excised and propagated on the same medium. After two weeks, the calli were multiplied or propagated by subculture on the same medium for another 2 weeks. Embryogenic callus pieces were sub-cultured on fresh medium 3 days before co-cultivation (to boost cell division activity). *Agrobacterium* strain LBA4404 harbouring binary T-DNA vectors were used for co-cultivation. *Agrobacterium* was inoculated on AB medium with the appropriate antibiotics and cultured for 3 days at 28° C. The bacteria were then collected and suspended in liquid co-cultivation medium to a density (OD600) of about 1. The suspension was then transferred to a petri dish and the calli immersed in the suspension for 15 minutes. The callus tissues were then blotted dry on a filter paper and transferred to solidified, co-cultivation medium and incubated for 3 days in the dark at 25° C. Co-cultivated calli were grown on 2,4-D-containing medium for 4 weeks in the dark at 28° C. in the presence of a suitable concentration of the selective agent. During this period, rapidly growing resistant callus islands developed. After transfer of this material to a regeneration medium and incubation in the light, the embryogenic potential was released and shoots developed in the next four to five weeks. Shoots were excised from the calli and incubated for 2 to 3 weeks on an auxin-containing medium from which they were transferred to soil. Hardened shoots were grown under high humidity and short days in a greenhouse. Seeds were then harvested three to five months after transplanting. The method yielded single locus transformants at a rate of over 50 (Aldemita and Hodges, Planta, 199 612-617, 1996; Chan et al., Plant Mol. Biol. 22 (3) 491-506, 1993, Hiei et al., Plant J., 6 (2) 271-282, 1994).

Example 32

Salt Stress Screen

Seeds were sown and seedlings selected by monitoring visual marker expression. Ten days after sowing, the seedlings were transplanted to plastic pots, 12 cm in diameter, filled with a 1:1 mixture of moist sand and vermiculite. The pots were soaked in fresh water before transplantation. Seedlings were then transplanted from tissue culture chambers to a greenhouse for growing and harvest of T1 seed. The pots were submitted to salt conditions one day after transplantation. Pots were watered 4 times a day at 8 am, 12 pm, 4 pm, and 9 pm with a salt-stress nutrient solution containing 25 mM NaCl and the components listed below.

NPK Nutrient mix, 20-20-20 Peters professional (Scotts, Marysville, Ohio, USA) at a concentration of 1 kg/$m^3$.

Magnesium chelate, Chelal Mg (BMS, Bornem, Belgium) at 333.33 ml/$m^3$

Iron chelate, Libfer (CIBA, Bradford, UK) at 21.67 g/$m^3$

NaCl 1.425 kg/m3

Salt concentration was monitored on a weekly basis and additions were made where necessary. Plants were grown under these conditions until the start of grain filling. They were then transferred to a different compartment of the greenhouse where they were irrigated daily with fresh water until seed harvest. Growth and yield parameters were recorded as detailed in Example 33.

Example 33

Evaluation and Results

Approximately 15 to 20 independent T0 rice transformants were generated. The primary transformants were transferred from a tissue culture chamber to a greenhouse for growing and harvest of T1 seed. At least 5 events for which the T1 progeny segregated 3:1 for presence/absence of the transgene were retained. For each of these events, approximately T1 seedlings containing the transgene (hetero- and homo-zygotes) and approximately 10 T1 seedlings lacking the transgene (nullizygotes) were selected by monitoring visual marker expression. 4 of the best performing T1 events were further evaluated in the T2 generation following the same evaluation procedure as for the T1 generation but with more individuals per event.

Statistical Analysis: F-Test

A two factor ANOVA (analysis of variants) was used as a statistical model for the overall evaluation of plant phenotypic characteristics. An F-test was carried out on all the parameters measured of all the plants of all the events transformed with the gene of the present invention. The F-test was carried out to check for an effect of the gene over all the transformation events and for an overall effect of the gene, also known as a global gene effect. The threshold for significance for a true global gene effect was set at a 5% probability level. A significant F-test value points to a gene effect, meaning that it is not only the presence or position of the gene that is causing the differences in phenotype.

32.1 Seed-Related Parameter Measurements

Mature primary panicles were harvested, bagged, barcode-labelled and then dried for three days in the oven at 37° C. The panicles were then threshed and all the seeds were collected and counted. Filled husks were separated from the empty ones using an air-blowing device. The empty husks were discarded and the remaining fraction was counted again. Filled husks were weighed on an analytical balance. The total seed yield was measured by weighing all filled husks harvested from a plant. The harvest index in the present invention is defined as a ratio of total seed yield and the aboveground area ($mm^2$) multiplied by a factor 106.

The Table R of results below show the p values from the F test for T1 and T2 evaluations. The percentage difference between the transgenics and the corresponding nullizygotes (or plants without the transgene) is also shown. For example, for total seed weight in the T1 generation, 2 events were positive for total seed weight (i.e., showed an increase in total seed weight (of >54%, with a p-value from the F-test of <0.1938) compared to the seed weight of corresponding nullizygote plants in conditions of salt stress). In the T2 generation, 1 event was positive for total seed weight (i.e., showed an increase in total seed weight (of 65%, with a p-value from the F-test of 0.0252) compared to the seed weight of corresponding nullizygote plants in conditions of salt stress).

TABLE R

T1 and T2 generation shaggy-like kinase transgenic plants and corresponding non-transgenic plants under salt-stress

| Phenotype | T1 | Diff | p-value | T2 | Diff | p-value |
|---|---|---|---|---|---|---|
| Area max | 1 event | 47% | 0.0254 | 1 event | 19% | 0.0951 |
| Number filled seeds | 1 event | 58% | 0.0376 | 1 event | 61% | 0.0313 |
| Total number seeds | 2 events | 41% | <0.191 | 1 event | 28% | 0.0999 |
| Flower per panicle | 1 event | 55% | 0.0177 | 1 event | 26% | 0.0072 |
| Total seed weight | 2 events | >54% | <0.1938 | 1 event | 65% | 0.0252 |
| TKW | | | | 1 event | 6% | 0.1008 |
| Harvest Index | 2 events | >57% | <0.0627 | 1 event | 54% | 0.0086 |

Transformation of Corn, Wheat, Soybean, Canola, Alfalfa with Sequences Useful in the Methods of the Invention Corn Transformation Transformation of maize (*Zea mays*) is performed with a modification of the method described by Ishida et al. (1996) Nature Biotech 14(6): 745-50. Transformation is genotype-dependent in corn and only specific genotypes are amenable to transformation and regeneration. The inbred line A188 (University of Minnesota) or hybrids with A188 as a parent are good sources of donor material for transformation, but other genotypes can be used successfully as well. Ears are harvested from corn plant approximately 11 days after pollination (DAP) when the length of the immature embryo is about 1 to 1.2 mm. Immature embryos are cocultivated with *Agrobacterium tumefaciens* containing the expression vector, and transgenic plants are recovered through organogenesis. Excised embryos are grown on callus induction medium, then maize regeneration medium, containing the selection agent (for example imidazolinone but various selection markers can be used). The Petri plates are incubated in the light at 25° C. for 2-3 weeks, or until shoots develop. The green shoots are transferred from each embryo to maize rooting medium and incubated at 25° C. for 2-3 weeks, until roots develop. The rooted shoots are transplanted to soil in the greenhouse. T1 seeds are produced from plants that exhibit tolerance to the selection agent and that contain a single copy of the T-DNA insert.

Wheat Transformation

Transformation of wheat is performed with the method described by Ishida et al. (1996) Nature Biotech 14(6): 745-50. The cultivar Bobwhite (available from CIMMYT, Mexico) is commonly used in transformation. Immature embryos are co-cultivated with *Agrobacterium tumefaciens* containing the expression vector, and transgenic plants are recovered through organogenesis. After incubation with *Agrobacterium*, the embryos are grown in vitro on callus induction medium, then regeneration medium, containing the selection agent (for example imidazolinone but various selection markers can be used). The Petri plates are incubated in the light at 25° C. for 2-3 weeks, or until shoots develop. The green shoots are transferred from each embryo to rooting medium and incubated at 25° C. for 2-3 weeks, until roots develop. The rooted shoots are transplanted to soil in the greenhouse. T1 seeds are produced from plants that exhibit tolerance to the selection agent and that contain a single copy of the T-DNA insert.

Soybean Transformation

Soybean is transformed according to a modification of the method described in the Texas A&M patent U.S. Pat. No. 5,164,310. Several commercial soybean varieties are amenable to transformation by this method. The cultivar Jack (available from the Illinois Seed foundation) is commonly used for transformation. Soybean seeds are sterilised for in vitro sowing. The hypocotyl, the radicle and one cotyledon are excised from seven-day old young seedlings. The epicotyl and the remaining cotyledon are further grown to develop axillary nodes. These axillary nodes are excised and incubated with *Agrobacterium tumefaciens* containing the expression vector. After the cocultivation treatment, the explants are washed and transferred to selection media. Regenerated shoots are excised and placed on a shoot elongation medium. Shoots no longer than 1 cm are placed on rooting medium until roots develop. The rooted shoots are transplanted to soil in the greenhouse. T1 seeds are produced from plants that exhibit tolerance to the selection agent and that contain a single copy of the T-DNA insert.

Rapeseed/Canola Transformation

Cotyledonary petioles and hypocotyls of 5-6 day old young seedling are used as explants for tissue culture and transformed according to Babic et al. (1998, Plant Cell Rep 17: 183-188). The commercial cultivar Westar (Agriculture Canada) is the standard variety used for transformation, but other varieties can also be used. Canola seeds are surface-sterilized for in vitro sowing. The cotyledon petiole explants with the cotyledon attached are excised from the in vitro seedlings, and inoculated with *Agrobacterium* (containing the expression vector) by dipping the cut end of the petiole explant into the bacterial suspension. The explants are then cultured for 2 days on MSBAP-3 medium containing 3 mg/l BAP, 3% sucrose, 0.7% Phytagar at 23° C., 16 hr light. After two days of co-cultivation with *Agrobacterium*, the petiole explants are transferred to MSBAP-3 medium containing 3 mg/l BAP, cefotaxime, carbenicillin, or timentin (300 mg/l) for 7 days, and then cultured on MSBAP-3 medium with cefotaxime, carbenicillin, or timentin and selection agent until shoot regeneration. When the shoots are 5-10 mm in length, they are cut and transferred to shoot elongation medium (MSBAP-0.5, containing 0.5 mg/l BAP). Shoots of about 2 cm in length are transferred to the rooting medium (MS0) for root induction. The rooted shoots are transplanted to soil in the greenhouse. T1 seeds are produced from plants that exhibit tolerance to the selection agent and that contain a single copy of the T-DNA insert.

Alfalfa Transformation

A regenerating clone of alfalfa (*Medicago sativa*) is transformed using the method of (McKersie et al., 1999 Plant Physiol 119: 839-847). Regeneration and transformation of alfalfa is genotype dependent and therefore a regenerating plant is required. Methods to obtain regenerating plants have been described. For example, these can be selected from the cultivar Rangelander (Agriculture Canada) or any other commercial alfalfa variety as described by Brown DCW and A Atanassov (1985. Plant Cell Tissue Organ Culture 4: 111-112). Alternatively, the RA3 variety (University of Wisconsin) has been selected for use in tissue culture (Walker et al., 1978 Am J Bot 65:654-659). Petiole explants are cocultivated with an overnight culture of *Agrobacterium tumefaciens* C58C1 pMP90 (McKersie et al., 1999 Plant Physiol 119: 839-847) or LBA4404 containing the expression vector. The explants are cocultivated for 3 d in the dark on SH induction medium containing 288 mg/L Pro, 53 mg/L thioproline, 4.35 g/L K2SO4, and 100 μm acetosyringinone. The explants are washed in half-strength Murashige-Skoog medium (Murashige and Skoog, 1962) and plated on the same SH induction medium without acetosyringinone but with a suitable selection agent and suitable antibiotic to inhibit *Agrobacterium* growth. After several weeks, somatic embryos are transferred to BOi2Y development medium containing no growth regulators, no antibiotics, and 50 g/L sucrose. Somatic embryos are subsequently germinated on half-strength Murashige-Skoog medium. Rooted seedlings were transplanted into pots and grown in a greenhouse. T1 seeds are produced from plants that exhibit tolerance to the selection agent and that contain a single copy of the T-DNA insert.

What is claimed is:

1. A method for increasing plant yield comprising:

(a) introducing and expressing in a plant, plant cell or plant part a nucleic acid encoding a class I homeodomain leucine zipper (HDZip) hox5 polypeptide; and (b) selecting for a plant having increased yield relative to a corresponding control plant, wherein said nucleic acid is:

a nucleic acid comprising the nucleotide sequence of SEQ ID NO: 1;

(ii) a nucleic acid encoding a polypeptide comprising the amino acid sequence of SEQ ID NO: 2;

(iii) a nucleic acid encoding a polypeptide having at least 90% sequence identity to the amino acid sequence of SEQ ID NO; 2; or (iv) a nucleic acid that hybridizes to the nucleic acid of (i) or (ii) under stringent hybridization conditions comprising hybridization in 1×SSC at 70° C., or 1×SSC and 50% formamide at 50° C., followed by washing in 0.3×SSC at 70° C.

2. The method of claim 1, wherein said nucleic acid encodes a polypeptide having at least 90% sequence identity to the amino acid sequence of SEQ ID NO: 2.

3. The method of claim 1, wherein said nucleic acid encodes a polypeptide having at least 95% sequence identity to the amino acid sequence of SEQ ID NO: 2.

4. The method of claim 1, wherein said nucleic acid comprises the nucleotide sequence of SEQ ID NO: 1.

5. The method of claim 1, wherein said nucleic acid encodes a polypeptide comprising the amino acid sequence of SEQ ID NO: 2.

6. The method of claim 1, wherein said nucleic acid encodes a polypeptide comprising from N-terminal to C-terminal: (i) acidic box; (ii) a class I homeodomain; and (iii) a leucine zipper with more than 5 heptads.

7. The method of claim 1, wherein said nucleic acid is overexpressed in said plant having increased yield.

8. The method of claim 1, wherein said nucleic acid is of plant origin.

9. The method of claim 1, wherein said nucleic acid is from a monocotyledonous plant.

10. The method of claim 9, wherein said monocotyledonous plant is from the family Poaceae.

11. The method of claim 9, wherein said monocotyledonous plant is *Oryza saliva.*

12. The method of claim 1, wherein said nucleic acid is operably linked to a constitutive promoter.

13. The method of claim 12, wherein said constitutive promoter is a GOS2 promoter.

14. The method of claim 12, wherein said constitutive promoter a GOS2 promoter from rice.

15. The method of claim 12, wherein said constitutive promoter comprises the nucleotide sequence of SEQ ID NO: 33 or SEQ ID NO: 178.

16. The method of claim 1, wherein said increased yield comprises increased total number of seeds, increased number of filled seeds, increased total seed yield, increased number of flowers per panicle, increased seed fill rate, increased harvest index (HI), increased thousand kernel weight (TKW), increased root length, and/or increased root diameter relative to a corresponding control plant.

17. The method of claim 16, wherein said increased yield comprises increased greenness index.

18. The method of claim 1, wherein said increased yield occurs under abiotic stress.

19. The method of claim 18, wherein said abiotic stress is osmotic stress.

20. The method of claim 18, wherein said abiotic stress is water stress, salt stress, oxidative stress, or ionic stress.

21. The method of claim 20, wherein said water stress is drought stress.

22. The method of claim 18, wherein said abiotic stress is reduced nutrient availability.

23. The method of claim 22, wherein said reduced nutrient availability is reduced nitrogen availability.

24. The method of claim 18, wherein said increased yield comprises increased total number of seeds, increased number of filled seeds, increased total seed yield, increased number of flowers per panicle, increased seed fill rate, increased HI, increased TKW, increased root length, and/or increased root diameter relative to a corresponding control plant.

25. A plant obtained from the method of claim 18, wherein said plant comprises said nucleic acid operably linked to a GOS2 promoter, and wherein said plant has increased yield relative to a corresponding control plant under salt stress, drought stress or reduced nutrient availability growth conditions.

26. A plant cell or plant part of the plant of claim 25, wherein said plant cell or plant part comprises said nucleic acid operably linked to said GOS2 promoter.

27. A seed or progeny of the plant of claim 25, wherein said seed or progeny comprises said nucleic acid operably linked to said GOS2 promoter.

28. An harvestable part of the plant of claim 25, wherein said harvest part comprises said nucleic acid operably linked to said GOS2 promoter.

29. The plant of claim 25, wherein said GOS2 promoter is a GOS2 promoter from rice.

30. The plant of claim 25, wherein said GOS2 promoter comprises the nucleotide sequence of SEQ ID NO: 33 or SEQ ID NO: 178.

31. The method of claim 1, wherein said plant is a monocotyledonous plant or a dicotyledonous plant.

32. The method of claim 1, wherein said plant is a crop plant or a cereal.

33. The method of claim 1, wherein said plant is a plant selected from the group consisting of soybean, sunflower, canola, alfalfa, rapeseed, cotton, tomato, potato, tobacco, sugarcane, rice, maize, wheat, barley, millet, rye, oats, triticale, and sorghum.

34. The plant of claim 25, wherein said plant is a monocotyledonous plant or a dicotyledonous plant.

35. The plant of claim 25, wherein said plant is a crop plant or a cereal.

36. The plant of claim 25, wherein said plant is as plant selected from the group consisting of soybean, sunflower, canola, alfalfa, rapeseed, cotton, tomato, potato, tobacco, sugarcane, rice, maize, wheat, barley, millet, rye, oats, triticale, and sorghum.

37. A product obtained from, or comprises, the plant of claim 25, or an harvestable part thereof, wherein said product comprises said nucleic acid.

38. A method for producing a transgenic plant having increased yield relative to a corresponding control plant, comprising:

(a) introducing and expressing in a plant or plant cell a nucleic acid encoding a class I homeodomain leucine zipper (HDZip) hox5 polypeptide;

(b) cultivating the plant or plant cell under conditions for promoting plant growth and development; and (c) selecting for a plant having increased yield relative to a corresponding control plant, wherein said nucleic acid is:

(i) a nucleic acid comprising the nucleotide sequence of SEQ ID NO: 1;

(ii) a nucleic acid encoding a polypeptide comprising the amino acid sequence of SEQ ID NO: 2;

(iii) a nucleic acid encoding a polypeptide having at least 90% sequence identity to the amino acid sequence of ID NO: 2; or (iv) a nucleic acid that hybridizes to the nucleic acid of (i) or (ii) under stringent hybridization conditions comprising hybridization in 1×SSC at 70° C., or 1×SSC and 50% formamide at 50° C., followed by washing in 0.3×SSC at 70° C.

39. The method of claim 38, wherein said nucleic acid encodes a polypeptide having at least 90% sequence identity to the amino acid sequence of SEQ ID NO: 2.

40. The method of claim 38, wherein said nucleic acid encodes a polypeptide having at least 95% sequence identity to the amino acid sequence of SEQ ID NO: 2.

41. The method of claim 38, wherein said nucleic acid comprises the nucleotide sequence of SEQ ID NO: 1.

42. The method of claim 38, wherein said nucleic acid encodes a polypeptide comprising the amino acid sequence of SEQ ID NO: 2.

43. The method of claim 38, wherein said nucleic acid encodes a polypeptide comprising from N-terminal to C-terminal: (i) an acidic box; (ii) a class I homeodomain; and (iii) a leucine zipper with more than 5 heptads.

44. The method of claim 38, wherein said increased yield occurs under increased abiotic stress.

45. The method of claim 38, further comprising obtaining a progeny from said plant having increased yield.

46. The method of claim 38, wherein said nucleic acid is operably linked to a constitutive promoter.

47. The method of claim 46, wherein said constitutive promoter is a GOS2 promoter.

48. The method of claim 46, wherein said constitutive promoter a GOS2 promoter from rice.

49. The method of claim 46, wherein said constitutive promoter comprises the nucleotide sequence of SEQ ID NO: 33 or SEQ ID NO: 178.

50. The method of claim 38, wherein said increased yield comprises increased total number of seeds, increased number of filled seeds, increased total seed yield, increased number of flowers per panicle, increased seed fill rate, increased harvest index (HI), increased thousand kernel weight (TKW), increased root length, and/or increased root diameter relative to a corresponding control plant.

51. The method of claim 38, wherein said plant is a monocotyledonous plant or a dicotyledonous plant.

52. The method of claim 38, wherein said plant is a crop plant or a cereal.

53. The method of claim 38, Wherein said plant is a plant selected from the group consisting of soybean, sunflower, canola, alfalfa, rapeseed, cotton, tomato, potato, tobacco, sugarcane, rice, maize, wheat, barley, millet, rye, oats, triticale, and sorghum.

54. A transgenic plant having increased yield relative to a corresponding control plant under salt stress, drought stress or reduced nutrient availability growth conditions, wherein said increased yield is resulted from increased expression of a nucleic acid encoding a class I homeodomain leucine zipper (HDZip) hox5 polypeptide, wherein said nucleic acid is operably linked to a GOS2 promoter, and wherein said nucleic acid is:

(i) a nucleic acid comprising the nucleotide sequence of SEQ ID NO: 1;

(ii) a nucleic acid encoding a polypeptide comprising the amino acid sequence of SEQ ID NO: 2;

(iii) a nucleic acid encoding a polypeptide having at least 90% sequence identity to the amino acid sequence of SEQ ID NO: 2; or (iv) a nucleic acid that hybridizes to the nucleic it of (i) or (ii) under stringent hybridization conditions comprising hybridization in 1×SSC at 70° C., or 1×SSC and 50% formamide at 50° C., followed by washing in 0.3×SSC at 70° C.

55. The transgenic plant of claim 54, wherein said nucleic acid encodes a polypeptide having at least 90% sequence identity to the amino acid sequence of SEQ ID NO: 2.

56. The transgenic plant of claim 54, wherein said nucleic acid encodes a polypeptide having at least 95% sequence identity to the amino acid sequence of SEQ ID NO: 2.

57. The transgenic plant of claim 54, wherein said nucleic acid comprises the nucleotide sequence of SEQ ID NO: 1.

58. The transgenic plant of claim 54, wherein said nucleic acid encodes a polypeptide comprising the amino acid sequence of SEQ ID NO: 2.

59. The transgenic plant of claim 54, wherein said nucleic acid encodes a polypeptide comprising from N-terminal to C-terminal: (i) an acidic box; (ii) a class I homeodomain; and (iii) a leucine zipper with more than 5 heptads.

60. The transgenic plant of claim 54, wherein said GOS2 promoter is a GOS2 promoter from rice.

61. The transgenic plant of claim 54, wherein said GOS2 promoter comprises the nucleotide sequence SEQ ID NO 33 or SEQ ID NO: 178.

62. The transgenic plant of claim 54, wherein said plant is a monocotyledonous plant or a dicotyledonous plant.

63. The transgenic plant of claim 54, Wherein said plant is a crop plant or a cereal.

64. The transgenic plant of claim 54, wherein said plant is a plant selected from the group consisting of soybean, sunflower, canola, alfalfa, rapeseed, cotton, tomato, potato, tobacco, sugarcane, rice, maize, wheat, barley, millet, rye, oats, triticale, and sorghum.

65. A plant cell or plant part of the transgenic plant of claim 54, wherein said plant cell or plant part comprises said nucleic acid operably linked to said GOS2 promoter.

66. A seed or progeny of the transgenic plant of claim 54, wherein said seed or progeny comprises said nucleic acid operably linked to said GOS2 promoter.

67. An harvestable part of the transgenic plant of claim 54, wherein said harvest part comprises said nucleic acid operably linked to said GOS2 promoter.

68. A product obtained from, or comprises, the transgenic plant of claim 54 or an harvestable part thereof, wherein said product comprises said nucleic acid.

69. The transgenic plant of claim 54, wherein said increased yield comprises increased total number of seeds, increased number of filled seeds, increased total seed yield, increased number of flowers per panicle, increased seed fill rate, increased harvest index (HI), increased thousand kernel weight (TKW), increased root length, and/or increased root diameter relative to a corresponding control plant.

* * * * *

SEQUENCE LISTING

```
<160> NUMBER OF SEQ ID NOS: 186

<210> SEQ ID NO 1
<211> LENGTH: 1050
<212> TYPE: DNA
<213> ORGANISM: Oryza sativa

<400> SEQUENCE: 1

atggatcccg gccgcgtcgt gttcgactcc ggcgtggcgc ggcgggcgtg ccccggcggc      60

gcgcagatgc ttctcttcgg cggcggcggc agcgccaaca gcggcggctt cttccgaggc     120

gtgccggcgg cggtgctggg gatggatgaa tcgcggtcgt cgtcgtcggc ggcggggggcg    180

ggggcgaagc ggccgttctt cacgacgcac gaggagctcc tggaggagga gtactacgac     240

gagcaggcgc cggagaagaa gcggcggctg acggcggagc aggtgcagat gctggagcgg     300

agcttcgagg aggagaacaa gctggagccg gagcggaaga cggagctcgc ccgccgcctc     360

ggcatggccc cccggcaggt cgccgtctgg ttccagaacc gccgcgcccg ctggaagacc     420

aagcagctcg agcacgactt cgaccgcctc aaggccgcct acgacgccct cgccgccgac     480

caccatgccc tcctctccga caacgaccgc ctccgcgcgc aggtaatctc attaaccgag     540

aagctgcaag acaaggagac gtcgccgtcg tcggcgacca tcaccaccgc ggcgcaggag     600

gtcgaccagc cggacgaaca cacggaggcc gcgtcaacca ccggcttcgc caccgtcgac     660

ggcgcattgg cggcgccacc gcccggccac cagcagccgc cgcataaaga tgatcttgtg     720

agcagcggcg gcaccaacga cgacggcgat ggcggcgcgg ccgtggtggt cttcgacgtc     780

accgagggcg ccaacgaccg cctcagctgc gagtcggcgt acttcgccga cgccgcggag     840

gcgtacgagc gcgactgcgc cgggcactac gccctctcgt cggaggagga ggacggcggc     900

gcggtcagcg acgagggctg cagcttcgac ctccccgacg ccgccgccgc cgccgccgcc     960

atgttcggcg ccgccggagt tgtgcaccac gacgccgcgg acgacgagga ggcgcagctc    1020

ggcagctgga ccgcctggtt ctggagctga                                     1050


<210> SEQ ID NO 2
<211> LENGTH: 349
<212> TYPE: PRT
<213> ORGANISM: Oryza sativa

<400> SEQUENCE: 2
```

```
Met Asp Pro Gly Arg Val Val Phe Asp Ser Gly Val Ala Arg Arg Ala
1               5                   10                  15

Cys Pro Gly Gly Ala Gln Met Leu Leu Phe Gly Gly Gly Gly Ser Ala
            20                  25                  30

Asn Ser Gly Gly Phe Phe Arg Gly Val Pro Ala Ala Val Leu Gly Met
        35                  40                  45

Asp Glu Ser Arg Ser Ser Ser Ser Ala Ala Gly Ala Gly Ala Lys Arg
    50                  55                  60

Pro Phe Phe Thr Thr His Glu Glu Leu Leu Glu Glu Glu Tyr Tyr Asp
65                  70                  75                  80

Glu Gln Ala Pro Glu Lys Lys Arg Arg Leu Thr Ala Glu Gln Val Gln
                85                  90                  95

Met Leu Glu Arg Ser Phe Glu Glu Glu Asn Lys Leu Glu Pro Glu Arg
            100                 105                 110

Lys Thr Glu Leu Ala Arg Arg Leu Gly Met Ala Pro Arg Gln Val Ala
        115                 120                 125

Val Trp Phe Gln Asn Arg Arg Ala Arg Trp Lys Thr Lys Gln Leu Glu
    130                 135                 140

His Asp Phe Asp Arg Leu Lys Ala Ala Tyr Asp Ala Leu Ala Ala Asp
145                 150                 155                 160

His His Ala Leu Leu Ser Asp Asn Asp Arg Leu Arg Ala Gln Val Ile
                165                 170                 175

Ser Leu Thr Glu Lys Leu Gln Asp Lys Glu Thr Ser Pro Ser Ser Ala
            180                 185                 190

Thr Ile Thr Thr Ala Ala Gln Glu Val Asp Gln Pro Asp Glu His Thr
        195                 200                 205

Glu Ala Ala Ser Thr Thr Gly Phe Ala Thr Val Asp Gly Ala Leu Ala
    210                 215                 220

Ala Pro Pro Pro Gly His Gln Gln Pro Pro His Lys Asp Asp Leu Val
225                 230                 235                 240

Ser Ser Gly Gly Thr Asn Asp Asp Gly Asp Gly Gly Ala Ala Val Val
                245                 250                 255

Val Phe Asp Val Thr Glu Gly Ala Asn Asp Arg Leu Ser Cys Glu Ser
            260                 265                 270

Ala Tyr Phe Ala Asp Ala Ala Glu Ala Tyr Glu Arg Asp Cys Ala Gly
        275                 280                 285

His Tyr Ala Leu Ser Ser Glu Glu Glu Asp Gly Gly Ala Val Ser Asp
    290                 295                 300

Glu Gly Cys Ser Phe Asp Leu Pro Asp Ala Ala Ala Ala Ala Ala Ala
305                 310                 315                 320

Met Phe Gly Ala Ala Gly Val Val His His Asp Ala Ala Asp Asp Glu
                325                 330                 335

Glu Ala Gln Leu Gly Ser Trp Thr Ala Trp Phe Trp Ser
            340                 345
```

<210> SEQ ID NO 3
<211> LENGTH: 1197
<212> TYPE: DNA
<213> ORGANISM: Oryza sativa

<400> SEQUENCE: 3

```
atggagtccg gccggctcat cttcagcacg gcgggctccg gcgccgggca gatgctcttc      60

ttggactgcg gcgctggcgg cggcggcgtc ggcggcgggg ccatgttcca tcgaggggcg     120
```

-continued

```
agaccggtgc tcggcatgga ggaaggaggg cgcggcgtca agcggccctt cttcaccacc    180

cccgacgagc tcctcgaaga ggagtactac gacgagcagc tcccggagaa gaagcggcgc    240

ctcacgccgg agcaggtgca tctgctggag aggagcttcg aggaggagaa caagctggag    300

ccggagcgga agacggagct ggcgcggaag ctagggctgc agccgcggca ggtcgccgtg    360

tggttccaga accgccgcgc gcgctggaag accaagcagc tcgagcgcga cttcgaccgc    420

ctcaaggcgt cgttcgacgc cctccgcgcc gaccacgacg ccctcctcca ggacaaccac    480

cgcctccact ctcaggtcat gtcgttgacc gagaagctgc aagagaagga gacgacgacc    540

gagggcagcg ccggcgcggc cgttgacgtc ccgggcttgc ctgcggcggc cgacgtgaag    600

gtcgccgtcc cggacgccga ggaaccggcg ctggaggagg cggcggcggc gttcgaggag    660

cagcaggagc agcaggtgaa ggccgaggac aggctgagca cgggcagcgg cgggagcgcg    720

gtggtggaca cggacgcgca actggtggtc gggtgcggcc ggcaagcatc tcgccgccgt    780

ggacagcagc gtggagtcgt acttcccggg cggcgacgag taccacgact gcgtgatggg    840

ccccatggac cacgccgcgg ggggcatcca gtcggaggag gacgacggcg ccggcagcga    900

cgagggctgc agctactacg ccgacgacgc cggcgtcctc ttcgccgacc acggccacca    960

ccaccaccac caacacgcgg acgacgacga ggaggacggc cagcagatca gctgctggtg   1020

gatgtggaac tagatttctc gcgcgcgcgc gtcgtcgtgc attcaattct cgtgttaaaa   1080

aaatcgttct ctttttcatt tttccgcttc tttgtctgta atgttgagtt tcgatcggct   1140

atgagaagga aggaggtgta tgcatgtgca tggtatggta gggtaacaca tcggtga      1197
```

<210> SEQ ID NO 4
<211> LENGTH: 343
<212> TYPE: PRT
<213> ORGANISM: Oryza sativa

<400> SEQUENCE: 4

```
Met Glu Ser Gly Arg Leu Ile Phe Ser Thr Ala Gly Ser Gly Ala Gly
1               5                   10                  15

Gln Met Leu Phe Leu Asp Cys Gly Ala Gly Gly Gly Gly Val Gly Gly
            20                  25                  30

Gly Ala Met Phe His Arg Gly Ala Arg Pro Val Leu Gly Met Glu Glu
        35                  40                  45

Gly Gly Arg Gly Val Lys Arg Pro Phe Phe Thr Thr Pro Asp Glu Leu
    50                  55                  60

Leu Glu Glu Glu Tyr Tyr Asp Glu Gln Leu Pro Glu Lys Lys Arg Arg
65                  70                  75                  80

Leu Thr Pro Glu Gln Val His Leu Leu Glu Arg Ser Phe Glu Glu Glu
                85                  90                  95

Asn Lys Leu Glu Pro Glu Arg Lys Thr Glu Leu Ala Arg Lys Leu Gly
            100                 105                 110

Leu Gln Pro Arg Gln Val Ala Val Trp Phe Gln Asn Arg Arg Ala Arg
        115                 120                 125

Trp Lys Thr Lys Gln Leu Glu Arg Asp Phe Asp Arg Leu Lys Ala Ser
    130                 135                 140

Phe Asp Ala Leu Arg Ala Asp His Asp Ala Leu Leu Gln Asp Asn His
145                 150                 155                 160

Arg Leu His Ser Gln Val Met Ser Leu Thr Glu Lys Leu Gln Glu Lys
                165                 170                 175

Glu Thr Thr Thr Glu Gly Ser Ala Gly Ala Ala Val Asp Val Pro Gly
            180                 185                 190
```

```
Leu Pro Ala Ala Ala Asp Val Lys Val Ala Val Pro Asp Ala Glu Glu
        195                 200                 205

Pro Ala Leu Glu Glu Ala Ala Ala Ala Phe Glu Glu Gln Gln Glu Gln
    210                 215                 220

Gln Val Lys Ala Glu Asp Arg Leu Ser Thr Gly Ser Gly Gly Ser Ala
225                 230                 235                 240

Val Val Asp Thr Asp Ala Gln Leu Val Val Gly Cys Gly Arg Gln His
                245                 250                 255

Leu Ala Ala Val Asp Ser Ser Val Glu Ser Tyr Phe Pro Gly Gly Asp
            260                 265                 270

Glu Tyr His Asp Cys Val Met Gly Pro Met Asp His Ala Ala Gly Gly
        275                 280                 285

Ile Gln Ser Glu Glu Asp Asp Gly Ala Gly Ser Asp Glu Gly Cys Ser
    290                 295                 300

Tyr Tyr Ala Asp Asp Ala Gly Val Leu Phe Ala Asp His Gly His His
305                 310                 315                 320

His His His Gln His Ala Asp Asp Asp Glu Glu Asp Gly Gln Gln Ile
                325                 330                 335

Ser Cys Trp Trp Met Trp Asn
            340
```

<210> SEQ ID NO 5
<211> LENGTH: 819
<212> TYPE: DNA
<213> ORGANISM: Zea mays

<400> SEQUENCE: 5

```
atggatccga gcgcggtcag tttcgactct ggcggcgcgc ggcggggcgg cggcgcgcag      60

atgctgctct tcggcggcgg aggcagcgcc aacagcaacg gcttcttccg aggtgttccg     120

atggcggtcc tgggcatgga cgacgcgacg cgcgtgggca agcggccctt cttcacgaca     180

cacgaggagc tcctagagga ggagtactac gacgagcagg cgccggagaa gaagcgccga     240

ctgacggcgg agcaggtgca gctgctggag cggagcttcg aagaagagaa caagctggag     300

ccggagcgca agaccgagct ggctcgccgc ctggggatgg cgccccgcca ggtagctgtt     360

tggttccaga accgccgcgc gcgctggaag accaagcaac tcgagaccga ctatgaccgc     420

ctcaaggctg cttacgacgc actcgccgcc gaccaccagg gcctcctggc cgacaacgat     480

aacctccggg cacaggtgat ctccctgacg gagaagctgc aaggcaagga gacatccccg     540

tcggcaacca ctgctgccca agaggtcgac cagccagacg aacacaccgc tgtgtcaggc     600

acggaagaac tgctggcgca gcagctcaag gacaacctcc acagcagcgg cgactgcact     660

ggccatggca ccctctcttc ggaagaagac gacggtggcg tggtcagtga cgagggctgc     720

agcttcgctc tcccggatgc catgttcgct gccgggttca cccaccatgg cgccgaggag     780

gtgcagctgg ccaactggac atccatgttc tggaactga                            819
```

<210> SEQ ID NO 6
<211> LENGTH: 272
<212> TYPE: PRT
<213> ORGANISM: Zea mays

<400> SEQUENCE: 6

```
Met Asp Pro Ser Ala Val Ser Phe Asp Ser Gly Gly Ala Arg Arg Gly
1               5                   10                  15

Gly Gly Ala Gln Met Leu Leu Phe Gly Gly Gly Gly Ser Ala Asn Ser
```

```
            20                  25                  30

Asn Gly Phe Phe Arg Gly Val Pro Met Ala Val Leu Gly Met Asp Asp
        35                  40                  45

Ala Thr Arg Val Gly Lys Arg Pro Phe Phe Thr Thr His Glu Glu Leu
    50                  55                  60

Leu Glu Glu Glu Tyr Tyr Asp Glu Gln Ala Pro Glu Lys Lys Arg Arg
65                  70                  75                  80

Leu Thr Ala Glu Gln Val Gln Leu Leu Glu Arg Ser Phe Glu Glu Glu
                85                  90                  95

Asn Lys Leu Glu Pro Glu Arg Lys Thr Glu Leu Ala Arg Arg Leu Gly
            100                 105                 110

Met Ala Pro Arg Gln Val Ala Val Trp Phe Gln Asn Arg Arg Ala Arg
        115                 120                 125

Trp Lys Thr Lys Gln Leu Glu Thr Asp Tyr Asp Arg Leu Lys Ala Ala
    130                 135                 140

Tyr Asp Ala Leu Ala Ala Asp His Gln Gly Leu Leu Ala Asp Asn Asp
145                 150                 155                 160

Asn Leu Arg Ala Gln Val Ile Ser Leu Thr Glu Lys Leu Gln Gly Lys
                165                 170                 175

Glu Thr Ser Pro Ser Ala Thr Thr Ala Ala Gln Glu Val Asp Gln Pro
            180                 185                 190

Asp Glu His Thr Ala Val Ser Gly Thr Glu Glu Leu Leu Ala Gln Gln
        195                 200                 205

Leu Lys Asp Asn Leu His Ser Ser Gly Asp Cys Thr Gly His Gly Thr
    210                 215                 220

Leu Ser Ser Glu Glu Asp Asp Gly Gly Val Val Ser Asp Glu Gly Cys
225                 230                 235                 240

Ser Phe Ala Leu Pro Asp Ala Met Phe Ala Ala Gly Phe Thr His His
                245                 250                 255

Gly Ala Glu Glu Val Gln Leu Ala Asn Trp Thr Ser Met Phe Trp Asn
            260                 265                 270


<210> SEQ ID NO 7
<211> LENGTH: 993
<212> TYPE: DNA
<213> ORGANISM: Zea mays

<400> SEQUENCE: 7

atggagtctg gacggctcat cttcaacgcg ccgggctctg gcgccgggca gatgctcttc      60

ctcgactgcg gcgcaggcgg cggtcccggc ggcggcttgt tccatcgagg cgggagaccg     120

atgcttggcc ttgaagaagg gcgcggcgta aaacggccct tcttcacctc gcccgacgag     180

ctcctcgagg aagagtacta cgacgagcag ctgccggaga agaagcgccg cctcacccca     240

gagcaggtgc ttctgctgga gaggagcttc gaggaggaga acaagctgga gccggagcgc     300

aagacggagc tggcgcgcaa gctgggcctg cagcctcgcc aggtggccgt ctggttccag     360

aaccgccgcg cccggtggaa gaccaagcag ctcgagcgcg acttcgaccg cctcaaggcc     420

tccttcgacg ctctccgagc ggaccacgac gccctcctcc aggacaacaa ccgcctccgc     480

tcacaggttg tgtcgttgac cgagaagctg caagagaagg aggatgcgac ggagggcggc     540

gccaccgctg acaccgccgc gccggcggtg gacgtcgagg cttccctggc cgacgacgtc     600

gaggagccag cagagcctgc ggcgacgttc gaggtgctgc aggaggtgaa gtccgaggac     660

aggctgagca ccggcagcgg cgggagcgcg gtggtggacg cggacgcgct gctgtacggc     720
```

```
aggttcgccg cggcagttga tagcagcgtg gagtcgtact tccccggcgg cgaggaccac    780

taccacgact gcgggacgat gggccccgtg aatcatggcg ccggaggagg catccagtcg    840

gacgacgacg gcgccggcag cgacgagggg tgcagctact acgccgacga agccgccgcc    900

gccgccgccg cgttcttcgc cggacacgcc acccaccacc acgcggacga ggacgaggac    960

gccggccaga tcagctggtg gatgtggaac tag                                  993


<210> SEQ ID NO 8
<211> LENGTH: 330
<212> TYPE: PRT
<213> ORGANISM: Zea mays

<400> SEQUENCE: 8

Met Glu Ser Gly Arg Leu Ile Phe Asn Ala Pro Gly Ser Gly Ala Gly
1               5                   10                  15

Gln Met Leu Phe Leu Asp Cys Gly Ala Gly Gly Gly Pro Gly Gly Gly
            20                  25                  30

Leu Phe His Arg Gly Gly Arg Pro Met Leu Gly Leu Glu Glu Gly Arg
        35                  40                  45

Gly Val Lys Arg Pro Phe Phe Thr Ser Pro Asp Glu Leu Leu Glu Glu
    50                  55                  60

Glu Tyr Tyr Asp Glu Gln Leu Pro Glu Lys Lys Arg Arg Leu Thr Pro
65                  70                  75                  80

Glu Gln Val Leu Leu Leu Glu Arg Ser Phe Glu Glu Glu Asn Lys Leu
                85                  90                  95

Glu Pro Glu Arg Lys Thr Glu Leu Ala Arg Lys Leu Gly Leu Gln Pro
            100                 105                 110

Arg Gln Val Ala Val Trp Phe Gln Asn Arg Arg Ala Arg Trp Lys Thr
        115                 120                 125

Lys Gln Leu Glu Arg Asp Phe Asp Arg Leu Lys Ala Ser Phe Asp Ala
    130                 135                 140

Leu Arg Ala Asp His Asp Ala Leu Leu Gln Asp Asn Asn Arg Leu Arg
145                 150                 155                 160

Ser Gln Val Val Ser Leu Thr Glu Lys Leu Gln Glu Lys Glu Asp Ala
                165                 170                 175

Thr Glu Gly Gly Ala Thr Ala Asp Thr Ala Ala Pro Ala Val Asp Val
            180                 185                 190

Glu Ala Ser Leu Ala Asp Asp Val Glu Glu Pro Ala Glu Pro Ala Ala
        195                 200                 205

Thr Phe Glu Val Leu Gln Glu Val Lys Ser Glu Asp Arg Leu Ser Thr
    210                 215                 220

Gly Ser Gly Gly Ser Ala Val Val Asp Ala Asp Ala Leu Leu Tyr Gly
225                 230                 235                 240

Arg Phe Ala Ala Ala Val Asp Ser Ser Val Glu Ser Tyr Phe Pro Gly
                245                 250                 255

Gly Glu Asp His Tyr His Asp Cys Gly Thr Met Gly Pro Val Asn His
            260                 265                 270

Gly Ala Gly Gly Gly Ile Gln Ser Asp Asp Asp Gly Ala Gly Ser Asp
        275                 280                 285

Glu Gly Cys Ser Tyr Tyr Ala Asp Glu Ala Ala Ala Ala Ala Ala Ala
    290                 295                 300

Phe Phe Ala Gly His Ala Thr His His His Ala Asp Glu Asp Glu Asp
305                 310                 315                 320

Ala Gly Gln Ile Ser Trp Trp Met Trp Asn
```

325 330

<210> SEQ ID NO 9
<211> LENGTH: 825
<212> TYPE: DNA
<213> ORGANISM: Saccharum officinarum

<400> SEQUENCE: 9

```
atggatccga gcgcggtcag tttcaactcc ggcggcgcgc ggcggggcgg cggcggcacg      60
cagatgctgc tcttcggcgg cggaggcagc gccaacagca acggcttctt ccgaggtgtt     120
ccgatggcgg tcctgggcat ggacgacgcg acgcgcgtgg gcaagcggcc cttcttcacc     180
acacacgagg agctcctgga ggaggagtac tacgacgagc aggcgcccga gaagaagcgc     240
cgtctgacgg cggagcaggt gcagctgctg gagcggagct tcgaggaaga gaacaagctg     300
gagcccgagc gcaagaccga gctggctcgc cgcctcggga tggcgccccg ccaggtggcc     360
gtctggttcc agaaccgccg cgcgcgctgg aagaccaagc agctcgagac cgactatgac     420
cacctcaagg ctgcctacga cgcgctcgcc gccgaccacc agggcctcct ggccgacaac     480
gatagcctcc gggcacaggt ggtctcccta acagagaagc tgcaaggcaa ggagacatcc     540
ccgtcggcca ccactgctgc ccaagaggtc gaccagccag acgaacacac cgcggcgtca     600
ggcactgaga aactgctggc gcagcagctc aaggacgacc tccacagcag cggcgactgc     660
actggccatg gtgccctctc ctcagaggaa gaagatggtg gtgtggtcag tgacgagggc     720
agctttgatc tcccggatgc catgtttgct gccggggtca cccaccatgg cgccgacgcc     780
gaggaggcac agctggccaa ctggacatcc tggttctgga actga                     825
```

<210> SEQ ID NO 10
<211> LENGTH: 274
<212> TYPE: PRT
<213> ORGANISM: Saccharum officinarum

<400> SEQUENCE: 10

```
Met Asp Pro Ser Ala Val Ser Phe Asn Ser Gly Gly Ala Arg Arg Gly
1               5                   10                  15

Gly Gly Gly Thr Gln Met Leu Leu Phe Gly Gly Gly Gly Ser Ala Asn
            20                  25                  30

Ser Asn Gly Phe Phe Arg Gly Val Pro Met Ala Val Leu Gly Met Asp
        35                  40                  45

Asp Ala Thr Arg Val Gly Lys Arg Pro Phe Phe Thr Thr His Glu Glu
    50                  55                  60

Leu Leu Glu Glu Glu Tyr Tyr Asp Glu Gln Ala Pro Glu Lys Lys Arg
65                  70                  75                  80

Arg Leu Thr Ala Glu Gln Val Gln Leu Leu Glu Arg Ser Phe Glu Glu
                85                  90                  95

Glu Asn Lys Leu Glu Pro Glu Arg Lys Thr Glu Leu Ala Arg Arg Leu
            100                 105                 110

Gly Met Ala Pro Arg Gln Val Ala Val Trp Phe Gln Asn Arg Arg Ala
        115                 120                 125

Arg Trp Lys Thr Lys Gln Leu Glu Thr Asp Tyr Asp His Leu Lys Ala
    130                 135                 140

Ala Tyr Asp Ala Leu Ala Ala Asp His Gln Gly Leu Leu Ala Asp Asn
145                 150                 155                 160

Asp Ser Leu Arg Ala Gln Val Val Ser Leu Thr Glu Lys Leu Gln Gly
                165                 170                 175
```

```
Lys Glu Thr Ser Pro Ser Ala Thr Thr Ala Ala Gln Glu Val Asp Gln
            180                 185                 190

Pro Asp Glu His Thr Ala Ala Ser Gly Thr Glu Lys Leu Leu Ala Gln
        195                 200                 205

Gln Leu Lys Asp Asp Leu His Ser Ser Gly Asp Cys Thr Gly His Gly
    210                 215                 220

Ala Leu Ser Ser Glu Glu Glu Asp Gly Gly Val Val Ser Asp Glu Gly
225                 230                 235                 240

Ser Phe Asp Leu Pro Asp Ala Met Phe Ala Ala Gly Val Thr His His
                245                 250                 255

Gly Ala Asp Ala Glu Glu Ala Gln Leu Ala Asn Trp Thr Ser Trp Phe
            260                 265                 270

Trp Asn


<210> SEQ ID NO 11
<211> LENGTH: 828
<212> TYPE: DNA
<213> ORGANISM: Sorghum bicolor

<400> SEQUENCE: 11

atggatccga gcgcggtcag tttcgactcc ggcggcgcgc ggcggggcgg cggcggcggc      60

ggcgcgcaga tgctgctctt cggcggcgga ggcagcgcca acagcaacgg cttcttccga     120

ggtgttccga tggcggtcct gggcatggac gacgcgacgc gcgtgggcaa gcggcctttc     180

ttcaccacgc acgaggagct cctggaggag gagtactacg acgagcaggc gcccgagaag     240

aagcgccgtc tgacggcgga gcaggtgcag ctgctggagc ggagcttcga ggaagagaac     300

aagctggagc cggagcgcaa gaccgagctg gctcgccgcc tcgggatggc gcctcgccag     360

gtggccgtct ggttccagaa ccgccgcgcg cgctggaaga ctaagcagct cgagaccgac     420

tatgaccgcc tcaaggctgc ctacgacgcg ctcgccgccg accaccaggg cctcctggcc     480

gacaacgata gcctccgggc acaggtgatc tccctaacgg ataagctgca acgcaaggag     540

acatccccgt cggcgaccac tgctgcccaa gaggtcgacc agccagacga acacaccgct     600

gcgtcaggca ctgagaaact gctggtgcag cagctcaagg acgacctcca cagcagcggc     660

gacttcactg gccatggtgc cctctcttca gaggaagagg atggtggtgt ggtcagcgac     720

gagggctgca gctttgatct cccggatgcc atgttcgctg ccggggtcac ccaccatggc     780

gccgaggagg cgcagctggc caactggaca tcctggttct ggaactga                  828


<210> SEQ ID NO 12
<211> LENGTH: 275
<212> TYPE: PRT
<213> ORGANISM: Sorghum bicolor

<400> SEQUENCE: 12

Met Asp Pro Ser Ala Val Ser Phe Asp Ser Gly Gly Ala Arg Arg Gly
1               5                   10                  15

Gly Gly Gly Gly Gly Ala Gln Met Leu Leu Phe Gly Gly Gly Gly Ser
            20                  25                  30

Ala Asn Ser Asn Gly Phe Phe Arg Gly Val Pro Met Ala Val Leu Gly
        35                  40                  45

Met Asp Asp Ala Thr Arg Val Gly Lys Arg Pro Phe Phe Thr Thr His
    50                  55                  60

Glu Glu Leu Leu Glu Glu Glu Tyr Tyr Asp Glu Gln Ala Pro Glu Lys
65                  70                  75                  80
```

-continued

```
Lys Arg Arg Leu Thr Ala Glu Gln Val Gln Leu Leu Glu Arg Ser Phe
                85                  90                  95

Glu Glu Glu Asn Lys Leu Glu Pro Glu Arg Lys Thr Glu Leu Ala Arg
            100                 105                 110

Arg Leu Gly Met Ala Pro Arg Gln Val Ala Val Trp Phe Gln Asn Arg
        115                 120                 125

Arg Ala Arg Trp Lys Thr Lys Gln Leu Glu Thr Asp Tyr Asp Arg Leu
    130                 135                 140

Lys Ala Ala Tyr Asp Ala Leu Ala Ala Asp His Gln Gly Leu Leu Ala
145                 150                 155                 160

Asp Asn Asp Ser Leu Arg Ala Gln Val Ile Ser Leu Thr Asp Lys Leu
                165                 170                 175

Gln Arg Lys Glu Thr Ser Pro Ser Ala Thr Thr Ala Ala Gln Glu Val
            180                 185                 190

Asp Gln Pro Asp Glu His Thr Ala Ala Ser Gly Thr Glu Lys Leu Leu
        195                 200                 205

Val Gln Gln Leu Lys Asp Asp Leu His Ser Ser Gly Asp Phe Thr Gly
    210                 215                 220

His Gly Ala Leu Ser Ser Glu Glu Glu Asp Gly Gly Val Val Ser Asp
225                 230                 235                 240

Glu Gly Cys Ser Phe Asp Leu Pro Asp Ala Met Phe Ala Ala Gly Val
                245                 250                 255

Thr His His Gly Ala Glu Glu Ala Gln Leu Ala Asn Trp Thr Ser Trp
            260                 265                 270

Phe Trp Asn
        275
```

<210> SEQ ID NO 13
<211> LENGTH: 1023
<212> TYPE: DNA
<213> ORGANISM: Triticum aestivum

<400> SEQUENCE: 13

```
atggagcccg gccggctcat cttcaacacg tcgggctccg gcaacggaca gatgctcttc     60

atggactgcg gcgcgggcgg catcgccggc gcggccggca tgttccatcg aggggtgaga    120

ccggtcctcg gcggcatgga agaagggcgc ggcgtgaagc ggcccttctt cacctcgccg    180

gatgacatgc tcgaggagga gtactacgac gagcagctcc cggagaagaa gcggcgcctc    240

accccggagc aggtccacct gctggagagg agcttcgagg aggagaacaa gctggagccg    300

gagaggaaga cggagctggc ccgcaagctc gggctgcagc cacgccaggt ggccgtctgg    360

ttccagaacc gccgcgcccg gtggaagaca aagacgctgg agcgcgactt cgaccgcctc    420

aaggcgtcct tcgacgccct ccgggccgac cacgacgccc tcctccagga caaccaccgg    480

ctccggtcac aggtggtaac gttgaccgag aagatgcaag ataaggaggc gccggaaggc    540

agcttcggtg cagccgccga cgcctcggag ccggagcagg cggcggcgga ggcgaaggct    600

tccttggccg acgccgagga gcaggccgcg gcagcggagg cgttcgaggt ggtgcagcag    660

cagctgcacg tgaaggacga ggagaggctg agcccgggga gcggcgggag cgcggtgctg    720

gacgcgaggg acgcgctgct cgggagcgga tgcggcctcg ccggcgtggt ggacagcagc    780

gtggactcgt actgcttccc ggggggcgcc ggcggcgacg agtaccacga gtgcgtggtg    840

ggccccgtgg cgggcggcat ccagtcggag gaggacgacg gcgcgggcag cgacgagggc    900

tgcagctact accccgacga cgccgccgtc ttcttcgccg ccgcgcaagg gcacggccac    960
```

```
catcgcacgg acgacgacga tcagcaggac gacggccaga tcagctactg gatgtggaac   1020

tag                                                                 1023


<210> SEQ ID NO 14
<211> LENGTH: 340
<212> TYPE: PRT
<213> ORGANISM: Triticum aestivum

<400> SEQUENCE: 14

Met Glu Pro Gly Arg Leu Ile Phe Asn Thr Ser Gly Ser Gly Asn Gly
1               5                   10                  15

Gln Met Leu Phe Met Asp Cys Gly Ala Gly Gly Ile Ala Gly Ala Ala
            20                  25                  30

Gly Met Phe His Arg Gly Val Arg Pro Val Leu Gly Gly Met Glu Glu
        35                  40                  45

Gly Arg Gly Val Lys Arg Pro Phe Phe Thr Ser Pro Asp Asp Met Leu
    50                  55                  60

Glu Glu Glu Tyr Tyr Asp Glu Gln Leu Pro Glu Lys Lys Arg Arg Leu
65                  70                  75                  80

Thr Pro Glu Gln Val His Leu Leu Glu Arg Ser Phe Glu Glu Glu Asn
                85                  90                  95

Lys Leu Glu Pro Glu Arg Lys Thr Glu Leu Ala Arg Lys Leu Gly Leu
            100                 105                 110

Gln Pro Arg Gln Val Ala Val Trp Phe Gln Asn Arg Arg Ala Arg Trp
        115                 120                 125

Lys Thr Lys Thr Leu Glu Arg Asp Phe Asp Arg Leu Lys Ala Ser Phe
    130                 135                 140

Asp Ala Leu Arg Ala Asp His Asp Ala Leu Leu Gln Asp Asn His Arg
145                 150                 155                 160

Leu Arg Ser Gln Val Val Thr Leu Thr Glu Lys Met Gln Asp Lys Glu
                165                 170                 175

Ala Pro Glu Gly Ser Phe Gly Ala Ala Ala Asp Ala Ser Glu Pro Glu
            180                 185                 190

Gln Ala Ala Ala Glu Ala Lys Ala Ser Leu Ala Asp Ala Glu Glu Gln
        195                 200                 205

Ala Ala Ala Ala Glu Ala Phe Glu Val Val Gln Gln Gln Leu His Val
    210                 215                 220

Lys Asp Glu Glu Arg Leu Ser Pro Gly Ser Gly Gly Ser Ala Val Leu
225                 230                 235                 240

Asp Ala Arg Asp Ala Leu Leu Gly Ser Gly Cys Gly Leu Ala Gly Val
                245                 250                 255

Val Asp Ser Ser Val Asp Ser Tyr Cys Phe Pro Gly Gly Ala Gly Gly
            260                 265                 270

Asp Glu Tyr His Glu Cys Val Val Gly Pro Val Ala Gly Gly Ile Gln
        275                 280                 285

Ser Glu Glu Asp Asp Gly Ala Gly Ser Asp Glu Gly Cys Ser Tyr Tyr
    290                 295                 300

Pro Asp Asp Ala Ala Val Phe Phe Ala Ala Ala Gln Gly His Gly His
305                 310                 315                 320

His Arg Thr Asp Asp Asp Asp Gln Gln Asp Asp Gly Gln Ile Ser Tyr
                325                 330                 335

Trp Met Trp Asn
            340
```

<210> SEQ ID NO 15
<211> LENGTH: 819
<212> TYPE: DNA
<213> ORGANISM: Arabidopsis thaliana

<400> SEQUENCE: 15
atggaatcca attcgttttt cttcgatcca tctgcttcac acggcaacag catgttcttc 60
cttgggaatc tcaatcccgt cgtccaagga ggaggagcaa gatcgatgat gaacatggag 120
gaaacttcga agcgaaggcc cttctttagc tcccctgagg atctctacga cgatgacttt 180
tacgacgacc agttgcctga aaagaagcgt cgcctcacta ccgaacaagt gcatctgctg 240
gagaaaagct tcgagacaga gaacaagcta gagcctgaac gcaagactca gcttgccaag 300
aagcttggtc tacagccaag gcaagtggct gtctggtttc agaatcgccg agctcgttgg 360
aaaacaaaac agcttgagag agactacgat cttctcaagt ccacttacga ccaacttctt 420
tctaactacg actccatcgt catggacaac gataagctca gatccgaggt tacttccctg 480
accgaaaagc ttcagggcaa acaagagaca gctaatgaac cacctggtca agtgcccgaa 540
ccaaaccaac ttgatccggt ttacattaat gcggcagcaa tcaaaaccga ggaccggtta 600
agttcaggga gcgttgggag cgcggtacta gacgacgacg cacctcaact actagacagc 660
tgtgactctt acttcccaag catcgtaccc atccaagaca acagcaacgc cagtgatcat 720
gacaatgacc ggagctgttt cgccgacgtc tttgtgccca ccacttcacc gtcgcacgat 780
catcacggtg aatcattggc tttctgggga tggccttag 819

<210> SEQ ID NO 16
<211> LENGTH: 272
<212> TYPE: PRT
<213> ORGANISM: Arabidopsis thaliana

<400> SEQUENCE: 16

Met Glu Ser Asn Ser Phe Phe Phe Asp Pro Ser Ala Ser His Gly Asn
1 5 10 15

Ser Met Phe Phe Leu Gly Asn Leu Asn Pro Val Val Gln Gly Gly Gly
20 25 30

Ala Arg Ser Met Met Asn Met Glu Glu Thr Ser Lys Arg Arg Pro Phe
35 40 45

Phe Ser Ser Pro Glu Asp Leu Tyr Asp Asp Asp Phe Tyr Asp Asp Gln
50 55 60

Leu Pro Glu Lys Lys Arg Arg Leu Thr Thr Glu Gln Val His Leu Leu
65 70 75 80

Glu Lys Ser Phe Glu Thr Glu Asn Lys Leu Glu Pro Glu Arg Lys Thr
85 90 95

Gln Leu Ala Lys Lys Leu Gly Leu Gln Pro Arg Gln Val Ala Val Trp
100 105 110

Phe Gln Asn Arg Arg Ala Arg Trp Lys Thr Lys Gln Leu Glu Arg Asp
115 120 125

Tyr Asp Leu Leu Lys Ser Thr Tyr Asp Gln Leu Leu Ser Asn Tyr Asp
130 135 140

Ser Ile Val Met Asp Asn Asp Lys Leu Arg Ser Glu Val Thr Ser Leu
145 150 155 160

Thr Glu Lys Leu Gln Gly Lys Gln Glu Thr Ala Asn Glu Pro Pro Gly
165 170 175

Gln Val Pro Glu Pro Asn Gln Leu Asp Pro Val Tyr Ile Asn Ala Ala
180 185 190

```
Ala Ile Lys Thr Glu Asp Arg Leu Ser Ser Gly Ser Val Gly Ser Ala
        195                 200                 205

Val Leu Asp Asp Asp Ala Pro Gln Leu Leu Asp Ser Cys Asp Ser Tyr
    210                 215                 220

Phe Pro Ser Ile Val Pro Ile Gln Asp Asn Ser Asn Ala Ser Asp His
225                 230                 235                 240

Asp Asn Asp Arg Ser Cys Phe Ala Asp Val Phe Val Pro Thr Thr Ser
                245                 250                 255

Pro Ser His Asp His His Gly Glu Ser Leu Ala Phe Trp Gly Trp Pro
            260                 265                 270


<210> SEQ ID NO 17
<211> LENGTH: 969
<212> TYPE: DNA
<213> ORGANISM: Daucus carota

<400> SEQUENCE: 17

atggcgggtc ggagggtgtt ctatggggag ggagccaata cgacgtcggc tagcctgttg      60

tttcatagtc aaagacctga gcctttcttt ctttctgcac cttctccttc tctaattggt     120

tcaaaatcca tggttagctt tcaagatgct aagcgaaaaa atccctacga tgggttcttt     180

atgcggtcat atgatgaaga agaaattggg gatgaagaat atgatgaata ctttcagcag     240

cctgagaaga agaggaggct caaggctgat caaatccagt ttcttgagaa aagttttgag     300

actgataaca agcttgagcc tgaaagaaaa gttcagcttg caaaagaact cggcttgcag     360

ccaagacagg ttgcgatatg gtttcagaac cgtcgagcac ggtggaagac caaaacacta     420

gaaaaagatt atgatgtatt gcaaaatagc tacaacagcc tcaaggctga ctatgacaat     480

ctacttgccg agaaagaaaa acttaaagcc gaggttctcg acctgacaga caagctactt     540

ctcaaagaag ataaggggag caagacagta gtttttgata agcaaaaggt gtctgcagca     600

ttccaacaag aacgtgttag taatgacata tctgtgggtg aagtactcag taactcagtt     660

atggactgca agcaagaaga tcataactct gtgaaaagtg atgcagttga ttctgacagt     720

ccacactaca gtgatgaagt ctactccagt tttatggagc cagtggatcg ctcttatgtt     780

tttgaacctg ctcagtcgga tatatctcaa gatgaagaag atgacatggg gaacaactta     840

tttctcccat catatcatgt tttctcaaag actgaagacg gtagttactc cgaccagcct     900

tcgaactctt cgtactttgg cttcccagtt gaagatcata cgtttggctt ttggggtact     960

gaattataa                                                             969


<210> SEQ ID NO 18
<211> LENGTH: 322
<212> TYPE: PRT
<213> ORGANISM: Daucus carota

<400> SEQUENCE: 18

Met Ala Gly Arg Arg Val Phe Tyr Gly Glu Gly Ala Asn Thr Thr Ser
1               5                   10                  15

Ala Ser Leu Leu Phe His Ser Gln Arg Pro Glu Pro Phe Phe Leu Ser
            20                  25                  30

Ala Pro Ser Pro Ser Leu Ile Gly Ser Lys Ser Met Val Ser Phe Gln
        35                  40                  45

Asp Ala Lys Arg Lys Asn Pro Tyr Asp Gly Phe Phe Met Arg Ser Tyr
    50                  55                  60

Asp Glu Glu Glu Ile Gly Asp Glu Glu Tyr Asp Glu Tyr Phe Gln Gln
65                  70                  75                  80
```

Pro Glu Lys Lys Arg Arg Leu Lys Ala Asp Gln Ile Gln Phe Leu Glu
85 90 95

Lys Ser Phe Glu Thr Asp Asn Lys Leu Glu Pro Glu Arg Lys Val Gln
100 105 110

Leu Ala Lys Glu Leu Gly Leu Gln Pro Arg Gln Val Ala Ile Trp Phe
115 120 125

Gln Asn Arg Arg Ala Arg Trp Lys Thr Lys Thr Leu Glu Lys Asp Tyr
130 135 140

Asp Val Leu Gln Asn Ser Tyr Asn Ser Leu Lys Ala Asp Tyr Asp Asn
145 150 155 160

Leu Leu Ala Glu Lys Glu Lys Leu Lys Ala Glu Val Leu Asp Leu Thr
165 170 175

Asp Lys Leu Leu Leu Lys Glu Asp Lys Gly Ser Lys Thr Val Val Phe
180 185 190

Asp Lys Gln Lys Val Ser Ala Ala Phe Gln Gln Glu Arg Val Ser Asn
195 200 205

Asp Ile Ser Val Gly Glu Val Leu Ser Asn Ser Val Met Asp Cys Lys
210 215 220

Gln Glu Asp His Asn Ser Val Lys Ser Asp Ala Val Asp Ser Asp Ser
225 230 235 240

Pro His Tyr Ser Asp Glu Val Tyr Ser Ser Phe Met Glu Pro Val Asp
245 250 255

Arg Ser Tyr Val Phe Glu Pro Ala Gln Ser Asp Ile Ser Gln Asp Glu
260 265 270

Glu Asp Asp Met Gly Asn Asn Leu Phe Leu Pro Ser Tyr His Val Phe
275 280 285

Ser Lys Thr Glu Asp Gly Ser Tyr Ser Asp Gln Pro Ser Asn Ser Ser
290 295 300

Tyr Phe Gly Phe Pro Val Glu Asp His Thr Phe Gly Phe Trp Gly Thr
305 310 315 320

Glu Leu

<210> SEQ ID NO 19
<211> LENGTH: 1038
<212> TYPE: DNA
<213> ORGANISM: Glycine max

<400> SEQUENCE: 19
atggcgagtg gcaagcttta tgcgggttca aacatgtcac ttctcctcca aaacgaaagg 60
ctcccttgct cctctgaagt ccttgagtct ctttgggctc agacctctaa ccctgcttcc 120
ttccaaggtt caaaacccgt ggttgatttt gagaatgtaa gtgggagcag gatgacggat 180
aggcctttct ttcaagcgtt ggagaaggaa gagaactgtg atgaggatta cgaggggtgt 240
ttccaccaac cggggaagaa aaggaggctc acaagcgaac aagttcagtt ccttgaaagg 300
aactttgagg tagagaacaa gcttgaaccc gaaaggaaag tccaacttgc aaaagagctt 360
ggcttgcagc caaggcaagt tgctatatgg ttccaaaacc gaagggcaag gttcaagacc 420
aagcagctag aaaaagacta tggcgtgttg aaagctagtt atgacagact caaaagtgac 480
tatgaaagtc ttgttcaaga gaatgacaag ttaaaagcag aggtgaattc tctggagagc 540
aaattgattc ttagagataa agagaaggag gagaattcgg atgacaagtc atctcctgat 600
gatgctgtca attcttcttc accccacaac aacaaggagc ctatggattt attaattatt 660
tcaaaaaatg caacaacaac aacaacatct gaaaatggga ccaaagtgtt gtcaccactc 720

```
ccactcccta ttatggtaac atgctgcaag caagaagatg ccaactcagc caaaagtgat    780

gtccttgatt cggatagccc acattgcact tcattcgtgg agcctgctga ttcctctcat    840

gcctttgaac cagaagacca ctcagaagac ttctcccaag atgaagagga taaccttagt    900

gaaaaccttt tgatgacctt cccttcttct tgttgcttac ctaaggttga agaacactgc    960

tatgacggcc ctcctgaaaa ctcttgtaat tttggcttcc aggttgagga tcaaaccttc   1020

tgtttctggc cctattga                                                 1038
```

<210> SEQ ID NO 20
<211> LENGTH: 345
<212> TYPE: PRT
<213> ORGANISM: Glycine max

<400> SEQUENCE: 20

```
Met Ala Ser Gly Lys Leu Tyr Ala Gly Ser Asn Met Ser Leu Leu Leu
1               5                   10                  15

Gln Asn Glu Arg Leu Pro Cys Ser Ser Glu Val Leu Glu Ser Leu Trp
            20                  25                  30

Ala Gln Thr Ser Asn Pro Ala Ser Phe Gln Gly Ser Lys Pro Val Val
        35                  40                  45

Asp Phe Glu Asn Val Ser Gly Ser Arg Met Thr Asp Arg Pro Phe Phe
    50                  55                  60

Gln Ala Leu Glu Lys Glu Glu Asn Cys Asp Glu Asp Tyr Glu Gly Cys
65                  70                  75                  80

Phe His Gln Pro Gly Lys Lys Arg Arg Leu Thr Ser Glu Gln Val Gln
                85                  90                  95

Phe Leu Glu Arg Asn Phe Glu Val Glu Asn Lys Leu Glu Pro Glu Arg
            100                 105                 110

Lys Val Gln Leu Ala Lys Glu Leu Gly Leu Gln Pro Arg Gln Val Ala
        115                 120                 125

Ile Trp Phe Gln Asn Arg Arg Ala Arg Phe Lys Thr Lys Gln Leu Glu
    130                 135                 140

Lys Asp Tyr Gly Val Leu Lys Ala Ser Tyr Asp Arg Leu Lys Ser Asp
145                 150                 155                 160

Tyr Glu Ser Leu Val Gln Glu Asn Asp Lys Leu Lys Ala Glu Val Asn
                165                 170                 175

Ser Leu Glu Ser Lys Leu Ile Leu Arg Asp Lys Glu Lys Glu Glu Asn
            180                 185                 190

Ser Asp Asp Lys Ser Ser Pro Asp Asp Ala Val Asn Ser Ser Ser Pro
        195                 200                 205

His Asn Asn Lys Glu Pro Met Asp Leu Leu Ile Ile Ser Lys Asn Ala
    210                 215                 220

Thr Thr Thr Thr Thr Ser Glu Asn Gly Thr Lys Val Leu Ser Pro Leu
225                 230                 235                 240

Pro Leu Pro Ile Met Val Thr Cys Cys Lys Gln Glu Asp Ala Asn Ser
                245                 250                 255

Ala Lys Ser Asp Val Leu Asp Ser Asp Ser Pro His Cys Thr Ser Phe
            260                 265                 270

Val Glu Pro Ala Asp Ser Ser His Ala Phe Glu Pro Glu Asp His Ser
        275                 280                 285

Glu Asp Phe Ser Gln Asp Glu Glu Asp Asn Leu Ser Glu Asn Leu Leu
    290                 295                 300

Met Thr Phe Pro Ser Ser Cys Cys Leu Pro Lys Val Glu Glu His Cys
```

305 310 315 320

Tyr Asp Gly Pro Pro Glu Asn Ser Cys Asn Phe Gly Phe Gln Val Glu
325 330 335

Asp Gln Thr Phe Cys Phe Trp Pro Tyr
340 345

<210> SEQ ID NO 21
<211> LENGTH: 858
<212> TYPE: DNA
<213> ORGANISM: Craterostigma plantagineum

<400> SEQUENCE: 21
atgaactctg ctcggatttt cttcgaccca tcttcccacg gcaacatgct gcagtttctt 60
gggaacgccg gcggcgattc atccgttttc cgaggaacaa gatcgtcgtc ggtgctgaac 120
atggaggaga gctcgttaaa acgacagatt ttcagcggcg gcggcggcga tgaattctac 180
gacgaggaat actacgacga gcagttgttg cctgagaaga agcgccgact caccgccgag 240
caggttcact tgcttgagaa gagcttcgag gctgagaaca agcttgagcc tgagcgaaag 300
gctgagctgg cgaagaagct cggattgcag ccgaggcaag tcgccatttg gttccaaaac 360
cgccgagcac ggtggaagac taagcagtta gagagggact acgacaagct taagtcttcc 420
tatgattctc ttctctcaac ctacgactct attcgccagg aaaacgacaa gctcaaagcc 480
gagctccttt ccctgaacga gaaattgcaa cccaaagacg acgacgaccc atcggccgaa 540
ataggtcgaa atctcagttc atcgtcgccg cctgtcgacg cggctgagcc gccgtgcctg 600
aagctgacgg tgaaggtgga ggaccgcctg agcacgggga gcaacggcag cgcagtaatg 660
gacggcgacg gacctcagca gctcctcgac gacagcggcg actcgtactt cgagaacgac 720
gaggaatacg actgcgccgc cgcaagtttg gctgctgcga aggaggacga cggcagcgat 780
gagggcgggt gttacttcac cgaggctctc gcggcggagg aggaggaggc gccgtttgct 840
tggtgtattt ggtcttaa 858

<210> SEQ ID NO 22
<211> LENGTH: 285
<212> TYPE: PRT
<213> ORGANISM: Craterostigma plantagineum

<400> SEQUENCE: 22

Met Asn Ser Ala Arg Ile Phe Phe Asp Pro Ser Ser His Gly Asn Met
1 5 10 15

Leu Gln Phe Leu Gly Asn Ala Gly Gly Asp Ser Ser Val Phe Arg Gly
20 25 30

Thr Arg Ser Ser Ser Val Leu Asn Met Glu Glu Ser Ser Leu Lys Arg
35 40 45

Gln Ile Phe Ser Gly Gly Gly Gly Asp Glu Phe Tyr Asp Glu Glu Tyr
50 55 60

Tyr Asp Glu Gln Leu Leu Pro Glu Lys Lys Arg Arg Leu Thr Ala Glu
65 70 75 80

Gln Val His Leu Leu Glu Lys Ser Phe Glu Ala Glu Asn Lys Leu Glu
85 90 95

Pro Glu Arg Lys Ala Glu Leu Ala Lys Lys Leu Gly Leu Gln Pro Arg
100 105 110

Gln Val Ala Ile Trp Phe Gln Asn Arg Arg Ala Arg Trp Lys Thr Lys
115 120 125

Gln Leu Glu Arg Asp Tyr Asp Lys Leu Lys Ser Ser Tyr Asp Ser Leu

```
    130                 135                 140

Leu Ser Thr Tyr Asp Ser Ile Arg Gln Glu Asn Asp Lys Leu Lys Ala
145                 150                 155                 160

Glu Leu Leu Ser Leu Asn Glu Lys Leu Gln Pro Lys Asp Asp Asp Asp
                165                 170                 175

Pro Ser Ala Glu Ile Gly Arg Asn Leu Ser Ser Ser Ser Pro Pro Val
            180                 185                 190

Asp Ala Ala Glu Pro Pro Cys Leu Lys Leu Thr Val Lys Val Glu Asp
        195                 200                 205

Arg Leu Ser Thr Gly Ser Asn Gly Ser Ala Val Met Asp Gly Asp Gly
    210                 215                 220

Pro Gln Gln Leu Leu Asp Asp Ser Gly Asp Ser Tyr Phe Glu Asn Asp
225                 230                 235                 240

Glu Glu Tyr Asp Cys Ala Ala Ala Ser Leu Ala Ala Ala Lys Glu Asp
                245                 250                 255

Asp Gly Ser Asp Glu Gly Gly Cys Tyr Phe Thr Glu Ala Leu Ala Ala
            260                 265                 270

Glu Glu Glu Glu Ala Pro Phe Ala Trp Cys Ile Trp Ser
        275                 280                 285
```

<210> SEQ ID NO 23
<211> LENGTH: 813
<212> TYPE: DNA
<213> ORGANISM: Gossypium hirsutum
<220> FEATURE:
<221> NAME/KEY: variation
<222> LOCATION: (808)..(808)
<223> OTHER INFORMATION: /replace="c" /replace="g" /replace="t"

<400> SEQUENCE: 23

```
atggagtctg gccgtctttt tttcaatccc tccactaccc accgcaacat gttgcttctc      60

gggaacactg aacccatctt tcgaggggca agaacaatgg ttagcatgga ggaaaaccca     120

aagaagcgac tgttcttcag ctcgccggag gatttgtacg acgaagagta ctacgacgag     180

cagttgcccg agaaaaagcg tcgccttacg tcggagcagg tgtatctgct agagaagagc     240

tttgaggcag agaacaagct ggagccggag aggaagagcc agttggccaa gaagttagga     300

ctgcaaccaa ggcaggtggc ggtatggttc cagaaccgcc gtgcaaggtg gaagacaaag     360

cagcttgaaa gggactatga cctcctcaaa tcttcctttg attcccttca gtccaattat     420

gacactattc tcaaagaaaa tgagaagctc aaatctgagg tagcttcctt gactgaaaaa     480

ctacaagcca aagatgtggc aacagaagca atagcaggtg aaaaggatga agggttagca     540

gctgagatgg cctccgccct ccaattcagt atgaaggtgg aggaccgtct tagtagcggc     600

agtgtcggaa gcgcggtggt ggatgaggat gccccacagc tggtggacag cggcaattcc     660

tactttccaa gcgatgaata ctccagaggc attggccctt tcgatggggt tcagtcggaa     720

gatgaggatg gcagtgataa ttgcgggagt tacttctccg atgtgttcgc aaccacagag     780

cagggagcat taggattgtg ggcctggatc taa                                 813
```

<210> SEQ ID NO 24
<211> LENGTH: 270
<212> TYPE: PRT
<213> ORGANISM: Gossypium hirsutum
<220> FEATURE:
<221> NAME/KEY: UNSURE
<222> LOCATION: (270)..(270)
<223> OTHER INFORMATION: Xaa can be any naturally occuring amino acid

<400> SEQUENCE: 24

Met Glu Ser Gly Arg Leu Phe Phe Asn Pro Ser Thr Thr His Arg Asn
1               5                   10                  15

Met Leu Leu Leu Gly Asn Thr Glu Pro Ile Phe Arg Gly Ala Arg Thr
            20                  25                  30

Met Val Ser Met Glu Glu Asn Pro Lys Lys Arg Leu Phe Phe Ser Ser
        35                  40                  45

Pro Glu Asp Leu Tyr Asp Glu Glu Tyr Tyr Asp Glu Gln Leu Pro Glu
    50                  55                  60

Lys Lys Arg Arg Leu Thr Ser Glu Gln Val Tyr Leu Leu Glu Lys Ser
65                  70                  75                  80

Phe Glu Ala Glu Asn Lys Leu Glu Pro Glu Arg Lys Ser Gln Leu Ala
                85                  90                  95

Lys Lys Leu Gly Leu Gln Pro Arg Gln Val Ala Val Trp Phe Gln Asn
            100                 105                 110

Arg Arg Ala Arg Trp Lys Thr Lys Gln Leu Glu Arg Asp Tyr Asp Leu
        115                 120                 125

Leu Lys Ser Ser Phe Asp Ser Leu Gln Ser Asn Tyr Asp Thr Ile Leu
    130                 135                 140

Lys Glu Asn Glu Lys Leu Lys Ser Glu Val Ala Ser Leu Thr Glu Lys
145                 150                 155                 160

Leu Gln Ala Lys Asp Val Ala Thr Glu Ala Ile Ala Gly Glu Lys Asp
                165                 170                 175

Glu Gly Leu Ala Ala Glu Met Ala Ser Ala Leu Gln Phe Ser Met Lys
            180                 185                 190

Val Glu Asp Arg Leu Ser Ser Gly Ser Val Gly Ser Ala Val Val Asp
        195                 200                 205

Glu Asp Ala Pro Gln Leu Val Asp Ser Gly Asn Ser Tyr Phe Pro Ser
    210                 215                 220

Asp Glu Tyr Ser Arg Gly Ile Gly Pro Phe Asp Gly Val Gln Ser Glu
225                 230                 235                 240

Asp Glu Asp Gly Ser Asp Asn Cys Gly Ser Tyr Phe Ser Asp Val Phe
                245                 250                 255

Ala Thr Thr Glu Gln Gly Ala Leu Gly Leu Trp Ala Trp Xaa
            260                 265                 270

<210> SEQ ID NO 25
<211> LENGTH: 858
<212> TYPE: DNA
<213> ORGANISM: Lycopersicon esculentum
<220> FEATURE:
<221> NAME/KEY: variation
<222> LOCATION: (294)..(294)
<223> OTHER INFORMATION: /replace="c" /replace="g" /replace="t"

<400> SEQUENCE: 25
atgggatctg ggcatatatt tttcgacccg tcgtcgtgtc acggcaacat gctgttcctt 60
gggagcggag atcctgtttt ccgaggacca agatcgacga tgatgaagat ggaggactcc 120
tcgaagaggc gacccttctt tagctcgccg gaggatctat atgacgagga atactacgac 180
gagcagtcac cggagaagaa gcgccgtctc actcctgagc aggtgcactt gttggagaag 240
agctttgaga cagaaaacaa gctggagccc gagcgcaaaa cccagctggc ctaaaagctg 300
gggctgcagc ccagacaggt ggctgtatgg ttccaaaacc gccgtgcccg gtggaagacc 360
aagcagctcg agagggatta tgatcagctc aaatcctctt atgactccct tctctctgat 420

-continued

```
tttgactccg ttcgcaaaga taacgataag ctcaaatctg aggttgtttc attgatggaa    480

aagttacagg ggaaagtggt tggaggagca gggggaaatg aaaaatctga catcttggag    540

gtggatgcta tgacgatcct tcaagtgaag gtgaaggctg gggaccggtt gagcagtggc    600

agtggtggga gcgcggtggt agatgagcat agttcacagc tggtggacag tggggactca    660

tattttcaca ctgatcatga ggagtatcca gggcctggag gatgcaatgt tcctccaccc    720

atggatggtt tacaatcgga ggaagatgat ggtagtgatg atcatggcag ttgccatggc    780

tacttctcta acgtctttgt ggcagaagag cagcaccatg aacaaggaga agagcctatt    840

ggatggttct ggtcttaa                                                  858
```

```
<210> SEQ ID NO 26
<211> LENGTH: 285
<212> TYPE: PRT
<213> ORGANISM: Lycopersicon esculentum
<220> FEATURE:
<221> NAME/KEY: UNSURE
<222> LOCATION: (98)..(98)
<223> OTHER INFORMATION: Xaa can be any naturally occuring amino acid

<400> SEQUENCE: 26

Met Gly Ser Gly His Ile Phe Phe Asp Pro Ser Ser Cys His Gly Asn
1               5                   10                  15

Met Leu Phe Leu Gly Ser Gly Asp Pro Val Phe Arg Gly Pro Arg Ser
            20                  25                  30

Thr Met Met Lys Met Glu Asp Ser Ser Lys Arg Arg Pro Phe Phe Ser
        35                  40                  45

Ser Pro Glu Asp Leu Tyr Asp Glu Glu Tyr Tyr Asp Glu Gln Ser Pro
    50                  55                  60

Glu Lys Lys Arg Arg Leu Thr Pro Glu Gln Val His Leu Leu Glu Lys
65                  70                  75                  80

Ser Phe Glu Thr Glu Asn Lys Leu Glu Pro Glu Arg Lys Thr Gln Leu
                85                  90                  95

Ala Xaa Lys Leu Gly Leu Gln Pro Arg Gln Val Ala Val Trp Phe Gln
            100                 105                 110

Asn Arg Arg Ala Arg Trp Lys Thr Lys Gln Leu Glu Arg Asp Tyr Asp
        115                 120                 125

Gln Leu Lys Ser Ser Tyr Asp Ser Leu Leu Ser Asp Phe Asp Ser Val
    130                 135                 140

Arg Lys Asp Asn Asp Lys Leu Lys Ser Glu Val Val Ser Leu Met Glu
145                 150                 155                 160

Lys Leu Gln Gly Lys Val Val Gly Gly Ala Gly Gly Asn Glu Lys Ser
                165                 170                 175

Asp Ile Leu Glu Val Asp Ala Met Thr Ile Leu Gln Val Lys Val Lys
            180                 185                 190

Ala Gly Asp Arg Leu Ser Ser Gly Ser Gly Gly Ser Ala Val Val Asp
        195                 200                 205

Glu His Ser Ser Gln Leu Val Asp Ser Gly Asp Ser Tyr Phe His Thr
    210                 215                 220

Asp His Glu Glu Tyr Pro Gly Pro Gly Gly Cys Asn Val Pro Pro Pro
225                 230                 235                 240

Met Asp Gly Leu Gln Ser Glu Glu Asp Asp Gly Ser Asp Asp His Gly
                245                 250                 255

Ser Cys His Gly Tyr Phe Ser Asn Val Phe Val Ala Glu Glu Gln His
            260                 265                 270
```

His Glu Gln Gly Glu Glu Pro Ile Gly Trp Phe Trp Ser
        275                 280                 285

<210> SEQ ID NO 27
<211> LENGTH: 972
<212> TYPE: DNA
<213> ORGANISM: Lycopersicon esculentum

<400> SEQUENCE: 27
atggctccag ggattctcta tggtggttct tctaatttcg atggcgtttt tactcaaaaa 60
cagagagacg tgttttcttc atctactgca ccgaaagggc atcttggttc cctttttgcc 120
cctgcctctt cttcttctaa tttcttggga tccagttcta tggtgagttt tcgcggtgtt 180
aatggaggga agagatcatt ctttgattcg ttcgatcagg atgacaatga agctgatgaa 240
ttgggggaat atcttcatca agcggagaag aagaggcgac ttactgacaa ccaagttcag 300
tttcttgaga agagttttgg ggaagagaac aaacttgaac cagaaagaaa agttcagctt 360
gctaaagaac ttggtctgca gcctcgccaa attgcaattt ggtttcagaa tcgtcgtgcg 420
cgatggaaga ctaagcagct cgagaaagat tatgatgaat tgaggaatag atacgatact 480
ctgaaatcaa attacaataa tcttctcaag gaaaaagaag atcttcgaac tgaagttttc 540
cgtctcaccg gtaagctgtt tatcaaagag aaaggaaatg ggcaattgga tttgcgcgat 600
gaacacaaac actccaatgc attggcaaaa gaaaccgtgg ttgatccaat gtccaatgta 660
ccagctctgg ttgttaagca ccagcaggaa gatttaagct ctgctaagag tgatgttttc 720
gactcagaaa gcccacgtta caccagtaga atgcattcct cagtcgtaga tcaggatgat 780
tctgctcgcg catttgaaac tgatcagtcg gattcatctc aggatgatga tgaaaacttc 840
agcaagaata tgctttctac tgccaaccta cttggcaaag acgcggatga tgattatccc 900
gcgacatcat caaatttgag ttactttgga tttccagttg aagaccaagg ttttggtttc 960
tggacttatt aa 972

<210> SEQ ID NO 28
<211> LENGTH: 323
<212> TYPE: PRT
<213> ORGANISM: Lycopersicon esculentum

<400> SEQUENCE: 28

Met Ala Pro Gly Ile Leu Tyr Gly Gly Ser Ser Asn Phe Asp Gly Val
1               5                   10                  15

Phe Thr Gln Lys Gln Arg Asp Val Phe Ser Ser Ser Thr Ala Pro Lys
            20                  25                  30

Gly His Leu Gly Ser Leu Phe Ala Pro Ala Ser Ser Ser Ser Asn Phe
        35                  40                  45

Leu Gly Ser Ser Ser Met Val Ser Phe Arg Gly Val Asn Gly Gly Lys
    50                  55                  60

Arg Ser Phe Phe Asp Ser Phe Asp Gln Asp Asp Asn Glu Ala Asp Glu
65                  70                  75                  80

Leu Gly Glu Tyr Leu His Gln Ala Glu Lys Lys Arg Arg Leu Thr Asp
                85                  90                  95

Asn Gln Val Gln Phe Leu Glu Lys Ser Phe Gly Glu Glu Asn Lys Leu
            100                 105                 110

Glu Pro Glu Arg Lys Val Gln Leu Ala Lys Glu Leu Gly Leu Gln Pro
        115                 120                 125

Arg Gln Ile Ala Ile Trp Phe Gln Asn Arg Arg Ala Arg Trp Lys Thr
    130                 135                 140

-continued

```
Lys Gln Leu Glu Lys Asp Tyr Asp Glu Leu Arg Asn Arg Tyr Asp Thr
145                 150                 155                 160

Leu Lys Ser Asn Tyr Asn Asn Leu Leu Lys Glu Lys Glu Asp Leu Arg
                165                 170                 175

Thr Glu Val Phe Arg Leu Thr Gly Lys Leu Phe Ile Lys Glu Lys Gly
            180                 185                 190

Asn Gly Gln Leu Asp Leu Arg Asp Glu His Lys His Ser Asn Ala Leu
        195                 200                 205

Ala Lys Glu Thr Val Val Asp Pro Met Ser Asn Val Pro Ala Leu Val
    210                 215                 220

Val Lys His Gln Gln Glu Asp Leu Ser Ser Ala Lys Ser Asp Val Phe
225                 230                 235                 240

Asp Ser Glu Ser Pro Arg Tyr Thr Ser Arg Met His Ser Ser Val Val
                245                 250                 255

Asp Gln Asp Asp Ser Ala Arg Ala Phe Glu Thr Asp Gln Ser Asp Ser
            260                 265                 270

Ser Gln Asp Asp Asp Glu Asn Phe Ser Lys Asn Met Leu Ser Thr Ala
        275                 280                 285

Asn Leu Leu Gly Lys Asp Ala Asp Asp Asp Tyr Pro Ala Thr Ser Ser
    290                 295                 300

Asn Leu Ser Tyr Phe Gly Phe Pro Val Glu Asp Gln Gly Phe Gly Phe
305                 310                 315                 320

Trp Thr Tyr


<210> SEQ ID NO 29
<211> LENGTH: 1014
<212> TYPE: DNA
<213> ORGANISM: Medicago sativa

<400> SEQUENCE: 29

atggcgggtg ggagagtttt ttcaaatggt cctgcaaata tttcaaatat aaatatgaat      60

attttgcttc agaatcaaca acaaactcct cgtggaaact cttctcaaca acctcttgat     120

tctcttttcc tttcttcttc tgcttctttc tttggttcaa gatctatggt gagttttgaa     180

gatgttcaag gaaggaaaag gcgcaacagg tctttctttg gaggatttga tcttgacgaa     240

aacggagagg atgagatgga tgagtacttt catcaatccg agaagaaacg gcgtctctca     300

gtggatcaag ttcagtttct tgagaaaagc tttgaggagg acaacaaact tgaaccagag     360

aggaaaacca agctagctaa agaccttggt ttgcagccac ggcaagttgc tatttggttt     420

caaaaccgtc gtgcaaggtg gaagactaaa cagcttgaga aggattatga ttctcttaat     480

gatggttatg agtctcttaa gacagagtat gacaaccttc tcaaagagaa agataggtta     540

caatctgagg tggcaagcct aactgaaaag gtacttgaaa gagagaaaca agagggaaaa     600

ttcaaacaag gtgaaagtga aacaaaggaa ttcttgaagg aaccaacaat taataagcct     660

ttggttgatt cagtttctga gggtgaagga tccaaattgt caattgttga ggcttctaat     720

aataataata ataataacaa acttgaagat attagttcag caaggagtga catattggat     780

tgtgaaagtc cacgctacac tgatggagtg ttagagacat gtgattcttc ctatgtattt     840

gaacctgaat atcaatcgga cctatcacaa gatgaagaag atcacaattt attgcctcct     900

tacatcttta caaaacttga agatgtgaat tactccgacc cgccacataa ttcaacaagt     960

tatggatttc aagaggaaga tcatcatcaa gctctttggc cttggtctta ttag         1014
```

<210> SEQ ID NO 30
<211> LENGTH: 337
<212> TYPE: PRT
<213> ORGANISM: Medicago sativa

<400> SEQUENCE: 30

Met Ala Gly Gly Arg Val Phe Ser Asn Gly Pro Ala Asn Ile Ser Asn
1 5 10 15

Ile Asn Met Asn Ile Leu Leu Gln Asn Gln Gln Gln Thr Pro Arg Gly
20 25 30

Asn Ser Ser Gln Gln Pro Leu Asp Ser Leu Phe Leu Ser Ser Ser Ala
35 40 45

Ser Phe Phe Gly Ser Arg Ser Met Val Ser Phe Glu Asp Val Gln Gly
50 55 60

Arg Lys Arg Arg Asn Arg Ser Phe Phe Gly Gly Phe Asp Leu Asp Glu
65 70 75 80

Asn Gly Glu Asp Glu Met Asp Glu Tyr Phe His Gln Ser Glu Lys Lys
85 90 95

Arg Arg Leu Ser Val Asp Gln Val Gln Phe Leu Glu Lys Ser Phe Glu
100 105 110

Glu Asp Asn Lys Leu Glu Pro Glu Arg Lys Thr Lys Leu Ala Lys Asp
115 120 125

Leu Gly Leu Gln Pro Arg Gln Val Ala Ile Trp Phe Gln Asn Arg Arg
130 135 140

Ala Arg Trp Lys Thr Lys Gln Leu Glu Lys Asp Tyr Asp Ser Leu Asn
145 150 155 160

Asp Gly Tyr Glu Ser Leu Lys Thr Glu Tyr Asp Asn Leu Leu Lys Glu
165 170 175

Lys Asp Arg Leu Gln Ser Glu Val Ala Ser Leu Thr Glu Lys Val Leu
180 185 190

Glu Arg Glu Lys Gln Glu Gly Lys Phe Lys Gln Gly Glu Ser Glu Thr
195 200 205

Lys Glu Phe Leu Lys Glu Pro Thr Ile Asn Lys Pro Leu Val Asp Ser
210 215 220

Val Ser Glu Gly Glu Gly Ser Lys Leu Ser Ile Val Glu Ala Ser Asn
225 230 235 240

Asn Asn Asn Asn Asn Asn Lys Leu Glu Asp Ile Ser Ser Ala Arg Ser
245 250 255

Asp Ile Leu Asp Cys Glu Ser Pro Arg Tyr Thr Asp Gly Val Leu Glu
260 265 270

Thr Cys Asp Ser Ser Tyr Val Phe Glu Pro Glu Tyr Gln Ser Asp Leu
275 280 285

Ser Gln Asp Glu Glu Asp His Asn Leu Leu Pro Pro Tyr Ile Phe Thr
290 295 300

Lys Leu Glu Asp Val Asn Tyr Ser Asp Pro Pro His Asn Ser Thr Ser
305 310 315 320

Tyr Gly Phe Gln Glu Glu Asp His His Gln Ala Leu Trp Pro Trp Ser
325 330 335

Tyr

<210> SEQ ID NO 31
<211> LENGTH: 843
<212> TYPE: DNA
<213> ORGANISM: Aquilegia formosa x Aquilegia pubescens

<400> SEQUENCE: 31

```
atggattcaa caacaagccg tcttttcttt gatggttcct gccatgggaa catgttgctt     60

ttagggagtg gagatcccgt tcttcgaggt tcaagatcat tcattaatat ggaagattct    120

ttgaaaagac gtccttttta tagttcaaca gatgaactaa ttgaagagga gttttatgat    180

gaacagctac ctgaaaagaa acgtcgtctt acttctgagc aggttcatct attggagaag    240

agctttgaga cagagaacaa gctggaacca gatcgtaaga cccagcttgc taagaagctt    300

gggttgcaac cgagacaagt tgcagtttgg tttcagaata gacgagctcg ttggaagact    360

aagcaactag agagagatta tgatcttctt aaagcttctt atgattccct tcgttctgat    420

tacgatgaca ttgttaaaga gaatgagaag ctcaaatctg aggtggtttc cttaactggg    480

aagttgcagg tcaaggaggg agctgggatg gagttaaatc agatatctga cccaccactc    540

tccactgaag aaaatgttga tgtaactacg atgcaattta atgttaaggt tgaggatcgc    600

ttgagctctg gcagtggggt aagtgctgtg gttgatgagg aatgtcgaca gcttgttgac    660

agtgttgatt cctatttccc tggcgatgac tatggtcaat gcataggccc agtagatgga    720

gtccagtcag aagaagatga cattagtgac gacagccgga gctatttctc agatgtcttt    780

ccagctgcac cagagcagaa ccaccaggag agtgagacat tgggttggtg ggactgggct    840

taa                                                                  843
```

<210> SEQ ID NO 32
<211> LENGTH: 280
<212> TYPE: PRT
<213> ORGANISM: Aquilegia formosa x Aquilegia pubescens

<400> SEQUENCE: 32

```
Met Asp Ser Thr Thr Ser Arg Leu Phe Phe Asp Gly Ser Cys His Gly
1               5                   10                  15

Asn Met Leu Leu Leu Gly Ser Gly Asp Pro Val Leu Arg Gly Ser Arg
            20                  25                  30

Ser Phe Ile Asn Met Glu Asp Ser Leu Lys Arg Arg Pro Phe Tyr Ser
        35                  40                  45

Ser Thr Asp Glu Leu Ile Glu Glu Glu Phe Tyr Asp Glu Gln Leu Pro
    50                  55                  60

Glu Lys Lys Arg Arg Leu Thr Ser Glu Gln Val His Leu Leu Glu Lys
65                  70                  75                  80

Ser Phe Glu Thr Glu Asn Lys Leu Glu Pro Asp Arg Lys Thr Gln Leu
                85                  90                  95

Ala Lys Lys Leu Gly Leu Gln Pro Arg Gln Val Ala Val Trp Phe Gln
            100                 105                 110

Asn Arg Arg Ala Arg Trp Lys Thr Lys Gln Leu Glu Arg Asp Tyr Asp
        115                 120                 125

Leu Leu Lys Ala Ser Tyr Asp Ser Leu Arg Ser Asp Tyr Asp Asp Ile
    130                 135                 140

Val Lys Glu Asn Glu Lys Leu Lys Ser Glu Val Val Ser Leu Thr Gly
145                 150                 155                 160

Lys Leu Gln Val Lys Glu Gly Ala Gly Met Glu Leu Asn Gln Ile Ser
                165                 170                 175

Asp Pro Pro Leu Ser Thr Glu Glu Asn Val Asp Val Thr Thr Met Gln
            180                 185                 190

Phe Asn Val Lys Val Glu Asp Arg Leu Ser Ser Gly Ser Gly Val Ser
        195                 200                 205

Ala Val Val Asp Glu Glu Cys Arg Gln Leu Val Asp Ser Val Asp Ser
```

```
    210                 215                 220

Tyr Phe Pro Gly Asp Asp Tyr Gly Gln Cys Ile Gly Pro Val Asp Gly
225                 230                 235                 240

Val Gln Ser Glu Glu Asp Asp Ile Ser Asp Asp Ser Arg Ser Tyr Phe
                245                 250                 255

Ser Asp Val Phe Pro Ala Ala Pro Glu Gln Asn His Gln Glu Ser Glu
            260                 265                 270

Thr Leu Gly Trp Trp Asp Trp Ala
        275                 280


<210> SEQ ID NO 33
<211> LENGTH: 2193
<212> TYPE: DNA
<213> ORGANISM: Oryza sativa

<400> SEQUENCE: 33

aatccgaaaa gtttctgcac cgttttcacc ccctaactaa caatataggg aacgtgtgct     60

aaatataaaa tgagacctta tatatgtagc gctgataact agaactatgc aagaaaaact    120

catccaccta ctttagtggc aatcgggcta aataaaaaag agtcgctaca ctagtttcgt    180

tttccttagt aattaagtgg gaaaatgaaa tcattattgc ttagaatata cgttcacatc    240

tctgtcatga agttaaatta ttcgaggtag ccataattgt catcaaactc ttcttgaata    300

aaaaaatctt tctagctgaa ctcaatgggt aaagagagag atttttttta aaaaaataga    360

atgaagatat tctgaacgta ttggcaaaga tttaaacata taattatata attttatagt    420

ttgtgcattc gtcatatcgc acatcattaa ggacatgtct tactccatcc caatttttat    480

ttagtaatta aagacaattg acttattttt attatttatc ttttttcgat tagatgcaag    540

gtacttacgc acacactttg tgctcatgtg catgtgtgag tgcacctcct caatacacgt    600

tcaactagca acacatctct aatatcactc gcctatttaa tacatttagg tagcaatatc    660

tgaattcaag cactccacca tcaccagacc acttttaata atatctaaaa tacaaaaaat    720

aattttacag aatagcatga aaagtatgaa acgaactatt taggtttttc acatacaaaa    780

aaaaaaagaa ttttgctcgt gcgcgagcgc caatctccca tattgggcac acaggcaaca    840

acagagtggc tgcccacaga acaacccaca aaaaacgatg atctaacgga ggacagcaag    900

tccgcaacaa ccttttaaca gcaggctttg cggccaggag agaggaggag aggcaaagaa    960

aaccaagcat cctcctcctc ccatctataa attcctcccc ccttttcccc tctctatata   1020

ggaggcatcc aagccaagaa gagggagagc accaaggaca cgcgactagc agaagccgag   1080

cgaccgcctt cttcgatcca tatcttccgg tcgagttctt ggtcgatctc ttccctcctc   1140

cacctcctcc tcacagggta tgtgcccttc ggttgttctt ggatttattg ttctaggttg   1200

tgtagtacgg gcgttgatgt taggaaaggg gatctgtatc tgtgatgatt cctgttcttg   1260

gatttgggat agaggggttc ttgatgttgc atgttatcgg ttcggtttga ttagtagtat   1320

ggttttcaat cgtctggaga gctctatgga aatgaaatgg tttagggtac ggaatcttgc   1380

gattttgtga gtaccttttg tttgaggtaa aatcagagca ccggtgattt tgcttggtgt   1440

aataaaagta cggttgtttg gtcctcgatt ctggtagtga tgcttctcga tttgacgaag   1500

ctatcctttg tttattccct attgaacaaa aataatccaa ctttgaagac ggtcccgttg   1560

atgagattga atgattgatt cttaagcctg tccaaaattt cgcagctggc ttgtttagat   1620

acagtagtcc ccatcacgaa attcatggaa acagttataa tcctcaggaa caggggattc   1680

cctgttcttc cgatttgctt tagtcccaga atttttttc ccaaatatct taaaaagtca    1740
```

```
ctttctggtt cagttcaatg aattgattgc tacaaataat gcttttatag cgttatccta   1800

gctgtagttc agttaatagg taatacccct atagtttagt caggagaaga acttatccga   1860

tttctgatct ccatttttaa ttatatgaaa tgaactgtag cataagcagt attcatttgg   1920

attatttttt ttattagctc tcaccccttc attattctga gctgaaagtc tggcatgaac   1980

tgtcctcaat tttgttttca aattcacatc gattatctat gcattatcct cttgtatcta   2040

cctgtagaag tttctttttg gttattcctt gactgcttga ttacagaaag aaatttatga   2100

agctgtaatc gggatagtta tactgcttgt tcttatgatt catttccttt gtgcagttct   2160

tggtgtagct tgccactttc accagcaaag ttc                                 2193


<210> SEQ ID NO 34
<211> LENGTH: 49
<212> TYPE: DNA
<213> ORGANISM: Artificial sequence
<220> FEATURE:
<223> OTHER INFORMATION: primer: prm6000

<400> SEQUENCE: 34

ggggacaagt ttgtacaaaa aagcaggctt aaacaatgga tcccggccg                  49


<210> SEQ ID NO 35
<211> LENGTH: 48
<212> TYPE: DNA
<213> ORGANISM: Artificial sequence
<220> FEATURE:
<223> OTHER INFORMATION: primer: prm6001

<400> SEQUENCE: 35

ggggaccact ttgtacaaga aagctgggtg atcagctcca gaaccagg                   48


<210> SEQ ID NO 36
<211> LENGTH: 834
<212> TYPE: DNA
<213> ORGANISM: Oryza sativa

<400> SEQUENCE: 36

atgaagcgac ccggcggtgc cggcggcggc ggaggcagcc catcgctcgt cacgatggct     60

aattctagtg atgatggata tggaggggtt gggatggagg cggaggggga cgtggaggag    120

gagatgatgg cgtgcggcgg cggcggggag aagaagcggc ggctgagcgt ggagcaggtt    180

cgcgcgctgg agcggagctt cgaggtggag aacaagcttg agcctgagcg gaaggcgcgg    240

ctggcgcgcg acctcggcct gcagccgcgc caggtcgccg tctggttcca gaaccgccgc    300

gcgcggtgga agaccaagca gctcgagcgc gactacgccg cgctccgcca ttcctacgac    360

tccctgcgcc tcgatcacga cgcgctccgc cgcgacaagg acgccctcct cgccgagatc    420

aaggagctga aggcgaagct cggggacgag gaggcggcgg cgagcttcac gtcggtgaag    480

gaggagccgg cggcctccga cggggccaccg gcggcgggat ttgggtcgtc cgacagcgac    540

tcaagcgcgg tgctgaacga cgtggacgcg gccggcgccg cgcccgcggc gacggacgcg    600

ctggctccgg aggcgtgcac gtttctcggt gcgccgcccg ccgcgggcgc gggcgcgggc    660

gcagcggcgg cggcgagcca cgaggaggtg ttcttccacg gcaatttcct caaggtggag    720

gaggacgaga cggggttcct cgacgacgac gagccgtgcg gcgggttctt cgccgacgat    780

cagcccccgc cgctctcgtc gtggtgggcc gaacccacgg agcactggaa ctga           834


<210> SEQ ID NO 37
```

<211> LENGTH: 277
<212> TYPE: PRT
<213> ORGANISM: Oryza sativa

<400> SEQUENCE: 37

```
Met Lys Arg Pro Gly Gly Ala Gly Gly Gly Gly Gly Ser Pro Ser Leu
1               5                   10                  15

Val Thr Met Ala Asn Ser Ser Asp Asp Gly Tyr Gly Gly Val Gly Met
            20                  25                  30

Glu Ala Glu Gly Asp Val Glu Glu Glu Met Met Ala Cys Gly Gly Gly
        35                  40                  45

Gly Glu Lys Lys Arg Arg Leu Ser Val Glu Gln Val Arg Ala Leu Glu
    50                  55                  60

Arg Ser Phe Glu Val Glu Asn Lys Leu Glu Pro Glu Arg Lys Ala Arg
65                  70                  75                  80

Leu Ala Arg Asp Leu Gly Leu Gln Pro Arg Gln Val Ala Val Trp Phe
                85                  90                  95

Gln Asn Arg Arg Ala Arg Trp Lys Thr Lys Gln Leu Glu Arg Asp Tyr
            100                 105                 110

Ala Ala Leu Arg His Ser Tyr Asp Ser Leu Arg Leu Asp His Asp Ala
        115                 120                 125

Leu Arg Arg Asp Lys Asp Ala Leu Leu Ala Glu Ile Lys Glu Leu Lys
    130                 135                 140

Ala Lys Leu Gly Asp Glu Glu Ala Ala Ala Ser Phe Thr Ser Val Lys
145                 150                 155                 160

Glu Glu Pro Ala Ala Ser Asp Gly Pro Pro Ala Ala Gly Phe Gly Ser
                165                 170                 175

Ser Asp Ser Asp Ser Ser Ala Val Leu Asn Asp Val Asp Ala Ala Gly
            180                 185                 190

Ala Ala Pro Ala Ala Thr Asp Ala Leu Ala Pro Glu Ala Cys Thr Phe
        195                 200                 205

Leu Gly Ala Pro Pro Ala Ala Gly Ala Gly Ala Gly Ala Ala Ala Ala
    210                 215                 220

Ala Ser His Glu Glu Val Phe Phe His Gly Asn Phe Leu Lys Val Glu
225                 230                 235                 240

Glu Asp Glu Thr Gly Phe Leu Asp Asp Asp Glu Pro Cys Gly Gly Phe
                245                 250                 255

Phe Ala Asp Asp Gln Pro Pro Pro Leu Ser Ser Trp Trp Ala Glu Pro
            260                 265                 270

Thr Glu His Trp Asn
        275
```

<210> SEQ ID NO 38
<211> LENGTH: 750
<212> TYPE: DNA
<213> ORGANISM: Oryza sativa

<400> SEQUENCE: 38

```
atggatgggg aggaggacag cgagtggatg atgatggacg ttggagggaa gggcgggaag      60

ggcggcggcg gcggcggcgc ggcggacagg aagaagcggt tcagcgagga gcagatcaag     120

tcgctggagt ccatgttcgc gacgcagacc aagctggagc cgaggcagaa gctgcagctc     180

gccagggagc tcggcctgca gcctcgccag gtcgccatct ggttccagaa caagcgcgcg     240

cggtggaagt ccaagcagct cgagcgcgag tactccgccc tccgcgacga ctacgacgcc     300

ctcctctgca gctacgagtc cctcaagaag gagaagctcg ccctcatcaa gcagctggag     360
```

-continued

```
aagctggcgg agatgctgca ggagccacgg gggaagtacg gcgataatgc cggggacgac    420

gcgcggtcgg gcggcgtcgc cggcatgaag aaggaggagt tcgtcggcgc gggcggcgcc    480

gccacgctct actcgtcggc cgagggtggc gggacgacga cgacgacgac ggccaagttg    540

atgccccact tcggcagcga cgacgtcgac gcggggctct tcctccggcc gtcgtcgcag    600

catcatccgc cgccgccgca cgccggtgcc ggcttcacgt cctccgagcc ggccgccgac    660

caccagtcct tcaacttcca ctcgagctgg ccgtcgtcca cggagcagac ctgcagcagc    720

acgccatggt gggaattcga gagcgagtga                                     750
```

<210> SEQ ID NO 39
<211> LENGTH: 249
<212> TYPE: PRT
<213> ORGANISM: Oryza sativa

<400> SEQUENCE: 39

```
Met Asp Gly Glu Glu Asp Ser Glu Trp Met Met Met Asp Val Gly Gly
1               5                   10                  15

Lys Gly Gly Lys Gly Gly Gly Gly Gly Gly Ala Ala Asp Arg Lys Lys
            20                  25                  30

Arg Phe Ser Glu Glu Gln Ile Lys Ser Leu Glu Ser Met Phe Ala Thr
        35                  40                  45

Gln Thr Lys Leu Glu Pro Arg Gln Lys Leu Gln Leu Ala Arg Glu Leu
    50                  55                  60

Gly Leu Gln Pro Arg Gln Val Ala Ile Trp Phe Gln Asn Lys Arg Ala
65                  70                  75                  80

Arg Trp Lys Ser Lys Gln Leu Glu Arg Glu Tyr Ser Ala Leu Arg Asp
                85                  90                  95

Asp Tyr Asp Ala Leu Leu Cys Ser Tyr Glu Ser Leu Lys Lys Glu Lys
            100                 105                 110

Leu Ala Leu Ile Lys Gln Leu Glu Lys Leu Ala Glu Met Leu Gln Glu
        115                 120                 125

Pro Arg Gly Lys Tyr Gly Asp Asn Ala Gly Asp Asp Ala Arg Ser Gly
    130                 135                 140

Gly Val Ala Gly Met Lys Lys Glu Glu Phe Val Gly Ala Gly Gly Ala
145                 150                 155                 160

Ala Thr Leu Tyr Ser Ser Ala Glu Gly Gly Gly Thr Thr Thr Thr Thr
                165                 170                 175

Thr Ala Lys Leu Met Pro His Phe Gly Ser Asp Asp Val Asp Ala Gly
            180                 185                 190

Leu Phe Leu Arg Pro Ser Ser Gln His His Pro Pro Pro Pro His Ala
        195                 200                 205

Gly Ala Gly Phe Thr Ser Ser Glu Pro Ala Ala Asp His Gln Ser Phe
    210                 215                 220

Asn Phe His Ser Ser Trp Pro Ser Ser Thr Glu Gln Thr Cys Ser Ser
225                 230                 235                 240

Thr Pro Trp Trp Glu Phe Glu Ser Glu
                245
```

<210> SEQ ID NO 40
<211> LENGTH: 945
<212> TYPE: DNA
<213> ORGANISM: Populus tremuloides

<400> SEQUENCE: 40

-continued

```
atggcgggtg gtaccggtgg ttctaattcc aatttgtctg ttttgcttca aagccaaaga     60

ggcccttgtg ctgcttcaca acctcttgaa tctttttttcc tttctggctc ttctccttct    120

tttcttggtt caagatccat gatgagtttt gaagatgttc atcaagcaaa cggatcaacc    180

aggccttttt tccgctcgtt tgatcacgaa gacaatggag acgatgatct ggatgaatat    240

tttcatcaac ctgaaaagaa gaggagactt actgttgatc aagttcagtt tcttgaaaag    300

agttttgagc ttgagaacaa gcttgaacct gaaaggaaaa tccagcttgc aaaggatctt    360

ggccttcagc cgcgtcaggt tgctatatgg tttcaaaacc gccgagcaag atggaagact    420

aaacagctgg aaaaggatta tgacgttttg caatctagct acaatagcct taaggctgac    480

tatgacaacc tcctcaagga gaaggagaaa ctaaaagctg aggttaatct tctcaccgac    540

aagttgctcc tcaaagagaa agagaaggga atctcagaat tgtctgataa agatgcatta    600

tcgcaagagc cacctaaaag ggctatagct gattcagctt ccgagggtga agtgtcgaaa    660

atctcaacag tggcctgtaa gcaggaagat atcagctcag ccaaaagcga catatttgat    720

tcagacagcc cacattacgc tgatggggtg cattcctcac tcttagaggc aggagattct    780

tcatatgttt tcgaacccga tcaatcagat ttgtcacaag atgaagaaga taactttagc    840

aagagcttat tgcctccata cgtctttccg aagcttgaag atgacgatta ctctgacccg    900

cctgcaagtt ttgaagatca tgccttttgg tcctggtcat actaa                     945


<210> SEQ ID NO 41
<211> LENGTH: 314
<212> TYPE: PRT
<213> ORGANISM: Populus tremuloides

<400> SEQUENCE: 41

Met Ala Gly Gly Thr Gly Gly Ser Asn Ser Asn Leu Ser Val Leu Leu
1               5                   10                  15

Gln Ser Gln Arg Gly Pro Cys Ala Ala Ser Gln Pro Leu Glu Ser Phe
            20                  25                  30

Phe Leu Ser Gly Ser Ser Pro Ser Phe Leu Gly Ser Arg Ser Met Met
        35                  40                  45

Ser Phe Glu Asp Val His Gln Ala Asn Gly Ser Thr Arg Pro Phe Phe
    50                  55                  60

Arg Ser Phe Asp His Glu Asp Asn Gly Asp Asp Asp Leu Asp Glu Tyr
65                  70                  75                  80

Phe His Gln Pro Glu Lys Lys Arg Arg Leu Thr Val Asp Gln Val Gln
                85                  90                  95

Phe Leu Glu Lys Ser Phe Glu Leu Glu Asn Lys Leu Glu Pro Glu Arg
            100                 105                 110

Lys Ile Gln Leu Ala Lys Asp Leu Gly Leu Gln Pro Arg Gln Val Ala
        115                 120                 125

Ile Trp Phe Gln Asn Arg Arg Ala Arg Trp Lys Thr Lys Gln Leu Glu
    130                 135                 140

Lys Asp Tyr Asp Val Leu Gln Ser Ser Tyr Asn Ser Leu Lys Ala Asp
145                 150                 155                 160

Tyr Asp Asn Leu Leu Lys Glu Lys Glu Lys Leu Lys Ala Glu Val Asn
                165                 170                 175

Leu Leu Thr Asp Lys Leu Leu Leu Lys Glu Lys Glu Lys Gly Ile Ser
            180                 185                 190

Glu Leu Ser Asp Lys Asp Ala Leu Ser Gln Glu Pro Pro Lys Arg Ala
        195                 200                 205
```

-continued

```
Ile Ala Asp Ser Ala Ser Glu Gly Glu Val Ser Lys Ile Ser Thr Val
    210                 215                 220

Ala Cys Lys Gln Glu Asp Ile Ser Ser Ala Lys Ser Asp Ile Phe Asp
225                 230                 235                 240

Ser Asp Ser Pro His Tyr Ala Asp Gly Val His Ser Ser Leu Leu Glu
                245                 250                 255

Ala Gly Asp Ser Ser Tyr Val Phe Glu Pro Asp Gln Ser Asp Leu Ser
            260                 265                 270

Gln Asp Glu Glu Asp Asn Phe Ser Lys Ser Leu Leu Pro Pro Tyr Val
        275                 280                 285

Phe Pro Lys Leu Glu Asp Asp Asp Tyr Ser Asp Pro Pro Ala Ser Phe
    290                 295                 300

Glu Asp His Ala Phe Trp Ser Trp Ser Tyr
305                 310
```

<210> SEQ ID NO 42
<211> LENGTH: 954
<212> TYPE: DNA
<213> ORGANISM: Populus tremuloides

<400> SEQUENCE: 42

```
atggcggctt gtggtggtgg tggtggtggt tctaatccca atttgtctgt tttagttcaa      60

agccaaagag gcccttgtgc tgcttctcaa cctcttgaag ctttttttcct ttctggctct    120

tctccttctt ttcttggttc aagatccatg atgagttttg cagatgttca ccaagcaaat    180

ggatcaacta gaccgttttt ccgcccatat gatcacgaag acaacggcga cgatgatttg    240

gatgaatatt ttcatcaacc tgaaaagaag aggagactta ctgttgatca agttcagttt    300

cttgaaagaa gttttgaggt tgagaacaag cttgaacccg aaaggaaaat ccagctggcg    360

aaggatcttg gcttgcagcc tcggcaggtt gccatatggt ttcaaaaccg ccgggcaaga    420

tggaagacga aacagcttga aaaagattat gaggttctgc aatctagcta caatggcctt    480

aaggctgact acgacaacct cttcaaggag aaggagaaac taaaagctga ggttaatctt    540

ctcaccaacg agttgctcct taaagagaaa gagaaaggaa gctcagaatt gtctgataaa    600

gatgcattat ctcaagagcc acccaaaaag gcaatagccg attcagcttc agagggtgaa    660

gtgtcgaaaa cttcaaccgt ggcctgccag caggaagata ttagctcagc caaaagtgat    720

atgtttgatt cagacagccc acattttgcg gatggggtac attcctcact cttagaggca    780

ggtgattctt cacatgtctt cgagcccgac caatcggatt tatcacaaga tgaagaagat    840

aacttgagca agagtctttt gcctccgtac gtctttccaa agcttgaaga tggtgattac    900

tctgacccgc cagcaagttt tgaagatcat gccttttggt gctggtcata ctaa          954
```

<210> SEQ ID NO 43
<211> LENGTH: 317
<212> TYPE: PRT
<213> ORGANISM: Populus tremuloides

<400> SEQUENCE: 43

```
Met Ala Ala Cys Gly Gly Gly Gly Gly Gly Ser Asn Pro Asn Leu Ser
1               5                   10                  15

Val Leu Val Gln Ser Gln Arg Gly Pro Cys Ala Ala Ser Gln Pro Leu
            20                  25                  30

Glu Ala Phe Phe Leu Ser Gly Ser Ser Pro Ser Phe Leu Gly Ser Arg
        35                  40                  45

Ser Met Met Ser Phe Ala Asp Val His Gln Ala Asn Gly Ser Thr Arg
```

```
    50                  55                  60

Pro Phe Phe Arg Pro Tyr Asp His Glu Asp Asn Gly Asp Asp Asp Leu
65                  70                  75                  80

Asp Glu Tyr Phe His Gln Pro Glu Lys Lys Arg Arg Leu Thr Val Asp
                85                  90                  95

Gln Val Gln Phe Leu Glu Arg Ser Phe Glu Val Glu Asn Lys Leu Glu
            100                 105                 110

Pro Glu Arg Lys Ile Gln Leu Ala Lys Asp Leu Gly Leu Gln Pro Arg
        115                 120                 125

Gln Val Ala Ile Trp Phe Gln Asn Arg Arg Ala Arg Trp Lys Thr Lys
    130                 135                 140

Gln Leu Glu Lys Asp Tyr Glu Val Leu Gln Ser Ser Tyr Asn Gly Leu
145                 150                 155                 160

Lys Ala Asp Tyr Asp Asn Leu Phe Lys Glu Lys Glu Lys Leu Lys Ala
                165                 170                 175

Glu Val Asn Leu Leu Thr Asn Glu Leu Leu Leu Lys Glu Lys Glu Lys
            180                 185                 190

Gly Ser Ser Glu Leu Ser Asp Lys Asp Ala Leu Ser Gln Glu Pro Pro
        195                 200                 205

Lys Lys Ala Ile Ala Asp Ser Ala Ser Glu Gly Glu Val Ser Lys Thr
    210                 215                 220

Ser Thr Val Ala Cys Gln Gln Glu Asp Ile Ser Ser Ala Lys Ser Asp
225                 230                 235                 240

Met Phe Asp Ser Asp Ser Pro His Phe Ala Asp Gly Val His Ser Ser
                245                 250                 255

Leu Leu Glu Ala Gly Asp Ser Ser His Val Phe Glu Pro Asp Gln Ser
            260                 265                 270

Asp Leu Ser Gln Asp Glu Glu Asp Asn Leu Ser Lys Ser Leu Leu Pro
        275                 280                 285

Pro Tyr Val Phe Pro Lys Leu Glu Asp Gly Asp Tyr Ser Asp Pro Pro
    290                 295                 300

Ala Ser Phe Glu Asp His Ala Phe Trp Cys Trp Ser Tyr
305                 310                 315
```

<210> SEQ ID NO 44
<211> LENGTH: 909
<212> TYPE: DNA
<213> ORGANISM: Populus tremuloides

<400> SEQUENCE: 44

```
atggcgggtg ataaagactg tggcagttct aaaatgacca tttttcttcg aaacggcagg      60

ctccctcctt gtgaatctct ctgtattctc acctctttta gcactcttca tggtgcaaaa     120

tctatggtta attttaggaa tgatggagga gacactgtag acatgtcttt tttccaacca     180

catgtcaaag aagaaagtag cgatgaggat tatgatgcgc accttaagcc atctgaaaag     240

aaaaggcggc ttacagctgc tcaagtccag tttcttgaga agagctttga ggcggagaat     300

aagcttgaac cagagaggaa gatgcagctt gctaaagaac tcggcttgca gcctcgccag     360

gttgcaatat ggtttcaaaa ccgtagagct cggttcaaga acaagcagct ggaaagggac     420

tacgactcct tgagaatcag ctttgacaaa ctcaaggctg attatgacaa actcctcctc     480

gagaagcaga atttgaaaaa cgagcttctt tcactgaaag aaaaattgct tagcagagag     540

gaaagtatgg aaagttcaga accatttgat gtcatccatt caccggatgc agaacttgag     600

cctattcctg atacagtgtc tgaaaatgtt tccgccattg tgccaatggt gacacccaaa     660
```

caagaagaaa gttcagctaa aaatgatgtt ttcaactcag acagcccacg ttcatttttg 720
gagccccgtg attgttatcg tgttttcgag tcagaccaac cagatttttc ccaagttgaa 780
gaagataatc tcaccaggag ctttctaccc cctccgtact ttccaaaact ctaccgagag 840
ccacctgcaa gttcacgtaa ttttgaattc tcagcggaag atcagccctt ttggtcctgg 900
atttactga 909

<210> SEQ ID NO 45
<211> LENGTH: 302
<212> TYPE: PRT
<213> ORGANISM: Populus tremuloides

<400> SEQUENCE: 45

Met Ala Gly Asp Lys Asp Cys Gly Ser Ser Lys Met Thr Ile Phe Leu
1 5 10 15

Arg Asn Gly Arg Leu Pro Pro Cys Glu Ser Leu Cys Ile Leu Thr Ser
20 25 30

Phe Ser Thr Leu His Gly Ala Lys Ser Met Val Asn Phe Arg Asn Asp
35 40 45

Gly Gly Asp Thr Val Asp Met Ser Phe Phe Gln Pro His Val Lys Glu
50 55 60

Glu Ser Ser Asp Glu Asp Tyr Asp Ala His Leu Lys Pro Ser Glu Lys
65 70 75 80

Lys Arg Arg Leu Thr Ala Ala Gln Val Gln Phe Leu Glu Lys Ser Phe
85 90 95

Glu Ala Glu Asn Lys Leu Glu Pro Glu Arg Lys Met Gln Leu Ala Lys
100 105 110

Glu Leu Gly Leu Gln Pro Arg Gln Val Ala Ile Trp Phe Gln Asn Arg
115 120 125

Arg Ala Arg Phe Lys Asn Lys Gln Leu Glu Arg Asp Tyr Asp Ser Leu
130 135 140

Arg Ile Ser Phe Asp Lys Leu Lys Ala Asp Tyr Asp Lys Leu Leu Leu
145 150 155 160

Glu Lys Gln Asn Leu Lys Asn Glu Leu Leu Ser Leu Lys Glu Lys Leu
165 170 175

Leu Ser Arg Glu Glu Ser Met Glu Ser Ser Glu Pro Phe Asp Val Ile
180 185 190

His Ser Pro Asp Ala Glu Leu Glu Pro Ile Pro Asp Thr Val Ser Glu
195 200 205

Asn Val Ser Ala Ile Val Pro Met Val Thr Pro Lys Gln Glu Glu Ser
210 215 220

Ser Ala Lys Asn Asp Val Phe Asn Ser Asp Ser Pro Arg Ser Phe Leu
225 230 235 240

Glu Pro Arg Asp Cys Tyr Arg Val Phe Glu Ser Asp Gln Pro Asp Phe
245 250 255

Ser Gln Val Glu Glu Asp Asn Leu Thr Arg Ser Phe Leu Pro Pro Pro
260 265 270

Tyr Phe Pro Lys Leu Tyr Arg Glu Pro Pro Ala Ser Ser Arg Asn Phe
275 280 285

Glu Phe Ser Ala Glu Asp Gln Pro Phe Trp Ser Trp Ile Tyr
290 295 300

<210> SEQ ID NO 46
<211> LENGTH: 975

<212> TYPE: DNA
<213> ORGANISM: Medicago truncatula

<400> SEQUENCE: 46
atggcaggtg gcaagctttt tggtggttct aatatgtcac ttttgcttca aaatgaaaga 60
ctcccttgta cttctgaagt ccttgaatct ctttgggttc acacccctgc ttcttttcaa 120
ggttcaaatt cagtggttaa ttttgagaat ggtggtggta gcaacagagt ggtaacagat 180
agacccttct ttcaacaact tgagaaagaa gagaattgtg gtgatgaaga ttatgaagca 240
tgctaccatc aacaaggaaa gaaaaggagg ctttcaagtg aacaagttca atttcttgaa 300
aagagttttg aggtagaaaa caagcttgaa cctgatagga aagttcaact tgcaaaagag 360
cttggtttgc aaccaagaca agttgctata tggtttcaaa acagaagggc aaggttcaaa 420
actaaacagc ttgaaaaaga ttatggcaca ttgaaagcta gctttgatag tctcaaagat 480
gattatgata atcttcttca agagaatgac aagttaaaag aagaggtgaa ttctctcaag 540
aacaaattga tcccaagaga taaagaaaaa gtgaattcag aagacaaatc atcaccagaa 600
gcaatcaatt cacctcataa caacatagat ccaatggata taatttcaat tacaaattca 660
gaaaatgggt ccaaaatgtc actccctaat atggtactaa aatgtaagca agaagatgcc 720
aattcagcta aaagtgatgt gcttgattct gatagcccac attgcaatga tgggaacaat 780
ctttcttctt tcatagagcc tacagattca gatttctcac aagatgaaga ggataatgat 840
aacttgagtc ataatctttt gactcttcct tgcttaccaa aagttgaaga tgtttgctat 900
gatgacccac atgaaaattc ttgtaatttt gggttccctg ttgaagatca aacctttgt 960
ttctggcctt attga 975

<210> SEQ ID NO 47
<211> LENGTH: 324
<212> TYPE: PRT
<213> ORGANISM: Medicago truncatula

<400> SEQUENCE: 47

Met Ala Gly Gly Lys Leu Phe Gly Gly Ser Asn Met Ser Leu Leu Leu
1 5 10 15

Gln Asn Glu Arg Leu Pro Cys Thr Ser Glu Val Leu Glu Ser Leu Trp
20 25 30

Val His Thr Pro Ala Ser Phe Gln Gly Ser Asn Ser Val Val Asn Phe
35 40 45

Glu Asn Gly Gly Gly Ser Asn Arg Val Val Thr Asp Arg Pro Phe Phe
50 55 60

Gln Gln Leu Glu Lys Glu Glu Asn Cys Gly Asp Glu Asp Tyr Glu Ala
65 70 75 80

Cys Tyr His Gln Gln Gly Lys Lys Arg Arg Leu Ser Ser Glu Gln Val
85 90 95

Gln Phe Leu Glu Lys Ser Phe Glu Val Glu Asn Lys Leu Glu Pro Asp
100 105 110

Arg Lys Val Gln Leu Ala Lys Glu Leu Gly Leu Gln Pro Arg Gln Val
115 120 125

Ala Ile Trp Phe Gln Asn Arg Arg Ala Arg Phe Lys Thr Lys Gln Leu
130 135 140

Glu Lys Asp Tyr Gly Thr Leu Lys Ala Ser Phe Asp Ser Leu Lys Asp
145 150 155 160

Asp Tyr Asp Asn Leu Leu Gln Glu Asn Asp Lys Leu Lys Glu Glu Val
165 170 175

```
Asn Ser Leu Lys Asn Lys Leu Ile Pro Arg Asp Lys Glu Lys Val Asn
            180                 185                 190

Ser Glu Asp Lys Ser Ser Pro Glu Ala Ile Asn Ser Pro His Asn Asn
        195                 200                 205

Ile Asp Pro Met Asp Ile Ile Ser Ile Thr Asn Ser Glu Asn Gly Ser
    210                 215                 220

Lys Met Ser Leu Pro Asn Met Val Leu Lys Cys Lys Gln Glu Asp Ala
225                 230                 235                 240

Asn Ser Ala Lys Ser Asp Val Leu Asp Ser Asp Ser Pro His Cys Asn
                245                 250                 255

Asp Gly Asn Asn Leu Ser Ser Phe Ile Glu Pro Thr Asp Ser Asp Phe
            260                 265                 270

Ser Gln Asp Glu Glu Asp Asn Asp Asn Leu Ser His Asn Leu Leu Thr
        275                 280                 285

Leu Pro Cys Leu Pro Lys Val Glu Asp Val Cys Tyr Asp Asp Pro His
    290                 295                 300

Glu Asn Ser Cys Asn Phe Gly Phe Pro Val Glu Asp Gln Thr Phe Cys
305                 310                 315                 320

Phe Trp Pro Tyr
```

<210> SEQ ID NO 48
<211> LENGTH: 984
<212> TYPE: DNA
<213> ORGANISM: Phaseolus vulgaris

<400> SEQUENCE: 48

```
atggcgggtg gcaagcttca tcctggttca aacatgtcac ttctcctcca aaacgacagg     60

ctcccttgct cctctgaagt ccttgagtct ctttgggctc acacctctaa cgctgcttcc    120

ttccaaggtt caaaatctat ggttgatttt gagaatgtta gtgggggcag ggtgacggat    180

aggccctttt ttcaagcgtt ggagaaggaa gataactgtg atgatgatta tgagggttgc    240

ttccatcaac cgggtaagaa aaggaggctc acaagcgaac aagttcagtt ccttgaaagg    300

aactttgagg tcgagaacaa gcttgaacct gaaaggaagg tccaacttgc aaaggagctt    360

ggcttgcagc caaggcaagt ggctatatgg ttccaaaacc gaagggcaag gttcaagacc    420

aagcagctag aaaaagatta tggcacattg aaagctagct atgacagact caaaggtgac    480

tatgaaagtc ttcttcaaga gaatgacaag ttaaaagcag aggtgaattc tctggagagc    540

aaattgattc ttagagataa agagaaggag aattcggacg acaagtcatc tcctgatgct    600

gtcaattcac cccacaaaga gcctatggat ttaatttcaa attcaacatc tgaaaatggg    660

accaaagtgt cactccctat tatggtaaca tgcaagcaag aagatgccaa ttcagccaaa    720

agtgatgtgc ttgattcgga cagcccacat tgcactgatg ggaaccatcc ctcttcattc    780

gtggagcctg ctgattcctc ccatgctttt gaaccagacc actccgactt ctcccaagat    840

gaagaggata atcttagtga aagccttttg accctccctt gcttaccaaa ggttgaagaa    900

gcctgctatg atgaccctcc tgaaaaccct tgtaattttg gcttccatgt cgaggatcaa    960

accttctgtt tctggcccta ttga                                           984
```

<210> SEQ ID NO 49
<211> LENGTH: 327
<212> TYPE: PRT
<213> ORGANISM: Phaseolus vulgaris

<400> SEQUENCE: 49

-continued

```
Met Ala Gly Gly Lys Leu His Pro Gly Ser Asn Met Ser Leu Leu Leu
1               5                   10                  15

Gln Asn Asp Arg Leu Pro Cys Ser Ser Glu Val Leu Glu Ser Leu Trp
            20                  25                  30

Ala His Thr Ser Asn Ala Ala Ser Phe Gln Gly Ser Lys Ser Met Val
        35                  40                  45

Asp Phe Glu Asn Val Ser Gly Gly Arg Val Thr Asp Arg Pro Phe Phe
    50                  55                  60

Gln Ala Leu Glu Lys Glu Asp Asn Cys Asp Asp Asp Tyr Glu Gly Cys
65                  70                  75                  80

Phe His Gln Pro Gly Lys Lys Arg Arg Leu Thr Ser Glu Gln Val Gln
                85                  90                  95

Phe Leu Glu Arg Asn Phe Glu Val Glu Asn Lys Leu Glu Pro Glu Arg
            100                 105                 110

Lys Val Gln Leu Ala Lys Glu Leu Gly Leu Gln Pro Arg Gln Val Ala
        115                 120                 125

Ile Trp Phe Gln Asn Arg Arg Ala Arg Phe Lys Thr Lys Gln Leu Glu
    130                 135                 140

Lys Asp Tyr Gly Thr Leu Lys Ala Ser Tyr Asp Arg Leu Lys Gly Asp
145                 150                 155                 160

Tyr Glu Ser Leu Leu Gln Glu Asn Asp Lys Leu Lys Ala Glu Val Asn
                165                 170                 175

Ser Leu Glu Ser Lys Leu Ile Leu Arg Asp Lys Glu Lys Glu Asn Ser
            180                 185                 190

Asp Asp Lys Ser Ser Pro Asp Ala Val Asn Ser Pro His Lys Glu Pro
        195                 200                 205

Met Asp Leu Ile Ser Asn Ser Thr Ser Glu Asn Gly Thr Lys Val Ser
    210                 215                 220

Leu Pro Ile Met Val Thr Cys Lys Gln Glu Asp Ala Asn Ser Ala Lys
225                 230                 235                 240

Ser Asp Val Leu Asp Ser Asp Ser Pro His Cys Thr Asp Gly Asn His
                245                 250                 255

Pro Ser Ser Phe Val Glu Pro Ala Asp Ser Ser His Ala Phe Glu Pro
            260                 265                 270

Asp His Ser Asp Phe Ser Gln Asp Glu Glu Asp Asn Leu Ser Glu Ser
        275                 280                 285

Leu Leu Thr Leu Pro Cys Leu Pro Lys Val Glu Glu Ala Cys Tyr Asp
    290                 295                 300

Asp Pro Pro Glu Asn Pro Cys Asn Phe Gly Phe His Val Glu Asp Gln
305                 310                 315                 320

Thr Phe Cys Phe Trp Pro Tyr
                325

<210> SEQ ID NO 50
<211> LENGTH: 957
<212> TYPE: DNA
<213> ORGANISM: Lotus corniculatus

<400> SEQUENCE: 50

atggcgggag ggagggtctt tagcggcggt tctgctgctc ctgcaaatgt ttccgatacc      60

agtcttttgc ttcagaatca acctcctgat tcttctctct tcctctctac ctctgcttct     120

tttctcggtt caagatccat ggtgagcttc gcagataata aattagggca aacgcggtcg     180

ttcttctccg cgtttgacct cgatgagaac ggcgatgagg tcatggacga gtactttcac     240
```

-continued

```
caatcggaga agaagcgccg tctctctgtt gaccaagttc agtttctgga gaagagcttc      300

gaggtggata acaagctcga acctgacagg aaaaccaaga ttgccaagga ccttggtttg      360

cagccacgcc aagtcgcaat ctggttccag aaccgccgtg cacggtggaa gacgaaacag      420

cttgagaagg attatgattc tctgcatagt agctttgaga gtctcaaatc caactatgat      480

aatcttctca aggagaaaga catgttaaaa gctgaggtgg caagtctcac tgagaaggtg      540

cttgcaagag agaatttgaa acaagttgaa agtgaaacaa agggattggt tgaaccaccc      600

caaaggcctt tacttgattc agtttcagag ggtgaagaat ctaaagtctc tgttggggct      660

tgtaaacatg aggatatcag ttcagccagg agtgagagtt tggattctga tagcccacgt      720

tacagggatg gatatggagt taactcagca gtgctagaga catgtgattc ttcttatgtg      780

gttgaacctg atcaatcgga tatgtcacag gatgaggaag acaacctgac caagaccctg      840

ttgcctccat acatgttttc caaacttgga gatatggatt actccgaccc gcctgaaagt      900

tcatgtaatt tcggatttcc ggaggaagat catgcccttt ggtcatggtc ttactga        957
```

<210> SEQ ID NO 51
<211> LENGTH: 318
<212> TYPE: PRT
<213> ORGANISM: Lotus corniculatus

<400> SEQUENCE: 51

```
Met Ala Gly Gly Arg Val Phe Ser Gly Gly Ser Ala Ala Pro Ala Asn
1               5                   10                  15

Val Ser Asp Thr Ser Leu Leu Leu Gln Asn Gln Pro Pro Asp Ser Ser
            20                  25                  30

Leu Phe Leu Ser Thr Ser Ala Ser Phe Leu Gly Ser Arg Ser Met Val
        35                  40                  45

Ser Phe Ala Asp Asn Lys Leu Gly Gln Thr Arg Ser Phe Phe Ser Ala
    50                  55                  60

Phe Asp Leu Asp Glu Asn Gly Asp Glu Val Met Asp Glu Tyr Phe His
65                  70                  75                  80

Gln Ser Glu Lys Lys Arg Arg Leu Ser Val Asp Gln Val Gln Phe Leu
                85                  90                  95

Glu Lys Ser Phe Glu Val Asp Asn Lys Leu Glu Pro Asp Arg Lys Thr
            100                 105                 110

Lys Ile Ala Lys Asp Leu Gly Leu Gln Pro Arg Gln Val Ala Ile Trp
        115                 120                 125

Phe Gln Asn Arg Arg Ala Arg Trp Lys Thr Lys Gln Leu Glu Lys Asp
    130                 135                 140

Tyr Asp Ser Leu His Ser Ser Phe Glu Ser Leu Lys Ser Asn Tyr Asp
145                 150                 155                 160

Asn Leu Leu Lys Glu Lys Asp Met Leu Lys Ala Glu Val Ala Ser Leu
                165                 170                 175

Thr Glu Lys Val Leu Ala Arg Glu Asn Leu Lys Gln Val Glu Ser Glu
            180                 185                 190

Thr Lys Gly Leu Val Glu Pro Pro Gln Arg Pro Leu Leu Asp Ser Val
        195                 200                 205

Ser Glu Gly Glu Glu Ser Lys Val Ser Val Gly Ala Cys Lys His Glu
    210                 215                 220

Asp Ile Ser Ser Ala Arg Ser Glu Ser Leu Asp Ser Asp Ser Pro Arg
225                 230                 235                 240

Tyr Arg Asp Gly Tyr Gly Val Asn Ser Ala Val Leu Glu Thr Cys Asp
```

-continued

```
                245                 250                 255

Ser Ser Tyr Val Val Glu Pro Asp Gln Ser Asp Met Ser Gln Asp Glu
            260                 265                 270

Glu Asp Asn Leu Thr Lys Thr Leu Leu Pro Pro Tyr Met Phe Ser Lys
        275                 280                 285

Leu Gly Asp Met Asp Tyr Ser Asp Pro Pro Glu Ser Ser Cys Asn Phe
    290                 295                 300

Gly Phe Pro Glu Glu Asp His Ala Leu Trp Ser Trp Ser Tyr
305                 310                 315
```

<210> SEQ ID NO 52
<211> LENGTH: 1602
<212> TYPE: DNA
<213> ORGANISM: Oryza sativa

<400> SEQUENCE: 52

```
atggactcgt cgacggtggg cgctccgggg agctcgctgc acggcgtgac ggggcgcgag     60

ccggcgttcg cgttctcgac ggaggtgggc ggcgaggacg cggcggcggc gagcaagttc    120

gacttgccgg tggactcgga gcacaaggcg aagacgatca ggttgctgtc gttcgcgaac    180

ccgcatatga ggacgttcca cctatcatgg atctccttct tctcctgctt cgtctccacc    240

ttcgccgccg cccctctcgt ccccatcatc cgcgacaacc tcaacctcac caaggccgac    300

atcggcaacg ccggcgtcgc ctccgtctcc ggctccatct tctccaggct cgccatgggc    360

gccatctgcg acatgctcgg cccgcgctac ggctgcgcct tcctcatcat gctcgccgcg    420

cccaccgtct tctgcatgtc gctcatcgac tccgccgcgg ggtacatcgc cgtgcgcttc    480

ctcatcggct tctccctcgc caccttcgtg tcatgccagt actggatgag caccatgttc    540

aacagcaaga tcatcggcct cgtcaacggc ctcgccgccg ggtggggaaa catgggcggc    600

ggcgcgacgc agctcatcat gccgctcgtc tacgacgtga tccgcaagtg cggcgcgacg    660

ccgttcacgg cgtggaggct ggcctacttc gtgccgggga cgctgcacgt ggtgatgggc    720

gtgctggtgc tgacgctggg gcaggacctc cccgacggca acctgcgcag cctgcagaag    780

aagggtgacg tcaacaggga cagcttctcc agggtgctct ggtacgccgt caccaactac    840

cgcacctgga tcttcgtcct cctctacggc tactccatgg gcgtcgagct caccaccgac    900

aacgtcatcg ccgagtactt ctacgatcgc ttcgacctcg acctccgcgt cgccggcatc    960

atcgccgcat ccttcggcat ggccaacatc gtcgcgcgcc ccaccggcgg cctcctctcg   1020

gacctcggcg cgcgctactt cggcatgcgc gcccgcctct ggaacatttg gatcctccag   1080

accgccggcg gcgcgttctg cctcctgctc ggccgcgcat ccaccctccc cacctccgtc   1140

gtctgcatgg tcctcttctc cttctgcgcg caggccgcct gcggcgccat cttcggcgtc   1200

atccccttcg tctcccgccg ctcgctcggc atcatctccg gcatgaccgg cgccggcggc   1260

aacttcggcg ccgggctcac gcagctgctc ttcttcacgt cgtcgaggta ctccacgggc   1320

acggggctgg agtacatggg catcatgatc atggcgtgca cgctgccggt ggtgctcgtc   1380

catttcccgc agtggggctc catgttcctc ccgcccaacg ccggcgccga ggaggagcac   1440

tactacggct ccgagtggag cgaacaggag aagagcaagg gcctccacgg tgcaagtctc   1500

aagttcgccg agaactcccg ctccgagcgt ggccgccgca acgtcatcaa cgccgccgcc   1560

gccgccgcca cgccgcccaa caactcgccg gagcacgcct aa                      1602
```

<210> SEQ ID NO 53
<211> LENGTH: 533

<212> TYPE: PRT
<213> ORGANISM: Oryza sativa

<400> SEQUENCE: 53

```
Met Asp Ser Ser Thr Val Gly Ala Pro Gly Ser Ser Leu His Gly Val
1               5                   10                  15

Thr Gly Arg Glu Pro Ala Phe Ala Phe Ser Thr Glu Val Gly Gly Glu
            20                  25                  30

Asp Ala Ala Ala Ala Ser Lys Phe Asp Leu Pro Val Asp Ser Glu His
        35                  40                  45

Lys Ala Lys Thr Ile Arg Leu Leu Ser Phe Ala Asn Pro His Met Arg
    50                  55                  60

Thr Phe His Leu Ser Trp Ile Ser Phe Phe Ser Cys Phe Val Ser Thr
65                  70                  75                  80

Phe Ala Ala Ala Pro Leu Val Pro Ile Ile Arg Asp Asn Leu Asn Leu
                85                  90                  95

Thr Lys Ala Asp Ile Gly Asn Ala Gly Val Ala Ser Val Ser Gly Ser
            100                 105                 110

Ile Phe Ser Arg Leu Ala Met Gly Ala Ile Cys Asp Met Leu Gly Pro
        115                 120                 125

Arg Tyr Gly Cys Ala Phe Leu Ile Met Leu Ala Ala Pro Thr Val Phe
    130                 135                 140

Cys Met Ser Leu Ile Asp Ser Ala Ala Gly Tyr Ile Ala Val Arg Phe
145                 150                 155                 160

Leu Ile Gly Phe Ser Leu Ala Thr Phe Val Ser Cys Gln Tyr Trp Met
                165                 170                 175

Ser Thr Met Phe Asn Ser Lys Ile Ile Gly Leu Val Asn Gly Leu Ala
            180                 185                 190

Ala Gly Trp Gly Asn Met Gly Gly Gly Ala Thr Gln Leu Ile Met Pro
        195                 200                 205

Leu Val Tyr Asp Val Ile Arg Lys Cys Gly Ala Thr Pro Phe Thr Ala
    210                 215                 220

Trp Arg Leu Ala Tyr Phe Val Pro Gly Thr Leu His Val Val Met Gly
225                 230                 235                 240

Val Leu Val Leu Thr Leu Gly Gln Asp Leu Pro Asp Gly Asn Leu Arg
                245                 250                 255

Ser Leu Gln Lys Lys Gly Asp Val Asn Arg Asp Ser Phe Ser Arg Val
            260                 265                 270

Leu Trp Tyr Ala Val Thr Asn Tyr Arg Thr Trp Ile Phe Val Leu Leu
        275                 280                 285

Tyr Gly Tyr Ser Met Gly Val Glu Leu Thr Thr Asp Asn Val Ile Ala
    290                 295                 300

Glu Tyr Phe Tyr Asp Arg Phe Asp Leu Asp Leu Arg Val Ala Gly Ile
305                 310                 315                 320

Ile Ala Ala Ser Phe Gly Met Ala Asn Ile Val Ala Arg Pro Thr Gly
                325                 330                 335

Gly Leu Leu Ser Asp Leu Gly Ala Arg Tyr Phe Gly Met Arg Ala Arg
            340                 345                 350

Leu Trp Asn Ile Trp Ile Leu Gln Thr Ala Gly Gly Ala Phe Cys Leu
        355                 360                 365

Leu Leu Gly Arg Ala Ser Thr Leu Pro Thr Ser Val Val Cys Met Val
    370                 375                 380

Leu Phe Ser Phe Cys Ala Gln Ala Ala Cys Gly Ala Ile Phe Gly Val
385                 390                 395                 400
```

```
Ile Pro Phe Val Ser Arg Arg Ser Leu Gly Ile Ile Ser Gly Met Thr
                405                 410                 415

Gly Ala Gly Gly Asn Phe Gly Ala Gly Leu Thr Gln Leu Leu Phe Phe
            420                 425                 430

Thr Ser Ser Arg Tyr Ser Thr Gly Thr Gly Leu Glu Tyr Met Gly Ile
        435                 440                 445

Met Ile Met Ala Cys Thr Leu Pro Val Val Leu Val His Phe Pro Gln
    450                 455                 460

Trp Gly Ser Met Phe Leu Pro Pro Asn Ala Gly Ala Glu Glu Glu His
465                 470                 475                 480

Tyr Tyr Gly Ser Glu Trp Ser Glu Gln Glu Lys Ser Lys Gly Leu His
                485                 490                 495

Gly Ala Ser Leu Lys Phe Ala Glu Asn Ser Arg Ser Glu Arg Gly Arg
            500                 505                 510

Arg Asn Val Ile Asn Ala Ala Ala Ala Ala Ala Thr Pro Pro Asn Asn
        515                 520                 525

Ser Pro Glu His Ala
    530
```

<210> SEQ ID NO 54
<211> LENGTH: 53
<212> TYPE: DNA
<213> ORGANISM: Artificial sequence
<220> FEATURE:
<223> OTHER INFORMATION: primer: prm07061

<400> SEQUENCE: 54
ggggacaagt ttgtacaaaa aagcaggctt aaacaatgga ctcgtcgacg gtg 53

<210> SEQ ID NO 55
<211> LENGTH: 50
<212> TYPE: DNA
<213> ORGANISM: Artificial sequence
<220> FEATURE:
<223> OTHER INFORMATION: primer: prm07062

<400> SEQUENCE: 55
ggggaccact ttgtacaaga aagctgggtc tcggtcgcag aattgtttac 50

<210> SEQ ID NO 56
<211> LENGTH: 3848
<212> TYPE: DNA
<213> ORGANISM: Artificial sequence
<220> FEATURE:
<223> OTHER INFORMATION: expression cassette

<400> SEQUENCE: 56
aatccgaaaa gtttctgcac cgttttcacc ccctaactaa caatataggg aacgtgtgct 60
aaatataaaa tgagacctta tatatgtagc gctgataact agaactatgc aagaaaaact 120
catccaccta ctttagtggc aatcgggcta aataaaaaag agtcgctaca ctagtttcgt 180
tttccttagt aattaagtgg gaaaatgaaa tcattattgc ttagaatata cgttcacatc 240
tctgtcatga agttaaatta ttcgaggtag ccataattgt catcaaactc ttcttgaata 300
aaaaaatctt tctagctgaa ctcaatgggt aaagagagag attttttta aaaaaataga 360 atgaagatat tctgaacgta ttggcaaaga tttaaacata taattatata attttatagt 420
ttgtgcattc gtcatatcgc acatcattaa ggacatgtct tactccatcc caatttttat 480
ttagtaatta aagacaattg acttattttt attatttatc ttttttcgat tagatgcaag 540

```
gtacttacgc acacactttg tgctcatgtg catgtgtgag tgcacctcct caatacacgt    600
tcaactagca acacatctct aatatcactc gcctatttaa tacatttagg tagcaatatc    660
tgaattcaag cactccacca tcaccagacc acttttaata atatctaaaa tacaaaaaat    720
aattttacag aatagcatga aaagtatgaa acgaactatt taggtttttc acatacaaaa    780
aaaaaaagaa ttttgctcgt gcgcgagcgc caatctccca tattgggcac acaggcaaca    840
acagagtggc tgcccacaga acaacccaca aaaaacgatg atctaacgga ggacagcaag    900
tccgcaacaa ccttttaaca gcaggctttg cggccaggag agaggaggag aggcaaagaa    960
aaccaagcat cctcctcctc ccatctataa attcctcccc ccttttcccc tctctatata   1020
ggaggcatcc aagccaagaa gagggagagc accaaggaca cgcgactagc agaagccgag   1080
cgaccgcctt cttcgatcca tatcttccgg tcgagttctt ggtcgatctc ttccctcctc   1140
cacctcctcc tcacagggta tgtgcccttc ggttgttctt ggatttattg ttctaggttg   1200
tgtagtacgg gcgttgatgt taggaaaggg gatctgtatc tgtgatgatt cctgttcttg   1260
gatttgggat agaggggttc ttgatgttgc atgttatcgg ttcggtttga ttagtagtat   1320
ggttttcaat cgtctggaga gctctatgga aatgaaatgg tttagggtac ggaatcttgc   1380
gattttgtga gtacctttg tttgaggtaa aatcagagca ccggtgattt tgcttggtgt    1440
aataaaagta cggttgtttg gtcctcgatt ctggtagtga tgcttctcga tttgacgaag   1500
ctatcctttg tttattccct attgaacaaa aataatccaa ctttgaagac ggtcccgttg   1560
atgagattga atgattgatt cttaagcctg tccaaaattt cgcagctggc ttgtttagat   1620
acagtagtcc ccatcacgaa attcatggaa acagttataa tcctcaggaa caggggattc   1680
cctgttcttc cgatttgctt tagtcccaga atttttttc ccaaatatct taaaaagtca    1740
ctttctggtt cagttcaatg aattgattgc tacaaataat gcttttatag cgttatccta   1800
gctgtagttc agttaatagg taatacccct atagtttagt caggagaaga acttatccga   1860
tttctgatct ccatttttaa ttatatgaaa tgaactgtag cataagcagt attcatttgg   1920
attatttttt ttattagctc tcaccccttc attattctga gctgaaagtc tggcatgaac   1980
tgtcctcaat tttgttttca aattcacatc gattatctat gcattatcct cttgtatcta   2040
cctgtagaag tttctttttg gttattcctt gactgcttga ttacagaaag aaatttatga   2100
agctgtaatc gggatagtta tactgcttgt tcttatgatt catttccttt gtgcagttct   2160
tggtgtagct tgccactttc accagcaaag ttcatttaaa tcaactaggg atatcacaag   2220
tttgtacaaa aaagcaggct taaacaatgg actcgtcgac ggtgggcgct ccggggagct   2280
cgctgcacgg cgtgacgggg cgcgagccgg cgttcgcgtt ctcgacggag gtgggcggcg   2340
aggacgcggc ggcggcgagc aagttcgact tgccggtgga ctcggagcac aaggcgaaga   2400
cgatcaggtt gctgtcgttc gcgaacccgc atatgaggac gttccaccta tcatggatct   2460
ccttcttctc ctgcttcgtc tccaccttcg ccgccgcccc tctcgtcccc atcatccgcg   2520
acaacctcaa cctcaccaag gccgacatcg gcaacgccgg cgtcgcctcc gtctccggct   2580
ccatcttctc caggctcgcc atgggcgcca tctgcgacat gctcggcccg cgctacggct   2640
gcgccttcct catcatgctc gccgcgccca ccgtcttctg catgtcgctc atcgactccg   2700
ccgcggggta catcgccgtg cgcttcctca tcggcttctc cctcgccacc ttcgtgtcat   2760
gccagtactg gatgagcacc atgttcaaca gcaagatcat cggcctcgtc aacggcctcg   2820
ccgccgggtg gggaaacatg ggcggcggcg cgacgcagct catcatgccg ctcgtctacg   2880
```

-continued

```
acgtgatccg caagtgcggc gcgacgccgt tcacggcgtg gaggctggcc tacttcgtgc   2940

cggggacgct gcacgtggtg atgggcgtgc tggtgctgac gctggggcag gacctccccg   3000

acggcaacct gcgcagcctg cagaagaagg gtgacgtcaa cagggacagc ttctccaggg   3060

tgctctggta cgccgtcacc aactaccgca cctggatctt cgtcctcctc tacggctact   3120

ccatgggcgt cgagctcacc accgacaacg tcatcgccga gtacttctac gatcgcttcg   3180

acctcgacct ccgcgtcgcc ggcatcatcg ccgcatcctt cggcatggcc aacatcgtcg   3240

cgcgccccac cggcggcctc ctctcggacc tcggcgcgcg ctacttcggc atgcgcgccc   3300

gcctctggaa catttggatc ctccagaccg ccggcggcgc gttctgcctc ctgctcggcc   3360

gcgcatccac cctccccacc tccgtcgtct gcatggtcct cttctccttc tgcgcgcagg   3420

ccgcctgcgg cgccatcttc ggcgtcatcc ccttcgtctc ccgccgctcg ctcggcatca   3480

tctccggcat gaccggcgcc ggcggcaact tcggcgccgg gctcacgcag ctgctcttct   3540

tcacgtcgtc gaggtactcc acgggcacgg ggctggagta catgggcatc atgatcatgg   3600

cgtgcacgct gccggtggtg ctcgtccatt tcccgcagtg gggctccatg ttcctcccgc   3660

ccaacgccgg cgccgaggag gagcactact acggctccga gtggagcgaa caggagaaga   3720

gcaagggcct ccacggtgca agtctcaagt tcgccgagaa ctcccgctcc gagcgtggcc   3780

gccgcaacgt catcaacgcc gccgccgccg ccgccacgcc gcccaacaac tcgccggagc   3840

acgcctaa                                                            3848
```

<210> SEQ ID NO 57
<211> LENGTH: 27
<212> TYPE: PRT
<213> ORGANISM: Artificial sequence
<220> FEATURE:
<223> OTHER INFORMATION: signature sequence 1
<220> FEATURE:
<221> NAME/KEY: VARIANT
<222> LOCATION: (1)..(1)
<223> OTHER INFORMATION: /replace=“Ser”
<220> FEATURE:
<221> NAME/KEY: VARIANT
<222> LOCATION: (2)..(2)
<223> OTHER INFORMATION: /replace=“Pro”
<220> FEATURE:
<221> NAME/KEY: VARIANT
<222> LOCATION: (3)..(3)
<223> OTHER INFORMATION: /replace=“Gly” /replace=“Ser” /replace=“Ala
<220> FEATURE:
<221> NAME/KEY: VARIANT
<222> LOCATION: (5)..(5)
<223> OTHER INFORMATION: /replace=”Val“ /replace=”Leu“
<220> FEATURE:
<221> NAME/KEY: VARIANT
<222> LOCATION: (6)..(6)
<223> OTHER INFORMATION: /replace=”Leu“ /replace=”Thr“
<220> FEATURE:
<221> NAME/KEY: VARIANT
<222> LOCATION: (7)..(7)
<223> OTHER INFORMATION: /replace=”Ala“ /replace=”Phe“ /replace=”Leu“
<220> FEATURE:
<221> NAME/KEY: VARIANT
<222> LOCATION: (8)..(8)
<223> OTHER INFORMATION: /replace=”Val“ /replace=”Met“ /replace=”Ile“
<220> FEATURE:
<221> NAME/KEY: VARIANT
<222> LOCATION: (9)..(9)
<223> OTHER INFORMATION: /replace=”Thr“ /replace=”Ile“ /replace=”Ala“
/replace=”Asn“
<220> FEATURE:
<221> NAME/KEY: VARIANT
<222> LOCATION: (12)..(12)
<223> OTHER INFORMATION: /replace=”Phe“
<220> FEATURE:

-continued

<221> NAME/KEY: VARIANT
<222> LOCATION: (13)..(13)
<223> OTHER INFORMATION: /replace="Cys" /replace="Thr"
<220> FEATURE:
<221> NAME/KEY: VARIANT
<222> LOCATION: (14)..(14)
<223> OTHER INFORMATION: /replace="Phe" /replace="Tyr"
<220> FEATURE:
<221> NAME/KEY: VARIANT
<222> LOCATION: (16)..(16)
<223> OTHER INFORMATION: /replace="Ile"
<220> FEATURE:
<221> NAME/KEY: VARIANT
<222> LOCATION: (19)..(19)
<223> OTHER INFORMATION: /replace="Ser"
<220> FEATURE:
<221> NAME/KEY: VARIANT
<222> LOCATION: (20)..(20)
<223> OTHER INFORMATION: /replace="Ile" /replace="Val"
<220> FEATURE:
<221> NAME/KEY: VARIANT
<222> LOCATION: (21)..(21)
<223> OTHER INFORMATION: /replace="Gly" /replace="Asn"
<220> FEATURE:
<221> NAME/KEY: VARIANT
<222> LOCATION: (23)..(23)
<223> OTHER INFORMATION: /replace="Ile" /replace="Asn"
<220> FEATURE:
<221> NAME/KEY: VARIANT
<222> LOCATION: (24)..(24)
<223> OTHER INFORMATION: /replace="Val"
<220> FEATURE:
<221> NAME/KEY: VARIANT
<222> LOCATION: (25)..(25)
<223> OTHER INFORMATION: /replace="Ser" /replace="His" /replace="Val"
<220> FEATURE:
<221> NAME/KEY: VARIANT
<222> LOCATION: (26)..(26)
<223> OTHER INFORMATION: /replace="Gln" /replace="Gly"

<400> SEQUENCE: 57

```
Asn Tyr Thr Trp Ile Phe Val Leu Leu Tyr Gly Tyr Ser Met Gly Val
1               5                   10                  15

Glu Leu Thr Thr Asp Asn Val Ile Ala Glu Tyr
            20                  25
```

<210> SEQ ID NO 58
<211> LENGTH: 10
<212> TYPE: PRT
<213> ORGANISM: Artificial sequence
<220> FEATURE:
<223> OTHER INFORMATION: signature sequence 2
<220> FEATURE:
<221> NAME/KEY: VARIANT
<222> LOCATION: (3)..(3)
<223> OTHER INFORMATION: /replace="Ala"
<220> FEATURE:
<221> NAME/KEY: VARIANT
<222> LOCATION: (7)..(7)
<223> OTHER INFORMATION: /replace="Thr"
<220> FEATURE:
<221> NAME/KEY: VARIANT
<222> LOCATION: (10)..(10)
<223> OTHER INFORMATION: /replace="Ser"

<400> SEQUENCE: 58

```
Leu Gly Pro Arg Tyr Gly Cys Ala Phe Leu
1               5                   10
```

<210> SEQ ID NO 59
<211> LENGTH: 18
<212> TYPE: PRT
<213> ORGANISM: Artificial sequence
<220> FEATURE:

<223> OTHER INFORMATION: signature sequence 3
<220> FEATURE:
<221> NAME/KEY: VARIANT
<222> LOCATION: (6)..(6)
<223> OTHER INFORMATION: /replace="Arg"
<220> FEATURE:
<221> NAME/KEY: VARIANT
<222> LOCATION: (9)..(9)
<223> OTHER INFORMATION: /replace="Ile"
<220> FEATURE:
<221> NAME/KEY: VARIANT
<222> LOCATION: (10)..(10)
<223> OTHER INFORMATION: /replace="Val"
<220> FEATURE:
<221> NAME/KEY: VARIANT
<222> LOCATION: (11)..(11)
<223> OTHER INFORMATION: /replace="Leu" /replace="Val"
<220> FEATURE:
<221> NAME/KEY: VARIANT
<222> LOCATION: (14)..(14)
<223> OTHER INFORMATION: /replace="Glu"
<220> FEATURE:
<221> NAME/KEY: VARIANT
<222> LOCATION: (17)..(17)
<223> OTHER INFORMATION: /replace="Asp"
<220> FEATURE:
<221> NAME/KEY: VARIANT
<222> LOCATION: (18)..(18)
<223> OTHER INFORMATION: /replace="Pro"

<400> SEQUENCE: 59

```
Ser Thr Phe Ala Ala Ala Pro Leu Val Pro Ile Ile Arg Asp Asn Leu
1               5                   10                  15

Asn Leu
```

<210> SEQ ID NO 60
<211> LENGTH: 10
<212> TYPE: PRT
<213> ORGANISM: Artificial sequence
<220> FEATURE:
<223> OTHER INFORMATION: signature sequence 4
<220> FEATURE:
<221> NAME/KEY: VARIANT
<222> LOCATION: (4)..(4)
<223> OTHER INFORMATION: /replace="Met"
<220> FEATURE:
<221> NAME/KEY: VARIANT
<222> LOCATION: (8)..(8)
<223> OTHER INFORMATION: /replace="Cys"

<400> SEQUENCE: 60

```
Val Arg Phe Leu Ile Gly Phe Ser Leu Ala
1               5                   10
```

<210> SEQ ID NO 61
<211> LENGTH: 12
<212> TYPE: PRT
<213> ORGANISM: Artificial sequence
<220> FEATURE:
<223> OTHER INFORMATION: signature sequence 5
<220> FEATURE:
<221> NAME/KEY: VARIANT
<222> LOCATION: (5)..(5)
<223> OTHER INFORMATION: /replace="Arg"
<220> FEATURE:
<221> NAME/KEY: VARIANT
<222> LOCATION: (8)..(8)
<223> OTHER INFORMATION: /replace="Thr"
<220> FEATURE:
<221> NAME/KEY: VARIANT
<222> LOCATION: (10)..(10)
<223> OTHER INFORMATION: /replace="Val"
<220> FEATURE:
<221> NAME/KEY: VARIANT
<222> LOCATION: (11)..(11)
<223> OTHER INFORMATION: /replace="Ser"
<220> FEATURE:
<221> NAME/KEY: VARIANT
<222> LOCATION: (12)..(12)
<223> OTHER INFORMATION: /replace="Ser"

<400> SEQUENCE: 61

Phe Val Ser Cys Gln Tyr Trp Met Ser Thr Met Phe
1 5 10

<210> SEQ ID NO 62
<211> LENGTH: 20
<212> TYPE: PRT
<213> ORGANISM: Artificial sequence
<220> FEATURE:
<223> OTHER INFORMATION: signature sequence 6
<220> FEATURE:
<221> NAME/KEY: VARIANT
<222> LOCATION: (2)..(2)
<223> OTHER INFORMATION: /replace="Gln" /replace="Ser" /replace="Met" /replace="His" /replace="Thr"
<220> FEATURE:
<221> NAME/KEY: VARIANT
<222> LOCATION: (4)..(4)
<223> OTHER INFORMATION: /replace="Val"
<220> FEATURE:
<221> NAME/KEY: VARIANT
<222> LOCATION: (13)..(13)
<223> OTHER INFORMATION: /replace="Thr"
<220> FEATURE:
<221> NAME/KEY: VARIANT
<222> LOCATION: (15)..(15)
<223> OTHER INFORMATION: /replace="Ala"
<220> FEATURE:
<221> NAME/KEY: VARIANT
<222> LOCATION: (17)..(17)
<223> OTHER INFORMATION: /replace="Leu"
<220> FEATURE:
<221> NAME/KEY: VARIANT
<222> LOCATION: (20)..(20)
<223> OTHER INFORMATION: /replace="Gly"

<400> SEQUENCE: 62

Lys Ala Asp Ile Gly Asn Ala Gly Val Ala Ser Val Ser Gly Ser Ile
1 5 10 15

Phe Ser Arg Leu
20

<210> SEQ ID NO 63
<211> LENGTH: 8
<212> TYPE: PRT
<213> ORGANISM: Artificial sequence
<220> FEATURE:
<223> OTHER INFORMATION: signature sequence 7
<220> FEATURE:
<221> NAME/KEY: VARIANT
<222> LOCATION: (3)..(3)
<223> OTHER INFORMATION: /replace="Thr" /replace="Cys"
<220> FEATURE:
<221> NAME/KEY: VARIANT
<222> LOCATION: (5)..(5)
<223> OTHER INFORMATION: /replace="Gly"

<400> SEQUENCE: 63

Asn Gly Leu Ala Ala Gly Trp Gly
1 5

<210> SEQ ID NO 64
<211> LENGTH: 13
<212> TYPE: PRT
<213> ORGANISM: Artificial sequence
<220> FEATURE:
<223> OTHER INFORMATION: signature sequence 8
<220> FEATURE:
<221> NAME/KEY: VARIANT
<222> LOCATION: (2)..(2)
<223> OTHER INFORMATION: /replace="Ser"
<220> FEATURE:
<221> NAME/KEY: VARIANT
<222> LOCATION: (4)..(4)
<223> OTHER INFORMATION: /replace="Val" /replace="Gln"
<220> FEATURE:
<221> NAME/KEY: VARIANT
<222> LOCATION: (7)..(7)
<223> OTHER INFORMATION: /replace="Pro"
<220> FEATURE:
<221> NAME/KEY: VARIANT
<222> LOCATION: (8)..(8)
<223> OTHER INFORMATION: /replace="Val" /replace="Ile"
<220> FEATURE:
<221> NAME/KEY: VARIANT
<222> LOCATION: (9)..(9)
<223> OTHER INFORMATION: /replace="Glu"
<220> FEATURE:
<221> NAME/KEY: VARIANT
<222> LOCATION: (11)..(11)
<223> OTHER INFORMATION: /replace="Ser" /replace="Asp"
<220> FEATURE:
<221> NAME/KEY: VARIANT
<222> LOCATION: (12)..(12)
<223> OTHER INFORMATION: /replace="Thr"
<220> FEATURE:
<221> NAME/KEY: VARIANT
<222> LOCATION: (13)..(13)
<223> OTHER INFORMATION: /replace="Ala" /replace="Thr"

<400> SEQUENCE: 64

Gly Ala Gly Leu Thr Gln Leu Leu Phe Phe Thr Ser Ser
1 5 10

<210> SEQ ID NO 65
<211> LENGTH: 1858
<212> TYPE: DNA
<213> ORGANISM: Phragmites australis

<400> SEQUENCE: 65
acaacagctc agatcaagca cctgcatttg cataagagct agcaagcaag caagtccaag 60
aaagaagcta gctagcttgt atcagatcaa gactcgagag gccagctatg gaggttggcg 120
cgccggggag ctcgctgcac ggcgtcacgg ggcgcgagcc ggcgttcgcc ttctcgacgt 180
ctgcggtgcc cgacgacgat gcagcgagca agttcgacct gccggtggac tcggagcaca 240
aggccaagag catccggctc ttctccttcg ccaacccgca catgcgcacc ttccatctct 300
cgtggatctc cttcttcacc tgcttcgtct ccaccttcgc cgccgcgccg ctcgtcccca 360
tcatccgcga caacctcaac ctcaccaagg ccgacatcgg caacgccggc gtggcctccg 420
tctcgggatc catcttctcc cgtctcgcca tgggcgccat ctgcgacctc ctcggcccgc 480
gctacggctg cgccttcctc atcatgctca cggcgcccac cgtcttctgc atgtccctca 540
tcgacgacgc agccggctac atcgtcgtca ggttcttgat cggcttctct ctggccacgt 600
tcgtgtcgtg ccagtactgg atgagcacca tgttcaatag caagatcatc gggacggtga 660
acgggctggc ggctgggtgg gggaacatgg gcggcggcgc cacgcagctc cccatgccgc 720
tcgtctacga cgtcatccgc aagtgcggcg cgacgccctt cacggcgtgg cgcatcgcct 780
acttcgtgcc ggggctaatg cacgtggtga tgggcatcct ggtgctcacg ctggggcagg 840
acctccccga cggcaacctg aggagcctcc agaagaaggg cgacgccaac aaggacaagt 900
tctccaaggt gctctggtac gccgtcacca actatcgcac ctggatcttc gtgctgctct 960

-continued acggctactg catgggcgtg gagctgacca ccgacaacgt catcgccgag tactactacg 1020
accacttcga cctagacctc cgcgtcgccg gcatcatcgc cgcttgcttc ggaatggcca 1080
acatcgtggc acggcccttg ggcggcatcc tctccgacat cggcgcgcgc tactggggca 1140
tgcgcgcgcg cctctggaac atctggatcc tccagactgc tggcggcgcc ttctgcctct 1200
ggctcggccg cgccagcacg cttcctgcct ccattaccgc catggtgctc ttctccttct 1260
gcgcccaggc cgcctgcggc gccattttcg gcgtcacccc tttcgtcacc cgccgctccc 1320
tcggcatcat gtccgggatg acgggggctg gcggcaactt cggcgcgggg ctcacgcagc 1380
tgctcttctt cacctcgtcc aagtactcca cgggcatggg gctggagtac atgggcatca 1440
tgatcatggc gtgcacgctg cccgtggtgt tcgtgcactt cccgcaatgg ggatccatgc 1500
tcctcccgcc cagcgccggc gccgtcgagg agcactacta cagctcggag tggagtgagg 1560
aggagaagag caaggggctc cacagctcca gcctcaagtt ttcagagaac tgccgttcag 1620
agcgcggcaa ccgcaacgtc atcctcgcgg caccaaacag cacgcccgag cacgtataag 1680
acgcacgtat atgtccgcat tcgtacccct gtgcgcgtat acgcatacgc cagcggtttg 1740
tttaataagg tgcgcatata tatatatgta actagctata atgcgtatca ccgttatgcg 1800
cacgcacacg aaatatatat aattcgatgt tgacgcatat acaaaaaaaa aaaaaaa 1858

<210> SEQ ID NO 66
<211> LENGTH: 523
<212> TYPE: PRT
<213> ORGANISM: Phragmites australis

<400> SEQUENCE: 66

Met Glu Val Gly Ala Pro Gly Ser Ser Leu His Gly Val Thr Gly Arg
1 5 10 15

Glu Pro Ala Phe Ala Phe Ser Thr Ser Ala Val Pro Asp Asp Asp Ala
20 25 30

Ala Ser Lys Phe Asp Leu Pro Val Asp Ser Glu His Lys Ala Lys Ser
35 40 45

Ile Arg Leu Phe Ser Phe Ala Asn Pro His Met Arg Thr Phe His Leu
50 55 60

Ser Trp Ile Ser Phe Phe Thr Cys Phe Val Ser Thr Phe Ala Ala Ala
65 70 75 80

Pro Leu Val Pro Ile Ile Arg Asp Asn Leu Asn Leu Thr Lys Ala Asp
85 90 95

Ile Gly Asn Ala Gly Val Ala Ser Val Ser Gly Ser Ile Phe Ser Arg
100 105 110

Leu Ala Met Gly Ala Ile Cys Asp Leu Leu Gly Pro Arg Tyr Gly Cys
115 120 125

Ala Phe Leu Ile Met Leu Thr Ala Pro Thr Val Phe Cys Met Ser Leu
130 135 140

Ile Asp Asp Ala Ala Gly Tyr Ile Val Val Arg Phe Leu Ile Gly Phe
145 150 155 160

Ser Leu Ala Thr Phe Val Ser Cys Gln Tyr Trp Met Ser Thr Met Phe
165 170 175

Asn Ser Lys Ile Ile Gly Thr Val Asn Gly Leu Ala Ala Gly Trp Gly
180 185 190

Asn Met Gly Gly Gly Ala Thr Gln Leu Pro Met Pro Leu Val Tyr Asp
195 200 205

Val Ile Arg Lys Cys Gly Ala Thr Pro Phe Thr Ala Trp Arg Ile Ala

-continued

```
    210                 215                 220

Tyr Phe Val Pro Gly Leu Met His Val Val Met Gly Ile Leu Val Leu
225                 230                 235                 240

Thr Leu Gly Gln Asp Leu Pro Asp Gly Asn Leu Arg Ser Leu Gln Lys
                245                 250                 255

Lys Gly Asp Ala Asn Lys Asp Lys Phe Ser Lys Val Leu Trp Tyr Ala
            260                 265                 270

Val Thr Asn Tyr Arg Thr Trp Ile Phe Val Leu Leu Tyr Gly Tyr Cys
        275                 280                 285

Met Gly Val Glu Leu Thr Thr Asp Asn Val Ile Ala Glu Tyr Tyr Tyr
    290                 295                 300

Asp His Phe Asp Leu Asp Leu Arg Val Ala Gly Ile Ile Ala Ala Cys
305                 310                 315                 320

Phe Gly Met Ala Asn Ile Val Ala Arg Pro Leu Gly Gly Ile Leu Ser
                325                 330                 335

Asp Ile Gly Ala Arg Tyr Trp Gly Met Arg Ala Arg Leu Trp Asn Ile
            340                 345                 350

Trp Ile Leu Gln Thr Ala Gly Gly Ala Phe Cys Leu Trp Leu Gly Arg
        355                 360                 365

Ala Ser Thr Leu Pro Ala Ser Ile Thr Ala Met Val Leu Phe Ser Phe
    370                 375                 380

Cys Ala Gln Ala Ala Cys Gly Ala Ile Phe Gly Val Thr Pro Phe Val
385                 390                 395                 400

Thr Arg Arg Ser Leu Gly Ile Met Ser Gly Met Thr Gly Ala Gly Gly
                405                 410                 415

Asn Phe Gly Ala Gly Leu Thr Gln Leu Leu Phe Phe Thr Ser Ser Lys
            420                 425                 430

Tyr Ser Thr Gly Met Gly Leu Glu Tyr Met Gly Ile Met Ile Met Ala
        435                 440                 445

Cys Thr Leu Pro Val Val Phe Val His Phe Pro Gln Trp Gly Ser Met
    450                 455                 460

Leu Leu Pro Pro Ser Ala Gly Ala Val Glu Glu His Tyr Tyr Ser Ser
465                 470                 475                 480

Glu Trp Ser Glu Glu Glu Lys Ser Lys Gly Leu His Ser Ser Ser Leu
                485                 490                 495

Lys Phe Ser Glu Asn Cys Arg Ser Glu Arg Gly Asn Arg Asn Val Ile
            500                 505                 510

Leu Ala Ala Pro Asn Ser Thr Pro Glu His Val
        515                 520
```

<210> SEQ ID NO 67
<211> LENGTH: 1691
<212> TYPE: DNA
<213> ORGANISM: Zea mays

<400> SEQUENCE: 67

```
ccaagggaaa gggatacatc acctgctgct ctagctctgc tatagcgcta gcagcaatat      60

aatggcggcc gtcggcgctc cggggagctc tctgcacgga gtcacggggc gcgagccggc     120

gttcgcattc tccacggagc acgaggaggc ggcgagcaat ggcggcaagt tcgacctgcc     180

ggtggactcg gagcacaagg cgaagagcgt ccggctcttc tccgtggcga acccgcacat     240

gcgcaccttc cacctctcct ggatctcctt cttcacctgc ttcgtgtcca ccttcgccgc     300

cgcgccgctg gtccccatca tccgcgacaa cctcaacctc accaaggccg acatcggcaa     360
```

```
cgcgggcgtg gcctccgtgt cgggctccat cttctcccgc ctcaccatgg gcgccgtctg    420

cgacctgctg ggcccgcgct acggctgcgc cttcctcatc atgctgtccg cgcccaccgt    480

gttctgcatg tcgctcatcg acgacgccgc gggctacatc accgtcaggt tcctcatcgg    540

cttctccctc gccaccttcg tctcctgcca gtactggatg agcaccatgt tcagcagcaa    600

gatcatcggc accgtcaacg ggctcgccgc cggatggggc aacatgggag gcggcgccac    660

gcagctcatc atgccgctcg tctacgacgt catccgcaag tgcggcgcca cgcccttcac    720

ggcgtggcgc ctcgcctact tcgtgccggg cctcatgcac gtcgtcatgg gcgtcctggt    780

gctcacgctg gggcaggacc tccccgacgg caacctcagg tcgctgcaga agaagggcaa    840

cgtcaacaag gacagcttct ccaaggtcat gtggtacgcc gtcatcaact accgcacctg    900

gatcttcgtc ctcctctacg gctactgcat gggcgtcgag ctcaccaccg acaacgtcat    960

cgccgagtac atgtacgacc gcttcgacct cgacctccgc gtcgccggga ccatcgccgc   1020

ctgcttcggc atggccaaca tcgtcgcgcg ccccatgggc ggcatcatgt ccgacatggg   1080

cgcgcgctac tggggcatgc gcgctcgcct ctggaacatc tggatcctcc agaccgccgg   1140

cggcgccttc tgcctctggc tgggacgcgc cagcaccctc cccgtctccg tcgtcgccat   1200

ggtgctcttc tccttctgcg cgcaggcggc ctgcggcgcc atcttcgggg tcatcccctt   1260

cgtctcccgc cgctccctcg gcatcatctc cggcatgacg ggcgccggcg gcaacttcgg   1320

cgcggggctc acgcagctgc tcttcttcac ctcctcaacc tactccacgg gcagggggct   1380

agagtacatg ggcatcatga tcatggcgtg cacgctacct gtggtgttcg tgcacttccc   1440

gcagtggggg tccatgttct tcccgcccag cgccaccgcc gacgaggagg gctactacgc   1500

ctccgagtgg aacgacgacg agaagagcaa gggactccat agcgccagcc tcaagtttgc   1560

cgagaacagc cgctcagagc gcggcaagcg aaacgtcatc caggccgatg ccgccgccac   1620

gccggagcat gtctaagtct actactaata agatggatcg atccatcatc catgttcacc   1680

tgctacctac c                                                        1691
```

<210> SEQ ID NO 68
<211> LENGTH: 524
<212> TYPE: PRT
<213> ORGANISM: Zea mays

<400> SEQUENCE: 68

```
Met Ala Ala Val Gly Ala Pro Gly Ser Ser Leu His Gly Val Thr Gly
1               5                   10                  15

Arg Glu Pro Ala Phe Ala Phe Ser Thr Glu His Glu Glu Ala Ala Ser
            20                  25                  30

Asn Gly Gly Lys Phe Asp Leu Pro Val Asp Ser Glu His Lys Ala Lys
        35                  40                  45

Ser Val Arg Leu Phe Ser Val Ala Asn Pro His Met Arg Thr Phe His
    50                  55                  60

Leu Ser Trp Ile Ser Phe Phe Thr Cys Phe Val Ser Thr Phe Ala Ala
65                  70                  75                  80

Ala Pro Leu Val Pro Ile Ile Arg Asp Asn Leu Asn Leu Thr Lys Ala
                85                  90                  95

Asp Ile Gly Asn Ala Gly Val Ala Ser Val Ser Gly Ser Ile Phe Ser
            100                 105                 110

Arg Leu Thr Met Gly Ala Val Cys Asp Leu Leu Gly Pro Arg Tyr Gly
        115                 120                 125

Cys Ala Phe Leu Ile Met Leu Ser Ala Pro Thr Val Phe Cys Met Ser
```

```
    130                 135                 140

Leu Ile Asp Asp Ala Ala Gly Tyr Ile Thr Val Arg Phe Leu Ile Gly
145                 150                 155                 160

Phe Ser Leu Ala Thr Phe Val Ser Cys Gln Tyr Trp Met Ser Thr Met
                165                 170                 175

Phe Ser Ser Lys Ile Ile Gly Thr Val Asn Gly Leu Ala Ala Gly Trp
            180                 185                 190

Gly Asn Met Gly Gly Gly Ala Thr Gln Leu Ile Met Pro Leu Val Tyr
        195                 200                 205

Asp Val Ile Arg Lys Cys Gly Ala Thr Pro Phe Thr Ala Trp Arg Leu
    210                 215                 220

Ala Tyr Phe Val Pro Gly Leu Met His Val Val Met Gly Val Leu Val
225                 230                 235                 240

Leu Thr Leu Gly Gln Asp Leu Pro Asp Gly Asn Leu Arg Ser Leu Gln
                245                 250                 255

Lys Lys Gly Asn Val Asn Lys Asp Ser Phe Ser Lys Val Met Trp Tyr
            260                 265                 270

Ala Val Ile Asn Tyr Arg Thr Trp Ile Phe Val Leu Leu Tyr Gly Tyr
        275                 280                 285

Cys Met Gly Val Glu Leu Thr Thr Asp Asn Val Ile Ala Glu Tyr Met
    290                 295                 300

Tyr Asp Arg Phe Asp Leu Asp Leu Arg Val Ala Gly Thr Ile Ala Ala
305                 310                 315                 320

Cys Phe Gly Met Ala Asn Ile Val Ala Arg Pro Met Gly Gly Ile Met
                325                 330                 335

Ser Asp Met Gly Ala Arg Tyr Trp Gly Met Arg Ala Arg Leu Trp Asn
            340                 345                 350

Ile Trp Ile Leu Gln Thr Ala Gly Gly Ala Phe Cys Leu Trp Leu Gly
        355                 360                 365

Arg Ala Ser Thr Leu Pro Val Ser Val Val Ala Met Val Leu Phe Ser
    370                 375                 380

Phe Cys Ala Gln Ala Ala Cys Gly Ala Ile Phe Gly Val Ile Pro Phe
385                 390                 395                 400

Val Ser Arg Arg Ser Leu Gly Ile Ile Ser Gly Met Thr Gly Ala Gly
                405                 410                 415

Gly Asn Phe Gly Ala Gly Leu Thr Gln Leu Leu Phe Phe Thr Ser Ser
            420                 425                 430

Thr Tyr Ser Thr Gly Arg Gly Leu Glu Tyr Met Gly Ile Met Ile Met
        435                 440                 445

Ala Cys Thr Leu Pro Val Val Phe Val His Phe Pro Gln Trp Gly Ser
    450                 455                 460

Met Phe Phe Pro Pro Ser Ala Thr Ala Asp Glu Glu Gly Tyr Tyr Ala
465                 470                 475                 480

Ser Glu Trp Asn Asp Asp Glu Lys Ser Lys Gly Leu His Ser Ala Ser
                485                 490                 495

Leu Lys Phe Ala Glu Asn Ser Arg Ser Glu Arg Gly Lys Arg Asn Val
            500                 505                 510

Ile Gln Ala Asp Ala Ala Ala Thr Pro Glu His Val
        515                 520
```

<210> SEQ ID NO 69
<211> LENGTH: 1789
<212> TYPE: DNA
<213> ORGANISM: Zea mays

<400> SEQUENCE: 69

```
acgcggggaa gcacaagcaa ccagccagct agtttccaag ggatcacctg ctctctagca     60
ctagcagcaa tggcggccgt cggcgctccg ggcagctctc tgcacggagt cacggggcgc    120
gagccggcgt tcgccttctc cacggagcac gaggaggcgg cgagcaatgg tggcaagttc    180
gacctgccgg tggactcaga gcacaaggcg aagagcgtcc gtctcttctc cgtggcgaac    240
ccacacatgc gcaccttcca cctctcctgg atctccttct tcacctgctt cgtgtccacc    300
ttcgccgccg cgccgctggt ccccatcatc cgcgacaacc tcaacctcac caaggccgac    360
atcggcaacg cgggcgtggc ctcggtgtcg ggctccatct tctcccgcct caccatgggc    420
gccgtctgcg acctgctggg cccgcgctac ggctgcgcct tcctcatcat gctgtccgcg    480
cccaccgtgt tctgcatgtc gctcatcgac gacgccgcgg gctacatcac cgtcaggttc    540
ctcatcggct tctccctcgc caccttcgtc tcctgccagt actggatgag caccatgttc    600
agcagcaaga tcatcggcac cgtcaacggg ctcgccgccg gatggggcac aatgggaagg    660
cggcgccacg cagctcatat gccgctcgtc tacgacgtca tccgcaagtg cggcgccacg    720
ccattcacgg cctggcgcct cgcctacttc gtgccgggcc tcatgcacgt cgtcatgggc    780
gtcctggtgc tcacgctggg gcaggacctc cccgacggca acctcaggtc gctgcagaag    840
aagggcaacg tcaacaagga cagcttctcc aaggtcatgt ggtacgccgt catcaactac    900
cgtacctgga tctttgtcct cctctacggc tactgcatgg gcgtcgagct caccaccgac    960
aacgtcatcg ccgagtacat gtacgaccgc ttcgacctcg acctccgcgt cgctgggacc   1020
atcgccgcct gcttcggcat ggccaacatc gtcgcacgcc ccatgggcgg catcatgtcc   1080
gacatgggcg cgcgctactg ggcatgcgc gctcgcctct ggaacatctg gatcctccag    1140
accgccggcg gcgccttctg cctctggctg gggcgcgcca gcaccctccc cgtctccgtc   1200
gtcgccatgg tgctcttctc cttctgcgcg caggcggcat gcggcgccat cttcggggtt   1260
atcccctttg tctcccgccg ctccctcggc atcatctccg gcatgacggg cgccggcggc   1320
aacttcggcg ccgggctcac gcagctgctc ttctttacct cctcgaccta ctccacgggc   1380
agggggctgg agtacatggg catcatgatc atggcgtgca cgctgcccgt ggtgttcgtg   1440
cacttccctc agtgggggtc catgttcttt ccgcccagcg ccaccgccga cgaggagggc   1500
tactacgcct ccgagtggaa cgacgacgag aagagcaagg gactccatag cgccagcctc   1560
aagttcgccg agaacagccg ctcagagcgc ggcaagcgaa acgtcatcca ggccgacgcc   1620
gccgccacgc cggagcatgt ctaagtctac tactaagatg gatcgatcga cgatcaccta   1680
tacctctttg tatgtacgaa tatgccttgt tattactgcg cgcgcgcata tacaatacac   1740
gtgtgctccg ttgacatgag ttagaaaaaa aaaaaaaaaa aaaaaaaaa               1789
```

<210> SEQ ID NO 70
<211> LENGTH: 524
<212> TYPE: PRT
<213> ORGANISM: Zea mays

<400> SEQUENCE: 70

```
Met Ala Ala Val Gly Ala Pro Gly Ser Ser Leu His Gly Val Thr Gly
1               5                   10                  15

Arg Glu Pro Ala Phe Ala Phe Ser Thr Glu His Glu Glu Ala Ala Ser
            20                  25                  30

Asn Gly Gly Lys Phe Asp Leu Pro Val Asp Ser Glu His Lys Ala Lys
        35                  40                  45
```

-continued

```
Ser Val Arg Leu Phe Ser Val Ala Asn Pro His Met Arg Thr Phe His
    50                  55                  60

Leu Ser Trp Ile Ser Phe Phe Thr Cys Phe Val Ser Thr Phe Ala Ala
65                  70                  75                  80

Ala Pro Leu Val Pro Ile Ile Arg Asp Asn Leu Asn Leu Thr Lys Ala
                85                  90                  95

Asp Ile Gly Asn Ala Gly Val Ala Ser Val Ser Gly Ser Ile Phe Ser
            100                 105                 110

Arg Leu Thr Met Gly Ala Val Cys Asp Leu Leu Gly Pro Arg Tyr Gly
        115                 120                 125

Cys Ala Phe Leu Ile Met Leu Ser Ala Pro Thr Val Phe Cys Met Ser
    130                 135                 140

Leu Ile Asp Asp Ala Ala Gly Tyr Ile Thr Val Arg Phe Leu Ile Gly
145                 150                 155                 160

Phe Ser Leu Ala Thr Phe Val Ser Cys Gln Tyr Trp Met Ser Thr Met
                165                 170                 175

Phe Ser Ser Lys Ile Ile Gly Thr Val Asn Gly Leu Ala Ala Gly Trp
            180                 185                 190

Gly Thr Met Gly Arg Arg Arg His Ala Ala His Met Pro Leu Val Tyr
        195                 200                 205

Asp Val Ile Arg Lys Cys Gly Ala Thr Pro Phe Thr Ala Trp Arg Leu
    210                 215                 220

Ala Tyr Phe Val Pro Gly Leu Met His Val Val Met Gly Val Leu Val
225                 230                 235                 240

Leu Thr Leu Gly Gln Asp Leu Pro Asp Gly Asn Leu Arg Ser Leu Gln
                245                 250                 255

Lys Lys Gly Asn Val Asn Lys Asp Ser Phe Ser Lys Val Met Trp Tyr
            260                 265                 270

Ala Val Ile Asn Tyr Arg Thr Trp Ile Phe Val Leu Leu Tyr Gly Tyr
        275                 280                 285

Cys Met Gly Val Glu Leu Thr Thr Asp Asn Val Ile Ala Glu Tyr Met
    290                 295                 300

Tyr Asp Arg Phe Asp Leu Asp Leu Arg Val Ala Gly Thr Ile Ala Ala
305                 310                 315                 320

Cys Phe Gly Met Ala Asn Ile Val Ala Arg Pro Met Gly Gly Ile Met
                325                 330                 335

Ser Asp Met Gly Ala Arg Tyr Trp Gly Met Arg Ala Arg Leu Trp Asn
            340                 345                 350

Ile Trp Ile Leu Gln Thr Ala Gly Gly Ala Phe Cys Leu Trp Leu Gly
        355                 360                 365

Arg Ala Ser Thr Leu Pro Val Ser Val Val Ala Met Val Leu Phe Ser
    370                 375                 380

Phe Cys Ala Gln Ala Ala Cys Gly Ala Ile Phe Gly Val Ile Pro Phe
385                 390                 395                 400

Val Ser Arg Arg Ser Leu Gly Ile Ile Ser Gly Met Thr Gly Ala Gly
                405                 410                 415

Gly Asn Phe Gly Ala Gly Leu Thr Gln Leu Leu Phe Phe Thr Ser Ser
            420                 425                 430

Thr Tyr Ser Thr Gly Arg Gly Leu Glu Tyr Met Gly Ile Met Ile Met
        435                 440                 445

Ala Cys Thr Leu Pro Val Val Phe Val His Phe Pro Gln Trp Gly Ser
    450                 455                 460
```

```
Met Phe Phe Pro Pro Ser Ala Thr Ala Asp Glu Glu Gly Tyr Tyr Ala
465                 470                 475                 480

Ser Glu Trp Asn Asp Asp Glu Lys Ser Lys Gly Leu His Ser Ala Ser
                485                 490                 495

Leu Lys Phe Ala Glu Asn Ser Arg Ser Glu Arg Gly Lys Arg Asn Val
            500                 505                 510

Ile Gln Ala Asp Ala Ala Ala Thr Pro Glu His Val
        515                 520


<210> SEQ ID NO 71
<211> LENGTH: 1837
<212> TYPE: DNA
<213> ORGANISM: Hordeum vulgare

<400> SEQUENCE: 71

gaattcgcgg ccgctccctt actacattgc aagccaagct caagagcagc agcaacagcc     60

accattagct gcttctagtt gttggcaaag atggaggtcg aggcgggcgc ccatggcgac    120

actgccgcga gcaagttcac gctgccggta gactccgagc acaaggccaa gtccttcagg    180

ctcttctcct tcgccaaccc gcacatgcgc accttccatc tctcgtggat ctccttcttc    240

acttgcttca tctccacctt cgccgcagcg ccccttgtcc ccatcattcg tgataacctc    300

aaccttgcca aggccgacat cggcaatgcc ggtgtggcat ccgtttctgg gtccatcttc    360

tccaggcttg ccatgggtgc catctgcgat ctcctcgggc cgcggtatgg atgtgcattc    420

ctcgtcatgc tctcggcacc gaccgttttc tgcatggccg ttatcgatga tgcctcaggg    480

tacatcgccg tccgctttct cattggcttc tcgcttgcta cgttcgtgtc atgccaatat    540

tggatgagca ccatgtttaa tagcaagatc atcggcacag tcaacggcct cgctgctgga    600

tggggcaaca tgggtggtgg cgccacgcag ctcatcatgc cgctcgtctt ccatgcaatc    660

cagaagtgtg gtgccacgcc cttcgtagcg tggcgtattg cctacttcgt gcccggaatg    720

atgcacatcg tgatgggctt gttggtactc accatggggc aagatctccc tgatgggaac    780

ctcgcaagtc tccagaagaa gggagacatg gccaaggaca agttctccaa ggtcctttgg    840

ggcgccgtta ccaactaccg aacatggatc tttgtcctcc tctatggcta ctgcatgggt    900

gtcgagctca ccaccgacaa tgtcattgcc gagtactact tcgaccactt ccacctagac    960

ctccgtgccg ccggtaccat cgctgcctgc ttcggcatgg ccaacatcgt cgcacgtcct   1020

acgggtggct acctctctga ccttggcgcc cgctatttcg gcatgcgtgc tcgcctctgg   1080

aatatctgga tcctccaaac cgctggtggc gctttctgca tctggctcgg tcgtgcatcg   1140

gccctccctg cctcggtgac cgccatggtc ctcttctcca tctgcgccca ggctgcgtgt   1200

ggtgctatct ttggtgtcgc acccttcgtc tccaggcgtt cccttggcat catttccggg   1260

ttgaccggtg ctggtggaaa cgtgggcgca gggctcacac agcttctctt cttcacgtca   1320

tcgcaatact ccactggtag gggtctcgag tacatgggca tcatgatcat ggcatgcacg   1380

ctgcccgtcg ctcttgtgca cttcccacaa tggggatcca tgttcttccc tgccagcgcc   1440

gacgccacgg aggaggagta ctacgcctcg gagtggtccg aagaggagaa agccaagggt   1500

ctccatatcg ccggccaaaa atttgctgag aattcccgct cggagcgcgg taggcgcaac   1560

gtcatccttg ccacgtccgc cacaccaccc aacaatacgc cccagcacgt atgagactgg   1620

attgtttttc atacctatgt acaagtactg aactacagtg cacgttcgta tatatatacg   1680

cctgcaacat cggctgtaat aaggcgtatg aatttacatt tgtagtgtag gcctgtgtaa   1740

tgcgtttctt acgcacgaaa tgtttggtct gtgcatgcac gcatgcgagg gtacctgtgc   1800
```

tctgaattta caacagcttt gaggcggccg cgaattc 1837

<210> SEQ ID NO 72
<211> LENGTH: 507
<212> TYPE: PRT
<213> ORGANISM: Hordeum vulgare

<400> SEQUENCE: 72

```
Met Glu Val Glu Ala Gly Ala His Gly Asp Thr Ala Ala Ser Lys Phe
1               5                   10                  15

Thr Leu Pro Val Asp Ser Glu His Lys Ala Lys Ser Phe Arg Leu Phe
            20                  25                  30

Ser Phe Ala Asn Pro His Met Arg Thr Phe His Leu Ser Trp Ile Ser
        35                  40                  45

Phe Phe Thr Cys Phe Ile Ser Thr Phe Ala Ala Ala Pro Leu Val Pro
    50                  55                  60

Ile Ile Arg Asp Asn Leu Asn Leu Ala Lys Ala Asp Ile Gly Asn Ala
65                  70                  75                  80

Gly Val Ala Ser Val Ser Gly Ser Ile Phe Ser Arg Leu Ala Met Gly
                85                  90                  95

Ala Ile Cys Asp Leu Leu Gly Pro Arg Tyr Gly Cys Ala Phe Leu Val
            100                 105                 110

Met Leu Ser Ala Pro Thr Val Phe Cys Met Ala Val Ile Asp Asp Ala
        115                 120                 125

Ser Gly Tyr Ile Ala Val Arg Phe Leu Ile Gly Phe Ser Leu Ala Thr
    130                 135                 140

Phe Val Ser Cys Gln Tyr Trp Met Ser Thr Met Phe Asn Ser Lys Ile
145                 150                 155                 160

Ile Gly Thr Val Asn Gly Leu Ala Ala Gly Trp Gly Asn Met Gly Gly
                165                 170                 175

Gly Ala Thr Gln Leu Ile Met Pro Leu Val Phe His Ala Ile Gln Lys
            180                 185                 190

Cys Gly Ala Thr Pro Phe Val Ala Trp Arg Ile Ala Tyr Phe Val Pro
        195                 200                 205

Gly Met Met His Ile Val Met Gly Leu Leu Val Leu Thr Met Gly Gln
    210                 215                 220

Asp Leu Pro Asp Gly Asn Leu Ala Ser Leu Gln Lys Lys Gly Asp Met
225                 230                 235                 240

Ala Lys Asp Lys Phe Ser Lys Val Leu Trp Gly Ala Val Thr Asn Tyr
                245                 250                 255

Arg Thr Trp Ile Phe Val Leu Leu Tyr Gly Tyr Cys Met Gly Val Glu
            260                 265                 270

Leu Thr Thr Asp Asn Val Ile Ala Glu Tyr Tyr Phe Asp His Phe His
        275                 280                 285

Leu Asp Leu Arg Ala Ala Gly Thr Ile Ala Ala Cys Phe Gly Met Ala
    290                 295                 300

Asn Ile Val Ala Arg Pro Thr Gly Gly Tyr Leu Ser Asp Leu Gly Ala
305                 310                 315                 320

Arg Tyr Phe Gly Met Arg Ala Arg Leu Trp Asn Ile Trp Ile Leu Gln
                325                 330                 335

Thr Ala Gly Gly Ala Phe Cys Ile Trp Leu Gly Arg Ala Ser Ala Leu
            340                 345                 350

Pro Ala Ser Val Thr Ala Met Val Leu Phe Ser Ile Cys Ala Gln Ala
        355                 360                 365
```

-continued

```
Ala Cys Gly Ala Ile Phe Gly Val Ala Pro Phe Val Ser Arg Arg Ser
    370                 375                 380

Leu Gly Ile Ile Ser Gly Leu Thr Gly Ala Gly Gly Asn Val Gly Ala
385                 390                 395                 400

Gly Leu Thr Gln Leu Leu Phe Phe Thr Ser Ser Gln Tyr Ser Thr Gly
                405                 410                 415

Arg Gly Leu Glu Tyr Met Gly Ile Met Ile Met Ala Cys Thr Leu Pro
            420                 425                 430

Val Ala Leu Val His Phe Pro Gln Trp Gly Ser Met Phe Phe Pro Ala
        435                 440                 445

Ser Ala Asp Ala Thr Glu Glu Glu Tyr Tyr Ala Ser Glu Trp Ser Glu
    450                 455                 460

Glu Glu Lys Ala Lys Gly Leu His Ile Ala Gly Gln Lys Phe Ala Glu
465                 470                 475                 480

Asn Ser Arg Ser Glu Arg Gly Arg Arg Asn Val Ile Leu Ala Thr Ser
                485                 490                 495

Ala Thr Pro Pro Asn Asn Thr Pro Gln His Val
            500                 505


<210> SEQ ID NO 73
<211> LENGTH: 1750
<212> TYPE: DNA
<213> ORGANISM: Triticum aestivum
<220> FEATURE:
<221> NAME/KEY: variation
<222> LOCATION: (1201)..(1201)
<223> OTHER INFORMATION: /replace="c" /replace="g" /replace="t"

<400> SEQUENCE: 73

tagttttgag tgcaactagg ctagctcaag aaagatggag gtgcaggccg gctctcatgc     60

cgacgccgcg gcgagcaagt tcacgctgcc ggtggactcc gagcacaagg ccaagtcctt    120

caggctcttc tccttcgcca acccccacat gcgcaccttt cacctctcgt ggatctcctt    180

cttcacctgc ttcgtctcca cctttgctgc ggcgcccctc gtgcccatca tccgcgacaa    240

cctcaacctt gccaaggctg acatcggcaa tgccggtgtc gcgtccgtgt ctgggtccat    300

cttctccagg ctggccatgg gcgctatctg tgacttgctt ggcccacggt atggttgtgc    360

cttcctcgtc atgctctcgg caccgaccgt cttctgcatg gccgtcatcg atgatgcctc    420

agggtacatc gccgtccggt tcctcattgg cttctccctc gccaccttcg tgtcatgcca    480

atactggatg agcaccatgt tcaatagcaa gatcattggc acggtcaatg gcttggctgc    540

aggctggggc aacatgggtg gcggcgccac gcagctcatc atgccgcttg tcttccacgc    600

aatccagaag tgtggcgcca cgcccttcgt ggcatggcgt attgcctact tcgtgccggg    660

aatgatgcac atcgtgatgg gcttgctggt cctcaccatg gggcaagatc tccctgacgg    720

gaaccttgcg agcctccara agaagggaga catggccaag gacaagttct ccaaggtcct    780

ttggggcgcy gtcaccaact accggacatg gatcttcgtc ctcctctacg gctactgcat    840

gggygtcgag ctcaccacsg acaatgtcat cgccgagtac tactacgacc acttccacct    900

agacctccgc gcygcwggca ccattgcygc ttgyttyggc atggcaaaca tygtcgcgcg    960

tcctatgggk ggctacctct cygaccttgg tgcccgctac tttggcatgc gtgctcgcct   1020

ttggaacatc tggatcctmc aaacygccgg tggcgctttc tgcatctggc tcggtcgtgc   1080

gtcagccctc cctgcctcag tgactgccat ggttctcttc tccatctgcg cccaagccgc   1140

gtgtggtgct gtatttggcg tcgcaccctt cgtttctaga cgttcccttg gcatcatctc   1200
```

-continued agggctgacc ggtgctggtg gaaacgtggg tgcrgggctc acgcagcttc tcttctttac 1260
ttcatcacaa tactccacyg gaaggggtct cgagtacatg ggcatcatga tcatggcatg 1320
cacgctgcct gtcgctcttg tgcacttccc acagtggggc tcgatgttct tcccggccag 1380
cgccgacgcc acagaggagg aatactatgc ctctgagtgg tcggaggagg agaagaacaa 1440
gggtctccat attgctggcc aaaagtttgc cgagaactca cgatcggagc gtggaaggcg 1500
caacgtcatc cttgccacgt ccgccacgcc acccaacaat acgccccagc acgtataaga 1560
ccggattgtt tttcatatac tatgtacaag tactgaacat cggctgtaat aaggtgtacg 1620
catttatatt tccagtgtag acttgtgtaa tgcgtttctt acgcacgaaa tgttttggtg 1680
tgtgcatgca cgcatgcgag gtacctgtgg tctgaattta cagcaacttt gagactaaaa 1740
aaaaaaaaaa 1750

<210> SEQ ID NO 74
<211> LENGTH: 507
<212> TYPE: PRT
<213> ORGANISM: Triticum aestivum

<400> SEQUENCE: 74

Met Glu Val Gln Ala Gly Ser His Ala Asp Ala Ala Ala Ser Lys Phe
1 5 10 15

Thr Leu Pro Val Asp Ser Glu His Lys Ala Lys Ser Phe Arg Leu Phe
20 25 30

Ser Phe Ala Asn Pro His Met Arg Thr Phe His Leu Ser Trp Ile Ser
35 40 45

Phe Phe Thr Cys Phe Val Ser Thr Phe Ala Ala Ala Pro Leu Val Pro
50 55 60

Ile Ile Arg Asp Asn Leu Asn Leu Ala Lys Ala Asp Ile Gly Asn Ala
65 70 75 80

Gly Val Ala Ser Val Ser Gly Ser Ile Phe Ser Arg Leu Ala Met Gly
85 90 95

Ala Ile Cys Asp Leu Leu Gly Pro Arg Tyr Gly Cys Ala Phe Leu Val
100 105 110

Met Leu Ser Ala Pro Thr Val Phe Cys Met Ala Val Ile Asp Asp Ala
115 120 125

Ser Gly Tyr Ile Ala Val Arg Phe Leu Ile Gly Phe Ser Leu Ala Thr
130 135 140

Phe Val Ser Cys Gln Tyr Trp Met Ser Thr Met Phe Asn Ser Lys Ile
145 150 155 160

Ile Gly Thr Val Asn Gly Leu Ala Ala Gly Trp Gly Asn Met Gly Gly
165 170 175

Gly Ala Thr Gln Leu Ile Met Pro Leu Val Phe His Ala Ile Gln Lys
180 185 190

Cys Gly Ala Thr Pro Phe Val Ala Trp Arg Ile Ala Tyr Phe Val Pro
195 200 205

Gly Met Met His Ile Val Met Gly Leu Leu Val Leu Thr Met Gly Gln
210 215 220

Asp Leu Pro Asp Gly Asn Leu Ala Ser Leu Gln Lys Lys Gly Asp Met
225 230 235 240

Ala Lys Asp Lys Phe Ser Lys Val Leu Trp Gly Ala Val Thr Asn Tyr
245 250 255

Arg Thr Trp Ile Phe Val Leu Leu Tyr Gly Tyr Cys Met Gly Val Glu
260 265 270

-continued

Leu Thr Thr Asp Asn Val Ile Ala Glu Tyr Tyr Tyr Asp His Phe His
275 280 285

Leu Asp Leu Arg Ala Ala Gly Thr Ile Ala Ala Cys Phe Gly Met Ala
290 295 300

Asn Ile Val Ala Arg Pro Met Gly Gly Tyr Leu Ser Asp Leu Gly Ala
305 310 315 320

Arg Tyr Phe Gly Met Arg Ala Arg Leu Trp Asn Ile Trp Ile Leu Gln
325 330 335

Thr Ala Gly Gly Ala Phe Cys Ile Trp Leu Gly Arg Ala Ser Ala Leu
340 345 350

Pro Ala Ser Val Thr Ala Met Val Leu Phe Ser Ile Cys Ala Gln Ala
355 360 365

Ala Cys Gly Ala Val Phe Gly Val Ala Pro Phe Val Ser Arg Arg Ser
370 375 380

Leu Gly Ile Ile Ser Gly Leu Thr Gly Ala Gly Gly Asn Val Gly Ala
385 390 395 400

Gly Leu Thr Gln Leu Leu Phe Phe Thr Ser Ser Gln Tyr Ser Thr Gly
405 410 415

Arg Gly Leu Glu Tyr Met Gly Ile Met Ile Met Ala Cys Thr Leu Pro
420 425 430

Val Ala Leu Val His Phe Pro Gln Trp Gly Ser Met Phe Phe Pro Ala
435 440 445

Ser Ala Asp Ala Thr Glu Glu Glu Tyr Tyr Ala Ser Glu Trp Ser Glu
450 455 460

Glu Glu Lys Asn Lys Gly Leu His Ile Ala Gly Gln Lys Phe Ala Glu
465 470 475 480

Asn Ser Arg Ser Glu Arg Gly Arg Arg Asn Val Ile Leu Ala Thr Ser
485 490 495

Ala Thr Pro Pro Asn Asn Thr Pro Gln His Val
500 505

<210> SEQ ID NO 75
<211> LENGTH: 1741
<212> TYPE: DNA
<213> ORGANISM: Hordeum vulgare

<400> SEQUENCE: 75
ttacaagctc catctgagag cagcagcaac caccattaga gacacactta gttgccagtg 60
cgactaagct agctagctcg aggaagatgg aggtggagtc gagctcgcat ggcgccggcg 120
acgaggctgc gagcaagttc tcgctgcccg tggactcgga gcacaaggcc aagtccatca 180
ggctcttctc cttcgccaac ccccacatgc gcaccttcca cctctcctgg atctccttct 240
tcacctgctt cgtctccacc ttcgctgccg cgcccctcgt ccctatcatc cgcgacaacc 300
taaacctcgc caaggccgac atcggcaacg ccggtgtggc gtccgtgtcc gggtctatct 360
tctcgaggct cgccatgggg gccatctgcg atctccttgg ccctcgatat ggatgcgcct 420
tcctcgtcat gctcgcagca cccaccgtct tctgcatgtc cctcatcgat gatgcggcgg 480
gctacatcac ggtccgcttc ctcatcggct tctccctcgc gacgtttgtg tcgtgccagt 540
attggatgag caccatgttc aacagcaaga tcatcggcac cgtcaacggc ctggcggccg 600
gctggggcaa catgggtggt ggtgccaccc agctcattat gccactcgtc ttccacgcca 660
tccagaagtg tggtgccacg cccttcgtcg catggcgcat cgcctacttc gtgccaggaa 720
tgatgcacgt ggtgatgggc ttgctcgtgc tcaccatggg acaggatctc cccgatggta 780

-continued

```
accttgcaag cctccagaag aagggggaga tggccaagga caagttctcc aaggttgtgt    840

ggggtgctgt tacaaactac cgtacatgga tcttcgttct tctttacgga tactgcatgg    900

gtgttgagct caccaccgac aacgtcatcg ccgagtacta cttcgaccac tttcaccttg    960

accttcgaac atccggcacc attgccgcct gttttggcat ggccaacatc gttgctcggc   1020

ctgcgggtgg ctacctctcc gacctcggtg cccgctactt cggcatgcgt gcccgcctct   1080

ggaacatctg gatcctccag accgctggtg gcgcattctg cctctggctc ggccgtgcaa   1140

aagccctccc cgaatccatc actgccatgg tcctcttctc catctgcgct caggcagcat   1200

gtggtgcagt ctttggtgtc atccccttcg tctcccgccg ctccctcggc atcatttcgg   1260

gcttgagtgg agccggtggg aactttggcg ccgggctgac acaattgctc ttcttcactt   1320

cgtcgaagta tggcaccggc agggggcttg agtacatggg tatcatgatc atggcctgca   1380

cgctccctgt ggcgcttgtg cacttcccac agtggggttc catgctcttg ccgccaaacg   1440

ccaacgccac cgaggaggag ttctatgccg ccgaatggag cgaggaggag aagaagaagg   1500

gtctccatat ccctggccaa aagtttgccg agaattcccg ctcggagcgt ggcaggcgca   1560

acgtcatcct tgccacagcc gccacacccc ccaacaacac tccccaacac gcataagact   1620

cgagcttttc tttacctgtg tacacgtaca gtgcgcgtat tatacacaca tcgatcgtgt   1680

atatacgcct ggaatccgca agcagtatgt tttttgaaaa aaaaaaagcg gccgcgaatt   1740

c                                                                   1741
```

```
<210> SEQ ID NO 76
<211> LENGTH: 509
<212> TYPE: PRT
<213> ORGANISM: Hordeum vulgare

<400> SEQUENCE: 76

Met Glu Val Glu Ser Ser Ser His Gly Ala Gly Asp Glu Ala Ala Ser
1               5                   10                  15

Lys Phe Ser Leu Pro Val Asp Ser Glu His Lys Ala Lys Ser Ile Arg
            20                  25                  30

Leu Phe Ser Phe Ala Asn Pro His Met Arg Thr Phe His Leu Ser Trp
        35                  40                  45

Ile Ser Phe Phe Thr Cys Phe Val Ser Thr Phe Ala Ala Ala Pro Leu
    50                  55                  60

Val Pro Ile Ile Arg Asp Asn Leu Asn Leu Ala Lys Ala Asp Ile Gly
65                  70                  75                  80

Asn Ala Gly Val Ala Ser Val Ser Gly Ser Ile Phe Ser Arg Leu Ala
                85                  90                  95

Met Gly Ala Ile Cys Asp Leu Leu Gly Pro Arg Tyr Gly Cys Ala Phe
            100                 105                 110

Leu Val Met Leu Ala Ala Pro Thr Val Phe Cys Met Ser Leu Ile Asp
        115                 120                 125

Asp Ala Ala Gly Tyr Ile Thr Val Arg Phe Leu Ile Gly Phe Ser Leu
    130                 135                 140

Ala Thr Phe Val Ser Cys Gln Tyr Trp Met Ser Thr Met Phe Asn Ser
145                 150                 155                 160

Lys Ile Ile Gly Thr Val Asn Gly Leu Ala Ala Gly Trp Gly Asn Met
                165                 170                 175

Gly Gly Gly Ala Thr Gln Leu Ile Met Pro Leu Val Phe His Ala Ile
            180                 185                 190
```

```
Gln Lys Cys Gly Ala Thr Pro Phe Val Ala Trp Arg Ile Ala Tyr Phe
        195                 200                 205

Val Pro Gly Met Met His Val Val Met Gly Leu Leu Val Leu Thr Met
    210                 215                 220

Gly Gln Asp Leu Pro Asp Gly Asn Leu Ala Ser Leu Gln Lys Lys Gly
225                 230                 235                 240

Glu Met Ala Lys Asp Lys Phe Ser Lys Val Val Trp Gly Ala Val Thr
                245                 250                 255

Asn Tyr Arg Thr Trp Ile Phe Val Leu Leu Tyr Gly Tyr Cys Met Gly
            260                 265                 270

Val Glu Leu Thr Thr Asp Asn Val Ile Ala Glu Tyr Tyr Phe Asp His
        275                 280                 285

Phe His Leu Asp Leu Arg Thr Ser Gly Thr Ile Ala Ala Cys Phe Gly
    290                 295                 300

Met Ala Asn Ile Val Ala Arg Pro Ala Gly Gly Tyr Leu Ser Asp Leu
305                 310                 315                 320

Gly Ala Arg Tyr Phe Gly Met Arg Ala Arg Leu Trp Asn Ile Trp Ile
                325                 330                 335

Leu Gln Thr Ala Gly Gly Ala Phe Cys Leu Trp Leu Gly Arg Ala Lys
            340                 345                 350

Ala Leu Pro Glu Ser Ile Thr Ala Met Val Leu Phe Ser Ile Cys Ala
        355                 360                 365

Gln Ala Ala Cys Gly Ala Val Phe Gly Val Ile Pro Phe Val Ser Arg
    370                 375                 380

Arg Ser Leu Gly Ile Ile Ser Gly Leu Ser Gly Ala Gly Gly Asn Phe
385                 390                 395                 400

Gly Ala Gly Leu Thr Gln Leu Leu Phe Phe Thr Ser Ser Lys Tyr Gly
                405                 410                 415

Thr Gly Arg Gly Leu Glu Tyr Met Gly Ile Met Ile Met Ala Cys Thr
            420                 425                 430

Leu Pro Val Ala Leu Val His Phe Pro Gln Trp Gly Ser Met Leu Leu
        435                 440                 445

Pro Pro Asn Ala Asn Ala Thr Glu Glu Glu Phe Tyr Ala Ala Glu Trp
    450                 455                 460

Ser Glu Glu Glu Lys Lys Lys Gly Leu His Ile Pro Gly Gln Lys Phe
465                 470                 475                 480

Ala Glu Asn Ser Arg Ser Glu Arg Gly Arg Arg Asn Val Ile Leu Ala
                485                 490                 495

Thr Ala Ala Thr Pro Pro Asn Asn Thr Pro Gln His Ala
            500                 505
```

<210> SEQ ID NO 77
<211> LENGTH: 1796
<212> TYPE: DNA
<213> ORGANISM: Triticum aestivum

<400> SEQUENCE: 77

```
aagctagcac caagcctcca aggagcaaga agagaagaag ccttgctcga tcaagcaagg      60

tcgaaatgga ggtggaggcc agcgcccatg gcgacacggc ggcgagcaag ttcacgctgc     120

ccgtggactc cgagcacaag gccaagtcct tcagactctt ctccttcgcc aacccccaca     180

tgcgtacctt ccacctctcc tggatatcct tcttcacctg cttcgtctcc accttcgcgg     240

cggcaccgtt ggtgcccatc atccgtgaca acctcaacct cgctaaggcc gacataggga     300

atgccggtgt ggcatctgtg tctgggtcca tcttctccag gcttgccatg ggtgccatct     360
```

```
gcgacctttt agggccgcgg tatggctgcg ccttcctcgt catgctctca gcacccactg    420
tgttttgcat ggctgctatc gacgatgcgt caggctacat cgccgtacgc ttcctcattg    480
gcttctccct cgccaccttc gtgtcatgcc aatattggat gagcaccatg ttcaacagta    540
agatcattgg cacggtgaat ggcctcgcgg ccggctgggg caacatgggc ggtggtgcca    600
cacaactcat catgccgctt gttttccatg ccatccaaaa gtgtggtgcc acacccttcg    660
tggcatggcg tattgcctat ttcgtgccgg gaatgatgca catcgtcatg ggttgcttg     720
tgctcactat gggccaagat ctccccgacg gcaaccttgc gagtctccag aagaaggggg    780
acatggccaa ggacaaattc tcgaaggtcc tttggggtgc ggtcaccaac taccggacat    840
ggatattcgt cctcctctac ggctactgca tgggtgtcga gctcaccacc gacaacgtca    900
tcgccgagta ctactacgac cacttccacc ttgaccttcg cgccgctggc accattgccg    960
cttgcttcgg catggccaac atcgtcgcgc gtcctatggg tggctatctc tctgaccttg   1020
gtgcccgcta cttcggcatg cgtgctcggc tctggaacat ctggatcctc cagaccgctg   1080
gtggcgcttt ctgcatctgg ctcggtcgtg catcggccct tcctgcctca gtcacggcca   1140
tggtcctctt ttccatttgt gcacaagctg cttgtggtgc tgtatttggc gtcgcaccct   1200
tcgtttccag gcgttccctt ggcatcatct ccgggctgac cggcgctggt ggcaatgttg   1260
gcgcagggct aacgcaactt cttttcttca catcgtcgca atactccacc gggaggggtc   1320
tcgagtacat gggcatcatg atcatggcat gcacattacc cgtcgctctg gtgcacttcc   1380
cccaatgggg ctccatgttc ttcccggcta gcgctgatgc cacggaagag gaatactatg   1440
cttctgagtg gtcggaggag gagaagggca agggtctcca tattacaggc caaaagttcg   1500
cagagaactc ccgctcagag cgcggcaggc gcaacgtcat ccttgccaca tccgccacgc   1560
cacccaacaa cacaccccag cacgtataag gcccttattt ttatgtcacc taagaatttt   1620
actgttcatc acgtatatat acaaaccgta tatctacgtc tgcagcccca gcgtaataag   1680
ttgtatgggg atttatgttt ctactagtaa acttaaggaa acgctgcttt tgcgttcctg   1740
ctctgtacgc atgaaatgta atatcaattt gagtccgaaa ttactacaaa aaaaaa       1796
```

<210> SEQ ID NO 78
<211> LENGTH: 507
<212> TYPE: PRT
<213> ORGANISM: Triticum aestivum

<400> SEQUENCE: 78

```
Met Glu Val Glu Ala Ser Ala His Gly Asp Thr Ala Ala Ser Lys Phe
1               5                   10                  15

Thr Leu Pro Val Asp Ser Glu His Lys Ala Lys Ser Phe Arg Leu Phe
            20                  25                  30

Ser Phe Ala Asn Pro His Met Arg Thr Phe His Leu Ser Trp Ile Ser
        35                  40                  45

Phe Phe Thr Cys Phe Val Ser Thr Phe Ala Ala Ala Pro Leu Val Pro
    50                  55                  60

Ile Ile Arg Asp Asn Leu Asn Leu Ala Lys Ala Asp Ile Gly Asn Ala
65                  70                  75                  80

Gly Val Ala Ser Val Ser Gly Ser Ile Phe Ser Arg Leu Ala Met Gly
                85                  90                  95

Ala Ile Cys Asp Leu Leu Gly Pro Arg Tyr Gly Cys Ala Phe Leu Val
            100                 105                 110

Met Leu Ser Ala Pro Thr Val Phe Cys Met Ala Ala Ile Asp Asp Ala
```

```
        115                 120                 125

Ser Gly Tyr Ile Ala Val Arg Phe Leu Ile Gly Phe Ser Leu Ala Thr
    130                 135                 140

Phe Val Ser Cys Gln Tyr Trp Met Ser Thr Met Phe Asn Ser Lys Ile
145                 150                 155                 160

Ile Gly Thr Val Asn Gly Leu Ala Ala Gly Trp Gly Asn Met Gly Gly
                165                 170                 175

Gly Ala Thr Gln Leu Ile Met Pro Leu Val Phe His Ala Ile Gln Lys
            180                 185                 190

Cys Gly Ala Thr Pro Phe Val Ala Trp Arg Ile Ala Tyr Phe Val Pro
        195                 200                 205

Gly Met Met His Ile Val Met Gly Leu Leu Val Leu Thr Met Gly Gln
    210                 215                 220

Asp Leu Pro Asp Gly Asn Leu Ala Ser Leu Gln Lys Lys Gly Asp Met
225                 230                 235                 240

Ala Lys Asp Lys Phe Ser Lys Val Leu Trp Gly Ala Val Thr Asn Tyr
                245                 250                 255

Arg Thr Trp Ile Phe Val Leu Leu Tyr Gly Tyr Cys Met Gly Val Glu
            260                 265                 270

Leu Thr Thr Asp Asn Val Ile Ala Glu Tyr Tyr Tyr Asp His Phe His
        275                 280                 285

Leu Asp Leu Arg Ala Ala Gly Thr Ile Ala Ala Cys Phe Gly Met Ala
    290                 295                 300

Asn Ile Val Ala Arg Pro Met Gly Gly Tyr Leu Ser Asp Leu Gly Ala
305                 310                 315                 320

Arg Tyr Phe Gly Met Arg Ala Arg Leu Trp Asn Ile Trp Ile Leu Gln
                325                 330                 335

Thr Ala Gly Gly Ala Phe Cys Ile Trp Leu Gly Arg Ala Ser Ala Leu
            340                 345                 350

Pro Ala Ser Val Thr Ala Met Val Leu Phe Ser Ile Cys Ala Gln Ala
        355                 360                 365

Ala Cys Gly Ala Val Phe Gly Val Ala Pro Phe Val Ser Arg Arg Ser
    370                 375                 380

Leu Gly Ile Ile Ser Gly Leu Thr Gly Ala Gly Gly Asn Val Gly Ala
385                 390                 395                 400

Gly Leu Thr Gln Leu Leu Phe Phe Thr Ser Ser Gln Tyr Ser Thr Gly
                405                 410                 415

Arg Gly Leu Glu Tyr Met Gly Ile Met Ile Met Ala Cys Thr Leu Pro
            420                 425                 430

Val Ala Leu Val His Phe Pro Gln Trp Gly Ser Met Phe Phe Pro Ala
        435                 440                 445

Ser Ala Asp Ala Thr Glu Glu Glu Tyr Tyr Ala Ser Glu Trp Ser Glu
    450                 455                 460

Glu Glu Lys Gly Lys Gly Leu His Ile Thr Gly Gln Lys Phe Ala Glu
465                 470                 475                 480

Asn Ser Arg Ser Glu Arg Gly Arg Arg Asn Val Ile Leu Ala Thr Ser
                485                 490                 495

Ala Thr Pro Pro Asn Asn Thr Pro Gln His Val
            500                 505
```

<210> SEQ ID NO 79
<211> LENGTH: 1744
<212> TYPE: DNA
<213> ORGANISM: Triticum aestivum

<400> SEQUENCE: 79
gcagtataat caagcaagct agctgcaagc cgaggagcct agctcgatca agcaaggtcg 60
aaatggaggt ggagtctagc gcccatggcg acgccgcggc gagcaagttc acgctgcctg 120
tggactccga gcacaaggcc aagtccttca ggctcttctc cttcgccaac ccccacatgc 180
gcaccttcca cctctcctgg atatccttct tcacctgctt tgtctccacc ttcgccgccg 240
cgccgttggt gcccatcatc cgtgacaacc tcaacctcgc caaggccgac atagggaatg 300
ccggtgtggc atctgtgtca gggtccatct tctccaggct tgccatgggc gccgtctgcg 360
accttttggg gccgcggtat ggctgtgcct tcctcgtcat gctctcagcg ccaacggtct 420
tctgcatggc cgtcatcgat gacgcctcgg ggtacatcgc tgtacgcttc ctcattggct 480
tctccctcgc cgcctttgtg tcctgccaat actggatgag caccatgttc aacagtaaga 540
tcattggcac ggtgaatggc ctcgcggccg gctggggcaa catggggggc ggtgccacac 600
aactcattat gccacttgtt ttccatgcca tccaaaagtg cggtgccaca cccttcgtgg 660
catggcgtat cgcctacttc gtgccgggaa tgatgcacat cgtcatgggg ttgcttgtcc 720
tcacaatggg ccaagatctc cccgacggca accttgcgag cctccagaag aagggagaca 780
tggccaagga caagttctcc aaggtccttt ggggcgccgt caccaactac cggacatgga 840
tcttcgtcct cctctacggc tactgcatgg gtgtcgagct caccactgac aacgtcatcg 900
ccgagtacta ctacgaccat ttccacctac accttcgcgc tgcaggcacc atcgccgcct 960
gctttggcat ggccaatatc gtcgcacgtc ctatgggagg ttacctctct gaccttggcg 1020
ctcgctactt tggtatgcgt gctcgcctat ggaacatctg gatcctccag accgccggcg 1080
gcgctttctg catctggctc ggtcgtgcat cggccctccc cgcctcagtg actgccatgg 1140
ttctcttctc catctgcgcc caagctgcat gtggcgctgt ctttggtgtt gcaccattcg 1200
tttccaggcg ttcccttggc atcatctctg ggttaaccgg cgctggtggc aatgtgggcg 1260
cggggctcac acaacttctc ttcttcactt cgtcgcaata ctccaccggg aggggtctcg 1320
agtacatggg catcatgatc atggcatgca cattacctat cactctggtg cacttcccac 1380
aatggggctc catgttcttc ccggccagtg ctgatgctac ggaggaggag tactacgctt 1440
ccgagtggtc agaggaggag aagggcaagg gtctccatat cgcaggccag aagtttgcag 1500
agaactcccg ctcggagcgt ggtaggcgca atgttatcct cgccacatcc gccacgccgc 1560
ccaacaatac accccagcat gtataaggcc cttgttttct gtcacctatg aattgtacgg 1620
ttcgtcacgt acatatacaa accgtatatc tacgtcggca gccccagcgt aataagttgt 1680
atggggattt atctttctac tagtaaactt aaggaaacgc tggttttgcg ttcctgctct 1740
gtac 1744

<210> SEQ ID NO 80
<211> LENGTH: 507
<212> TYPE: PRT
<213> ORGANISM: Triticum aestivum

<400> SEQUENCE: 80

Met Glu Val Glu Ser Ser Ala His Gly Asp Ala Ala Ala Ser Lys Phe
1               5                   10                  15

Thr Leu Pro Val Asp Ser Glu His Lys Ala Lys Ser Phe Arg Leu Phe
            20                  25                  30

Ser Phe Ala Asn Pro His Met Arg Thr Phe His Leu Ser Trp Ile Ser
        35                  40                  45

```
Phe Phe Thr Cys Phe Val Ser Thr Phe Ala Ala Ala Pro Leu Val Pro
    50                  55                  60

Ile Ile Arg Asp Asn Leu Asn Leu Ala Lys Ala Asp Ile Gly Asn Ala
65                  70                  75                  80

Gly Val Ala Ser Val Ser Gly Ser Ile Phe Ser Arg Leu Ala Met Gly
                85                  90                  95

Ala Val Cys Asp Leu Leu Gly Pro Arg Tyr Gly Cys Ala Phe Leu Val
            100                 105                 110

Met Leu Ser Ala Pro Thr Val Phe Cys Met Ala Val Ile Asp Asp Ala
        115                 120                 125

Ser Gly Tyr Ile Ala Val Arg Phe Leu Ile Gly Phe Ser Leu Ala Ala
    130                 135                 140

Phe Val Ser Cys Gln Tyr Trp Met Ser Thr Met Phe Asn Ser Lys Ile
145                 150                 155                 160

Ile Gly Thr Val Asn Gly Leu Ala Ala Gly Trp Gly Asn Met Gly Gly
                165                 170                 175

Gly Ala Thr Gln Leu Ile Met Pro Leu Val Phe His Ala Ile Gln Lys
            180                 185                 190

Cys Gly Ala Thr Pro Phe Val Ala Trp Arg Ile Ala Tyr Phe Val Pro
        195                 200                 205

Gly Met Met His Ile Val Met Gly Leu Leu Val Leu Thr Met Gly Gln
    210                 215                 220

Asp Leu Pro Asp Gly Asn Leu Ala Ser Leu Gln Lys Lys Gly Asp Met
225                 230                 235                 240

Ala Lys Asp Lys Phe Ser Lys Val Leu Trp Gly Ala Val Thr Asn Tyr
                245                 250                 255

Arg Thr Trp Ile Phe Val Leu Leu Tyr Gly Tyr Cys Met Gly Val Glu
            260                 265                 270

Leu Thr Thr Asp Asn Val Ile Ala Glu Tyr Tyr Tyr Asp His Phe His
        275                 280                 285

Leu His Leu Arg Ala Ala Gly Thr Ile Ala Ala Cys Phe Gly Met Ala
    290                 295                 300

Asn Ile Val Ala Arg Pro Met Gly Gly Tyr Leu Ser Asp Leu Gly Ala
305                 310                 315                 320

Arg Tyr Phe Gly Met Arg Ala Arg Leu Trp Asn Ile Trp Ile Leu Gln
                325                 330                 335

Thr Ala Gly Gly Ala Phe Cys Ile Trp Leu Gly Arg Ala Ser Ala Leu
            340                 345                 350

Pro Ala Ser Val Thr Ala Met Val Leu Phe Ser Ile Cys Ala Gln Ala
        355                 360                 365

Ala Cys Gly Ala Val Phe Gly Val Ala Pro Phe Val Ser Arg Arg Ser
    370                 375                 380

Leu Gly Ile Ile Ser Gly Leu Thr Gly Ala Gly Gly Asn Val Gly Ala
385                 390                 395                 400

Gly Leu Thr Gln Leu Leu Phe Phe Thr Ser Ser Gln Tyr Ser Thr Gly
                405                 410                 415

Arg Gly Leu Glu Tyr Met Gly Ile Met Ile Met Ala Cys Thr Leu Pro
            420                 425                 430

Ile Thr Leu Val His Phe Pro Gln Trp Gly Ser Met Phe Phe Pro Ala
        435                 440                 445

Ser Ala Asp Ala Thr Glu Glu Glu Tyr Tyr Ala Ser Glu Trp Ser Glu
    450                 455                 460
```

```
Glu Glu Lys Gly Lys Gly Leu His Ile Ala Gly Gln Lys Phe Ala Glu
465                 470                 475                 480

Asn Ser Arg Ser Glu Arg Gly Arg Arg Asn Val Ile Leu Ala Thr Ser
                485                 490                 495

Ala Thr Pro Pro Asn Asn Thr Pro Gln His Val
            500                 505


<210> SEQ ID NO 81
<211> LENGTH: 1704
<212> TYPE: DNA
<213> ORGANISM: Hordeum vulgare

<400> SEQUENCE: 81

caccactgca agcatattta ggcttagtta gctccaagga gcaaagctaa aaagaaccta     60

gctaggctag ctcgatccag ctagctcagt agatatggag gtggaggccg gagctcatgg    120

cgatgcggcg gcgagcaagt tcacgctgcc cgtggactcc gagcacaagg ccaagtcctt    180

caggctcttc tccttcgcca acccgcacat gcgcaccttc cacctctcgt ggatctcctt    240

cttcacctgc ttcgtctcca cctttgccgc tgctccgttg gtgcccatca tccgcgacaa    300

cctcaacctc gccaaggccg acatcggcaa tgccggtgtg gcgtccgtgt ccggctccat    360

cttctcgagg ctcgccatgg gcgccatttg tgacctgctt ggcccgcggt acggttgtgc    420

ctttctcgtc atgctatcgg cgccaaccgt cttctgcatg gccgtcatcg acgacgcgtc    480

gggatacatc gcagtccgct tcctcatcgg cttctccctc gcaaccttcg tgtcatgcca    540

gtactggatg agcacaatgt tcaacagtaa aatcatcggc acggttaatg gcctcgcagc    600

cgggtggggc aacatgggtg gcggggccac acagctcatc atgcccctcg tcttccatgc    660

catccaaaag tgtggtgcca caccctttgt ggcatggcgt atcgcctact tcgtgccggg    720

gatgatgcac atcgtgatgg gcctactcgt gctcaccatg ggacaagacc tccctgatgg    780

gaacctcgca agcctgcaga agaagggaga catggccaag gacaagttct ccaaggtcct    840

ttggggcgcc gttaccaact accggacatg gatctttgtc ctcctctatg gctactgcat    900

gggtgtcgag ctcaccactg gcaatgtcat tgccgagtac tacttcgatc acttccacct    960

aaacctccgt gccgccggta ccatcgccgc ttgcttcggc atggccaaca tcgtcgcacg   1020

tcctatgggc ggctacctct ccgaccttgg tgctcgctac ttcggtatgc gtgctcgcct   1080

ttggaacatc tggatccttc agacagctgg cggcgccttt tgcatctggc ttgggcgcgc   1140

ctcggccctc cccgcctcag tgactgccat ggtcctcttc tccatctgcg cccaggctgc   1200

gtgtggtgct atctttggtg tcgaaccctt cgtctccagg cgttcccttg gcatcatttc   1260

cgggttgacc ggtgctggtg gaaacgtggg cgcagggctc acacagcttc tcttcttcac   1320

ttcgtcgcaa tactccactg gcaggggtct tgagtacatg ggcatcatga tcatggcatg   1380

caccttaccc gtcgctctcg ttcacttccc tcagtggggc tctatgttct tggctgccag   1440

tgccgacgcc acggaggagg agtactacgc ctcagagtgg tcagaggagg agaagagcaa   1500

gggtctccat atcgcaggac aaaagtttgc tgagaactcc cgctcggaac gcggcaggcg   1560

caacgtcatc cttgccacat ccgccacacc acccaacaac acgcccctac acgtataagt   1620

ttcaaatttt gtgttacaca agaaatgtac atcttgctga gtatatatac acatcgtata   1680

ttttagtaaa aaaaaaaaaa aaaa                                          1704


<210> SEQ ID NO 82
<211> LENGTH: 507
<212> TYPE: PRT
```

<213> ORGANISM: Hordeum vulgare

<400> SEQUENCE: 82

```
Met Glu Val Glu Ala Gly Ala His Gly Asp Ala Ala Ala Ser Lys Phe
1               5                   10                  15

Thr Leu Pro Val Asp Ser Glu His Lys Ala Lys Ser Phe Arg Leu Phe
            20                  25                  30

Ser Phe Ala Asn Pro His Met Arg Thr Phe His Leu Ser Trp Ile Ser
        35                  40                  45

Phe Phe Thr Cys Phe Val Ser Thr Phe Ala Ala Ala Pro Leu Val Pro
    50                  55                  60

Ile Ile Arg Asp Asn Leu Asn Leu Ala Lys Ala Asp Ile Gly Asn Ala
65                  70                  75                  80

Gly Val Ala Ser Val Ser Gly Ser Ile Phe Ser Arg Leu Ala Met Gly
                85                  90                  95

Ala Ile Cys Asp Leu Leu Gly Pro Arg Tyr Gly Cys Ala Phe Leu Val
            100                 105                 110

Met Leu Ser Ala Pro Thr Val Phe Cys Met Ala Val Ile Asp Asp Ala
        115                 120                 125

Ser Gly Tyr Ile Ala Val Arg Phe Leu Ile Gly Phe Ser Leu Ala Thr
    130                 135                 140

Phe Val Ser Cys Gln Tyr Trp Met Ser Thr Met Phe Asn Ser Lys Ile
145                 150                 155                 160

Ile Gly Thr Val Asn Gly Leu Ala Ala Gly Trp Gly Asn Met Gly Gly
                165                 170                 175

Gly Ala Thr Gln Leu Ile Met Pro Leu Val Phe His Ala Ile Gln Lys
            180                 185                 190

Cys Gly Ala Thr Pro Phe Val Ala Trp Arg Ile Ala Tyr Phe Val Pro
        195                 200                 205

Gly Met Met His Ile Val Met Gly Leu Leu Val Leu Thr Met Gly Gln
    210                 215                 220

Asp Leu Pro Asp Gly Asn Leu Ala Ser Leu Gln Lys Lys Gly Asp Met
225                 230                 235                 240

Ala Lys Asp Lys Phe Ser Lys Val Leu Trp Gly Ala Val Thr Asn Tyr
                245                 250                 255

Arg Thr Trp Ile Phe Val Leu Leu Tyr Gly Tyr Cys Met Gly Val Glu
            260                 265                 270

Leu Thr Thr Gly Asn Val Ile Ala Glu Tyr Tyr Phe Asp His Phe His
        275                 280                 285

Leu Asn Leu Arg Ala Ala Gly Thr Ile Ala Ala Cys Phe Gly Met Ala
    290                 295                 300

Asn Ile Val Ala Arg Pro Met Gly Gly Tyr Leu Ser Asp Leu Gly Ala
305                 310                 315                 320

Arg Tyr Phe Gly Met Arg Ala Arg Leu Trp Asn Ile Trp Ile Leu Gln
                325                 330                 335

Thr Ala Gly Gly Ala Phe Cys Ile Trp Leu Gly Arg Ala Ser Ala Leu
            340                 345                 350

Pro Ala Ser Val Thr Ala Met Val Leu Phe Ser Ile Cys Ala Gln Ala
        355                 360                 365

Ala Cys Gly Ala Ile Phe Gly Val Glu Pro Phe Val Ser Arg Arg Ser
    370                 375                 380

Leu Gly Ile Ile Ser Gly Leu Thr Gly Ala Gly Gly Asn Val Gly Ala
385                 390                 395                 400
```

-continued

```
Gly Leu Thr Gln Leu Leu Phe Phe Thr Ser Ser Gln Tyr Ser Thr Gly
                405                 410                 415

Arg Gly Leu Glu Tyr Met Gly Ile Met Ile Met Ala Cys Thr Leu Pro
            420                 425                 430

Val Ala Leu Val His Phe Pro Gln Trp Gly Ser Met Phe Leu Ala Ala
        435                 440                 445

Ser Ala Asp Ala Thr Glu Glu Glu Tyr Tyr Ala Ser Glu Trp Ser Glu
    450                 455                 460

Glu Glu Lys Ser Lys Gly Leu His Ile Ala Gly Gln Lys Phe Ala Glu
465                 470                 475                 480

Asn Ser Arg Ser Glu Arg Gly Arg Arg Asn Val Ile Leu Ala Thr Ser
                485                 490                 495

Ala Thr Pro Pro Asn Asn Thr Pro Leu His Val
            500                 505


<210> SEQ ID NO 83
<211> LENGTH: 1825
<212> TYPE: DNA
<213> ORGANISM: Hordeum vulgare

<400> SEQUENCE: 83

tctcagttgc cactgcagct gatcaagcaa gctagctcca aacctccaag gaggaagcag      60

agaaggagac tagctcgatc aagcaaggtc caaatggagg tggaggctgg tgcccatggc     120

gacacggcgg cgagcaagtt cacgttgccc gtggactccg agcacaaggc caagtccttc     180

aggctcttct ccttcgccaa cccacacatg cgcacctttc acctatcgtg gatatccttc     240

ttcacatgct tcgtctccac ctttgccgcg gcgcccctgg tgcccatcat ccgcgacaac     300

ctgaacctcg ccaaggccga catagggaat gccggtgtgg catctgtgtc tgggtctatc     360

ttctcgaggc ttgccatggg cgccatctgc gaccttttgg ggccgcggta tgggtgtgcc     420

ttcctcgtca tgctctcagc gccaaccgtc ttctgcatgg ccgtcatcga tgacgcctca     480

gggtacatcg ccgtacgctt cctcatcggc ttctcccttg ccacctttgt gtcgtgccaa     540

tactggatga gcaccatgtt caacagtaaa atcatcggca cggtcaatgg cctcgcggcc     600

ggctggggca acatgggcgg tggtgccaca caactcatca tgccgcttgt tttccacgcc     660

atccaaaaat gtggtgccac accatttgtg gcatggcgta ttgcctactt cgtgcccgga     720

atgatgcaca tcgtgatggg cttgctggta ctcaccatgg ggcaagatct ccctgatggg     780

aacctcgcga gcctccagaa gagaggagac atggccaagg acaagttctc caaggtcctt     840

tggggcgccg tcaccaacta ccggacatgg atctttgtcc tcctatatgg ctactgcatg     900

ggtgtcgaac tcaccactga caatgtcatt gccgagtact acttcgacca cttccaccta     960

gaccttcgcg ccgctggtac catcgccgcc tgcttcggta tggccaacat agtcgcacgt    1020

cctatgggcg gctacctctc tgaccttggc gcccgctatt tcggcatgcg tgccctttgg    1080

aacatctgga tcctccaaac cgctggtggc gctttctgca tctggctcgg tcgtgcatcg    1140

gccctccctg cctcggtgac cgccatggtc ctcttctcca tctgtgccca ggctgcctgt    1200

ggtgctatct ttggtgtcgc acccttcgtc tccaggcgtt cccttggcat catttccggg    1260

ttgaccggtg ccggtggaaa cgtgggcgca ggactcacac aacttctatt cttcacctca    1320

tcgcaatact ccactggtag gggtctcgag tacatgggca tcatgatcat ggcatgcacg    1380

ctgcccgtcg ctcttgtgca ctttccgcaa tggggatcca tgttcttccc ggccagcgct    1440

gatgccactg aggaggagta ctatgcttcc gagtggtcgg aggaggagaa gggcaagggt    1500
```

-continued

```
ctccatatcg caggccaaaa gttcgccgag aactcccgct cggagcgcgg caggcgcaac   1560

gtcatctttg ccacatccgc cacgccgccc aacaacacac cccagcaggt ataaggcatt   1620

tttttttgtt acctatgaat tttacagctc atggcgtata tatacaaaca gtatatttac   1680

gtttgcagcc ccagcgtaat aagttgtatg ggggtttatc tttttactat ggtaaaccta   1740

aggacatgta ttgtcaaatt gagtccgaaa ttaatacatg aacagtgttg atgtttgtgt   1800

atgcttgaaa aaaaaaaaaa aaaaa                                         1825


<210> SEQ ID NO 84
<211> LENGTH: 506
<212> TYPE: PRT
<213> ORGANISM: Hordeum vulgare

<400> SEQUENCE: 84

Met Glu Val Glu Ala Gly Ala His Gly Asp Thr Ala Ala Ser Lys Phe
1               5                   10                  15

Thr Leu Pro Val Asp Ser Glu His Lys Ala Lys Ser Phe Arg Leu Phe
            20                  25                  30

Ser Phe Ala Asn Pro His Met Arg Thr Phe His Leu Ser Trp Ile Ser
        35                  40                  45

Phe Phe Thr Cys Phe Val Ser Thr Phe Ala Ala Ala Pro Leu Val Pro
    50                  55                  60

Ile Ile Arg Asp Asn Leu Asn Leu Ala Lys Ala Asp Ile Gly Asn Ala
65                  70                  75                  80

Gly Val Ala Ser Val Ser Gly Ser Ile Phe Ser Arg Leu Ala Met Gly
                85                  90                  95

Ala Ile Cys Asp Leu Leu Gly Pro Arg Tyr Gly Cys Ala Phe Leu Val
            100                 105                 110

Met Leu Ser Ala Pro Thr Val Phe Cys Met Ala Val Ile Asp Asp Ala
        115                 120                 125

Ser Gly Tyr Ile Ala Val Arg Phe Leu Ile Gly Phe Ser Leu Ala Thr
    130                 135                 140

Phe Val Ser Cys Gln Tyr Trp Met Ser Thr Met Phe Asn Ser Lys Ile
145                 150                 155                 160

Ile Gly Thr Val Asn Gly Leu Ala Ala Gly Trp Gly Asn Met Gly Gly
                165                 170                 175

Gly Ala Thr Gln Leu Ile Met Pro Leu Val Phe His Ala Ile Gln Lys
            180                 185                 190

Cys Gly Ala Thr Pro Phe Val Ala Trp Arg Ile Ala Tyr Phe Val Pro
        195                 200                 205

Gly Met Met His Ile Val Met Gly Leu Leu Val Leu Thr Met Gly Gln
    210                 215                 220

Asp Leu Pro Asp Gly Asn Leu Ala Ser Leu Gln Lys Arg Gly Asp Met
225                 230                 235                 240

Ala Lys Asp Lys Phe Ser Lys Val Leu Trp Gly Ala Val Thr Asn Tyr
                245                 250                 255

Arg Thr Trp Ile Phe Val Leu Leu Tyr Gly Tyr Cys Met Gly Val Glu
            260                 265                 270

Leu Thr Thr Asp Asn Val Ile Ala Glu Tyr Tyr Phe Asp His Phe His
        275                 280                 285

Leu Asp Leu Arg Ala Ala Gly Thr Ile Ala Ala Cys Phe Gly Met Ala
    290                 295                 300

Asn Ile Val Ala Arg Pro Met Gly Gly Tyr Leu Ser Asp Leu Gly Ala
305                 310                 315                 320
```

```
Arg Tyr Phe Gly Met Arg Ala Leu Trp Asn Ile Trp Ile Leu Gln Thr
                325                 330                 335

Ala Gly Gly Ala Phe Cys Ile Trp Leu Gly Arg Ala Ser Ala Leu Pro
            340                 345                 350

Ala Ser Val Thr Ala Met Val Leu Phe Ser Ile Cys Ala Gln Ala Ala
        355                 360                 365

Cys Gly Ala Ile Phe Gly Val Ala Pro Phe Val Ser Arg Arg Ser Leu
    370                 375                 380

Gly Ile Ile Ser Gly Leu Thr Gly Ala Gly Gly Asn Val Gly Ala Gly
385                 390                 395                 400

Leu Thr Gln Leu Leu Phe Phe Thr Ser Ser Gln Tyr Ser Thr Gly Arg
                405                 410                 415

Gly Leu Glu Tyr Met Gly Ile Met Ile Met Ala Cys Thr Leu Pro Val
            420                 425                 430

Ala Leu Val His Phe Pro Gln Trp Gly Ser Met Phe Phe Pro Ala Ser
        435                 440                 445

Ala Asp Ala Thr Glu Glu Glu Tyr Tyr Ala Ser Glu Trp Ser Glu Glu
    450                 455                 460

Glu Lys Gly Lys Gly Leu His Ile Ala Gly Gln Lys Phe Ala Glu Asn
465                 470                 475                 480

Ser Arg Ser Glu Arg Gly Arg Arg Asn Val Ile Phe Ala Thr Ser Ala
                485                 490                 495

Thr Pro Pro Asn Asn Thr Pro Gln Gln Val
            500                 505


<210> SEQ ID NO 85
<211> LENGTH: 1885
<212> TYPE: DNA
<213> ORGANISM: Prunus persica

<400> SEQUENCE: 85

catttagtct aagtagtttc taaattcgaa acttgagtgc tgaaactcga gattcaaaat     60

ccaaactcca aaccccaaat tcaaaacccc aaaaacatgg ccgaagtcga aggtgaaccc    120

ggaagctcca tgcatggagt gacaggcaga gagcaaacct ttgcgttctc ggtagcttcc    180

cccatcgtcc caacagaccc aacagccaaa tttgacctac cagttgattc agagcacaag    240

gccaaagttt tcaaaatctt ctctttggcc aaccctcaca tgagaacttt ccacttgtct    300

tggatctctt tcttcacttg ctttgtctca acttttgcag cggccccact tgtccctata    360

atccgagaca acctcaacct cacaaagcaa gacattggaa atgctggggt tgcctctgtc    420

tcaggcagca tattctcaag acttgtaatg ggtgcagtgt gtgatttgct agggccacga    480

tatgggtgtg cctttctcat aatgctcagc gcacccactg tgttttgcat gtcatttgta    540

tctgatgctg gggctactt ggcagtgaga ttcatgattg gtttttcgct tgctacattc    600

gtgtcatgcc agtattggat gagtaccatg tttaacagta agattattgg gctggttaat    660

gggacagctg ctgggtgggg aaacatgggt ggtggggcca cccagctctt gatgccattg    720

gtgtttgata taattggaag agttggtgca actcctttca ctgcttggag aattgccttt    780

ttcattcctg gctggcttca tgtcattatg ggaataatgg tcttgaccct tggccaagac    840

ttgcctgatg ggaatcttgc tgccctgcaa aagaagggtg atgttgccaa agatcaattc    900

tccaaggtat tgtggcatgc tgtaacaaat tacaggacat ggatctttgt ccttctctat    960

ggctactcca tgggtgttga attgtccact gataatgtca ttgctgaata cttctatgac   1020
```

```
aggttcaatc tcaagcttca cacagctgga atcattgctg caacatttgg catggccaac   1080

ctagtagccc gtccctttgg aggatttgcg tctgatcgag cagccaggta ctttggcatg   1140

aggggcaggc tatggactct ttggatcctc caaacactag gaggagtctt ctgcatctgg   1200

ctcggccgag caaactcact ccccattgcg gtctttgcca tgatcctctt ctctgtagga   1260

gcccaagctg catgcggagc cacctttggc gtcatcccct tcatctcccg gcgatccctc   1320

ggcatcatat cgggcctcac tggagcgggt gggaacttcg ggtccgggct gacccaacta   1380

gtgttcttct caagctcagc attctcaact gcgacagggt tgtctctgat gggggtaatg   1440

atcgtgtgct gcacacttcc agtgactttg gtgcacttcc ctcagtgggg gagcatgttc   1500

cttccgcctt caaaagatgt cgtgaaatcg acggaagagt tttactatgg agctgagtgg   1560

aatgaggagg agaagcagaa ggggctacac cagcagagtt tgaggtttgc agagaatagt   1620

aggtctgagc gtggtaggcg tgttgcctca gctccaaccc cacccaacac cacaccttcc   1680

catgtttagg ttatgttatg atctcatgag aattgtttct ttgaaatgct ttgcaaactc   1740

ctcatgcgcc caattattct ccttaagttg accgagaagc ttacttctct cttggggaaa   1800

ttttttcttt attattatca gttttttccc aagcatataa gtgaactgat gattattttt   1860

atttcagaaa aaaaaaaaaa aaaaa                                         1885
```

<210> SEQ ID NO 86
<211> LENGTH: 530
<212> TYPE: PRT
<213> ORGANISM: Prunus persica

<400> SEQUENCE: 86

```
Met Ala Glu Val Glu Gly Glu Pro Gly Ser Ser Met His Gly Val Thr
1               5                   10                  15

Gly Arg Glu Gln Thr Phe Ala Phe Ser Val Ala Ser Pro Ile Val Pro
            20                  25                  30

Thr Asp Pro Thr Ala Lys Phe Asp Leu Pro Val Asp Ser Glu His Lys
        35                  40                  45

Ala Lys Val Phe Lys Ile Phe Ser Leu Ala Asn Pro His Met Arg Thr
    50                  55                  60

Phe His Leu Ser Trp Ile Ser Phe Phe Thr Cys Phe Val Ser Thr Phe
65                  70                  75                  80

Ala Ala Ala Pro Leu Val Pro Ile Ile Arg Asp Asn Leu Asn Leu Thr
                85                  90                  95

Lys Gln Asp Ile Gly Asn Ala Gly Val Ala Ser Val Ser Gly Ser Ile
            100                 105                 110

Phe Ser Arg Leu Val Met Gly Ala Val Cys Asp Leu Leu Gly Pro Arg
        115                 120                 125

Tyr Gly Cys Ala Phe Leu Ile Met Leu Ser Ala Pro Thr Val Phe Cys
    130                 135                 140

Met Ser Phe Val Ser Asp Ala Gly Gly Tyr Leu Ala Val Arg Phe Met
145                 150                 155                 160

Ile Gly Phe Ser Leu Ala Thr Phe Val Ser Cys Gln Tyr Trp Met Ser
                165                 170                 175

Thr Met Phe Asn Ser Lys Ile Ile Gly Leu Val Asn Gly Thr Ala Ala
            180                 185                 190

Gly Trp Gly Asn Met Gly Gly Gly Ala Thr Gln Leu Leu Met Pro Leu
        195                 200                 205

Val Phe Asp Ile Ile Gly Arg Val Gly Ala Thr Pro Phe Thr Ala Trp
    210                 215                 220
```

```
Arg Ile Ala Phe Phe Ile Pro Gly Trp Leu His Val Ile Met Gly Ile
225                 230                 235                 240

Met Val Leu Thr Leu Gly Gln Asp Leu Pro Asp Gly Asn Leu Ala Ala
                245                 250                 255

Leu Gln Lys Lys Gly Asp Val Ala Lys Asp Gln Phe Ser Lys Val Leu
            260                 265                 270

Trp His Ala Val Thr Asn Tyr Arg Thr Trp Ile Phe Val Leu Leu Tyr
        275                 280                 285

Gly Tyr Ser Met Gly Val Glu Leu Ser Thr Asp Asn Val Ile Ala Glu
    290                 295                 300

Tyr Phe Tyr Asp Arg Phe Asn Leu Lys Leu His Thr Ala Gly Ile Ile
305                 310                 315                 320

Ala Ala Thr Phe Gly Met Ala Asn Leu Val Ala Arg Pro Phe Gly Gly
                325                 330                 335

Phe Ala Ser Asp Arg Ala Ala Arg Tyr Phe Gly Met Arg Gly Arg Leu
            340                 345                 350

Trp Thr Leu Trp Ile Leu Gln Thr Leu Gly Gly Val Phe Cys Ile Trp
        355                 360                 365

Leu Gly Arg Ala Asn Ser Leu Pro Ile Ala Val Phe Ala Met Ile Leu
    370                 375                 380

Phe Ser Val Gly Ala Gln Ala Ala Cys Gly Ala Thr Phe Gly Val Ile
385                 390                 395                 400

Pro Phe Ile Ser Arg Arg Ser Leu Gly Ile Ile Ser Gly Leu Thr Gly
                405                 410                 415

Ala Gly Gly Asn Phe Gly Ser Gly Leu Thr Gln Leu Val Phe Phe Ser
            420                 425                 430

Ser Ser Ala Phe Ser Thr Ala Thr Gly Leu Ser Leu Met Gly Val Met
        435                 440                 445

Ile Val Cys Cys Thr Leu Pro Val Thr Leu Val His Phe Pro Gln Trp
    450                 455                 460

Gly Ser Met Phe Leu Pro Pro Ser Lys Asp Val Val Lys Ser Thr Glu
465                 470                 475                 480

Glu Phe Tyr Tyr Gly Ala Glu Trp Asn Glu Glu Glu Lys Gln Lys Gly
                485                 490                 495

Leu His Gln Gln Ser Leu Arg Phe Ala Glu Asn Ser Arg Ser Glu Arg
            500                 505                 510

Gly Arg Arg Val Ala Ser Ala Pro Thr Pro Pro Asn Thr Thr Pro Ser
        515                 520                 525

His Val
    530
```

<210> SEQ ID NO 87
<211> LENGTH: 1962
<212> TYPE: DNA
<213> ORGANISM: Prunus persica

<400> SEQUENCE: 87

```
gcttcattta gtctaagtag tttctaaatt cgaaactcga gttttgaaac tcgagattca      60

aaatccaaac tccaaacccc aaataatggc cgaagtcgaa ggtgaacccg gaagctccat     120

gcatggagtg acaggcagag agcaaacctt tgcgttctca gtagcttccc ccatcgtccc     180

aacagaccca acagctaaat ttgacctacc tgttgattca gagcacaagg ccaaagtttt     240

caaaatcttc tctttggcca acccgcacat gagaaccttc cacttgtctt ggatctcctt     300
```

```
cttcacttgc tttgtctcaa cttttgcagc ggccccactt gtccctataa tccgagacaa    360

cctcaacctc acaaagcaag acattggaaa tgctggggtt gcctctgtct caggcagcat    420

attctcaaga cttgtaatgg gtgcagtgtg tgatttgcta gggccacgat atgggtgtgc    480

ctttctcata atgctcagcg cacccactgt gttttgcatg tcatttgtat ctgatgctgg    540

gggctacttg gcagtgagat tcatgattgg tttttcgctt gctacattcg tgtcatgcca    600

gtattggatg agtaccatgt ttaacagtaa gattattggg ctggttaatg ggacagctgc    660

tgggtgggga aacatgggtg gtggggccac ccagctcttg atgccattgg tgtttgatat    720

aattggaaga gttggtgcaa ctcctttcac tgcttggaga attgcctttt tcatccctgg    780

ctggcttcat gtcattatgg gaataatggt cttgaccctt ggccaagact tgcctgatgg    840

aaatcttgct gccctgcaaa agaagggtga tgttgccaaa gatcaattct ccaaggtatt    900

gtggcatgct ataacaaact acaggacatg gatctttgtc cttctctatg gctactccat    960

gggtgttgaa ttgtccattg ataatgtcat tgctgaatac ttctatgaca ggttcaatct   1020

caagcttcac acagctggaa tcattgctgc agcatttggc atggccaaca tagtggcccg   1080

tccctttgga ggatttgcgt ctgatcgagc agccaggtac tttggcatga ggggcaggct   1140

atggactctt tggatcctcc aaacactagg aggagtcttt tgcatctggc tcggccgagc   1200

aaactcactc cccattgcgg tctttgccat gatcctcttc tctgtaggag cccaagctgc   1260

atgcggagcc acctttggcg tcatcccctt catctcccgg cgatccctcg gcatcatatc   1320

gggcctcact ggagcgggtg ggaacttcgg atccgggctg acccaactag tgttcttctc   1380

aagcgcagca ttctcaactg cgacagggtt gtctctgatg gggtaatga tcgtgtgctg    1440

cacacttcca gtgactttgg tgcacttccc tcagtggggg agcatgttcc ttccgccttc   1500

aaaagatgtc gtgaaatcaa cggaagagtt ttactatgga gctgagtgga atgaggagga   1560

gaagcagaag ggctacacc agcagagttt gaggtttgca gagaatagta ggtctgagcg    1620

tggtaggcgt gttgcctcag ctccaacccc acccaacacc acaccttccc atgtttagtc   1680

aaacaaggga aaaaggtcaa catgcaccaa ggtgcatatg tggtgtggaa caaaccaata   1740

atcagagaag tgctattttg tatcatctca atcaatcata tgtgtactgt atttctatta   1800

gaaatacaag agatgatcag ttgagttgat acaagtagtt ttatttgtaa tgaaaataga   1860

gttgccatat agcgtgtgcc tctatatatg tatcttgtac acaaatgttt ttactttcaa   1920

ggtttaaact tatgataatt ttcaaaaaaa aaaaaaaaaa aa                      1962
```

<210> SEQ ID NO 88
<211> LENGTH: 530
<212> TYPE: PRT
<213> ORGANISM: Prunus persica

<400> SEQUENCE: 88

```
Met Ala Glu Val Glu Gly Glu Pro Gly Ser Ser Met His Gly Val Thr
1               5                   10                  15

Gly Arg Glu Gln Thr Phe Ala Phe Ser Val Ala Ser Pro Ile Val Pro
            20                  25                  30

Thr Asp Pro Thr Ala Lys Phe Asp Leu Pro Val Asp Ser Glu His Lys
        35                  40                  45

Ala Lys Val Phe Lys Ile Phe Ser Leu Ala Asn Pro His Met Arg Thr
    50                  55                  60

Phe His Leu Ser Trp Ile Ser Phe Phe Thr Cys Phe Val Ser Thr Phe
65                  70                  75                  80
```

```
Ala Ala Ala Pro Leu Val Pro Ile Ile Arg Asp Asn Leu Asn Leu Thr
                85                  90                  95

Lys Gln Asp Ile Gly Asn Ala Gly Val Ala Ser Val Ser Gly Ser Ile
            100                 105                 110

Phe Ser Arg Leu Val Met Gly Ala Val Cys Asp Leu Leu Gly Pro Arg
        115                 120                 125

Tyr Gly Cys Ala Phe Leu Ile Met Leu Ser Ala Pro Thr Val Phe Cys
    130                 135                 140

Met Ser Phe Val Ser Asp Ala Gly Gly Tyr Leu Ala Val Arg Phe Met
145                 150                 155                 160

Ile Gly Phe Ser Leu Ala Thr Phe Val Ser Cys Gln Tyr Trp Met Ser
                165                 170                 175

Thr Met Phe Asn Ser Lys Ile Ile Gly Leu Val Asn Gly Thr Ala Ala
            180                 185                 190

Gly Trp Gly Asn Met Gly Gly Gly Ala Thr Gln Leu Leu Met Pro Leu
        195                 200                 205

Val Phe Asp Ile Ile Gly Arg Val Gly Ala Thr Pro Phe Thr Ala Trp
    210                 215                 220

Arg Ile Ala Phe Phe Ile Pro Gly Trp Leu His Val Ile Met Gly Ile
225                 230                 235                 240

Met Val Leu Thr Leu Gly Gln Asp Leu Pro Asp Gly Asn Leu Ala Ala
                245                 250                 255

Leu Gln Lys Lys Gly Asp Val Ala Lys Asp Gln Phe Ser Lys Val Leu
            260                 265                 270

Trp His Ala Ile Thr Asn Tyr Arg Thr Trp Ile Phe Val Leu Leu Tyr
        275                 280                 285

Gly Tyr Ser Met Gly Val Glu Leu Ser Ile Asp Asn Val Ile Ala Glu
    290                 295                 300

Tyr Phe Tyr Asp Arg Phe Asn Leu Lys Leu His Thr Ala Gly Ile Ile
305                 310                 315                 320

Ala Ala Ala Phe Gly Met Ala Asn Ile Val Ala Arg Pro Phe Gly Gly
                325                 330                 335

Phe Ala Ser Asp Arg Ala Ala Arg Tyr Phe Gly Met Arg Gly Arg Leu
            340                 345                 350

Trp Thr Leu Trp Ile Leu Gln Thr Leu Gly Gly Val Phe Cys Ile Trp
        355                 360                 365

Leu Gly Arg Ala Asn Ser Leu Pro Ile Ala Val Phe Ala Met Ile Leu
    370                 375                 380

Phe Ser Val Gly Ala Gln Ala Ala Cys Gly Ala Thr Phe Gly Val Ile
385                 390                 395                 400

Pro Phe Ile Ser Arg Arg Ser Leu Gly Ile Ile Ser Gly Leu Thr Gly
                405                 410                 415

Ala Gly Gly Asn Phe Gly Ser Gly Leu Thr Gln Leu Val Phe Phe Ser
            420                 425                 430

Ser Ala Ala Phe Ser Thr Ala Thr Gly Leu Ser Leu Met Gly Val Met
        435                 440                 445

Ile Val Cys Cys Thr Leu Pro Val Thr Leu Val His Phe Pro Gln Trp
    450                 455                 460

Gly Ser Met Phe Leu Pro Pro Ser Lys Asp Val Val Lys Ser Thr Glu
465                 470                 475                 480

Glu Phe Tyr Tyr Gly Ala Glu Trp Asn Glu Glu Glu Lys Gln Lys Gly
                485                 490                 495

Leu His Gln Gln Ser Leu Arg Phe Ala Glu Asn Ser Arg Ser Glu Arg
```

-continued 500 505 510

Gly Arg Arg Val Ala Ser Ala Pro Thr Pro Pro Asn Thr Thr Pro Ser
515 520 525

His Val
530

<210> SEQ ID NO 89
<211> LENGTH: 1890
<212> TYPE: DNA
<213> ORGANISM: Glycine max

<400> SEQUENCE: 89
tcacactttc ttccttaatt ttctagctct tgctacgtac ttgaattcaa ttagttatta 60
atggctgaga ttgagggttc tcccggaagc tccatgcatg gagtaacagg aagagaacaa 120
acatttgtag cctcagttgc ttctccaatt gtccctacag acaccacagc caaatttgct 180
ctcccagtgg attcagaaca caaggccaag gttttcaaac tcttctccct ggccaatccc 240
cacatgagaa ccttccacct ttcttggatc tccttcttca cctgcttcgt ctcgacattc 300
gcagcagcac ctcttgtgcc catcatccgc gacaacctta acctcaccaa aagcgacatt 360
ggaaacgccg gggttgcttc tgtctccgga agcatcttct caaggctcgc aatgggtgca 420
gtctgtgaca tgttgggtcc acgctatggc tgcgccttcc tcatcatgct ttcggcccct 480
acggtgttct gcatgtcctt tgtgaaagat gctgcggggt acatagcggt tcggttcttg 540
attgggttct cgttggcgac gtttgtgtcg tgccagtact ggatgagcac gatgttcaac 600
agtaagatta tagggcttgc gaatgggact gctgcggggt gggggaacat gggtggtgga 660
gccactcagc tcataatgcc tttggtgtat gagcttatca gaagagctgg ggctactccc 720
ttcactgctt ggaggattgc cttctttgtt ccgggtttca tgcatgtcat catggggatt 780
cttgtcctca ctctaggcca ggacttgcct gatggaaacc tcggggcctt gcggaagaag 840
ggtgatgtag ctaaagacaa gttttccaag gtgctatggt atgccataac aaattacagg 900
acatggattt ttgctctcct ctatgggtac tccatgggag ttgaattaac aactgacaat 960
gtcattgctg agtatttcta tgacagattt aatctcaagc tacacactgc tggaatcatt 1020
gctgcttcat ttggaatggc aaacttagtt gctcgacctt ttggtggata tgcttcagat 1080
gttgcagcca ggctgtttgg catgagggga agactctgga ccctttggat cctccaaacc 1140
ttaggagggg ttttctgtat ttggcttggc cgtgccaatt ctcttcctat tgctgtattg 1200
gccatgatcc tgttctctat aggagctcaa gctgcatgtg gtgcaacttt tggcatcatt 1260
cctttcatct caagaaggtc tttggggatc atatcaggtc taactggtgc aggtggaaac 1320
tttgggtctg gcctcaccca attggtcttc ttttcaacct ccaaattctc tactgccaca 1380
ggtctctcct tgatgggtgt aatgatagtg gcttgcactc taccagtgag tgttgttcac 1440
ttcccacagt ggggtagcat gtttctacca ccctcaaaag atgtcagcaa atccactgaa 1500
gaattctatt acacctctga atggaatgag gaagagaagc agaagggttt gcaccagcaa 1560
agtctcaaat ttgctgagaa tagccgatct gagagaggaa agcgagtggc ttcagcacca 1620
acacctccaa atgcaactcc cactcatgtc tagccatagc acttcaatca aagaagatca 1680
tgaaacataa ttactgagca gtattgggaa tgaagaacca tgagttgaag aattttctaa 1740
taagaaatct tgtaacatgt agacatagaa tgttctggtt ctggtttgcg tgtggtgtaa 1800
gagttgtcta cttgtggtaa gtcataagta tcataatcag tatgtcaatg cagatcttga 1860
tgctgagtat caatagtatc aaaaaaaaaa 1890

<210> SEQ ID NO 90
<211> LENGTH: 530
<212> TYPE: PRT
<213> ORGANISM: Glycine max

<400> SEQUENCE: 90

Met Ala Glu Ile Glu Gly Ser Pro Gly Ser Ser Met His Gly Val Thr
1 5 10 15

Gly Arg Glu Gln Thr Phe Val Ala Ser Val Ala Ser Pro Ile Val Pro
20 25 30

Thr Asp Thr Thr Ala Lys Phe Ala Leu Pro Val Asp Ser Glu His Lys
35 40 45

Ala Lys Val Phe Lys Leu Phe Ser Leu Ala Asn Pro His Met Arg Thr
50 55 60

Phe His Leu Ser Trp Ile Ser Phe Phe Thr Cys Phe Val Ser Thr Phe
65 70 75 80

Ala Ala Ala Pro Leu Val Pro Ile Ile Arg Asp Asn Leu Asn Leu Thr
85 90 95

Lys Ser Asp Ile Gly Asn Ala Gly Val Ala Ser Val Ser Gly Ser Ile
100 105 110

Phe Ser Arg Leu Ala Met Gly Ala Val Cys Asp Met Leu Gly Pro Arg
115 120 125

Tyr Gly Cys Ala Phe Leu Ile Met Leu Ser Ala Pro Thr Val Phe Cys
130 135 140

Met Ser Phe Val Lys Asp Ala Ala Gly Tyr Ile Ala Val Arg Phe Leu
145 150 155 160

Ile Gly Phe Ser Leu Ala Thr Phe Val Ser Cys Gln Tyr Trp Met Ser
165 170 175

Thr Met Phe Asn Ser Lys Ile Ile Gly Leu Ala Asn Gly Thr Ala Ala
180 185 190

Gly Trp Gly Asn Met Gly Gly Gly Ala Thr Gln Leu Ile Met Pro Leu
195 200 205

Val Tyr Glu Leu Ile Arg Arg Ala Gly Ala Thr Pro Phe Thr Ala Trp
210 215 220

Arg Ile Ala Phe Phe Val Pro Gly Phe Met His Val Ile Met Gly Ile
225 230 235 240

Leu Val Leu Thr Leu Gly Gln Asp Leu Pro Asp Gly Asn Leu Gly Ala
245 250 255

Leu Arg Lys Lys Gly Asp Val Ala Lys Asp Lys Phe Ser Lys Val Leu
260 265 270

Trp Tyr Ala Ile Thr Asn Tyr Arg Thr Trp Ile Phe Ala Leu Leu Tyr
275 280 285

Gly Tyr Ser Met Gly Val Glu Leu Thr Thr Asp Asn Val Ile Ala Glu
290 295 300

Tyr Phe Tyr Asp Arg Phe Asn Leu Lys Leu His Thr Ala Gly Ile Ile
305 310 315 320

Ala Ala Ser Phe Gly Met Ala Asn Leu Val Ala Arg Pro Phe Gly Gly
325 330 335

Tyr Ala Ser Asp Val Ala Ala Arg Leu Phe Gly Met Arg Gly Arg Leu
340 345 350

Trp Thr Leu Trp Ile Leu Gln Thr Leu Gly Gly Val Phe Cys Ile Trp
355 360 365

Leu Gly Arg Ala Asn Ser Leu Pro Ile Ala Val Leu Ala Met Ile Leu

```
    370                 375                 380

Phe Ser Ile Gly Ala Gln Ala Ala Cys Gly Ala Thr Phe Gly Ile Ile
385                 390                 395                 400

Pro Phe Ile Ser Arg Arg Ser Leu Gly Ile Ile Ser Gly Leu Thr Gly
                405                 410                 415

Ala Gly Gly Asn Phe Gly Ser Gly Leu Thr Gln Leu Val Phe Phe Ser
            420                 425                 430

Thr Ser Lys Phe Ser Thr Ala Thr Gly Leu Ser Leu Met Gly Val Met
        435                 440                 445

Ile Val Ala Cys Thr Leu Pro Val Ser Val Val His Phe Pro Gln Trp
    450                 455                 460

Gly Ser Met Phe Leu Pro Pro Ser Lys Asp Val Ser Lys Ser Thr Glu
465                 470                 475                 480

Glu Phe Tyr Tyr Thr Ser Glu Trp Asn Glu Glu Glu Lys Gln Lys Gly
                485                 490                 495

Leu His Gln Gln Ser Leu Lys Phe Ala Glu Asn Ser Arg Ser Glu Arg
            500                 505                 510

Gly Lys Arg Val Ala Ser Ala Pro Thr Pro Pro Asn Ala Thr Pro Thr
        515                 520                 525

His Val
    530


<210> SEQ ID NO 91
<211> LENGTH: 1990
<212> TYPE: DNA
<213> ORGANISM: Lotus japonicus

<400> SEQUENCE: 91

gcacaagttt ttctctgttg catgttctgt ttctgaatta ctttaattac ttcacacaac     60

aacattcaac aatggttgaa attgaaggat ctccaggaac ctccatgcat ggagtaacag    120

ggagggaaca aaccttcata tcctcagttt cttccccaat ggtcccaaca gacaccacag    180

ccaaattcga tttaccagtt gattcacagc acaaagccaa agttttcaaa ctgttctcat    240

tagctaatcc tcacatgaca accttccact tatcatggat ttccttcttc acctgctttg    300

tctctacctt tgcagcagct cctcttgtcc ccatcatccg agacaacctc aatctcacca    360

aaagcgacat tggcaacgcc ggtgtcgcgt ctgtctccgg cagcattttc tccaggctca    420

ccatgggtgt aatttgtgac ctcttaggcc cacgttacgg gtgtgccttc ctgatcatgc    480

tgtctgcacc aactgtgttc tgcatgtcgt ttgtgaatga tgctgcaggc tacattgtgg    540

ttcggttcat gatcgggttc tcattggcca cgtttgtttc gtgccagtac tggatgagta    600

ccatgtttaa cagtaagatt attgggcttg ttaatggaac tgcagctggt tggggtaaca    660

tgggtggtgg agccactcag ctcatcatgc ctattgtcta tgaattgatc aggagagcgg    720

ggtccactgg gttcactgct tggaggattg ccttcttcat ccctggtttc atgcatgttt    780

tcatggggat ccttgtctta acccttggcc aagacttgcc tgatggcaac ctcagtgccc    840

tccagaagaa gggtgatgtt gctaaagaca aattctccaa ggtgttatgg tatgccataa    900

caaattacag gacatggatc tttgcacttc tctatggata ctctatggga gtcgaattaa    960

ccactgacaa tgtcattgct gagtattttt atgacagatt taatctgaag ttgcacacag   1020

ttggaatcat tgctgcttct tttggaatgg caaatcttgt tgctcgcccc tttggcggat   1080

atgtatctga tgttgcagcc cggttgtttg gtatgagagg aagactgtgg actctgtgga   1140

tcctccaaac acttggagga gtgttctgta tatggcttgg gcgtgcgaat tcacttccaa   1200
```

```
ttgcggtgtt ggcgatgatc cttttctcag ttggagctca agctgcttgt ggtgcaacat   1260
ttggaatcat tcctttcatc tcaaaaaggt ctttggggat catttcaggt ctaactggtg   1320
caggtggcaa ctttggttct ggattgacac agttggtatt cttttctact tcaagattct   1380
ccacaggtgc aggattgtca tggatgggtg tgatgattgt tggttgcact cttccggtga   1440
ctcttgttca cttcccacag tggggtagca tgttccttcc tccttcaaaa gacatcaaca   1500
agtccagtga ggaacactat tacactgctg aatgggatga ggaagagagg aagaaggggt   1560
tgcactctca aagtcttaag tttgcagaga atagtcgctc tgagagagga aaacgtgttt   1620
cctctgctcc aactcctcca aacacaaccc ctacccatgt ctaagatgga tggatgatca   1680
ccacagtgga aagctaatga ggaaaagagt atatggatcc cttgattgaa taatttatcc   1740
ttaagccttt aaagatactt tggcatccag aaatttggtg tttgcccttc aaattctact   1800
tgttatagaa atttggtgtg attttctata agggactttg gtgtctgtgg gagtgtgggt   1860
ctatcagtta attatacaaa caggtggtgt acaaaaataa tatattgagt tttttaattt   1920
tggtgtgata tatattaatg aatgttactc aaaaaaaaaa aaaaaaaaaa actcgagggg   1980
gggcccggta                                                          1990
```

<210> SEQ ID NO 92
<211> LENGTH: 530
<212> TYPE: PRT
<213> ORGANISM: Lotus japonicus

<400> SEQUENCE: 92

```
Met Val Glu Ile Glu Gly Ser Pro Gly Thr Ser Met His Gly Val Thr
1               5                   10                  15

Gly Arg Glu Gln Thr Phe Ile Ser Ser Val Ser Ser Pro Met Val Pro
            20                  25                  30

Thr Asp Thr Thr Ala Lys Phe Asp Leu Pro Val Asp Ser Gln His Lys
        35                  40                  45

Ala Lys Val Phe Lys Leu Phe Ser Leu Ala Asn Pro His Met Thr Thr
    50                  55                  60

Phe His Leu Ser Trp Ile Ser Phe Phe Thr Cys Phe Val Ser Thr Phe
65                  70                  75                  80

Ala Ala Ala Pro Leu Val Pro Ile Ile Arg Asp Asn Leu Asn Leu Thr
                85                  90                  95

Lys Ser Asp Ile Gly Asn Ala Gly Val Ala Ser Val Ser Gly Ser Ile
            100                 105                 110

Phe Ser Arg Leu Thr Met Gly Val Ile Cys Asp Leu Leu Gly Pro Arg
        115                 120                 125

Tyr Gly Cys Ala Phe Leu Ile Met Leu Ser Ala Pro Thr Val Phe Cys
    130                 135                 140

Met Ser Phe Val Asn Asp Ala Ala Gly Tyr Ile Val Val Arg Phe Met
145                 150                 155                 160

Ile Gly Phe Ser Leu Ala Thr Phe Val Ser Cys Gln Tyr Trp Met Ser
                165                 170                 175

Thr Met Phe Asn Ser Lys Ile Ile Gly Leu Val Asn Gly Thr Ala Ala
            180                 185                 190

Gly Trp Gly Asn Met Gly Gly Gly Ala Thr Gln Leu Ile Met Pro Ile
        195                 200                 205

Val Tyr Glu Leu Ile Arg Arg Ala Gly Ser Thr Gly Phe Thr Ala Trp
    210                 215                 220
```

```
Arg Ile Ala Phe Phe Ile Pro Gly Phe Met His Val Phe Met Gly Ile
225                 230                 235                 240

Leu Val Leu Thr Leu Gly Gln Asp Leu Pro Asp Gly Asn Leu Ser Ala
                245                 250                 255

Leu Gln Lys Lys Gly Asp Val Ala Lys Asp Lys Phe Ser Lys Val Leu
            260                 265                 270

Trp Tyr Ala Ile Thr Asn Tyr Arg Thr Trp Ile Phe Ala Leu Leu Tyr
        275                 280                 285

Gly Tyr Ser Met Gly Val Glu Leu Thr Thr Asp Asn Val Ile Ala Glu
    290                 295                 300

Tyr Phe Tyr Asp Arg Phe Asn Leu Lys Leu His Thr Val Gly Ile Ile
305                 310                 315                 320

Ala Ala Ser Phe Gly Met Ala Asn Leu Val Ala Arg Pro Phe Gly Gly
                325                 330                 335

Tyr Val Ser Asp Val Ala Ala Arg Leu Phe Gly Met Arg Gly Arg Leu
            340                 345                 350

Trp Thr Leu Trp Ile Leu Gln Thr Leu Gly Gly Val Phe Cys Ile Trp
        355                 360                 365

Leu Gly Arg Ala Asn Ser Leu Pro Ile Ala Val Leu Ala Met Ile Leu
    370                 375                 380

Phe Ser Val Gly Ala Gln Ala Ala Cys Gly Ala Thr Phe Gly Ile Ile
385                 390                 395                 400

Pro Phe Ile Ser Lys Arg Ser Leu Gly Ile Ile Ser Gly Leu Thr Gly
                405                 410                 415

Ala Gly Gly Asn Phe Gly Ser Gly Leu Thr Gln Leu Val Phe Phe Ser
            420                 425                 430

Thr Ser Arg Phe Ser Thr Gly Ala Gly Leu Ser Trp Met Gly Val Met
        435                 440                 445

Ile Val Gly Cys Thr Leu Pro Val Thr Leu Val His Phe Pro Gln Trp
    450                 455                 460

Gly Ser Met Phe Leu Pro Pro Ser Lys Asp Ile Asn Lys Ser Ser Glu
465                 470                 475                 480

Glu His Tyr Tyr Thr Ala Glu Trp Asp Glu Glu Glu Arg Lys Lys Gly
                485                 490                 495

Leu His Ser Gln Ser Leu Lys Phe Ala Glu Asn Ser Arg Ser Glu Arg
            500                 505                 510

Gly Lys Arg Val Ser Ser Ala Pro Thr Pro Pro Asn Thr Thr Pro Thr
        515                 520                 525

His Val
    530
```

<210> SEQ ID NO 93
<211> LENGTH: 1838
<212> TYPE: DNA
<213> ORGANISM: Nicotiana tabacum

<400> SEQUENCE: 93

```
ttaaagaaga aattaaaaat ggttgatatt gaaggatcac caggtagttc tatgcatgga      60

gttacaggta gagaaccagt tcttgctttc tctgttgcat ctccaatggt acaaactgat     120

accactgcac attttaaagt tccggtcgat tctgaacaca aggccaaggt tttcaaattc     180

tactcatttt caaaacctca cggtctaact tttcaacttt cttggatttc tttctttact     240

tgttttgttt ctacttttgc tgctgcccct ttagttccta ttattagaga caaccttaac     300

ttgaccaaaa tggacgttgg taatgctggg gttgcctctg tttccggaag tattctatct     360
```

-continued

```
aggcttgcaa tgggtgcgat ttgtgacatg ttgggaccaa gatatggatg cgcgtttctt    420

atcatgttat cagctccgac tgttttttgc atgtctttcg tgtcttcggc tggtggctac    480

gttgctgtga gattcatgat tggattctca ctcgcgacgt ttgtgtcgtg tcaatattgg    540

atgagtacga tgtttaatag tcagattatt ggacttgtta atggaacagc agcaggatgg    600

ggaaatatgg ggggtggagc tactcagctt attatgccta ttctctatga tattattaga    660

agagcaggag ccaccccttt tactgcttgg agaattgctt tctttattcc tggttggctt    720

catgttatta tgggaatttt agtgttaact cttggccaag atttgcctga tggtaacctt    780

gcttccctac agaagaaagg cgatgtttct aaagataagt tctctaagat attgtggtat    840

gctgcaacaa attacaggac atggatcttt gtcctgctct atggttactc catgggagtt    900

gaattgacta cagataatgt gattgctgag tacttctttg atagatttga tctaaagctt    960

cacacggctg gaatcattgc tgccacattt ggtatggcta atctcttagc tcgacctttt   1020

ggaggatggt catcagatat tgcagccaaa cattttggaa tgagaggcag attatggaac   1080

ttatggattt tacaaacact tggtggtgtt ttctgtttct tacttggaaa agcaaacaca   1140

cttcctatgg ctatagcttg gatgatcata ttctccttag gtgctcaagc agcatgtgga   1200

gctacatttg gtattattcc tttcatttcg cgtcgatcgt taggtataat ctcaggtatg   1260

acaggagctg gaggaaattt tggttctgga ttgacacaac tcttgttttt cacaactaca   1320

aaatggtcaa cagaaacagg attgagttat atggggatta tgattatagc ttgtacactt   1380

cctgtatctt tggttcattt cccacaatgg ggaagtatgt tttgcctcc aactaaagat    1440

cctgttaaga gtactgaaga gcattacttc acgtctgagt acactgaggc tgagaagcaa   1500

aagggtatgc accaaaaacag catcaagttt gctgaaaact gtcggtcgga gcgtggtaag   1560

cgtgtgggtt cagctcttac tccgcctaat gtaacgccaa accgtgtctg agcttgagtc   1620

tcacggatca gtacggagaa atagtgattt tgaaaagctt acttgcttaa ttggtgtttg   1680

tatcaacaca ataaacgtgt gatatgtgtc ttttaatgag ctttatatta cccaagtgtg   1740

agtagttaat ttgtattatc actttgtgtt gtgagactga tcttaatatt aaaacagttg   1800

atttggtgta aactttcatt aaaaaaaaaa aaaaaaaa                           1838
```

<210> SEQ ID NO 94
<211> LENGTH: 530
<212> TYPE: PRT
<213> ORGANISM: Nicotiana tabacum

<400> SEQUENCE: 94

```
Met Val Asp Ile Glu Gly Ser Pro Gly Ser Ser Met His Gly Val Thr
1               5                   10                  15

Gly Arg Glu Pro Val Leu Ala Phe Ser Val Ala Ser Pro Met Val Gln
            20                  25                  30

Thr Asp Thr Thr Ala His Phe Lys Val Pro Val Asp Ser Glu His Lys
        35                  40                  45

Ala Lys Val Phe Lys Phe Tyr Ser Phe Ser Lys Pro His Gly Leu Thr
    50                  55                  60

Phe Gln Leu Ser Trp Ile Ser Phe Phe Thr Cys Phe Val Ser Thr Phe
65                  70                  75                  80

Ala Ala Ala Pro Leu Val Pro Ile Ile Arg Asp Asn Leu Asn Leu Thr
                85                  90                  95

Lys Met Asp Val Gly Asn Ala Gly Val Ala Ser Val Ser Gly Ser Ile
            100                 105                 110
```

-continued

```
Leu Ser Arg Leu Ala Met Gly Ala Ile Cys Asp Met Leu Gly Pro Arg
        115                 120                 125

Tyr Gly Cys Ala Phe Leu Ile Met Leu Ser Ala Pro Thr Val Phe Cys
    130                 135                 140

Met Ser Phe Val Ser Ser Ala Gly Gly Tyr Val Ala Val Arg Phe Met
145                 150                 155                 160

Ile Gly Phe Ser Leu Ala Thr Phe Val Ser Cys Gln Tyr Trp Met Ser
                165                 170                 175

Thr Met Phe Asn Ser Gln Ile Ile Gly Leu Val Asn Gly Thr Ala Ala
            180                 185                 190

Gly Trp Gly Asn Met Gly Gly Gly Ala Thr Gln Leu Ile Met Pro Ile
        195                 200                 205

Leu Tyr Asp Ile Ile Arg Arg Ala Gly Ala Thr Pro Phe Thr Ala Trp
    210                 215                 220

Arg Ile Ala Phe Phe Ile Pro Gly Trp Leu His Val Ile Met Gly Ile
225                 230                 235                 240

Leu Val Leu Thr Leu Gly Gln Asp Leu Pro Asp Gly Asn Leu Ala Ser
                245                 250                 255

Leu Gln Lys Lys Gly Asp Val Ser Lys Asp Lys Phe Ser Lys Ile Leu
            260                 265                 270

Trp Tyr Ala Ala Thr Asn Tyr Arg Thr Trp Ile Phe Val Leu Leu Tyr
        275                 280                 285

Gly Tyr Ser Met Gly Val Glu Leu Thr Thr Asp Asn Val Ile Ala Glu
    290                 295                 300

Tyr Phe Phe Asp Arg Phe Asp Leu Lys Leu His Thr Ala Gly Ile Ile
305                 310                 315                 320

Ala Ala Thr Phe Gly Met Ala Asn Leu Leu Ala Arg Pro Phe Gly Gly
                325                 330                 335

Trp Ser Ser Asp Ile Ala Ala Lys His Phe Gly Met Arg Gly Arg Leu
            340                 345                 350

Trp Asn Leu Trp Ile Leu Gln Thr Leu Gly Gly Val Phe Cys Phe Leu
        355                 360                 365

Leu Gly Lys Ala Asn Thr Leu Pro Met Ala Ile Ala Trp Met Ile Ile
    370                 375                 380

Phe Ser Leu Gly Ala Gln Ala Ala Cys Gly Ala Thr Phe Gly Ile Ile
385                 390                 395                 400

Pro Phe Ile Ser Arg Arg Ser Leu Gly Ile Ile Ser Gly Met Thr Gly
                405                 410                 415

Ala Gly Gly Asn Phe Gly Ser Gly Leu Thr Gln Leu Leu Phe Phe Thr
            420                 425                 430

Thr Thr Lys Trp Ser Thr Glu Thr Gly Leu Ser Tyr Met Gly Ile Met
        435                 440                 445

Ile Ile Ala Cys Thr Leu Pro Val Ser Leu Val His Phe Pro Gln Trp
    450                 455                 460

Gly Ser Met Phe Leu Pro Pro Thr Lys Asp Pro Val Lys Ser Thr Glu
465                 470                 475                 480

Glu His Tyr Phe Thr Ser Glu Tyr Thr Glu Ala Glu Lys Gln Lys Gly
                485                 490                 495

Met His Gln Asn Ser Ile Lys Phe Ala Glu Asn Cys Arg Ser Glu Arg
            500                 505                 510

Gly Lys Arg Val Gly Ser Ala Leu Thr Pro Pro Asn Val Thr Pro Asn
        515                 520                 525
```

Arg Val
530

<210> SEQ ID NO 95
<211> LENGTH: 1646
<212> TYPE: DNA
<213> ORGANISM: Lycopersicon esculentum

<400> SEQUENCE: 95
gcctaaaatg ggtgatattg aaggatcacc aggaagttca atgcatggtg ttactggtag 60
agagccagtt cttgcatttt cagttgcttc actaattgta ccaactgata catcagccaa 120
tttcaaagtc cctgttgatt ctgaacataa agctaaagtt tttaaatttt attcgttttc 180
gaaacctcat ggactaacgt ttcaactctc atggatttca ttttgtactt gtttcgtatc 240
gacttttgct gcagcccctt tagtccctat tattagggac aatcttaatc taactaaaat 300
ggatgttggt aatgctggag ttgcctctgt ttcgggtagt atcttgtcta ggctagctat 360
gggcgcgatt tgtgacatgt taggtcctag atatggttgc gcgttcctta taatgttatc 420
agccccaact gttttatgta tgtcttttgt gtcatcggct ggagggtacg ttgctgtgag 480
gtttatgatt gggttttcac tagcaacgtt tgtgtcatgt cagtattgga tgagtacgat 540
gtttaatagt caaatcattg gacttgtgaa tggtacagct gctggatggg gtaatatggg 600
tggtggtgct actcaactta ttatgccttt gctctacgat ataatacgta gagcaggggc 660
aaccccgttc actgcttgga gaatcgcatt ttttattcct ggatggcttc atgttattat 720
gggaatttta gttttaactc ttggacaaga tttacctgat ggtaacctcg cttctttaca 780
gaagaaaggc gatgtttcta aagataaatt ctcaaagata ttatggtatg ctgcaacaaa 840
ttacagaaca tggatccttg ttctgctcta tggatactca atgggagttg aattaactac 900
agataacgtg attgctgagt atttcttcga tagatttgat ttgaagcttc atacggctgg 960
aatcatcgct gcaacatttg gcatggctaa cttattagcg cgaccatttg gaggatggtc 1020
atcagatgtt gcagctaaac atttcgggat gagaggcaga ttatggaatt catggatttt 1080
acaaacactt ggtggtgtgt tctgtttact acttggaagg gctactacac ttcctctggc 1140
tattacttgg atgatcatat tctcaatagg tgcacaagca gcatgtggtg taacgtttgg 1200
aattattccc tttatttcgc gaagatcatt aggtataata tcaggtatga caggagctgg 1260
aggcaatttt ggttccggat tgacacaact actgtttttc acgagtacaa agtactcgac 1320
aggaacagga ctaacgtata tggggatgat gatcatcgcg tgtacacttc cagtaatgtt 1380
agttcgtttt ccacagtggg gtagtatgtt tttgcctcca tctaaagatc ctattaaggg 1440
tactgaagaa cattattttg gttctgagta tactgaggat gagaaacaaa agggaatgca 1500
ccagaacagc atcaagttcg cggaaaacag caggacagag cgtgggaaga agcgcgttgg 1560
ttcagcacct actccgccta atgtaacacc aaatcgcgtc tgatggggaa aaaaattaaa 1620
atacttactt cgcagttcat gctcgt 1646

<210> SEQ ID NO 96
<211> LENGTH: 531
<212> TYPE: PRT
<213> ORGANISM: Lycopersicon esculentum

<400> SEQUENCE: 96

Met Gly Asp Ile Glu Gly Ser Pro Gly Ser Ser Met His Gly Val Thr
1               5                   10                  15

Gly Arg Glu Pro Val Leu Ala Phe Ser Val Ala Ser Leu Ile Val Pro

-continued

```
            20                  25                  30

Thr Asp Thr Ser Ala Asn Phe Lys Val Pro Val Asp Ser Glu His Lys
        35                  40                  45

Ala Lys Val Phe Lys Phe Tyr Ser Phe Ser Lys Pro His Gly Leu Thr
    50                  55                  60

Phe Gln Leu Ser Trp Ile Ser Phe Cys Thr Cys Phe Val Ser Thr Phe
65                  70                  75                  80

Ala Ala Ala Pro Leu Val Pro Ile Ile Arg Asp Asn Leu Asn Leu Thr
                85                  90                  95

Lys Met Asp Val Gly Asn Ala Gly Val Ala Ser Val Ser Gly Ser Ile
            100                 105                 110

Leu Ser Arg Leu Ala Met Gly Ala Ile Cys Asp Met Leu Gly Pro Arg
        115                 120                 125

Tyr Gly Cys Ala Phe Leu Ile Met Leu Ser Ala Pro Thr Val Leu Cys
    130                 135                 140

Met Ser Phe Val Ser Ser Ala Gly Gly Tyr Val Ala Val Arg Phe Met
145                 150                 155                 160

Ile Gly Phe Ser Leu Ala Thr Phe Val Ser Cys Gln Tyr Trp Met Ser
                165                 170                 175

Thr Met Phe Asn Ser Gln Ile Ile Gly Leu Val Asn Gly Thr Ala Ala
            180                 185                 190

Gly Trp Gly Asn Met Gly Gly Gly Ala Thr Gln Leu Ile Met Pro Leu
        195                 200                 205

Leu Tyr Asp Ile Ile Arg Arg Ala Gly Ala Thr Pro Phe Thr Ala Trp
    210                 215                 220

Arg Ile Ala Phe Phe Ile Pro Gly Trp Leu His Val Ile Met Gly Ile
225                 230                 235                 240

Leu Val Leu Thr Leu Gly Gln Asp Leu Pro Asp Gly Asn Leu Ala Ser
                245                 250                 255

Leu Gln Lys Lys Gly Asp Val Ser Lys Asp Lys Phe Ser Lys Ile Leu
            260                 265                 270

Trp Tyr Ala Ala Thr Asn Tyr Arg Thr Trp Ile Leu Val Leu Leu Tyr
        275                 280                 285

Gly Tyr Ser Met Gly Val Glu Leu Thr Thr Asp Asn Val Ile Ala Glu
    290                 295                 300

Tyr Phe Phe Asp Arg Phe Asp Leu Lys Leu His Thr Ala Gly Ile Ile
305                 310                 315                 320

Ala Ala Thr Phe Gly Met Ala Asn Leu Leu Ala Arg Pro Phe Gly Gly
                325                 330                 335

Trp Ser Ser Asp Val Ala Ala Lys His Phe Gly Met Arg Gly Arg Leu
            340                 345                 350

Trp Asn Ser Trp Ile Leu Gln Thr Leu Gly Gly Val Phe Cys Leu Leu
        355                 360                 365

Leu Gly Arg Ala Thr Thr Leu Pro Leu Ala Ile Thr Trp Met Ile Ile
    370                 375                 380

Phe Ser Ile Gly Ala Gln Ala Ala Cys Gly Val Thr Phe Gly Ile Ile
385                 390                 395                 400

Pro Phe Ile Ser Arg Arg Ser Leu Gly Ile Ile Ser Gly Met Thr Gly
                405                 410                 415

Ala Gly Gly Asn Phe Gly Ser Gly Leu Thr Gln Leu Leu Phe Phe Thr
            420                 425                 430

Ser Thr Lys Tyr Ser Thr Gly Thr Gly Leu Thr Tyr Met Gly Met Met
        435                 440                 445
```

```
Ile Ile Ala Cys Thr Leu Pro Val Met Leu Val Arg Phe Pro Gln Trp
    450                 455                 460

Gly Ser Met Phe Leu Pro Pro Ser Lys Asp Pro Ile Lys Gly Thr Glu
465                 470                 475                 480

Glu His Tyr Phe Gly Ser Glu Tyr Thr Glu Asp Glu Lys Gln Lys Gly
                485                 490                 495

Met His Gln Asn Ser Ile Lys Phe Ala Glu Asn Ser Arg Thr Glu Arg
            500                 505                 510

Gly Lys Lys Arg Val Gly Ser Ala Pro Thr Pro Pro Asn Val Thr Pro
        515                 520                 525

Asn Arg Val
    530
```

<210> SEQ ID NO 97
<211> LENGTH: 1680
<212> TYPE: DNA
<213> ORGANISM: Populus tremula x Populus tremuloides

<400> SEQUENCE: 97

```
cttccctagt ctgaaactcc tatcacaatc cggtttggaa gagaatagag gaagggaatg     60

gctgacgttg agggttcccc gggtagttcc atgcatggag tgacaggcag agaacaaagc    120

tttgcctttt cggttgcctc tcctacagtc ccgacggata caacagcaaa atttgccttg    180

ccagttgatt ctgagcacaa ggccaaagtg ttcaagattt tctcttttgc taaccctcat    240

atgagaacat ttcacctttc ttggatatca ttcttcactt gttttgtctc cacttttgct    300

gcagcacccc ttgttcctat cattcgggac aacctcaatt taaccaaaag tgacatcggt    360

aatgctggtg ttgcttctgt ctctggaagc atcttctcta ggcttgtaat gggtgcagtt    420

tgtgacctct tggggccgcg atatgggtgt gcgtttctga tcatgctctc agccccaact    480

gtgttttgca tgtcgtttgt ggactcagct ggaggatacc tagcagtccg tttcatgatt    540

ggattctctc ttgcaacgtt cgtgtcatgc cagtactgga tgagcacaat gtttaacagc    600

aagattatcg gactcgtcaa tggaaccgca gccggttggg gcaatatggg tggaggtgca    660

actcagctcg taatgccctt ggtctacgag ctcattaagc gagctggttc aacttcattc    720

agtgcttgga ggatagcatt ttttgtccca ggatggcttc atgttatcat gggaatcttg    780

gtcttgaatc taggccaaga cttgcctgat gggaatctcg gtgccctaaa gaagaagggt    840

gatgttgcta aagataagtt ctccaaggta ctctggtatg ctgttacaaa ctataggacc    900

tggatctttg tccttctcta tggctactcc atgggagttg aattatccac cgacaatgtt    960

atcgccgagt acttctataa caggttcgat ctaaagcttc acacagcagg tgtcattgct   1020

gctacctttg gtatggctaa ccttgtagct cgtccctttg gtggatattt ttctgatgta   1080

gcagcaaggt acttcgggat gagaggcagg ttatgggtgc tctggatttt acagacactt   1140

ggaggagttt tctgtacttg gctcggtcga gctaattcac ttccccttgc tgtcaccgct   1200

atgattctct tctctattgg agcgcaagcc gcatgtggag caacttttgg tatcattccc   1260

tttatttctc gacgatcatt gggcatcata tccggcctaa ctggtgcagg tggaaatttt   1320

gggtccggat tgacacaact agtattcttt tcgagctcaa gtttgtccac agctgcaggt   1380

ctatcctgga tgggtgtcat gatttgcggc tgcactctcc ctgtgacatt ggtttacttc   1440

ccacaatggg gcggcatgtt ctttccgcct tctaaagacg tagtgaagtc aacagaagaa   1500

tcctattatg catcagagtg ggatgaggac gagaagcaaa ggggcatgca ccagaaaagc   1560
```

```
ctcaagtttg cggagaacag ccgatctgaa cgtggcaagc gcattgcctc tgcaccaaca   1620

ccaccaagta ccacaccaaa ccgtgtgtag atcaaagcgt tggccatgct tctatagtgc   1680


<210> SEQ ID NO 98
<211> LENGTH: 529
<212> TYPE: PRT
<213> ORGANISM: Populus tremula x Populus tremuloides

<400> SEQUENCE: 98

Met Ala Asp Val Glu Gly Ser Pro Gly Ser Ser Met His Gly Val Thr
1               5                   10                  15

Gly Arg Glu Gln Ser Phe Ala Phe Ser Val Ala Ser Pro Thr Val Pro
            20                  25                  30

Thr Asp Thr Thr Ala Lys Phe Ala Leu Pro Val Asp Ser Glu His Lys
        35                  40                  45

Ala Lys Val Phe Lys Ile Phe Ser Phe Ala Asn Pro His Met Arg Thr
    50                  55                  60

Phe His Leu Ser Trp Ile Ser Phe Phe Thr Cys Phe Val Ser Thr Phe
65                  70                  75                  80

Ala Ala Ala Pro Leu Val Pro Ile Ile Arg Asp Asn Leu Asn Leu Thr
                85                  90                  95

Lys Ser Asp Ile Gly Asn Ala Gly Val Ala Ser Val Ser Gly Ser Ile
            100                 105                 110

Phe Ser Arg Leu Val Met Gly Ala Val Cys Asp Leu Leu Gly Pro Arg
        115                 120                 125

Tyr Gly Cys Ala Phe Leu Ile Met Leu Ser Ala Pro Thr Val Phe Cys
    130                 135                 140

Met Ser Phe Val Asp Ser Ala Gly Gly Tyr Leu Ala Val Arg Phe Met
145                 150                 155                 160

Ile Gly Phe Ser Leu Ala Thr Phe Val Ser Cys Gln Tyr Trp Met Ser
                165                 170                 175

Thr Met Phe Asn Ser Lys Ile Ile Gly Leu Val Asn Gly Thr Ala Ala
            180                 185                 190

Gly Trp Gly Asn Met Gly Gly Gly Ala Thr Gln Leu Val Met Pro Leu
        195                 200                 205

Val Tyr Glu Leu Ile Lys Arg Ala Gly Ser Thr Ser Phe Ser Ala Trp
    210                 215                 220

Arg Ile Ala Phe Phe Val Pro Gly Trp Leu His Val Ile Met Gly Ile
225                 230                 235                 240

Leu Val Leu Asn Leu Gly Gln Asp Leu Pro Asp Gly Asn Leu Gly Ala
                245                 250                 255

Leu Lys Lys Lys Gly Asp Val Ala Lys Asp Lys Phe Ser Lys Val Leu
            260                 265                 270

Trp Tyr Ala Val Thr Asn Tyr Arg Thr Trp Ile Phe Val Leu Leu Tyr
        275                 280                 285

Gly Tyr Ser Met Gly Val Glu Leu Ser Thr Asp Asn Val Ile Ala Glu
    290                 295                 300

Tyr Phe Tyr Asn Arg Phe Asp Leu Lys Leu His Thr Ala Gly Val Ile
305                 310                 315                 320

Ala Ala Thr Phe Gly Met Ala Asn Leu Val Ala Arg Pro Phe Gly Gly
                325                 330                 335

Tyr Phe Ser Asp Val Ala Ala Arg Tyr Phe Gly Met Arg Gly Arg Leu
            340                 345                 350

Trp Val Leu Trp Ile Leu Gln Thr Leu Gly Gly Val Phe Cys Thr Trp
```

```
        355                 360                 365

Leu Gly Arg Ala Asn Ser Leu Pro Leu Ala Val Thr Ala Met Ile Leu
    370                 375                 380

Phe Ser Ile Gly Ala Gln Ala Ala Cys Gly Ala Thr Phe Gly Ile Ile
385                 390                 395                 400

Pro Phe Ile Ser Arg Arg Ser Leu Gly Ile Ile Ser Gly Leu Thr Gly
                405                 410                 415

Ala Gly Gly Asn Phe Gly Ser Gly Leu Thr Gln Leu Val Phe Phe Ser
            420                 425                 430

Ser Ser Ser Leu Ser Thr Ala Ala Gly Leu Ser Trp Met Gly Val Met
        435                 440                 445

Ile Cys Gly Cys Thr Leu Pro Val Thr Leu Val Tyr Phe Pro Gln Trp
    450                 455                 460

Gly Gly Met Phe Phe Pro Pro Ser Lys Asp Val Val Lys Ser Thr Glu
465                 470                 475                 480

Glu Ser Tyr Tyr Ala Ser Glu Trp Asp Glu Asp Glu Lys Gln Arg Gly
                485                 490                 495

Met His Gln Lys Ser Leu Lys Phe Ala Glu Asn Ser Arg Ser Glu Arg
            500                 505                 510

Gly Lys Arg Ile Ala Ser Ala Pro Thr Pro Pro Ser Thr Thr Pro Asn
        515                 520                 525

Arg


<210> SEQ ID NO 99
<211> LENGTH: 1611
<212> TYPE: DNA
<213> ORGANISM: Nicotiana tabacum

<400> SEQUENCE: 99

ttaaaaaaaa aatgggtgat attgagggcg aaccagggag ttccatgcat ggagtcactg      60

gtagagagcc agttcttgct ttctcagtgg cttctccgat ggtgccaact gataccactg     120

caaaatttc agtaccagtt gatactgaac acaaagccaa gatttttaag ttctattcat     180

tttcaaagcc acatggtctt actttccagc tctcctggat ttctttcttc acttgttttg     240

tttcaacttt tgccgctgcc cctttagttc ctatcattag ggacaacctt aatttaacca     300

aaatggatgt tggtaatgcc ggagttgctt ccgtttccgg aagtatttta tctaggcttg     360

ttatgggtgc agtttgtgat atgttagggc caagatatgg ctgtgcattt ctgattatgt     420

tgtcagcccc aactgtattt tgcatgtcat ttgtgtcgtc ggctggagga tatgttgctg     480

tccggttcat gatcggattc tcgctagcaa catttgtgtc gtgccaatat tggatgagta     540

ctatgtttaa tagtcagatt ataggacttg tcaatgggac agctgcagga tggggaaata     600

tgggtggtgg tgcgactcaa cttattatgc caattgtgta tgatataata agaagagcag     660

gagcaactcc attcactgct tggagaattg catttttcat tcctggctgg cttcatattg     720

tgatgggtat tttggtgttg actcttggcc aagatttgcc tgatgggaac cgtggtgatt     780

tacagaagaa gggtgatgtt tctaaagata aattctccaa catattgtgg tacgctgcaa     840

caaactacag gacgtggatc tttgttcttc tctacggata ctctatggga gttgaactgt     900

ctacagacaa cgtaattgcg gagtacttct tcgacagatt tgatctaaag cttcacacag     960

cgggaattat tgcagcgacc tttggtatgg ctaatttatt agctcgtcca ttcggaggat    1020

tttcttcaga ttacgcagcc aaaagattcg gcatgagagg cagactttgg gtcctttgga    1080

tattacaaac actgggagga gtattctgcg tcctgttggg ccgttcaaat cctctgccca    1140
```

```
tagccgtcac attcatgatc cttttctcta ttggtgctca agctgcatgt ggtgcaacat   1200

tcggtattat tccattcatt tctcgccgat ccttaggtat aatctcagga atgactgggg   1260

ctggaggaaa tttcggttct ggattgacac aactgttgtt cttcacgagc tcaaaatact   1320

cgacagcaac agggctaact tacatgggac taatgatcat aggatgcact cttccagtga   1380

ctttctgtca tttcccacaa tggggaagta tgtttttccc accaacgaaa gaccctgtta   1440

agggaagtga ggaacattat tatgccgcag agtataccga agctgagagg cagaaaggta   1500

tgcaccaaaa cagcttgaag ttcgccgaga actgccgatc ggagcgtggc aagcgcgtgg   1560

gatcggcacc tactcctcca aatttaacgc ctaatcgtgt ctgagatccc g            1611
```

```
<210> SEQ ID NO 100
<211> LENGTH: 530
<212> TYPE: PRT
<213> ORGANISM: Nicotiana tabacum

<400> SEQUENCE: 100

Met Gly Asp Ile Glu Gly Glu Pro Gly Ser Ser Met His Gly Val Thr
1               5                   10                  15

Gly Arg Glu Pro Val Leu Ala Phe Ser Val Ala Ser Pro Met Val Pro
            20                  25                  30

Thr Asp Thr Thr Ala Lys Phe Ser Val Pro Val Asp Thr Glu His Lys
        35                  40                  45

Ala Lys Ile Phe Lys Phe Tyr Ser Phe Ser Lys Pro His Gly Leu Thr
    50                  55                  60

Phe Gln Leu Ser Trp Ile Ser Phe Phe Thr Cys Phe Val Ser Thr Phe
65                  70                  75                  80

Ala Ala Ala Pro Leu Val Pro Ile Ile Arg Asp Asn Leu Asn Leu Thr
                85                  90                  95

Lys Met Asp Val Gly Asn Ala Gly Val Ala Ser Val Ser Gly Ser Ile
            100                 105                 110

Leu Ser Arg Leu Val Met Gly Ala Val Cys Asp Met Leu Gly Pro Arg
        115                 120                 125

Tyr Gly Cys Ala Phe Leu Ile Met Leu Ser Ala Pro Thr Val Phe Cys
    130                 135                 140

Met Ser Phe Val Ser Ser Ala Gly Gly Tyr Val Ala Val Arg Phe Met
145                 150                 155                 160

Ile Gly Phe Ser Leu Ala Thr Phe Val Ser Cys Gln Tyr Trp Met Ser
                165                 170                 175

Thr Met Phe Asn Ser Gln Ile Ile Gly Leu Val Asn Gly Thr Ala Ala
            180                 185                 190

Gly Trp Gly Asn Met Gly Gly Gly Ala Thr Gln Leu Ile Met Pro Ile
        195                 200                 205

Val Tyr Asp Ile Ile Arg Arg Ala Gly Ala Thr Pro Phe Thr Ala Trp
    210                 215                 220

Arg Ile Ala Phe Phe Ile Pro Gly Trp Leu His Ile Val Met Gly Ile
225                 230                 235                 240

Leu Val Leu Thr Leu Gly Gln Asp Leu Pro Asp Gly Asn Arg Gly Asp
                245                 250                 255

Leu Gln Lys Lys Gly Asp Val Ser Lys Asp Lys Phe Ser Asn Ile Leu
            260                 265                 270

Trp Tyr Ala Ala Thr Asn Tyr Arg Thr Trp Ile Phe Val Leu Leu Tyr
        275                 280                 285
```

```
Gly Tyr Ser Met Gly Val Glu Leu Ser Thr Asp Asn Val Ile Ala Glu
    290                 295                 300

Tyr Phe Phe Asp Arg Phe Asp Leu Lys Leu His Thr Ala Gly Ile Ile
305                 310                 315                 320

Ala Ala Thr Phe Gly Met Ala Asn Leu Leu Ala Arg Pro Phe Gly Gly
                325                 330                 335

Phe Ser Ser Asp Tyr Ala Ala Lys Arg Phe Gly Met Arg Gly Arg Leu
            340                 345                 350

Trp Val Leu Trp Ile Leu Gln Thr Leu Gly Gly Val Phe Cys Val Leu
        355                 360                 365

Leu Gly Arg Ser Asn Pro Leu Pro Ile Ala Val Thr Phe Met Ile Leu
    370                 375                 380

Phe Ser Ile Gly Ala Gln Ala Ala Cys Gly Ala Thr Phe Gly Ile Ile
385                 390                 395                 400

Pro Phe Ile Ser Arg Arg Ser Leu Gly Ile Ile Ser Gly Met Thr Gly
                405                 410                 415

Ala Gly Gly Asn Phe Gly Ser Gly Leu Thr Gln Leu Leu Phe Phe Thr
            420                 425                 430

Ser Ser Lys Tyr Ser Thr Ala Thr Gly Leu Thr Tyr Met Gly Leu Met
        435                 440                 445

Ile Ile Gly Cys Thr Leu Pro Val Thr Phe Cys His Phe Pro Gln Trp
    450                 455                 460

Gly Ser Met Phe Phe Pro Pro Thr Lys Asp Pro Val Lys Gly Ser Glu
465                 470                 475                 480

Glu His Tyr Tyr Ala Ala Glu Tyr Thr Glu Ala Glu Arg Gln Lys Gly
                485                 490                 495

Met His Gln Asn Ser Leu Lys Phe Ala Glu Asn Cys Arg Ser Glu Arg
            500                 505                 510

Gly Lys Arg Val Gly Ser Ala Pro Thr Pro Pro Asn Leu Thr Pro Asn
        515                 520                 525

Arg Val
    530
```

<210> SEQ ID NO 101
<211> LENGTH: 1992
<212> TYPE: DNA
<213> ORGANISM: Nicotiana plumbaginifolia

<400> SEQUENCE: 101

```
ttcactttca acatttaatc aatcttagtg ctatcagttt attttcctta agaaaaaaaa     60

tggctgatat tgagggagaa ccagggagtt ctatgcatgg agtcactggt agagagccag    120

ttcttgcttt ctcagtggct tctccaatgg tgccaactga taccactgct aaattttcag    180

taccagttga tactgaacac aaagccaagg tttttaaatt ttattcattt tcaaagcctc    240

atggacttac tttccagctc tcctggattt ctttcttcac ttgttttgta tcaacttttg    300

ctgctgctcc tttagttcct ctcattaggg acaaccttaa tttaaccaaa atggatgttg    360

gtaatgccgg agttgcttcc gtttctggaa gtattttatc taggcttgtt atgggtgcag    420

tttgtgatat gttagggcca agatacggct gtgcatttct gattatgttg tcagccccaa    480

ctgtattttg tatgtcgttc gtgtcgtcgg ctggaggata tgttgctgtc cggttcatga    540

tcggattctc gctcgcaaca tttgtgtcgt gccaatattg gatgagtact atgtttaata    600

gtcagattat aggacttgtc aatggaacag ctgctgggtg gggaaatatg ggtggtggtg    660

cgactcaact tattatgcca attctgtatg atataataag aaaagcagga gcaactccat    720
```

-continued

```
tcactgcttg gagaattgca tttttcattc ctggctggct tcatgttgta atgggtattt    780
tggtgttgac tcttggtcaa gatttgcctg atggaaaccg tggtgattta cagaagaagg    840
gtggtgtttc taaagataaa ttcaccaaca tattgtggta cgctgcaaca aactacagga    900
cgtggatctt tgtccttctc tacggatact ctatgggagt tgaactgtct accgacaacg    960
taattgcaga gtacttcttc gacagatttg atctaaagct tcacacagcg ggaatcatcg   1020
cagccacatt tggtatggca aatttattag ctcgtccatt cggagggttt tcttcagatt   1080
tcgcagccaa aagattcggc atgaggggta gactttgggt cctttggata ttacaaacac   1140
ttggaggagt attctgtgtc ctgttgggcc gttcaaattc tctgcccata gctgtcacat   1200
tcatgatcct tttctcagtt ggtgctcaag ctgcatgtgg tgcaacattc ggtattattc   1260
ccttcatatc tcgtcgatca ttaggtataa tctcgggaat gactggagct ggaggcaatt   1320
tcggttctgg attgacacaa ctgctgtttt tcacaagctc aaaatactcg acagcaacag   1380
ggctaactta tatggggatg atgatcattg gatgcactct tcctgtgaca ctatgtcatt   1440
tcccacaatg ggaagcatg tttttcccac caacaaaaga tccagttaag ggaagtgagg   1500
aacattatta tgccgcagag tatacagaag ctgagaggca gaaaggtatg catcaaaaca   1560
gcttgaaatt cgccgagaac tgtcgatcgg agcgtggcaa gcgcgtggga tcggcaccta   1620
ctcctccaaa tttaacgcct aaccgtgtct gagtttctca gatttgataa ttttctctaa   1680
ggggatggat cattgtcaat ctctgattgg atgaagattc aatgagctga gtctcaataa   1740
gcatattatt tttaaagaat gtatctttat ttttcttgtc ctttcttctt cttcttcttc   1800
tttttcttgg aatctactta taagttttat gttttttttt ttaaatgaag tatatatatg   1860
acgcattgtg tatctttcct cttgcttttt acatctgaat attcgtatga gccaatgggt   1920
tgttgtagaa tcaaaagtaa tattaataaa acttttgact tccaaaaaaa aaaaaaaaaa   1980
aaaaaaaaaa aa                                                       1992
```

```
<210> SEQ ID NO 102
<211> LENGTH: 530
<212> TYPE: PRT
<213> ORGANISM: Nicotiana plumbaginifolia

<400> SEQUENCE: 102

Met Ala Asp Ile Glu Gly Glu Pro Gly Ser Ser Met His Gly Val Thr
1               5                   10                  15

Gly Arg Glu Pro Val Leu Ala Phe Ser Val Ala Ser Pro Met Val Pro
            20                  25                  30

Thr Asp Thr Thr Ala Lys Phe Ser Val Pro Val Asp Thr Glu His Lys
        35                  40                  45

Ala Lys Val Phe Lys Phe Tyr Ser Phe Ser Lys Pro His Gly Leu Thr
    50                  55                  60

Phe Gln Leu Ser Trp Ile Ser Phe Phe Thr Cys Phe Val Ser Thr Phe
65                  70                  75                  80

Ala Ala Ala Pro Leu Val Pro Leu Ile Arg Asp Asn Leu Asn Leu Thr
                85                  90                  95

Lys Met Asp Val Gly Asn Ala Gly Val Ala Ser Val Ser Gly Ser Ile
            100                 105                 110

Leu Ser Arg Leu Val Met Gly Ala Val Cys Asp Met Leu Gly Pro Arg
        115                 120                 125

Tyr Gly Cys Ala Phe Leu Ile Met Leu Ser Ala Pro Thr Val Phe Cys
    130                 135                 140
```

```
Met Ser Phe Val Ser Ser Ala Gly Gly Tyr Val Ala Val Arg Phe Met
145                 150                 155                 160

Ile Gly Phe Ser Leu Ala Thr Phe Val Ser Cys Gln Tyr Trp Met Ser
                165                 170                 175

Thr Met Phe Asn Ser Gln Ile Ile Gly Leu Val Asn Gly Thr Ala Ala
            180                 185                 190

Gly Trp Gly Asn Met Gly Gly Gly Ala Thr Gln Leu Ile Met Pro Ile
        195                 200                 205

Leu Tyr Asp Ile Ile Arg Lys Ala Gly Ala Thr Pro Phe Thr Ala Trp
    210                 215                 220

Arg Ile Ala Phe Phe Ile Pro Gly Trp Leu His Val Val Met Gly Ile
225                 230                 235                 240

Leu Val Leu Thr Leu Gly Gln Asp Leu Pro Asp Gly Asn Arg Gly Asp
                245                 250                 255

Leu Gln Lys Lys Gly Gly Val Ser Lys Asp Lys Phe Thr Asn Ile Leu
            260                 265                 270

Trp Tyr Ala Ala Thr Asn Tyr Arg Thr Trp Ile Phe Val Leu Leu Tyr
        275                 280                 285

Gly Tyr Ser Met Gly Val Glu Leu Ser Thr Asp Asn Val Ile Ala Glu
    290                 295                 300

Tyr Phe Phe Asp Arg Phe Asp Leu Lys Leu His Thr Ala Gly Ile Ile
305                 310                 315                 320

Ala Ala Thr Phe Gly Met Ala Asn Leu Leu Ala Arg Pro Phe Gly Gly
                325                 330                 335

Phe Ser Ser Asp Phe Ala Ala Lys Arg Phe Gly Met Arg Gly Arg Leu
            340                 345                 350

Trp Val Leu Trp Ile Leu Gln Thr Leu Gly Gly Val Phe Cys Val Leu
        355                 360                 365

Leu Gly Arg Ser Asn Ser Leu Pro Ile Ala Val Thr Phe Met Ile Leu
    370                 375                 380

Phe Ser Val Gly Ala Gln Ala Ala Cys Gly Ala Thr Phe Gly Ile Ile
385                 390                 395                 400

Pro Phe Ile Ser Arg Arg Ser Leu Gly Ile Ile Ser Gly Met Thr Gly
                405                 410                 415

Ala Gly Gly Asn Phe Gly Ser Gly Leu Thr Gln Leu Leu Phe Phe Thr
            420                 425                 430

Ser Ser Lys Tyr Ser Thr Ala Thr Gly Leu Thr Tyr Met Gly Met Met
        435                 440                 445

Ile Ile Gly Cys Thr Leu Pro Val Thr Leu Cys His Phe Pro Gln Trp
    450                 455                 460

Gly Ser Met Phe Phe Pro Pro Thr Lys Asp Pro Val Lys Gly Ser Glu
465                 470                 475                 480

Glu His Tyr Tyr Ala Ala Glu Tyr Thr Glu Ala Glu Arg Gln Lys Gly
                485                 490                 495

Met His Gln Asn Ser Leu Lys Phe Ala Glu Asn Cys Arg Ser Glu Arg
            500                 505                 510

Gly Lys Arg Val Gly Ser Ala Pro Thr Pro Pro Asn Leu Thr Pro Asn
        515                 520                 525

Arg Val
    530
```

<210> SEQ ID NO 103
<211> LENGTH: 2060

<212> TYPE: DNA
<213> ORGANISM: Lycopersicon esculentum

<400> SEQUENCE: 103
tattctcaat acatttcaaa tcaatcattt ataaaattaa ccagttattt cctcaattga 60
agaaatggct gatgtagaag gatcaccggg gagttctatg catggagtca ccggaagaga 120
acctgttctc gctttctccg tggcttctcc aatggtgcct acggatacct ccgccaaatt 180
ttcagtaccg gtggacactg aacacaaggc taaacaattt aagttttatt cgttttcgaa 240
gcctcatgga cttacgttcc agctctcctg gatctccttt ttcacttgtt tcgtttcgac 300
ttttgctgct gcacctttag ttcctattat tagggacaat cttaatttga caaaaatgga 360
tgttggtaac gctggggttg cttccgtatc cggaagtatt ttatctaggc ttacgatggg 420
tgcggtttgt gatttgttgg gtccaaggta tgggtgcgct tttcttatca tgttgtcagc 480
gccaactgtt ttttgtatgt cttttgtttc atccgctggt ggctacgtag ctgtccggtt 540
catgattggg ttttcgctcg caacgtttgt gtcttgtcaa tattggatga gtactatgtt 600
taatagtaag atcatagggc tagtgaacgg aacggctgct ggatggggta atatgggtgg 660
aggtgcaact caactcatta tgccactttt gtatgatata attcgaaggg cgggtgcaac 720
tccgttcact gcttggagaa ttgcattttt tattcctgga tggcttcatg tggtgatggg 780
tattttagtg ttgactcttg gccaagattt acccgacgga aatcgtggca ctttacagaa 840
gacgggtact gttgctaaag ataaattcgg taacatattg tggtatgctg caacaaacta 900
caggacatgg atctttgttc ttctctatgg atactctatg ggagttgaac tgtcaacaga 960
caacgtcatt gctgagtact tcttcgacag atttgatcta aagcttagca cagcggggat 1020
cattgctgcc acatttggta tggctaacct tttggctcga ccatttggag gattttcttc 1080
tgattacgca gcaaagaaat tcggtatgag agggagactt tgggttttgt ggattttaca 1140
aacacttgga ggagtatttt gtgttctttt gggtcgttcg aattctctac cacttgcggt 1200
aacctttatg atccttttct caatcggagc tcaagctgct tgtggtgcaa cttttggtat 1260
tattccattc atttctcgac gatcgttagg aattataagc ggaatgacag gggcaggtgg 1320
aaattttggt tctggattga ctcaattgtt gtttttcacg agctcaaagt actcgacagc 1380
gacagggtta acttacatgg gattcatgat cataggatgc actcttcctg ttacattttg 1440
tcatttccca caatggggaa gcatgttttt gccaccaaca aaagatccag tcaagggaac 1500
ggaagaacat tattatactt cagagtacac agaggccgag aggcaaaaag ggatgcacca 1560
aaacagcttg aaattcgctg aaaattgccg atcagagcgt ggtaagcgtg ttggttccgc 1620
accaacccca ccaaatttga caccaaatcg tgtttgatga tctttatgag gaatggatag 1680
tcttgaatct gtgatttaaa tttaaggttc aatgtgctga gtcgtctcaa taagcaaaat 1740
ctatcttgat ttttcttctt tgtttttttt ttataatgat attgcttgtt gatctttcca 1800
gacaaatacc ttgaatccac gaaggtgtat gcttttttttt taatgaagta tatataatat 1860
attactcatt gtgtatgttt tctattgctt ttttcaaaag aatattctat ggccaatggt 1920
ggttgtgttt tactctgtag attcaaaagt gtattataat aaaactcttg acttgtaaga 1980
aggggactga tcatttattc cagttgattt atagaaagtt cgtgaaaaaa aaaaaaaaaa 2040
aaaaaaaaaa aaaaaaaaaa 2060

<210> SEQ ID NO 104
<211> LENGTH: 530
<212> TYPE: PRT

<213> ORGANISM: Lycopersicon esculentum

<400> SEQUENCE: 104

```
Met Ala Asp Val Glu Gly Ser Pro Gly Ser Ser Met His Gly Val Thr
1               5                   10                  15

Gly Arg Glu Pro Val Leu Ala Phe Ser Val Ala Ser Pro Met Val Pro
            20                  25                  30

Thr Asp Thr Ser Ala Lys Phe Ser Val Pro Val Asp Thr Glu His Lys
        35                  40                  45

Ala Lys Gln Phe Lys Phe Tyr Ser Phe Ser Lys Pro His Gly Leu Thr
    50                  55                  60

Phe Gln Leu Ser Trp Ile Ser Phe Phe Thr Cys Phe Val Ser Thr Phe
65                  70                  75                  80

Ala Ala Ala Pro Leu Val Pro Ile Ile Arg Asp Asn Leu Asn Leu Thr
                85                  90                  95

Lys Met Asp Val Gly Asn Ala Gly Val Ala Ser Val Ser Gly Ser Ile
            100                 105                 110

Leu Ser Arg Leu Thr Met Gly Ala Val Cys Asp Leu Leu Gly Pro Arg
        115                 120                 125

Tyr Gly Cys Ala Phe Leu Ile Met Leu Ser Ala Pro Thr Val Phe Cys
    130                 135                 140

Met Ser Phe Val Ser Ser Ala Gly Gly Tyr Val Ala Val Arg Phe Met
145                 150                 155                 160

Ile Gly Phe Ser Leu Ala Thr Phe Val Ser Cys Gln Tyr Trp Met Ser
                165                 170                 175

Thr Met Phe Asn Ser Lys Ile Ile Gly Leu Val Asn Gly Thr Ala Ala
            180                 185                 190

Gly Trp Gly Asn Met Gly Gly Gly Ala Thr Gln Leu Ile Met Pro Leu
        195                 200                 205

Leu Tyr Asp Ile Ile Arg Arg Ala Gly Ala Thr Pro Phe Thr Ala Trp
    210                 215                 220

Arg Ile Ala Phe Phe Ile Pro Gly Trp Leu His Val Val Met Gly Ile
225                 230                 235                 240

Leu Val Leu Thr Leu Gly Gln Asp Leu Pro Asp Gly Asn Arg Gly Thr
                245                 250                 255

Leu Gln Lys Thr Gly Thr Val Ala Lys Asp Lys Phe Gly Asn Ile Leu
            260                 265                 270

Trp Tyr Ala Ala Thr Asn Tyr Arg Thr Trp Ile Phe Val Leu Leu Tyr
        275                 280                 285

Gly Tyr Ser Met Gly Val Glu Leu Ser Thr Asp Asn Val Ile Ala Glu
    290                 295                 300

Tyr Phe Phe Asp Arg Phe Asp Leu Lys Leu Ser Thr Ala Gly Ile Ile
305                 310                 315                 320

Ala Ala Thr Phe Gly Met Ala Asn Leu Leu Ala Arg Pro Phe Gly Gly
                325                 330                 335

Phe Ser Ser Asp Tyr Ala Ala Lys Lys Phe Gly Met Arg Gly Arg Leu
            340                 345                 350

Trp Val Leu Trp Ile Leu Gln Thr Leu Gly Gly Val Phe Cys Val Leu
        355                 360                 365

Leu Gly Arg Ser Asn Ser Leu Pro Leu Ala Val Thr Phe Met Ile Leu
    370                 375                 380

Phe Ser Ile Gly Ala Gln Ala Ala Cys Gly Ala Thr Phe Gly Ile Ile
385                 390                 395                 400
```

```
Pro Phe Ile Ser Arg Arg Ser Leu Gly Ile Ile Ser Gly Met Thr Gly
                405                 410                 415

Ala Gly Gly Asn Phe Gly Ser Gly Leu Thr Gln Leu Leu Phe Phe Thr
            420                 425                 430

Ser Ser Lys Tyr Ser Thr Ala Thr Gly Leu Thr Tyr Met Gly Phe Met
        435                 440                 445

Ile Ile Gly Cys Thr Leu Pro Val Thr Phe Cys His Phe Pro Gln Trp
    450                 455                 460

Gly Ser Met Phe Leu Pro Pro Thr Lys Asp Pro Val Lys Gly Thr Glu
465                 470                 475                 480

Glu His Tyr Tyr Thr Ser Glu Tyr Thr Glu Ala Glu Arg Gln Lys Gly
                485                 490                 495

Met His Gln Asn Ser Leu Lys Phe Ala Glu Asn Cys Arg Ser Glu Arg
            500                 505                 510

Gly Lys Arg Val Gly Ser Ala Pro Thr Pro Pro Asn Leu Thr Pro Asn
        515                 520                 525

Arg Val
    530


<210> SEQ ID NO 105
<211> LENGTH: 1902
<212> TYPE: DNA
<213> ORGANISM: Arabidopsis thaliana

<400> SEQUENCE: 105

agtgtgagta atttagcttg aatcaaatct caaacttgca aagaaacttg aaatatttta      60

taacaatggg tgattctact ggtgagccgg ggagctccat gcatggagtc accggtagag     120

aacaaagctt tgcattctcg gtgcaatcac caattgtgca taccgacaag acggccaagt     180

tcgaccttcc ggtggacaca gagcataagg caacggtttt caagctcttc tccttcgcca     240

aacctcacat gagaacgttc catctctcgt ggatctcttt ctccacatgt tttgtctcga     300

ctttcgcagc tgcaccactt gtccctatca tccgggagaa tctcaacctc accaaacaag     360

acattggaaa cgccggagtt gcctctgtct ctgggagtat cttctctagg ctcgtgatgg     420

gagccgtgtg tgatcttttg ggtccccgtt acggttgtgc cttccttgtg atgttgtctg     480

ccccaacggt gttctccatg agcttcgtga gtgacgcagc aggcttcata acggtgaggt     540

tcatgattgg tttttgcctg gcgacgtttg tgtcttgtca atactggatg agcactatgt     600

tcaacagtca gatcattggt ctggtgaatg ggacagcagc cggatgggga aacatgggtg     660

gcggcataac gcagttgctc atgcccattg tgtatgaaat cattaggcgc tgcggttcca     720

cagccttcac ggcctggagg atcgccttct ttgtacccgg ttggttgcac atcatcatgg     780

gaatcttggt gctcaatcta ggtcaagatc tgccagatgg aaatcgagct accttggaga     840

aagcgggaga agttgccaaa gacaaattcg gaaagattct gtggtatgcc gttacaaact     900

acaggacttg gatcttcgtt cttctctacg gatactccat gggagttgag ttgagcactg     960

ataatgttat cgccgagtac ttctttgaca ggtttcactt gaagctccac acagcagggc    1020

tcatagcagc atgtttcgga atggccaatt tctttgctcg tccagcagga ggctacgcat    1080

ctgactttgc agccaagtac ttcgggatga gagggaggtt gtggacgttg tggatcatac    1140

agacggctgg tggcctcttc tgtgtgtggc tcggccgcgc caacaccctt gtaactgccg    1200

ttgtggctat ggtgctcttc tctatggggg cacaagctgc ttgcggagcc acctttgcaa    1260

ttgtgccctt tgtctcccgg cgagctctag gcatcatctc gggtttaacc ggggctggag    1320
```

```
ggaactttgg atcagggctc acacaactcc tcttcttctc gacctcacac ttcacaactg   1380

aacaagggct aacgtggatg ggagtgatga tagtcgcttg cacgttacct gtgaccttag   1440

ttcactttcc tcaatgggga agcatgttct tgcctccttc cacagatcca gtgaaaggta   1500

cagaggctca ttattatggt tctgagtgga atgagcagga gaagcagaag aacatgcatc   1560

aaggaagcct ccggtttgcc gagaacgcca agtcagaggg tggacgccgc gtccgctctg   1620

ctgctacgcc gcctgagaac acacccaaca atgtttgatc atacattcca cccacggtgg   1680

aatggtgaag gatgatcgca tataagaata tgtcacacag tgaaaaaaaa aaatgcaaat   1740

gttatcaatg cttgcataac attactatct atctttcatt tactaaacaa accttttgct   1800

ttttgccttg aaatcttttt attatatatc aaaatatatc tctatgtctt gaggtttgat   1860

tattttgcat atatcattaa tgatttgata atattggaac tg                      1902
```

```
<210> SEQ ID NO 106
<211> LENGTH: 530
<212> TYPE: PRT
<213> ORGANISM: Arabidopsis thaliana

<400> SEQUENCE: 106

Met Gly Asp Ser Thr Gly Glu Pro Gly Ser Ser Met His Gly Val Thr
1               5                   10                  15

Gly Arg Glu Gln Ser Phe Ala Phe Ser Val Gln Ser Pro Ile Val His
            20                  25                  30

Thr Asp Lys Thr Ala Lys Phe Asp Leu Pro Val Asp Thr Glu His Lys
        35                  40                  45

Ala Thr Val Phe Lys Leu Phe Ser Phe Ala Lys Pro His Met Arg Thr
    50                  55                  60

Phe His Leu Ser Trp Ile Ser Phe Ser Thr Cys Phe Val Ser Thr Phe
65                  70                  75                  80

Ala Ala Ala Pro Leu Val Pro Ile Ile Arg Glu Asn Leu Asn Leu Thr
                85                  90                  95

Lys Gln Asp Ile Gly Asn Ala Gly Val Ala Ser Val Ser Gly Ser Ile
            100                 105                 110

Phe Ser Arg Leu Val Met Gly Ala Val Cys Asp Leu Leu Gly Pro Arg
        115                 120                 125

Tyr Gly Cys Ala Phe Leu Val Met Leu Ser Ala Pro Thr Val Phe Ser
    130                 135                 140

Met Ser Phe Val Ser Asp Ala Ala Gly Phe Ile Thr Val Arg Phe Met
145                 150                 155                 160

Ile Gly Phe Cys Leu Ala Thr Phe Val Ser Cys Gln Tyr Trp Met Ser
                165                 170                 175

Thr Met Phe Asn Ser Gln Ile Ile Gly Leu Val Asn Gly Thr Ala Ala
            180                 185                 190

Gly Trp Gly Asn Met Gly Gly Gly Ile Thr Gln Leu Leu Met Pro Ile
        195                 200                 205

Val Tyr Glu Ile Ile Arg Arg Cys Gly Ser Thr Ala Phe Thr Ala Trp
    210                 215                 220

Arg Ile Ala Phe Phe Val Pro Gly Trp Leu His Ile Ile Met Gly Ile
225                 230                 235                 240

Leu Val Leu Asn Leu Gly Gln Asp Leu Pro Asp Gly Asn Arg Ala Thr
                245                 250                 255

Leu Glu Lys Ala Gly Glu Val Ala Lys Asp Lys Phe Gly Lys Ile Leu
            260                 265                 270
```

```
Trp Tyr Ala Val Thr Asn Tyr Arg Thr Trp Ile Phe Val Leu Leu Tyr
        275                 280                 285

Gly Tyr Ser Met Gly Val Glu Leu Ser Thr Asp Asn Val Ile Ala Glu
    290                 295                 300

Tyr Phe Phe Asp Arg Phe His Leu Lys Leu His Thr Ala Gly Leu Ile
305                 310                 315                 320

Ala Ala Cys Phe Gly Met Ala Asn Phe Phe Ala Arg Pro Ala Gly Gly
                325                 330                 335

Tyr Ala Ser Asp Phe Ala Ala Lys Tyr Phe Gly Met Arg Gly Arg Leu
            340                 345                 350

Trp Thr Leu Trp Ile Ile Gln Thr Ala Gly Gly Leu Phe Cys Val Trp
        355                 360                 365

Leu Gly Arg Ala Asn Thr Leu Val Thr Ala Val Val Ala Met Val Leu
    370                 375                 380

Phe Ser Met Gly Ala Gln Ala Ala Cys Gly Ala Thr Phe Ala Ile Val
385                 390                 395                 400

Pro Phe Val Ser Arg Arg Ala Leu Gly Ile Ile Ser Gly Leu Thr Gly
                405                 410                 415

Ala Gly Gly Asn Phe Gly Ser Gly Leu Thr Gln Leu Leu Phe Phe Ser
            420                 425                 430

Thr Ser His Phe Thr Thr Glu Gln Gly Leu Thr Trp Met Gly Val Met
        435                 440                 445

Ile Val Ala Cys Thr Leu Pro Val Thr Leu Val His Phe Pro Gln Trp
    450                 455                 460

Gly Ser Met Phe Leu Pro Pro Ser Thr Asp Pro Val Lys Gly Thr Glu
465                 470                 475                 480

Ala His Tyr Tyr Gly Ser Glu Trp Asn Glu Gln Glu Lys Gln Lys Asn
                485                 490                 495

Met His Gln Gly Ser Leu Arg Phe Ala Glu Asn Ala Lys Ser Glu Gly
            500                 505                 510

Gly Arg Arg Val Arg Ser Ala Ala Thr Pro Pro Glu Asn Thr Pro Asn
        515                 520                 525

Asn Val
    530
```

<210> SEQ ID NO 107
<211> LENGTH: 1870
<212> TYPE: DNA
<213> ORGANISM: Lycopersicon esculentum

<400> SEQUENCE: 107

```
tttcaaatca atcatttata aaattaacca gttatttcct caattgaaga aatgactgat      60

gtagaaggat caccggggag ttctatgcat ggagtcaccg gaagagaacc tgttctcgct     120

ttctccgtgg cttctccaat ggtgcctacg gatacctccg ccaagttttc agtaccggtg     180

gatactgaac acaaggctaa acaatttaag ttttattcgt tttcgaagcc tcatggactt     240

acgttccagc tctcctggat ctcctttttc acttgtttcg tttcgacttt tgctgctgca     300

cctttagttc ctattattag ggacaatctt aatttgacaa aaatggatgt cggtaacgct     360

ggggttgctt ccgtatccgg aagtatttta tctaggctta cgatgggtgc ggtttgtgat     420

ttgttgggtc caaggtatgg gtgcgctttt cttatcatgt tgtcggcccc aactgttttt     480

tgtatgtcct ttgtttcatc cgctggtggc tacgtagccg tccggttcat gattgggttt     540

tccctcgcaa cgtttgtgtc gtgtcaatat tggatgagta ctatgtttaa tagtaagatc     600
```

-continued

```
atagggctag tgaacggaac ggctgctgga tggggtaata tgggtggagg tgcaactcaa    660

ctcattatgc cacttttgta tgatataatt cggagggcgg gtgcaattcc gttcactgct    720

tggagaattg catttttttat tcctggatgg cttcatgtgg tgatgggtat tttagtgttg   780

actcttggcc aagatttacc cgacggaaat cgtggcactt tacagaagac gggtactgtt    840

gctaaagata aattcggtaa catattgtgg tatgctgcaa caaactacag gacatggatc    900

tttgttcttc tctatggata ctctatggga gttgaactgt caacagacaa cgtcattgct    960

gagtacttct tcgacagatt tgatctaaag cttagcacag cggggatcat tgctgccaca   1020

tttggtatgg ctaacctttt ggctcgacca tttggaggat tttcttctga ttacgcagca   1080

aagaaattcg gtatgagagg gagactttgg gttttgtgga ttttacaaac acttggagga   1140

gtattttgtg ttcttttggg tcgttcgaat tctctaccac ttgctgtaac ctttatgatc   1200

cttttctcaa tcggagctca agctgcttgt ggtgcaactt ttggtattat tccattcatt   1260

tctcgacgat cgttaggaat tataagcgga atgacagggg caggtggaaa ttttggttct   1320

ggattgactc aattgttgtt tttcacgagc tcaaagtact cgacagcgac agggttaact   1380

tacatgggat tcatgatcat aggatgcact cttcctgtta cattttgtca tttcccacaa   1440

tggggaagca tgtttctccc accaacaaaa gatccagtca agggaacgga agaacattat   1500

tatacttcag agtacacaga ggcagagagg caaaaaggga tgcaccaaaa cagcttgaaa   1560

ttcgctgaaa attgccgatc ggagcgtggt aagcgcgttg gttccgcacc cactccacca   1620

aatttgacac caaaccgtgt ctgatcggat tgatgatcgt caatctttag ttcaatgagc   1680

tgagttgttt caataagcaa aataagtcct gatttttttt tcttctttct tttttgtttt   1740

tttcttaaat gatgttgctt gtcaatacgc tggaatctac taaggtgtat gtggttttaa   1800

atttacgtat atataatata tatatatata tatattacac attttaatgt taaaaaaaaa   1860

aaaaaaaaaa                                                          1870
```

<210> SEQ ID NO 108
<211> LENGTH: 530
<212> TYPE: PRT
<213> ORGANISM: Lycopersicon esculentum

<400> SEQUENCE: 108

```
Met Thr Asp Val Glu Gly Ser Pro Gly Ser Ser Met His Gly Val Thr
1               5                   10                  15

Gly Arg Glu Pro Val Leu Ala Phe Ser Val Ala Ser Pro Met Val Pro
            20                  25                  30

Thr Asp Thr Ser Ala Lys Phe Ser Val Pro Val Asp Thr Glu His Lys
        35                  40                  45

Ala Lys Gln Phe Lys Phe Tyr Ser Phe Ser Lys Pro His Gly Leu Thr
    50                  55                  60

Phe Gln Leu Ser Trp Ile Ser Phe Phe Thr Cys Phe Val Ser Thr Phe
65                  70                  75                  80

Ala Ala Ala Pro Leu Val Pro Ile Ile Arg Asp Asn Leu Asn Leu Thr
                85                  90                  95

Lys Met Asp Val Gly Asn Ala Gly Val Ala Ser Val Ser Gly Ser Ile
            100                 105                 110

Leu Ser Arg Leu Thr Met Gly Ala Val Cys Asp Leu Leu Gly Pro Arg
        115                 120                 125

Tyr Gly Cys Ala Phe Leu Ile Met Leu Ser Ala Pro Thr Val Phe Cys
    130                 135                 140
```

```
Met Ser Phe Val Ser Ser Ala Gly Gly Tyr Val Ala Val Arg Phe Met
145                 150                 155                 160

Ile Gly Phe Ser Leu Ala Thr Phe Val Ser Cys Gln Tyr Trp Met Ser
                165                 170                 175

Thr Met Phe Asn Ser Lys Ile Ile Gly Leu Val Asn Gly Thr Ala Ala
            180                 185                 190

Gly Trp Gly Asn Met Gly Gly Gly Ala Thr Gln Leu Ile Met Pro Leu
        195                 200                 205

Leu Tyr Asp Ile Ile Arg Arg Ala Gly Ala Ile Pro Phe Thr Ala Trp
    210                 215                 220

Arg Ile Ala Phe Phe Ile Pro Gly Trp Leu His Val Val Met Gly Ile
225                 230                 235                 240

Leu Val Leu Thr Leu Gly Gln Asp Leu Pro Asp Gly Asn Arg Gly Thr
                245                 250                 255

Leu Gln Lys Thr Gly Thr Val Ala Lys Asp Lys Phe Gly Asn Ile Leu
            260                 265                 270

Trp Tyr Ala Ala Thr Asn Tyr Arg Thr Trp Ile Phe Val Leu Leu Tyr
        275                 280                 285

Gly Tyr Ser Met Gly Val Glu Leu Ser Thr Asp Asn Val Ile Ala Glu
    290                 295                 300

Tyr Phe Phe Asp Arg Phe Asp Leu Lys Leu Ser Thr Ala Gly Ile Ile
305                 310                 315                 320

Ala Ala Thr Phe Gly Met Ala Asn Leu Leu Ala Arg Pro Phe Gly Gly
                325                 330                 335

Phe Ser Ser Asp Tyr Ala Ala Lys Lys Phe Gly Met Arg Gly Arg Leu
            340                 345                 350

Trp Val Leu Trp Ile Leu Gln Thr Leu Gly Gly Val Phe Cys Val Leu
        355                 360                 365

Leu Gly Arg Ser Asn Ser Leu Pro Leu Ala Val Thr Phe Met Ile Leu
    370                 375                 380

Phe Ser Ile Gly Ala Gln Ala Ala Cys Gly Ala Thr Phe Gly Ile Ile
385                 390                 395                 400

Pro Phe Ile Ser Arg Arg Ser Leu Gly Ile Ile Ser Gly Met Thr Gly
                405                 410                 415

Ala Gly Gly Asn Phe Gly Ser Gly Leu Thr Gln Leu Leu Phe Phe Thr
            420                 425                 430

Ser Ser Lys Tyr Ser Thr Ala Thr Gly Leu Thr Tyr Met Gly Phe Met
        435                 440                 445

Ile Ile Gly Cys Thr Leu Pro Val Thr Phe Cys His Phe Pro Gln Trp
    450                 455                 460

Gly Ser Met Phe Leu Pro Pro Thr Lys Asp Pro Val Lys Gly Thr Glu
465                 470                 475                 480

Glu His Tyr Tyr Thr Ser Glu Tyr Thr Glu Ala Glu Arg Gln Lys Gly
                485                 490                 495

Met His Gln Asn Ser Leu Lys Phe Ala Glu Asn Cys Arg Ser Glu Arg
            500                 505                 510

Gly Lys Arg Val Gly Ser Ala Pro Thr Pro Pro Asn Leu Thr Pro Asn
        515                 520                 525

Arg Val
    530
```

<210> SEQ ID NO 109
<211> LENGTH: 1832
<212> TYPE: DNA

<213> ORGANISM: Brassica napus

<400> SEQUENCE: 109

```
cacattcttg tgaaagaact taaacatttt gcatcaatgg gtgattctac tggcgagccg     60
ggaagctcca tgcatggagt gaccggtaga gaacaaacat ttgctttctc ggtggcttca    120
ccgattgtcc caaccgacaa gacagcaaag ttcgacctgc cggtggactc ggagcataag    180
gcaacggttt tcaagctctt ctccttcgcc aaacctcaca tgcgaacgtt ccatctctcg    240
tggatctctt tctccacgtg ttttgtctcg acgtttgcgg ctgcaccact tgtccccatc    300
atccgagaga atctcaacct cacgaaacaa gacatcggta acgcaggagt tgcgtccgtc    360
tcggggagta tcttctctag gctggtgatg ggagcagtgt gtgatcttct cggtccacgt    420
tacggctgtg ccttccttgt tatgctttcc gcaccaacgg tgttctcaat gagcttcgtg    480
agtggagccg caggattcat aacggtgagg ttcatgattg ggttctgtct agcaacgttt    540
gtgtcttgtc aatatggaat gagtactatg ttcaatagtc agatcatcgg tctggtgaac    600
ggtacagccg ccgggtgggg aaacatgggt ggtggcataa cgcagttgct catgccggtt    660
gtctatgaga tcataaggcg ctgtggtgca acagcgttca cggcctggag gcttgccttc    720
ttcgtccctg gttggttgca catcatcatg ggagtcttgg tgctcaatct aggtcaagat    780
ttgccagatg gtaaccgaag tgccttggag aaaaagggag aagttgccaa agacaaattc    840
ggaaagatta tgtggtacgc cgtcacaaac tacaggactt ggatctttgt tcttctctat    900
ggatactcca tgggagttga gctgagcact gacaatgtta tcgccgaata cttctttgac    960
aggttccact tgaagcttca cacagctgga atcatagcag catgtttcgg aatggccaac   1020
ttctttgctc gtccagcagg aggctatgca tctgaccttg cagccaaata cttcgggatg   1080
agagggaggt tatgggcgtt gtggatcatt cagacagcag gtggtgtctt ctgcgtgtgg   1140
ctcggccgtg ccaacaccct cgttactgcc gttgtagcta tggtcctctt ctctttagga   1200
gcacaagccg cttgtggagc caccttcgca atcgttccct ttgtttctcg gcgagccctt   1260
ggtatcatct caggtttaac cggtgctgga ggaaactttg ggtcagggct cacacagctc   1320
atcttcttct cgacctcaag gttcacaacc gaacaagggc taacatggat gggagtgatg   1380
atagttgcct gcacgttgcc tgtgacttta atccacttcc ctcagtgggg aagcatgttc   1440
ttgcctcctt ctaccgatcc agtcaaaggt ccgaaggagc actattatgc ttcagagtgg   1500
aatgagcagg agaaggagaa gaacatgcat cagggaagcc tcaggtttgc taagaacgcc   1560
aagtctgagg gcggccgccg tgtccgttct gctgctaccc cgcctgagaa cacaccaaac   1620
aatgtttgat cataccagcc acaaggaaag tgtgaaggat ggtcgcagat aagaatttat   1680
atgtcccaca gtgaaaacaa atgcgtatgt tatcaatgct tgctggacgt tatttgttgt   1740
gtatctttct ttttttcact gaagaaacat ttgttttgtt tacggcttca agaaatattt   1800
ttctaatcaa aatgtctacc tcttgcgaca tt                                 1832
```

<210> SEQ ID NO 110
<211> LENGTH: 530
<212> TYPE: PRT
<213> ORGANISM: Brassica napus

<400> SEQUENCE: 110

```
Met Gly Asp Ser Thr Gly Glu Pro Gly Ser Ser Met His Gly Val Thr
1               5                   10                  15

Gly Arg Glu Gln Thr Phe Ala Phe Ser Val Ala Ser Pro Ile Val Pro
            20                  25                  30
```

-continued

```
Thr Asp Lys Thr Ala Lys Phe Asp Leu Pro Val Asp Ser Glu His Lys
        35                  40                  45

Ala Thr Val Phe Lys Leu Phe Ser Phe Ala Lys Pro His Met Arg Thr
    50                  55                  60

Phe His Leu Ser Trp Ile Ser Phe Ser Thr Cys Phe Val Ser Thr Phe
65                  70                  75                  80

Ala Ala Ala Pro Leu Val Pro Ile Ile Arg Glu Asn Leu Asn Leu Thr
                85                  90                  95

Lys Gln Asp Ile Gly Asn Ala Gly Val Ala Ser Val Ser Gly Ser Ile
            100                 105                 110

Phe Ser Arg Leu Val Met Gly Ala Val Cys Asp Leu Leu Gly Pro Arg
        115                 120                 125

Tyr Gly Cys Ala Phe Leu Val Met Leu Ser Ala Pro Thr Val Phe Ser
    130                 135                 140

Met Ser Phe Val Ser Gly Ala Ala Gly Phe Ile Thr Val Arg Phe Met
145                 150                 155                 160

Ile Gly Phe Cys Leu Ala Thr Phe Val Ser Cys Gln Tyr Gly Met Ser
                165                 170                 175

Thr Met Phe Asn Ser Gln Ile Ile Gly Leu Val Asn Gly Thr Ala Ala
            180                 185                 190

Gly Trp Gly Asn Met Gly Gly Gly Ile Thr Gln Leu Leu Met Pro Val
        195                 200                 205

Val Tyr Glu Ile Ile Arg Arg Cys Gly Ala Thr Ala Phe Thr Ala Trp
    210                 215                 220

Arg Leu Ala Phe Phe Val Pro Gly Trp Leu His Ile Ile Met Gly Val
225                 230                 235                 240

Leu Val Leu Asn Leu Gly Gln Asp Leu Pro Asp Gly Asn Arg Ser Ala
                245                 250                 255

Leu Glu Lys Lys Gly Glu Val Ala Lys Asp Lys Phe Gly Lys Ile Met
            260                 265                 270

Trp Tyr Ala Val Thr Asn Tyr Arg Thr Trp Ile Phe Val Leu Leu Tyr
        275                 280                 285

Gly Tyr Ser Met Gly Val Glu Leu Ser Thr Asp Asn Val Ile Ala Glu
    290                 295                 300

Tyr Phe Phe Asp Arg Phe His Leu Lys Leu His Thr Ala Gly Ile Ile
305                 310                 315                 320

Ala Ala Cys Phe Gly Met Ala Asn Phe Phe Ala Arg Pro Ala Gly Gly
                325                 330                 335

Tyr Ala Ser Asp Leu Ala Ala Lys Tyr Phe Gly Met Arg Gly Arg Leu
            340                 345                 350

Trp Ala Leu Trp Ile Ile Gln Thr Ala Gly Gly Val Phe Cys Val Trp
        355                 360                 365

Leu Gly Arg Ala Asn Thr Leu Val Thr Ala Val Val Ala Met Val Leu
    370                 375                 380

Phe Ser Leu Gly Ala Gln Ala Ala Cys Gly Ala Thr Phe Ala Ile Val
385                 390                 395                 400

Pro Phe Val Ser Arg Arg Ala Leu Gly Ile Ile Ser Gly Leu Thr Gly
                405                 410                 415

Ala Gly Gly Asn Phe Gly Ser Gly Leu Thr Gln Leu Ile Phe Phe Ser
            420                 425                 430

Thr Ser Arg Phe Thr Thr Glu Gln Gly Leu Thr Trp Met Gly Val Met
        435                 440                 445
```

-continued

```
Ile Val Ala Cys Thr Leu Pro Val Thr Leu Ile His Phe Pro Gln Trp
    450                 455                 460

Gly Ser Met Phe Leu Pro Pro Ser Thr Asp Pro Val Lys Gly Pro Lys
465                 470                 475                 480

Glu His Tyr Tyr Ala Ser Glu Trp Asn Glu Gln Glu Lys Glu Lys Asn
                485                 490                 495

Met His Gln Gly Ser Leu Arg Phe Ala Lys Asn Ala Lys Ser Glu Gly
            500                 505                 510

Gly Arg Arg Val Arg Ser Ala Ala Thr Pro Pro Glu Asn Thr Pro Asn
        515                 520                 525

Asn Val
    530
```

<210> SEQ ID NO 111
<211> LENGTH: 1584
<212> TYPE: DNA
<213> ORGANISM: Arabidopsis thaliana

<400> SEQUENCE: 111

```
atggccgatg gttttggtga accgggaagc tcaatgcatg gagtcaccgg cagagaacaa     60

agctatgcat tctctgtcga gtctccggca gttccttccg actcatcagc aaaattttct    120

ctccccgtgg acaccgaaca caaagccaaa gtcttcaaac tcttatcctt tgaagctcca    180

catatgagaa ctttccatct tgcttggatc tcattcttca cttgcttcat ttccactttc    240

gctgctgctc ctcttgtccc catcattaga gataacctta atctcacaag acaagatgtc    300

ggaaatgctg gtgttgcttc tgtctctggc agtatcttct ctaggcttgt tatgggagca    360

gtttgtgatc tccttgggcc acgttatggc tgtgctttcc tcgtcatgct ctctgctcca    420

accgtcttct ccatgtcttt cgttggtggt gccggagggt acataacggt gaggttcatg    480

atcgggttct gcctggcgac tttcgtgtca tgccagtatt ggatgagcac aatgttcaat    540

ggtcagatca taggtctagt gaacgggaca gcggcagggt gggggaacat gggcggtggg    600

gtcactcagt tgctcatgcc aatggtctat gagatcatcc gacggttagg gtccacgtcc    660

ttcaccgcat ggaggatggc tttcttcgtc cccgggtgga tgcacatcat catggggatc    720

ttggtcttga ctctagggca agacctccct gatggtaata gaagcacact cgagaagaaa    780

ggtgcagtta ctaaagacaa gttctcaaag gttttatggt acgcgatcac gaactatagg    840

acatgggttt tcgtgctgct atatggatac tccatgggag tagagctcac aaccgataac    900

gtcatcgctg agtacttttt cgacaggttc catcttaagc ttcataccgc cggtataatc    960

gcggcaagct ttggtatggc aaacttcttt gcccgtccta ttggtggttg ggcctcagat   1020

attgcggcta gacgcttcgg catgagaggc cgtctctgga ccctatggat catccaaacc   1080

ttaggcggtt tcttctgcct atggctaggc cgagccacca cgctcccgac cgcggttgtc   1140

ttcatgatcc tcttctctct cggcgctcaa gccgcttgtg gagctacctt tgctatcata   1200

cctttcatct cacgccgctc cttagggatc atctctggtc ttactggagc tggtggaaac   1260

ttcggctctg gtttgaccca actcgtattc ttctcgacct caacgttctc cacggaacaa   1320

gggctgacat ggatgggggt gatgattatg gcgtgtacat tacccgtcac tttagtgcac   1380

ttcccgcaat ggggaagcat gtttttgcct tccacggaag atgaagtgaa gtctacggag   1440

gagtattatt acatgaaaga gtggacagag accgagaagc gaaagggtat gcatgaaggg   1500

agtttgaagt tcgccgtgaa tagtagatcg gagcgtggac ggcgcgtggc ttctgcaccg   1560

tctcctccgc cggaacacgt ttaa                                          1584
```

<210> SEQ ID NO 112
<211> LENGTH: 527
<212> TYPE: PRT
<213> ORGANISM: Arabidopsis thaliana

<400> SEQUENCE: 112

Met Ala Asp Gly Phe Gly Glu Pro Gly Ser Ser Met His Gly Val Thr
1 5 10 15

Gly Arg Glu Gln Ser Tyr Ala Phe Ser Val Glu Ser Pro Ala Val Pro
20 25 30

Ser Asp Ser Ser Ala Lys Phe Ser Leu Pro Val Asp Thr Glu His Lys
35 40 45

Ala Lys Val Phe Lys Leu Leu Ser Phe Glu Ala Pro His Met Arg Thr
50 55 60

Phe His Leu Ala Trp Ile Ser Phe Phe Thr Cys Phe Ile Ser Thr Phe
65 70 75 80

Ala Ala Ala Pro Leu Val Pro Ile Ile Arg Asp Asn Leu Asn Leu Thr
85 90 95

Arg Gln Asp Val Gly Asn Ala Gly Val Ala Ser Val Ser Gly Ser Ile
100 105 110

Phe Ser Arg Leu Val Met Gly Ala Val Cys Asp Leu Leu Gly Pro Arg
115 120 125

Tyr Gly Cys Ala Phe Leu Val Met Leu Ser Ala Pro Thr Val Phe Ser
130 135 140

Met Ser Phe Val Gly Gly Ala Gly Gly Tyr Ile Thr Val Arg Phe Met
145 150 155 160

Ile Gly Phe Cys Leu Ala Thr Phe Val Ser Cys Gln Tyr Trp Met Ser
165 170 175

Thr Met Phe Asn Gly Gln Ile Ile Gly Leu Val Asn Gly Thr Ala Ala
180 185 190

Gly Trp Gly Asn Met Gly Gly Gly Val Thr Gln Leu Leu Met Pro Met
195 200 205

Val Tyr Glu Ile Ile Arg Arg Leu Gly Ser Thr Ser Phe Thr Ala Trp
210 215 220

Arg Met Ala Phe Phe Val Pro Gly Trp Met His Ile Ile Met Gly Ile
225 230 235 240

Leu Val Leu Thr Leu Gly Gln Asp Leu Pro Asp Gly Asn Arg Ser Thr
245 250 255

Leu Glu Lys Lys Gly Ala Val Thr Lys Asp Lys Phe Ser Lys Val Leu
260 265 270

Trp Tyr Ala Ile Thr Asn Tyr Arg Thr Trp Val Phe Val Leu Leu Tyr
275 280 285

Gly Tyr Ser Met Gly Val Glu Leu Thr Thr Asp Asn Val Ile Ala Glu
290 295 300

Tyr Phe Phe Asp Arg Phe His Leu Lys Leu His Thr Ala Gly Ile Ile
305 310 315 320

Ala Ala Ser Phe Gly Met Ala Asn Phe Phe Ala Arg Pro Ile Gly Gly
325 330 335

Trp Ala Ser Asp Ile Ala Ala Arg Arg Phe Gly Met Arg Gly Arg Leu
340 345 350

Trp Thr Leu Trp Ile Ile Gln Thr Leu Gly Gly Phe Phe Cys Leu Trp
355 360 365

Leu Gly Arg Ala Thr Thr Leu Pro Thr Ala Val Val Phe Met Ile Leu

```
    370                 375                 380

Phe Ser Leu Gly Ala Gln Ala Ala Cys Gly Ala Thr Phe Ala Ile Ile
385                 390                 395                 400

Pro Phe Ile Ser Arg Arg Ser Leu Gly Ile Ile Ser Gly Leu Thr Gly
                405                 410                 415

Ala Gly Gly Asn Phe Gly Ser Gly Leu Thr Gln Leu Val Phe Phe Ser
            420                 425                 430

Thr Ser Thr Phe Ser Thr Glu Gln Gly Leu Thr Trp Met Gly Val Met
        435                 440                 445

Ile Met Ala Cys Thr Leu Pro Val Thr Leu Val His Phe Pro Gln Trp
    450                 455                 460

Gly Ser Met Phe Leu Pro Ser Thr Glu Asp Glu Val Lys Ser Thr Glu
465                 470                 475                 480

Glu Tyr Tyr Tyr Met Lys Glu Trp Thr Glu Thr Glu Lys Arg Lys Gly
                485                 490                 495

Met His Glu Gly Ser Leu Lys Phe Ala Val Asn Ser Arg Ser Glu Arg
            500                 505                 510

Gly Arg Arg Val Ala Ser Ala Pro Ser Pro Pro Pro Glu His Val
        515                 520                 525


<210> SEQ ID NO 113
<211> LENGTH: 1709
<212> TYPE: PRT
<213> ORGANISM: Arabidopsis thaliana

<400> SEQUENCE: 113

Ala Ala Ala Cys Thr Thr Gly Ala Ala Thr Thr Thr Thr Cys Thr Cys
1               5                   10                  15

Ala Ala Ala Gly Gly Ala Ala Cys Thr Thr Gly Ala Thr Ala Cys Gly
            20                  25                  30

Thr Thr Thr Ala Ala Ala Ala Thr Ala Cys Ala Thr Gly Gly Gly Thr
        35                  40                  45

Thr Cys Thr Ala Cys Thr Gly Ala Thr Gly Ala Gly Cys Cys Cys Gly
    50                  55                  60

Gly Ala Ala Gly Thr Thr Cys Cys Ala Thr Gly Cys Ala Thr Gly Gly
65                  70                  75                  80

Ala Gly Thr Thr Ala Cys Cys Gly Gly Thr Ala Gly Ala Gly Ala Ala
                85                  90                  95

Cys Ala Gly Ala Gly Cys Thr Ala Thr Gly Cys Thr Thr Thr Cys Thr
            100                 105                 110

Cys Gly Gly Thr Ala Gly Ala Thr Gly Gly Thr Ala Gly Thr Gly Ala
        115                 120                 125

Gly Cys Cys Gly Ala Cys Cys Ala Ala Cys Ala Cys Ala Ala Ala Gly
    130                 135                 140

Ala Ala Ala Ala Ala Gly Thr Ala Cys Ala Ala Thr Cys Thr Gly Cys
145                 150                 155                 160

Cys Gly Gly Thr Gly Gly Ala Cys Gly Cys Gly Gly Ala Gly Gly Ala
                165                 170                 175

Thr Ala Ala Gly Gly Cys Ala Ala Cys Gly Gly Thr Thr Thr Thr Cys
            180                 185                 190

Ala Ala Gly Cys Thr Cys Thr Thr Cys Thr Cys Cys Thr Thr Cys Gly
        195                 200                 205

Cys Cys Ala Ala Ala Cys Cys Thr Cys Ala Cys Ala Thr Gly Ala Gly
    210                 215                 220
```

```
Ala Ala Cys Gly Thr Thr Cys Cys Ala Cys Cys Thr Cys Thr Cys Gly
225                 230                 235                 240

Thr Gly Gly Ala Thr Cys Thr Cys Thr Thr Thr Cys Thr Cys Cys Ala
                245                 250                 255

Cys Ala Thr Gly Thr Thr Thr Thr Gly Thr Thr Thr Cys Gly Ala Cys
            260                 265                 270

Gly Thr Thr Cys Gly Cys Ala Gly Cys Thr Gly Cys Ala Cys Cys Ala
        275                 280                 285

Cys Thr Thr Ala Thr Cys Cys Cys Gly Ala Thr Cys Ala Thr Cys Ala
    290                 295                 300

Gly Gly Gly Ala Gly Ala Ala Thr Cys Thr Thr Ala Ala Cys Cys Thr
305                 310                 315                 320

Cys Ala Cys Cys Ala Ala Ala Cys Ala Thr Gly Ala Cys Ala Thr Thr
                325                 330                 335

Gly Gly Ala Ala Ala Cys Gly Cys Thr Gly Gly Ala Gly Thr Thr Gly
            340                 345                 350

Cys Cys Thr Cys Cys Gly Thr Cys Thr Cys Gly Gly Gly Gly Ala Gly
        355                 360                 365

Thr Ala Thr Cys Thr Thr Cys Thr Cys Thr Ala Gly Gly Cys Thr Cys
    370                 375                 380

Gly Thr Gly Ala Thr Gly Gly Gly Ala Gly Cys Cys Gly Thr Gly Thr
385                 390                 395                 400

Gly Thr Gly Ala Thr Cys Thr Thr Thr Thr Gly Gly Gly Thr Cys Cys
                405                 410                 415

Thr Cys Gly Thr Thr Ala Cys Gly Gly Thr Thr Gly Thr Gly Cys Cys
            420                 425                 430

Thr Thr Cys Cys Thr Thr Gly Thr Gly Ala Thr Gly Thr Thr Gly Thr
        435                 440                 445

Cys Thr Gly Cys Cys Cys Cys Ala Ala Cys Gly Gly Thr Gly Thr Thr
    450                 455                 460

Cys Thr Cys Cys Ala Thr Gly Ala Gly Cys Thr Thr Cys Gly Thr Gly
465                 470                 475                 480

Ala Gly Thr Gly Ala Cys Gly Cys Ala Gly Cys Ala Gly Gly Cys Thr
                485                 490                 495

Thr Cys Ala Thr Ala Ala Cys Gly Gly Thr Gly Ala Gly Gly Thr Thr
            500                 505                 510

Cys Ala Thr Gly Ala Thr Thr Gly Gly Thr Thr Thr Thr Thr Gly Cys
        515                 520                 525

Cys Thr Gly Gly Cys Gly Ala Cys Gly Thr Thr Thr Gly Thr Gly Thr
    530                 535                 540

Cys Thr Thr Gly Thr Cys Ala Ala Thr Ala Cys Thr Gly Gly Ala Thr
545                 550                 555                 560

Gly Ala Gly Cys Ala Cys Thr Ala Thr Gly Thr Thr Cys Ala Ala Cys
                565                 570                 575

Ala Gly Thr Cys Ala Gly Ala Thr Cys Ala Thr Cys Gly Gly Thr Cys
            580                 585                 590

Thr Gly Gly Thr Gly Ala Ala Cys Gly Gly Gly Ala Cys Ala Gly Cys
        595                 600                 605

Ala Gly Cys Cys Gly Gly Ala Thr Gly Gly Gly Gly Ala Ala Ala Cys
    610                 615                 620

Ala Thr Gly Gly Gly Thr Gly Gly Cys Gly Gly Cys Ala Thr Ala Ala
625                 630                 635                 640

Cys Gly Cys Ala Gly Thr Thr Gly Cys Thr Cys Ala Thr Gly Cys Cys
```

-continued

```
                645                 650                 655

Cys Ala Thr Thr Gly Thr Gly Thr Ala Thr Gly Ala Ala Ala Thr Cys
            660                 665                 670

Ala Thr Thr Ala Gly Gly Cys Gly Cys Thr Gly Cys Gly Gly Ala Thr
        675                 680                 685

Cys Ala Ala Cys Ala Gly Cys Gly Thr Thr Cys Ala Cys Gly Gly Cys
    690                 695                 700

Cys Thr Gly Gly Ala Gly Gly Ala Thr Cys Gly Cys Cys Thr Thr Cys
705                 710                 715                 720

Thr Thr Thr Gly Thr Cys Cys Cys Cys Gly Gly Thr Thr Gly Gly Thr
                725                 730                 735

Thr Gly Cys Ala Cys Ala Thr Cys Ala Thr Cys Ala Thr Gly Gly Gly
            740                 745                 750

Ala Ala Thr Cys Thr Thr Gly Gly Thr Gly Cys Thr Cys Ala Cys Gly
        755                 760                 765

Cys Thr Ala Gly Gly Thr Cys Ala Ala Gly Ala Thr Cys Thr Gly Cys
    770                 775                 780

Cys Ala Gly Gly Thr Gly Gly Ala Ala Ala Cys Ala Gly Ala Gly Cys
785                 790                 795                 800

Thr Gly Cys Cys Ala Thr Gly Gly Ala Gly Ala Ala Ala Gly Cys Gly
                805                 810                 815

Gly Gly Ala Gly Ala Ala Gly Thr Thr Gly Cys Cys Ala Ala Ala Gly
            820                 825                 830

Ala Cys Ala Ala Ala Thr Thr Cys Gly Gly Ala Ala Ala Gly Ala Thr
        835                 840                 845

Thr Cys Thr Ala Thr Gly Gly Thr Ala Cys Gly Cys Cys Gly Thr Thr
    850                 855                 860

Ala Cys Ala Ala Ala Thr Thr Ala Cys Ala Gly Gly Ala Cys Thr Thr
865                 870                 875                 880

Gly Gly Ala Thr Thr Thr Thr Cys Gly Thr Thr Cys Thr Thr Cys Thr
                885                 890                 895

Gly Thr Ala Thr Gly Gly Ala Thr Ala Thr Thr Cys Cys Ala Thr Gly
            900                 905                 910

Gly Gly Ala Gly Thr Thr Gly Ala Gly Thr Thr Ala Ala Gly Cys Ala
        915                 920                 925

Cys Ala Gly Ala Cys Ala Ala Thr Gly Thr Thr Ala Thr Cys Gly Cys
    930                 935                 940

Cys Gly Ala Gly Thr Ala Cys Thr Thr Cys Thr Thr Thr Gly Ala Thr
945                 950                 955                 960

Ala Gly Gly Thr Thr Thr Cys Ala Cys Thr Thr Gly Ala Ala Gly Cys
                965                 970                 975

Thr Thr Cys Ala Cys Ala Cys Ala Gly Cys Gly Gly Gly Gly Ala Thr
            980                 985                 990

Thr Ala Thr Ala Gly Cys Ala Gly  Cys Ala Thr Gly Thr  Thr Thr Cys
        995                 1000                 1005

Gly Gly  Ala Ala Thr Gly Gly  Cys Cys Ala Ala Thr  Thr Thr Cys
    1010                 1015                 1020

Thr Thr  Thr Gly Cys Thr Cys  Gly Thr Cys Cys Ala  Gly Cys Ala
    1025                 1030                 1035

Gly Gly  Ala Gly Gly Cys Thr  Gly Gly Gly Cys Ala  Thr Cys Thr
    1040                 1045                 1050

Gly Ala  Cys Ala Thr Thr Gly  Cys Ala Gly Cys Cys  Ala Ala Gly
    1055                 1060                 1065
```

```
Cys Gly  Cys Thr Thr Cys Gly  Gly Ala Ala Thr Gly  Cys Gly Ala
    1070                 1075                 1080

Gly Gly  Gly Ala Gly Gly Thr  Thr Gly Thr Gly Gly  Ala Cys Thr
    1085                 1090                 1095

Thr Thr  Gly Thr Gly Gly Ala  Thr Cys Ala Thr Thr  Cys Ala Gly
    1100                 1105                 1110

Ala Cys  Gly Thr Cys Cys Gly  Gly Thr Gly Gly Thr  Cys Thr Cys
    1115                 1120                 1125

Thr Thr  Thr Thr Gly Thr Gly  Thr Gly Thr Gly Gly  Cys Thr Cys
    1130                 1135                 1140

Gly Gly  Ala Cys Gly Thr Gly  Cys Cys Ala Ala Cys  Ala Cys Cys
    1145                 1150                 1155

Cys Thr  Cys Gly Thr Cys Ala  Cys Thr Gly Cys Cys  Gly Thr Thr
    1160                 1165                 1170

Gly Thr  Ala Thr Cys Thr Ala  Thr Gly Gly Thr Cys  Cys Thr Cys
    1175                 1180                 1185

Thr Thr  Cys Thr Cys Thr Thr  Thr Ala Gly Gly Ala  Gly Cys Ala
    1190                 1195                 1200

Cys Ala  Ala Gly Cys Cys Gly  Cys Thr Thr Gly Cys  Gly Gly Ala
    1205                 1210                 1215

Gly Cys  Cys Ala Cys Cys Thr  Thr Thr Gly Cys Thr  Ala Thr Cys
    1220                 1225                 1230

Gly Thr  Gly Cys Cys Cys Thr  Thr Thr Gly Thr Cys  Thr Cys Cys
    1235                 1240                 1245

Cys Gly  Gly Cys Gly Ala Gly  Cys Thr Cys Thr Ala  Gly Gly Cys
    1250                 1255                 1260

Ala Thr  Thr Ala Thr Cys Thr  Cys Gly Gly Gly Thr  Thr Thr Ala
    1265                 1270                 1275

Ala Cys  Cys Gly Gly Gly Gly  Cys Thr Gly Gly Ala  Gly Gly Gly
    1280                 1285                 1290

Ala Ala  Cys Thr Thr Thr Gly  Gly Gly Thr Cys Ala  Gly Gly Ala
    1295                 1300                 1305

Cys Thr  Cys Ala Cys Ala Cys  Ala Gly Cys Thr Cys  Gly Thr Cys
    1310                 1315                 1320

Thr Thr  Thr Thr Thr Cys Thr  Cys Gly Ala Cys Thr  Thr Cys Gly
    1325                 1330                 1335

Cys Gly  Cys Thr Thr Cys Ala  Cys Ala Ala Cys Thr  Gly Ala Ala
    1340                 1345                 1350

Gly Ala  Ala Gly Gly Gly Cys  Thr Ala Ala Cys Gly  Thr Gly Gly
    1355                 1360                 1365

Ala Thr  Gly Gly Gly Ala Gly  Thr Gly Ala Thr Gly  Ala Thr Ala
    1370                 1375                 1380

Gly Thr  Thr Gly Cys Thr Thr  Gly Cys Ala Cys Gly  Thr Thr Gly
    1385                 1390                 1395

Cys Cys  Thr Gly Thr Thr Ala  Cys Cys Thr Thr Ala  Ala Thr Cys
    1400                 1405                 1410

Cys Ala  Cys Thr Thr Thr Cys  Cys Thr Cys Ala Gly  Thr Gly Gly
    1415                 1420                 1425

Gly Gly  Ala Ala Gly Cys Ala  Thr Gly Thr Thr Cys  Thr Thr Cys
    1430                 1435                 1440

Cys Cys  Thr Cys Cys Thr Thr  Cys Cys Ala Ala Cys  Gly Ala Thr
    1445                 1450                 1455
```

-continued

```
Thr Cys  Gly Gly Thr Cys Gly  Ala Cys Gly Cys Thr  Ala Cys Gly
    1460                 1465                 1470

Gly Ala  Gly Cys Ala Cys Thr  Ala Thr Thr Ala Thr  Gly Thr Thr
    1475                 1480                 1485

Gly Gly  Cys Gly Ala Ala Thr  Ala Thr Ala Gly Thr  Ala Ala Gly
    1490                 1495                 1500

Gly Ala  Gly Gly Ala Gly Cys  Ala Gly Cys Ala Gly  Ala Thr Thr
    1505                 1510                 1515

Gly Gly  Cys Ala Thr Gly Cys  Ala Thr Thr Thr Ala  Ala Ala Ala
    1520                 1525                 1530

Ala Gly  Cys Ala Ala Ala Cys  Thr Gly Thr Thr Thr  Gly Cys Thr
    1535                 1540                 1545

Gly Ala  Thr Gly Gly Ala Gly  Cys Cys Ala Ala Gly  Ala Cys Cys
    1550                 1555                 1560

Gly Ala  Gly Gly Gly Ala Gly  Gly Cys Ala Gly Cys  Ala Gly Cys
    1565                 1570                 1575

Gly Thr  Cys Cys Ala Cys Ala  Ala Ala Gly Gly Gly  Ala Ala Cys
    1580                 1585                 1590

Gly Cys  Ala Ala Cys Cys Ala  Ala Cys Ala Ala Thr  Gly Cys Thr
    1595                 1600                 1605

Thr Gly  Ala Thr Cys Ala Thr  Gly Thr Gly Thr Cys  Ala Thr Thr
    1610                 1615                 1620

Gly Ala  Thr Ala Thr Cys Ala  Ala Gly Ala Ala Ala  Thr Thr Ala
    1625                 1630                 1635

Ala Thr  Ala Ala Thr Thr Thr  Cys Ala Cys Thr Thr  Ala Thr Gly
    1640                 1645                 1650

Thr Gly  Ala Ala Ala Thr Gly  Gly Ala Cys Ala Thr  Ala Ala Ala
    1655                 1660                 1665

Cys Thr  Gly Thr Thr Gly Gly  Ala Ala Ala Ala Thr  Ala Ala Ala
    1670                 1675                 1680

Gly Ala  Ala Cys Cys Ala Thr  Thr Thr Cys Thr Thr  Thr Cys Ala
    1685                 1690                 1695

Thr Cys  Ala Thr Thr Thr Gly  Cys Thr Thr Thr
    1700                 1705
```

<210> SEQ ID NO 114
<211> LENGTH: 522
<212> TYPE: PRT
<213> ORGANISM: Arabidopsis thaliana

<400> SEQUENCE: 114

```
Met Gly Ser Thr Asp Glu Pro Gly Ser Ser Met His Gly Val Thr Gly
1               5                   10                  15

Arg Glu Gln Ser Tyr Ala Phe Ser Val Asp Gly Ser Glu Pro Thr Asn
            20                  25                  30

Thr Lys Lys Lys Tyr Asn Leu Pro Val Asp Ala Glu Asp Lys Ala Thr
        35                  40                  45

Val Phe Lys Leu Phe Ser Phe Ala Lys Pro His Met Arg Thr Phe His
    50                  55                  60

Leu Ser Trp Ile Ser Phe Ser Thr Cys Phe Val Ser Thr Phe Ala Ala
65                  70                  75                  80

Ala Pro Leu Ile Pro Ile Ile Arg Glu Asn Leu Asn Leu Thr Lys His
                85                  90                  95

Asp Ile Gly Asn Ala Gly Val Ala Ser Val Ser Gly Ser Ile Phe Ser
            100                 105                 110
```

```
Arg Leu Val Met Gly Ala Val Cys Asp Leu Leu Gly Pro Arg Tyr Gly
        115                 120                 125

Cys Ala Phe Leu Val Met Leu Ser Ala Pro Thr Val Phe Ser Met Ser
    130                 135                 140

Phe Val Ser Asp Ala Ala Gly Phe Ile Thr Val Arg Phe Met Ile Gly
145                 150                 155                 160

Phe Cys Leu Ala Thr Phe Val Ser Cys Gln Tyr Trp Met Ser Thr Met
                165                 170                 175

Phe Asn Ser Gln Ile Ile Gly Leu Val Asn Gly Thr Ala Ala Gly Trp
            180                 185                 190

Gly Asn Met Gly Gly Gly Ile Thr Gln Leu Leu Met Pro Ile Val Tyr
        195                 200                 205

Glu Ile Ile Arg Arg Cys Gly Ser Thr Ala Phe Thr Ala Trp Arg Ile
    210                 215                 220

Ala Phe Phe Val Pro Gly Trp Leu His Ile Ile Met Gly Ile Leu Val
225                 230                 235                 240

Leu Thr Leu Gly Gln Asp Leu Pro Gly Gly Asn Arg Ala Ala Met Glu
                245                 250                 255

Lys Ala Gly Glu Val Ala Lys Asp Lys Phe Gly Lys Ile Leu Trp Tyr
            260                 265                 270

Ala Val Thr Asn Tyr Arg Thr Trp Ile Phe Val Leu Leu Tyr Gly Tyr
        275                 280                 285

Ser Met Gly Val Glu Leu Ser Thr Asp Asn Val Ile Ala Glu Tyr Phe
    290                 295                 300

Phe Asp Arg Phe His Leu Lys Leu His Thr Ala Gly Ile Ile Ala Ala
305                 310                 315                 320

Cys Phe Gly Met Ala Asn Phe Phe Ala Arg Pro Ala Gly Gly Trp Ala
                325                 330                 335

Ser Asp Ile Ala Ala Lys Arg Phe Gly Met Arg Gly Arg Leu Trp Thr
            340                 345                 350

Leu Trp Ile Ile Gln Thr Ser Gly Gly Leu Phe Cys Val Trp Leu Gly
        355                 360                 365

Arg Ala Asn Thr Leu Val Thr Ala Val Val Ser Met Val Leu Phe Ser
    370                 375                 380

Leu Gly Ala Gln Ala Ala Cys Gly Ala Thr Phe Ala Ile Val Pro Phe
385                 390                 395                 400

Val Ser Arg Arg Ala Leu Gly Ile Ile Ser Gly Leu Thr Gly Ala Gly
                405                 410                 415

Gly Asn Phe Gly Ser Gly Leu Thr Gln Leu Val Phe Phe Ser Thr Ser
            420                 425                 430

Arg Phe Thr Thr Glu Glu Gly Leu Thr Trp Met Gly Val Met Ile Val
        435                 440                 445

Ala Cys Thr Leu Pro Val Thr Leu Ile His Phe Pro Gln Trp Gly Ser
    450                 455                 460

Met Phe Phe Pro Pro Ser Asn Asp Ser Val Asp Ala Thr Glu His Tyr
465                 470                 475                 480

Tyr Val Gly Glu Tyr Ser Lys Glu Glu Gln Gln Ile Gly Met His Leu
                485                 490                 495

Lys Ser Lys Leu Phe Ala Asp Gly Ala Lys Thr Glu Gly Gly Ser Ser
            500                 505                 510

Val His Lys Gly Asn Ala Thr Asn Asn Ala
        515                 520
```

<210> SEQ ID NO 115
<211> LENGTH: 1709
<212> TYPE: DNA
<213> ORGANISM: Arabidopsis thaliana

<400> SEQUENCE: 115
aaacttgaat tttctcaaag gaacttgata cgtttaaaat acatgggttc tactgatgag 60
cccagaagtt ccatgcatgg agttaccggt agagaacaga gctatgcttt ctcggtagat 120
ggtagtgagc cgaccaacac aaagaaaaag tacaatctgc cggtggacgc ggaggataag 180
gcaacggttt tcaagctctt ctccttcgcc aaacctcaca tgagaacgtt ccacctctcg 240
tggatctctt tctccacatg ttttgtttcg acgttcgcag ctgcaccact tatcccgatc 300
atcagggaga atcttaacct caccaaacat gacattggaa acgctggagt tgcctccgtc 360
tcggggagta tcttctctag gctcgtgatg ggagccgtgt gtgatctttt gggtcctcgt 420
tacggttgtg ccttccttgt gatgttgtct gccccaacgg tgttctccat gagcttcgtg 480
agtgacgcag caggcttcat aacggtgagg ttcatgattg gtttttgcct ggcgacgttt 540
gtgtcttgtc aatactggat gagcactatg ttcaacagtc agatcatcgg tctggtgaac 600
gggacagcag ccggatgggg aaacatgggt ggcggcataa cgcagttgct catgcccatt 660
gtgtatgaaa tcattaggcg ctgcggatca acagcgttca cggcctggag gatcgccttc 720
tttgtccccg gttggttgca catcatcatg ggaatcttgg tgctcacgct aggtcaagat 780
ctgccaggtg gaaacagagc tgccatggag aaagcgggag aagttgccaa agacaaattc 840
ggaaagattc tatggtacgc cgttacaaat tacaggactt ggattttcgt tcttctgtat 900
ggatattcca tgggagttga gttaagcaca gacaatgtta tcgccgagta cttctttgac 960
aggtttcact tgaagcttca cacagcgggg attatagcag catgtttcgg aatggccaat 1020
ttctttgctc gtccagcagg aggctgggca tctgacattg cagccaagcg cttcggaatg 1080
cgagggaggt tgtggacttt gtggatcatt cagacgtccg gtggtctctt ttgtgtgtgg 1140
ctcggacgtg ccaacaccct cgtcactgcc gttgtatcta tggtcctctt ctctttagga 1200
gcacaagccg cttgcggagc cacctttgct atcgtgccct ttgtctcccg gcgagctcta 1260
ggcattatct cgggtttaac cggggctgga gggaactttg ggtcaggact cacacagctc 1320
gtcttttcct cgacttcgcg cttcacaact gaagaagggc taacgtggat gggagtgatg 1380
atagttgctt gcacgttgcc tgttacctta atccactttc ctcagtgggg aagcatgttc 1440
ttccctcctt ccaacgattc ggtcgacgct acggagcact attatgttgg cgaatatagt 1500
aaggaggagc agcagattgg catgcattta aaaagcaaac tgtttgctga tggagccaag 1560
accgagggag gcagcagcgt ccacaaaggg aacgcaacca acaatgcttg atcatgtgtc 1620
attgatatca agaaattaat aatttcactt atgtgaaatg gacataaact gttggaaaat 1680
aaagaaccat ttctttcatc atttgcttt 1709

<210> SEQ ID NO 116
<211> LENGTH: 522
<212> TYPE: PRT
<213> ORGANISM: Arabidopsis thaliana

<400> SEQUENCE: 116

Met Gly Ser Thr Asp Glu Pro Arg Ser Ser Met His Gly Val Thr Gly
1 5 10 15

Arg Glu Gln Ser Tyr Ala Phe Ser Val Asp Gly Ser Glu Pro Thr Asn
20 25 30

-continued

```
Thr Lys Lys Lys Tyr Asn Leu Pro Val Asp Ala Glu Asp Lys Ala Thr
        35                  40                  45

Val Phe Lys Leu Phe Ser Phe Ala Lys Pro His Met Arg Thr Phe His
    50                  55                  60

Leu Ser Trp Ile Ser Phe Ser Thr Cys Phe Val Ser Thr Phe Ala Ala
65                  70                  75                  80

Ala Pro Leu Ile Pro Ile Ile Arg Glu Asn Leu Asn Leu Thr Lys His
                85                  90                  95

Asp Ile Gly Asn Ala Gly Val Ala Ser Val Ser Gly Ser Ile Phe Ser
            100                 105                 110

Arg Leu Val Met Gly Ala Val Cys Asp Leu Leu Gly Pro Arg Tyr Gly
        115                 120                 125

Cys Ala Phe Leu Val Met Leu Ser Ala Pro Thr Val Phe Ser Met Ser
    130                 135                 140

Phe Val Ser Asp Ala Ala Gly Phe Ile Thr Val Arg Phe Met Ile Gly
145                 150                 155                 160

Phe Cys Leu Ala Thr Phe Val Ser Cys Gln Tyr Trp Met Ser Thr Met
                165                 170                 175

Phe Asn Ser Gln Ile Ile Gly Leu Val Asn Gly Thr Ala Ala Gly Trp
            180                 185                 190

Gly Asn Met Gly Gly Gly Ile Thr Gln Leu Leu Met Pro Ile Val Tyr
        195                 200                 205

Glu Ile Ile Arg Arg Cys Gly Ser Thr Ala Phe Thr Ala Trp Arg Ile
    210                 215                 220

Ala Phe Phe Val Pro Gly Trp Leu His Ile Ile Met Gly Ile Leu Val
225                 230                 235                 240

Leu Thr Leu Gly Gln Asp Leu Pro Gly Gly Asn Arg Ala Ala Met Glu
                245                 250                 255

Lys Ala Gly Glu Val Ala Lys Asp Lys Phe Gly Lys Ile Leu Trp Tyr
            260                 265                 270

Ala Val Thr Asn Tyr Arg Thr Trp Ile Phe Val Leu Leu Tyr Gly Tyr
        275                 280                 285

Ser Met Gly Val Glu Leu Ser Thr Asp Asn Val Ile Ala Glu Tyr Phe
    290                 295                 300

Phe Asp Arg Phe His Leu Lys Leu His Thr Ala Gly Ile Ile Ala Ala
305                 310                 315                 320

Cys Phe Gly Met Ala Asn Phe Phe Ala Arg Pro Ala Gly Gly Trp Ala
                325                 330                 335

Ser Asp Ile Ala Ala Lys Arg Phe Gly Met Arg Gly Arg Leu Trp Thr
            340                 345                 350

Leu Trp Ile Ile Gln Thr Ser Gly Gly Leu Phe Cys Val Trp Leu Gly
        355                 360                 365

Arg Ala Asn Thr Leu Val Thr Ala Val Val Ser Met Val Leu Phe Ser
    370                 375                 380

Leu Gly Ala Gln Ala Ala Cys Gly Ala Thr Phe Ala Ile Val Pro Phe
385                 390                 395                 400

Val Ser Arg Arg Ala Leu Gly Ile Ile Ser Gly Leu Thr Gly Ala Gly
                405                 410                 415

Gly Asn Phe Gly Ser Gly Leu Thr Gln Leu Val Phe Phe Ser Thr Ser
            420                 425                 430

Arg Phe Thr Thr Glu Glu Gly Leu Thr Trp Met Gly Val Met Ile Val
        435                 440                 445
```

-continued

```
Ala Cys Thr Leu Pro Val Thr Leu Ile His Phe Pro Gln Trp Gly Ser
    450                 455                 460

Met Phe Phe Pro Pro Ser Asn Asp Ser Val Asp Ala Thr Glu His Tyr
465                 470                 475                 480

Tyr Val Gly Glu Tyr Ser Lys Glu Glu Gln Gln Ile Gly Met His Leu
                485                 490                 495

Lys Ser Lys Leu Phe Ala Asp Gly Ala Lys Thr Glu Gly Gly Ser Ser
            500                 505                 510

Val His Lys Gly Asn Ala Thr Asn Asn Ala
        515                 520


<210> SEQ ID NO 117
<211> LENGTH: 1620
<212> TYPE: DNA
<213> ORGANISM: Arabidopsis thaliana

<400> SEQUENCE: 117

atgactcaca accattctaa tgaagaaggc tccattggaa cctccttgca tggagttaca      60

gcaagagaac aagtcttctc tttctccgtc gatgcttcgt ctcaaacagt ccaatcagac     120

gatccaacag ctaaattcgc ccttccggtt gattccgaac atcgagccaa agtgttcaac     180

ccactctctt ttgctaaacc tcacatgaga gccttccact taggatggct ctcattcttc     240

acatgcttca tctccacctt cgcggcagca ccattagtcc ccatcatccg cgacaacctc     300

gacctcacta aaaccgacat tggaaacgcc ggagtcgcat ccgtctctgg tgccattttc     360

tcaaggttag ccatgggagc ggtttgtgat ctcctcggtg cacgatatgg gactgccttc     420

tccctcatgc taaccgcccc aaccgtcttc tcaatgtcgt ttgtgggtgg ccctagcgga     480

tacttaggcg tccggttcat gatcggattc tgtctcgcca cgtttgtatc atgccagtat     540

tggaccagcg ttatgttcaa cggtaagatc ataggactag tgaacggctg tgcaggcggg     600

tggggtgata tgggcggtgg agtgactcaa ctcctaatgc cgatggtctt ccacgtcatc     660

aaacttgccg gagccactcc gttcatggcc tggcggatag ctttcttcgt tcccggattt     720

cttcaagttg ttatgggcat tctcgtcctc agtctcggcc aagatctccc tgacggtaac     780

ctaagtaccc ttcagaagag tggtcaagtc tctaaagaca aattctccaa ggttttctgg     840

tttgctgtga agaactacag aacatggatt ttattcgttc tttatggatc ttccatggga     900

attgaattaa ctatcaacaa cgttatctcc ggatattttt acgacaggtt taaccttaag     960

cttcaaacag ctggtatagt agcagccagc tttggaatgg ctaacttcat cgcccgtccc    1020

ttcggtggtt acgcttctga tgtagcggct cgggtttttg gcatgagagg ccggttatgg    1080

accttatgga tctttcaaac cgtaggagct cttttctgta tctggctagg tcgagctagt    1140

tcacttccca tagcaatcct agcaatgatg ctcttctcaa tcggtacaca agcagcttgc    1200

ggagccctct tcggagttgc accttttgtc tcgcgccgct ctctagggct catatcggga    1260

ctaaccggcg caggaggaaa cttcgggtcc ggtttgactc aactgctttt cttctcatca    1320

gcgaggttta gtacagctga gggactctca ttgatgggcg ttatggcggt tttgtgcaca    1380

ctcccagttg cgtttataca ttttccgcaa tggggaagca tgtttttaag accgtcgacc    1440

gatggagaaa gatcacagga ggaatattat tacggttctg agtggacgga gaatgagaaa    1500

caacaaggat tgcacgaagg aagcatcaaa tttgcagaga atagtaggtc agagagaggc    1560

cggaaagtag ctttggctaa cattccaacg ccggagaacg gaactccaag tcatgtttga    1620


<210> SEQ ID NO 118
```

<211> LENGTH: 539
<212> TYPE: PRT
<213> ORGANISM: Arabidopsis thaliana

<400> SEQUENCE: 118

```
Met Thr His Asn His Ser Asn Glu Glu Gly Ser Ile Gly Thr Ser Leu
1               5                   10                  15

His Gly Val Thr Ala Arg Glu Gln Val Phe Ser Phe Ser Val Asp Ala
            20                  25                  30

Ser Ser Gln Thr Val Gln Ser Asp Asp Pro Thr Ala Lys Phe Ala Leu
        35                  40                  45

Pro Val Asp Ser Glu His Arg Ala Lys Val Phe Asn Pro Leu Ser Phe
    50                  55                  60

Ala Lys Pro His Met Arg Ala Phe His Leu Gly Trp Leu Ser Phe Phe
65                  70                  75                  80

Thr Cys Phe Ile Ser Thr Phe Ala Ala Ala Pro Leu Val Pro Ile Ile
                85                  90                  95

Arg Asp Asn Leu Asp Leu Thr Lys Thr Asp Ile Gly Asn Ala Gly Val
            100                 105                 110

Ala Ser Val Ser Gly Ala Ile Phe Ser Arg Leu Ala Met Gly Ala Val
        115                 120                 125

Cys Asp Leu Leu Gly Ala Arg Tyr Gly Thr Ala Phe Ser Leu Met Leu
    130                 135                 140

Thr Ala Pro Thr Val Phe Ser Met Ser Phe Val Gly Gly Pro Ser Gly
145                 150                 155                 160

Tyr Leu Gly Val Arg Phe Met Ile Gly Phe Cys Leu Ala Thr Phe Val
                165                 170                 175

Ser Cys Gln Tyr Trp Thr Ser Val Met Phe Asn Gly Lys Ile Ile Gly
            180                 185                 190

Leu Val Asn Gly Cys Ala Gly Gly Trp Gly Asp Met Gly Gly Gly Val
        195                 200                 205

Thr Gln Leu Leu Met Pro Met Val Phe His Val Ile Lys Leu Ala Gly
    210                 215                 220

Ala Thr Pro Phe Met Ala Trp Arg Ile Ala Phe Phe Val Pro Gly Phe
225                 230                 235                 240

Leu Gln Val Val Met Gly Ile Leu Val Leu Ser Leu Gly Gln Asp Leu
                245                 250                 255

Pro Asp Gly Asn Leu Ser Thr Leu Gln Lys Ser Gly Gln Val Ser Lys
            260                 265                 270

Asp Lys Phe Ser Lys Val Phe Trp Phe Ala Val Lys Asn Tyr Arg Thr
        275                 280                 285

Trp Ile Leu Phe Val Leu Tyr Gly Ser Ser Met Gly Ile Glu Leu Thr
    290                 295                 300

Ile Asn Asn Val Ile Ser Gly Tyr Phe Tyr Asp Arg Phe Asn Leu Lys
305                 310                 315                 320

Leu Gln Thr Ala Gly Ile Val Ala Ala Ser Phe Gly Met Ala Asn Phe
                325                 330                 335

Ile Ala Arg Pro Phe Gly Gly Tyr Ala Ser Asp Val Ala Ala Arg Val
            340                 345                 350

Phe Gly Met Arg Gly Arg Leu Trp Thr Leu Trp Ile Phe Gln Thr Val
        355                 360                 365

Gly Ala Leu Phe Cys Ile Trp Leu Gly Arg Ala Ser Ser Leu Pro Ile
    370                 375                 380

Ala Ile Leu Ala Met Met Leu Phe Ser Ile Gly Thr Gln Ala Ala Cys
```

385 390 395 400

Gly Ala Leu Phe Gly Val Ala Pro Phe Val Ser Arg Arg Ser Leu Gly
405 410 415

Leu Ile Ser Gly Leu Thr Gly Ala Gly Gly Asn Phe Gly Ser Gly Leu
420 425 430

Thr Gln Leu Leu Phe Phe Ser Ser Ala Arg Phe Ser Thr Ala Glu Gly
435 440 445

Leu Ser Leu Met Gly Val Met Ala Val Leu Cys Thr Leu Pro Val Ala
450 455 460

Phe Ile His Phe Pro Gln Trp Gly Ser Met Phe Leu Arg Pro Ser Thr
465 470 475 480

Asp Gly Glu Arg Ser Gln Glu Glu Tyr Tyr Tyr Gly Ser Glu Trp Thr
485 490 495

Glu Asn Glu Lys Gln Gln Gly Leu His Glu Gly Ser Ile Lys Phe Ala
500 505 510

Glu Asn Ser Arg Ser Glu Arg Gly Arg Lys Val Ala Leu Ala Asn Ile
515 520 525

Pro Thr Pro Glu Asn Gly Thr Pro Ser His Val
530 535

<210> SEQ ID NO 119
<211> LENGTH: 1629
<212> TYPE: DNA
<213> ORGANISM: Arabidopsis thaliana

<400> SEQUENCE: 119
atggctcaca accattctaa tgaagacggc tctattggaa cctccttgca tggagtcacg 60
gcaagggagc aagtcttctc cttctccgtc caagaagatg tcccttcatc tcaagccgtc 120
cgaacaaacg atccaacggc taagtttgcc ctaccagtgg actccgaaca tagggcaaaa 180
gtgttcaaac cactatcatt cgctaaacca catatgagag ccttccactt aggatggatc 240
tctttcttca cttgcttcat ctccaccttc gcagccgcac ctctagtccc cgtcattcgc 300
gacaatctcg acctgaccaa aaccgacatc ggaaatgctg gagttgcatc agtttccggc 360
gccattttct cgagactcgc tatgggtgct gtatgtgacc ttctaggggc acgttatgga 420
accgccttct cacttatgct tacagctcca gcagttttct ccatgtcgtt cgtagctgac 480
gcgggaagct acttagccgt aaggttcatg atcggttttt gcttagcaac gttcgtatca 540
tgtcagtact ggacgagtgt tatgttcact ggaaagatta tcggactcgt taacggatgt 600
gctggagggt ggggagatat gggaggagga gtgactcagc tactaatgcc aatggtcttc 660
cacgtcatca aactcaccgg agccactccc ttcacggctt ggaggttcgc cttcttcatc 720
cccggcattc ttcagatagt tatgggtatt ctcgttctca ctctcggcca agatcttccc 780
gatggtaacc tcagtactct ccaaaagagt ggtcaagttt ctaaagacaa attctccaag 840
gtcttttggt tcgctgtgaa aaactataga acatggatct tattcatgct ctatggattt 900
tctatgggag ttgaattaac gatcaacaac gttatatctg gatacttcta cgataggttt 960
aaccttacgc ttcacacagc tggtattata gcagccagct ttggtatggc aaacttcttt 1020
gcccgtcctt ttggtggcta cgcttcagat gtagctgcac ggctcttcgg tatgagggga 1080
cggttatgga tcttgtggat cttacaaact gttggagctc tcttttgcat ctggcttggt 1140
cgtgctagtt cactacctat agctatctta gccatgatgc ttttttccat gggcacacaa 1200
gctgcttgtg gagctctctt tggtgttgct ccttttgttt cccgccgttc tcttggactt 1260

```
atctcgggat taactggtgc tggtggaaat tttgggtcgg gagttactca acttcttttc   1320

ttctcttcct cgaggtttag tacggcggaa ggactatcgt tgatgggcgt tatggctgtt   1380

gtgtgctctc ttccggttgc gtttatacat tttccgcagt ggggaagcat gttcttgagg   1440

ccatcacaag atggagagaa atcaaaggaa gagcattact atggagcgga atggacagag   1500

gaagagaaga gcttaggact acacgaagga agcattaaat ttgctgaaaa cagccggtca   1560

gagagaggcc gcaaggcgat gttggctgat attccaacgc cggaaaccgg atctccggct   1620

catgtctag                                                           1629


<210> SEQ ID NO 120
<211> LENGTH: 542
<212> TYPE: PRT
<213> ORGANISM: Arabidopsis thaliana

<400> SEQUENCE: 120

Met Ala His Asn His Ser Asn Glu Asp Gly Ser Ile Gly Thr Ser Leu
1               5                   10                  15

His Gly Val Thr Ala Arg Glu Gln Val Phe Ser Phe Ser Val Gln Glu
            20                  25                  30

Asp Val Pro Ser Ser Gln Ala Val Arg Thr Asn Asp Pro Thr Ala Lys
        35                  40                  45

Phe Ala Leu Pro Val Asp Ser Glu His Arg Ala Lys Val Phe Lys Pro
    50                  55                  60

Leu Ser Phe Ala Lys Pro His Met Arg Ala Phe His Leu Gly Trp Ile
65                  70                  75                  80

Ser Phe Phe Thr Cys Phe Ile Ser Thr Phe Ala Ala Ala Pro Leu Val
                85                  90                  95

Pro Val Ile Arg Asp Asn Leu Asp Leu Thr Lys Thr Asp Ile Gly Asn
            100                 105                 110

Ala Gly Val Ala Ser Val Ser Gly Ala Ile Phe Ser Arg Leu Ala Met
        115                 120                 125

Gly Ala Val Cys Asp Leu Leu Gly Ala Arg Tyr Gly Thr Ala Phe Ser
    130                 135                 140

Leu Met Leu Thr Ala Pro Ala Val Phe Ser Met Ser Phe Val Ala Asp
145                 150                 155                 160

Ala Gly Ser Tyr Leu Ala Val Arg Phe Met Ile Gly Phe Cys Leu Ala
                165                 170                 175

Thr Phe Val Ser Cys Gln Tyr Trp Thr Ser Val Met Phe Thr Gly Lys
            180                 185                 190

Ile Ile Gly Leu Val Asn Gly Cys Ala Gly Gly Trp Gly Asp Met Gly
        195                 200                 205

Gly Gly Val Thr Gln Leu Leu Met Pro Met Val Phe His Val Ile Lys
    210                 215                 220

Leu Thr Gly Ala Thr Pro Phe Thr Ala Trp Arg Phe Ala Phe Phe Ile
225                 230                 235                 240

Pro Gly Ile Leu Gln Ile Val Met Gly Ile Leu Val Leu Thr Leu Gly
                245                 250                 255

Gln Asp Leu Pro Asp Gly Asn Leu Ser Thr Leu Gln Lys Ser Gly Gln
            260                 265                 270

Val Ser Lys Asp Lys Phe Ser Lys Val Phe Trp Phe Ala Val Lys Asn
        275                 280                 285

Tyr Arg Thr Trp Ile Leu Phe Met Leu Tyr Gly Phe Ser Met Gly Val
    290                 295                 300
```

```
Glu Leu Thr Ile Asn Asn Val Ile Ser Gly Tyr Phe Tyr Asp Arg Phe
305                 310                 315                 320

Asn Leu Thr Leu His Thr Ala Gly Ile Ile Ala Ala Ser Phe Gly Met
                325                 330                 335

Ala Asn Phe Phe Ala Arg Pro Phe Gly Gly Tyr Ala Ser Asp Val Ala
            340                 345                 350

Ala Arg Leu Phe Gly Met Arg Gly Arg Leu Trp Ile Leu Trp Ile Leu
        355                 360                 365

Gln Thr Val Gly Ala Leu Phe Cys Ile Trp Leu Gly Arg Ala Ser Ser
    370                 375                 380

Leu Pro Ile Ala Ile Leu Ala Met Met Leu Phe Ser Met Gly Thr Gln
385                 390                 395                 400

Ala Ala Cys Gly Ala Leu Phe Gly Val Ala Pro Phe Val Ser Arg Arg
                405                 410                 415

Ser Leu Gly Leu Ile Ser Gly Leu Thr Gly Ala Gly Gly Asn Phe Gly
            420                 425                 430

Ser Gly Val Thr Gln Leu Leu Phe Phe Ser Ser Ser Arg Phe Ser Thr
        435                 440                 445

Ala Glu Gly Leu Ser Leu Met Gly Val Met Ala Val Val Cys Ser Leu
    450                 455                 460

Pro Val Ala Phe Ile His Phe Pro Gln Trp Gly Ser Met Phe Leu Arg
465                 470                 475                 480

Pro Ser Gln Asp Gly Glu Lys Ser Lys Glu Glu His Tyr Tyr Gly Ala
                485                 490                 495

Glu Trp Thr Glu Glu Glu Lys Ser Leu Gly Leu His Glu Gly Ser Ile
            500                 505                 510

Lys Phe Ala Glu Asn Ser Arg Ser Glu Arg Gly Arg Lys Ala Met Leu
        515                 520                 525

Ala Asp Ile Pro Thr Pro Glu Thr Gly Ser Pro Ala His Val
    530                 535                 540
```

<210> SEQ ID NO 121
<211> LENGTH: 1605
<212> TYPE: DNA
<213> ORGANISM: Daucus carota

<400> SEQUENCE: 121

```
atgggtgaca tggaaggttc cccgggttcc tccatgcacg gtgttaccgg tcgtgaaccg      60

tccctggctt tctccgttgc ttcccgtatc gacacctccg ctgaattcca cgttccggtt     120

gactccgaac acaaagctaa agttttcaaa ttcaaatcct tctccccgcc gcacggtctg     180

cagttccagc tgacctggat ctccttcccg acctgcttcg tttccacctt cgctgctcgt     240

ccgctggttg ttatcatccg tgacaacctg aacccgacca aaatggacgt tggtaacgct     300

ggtgttgctt ccgttaccgg ttccatcctg tcccgtggtg ctatgggtgc tatctgcgac     360

atgctgggtc cgcgttacgg ttgcgctttc ctgatcatgc tgtccgctcc gaaagttctg     420

tgcatgtcct tcgtttcctc cgctggtggt tacgttgctg ttcgtttcat gatcggtttc     480

tccctggcta ccttcgtttc ctgccgttac tggatgtcca cctccatgca ctccgacatc     540

atcggtctgg ttaacggtac cgctgctggt tggggtaaca tgaccggtgg tgctacccag     600

ctgatcatgc cgctgctgta cgacatcatc cgtgaagctg gtgctacccc gttcaccgct     660

tggcgtatcg ctctgttcat cccgggttgg ctgcacgtta tctccggtat cctggttctg     720

accctgggtc aggacctgcc ggacggtaac gctcagaacg aagcttccct gcgtaaaaaa     780
```

```
ggtcgtgttc acaaagacaa attctccaaa atcctgcgtt acgctgctac caactaccgt    840

acctggatcc tggttctgct gtacggttac tccatgggtg ttgaactgac caccgacaac    900

gttatcgctg aatacttctt cgaccgtttc gacctgaaac tgcacacccc gggtatcatc    960

gctgctacct tcggtatggc taacctgctg gctcgtccgt tcggtggttg gtcctccgac   1020

gttgctgcta aacacttcgg tatgcgtggt cgtcactgga actcctggga cctgcagacc   1080

ctgggtggtg ttttctgcct gctgctggtt cgtgctacca cctccccgat cgacgctctg   1140

gctatcacct ggatgatcat cttctccatc ggtgctcagg ctgctaccgg tgttaccttc   1200

ggtatcatcc cgttcatctc ccgtcgttac ctgggtatca tctcccagat gaccggtgct   1260

aacggtaact tcggttccgg tcagacccag ccgctggaat tcgactccac caaatacaac   1320

accggtctgg gtctgaccta catgggtatg atgatcatcg cttgcaccct gccgccgatg   1380

ctggtttggt tctggcagga cggttccatg ttcctgccgc cgtccaaaga cccgatcaaa   1440

ggtaccgaac cggaacacta cttcggttcc gaatacaccg aagacgaaaa agttaaaggt   1500

atgcaccaga actccatcaa attcgctgaa aactcccgta ccgaattcgg taaaaaacgt   1560

gttggttccg ctccgacccc gccgaacgtt taccccaacc gtgtt                   1605
```

<210> SEQ ID NO 122
<211> LENGTH: 535
<212> TYPE: PRT
<213> ORGANISM: Daucus carota

<400> SEQUENCE: 122

```
Met Gly Asp Met Glu Gly Ser Pro Gly Ser Ser Met His Gly Val Thr
1               5                   10                  15

Gly Arg Glu Pro Ser Leu Ala Phe Ser Val Ala Ser Arg Ile Asp Thr
            20                  25                  30

Ser Ala Glu Phe His Val Pro Val Asp Ser Glu His Lys Ala Lys Val
        35                  40                  45

Phe Lys Phe Lys Ser Phe Ser Pro Pro His Gly Leu Gln Phe Gln Leu
    50                  55                  60

Thr Trp Ile Ser Phe Pro Thr Cys Phe Val Ser Thr Phe Ala Ala Arg
65                  70                  75                  80

Pro Leu Val Val Ile Ile Arg Asp Asn Leu Asn Pro Thr Lys Met Asp
                85                  90                  95

Val Gly Asn Ala Gly Val Ala Ser Val Thr Gly Ser Ile Leu Ser Arg
            100                 105                 110

Gly Ala Met Gly Ala Ile Cys Asp Met Leu Gly Pro Arg Tyr Gly Cys
        115                 120                 125

Ala Phe Leu Ile Met Leu Ser Ala Pro Lys Val Leu Cys Met Ser Phe
    130                 135                 140

Val Ser Ser Ala Gly Gly Tyr Val Ala Val Arg Phe Met Ile Gly Phe
145                 150                 155                 160

Ser Leu Ala Thr Phe Val Ser Cys Arg Tyr Trp Met Ser Thr Ser Met
                165                 170                 175

His Ser Asp Ile Ile Gly Leu Val Asn Gly Thr Ala Ala Gly Trp Gly
            180                 185                 190

Asn Met Thr Gly Gly Ala Thr Gln Leu Ile Met Pro Leu Leu Tyr Asp
        195                 200                 205

Ile Ile Arg Glu Ala Gly Ala Thr Pro Phe Thr Ala Trp Arg Ile Ala
    210                 215                 220

Leu Phe Ile Pro Gly Trp Leu His Val Ile Ser Gly Ile Leu Val Leu
```

```
225                 230                 235                 240

Thr Leu Gly Gln Asp Leu Pro Asp Gly Asn Ala Gln Asn Glu Ala Ser
                245                 250                 255

Leu Arg Lys Lys Gly Arg Val His Lys Asp Lys Phe Ser Lys Ile Leu
            260                 265                 270

Arg Tyr Ala Ala Thr Asn Tyr Arg Thr Trp Ile Leu Val Leu Leu Tyr
        275                 280                 285

Gly Tyr Ser Met Gly Val Glu Leu Thr Thr Asp Asn Val Ile Ala Glu
    290                 295                 300

Tyr Phe Phe Asp Arg Phe Asp Leu Lys Leu His Thr Pro Gly Ile Ile
305                 310                 315                 320

Ala Ala Thr Phe Gly Met Ala Asn Leu Leu Ala Arg Pro Phe Gly Gly
                325                 330                 335

Trp Ser Ser Asp Val Ala Ala Lys His Phe Gly Met Arg Gly Arg His
            340                 345                 350

Trp Asn Ser Trp Asp Leu Gln Thr Leu Gly Gly Val Phe Cys Leu Leu
        355                 360                 365

Leu Val Arg Ala Thr Thr Ser Pro Ile Asp Ala Leu Ala Ile Thr Trp
    370                 375                 380

Met Ile Ile Phe Ser Ile Gly Ala Gln Ala Ala Thr Gly Val Thr Phe
385                 390                 395                 400

Gly Ile Ile Pro Phe Ile Ser Arg Arg Tyr Leu Gly Ile Ile Ser Gln
                405                 410                 415

Met Thr Gly Ala Asn Gly Asn Phe Gly Ser Gly Gln Thr Gln Pro Leu
            420                 425                 430

Glu Phe Asp Ser Thr Lys Tyr Asn Thr Gly Leu Gly Leu Thr Tyr Met
        435                 440                 445

Gly Met Met Ile Ile Ala Cys Thr Leu Pro Pro Met Leu Val Trp Phe
    450                 455                 460

Trp Gln Asp Gly Ser Met Phe Leu Pro Pro Ser Lys Asp Pro Ile Lys
465                 470                 475                 480

Gly Thr Glu Pro Glu His Tyr Phe Gly Ser Glu Tyr Thr Glu Asp Glu
                485                 490                 495

Lys Val Lys Gly Met His Gln Asn Ser Ile Lys Phe Ala Glu Asn Ser
            500                 505                 510

Arg Thr Glu Phe Gly Lys Lys Arg Val Gly Ser Ala Pro Thr Pro Pro
        515                 520                 525

Asn Val Tyr Pro Asn Arg Val
    530                 535
```

<210> SEQ ID NO 123
<211> LENGTH: 1200
<212> TYPE: DNA
<213> ORGANISM: Zea mays

<400> SEQUENCE: 123

```
cagcaagatc atcggcaccg tcaacgggct cgccgccgga tggggcaaca tgggaggcgg      60

cgccacgcag ctcatcatgc cgctcgtcta cgacgtcatc cgcaagtgcg gcgccacgcc     120

attcacggcc tggcgcctcg cctacttcgt gccgggcctc atgcacgtcg tcatgggcgt     180

cctggtgctc acgctggggc aggacctccc cgacggcaac ctcaggtcgc tgcagaagaa     240

gggcaacgtc aacaaggaca gcttctccaa ggtcatgtgg tacgccgtca tcaactaccg     300

tacctggatc ttcgtcctcc tctacggcta ctgcatgggc gtcgagctca ccaccgacaa     360
```

```
cgtcatcgcc gagtacatgt acgaccgctt cgacctcgac ctccgcgtcg ccgggaccat    420

cgccgcctgc ttcggcatgg ccaacatcgt cgcacgccct atgggcggca tcatgtcgga    480

catgggcgcg cgctactggg gcatgcgcgc tcgcctctgg aacatctgga tcctccagac    540

cgccggcggc gccttctgcc tctggctggg acgcgccagc accctccccg tctccgtcgt    600

cgccatggtg ctcttctcct tctgcgcgca ggcggcctgc ggcgccatct tcggggtcat    660

ccccttcgtc tcccgccgct ccctcggcat catctccggc atgacgggcg ccggcggcaa    720

cttcggcgcc gggctcacgc agctgctctt ctttacctcc tcgacctact ccacgggcag    780

ggggctggag tacatgggca tcatgatcat ggcgtgcacg ctgccggtgg tgttcgtgca    840

cttcccgcag tgggggtcca tgttcttccc gcccagcgcc accgccgacg aggagggcta    900

ctacgcctcc gagtggaacg acgacgagaa gagcaaggga ctccatagcg ctagcctcaa    960

gttcgccgag aacagccgct cagagcgcgg caagcgcaac gtcatccagg ccgacgccgc   1020

cgccacgccg gagcatgtct aagttcacta ctaagatgga tcgatcgacg atcacctata   1080

cctctttgta tgtacgaata tgccttgtta ttactgtgcg cgcgcatata caatacacgt   1140

gtgctccgtt gacatgagtt atatagcact aaaaacttct tttgaaaaaa aaaaaaaaaa   1200
```

```
<210> SEQ ID NO 124
<211> LENGTH: 346
<212> TYPE: PRT
<213> ORGANISM: Zea mays

<400> SEQUENCE: 124

Ser Lys Ile Ile Gly Thr Val Asn Gly Leu Ala Ala Gly Trp Gly Asn
1               5                   10                  15

Met Gly Gly Gly Ala Thr Gln Leu Ile Met Pro Leu Val Tyr Asp Val
            20                  25                  30

Ile Arg Lys Cys Gly Ala Thr Pro Phe Thr Ala Trp Arg Leu Ala Tyr
        35                  40                  45

Phe Val Pro Gly Leu Met His Val Val Met Gly Val Leu Val Leu Thr
    50                  55                  60

Leu Gly Gln Asp Leu Pro Asp Gly Asn Leu Arg Ser Leu Gln Lys Lys
65                  70                  75                  80

Gly Asn Val Asn Lys Asp Ser Phe Ser Lys Val Met Trp Tyr Ala Val
                85                  90                  95

Ile Asn Tyr Arg Thr Trp Ile Phe Val Leu Leu Tyr Gly Tyr Cys Met
            100                 105                 110

Gly Val Glu Leu Thr Thr Asp Asn Val Ile Ala Glu Tyr Met Tyr Asp
        115                 120                 125

Arg Phe Asp Leu Asp Leu Arg Val Ala Gly Thr Ile Ala Ala Cys Phe
    130                 135                 140

Gly Met Ala Asn Ile Val Ala Arg Pro Met Gly Gly Ile Met Ser Asp
145                 150                 155                 160

Met Gly Ala Arg Tyr Trp Gly Met Arg Ala Arg Leu Trp Asn Ile Trp
                165                 170                 175

Ile Leu Gln Thr Ala Gly Gly Ala Phe Cys Leu Trp Leu Gly Arg Ala
            180                 185                 190

Ser Thr Leu Pro Val Ser Val Val Ala Met Val Leu Phe Ser Phe Cys
        195                 200                 205

Ala Gln Ala Ala Cys Gly Ala Ile Phe Gly Val Ile Pro Phe Val Ser
    210                 215                 220

Arg Arg Ser Leu Gly Ile Ile Ser Gly Met Thr Gly Ala Gly Gly Asn
```

-continued

```
225                 230                 235                 240

Phe Gly Ala Gly Leu Thr Gln Leu Leu Phe Phe Thr Ser Ser Thr Tyr
                245                 250                 255

Ser Thr Gly Arg Gly Leu Glu Tyr Met Gly Ile Met Ile Met Ala Cys
            260                 265                 270

Thr Leu Pro Val Val Phe Val His Phe Pro Gln Trp Gly Ser Met Phe
        275                 280                 285

Phe Pro Pro Ser Ala Thr Ala Asp Glu Glu Gly Tyr Tyr Ala Ser Glu
    290                 295                 300

Trp Asn Asp Asp Glu Lys Ser Lys Gly Leu His Ser Ala Ser Leu Lys
305                 310                 315                 320

Phe Ala Glu Asn Ser Arg Ser Glu Arg Gly Lys Arg Asn Val Ile Gln
                325                 330                 335

Ala Asp Ala Ala Ala Thr Pro Glu His Val
            340                 345


<210> SEQ ID NO 125
<211> LENGTH: 1965
<212> TYPE: DNA
<213> ORGANISM: Oryza sativa

<400> SEQUENCE: 125

ggtggaggag agtgaggacg gcccacgcgg acgagcagag agtggcgggc tcagtgtcgg     60

gctcgccgga gtccgcgcaa tccggccgtt catgcttcat tctctcggac attaacctgg    120

tttacttgta agaaagtaga gccatggact cctcatacca gcatgacaag cctctgctgg    180

atgaagagaa ctcctcgcaa gtgacccttg aatatacagg tgatggatct gtttgcatcc    240

gtgggcatcc tgctttaagg aaacatacag ggaactggaa gggttcctca ttagccatcg    300

ttttttcatt ctgctcttat ctggccttta cttcaattgt aaaaaaccta gtcagttatc    360

tcacaaaagt tctacatgaa acaaacgtgg ccgctgcaag agatgttgca acttggtcag    420

gaacaagtta tcttgcacct ctggttggag ccttcttagc tgattcatat ctggggaagt    480

actgtacaat tctgatcttc tgcacgatct tcattatcgg attgatgatg ttgcttctgt    540

cagcagcagt tccattaatc tctactggtc ctcactcatg gatcatatgg acagatccag    600

tctcttctca gaacatcata ttctttgtcg gtttgtacat ggttgcttta gggtatggtg    660

cacagtgccc ctgcatatca tcatttggtg ctgatcaatt tgatgacact gatgaaaatg    720

agagaacaaa aaagagttct tttttcaatt ggacctattt cgtagccaat gcgggctcat    780

tgatctcggg gactgttatt gtgtgggtgc aagatcacaa aggttggatc tggggtttta    840

ccatttctgc actatttgtg tatttaggtt ttggtacttt tatctttggc tcctctatgt    900

atgatttcag aaacctggag gaagcccctc ttgcgagaat atgccaggtt gttgttgctg    960

ctattcacaa acgcgataaa gatttgccat gtgattcctc agttctttat gagtttctgg   1020

ggcagagttc agcaatcgaa ggcagccgaa aattggagca tacaactgga cttaagttct   1080

ttgatagagc tgcaatggtg acaccatctg attttgaatc tgatggccta ctaaacacat   1140

ggaagatttg cacagtcact caagtggagg aactgaagat tttgatcagg atgttccccg   1200

tttgggcaac gatgatatta tttgctgcag ttctggacaa catgttttcg acattcatag   1260

aacaggggat ggtgatggag aaacacatcg gctctttcga aatacctgcg gcgtccttcc   1320

aatccattga tgtcattgct gtccttatac tagttccagt ctatgaaaga gtccttgttc   1380

cagtgttcag aaaattcact ggcagagcaa atggcattac tccactgcag cgaatgggga   1440
```

-continued

```
tcggcctgtt cttttccatg ctctccatgg tatcagcagc attggtggag agtaatcggt   1500

tgcggattgc gcaggatgaa ggtttggtgc acaggaaggt ggctgttcca atgagcatcc   1560

tgtggcaggg accccagtac ttcctgatag gcgtgggaga ggtgttctca aacattgggt   1620

taactgaatt tttctaccag gaatcaccgg acgccatgag aagcttatgt ctcgcattct   1680

cacttgctaa cgtttcggca ggaagttacc tcagctcgtt tatcgtttct cttgtgccag   1740

tgttcacagc cagagaaggc agtcctggat ggatacctga taacttgaac gaagggcatt   1800

tggatcggtt cttctggatg atggctggct tgtgtttctt gaatatgctg gcctttgtgt   1860

tctgtgccat gaggtacaaa tgtaagaagg cttcctgaac cttgttaaca ttagcaatat   1920

aatggtggtg gaaaaggaca attgtgttgc aaaaaaaaaa aaaaa                   1965


<210> SEQ ID NO 126
<211> LENGTH: 584
<212> TYPE: PRT
<213> ORGANISM: Oryza sativa

<400> SEQUENCE: 126

Met Asp Ser Ser Tyr Gln His Asp Lys Pro Leu Leu Asp Glu Glu Asn
1               5                   10                  15

Ser Ser Gln Val Thr Leu Glu Tyr Thr Gly Asp Gly Ser Val Cys Ile
            20                  25                  30

Arg Gly His Pro Ala Leu Arg Lys His Thr Gly Asn Trp Lys Gly Ser
        35                  40                  45

Ser Leu Ala Ile Val Phe Ser Phe Cys Ser Tyr Leu Ala Phe Thr Ser
    50                  55                  60

Ile Val Lys Asn Leu Val Ser Tyr Leu Thr Lys Val Leu His Glu Thr
65                  70                  75                  80

Asn Val Ala Ala Ala Arg Asp Val Ala Thr Trp Ser Gly Thr Ser Tyr
                85                  90                  95

Leu Ala Pro Leu Val Gly Ala Phe Leu Ala Asp Ser Tyr Leu Gly Lys
            100                 105                 110

Tyr Cys Thr Ile Leu Ile Phe Cys Thr Ile Phe Ile Ile Gly Leu Met
        115                 120                 125

Met Leu Leu Leu Ser Ala Ala Val Pro Leu Ile Ser Thr Gly Pro His
    130                 135                 140

Ser Trp Ile Ile Trp Thr Asp Pro Val Ser Ser Gln Asn Ile Ile Phe
145                 150                 155                 160

Phe Val Gly Leu Tyr Met Val Ala Leu Gly Tyr Gly Ala Gln Cys Pro
                165                 170                 175

Cys Ile Ser Ser Phe Gly Ala Asp Gln Phe Asp Asp Thr Asp Glu Asn
            180                 185                 190

Glu Arg Thr Lys Lys Ser Ser Phe Phe Asn Trp Thr Tyr Phe Val Ala
        195                 200                 205

Asn Ala Gly Ser Leu Ile Ser Gly Thr Val Ile Val Trp Val Gln Asp
    210                 215                 220

His Lys Gly Trp Ile Trp Gly Phe Thr Ile Ser Ala Leu Phe Val Tyr
225                 230                 235                 240

Leu Gly Phe Gly Thr Phe Ile Phe Gly Ser Ser Met Tyr Asp Phe Arg
                245                 250                 255

Asn Leu Glu Glu Ala Pro Leu Ala Arg Ile Cys Gln Val Val Val Ala
            260                 265                 270

Ala Ile His Lys Arg Asp Lys Asp Leu Pro Cys Asp Ser Ser Val Leu
        275                 280                 285
```

```
Tyr Glu Phe Leu Gly Gln Ser Ser Ala Ile Glu Gly Ser Arg Lys Leu
    290                 295                 300

Glu His Thr Thr Gly Leu Lys Phe Phe Asp Arg Ala Ala Met Val Thr
305                 310                 315                 320

Pro Ser Asp Phe Glu Ser Asp Gly Leu Leu Asn Thr Trp Lys Ile Cys
                325                 330                 335

Thr Val Thr Gln Val Glu Glu Leu Lys Ile Leu Ile Arg Met Phe Pro
            340                 345                 350

Val Trp Ala Thr Met Ile Leu Phe Ala Ala Val Leu Asp Asn Met Phe
        355                 360                 365

Ser Thr Phe Ile Glu Gln Gly Met Val Met Glu Lys His Ile Gly Ser
    370                 375                 380

Phe Glu Ile Pro Ala Ala Ser Phe Gln Ser Ile Asp Val Ile Ala Val
385                 390                 395                 400

Leu Ile Leu Val Pro Val Tyr Glu Arg Val Leu Val Pro Val Phe Arg
                405                 410                 415

Lys Phe Thr Gly Arg Ala Asn Gly Ile Thr Pro Leu Gln Arg Met Gly
            420                 425                 430

Ile Gly Leu Phe Phe Ser Met Leu Ser Met Val Ser Ala Ala Leu Val
        435                 440                 445

Glu Ser Asn Arg Leu Arg Ile Ala Gln Asp Glu Gly Leu Val His Arg
    450                 455                 460

Lys Val Ala Val Pro Met Ser Ile Leu Trp Gln Gly Pro Gln Tyr Phe
465                 470                 475                 480

Leu Ile Gly Val Gly Glu Val Phe Ser Asn Ile Gly Leu Thr Glu Phe
                485                 490                 495

Phe Tyr Gln Glu Ser Pro Asp Ala Met Arg Ser Leu Cys Leu Ala Phe
            500                 505                 510

Ser Leu Ala Asn Val Ser Ala Gly Ser Tyr Leu Ser Ser Phe Ile Val
        515                 520                 525

Ser Leu Val Pro Val Phe Thr Ala Arg Glu Gly Ser Pro Gly Trp Ile
    530                 535                 540

Pro Asp Asn Leu Asn Glu Gly His Leu Asp Arg Phe Phe Trp Met Met
545                 550                 555                 560

Ala Gly Leu Cys Phe Leu Asn Met Leu Ala Phe Val Phe Cys Ala Met
                565                 570                 575

Arg Tyr Lys Cys Lys Lys Ala Ser
            580
```

<210> SEQ ID NO 127
<211> LENGTH: 405
<212> TYPE: DNA
<213> ORGANISM: Arabidopsis thaliana

<400> SEQUENCE: 127

```
tcatactcac agaacagaaa ccctaatttc ctcaaagcaa tctcgtttca tcttccgcaa     60

acgaaaccct cgagagttgt tactcctcct cctcctctgg tgcatgataa agcggcctca    120

gggtttgctg cggcgctcgt tagcgtttgt caatcgaaga attgtcttgg tcggactcaa    180

gaagatgtca gaagattgat ggagtttctt gtgggagaag aaaagaagag gaacaaggtc    240

ttagtcaatg atgttgttga gagaggtaaa tttggtaaac acttcaaggg cttggtcaag    300

atgttgattg caagaggtaa atctgggatt ctggtggatg ttttaatgga atttgagaga    360

atctgtaatg aattggtctc aaaaaaactt gtctgggttt cttga                    405
```

<210> SEQ ID NO 128
<211> LENGTH: 135
<212> TYPE: PRT
<213> ORGANISM: Arabidopsis thaliana

<400> SEQUENCE: 128

```
Ala Ser Tyr Ser Gln Asn Arg Asn Pro Asn Phe Leu Lys Ala Ile Ser
1               5                   10                  15

Phe His Leu Pro Gln Thr Lys Pro Ser Arg Val Val Thr Pro Pro Pro
            20                  25                  30

Pro Leu Val His Asp Lys Ala Ala Ser Gly Phe Ala Ala Ala Leu Val
        35                  40                  45

Ser Val Cys Gln Ser Lys Asn Cys Leu Gly Arg Thr Gln Glu Asp Val
    50                  55                  60

Arg Arg Leu Met Glu Phe Leu Val Gly Glu Glu Lys Lys Arg Asn Lys
65                  70                  75                  80

Val Leu Val Asn Asp Val Val Glu Arg Gly Lys Phe Gly Lys His Phe
                85                  90                  95

Lys Gly Leu Val Lys Met Leu Ile Ala Arg Gly Lys Ser Gly Ile Leu
            100                 105                 110

Val Asp Val Leu Met Glu Phe Glu Arg Ile Cys Asn Glu Leu Val Ser
        115                 120                 125

Lys Lys Leu Val Trp Val Ser
    130                 135
```

<210> SEQ ID NO 129
<211> LENGTH: 576
<212> TYPE: DNA
<213> ORGANISM: Arabidopsis thaliana

<400> SEQUENCE: 129

```
atggatactc tctcagcatc cgtttcatcc ttgaacctcc cttctcttcc tccaccaccg     60

cagccaccgt tgagatccat ctccagccgc tttaaatcca ccgtaaacgc caccacttct    120

gcttcatcta ccaatctttc aaaaccaaca tcgtcttcac cttcttcagc atcatactca    180

cagaacagaa accctaattt cctcaaagca atctcgtttc atcttccgca aacgaaaccc    240

tcgagagttg ttactcctcc tcctcctctg gtgcatgata aagcggcctc agggtttgct    300

gcggcgctcg ttagcgtttg tcaatcgaag aattgtcttg gtcggactca agaagatgtc    360

agaagattga tggagtttct tgtgggagaa gaaaagaaga ggaacaaggt cttagtcaat    420

gatgttgttg agagaggtaa atttggtaaa cacttcaagg gcttggtcaa gatgttgatt    480

gcaagaggta aatctgggat tctggtggat gttttaatgg aatttgagag aatctgtaat    540

gaattggtct caaaaaaact tgtctgggtt tcttga                              576
```

<210> SEQ ID NO 130
<211> LENGTH: 191
<212> TYPE: PRT
<213> ORGANISM: Arabidopsis thaliana

<400> SEQUENCE: 130

```
Met Asp Thr Leu Ser Ala Ser Val Ser Ser Leu Asn Leu Pro Ser Leu
1               5                   10                  15

Pro Pro Pro Pro Gln Pro Pro Leu Arg Ser Ile Ser Ser Arg Phe Lys
            20                  25                  30

Ser Thr Val Asn Ala Thr Thr Ser Ala Ser Ser Thr Asn Leu Ser Lys
```

```
        35                  40                  45

Pro Thr Ser Ser Ser Pro Ser Ser Ala Ser Tyr Ser Gln Asn Arg Asn
    50                  55                  60

Pro Asn Phe Leu Lys Ala Ile Ser Phe His Leu Pro Gln Thr Lys Pro
65                  70                  75                  80

Ser Arg Val Val Thr Pro Pro Pro Pro Leu Val His Asp Lys Ala Ala
                85                  90                  95

Ser Gly Phe Ala Ala Ala Leu Val Ser Val Cys Gln Ser Lys Asn Cys
            100                 105                 110

Leu Gly Arg Thr Gln Glu Asp Val Arg Arg Leu Met Glu Phe Leu Val
        115                 120                 125

Gly Glu Glu Lys Lys Arg Asn Lys Val Leu Val Asn Asp Val Val Glu
    130                 135                 140

Arg Gly Lys Phe Gly Lys His Phe Lys Gly Leu Val Lys Met Leu Ile
145                 150                 155                 160

Ala Arg Gly Lys Ser Gly Ile Leu Val Asp Val Leu Met Glu Phe Glu
                165                 170                 175

Arg Ile Cys Asn Glu Leu Val Ser Lys Lys Leu Val Trp Val Ser
            180                 185                 190


<210> SEQ ID NO 131
<211> LENGTH: 57
<212> TYPE: PRT
<213> ORGANISM: Arabidopsis thaliana

<400> SEQUENCE: 131

Met Asp Thr Leu Ser Ala Ser Val Ser Ser Leu Asn Leu Pro Ser Leu
1               5                   10                  15

Pro Pro Pro Pro Gln Pro Pro Leu Arg Ser Ile Ser Ser Arg Phe Lys
            20                  25                  30

Ser Thr Val Asn Ala Thr Thr Ser Ala Ser Ser Thr Asn Leu Ser Lys
        35                  40                  45

Pro Thr Ser Ser Ser Pro Ser Ser Ser
    50                  55


<210> SEQ ID NO 132
<211> LENGTH: 32
<212> TYPE: PRT
<213> ORGANISM: Chlamydomonas

<400> SEQUENCE: 132

Met Ala Met Ala Met Arg Ser Thr Phe Ala Ala Arg Val Gly Ala Lys
1               5                   10                  15

Pro Ala Val Arg Gly Ala Arg Pro Ala Ser Arg Met Ser Cys Met Ala
            20                  25                  30


<210> SEQ ID NO 133
<211> LENGTH: 32
<212> TYPE: PRT
<213> ORGANISM: Chlamydomonas

<400> SEQUENCE: 133

Met Gln Val Thr Met Lys Ser Ser Ala Val Ser Gly Gln Arg Val Gly
1               5                   10                  15

Gly Ala Arg Val Ala Thr Arg Ser Val Arg Arg Ala Gln Leu Gln Val
            20                  25                  30


<210> SEQ ID NO 134
```

<211> LENGTH: 52
<212> TYPE: PRT
<213> ORGANISM: Arabidopsis thaliana

<400> SEQUENCE: 134

Met Ala Ser Leu Met Leu Ser Leu Gly Ser Thr Ser Leu Leu Pro Arg
1 5 10 15

Glu Ile Asn Lys Asp Lys Leu Lys Leu Gly Thr Ser Ala Ser Asn Pro
20 25 30

Phe Leu Lys Ala Lys Ser Phe Ser Arg Val Thr Met Thr Val Ala Val
35 40 45

Lys Pro Ser Arg
50

<210> SEQ ID NO 135
<211> LENGTH: 54
<212> TYPE: PRT
<213> ORGANISM: Arabidopsis thaliana

<400> SEQUENCE: 135

Met Ala Thr Gln Phe Ser Ala Ser Val Ser Leu Gln Thr Ser Cys Leu
1 5 10 15

Ala Thr Thr Arg Ile Ser Phe Gln Lys Pro Ala Leu Ile Ser Asn His
20 25 30

Gly Lys Thr Asn Leu Ser Phe Asn Leu Arg Arg Ser Ile Pro Ser Arg
35 40 45

Arg Leu Ser Val Ser Cys
50

<210> SEQ ID NO 136
<211> LENGTH: 70
<212> TYPE: PRT
<213> ORGANISM: Arabidopsis thaliana

<400> SEQUENCE: 136

Met Ala Ser Ile Ala Ala Ser Ala Ser Ile Ser Leu Gln Ala Arg Pro
1 5 10 15

Arg Gln Leu Ala Ile Ala Ala Ser Gln Val Lys Ser Phe Ser Asn Gly
20 25 30

Arg Arg Ser Ser Leu Ser Phe Asn Leu Arg Gln Leu Pro Thr Arg Leu
35 40 45

Thr Val Ser Cys Ala Ala Lys Pro Glu Thr Val Asp Lys Val Cys Ala
50 55 60

Val Val Arg Lys Gln Leu
65 70

<210> SEQ ID NO 137
<211> LENGTH: 74
<212> TYPE: PRT
<213> ORGANISM: Arabidopsis thaliana

<400> SEQUENCE: 137

Met Ala Ser Ile Ala Thr Ser Ala Ser Thr Ser Leu Gln Ala Arg Pro
1 5 10 15

Arg Gln Leu Val Ile Gly Ala Lys Gln Val Lys Ser Phe Ser Tyr Gly
20 25 30

Ser Arg Ser Asn Leu Ser Phe Asn Leu Arg Gln Leu Pro Thr Arg Leu
35 40 45

Thr Val Tyr Cys Ala Ala Lys Pro Glu Thr Val Asp Lys Val Cys Ala 50 55 60

Val Val Arg Lys Gln Leu Ser Leu Lys Glu
65 70

<210> SEQ ID NO 138
<211> LENGTH: 51
<212> TYPE: PRT
<213> ORGANISM: Arabidopsis thaliana

<400> SEQUENCE: 138

Met Ala Ser Ser Ala Ala Ala Ile Val Ser Gly Ser Pro Phe Arg Ser
1 5 10 15

Ser Pro Leu Ile His Asn His His Ala Ser Arg Tyr Ala Pro Gly Ser
20 25 30

Ile Ser Val Val Ser Leu Pro Arg Gln Val Ser Arg Arg Gly Leu Ser
35 40 45

Val Lys Ser
50

<210> SEQ ID NO 139
<211> LENGTH: 100
<212> TYPE: PRT
<213> ORGANISM: Brassica napus

<400> SEQUENCE: 139

Met Ala Thr Ala Asn Ala Leu Ser Ser Pro Ser Val Leu Cys Ser Ser
1 5 10 15

Arg Gln Gly Lys Leu Ser Gly Gly Ser Gln Gln Lys Gly Gln Arg Val
20 25 30

Ser Tyr Arg Lys Ala Asn Arg Arg Phe Ser Leu Arg Ala Asn Val Lys
35 40 45

Glu Ile Ala Phe Asp Gln Ser Ser Arg Ala Ala Leu Gln Ala Gly Ile
50 55 60

Asp Lys Leu Ala Asp Ala Val Gly Leu Thr Leu Gly Pro Arg Gly Arg
65 70 75 80

Asn Val Val Leu Asp Glu Phe Gly Ser Pro Lys Val Val Asn Asp Gly
85 90 95

Val Thr Ile Ala
100

<210> SEQ ID NO 140
<211> LENGTH: 100
<212> TYPE: PRT
<213> ORGANISM: Hordeum vulgare

<400> SEQUENCE: 140

Met Ala Pro Thr Val Met Ala Ser Ser Ala Thr Ser Val Ala Pro Phe
1 5 10 15

Gln Gly Leu Lys Ser Thr Ala Gly Leu Pro Val Ser Arg Arg Ser Asn
20 25 30

Ala Ser Ser Ala Ser Val Ser Asn Gly Gly Arg Ile Arg Cys Met Gln
35 40 45

Val Trp Pro Ile Glu Gly Ile Lys Lys Phe Glu Thr Leu Ser Tyr Leu
50 55 60

Pro Pro Leu Ser Thr Glu Ala Leu Leu Lys Gln Val Asp Tyr Leu Ile
65 70 75 80

Arg Ser Lys Trp Val Pro Cys Leu Glu Phe Ser Lys Val Gly Phe Ile
85 90 95

Phe Arg Glu His
            100

<210> SEQ ID NO 141
<211> LENGTH: 100
<212> TYPE: PRT
<213> ORGANISM: Medicago truncatula

<400> SEQUENCE: 141

Met Thr Thr Ile Phe Arg Leu Ala Ser Ser Ser Ser Pro Ser Leu Arg
1               5                   10                  15

His Asp Ala Thr Pro His Asn Phe His Ile Arg Lys Thr Ser Ile Ser
            20                  25                  30

Asn Thr Phe Ser Phe Ser Ser Lys Asn Ser Leu Ser Phe Lys Arg Ile
        35                  40                  45

Leu Thr Ser Gly Gly Ser Arg Arg Phe Ile Val Ala Ala Ser Pro Pro
    50                  55                  60

Thr Glu Asp Ala Val Val Ala Thr Glu Pro Leu Thr Lys Gln Asp Leu
65                  70                  75                  80

Ile Asp Tyr Leu Ala Ser Gly Cys Lys Thr Lys Asp Lys Trp Arg Ile
                85                  90                  95

Gly Thr Glu His
            100

<210> SEQ ID NO 142
<211> LENGTH: 100
<212> TYPE: PRT
<213> ORGANISM: Spinacia oleracea

<400> SEQUENCE: 142

Met Glu Thr Ser Met Ala Cys Cys Ser Arg Ser Ile Val Leu Pro Arg
1               5                   10                  15

Val Ser Pro Gln His Ser Ser Ala Leu Val Pro Ser Ser Ile Asn Leu
            20                  25                  30

Lys Ser Leu Lys Ser Ser Ser Leu Phe Gly Glu Ser Leu Arg Met Thr
        35                  40                  45

Thr Lys Ser Ser Val Arg Val Asn Lys Ala Lys Asn Ser Ser Leu Val
    50                  55                  60

Thr Lys Cys Glu Leu Gly Asp Ser Leu Glu Glu Phe Leu Ala Lys Ala
65                  70                  75                  80

Thr Thr Asp Lys Gly Leu Ile Arg Leu Met Met Cys Met Gly Glu Ala
                85                  90                  95

Leu Arg Thr Ile
            100

<210> SEQ ID NO 143
<211> LENGTH: 1236
<212> TYPE: DNA
<213> ORGANISM: Oryza sativa

<400> SEQUENCE: 143
ggtcagccaa tacattgatc cgttgccaat catgcaaagt attttggctg tggccgagtg      60
ccggaattga taattgtgtt ctgactaaat taaatgacca gaagtcgcta tcttccaatg     120
tatccgaaac ctggattaaa caatcctgtt ctgttctcta gcccctcctg catggccgga     180
ttgttttttt gacatgtttt cttgactgag gcctgtttgt tctaaacttt ttcttcaaac     240
ttttaacttt ttcatcacat cagaactttt ctacacatat aaacttttaa cttttccgtc     300
acatcgttcc aatttcaatc aaactttcaa ttttggcgtg aactaaacac accctgagtc 360
ttttattgct cctccgtacg ggttggctgg ttgagaatag gtattttcag agagaaaatc 420
tagatattgg gaggaacttg gcatgaatgg ccactatatt tagagcaatt ctacggtcct 480
tgaggaggta ccatgaggta ccaaaatttt agtgtaaatt ttagtatctc attataacta 540
ggtattatga ggtaccaaat ttacaataga aaaaatagta cttcatggta ctttcttaag 600
taccgtaaaa ttgctcctat atttaagggg atgtttatat ctatccatat ccataatttg 660
attttgataa gaaaaaatgt gagcacacca agcatgtcca tgaccttgca ctcttggctc 720
actcgtcaac tgtgaagaac ctcaaaaatg ctcaatatag ctacaggtgc ctgaaaaaat 780
aactttaaag ttttgaacat cgatttcact aaacaacaat tattatctcc ctctgaaaga 840
tgatagttta gaactctaga atcattgtcg gcggagaaag taaattattt tccccaaatt 900
tccagctatg aaaaaaccct caccaaacac catcaaacaa gagttcacca aaccgcccat 960
gcggccatgc tgtcacgcaa cgcaccgcat tgcctgatgg ccgctcgatg catgcatgct 1020
tccccgtgca catatccgac agacgcgccg tgtcagcgag ctcctcgacc gacctgtgta 1080
gcccatgcaa gcatccaccc ccgccacgta cacccccctcc tcctccctac gtgtcaccgc 1140
tctctccacc tatatatgcc cacctggccc ctctcctccc atctccactt cacccgatcg 1200
cttcttcttc ttcttcgttg cattcatctt gctagc 1236

<210> SEQ ID NO 144
<211> LENGTH: 55
<212> TYPE: DNA
<213> ORGANISM: Artificial sequence
<220> FEATURE:
<223> OTHER INFORMATION: primer: prm00735

<400> SEQUENCE: 144
ggggacaagt ttgtacaaaa aagcaggctt cacaatggat actctctcag catcc 55

<210> SEQ ID NO 145
<211> LENGTH: 50
<212> TYPE: DNA
<213> ORGANISM: Artificial sequence
<220> FEATURE:
<223> OTHER INFORMATION: primer: prm00736

<400> SEQUENCE: 145
ggggaccact ttgtacaaga aagctgggtt gtatcatcaa gaaacccaga 50

<210> SEQ ID NO 146
<211> LENGTH: 1592
<212> TYPE: DNA
<213> ORGANISM: Oryza sativa

<400> SEQUENCE: 146
caaaagcaag aggaggaggc cgcggctagc gagcgagcga gagagagggg agaagaagag 60
gtgggacagc cgggagatcc atccctgtgg agaggaggga gggaggaagg aggcgttgga 120
ggaggagagg ttgaccgata gatccattgc ggagttgagt gttgatgcaa agctgattcg 180
ccatcgttta gctttttata agagatgggt tcagtagggg ttgcgccgtc tgggttaaag 240
aacagcagta gcaccagcat gggtgctgag aagttgcctg atcagatgca tgatctgaag 300
ataagggacg ataaggaagt tgaagcgact attattaacg gcaagggaac agaaaccggc 360
cacataattg tcacaactac tggtggcaga aatggtcagc cgaaacagac agttagctac 420

```
atggctgagc gtattgtagg gcaaggttca tttgggattg tcttccaggc aaaatgtctg     480

gagacaggtg agacagttgc tatcaagaag gttcttcagg ataagcgcta caagaaccgt     540

gagcttcaga ccatgcgcct tcttgaccac ccaaatgttg tagctctgaa gcactgtttc     600

ttctctacaa ctgagaagga tgaactgtat ctaaacttgg ttcttgagta tgtgcctgaa     660

actgttcatc gtgttgtgaa gcattacaac aagatgaacc agcgtatgcc acttatctat     720

gtgaagctgt atatgtacca gatttgtagg gcattagctt acatccataa tagcatcgga     780

gtttgccaca gagatatcaa gccacagaat cttctggtaa acccacatac ccatcaactc     840

aagctatgtg actttgggag tgcaaaagtt ctggtcaagg gagaaccgaa catatcgtac     900

atttgctccc gatactatag ggctccggag ctcatatttg gtgccaccga atacactaca     960

gctattgaca tctggtctgc tggatgtgtt cttgctgaac ttatgttagg gcagcctctg    1020

tttcctggtg aaagtggtgt agaccaactt gtggaaatca tcaaggtcct tggaacacct    1080

acaagggagg aaattaaatg catgaatcca aactataccg agttcaagtt tccacagatt    1140

aaagcacacc catggcacaa ggtattccat aaaaggttgc ctccagaagc tgttgatctt    1200

gtctctaggc tgctccagta ctcacccaac ctaagatgca ctgctgtgga agcacttgtt    1260

cacccattct ttgatgagct tcgagaccct aatgctcgcc ttccgaatgg ccgctttttg    1320

cctcctctct tcaacttcaa gcctcatgaa ctgaaaggaa tcccatcaga tattatggcg    1380

aaattgatcc cagaacatgt gaagaagcaa tgctcctatg caggagtatg agacagcttc    1440

cgcacgaccc ccctggaaat ttccatgaca agtgcccatt tcctcccccc tggacgacga    1500

tggatcgtca gcatatgcgt gcatgatggt tggtgaggat gtgaagttac gttgttgttg    1560

tgtgaccacc tagagcttga acagaaggaa aa                                  1592
```

<210> SEQ ID NO 147
<211> LENGTH: 408
<212> TYPE: PRT
<213> ORGANISM: Oryza sativa

<400> SEQUENCE: 147

```
Met Gly Ser Val Gly Val Ala Pro Ser Gly Leu Lys Asn Ser Ser Ser
1               5                   10                  15

Thr Ser Met Gly Ala Glu Lys Leu Pro Asp Gln Met His Asp Leu Lys
            20                  25                  30

Ile Arg Asp Asp Lys Glu Val Glu Ala Thr Ile Ile Asn Gly Lys Gly
        35                  40                  45

Thr Glu Thr Gly His Ile Ile Val Thr Thr Thr Gly Gly Arg Asn Gly
    50                  55                  60

Gln Pro Lys Gln Thr Val Ser Tyr Met Ala Glu Arg Ile Val Gly Gln
65                  70                  75                  80

Gly Ser Phe Gly Ile Val Phe Gln Ala Lys Cys Leu Glu Thr Gly Glu
                85                  90                  95

Thr Val Ala Ile Lys Lys Val Leu Gln Asp Lys Arg Tyr Lys Asn Arg
            100                 105                 110

Glu Leu Gln Thr Met Arg Leu Leu Asp His Pro Asn Val Val Ala Leu
        115                 120                 125

Lys His Cys Phe Phe Ser Thr Thr Glu Lys Asp Glu Leu Tyr Leu Asn
    130                 135                 140

Leu Val Leu Glu Tyr Val Pro Glu Thr Val His Arg Val Val Lys His
145                 150                 155                 160

Tyr Asn Lys Met Asn Gln Arg Met Pro Leu Ile Tyr Val Lys Leu Tyr
```

```
                165                 170                 175

Met Tyr Gln Ile Cys Arg Ala Leu Ala Tyr Ile His Asn Ser Ile Gly
            180                 185                 190

Val Cys His Arg Asp Ile Lys Pro Gln Asn Leu Leu Val Asn Pro His
        195                 200                 205

Thr His Gln Leu Lys Leu Cys Asp Phe Gly Ser Ala Lys Val Leu Val
    210                 215                 220

Lys Gly Glu Pro Asn Ile Ser Tyr Ile Cys Ser Arg Tyr Tyr Arg Ala
225                 230                 235                 240

Pro Glu Leu Ile Phe Gly Ala Thr Glu Tyr Thr Thr Ala Ile Asp Ile
                245                 250                 255

Trp Ser Ala Gly Cys Val Leu Ala Glu Leu Met Leu Gly Gln Pro Leu
            260                 265                 270

Phe Pro Gly Glu Ser Gly Val Asp Gln Leu Val Glu Ile Ile Lys Val
        275                 280                 285

Leu Gly Thr Pro Thr Arg Glu Glu Ile Lys Cys Met Asn Pro Asn Tyr
    290                 295                 300

Thr Glu Phe Lys Phe Pro Gln Ile Lys Ala His Pro Trp His Lys Val
305                 310                 315                 320

Phe His Lys Arg Leu Pro Pro Glu Ala Val Asp Leu Val Ser Arg Leu
                325                 330                 335

Leu Gln Tyr Ser Pro Asn Leu Arg Cys Thr Ala Val Glu Ala Leu Val
            340                 345                 350

His Pro Phe Phe Asp Glu Leu Arg Asp Pro Asn Ala Arg Leu Pro Asn
        355                 360                 365

Gly Arg Phe Leu Pro Pro Leu Phe Asn Phe Lys Pro His Glu Leu Lys
    370                 375                 380

Gly Ile Pro Ser Asp Ile Met Ala Lys Leu Ile Pro Glu His Val Lys
385                 390                 395                 400

Lys Gln Cys Ser Tyr Ala Gly Val
                405


<210> SEQ ID NO 148
<211> LENGTH: 1800
<212> TYPE: DNA
<213> ORGANISM: Oryza sativa

<400> SEQUENCE: 148

ctctccgaat cctcccccgc attccgcgcc ggagctgagg agggacagcg agccagcgag     60

ggaggtgggg caatccagcg agcgccagat cgtgccgcca gccccgctcc gtcctctctc    120

cggcgaccct ccgccccgcc tgatcccgtg gtggatcaac tacaactcat ctttaggaaa    180

gcctcttgaa cattagcctt gtgtgccttt caacagtatg gcctcggtag gtgtggtgcg    240

ttcttccttg ggtttcaga acgaaacaag tacaagtggc gatgccgacc gacttccgaa    300

tgagatgagc aatatgagta taagggatga taataaggac attgacgaca tagttgtcaa    360

tggcaatggg acagaacctg gtcatgttat tgtgacaagc attgatggaa gaaatggaca    420

ggctaaacag accattagct acatggccga gcgtgtcgta ggtcatggat cctttggaac    480

tgttttccag gccaagtgcc tggaaaccgg tgagactgtg gctataaaga aggttcttca    540

agacaagaga tataagaacc gtgagctgca aacaatgcga gttcttgacc acccaaatgt    600

ggtgtcacta aagcattgtt ttttctcaaa gactgagaag gaggagcttt acctcaattt    660

ggtgcttgag tatgtgccag agactgctca ccgtgtaatt aaacattaca acaagatgaa    720
```

```
ccaacgcatg ccattgatat atgcaaaact atacatgtat cagatatgca gagctttggc    780

gtacattcac aacaccattg gcgtgtgtca cagggatatc aagccacaaa atcttctggt    840

gaacccacat actcatcagc tgaaattatg tgacttcggc agcgcgaaag tcttggtaaa    900

aggagaacca aatatttctt acatctgttc aaggtactac agagctccag agctcatatt    960

tggtgctact gaatacacaa cagcgattga tgtttggtct gccggttgtg tgcttgctga   1020

actcctcctg ggcagcctc tattccctgg cgacagtggc gttgatcagc ttgttgaaat   1080

catcaaggtt ctgggtaccc ctacacgaga ggagattaag tgcatgaacc caaattacac   1140

cgagtttaaa tttccgcaaa tcaaagctca cccatggcac aagatcttcc ataaaagaat   1200

gcctgctgaa gcagtcgatc tcgtctccag gcttttgcag tattcaccat acctccggtc   1260

cactgcttcg gaagcattga tccatccctt cttcgatgaa ctccgtgatc caaacacccg   1320

cttaccgaac ggccgtttcc ttcctcctct cttcaacttc aagccccatg aactgaaggg   1380

tatgccaatg gaattcctgg tgaagcttat ccccgaacat gctcgaaagc aatgcgcgtt   1440

tgtaggatgg tgatttctga ggtcagcatg aaaactagtt cagaatttct tcaccgtcct   1500

ccattagaaa gcagagatga accctgtgtg cagccatttg ggaaagctgg tgcatatgga   1560

agtggaacta catttttttg tccgagattc tgacgccgcg tattcttttc ccccctccca   1620

ctttgctgct gccggtgtaa ccaaaaaatc atccacggtt ctgtaaagtt gatgaagaag   1680

agtgtaaaat caggttgaaa actgaattcg atcggtttgt caagattgta gcaacatgca   1740

aggaaggatg ttgcacactt tgtatggcaa tgttcgttcg gtccaaatat ttggacatgg   1800
```

<210> SEQ ID NO 149
<211> LENGTH: 411
<212> TYPE: PRT
<213> ORGANISM: Oryza sativa

<400> SEQUENCE: 149

```
Met Ala Ser Val Gly Val Val Arg Ser Ser Leu Gly Phe Gln Asn Glu
1               5                   10                  15

Thr Ser Thr Ser Gly Asp Ala Asp Arg Leu Pro Asn Glu Met Ser Asn
            20                  25                  30

Met Ser Ile Arg Asp Asp Asn Lys Asp Ile Asp Asp Ile Val Val Asn
        35                  40                  45

Gly Asn Gly Thr Glu Pro Gly His Val Ile Val Thr Ser Ile Asp Gly
    50                  55                  60

Arg Asn Gly Gln Ala Lys Gln Thr Ile Ser Tyr Met Ala Glu Arg Val
65                  70                  75                  80

Val Gly His Gly Ser Phe Gly Thr Val Phe Gln Ala Lys Cys Leu Glu
                85                  90                  95

Thr Gly Glu Thr Val Ala Ile Lys Lys Val Leu Gln Asp Lys Arg Tyr
            100                 105                 110

Lys Asn Arg Glu Leu Gln Thr Met Arg Val Leu Asp His Pro Asn Val
        115                 120                 125

Val Ser Leu Lys His Cys Phe Phe Ser Lys Thr Glu Lys Glu Glu Leu
    130                 135                 140

Tyr Leu Asn Leu Val Leu Glu Tyr Val Pro Glu Thr Ala His Arg Val
145                 150                 155                 160

Ile Lys His Tyr Asn Lys Met Asn Gln Arg Met Pro Leu Ile Tyr Ala
                165                 170                 175

Lys Leu Tyr Met Tyr Gln Ile Cys Arg Ala Leu Ala Tyr Ile His Asn
            180                 185                 190
```

```
Thr Ile Gly Val Cys His Arg Asp Ile Lys Pro Gln Asn Leu Leu Val
        195                 200                 205

Asn Pro His Thr His Gln Leu Lys Leu Cys Asp Phe Gly Ser Ala Lys
    210                 215                 220

Val Leu Val Lys Gly Glu Pro Asn Ile Ser Tyr Ile Cys Ser Arg Tyr
225                 230                 235                 240

Tyr Arg Ala Pro Glu Leu Ile Phe Gly Ala Thr Glu Tyr Thr Thr Ala
                245                 250                 255

Ile Asp Val Trp Ser Ala Gly Cys Val Leu Ala Glu Leu Leu Leu Gly
            260                 265                 270

Gln Pro Leu Phe Pro Gly Asp Ser Gly Val Asp Gln Leu Val Glu Ile
        275                 280                 285

Ile Lys Val Leu Gly Thr Pro Thr Arg Glu Glu Ile Lys Cys Met Asn
    290                 295                 300

Pro Asn Tyr Thr Glu Phe Lys Phe Pro Gln Ile Lys Ala His Pro Trp
305                 310                 315                 320

His Lys Ile Phe His Lys Arg Met Pro Ala Glu Ala Val Asp Leu Val
                325                 330                 335

Ser Arg Leu Leu Gln Tyr Ser Pro Tyr Leu Arg Ser Thr Ala Ser Glu
            340                 345                 350

Ala Leu Ile His Pro Phe Phe Asp Glu Leu Arg Asp Pro Asn Thr Arg
        355                 360                 365

Leu Pro Asn Gly Arg Phe Leu Pro Pro Leu Phe Asn Phe Lys Pro His
    370                 375                 380

Glu Leu Lys Gly Met Pro Met Glu Phe Leu Val Lys Leu Ile Pro Glu
385                 390                 395                 400

His Ala Arg Lys Gln Cys Ala Phe Val Gly Trp
                405                 410


<210> SEQ ID NO 150
<211> LENGTH: 2261
<212> TYPE: DNA
<213> ORGANISM: Oryza sativa

<400> SEQUENCE: 150

ttggggcgga gagacgggag agagaggaga ggagtcgaac tagggttagt gaggtgaagg      60

ggggcgattt tgctcatcgc cctccgccta gatcgaatcc gaatcccgcc tcctcctcct     120

cctcctcctc cccccgcgcc gatcttgccc cgctccctcg ccgcagctgc gggcttgccc     180

tagcccgccg catcgccgac gtactacgcc cgctcggctc caggctccag atccggcctc     240

cagggcgtgc ccgctgctgg acggcgctct cccgcgtccg tggctacctc ctcctccggg     300

tttgcgttgc cgtcgccgaa gcgatccgtt ggtggattgt gtgtagctct gtaacaaagg     360

atcttggtcc ataggagtga accagaaggt acaaaacttc ttggctatta tgacatcggt     420

gggtctagta gattcttcat caggtttccc ggaaacgagt actagtggag ccactgatcg     480

tctgacagat gatatcagcg agatgagcat aagagataag gaagttgaag ctgtagtggt     540

cagtggcaat agtatggaca taggtcacac tattgtgaca actgttggtg gaagaaatgg     600

gcagccaaag cagacaatta gttacatcgc agagcgtgct gttgggcgtg gttcatttgg     660

agttgtcttc caggctaagt gtctagaaac tggtgagaga gttgctgtaa agaaagttct     720

tcaagatgcg agatacaaga accgggagct gcaaacgatg caagttctcg atcacccaaa     780

tgttgcatgc ttgaagcatt acttttgctc gactactgcg aaggaggagc tatacctcaa     840
```

-continued

```
cttggttctt gaatatgtgc cagaaactgt tcatcgtgtt attagacatt acaataagat    900

gagccaacgc atgccattga tttatgttaa actttatatg taccagattt gtagggcttt    960

ggcatacatt cataactgtg tgggagtatg ccacagagat ataaagccac agaatatatt   1020

ggtgaatcca cataatcatc agttgaaatt gtgtgacttt ggcagtgcaa aagtcctggt   1080

gaaaggggaa ccaaatattt catatatctg ttctagatac tacagagccc cagcactcat   1140

atttggggct acagagtaca cgacagctat tgatgtgtgg tctgctggct gtgttcttgc   1200

tgaactactt ctagggcagc ctgtttttcc tggtgacagt ggcgtcgacc aacttgttga   1260

aattatcaag gtactgggta ctccaacaag ggaagaaatc aaacatatga atccgaacta   1320

cactgagttt aagttccccc aaatcaaagc tcacccatgg cacaagatct ttcataaaag   1380

aatgccatct gaagctgtag atcttgtgtc tcggcttctg cagtactcac cacacctccg   1440

gtgcagtgca ttggaggtgt taattcatcc attcttcgat gaactacgag atccaaatgc   1500

tcgcttacca aatggccgta ctcttccccc actattcaat ttcaagcctc gtgagctgaa   1560

aggagcatca atggaatttc ttgtgaagtt ggttccacag catgctaaga agcaatgtgc   1620

cttcttagga ttatgagcag acagttcata cactaatcgg gtattacgtt ggtctacttg   1680

gttccgtaga acagcatggc ctgcagtatt attgaatggg ccctaatttt gttctacgtg   1740

caccctgctt gggcatgcct tctaccatca tattctgtaa agcagatgaa gacatggagt   1800

gagtggttat tgattggggc ttgtatattg gtctgccctt gacttgagaa ctttattcac   1860

tctgctgtat caagcaagaa agaacacgta tgtatgcttg agccatattt cattccagag   1920

cctctatcag gtttcaccga ccatcagatt taagtcttcc agtttgtagg gctaagccaa   1980

aaaagttcta tgtgtgaaga gttggagaca tctgtttggt tacaagctat ttgattgtat   2040

ttgatcattc ttttgtatta acactctgat aaacttacat gagttaattc tattgttatg   2100

tgatatagtt gtgtgccact tttaaacacc taaacaactc tgttcaatgt tgaaatgttt   2160

ggcatgtatc aacatatcac ctcattattt cgaggttgat tttgtacacc tgatatctgt   2220

tagcttgaat gcttgattac aagcaaatga ttaaatattt t                       2261
```

```
<210> SEQ ID NO 151
<211> LENGTH: 408
<212> TYPE: PRT
<213> ORGANISM: Oryza sativa

<400> SEQUENCE: 151

Met Thr Ser Val Gly Leu Val Asp Ser Ser Ser Gly Phe Pro Glu Thr
1               5                   10                  15

Ser Thr Ser Gly Ala Thr Asp Arg Leu Thr Asp Asp Ile Ser Glu Met
            20                  25                  30

Ser Ile Arg Asp Lys Glu Val Glu Ala Val Val Val Ser Gly Asn Ser
        35                  40                  45

Met Asp Ile Gly His Thr Ile Val Thr Thr Val Gly Gly Arg Asn Gly
    50                  55                  60

Gln Pro Lys Gln Thr Ile Ser Tyr Ile Ala Glu Arg Ala Val Gly Arg
65                  70                  75                  80

Gly Ser Phe Gly Val Val Phe Gln Ala Lys Cys Leu Glu Thr Gly Glu
                85                  90                  95

Arg Val Ala Val Lys Lys Val Leu Gln Asp Ala Arg Tyr Lys Asn Arg
            100                 105                 110

Glu Leu Gln Thr Met Gln Val Leu Asp His Pro Asn Val Ala Cys Leu
        115                 120                 125
```

-continued

```
Lys His Tyr Phe Cys Ser Thr Thr Ala Lys Glu Glu Leu Tyr Leu Asn
    130                 135                 140

Leu Val Leu Glu Tyr Val Pro Glu Thr Val His Arg Val Ile Arg His
145                 150                 155                 160

Tyr Asn Lys Met Ser Gln Arg Met Pro Leu Ile Tyr Val Lys Leu Tyr
                165                 170                 175

Met Tyr Gln Ile Cys Arg Ala Leu Ala Tyr Ile His Asn Cys Val Gly
            180                 185                 190

Val Cys His Arg Asp Ile Lys Pro Gln Asn Ile Leu Val Asn Pro His
        195                 200                 205

Asn His Gln Leu Lys Leu Cys Asp Phe Gly Ser Ala Lys Val Leu Val
    210                 215                 220

Lys Gly Glu Pro Asn Ile Ser Tyr Ile Cys Ser Arg Tyr Tyr Arg Ala
225                 230                 235                 240

Pro Ala Leu Ile Phe Gly Ala Thr Glu Tyr Thr Thr Ala Ile Asp Val
                245                 250                 255

Trp Ser Ala Gly Cys Val Leu Ala Glu Leu Leu Leu Gly Gln Pro Val
            260                 265                 270

Phe Pro Gly Asp Ser Gly Val Asp Gln Leu Val Glu Ile Ile Lys Val
        275                 280                 285

Leu Gly Thr Pro Thr Arg Glu Glu Ile Lys His Met Asn Pro Asn Tyr
    290                 295                 300

Thr Glu Phe Lys Phe Pro Gln Ile Lys Ala His Pro Trp His Lys Ile
305                 310                 315                 320

Phe His Lys Arg Met Pro Ser Glu Ala Val Asp Leu Val Ser Arg Leu
                325                 330                 335

Leu Gln Tyr Ser Pro His Leu Arg Cys Ser Ala Leu Glu Val Leu Ile
            340                 345                 350

His Pro Phe Phe Asp Glu Leu Arg Asp Pro Asn Ala Arg Leu Pro Asn
        355                 360                 365

Gly Arg Thr Leu Pro Pro Leu Phe Asn Phe Lys Pro Arg Glu Leu Lys
    370                 375                 380

Gly Ala Ser Met Glu Phe Leu Val Lys Leu Val Pro Gln His Ala Lys
385                 390                 395                 400

Lys Gln Cys Ala Phe Leu Gly Leu
                405
```

<210> SEQ ID NO 152
<211> LENGTH: 1634
<212> TYPE: DNA
<213> ORGANISM: Arabidopsis thaliana

<400> SEQUENCE: 152

```
acaaaataat ataaagtaaa aatatttcat aattcgtctc tcaccggaaa aataaataaa      60

gttagagaga gagattcata atcatcaaac ccacaaatcc tttttttttt tttttgttaa     120

aacccacaaa tccttactcg tacggatctc tctctcttta atatcctaat tcttctcttc     180

atcgatctga gatttttacg ttttcatcgg cttgaaagtt tgaagagttt tgtagcctga     240

aaaatggcgt cagtgggtat agctcctaat cctggagcaa gagactctac tggtgttgat     300

aaattgcctg aagaaatgaa tgacatgaaa attcgtgacg ataaagaaat ggaagcgaca     360

gtggtagatg gaaatggaac agagactgga catatcattg tgactactat tggtggtaga     420

aatggccaac caaaacagac aattagctac atggctgagc gtgttgttgg tcacggatct     480
```

-continued

```
tttggtgttg tgttccaagc gaaatgtctt gagacaggag aaactgttgc gataaagaaa    540

gttttacaag ataggaggta caagaaccgt gagcttcaaa ccatgaggct acttgaccat    600

cctaatgttg tgtctctgaa acattgtttc ttctcaacca ctgaaaaaga tgagctttac    660

ctcaatcttg ttcttgagta cgttccagaa actgttcatc gtgttatcaa acactacaac    720

aaactgaatc agagaatgcc tcttatatac gtcaaacttt acacttatca gatttttaga    780

gccttatctt acattcaccg atgcattggt gtgtgtcatc gtgacataaa acctcaaaac    840

ttgttggtaa atccgcacac tcatcaagta aagctatgtg attttggaag tgcaaaagta    900

ttggtaaaag gagaaccaaa catttcctac atctgctcga ggtattacag agcacctgaa    960

cttatttttg gagcaaccga gtatacgaca gccattgatg tctggtctgc aggatgtgtt   1020

ctagctgaac tattgcttgg acagcccttg ttccctggtg agagcggtgt tgatcaactt   1080

gtagagatta tcaaggtctt gggaacgcct actagagaag aaatcaagtg catgaaccca   1140

aactacacgg aattcaaatt ccctcagatt aaagctcatc catggcacaa gatttttccac   1200

aaacgcatgc ctccagaagc tgttgatttg gtctcaagac ttcttcaata ctctcctaat   1260

ctacgaagtg ccgctctcga cacattagtc cacccattct ttgatgagtt aagagaccca   1320

aacgcacgtc tacctaatgg acgtttcctt ccaccgcttt tcaacttcaa gcctcacgag   1380

ctgaaaggtg taccattgga gatggtagct aagttagtac ctgagcatgc aaggaagcag   1440

tgtccttggc tcggtttgtg atttcctctt aatgtagcat gaacacaaca aacacttctt   1500

ataaattacc tctctatgta tcaatatgtc acaaactgat atgcaccctt tgtttgttgt   1560

atgagtagag aaaaaaagag ttattactat ggttggttgg ttcataatgt aaaagcccac   1620

caagattttt tatc                                                     1634
```

<210> SEQ ID NO 153
<211> LENGTH: 405
<212> TYPE: PRT
<213> ORGANISM: Arabidopsis thaliana

<400> SEQUENCE: 153

```
Met Ala Ser Val Gly Ile Ala Pro Asn Pro Gly Ala Arg Asp Ser Thr
1               5                   10                  15

Gly Val Asp Lys Leu Pro Glu Glu Met Asn Asp Met Lys Ile Arg Asp
            20                  25                  30

Asp Lys Glu Met Glu Ala Thr Val Val Asp Gly Asn Gly Thr Glu Thr
        35                  40                  45

Gly His Ile Ile Val Thr Thr Ile Gly Gly Arg Asn Gly Gln Pro Lys
    50                  55                  60

Gln Thr Ile Ser Tyr Met Ala Glu Arg Val Val Gly His Gly Ser Phe
65                  70                  75                  80

Gly Val Val Phe Gln Ala Lys Cys Leu Glu Thr Gly Glu Thr Val Ala
                85                  90                  95

Ile Lys Lys Val Leu Gln Asp Arg Arg Tyr Lys Asn Arg Glu Leu Gln
            100                 105                 110

Thr Met Arg Leu Leu Asp His Pro Asn Val Val Ser Leu Lys His Cys
        115                 120                 125

Phe Phe Ser Thr Thr Glu Lys Asp Glu Leu Tyr Leu Asn Leu Val Leu
    130                 135                 140

Glu Tyr Val Pro Glu Thr Val His Arg Val Ile Lys His Tyr Asn Lys
145                 150                 155                 160

Leu Asn Gln Arg Met Pro Leu Ile Tyr Val Lys Leu Tyr Thr Tyr Gln
```

```
                165                 170                 175

Ile Phe Arg Ala Leu Ser Tyr Ile His Arg Cys Ile Gly Val Cys His
            180                 185                 190

Arg Asp Ile Lys Pro Gln Asn Leu Leu Val Asn Pro His Thr His Gln
        195                 200                 205

Val Lys Leu Cys Asp Phe Gly Ser Ala Lys Val Leu Val Lys Gly Glu
    210                 215                 220

Pro Asn Ile Ser Tyr Ile Cys Ser Arg Tyr Tyr Arg Ala Pro Glu Leu
225                 230                 235                 240

Ile Phe Gly Ala Thr Glu Tyr Thr Thr Ala Ile Asp Val Trp Ser Ala
                245                 250                 255

Gly Cys Val Leu Ala Glu Leu Leu Leu Gly Gln Pro Leu Phe Pro Gly
            260                 265                 270

Glu Ser Gly Val Asp Gln Leu Val Glu Ile Ile Lys Val Leu Gly Thr
        275                 280                 285

Pro Thr Arg Glu Glu Ile Lys Cys Met Asn Pro Asn Tyr Thr Glu Phe
    290                 295                 300

Lys Phe Pro Gln Ile Lys Ala His Pro Trp His Lys Ile Phe His Lys
305                 310                 315                 320

Arg Met Pro Pro Glu Ala Val Asp Leu Val Ser Arg Leu Leu Gln Tyr
                325                 330                 335

Ser Pro Asn Leu Arg Ser Ala Ala Leu Asp Thr Leu Val His Pro Phe
            340                 345                 350

Phe Asp Glu Leu Arg Asp Pro Asn Ala Arg Leu Pro Asn Gly Arg Phe
        355                 360                 365

Leu Pro Pro Leu Phe Asn Phe Lys Pro His Glu Leu Lys Gly Val Pro
    370                 375                 380

Leu Glu Met Val Ala Lys Leu Val Pro Glu His Ala Arg Lys Gln Cys
385                 390                 395                 400

Pro Trp Leu Gly Leu
                405


<210> SEQ ID NO 154
<211> LENGTH: 1669
<212> TYPE: DNA
<213> ORGANISM: Arabidopsis thaliana

<400> SEQUENCE: 154

cagaccaaca acaaaaagga gataaagaga agaggattca tcatcatcaa tcaatccttc      60

attttatgga tctactcata tcttgattct tccttctatc tctccctttt cttccatctc     120

tttttctctg ggtttccccg atttgaagag cgtgacaaag gaagaatctt ttattaaaac     180

aaattcttct gttttaatct tgggatggcc tcggtgggca tagagcctag tgccgcggtt     240

agagaatcta ctggaaacgt tactgatgct gatagattac ccgaggagat gaaggacatg     300

aaaattcaag atgataaaga aatggaagct acgattgtta atggcaatgt gactgagact     360

ggccatataa tagtaactac tataggagga agaaatggcc agccaaaaca gacaatcagt     420

tacatggcgg agcgagttgt tggacatggc tcctttggtg ttgtgtttca ggccaaatgt     480

ttagaaacag gagaaactgt tgctataaag aaagttctac aagatcggag gtacaagaat     540

cgtgagcttc aaacaatgag gctacttgac catccaaatg ttgtgtcttt gaaacattgt     600

ttcttctcta caaccgaaaa agatgagctt tatctcaact tggttctgga atacgttccg     660

gaaactgtgc accgcgtcat caaacactac aacaaactta accaacgaat gcctctcgtt     720
```

```
tacgtcaaac tttacactta tcagattttt aggtccttat cctacattca ccgatgtatc    780
ggcgtatgtc atcgagacat caaacctcaa aacttgttgg taaatccaca cactcatcaa    840
gtgaaactat gcgattttgg aagtgcgaaa gtattggtta aaggagagcc aaacatttca    900
tacatttgct cgaggtatta cagagcacct gagctcattt ttggagccac cgagtatact    960
acagccattg atgtctggtc tgcaggatgt gttctcgccg agcttcttct cgggcagcca   1020
ttgttcccgg gtgagagcgg tgttgatcaa cttgtagaga ttataaaggt tttgggaaca   1080
ccaacaaggg aagaaatcaa atgcatgaac ccgaattaca cagagttcaa atttcctcag   1140
attaaagctc atccatggca taagattttc cacaagagaa tgcctccaga agctgttgat   1200
ttggtctcaa ggcttcttca atactctccc aatctccgtt gtgctgctct tgattcattg   1260
gtccacccat tctttgacga gctaagagat ccgaatgcgc gattacccaa cggacgtttc   1320
cttccaccgc tctttaactt taagcctcat gaacttaaag gtgtgcctgt ggagatggtg   1380
gcgaagttag ttccagaaca tgcgaggaag caatgtccgt ggctcagttt gtgatttgtt   1440
ctcacctgca aacacgaaaa ctagagcaaa gcagtcgaga tattcatctc ttctcttctc   1500
tctccttctc tgtattaata ttattataat gatcatatct caatctgatg atttagtaac   1560
cctttgtttg ttgtatgagt agagaaagag tgaatcattt gtgggggtta tgatattgta   1620
taagccaaca aagattattt tttaaagaga gtttcgtgtt ttctgtctc               1669
```

```
<210> SEQ ID NO 155
<211> LENGTH: 409
<212> TYPE: PRT
<213> ORGANISM: Arabidopsis thaliana

<400> SEQUENCE: 155

Met Ala Ser Val Gly Ile Glu Pro Ser Ala Ala Val Arg Glu Ser Thr
1               5                   10                  15

Gly Asn Val Thr Asp Ala Asp Arg Leu Pro Glu Glu Met Lys Asp Met
            20                  25                  30

Lys Ile Gln Asp Asp Lys Glu Met Glu Ala Thr Ile Val Asn Gly Asn
        35                  40                  45

Val Thr Glu Thr Gly His Ile Ile Val Thr Thr Ile Gly Gly Arg Asn
    50                  55                  60

Gly Gln Pro Lys Gln Thr Ile Ser Tyr Met Ala Glu Arg Val Val Gly
65                  70                  75                  80

His Gly Ser Phe Gly Val Val Phe Gln Ala Lys Cys Leu Glu Thr Gly
                85                  90                  95

Glu Thr Val Ala Ile Lys Lys Val Leu Gln Asp Arg Arg Tyr Lys Asn
            100                 105                 110

Arg Glu Leu Gln Thr Met Arg Leu Leu Asp His Pro Asn Val Val Ser
        115                 120                 125

Leu Lys His Cys Phe Phe Ser Thr Thr Glu Lys Asp Glu Leu Tyr Leu
    130                 135                 140

Asn Leu Val Leu Glu Tyr Val Pro Glu Thr Val His Arg Val Ile Lys
145                 150                 155                 160

His Tyr Asn Lys Leu Asn Gln Arg Met Pro Leu Val Tyr Val Lys Leu
                165                 170                 175

Tyr Thr Tyr Gln Ile Phe Arg Ser Leu Ser Tyr Ile His Arg Cys Ile
            180                 185                 190

Gly Val Cys His Arg Asp Ile Lys Pro Gln Asn Leu Leu Val Asn Pro
        195                 200                 205
```

-continued

```
His Thr His Gln Val Lys Leu Cys Asp Phe Gly Ser Ala Lys Val Leu
    210                 215                 220

Val Lys Gly Glu Pro Asn Ile Ser Tyr Ile Cys Ser Arg Tyr Tyr Arg
225                 230                 235                 240

Ala Pro Glu Leu Ile Phe Gly Ala Thr Glu Tyr Thr Thr Ala Ile Asp
                245                 250                 255

Val Trp Ser Ala Gly Cys Val Leu Ala Glu Leu Leu Leu Gly Gln Pro
            260                 265                 270

Leu Phe Pro Gly Glu Ser Gly Val Asp Gln Leu Val Glu Ile Ile Lys
        275                 280                 285

Val Leu Gly Thr Pro Thr Arg Glu Glu Ile Lys Cys Met Asn Pro Asn
    290                 295                 300

Tyr Thr Glu Phe Lys Phe Pro Gln Ile Lys Ala His Pro Trp His Lys
305                 310                 315                 320

Ile Phe His Lys Arg Met Pro Pro Glu Ala Val Asp Leu Val Ser Arg
                325                 330                 335

Leu Leu Gln Tyr Ser Pro Asn Leu Arg Cys Ala Ala Leu Asp Ser Leu
            340                 345                 350

Val His Pro Phe Phe Asp Glu Leu Arg Asp Pro Asn Ala Arg Leu Pro
        355                 360                 365

Asn Gly Arg Phe Leu Pro Pro Leu Phe Asn Phe Lys Pro His Glu Leu
    370                 375                 380

Lys Gly Val Pro Val Glu Met Val Ala Lys Leu Val Pro Glu His Ala
385                 390                 395                 400

Arg Lys Gln Cys Pro Trp Leu Ser Leu
                405
```

<210> SEQ ID NO 156
<211> LENGTH: 1496
<212> TYPE: DNA
<213> ORGANISM: Arabidopsis thaliana

<400> SEQUENCE: 156

```
ctcagatcga tgaagagaag aattaggatt tttacgtttt catcggcttg aaagtttgaa      60

gagttttgta gcctgaaaaa tggcgtcagt gggtatagct cctaatcctg gagcaagaga     120

ctctactggt gttgataaat tgcctgaaga aatgaatgac atgaaaattc gtgacgataa     180

agaaatggaa gcgacagtgg tagatggaaa tggaacagag actggacata tcattgtgac     240

tactattggt ggtagaaatg gccaaccaaa acagacaatt agctacatgg ctgagcgtgt     300

tgttggtcac ggatcttttg gtgttgtgtt ccaagcgaaa tgtcttgaga caggagaaac     360

tgttgcgata aagaaagttt tacaagatag gaggtacaag aaccgtgagc ttcaaaccat     420

gaggctactt gaccatccta atgttgtgtc tctgaaacat tgtttcttct caaccactga     480

aaaagatgag ctttacctca atcttgttct tgagtacgtt ccagaaactg ttcatcgtgt     540

tatcaaacac tacaacaaac tgaatcagag aatgcctctt atatacgtca aactttacac     600

ttatcagatt tttagagcct tatcttacat tcaccgatgc attggtgtgt gtcatcgtga     660

cataaaacct caaaacttgt tggtaaatcc gcacactcat caagtaaagc tatgtgattt     720

tggaagtgca aaagtattgg taaaaggaga accaaacatt tcctacatct gctcgaggta     780

ttacagagca cctgaactta tttttggagc aaccgagtat acgacagcca ttgatgtctg     840

gtctgcagga tgtgttctag ctgaactatt gcttggacag cccttgttcc ctggtgagag     900

cggtgttgat caacttgtac acattatcaa ggtcttggga acgcctacta gagaagaaat     960
```

```
caagtgcatg aacccaaact acacggaatt caaattccct cagattaaag ctcatccatg   1020

gcacaagatt ttccacaaac gcatgcctcc agaagctgtt gatttggtct caagacttct   1080

tcaatactct cctaatctac gaagtgccgc tctcgacaca ttagtccacc cattctttga   1140

tgagttaaga gacccaaacg cacgtctacc taatggacgt ttccttccac cggcttttca   1200

cttcaagcct cacgagctga aaggtgtacc attggagatg gtagctaagt tagtacctga   1260

gcatgcaagg aagcagtgtc cttggctcgg tttgtgattt cctcttaatg tagcatgaac   1320

acaacaaaca cttcttataa attacctctc tatgtatcaa tatgtcacaa actgatatgc   1380

accctttgtt tgttgtatga gtagagaaaa aaagagttat tactatggtt ggttggttca   1440

taatgtaaaa gcccaccaag attttttatc tagataaaga gtttgctaaa aaaaaa        1496
```

<210> SEQ ID NO 157
<211> LENGTH: 405
<212> TYPE: PRT
<213> ORGANISM: Arabidopsis thaliana

<400> SEQUENCE: 157

```
Met Ala Ser Val Gly Ile Ala Pro Asn Pro Gly Ala Arg Asp Ser Thr
1               5                   10                  15

Gly Val Asp Lys Leu Pro Glu Glu Met Asn Asp Met Lys Ile Arg Asp
            20                  25                  30

Asp Lys Glu Met Glu Ala Thr Val Val Asp Gly Asn Gly Thr Glu Thr
        35                  40                  45

Gly His Ile Ile Val Thr Thr Ile Gly Gly Arg Asn Gly Gln Pro Lys
    50                  55                  60

Gln Thr Ile Ser Tyr Met Ala Glu Arg Val Val Gly His Gly Ser Phe
65                  70                  75                  80

Gly Val Val Phe Gln Ala Lys Cys Leu Glu Thr Gly Glu Thr Val Ala
                85                  90                  95

Ile Lys Lys Val Leu Gln Asp Arg Arg Tyr Lys Asn Arg Glu Leu Gln
            100                 105                 110

Thr Met Arg Leu Leu Asp His Pro Asn Val Val Ser Leu Lys His Cys
        115                 120                 125

Phe Phe Ser Thr Thr Glu Lys Asp Glu Leu Tyr Leu Asn Leu Val Leu
    130                 135                 140

Glu Tyr Val Pro Glu Thr Val His Arg Val Ile Lys His Tyr Asn Lys
145                 150                 155                 160

Leu Asn Gln Arg Met Pro Leu Ile Tyr Val Lys Leu Tyr Thr Tyr Gln
                165                 170                 175

Ile Phe Arg Ala Leu Ser Tyr Ile His Arg Cys Ile Gly Val Cys His
            180                 185                 190

Arg Asp Ile Lys Pro Gln Asn Leu Leu Val Asn Pro His Thr His Gln
        195                 200                 205

Val Lys Leu Cys Asp Phe Gly Ser Ala Lys Val Leu Val Lys Gly Glu
    210                 215                 220

Pro Asn Ile Ser Tyr Ile Cys Ser Arg Tyr Tyr Arg Ala Pro Glu Leu
225                 230                 235                 240

Ile Phe Gly Ala Thr Glu Tyr Thr Thr Ala Ile Asp Val Trp Ser Ala
                245                 250                 255

Gly Cys Val Leu Ala Glu Leu Leu Leu Gly Gln Pro Leu Phe Pro Gly
            260                 265                 270

Glu Ser Gly Val Asp Gln Leu Val His Ile Ile Lys Val Leu Gly Thr
        275                 280                 285
```

```
Pro Thr Arg Glu Glu Ile Lys Cys Met Asn Pro Asn Tyr Thr Glu Phe
    290                 295                 300

Lys Phe Pro Gln Ile Lys Ala His Pro Trp His Lys Ile Phe His Lys
305                 310                 315                 320

Arg Met Pro Pro Glu Ala Val Asp Leu Val Ser Arg Leu Leu Gln Tyr
                325                 330                 335

Ser Pro Asn Leu Arg Ser Ala Ala Leu Asp Thr Leu Val His Pro Phe
            340                 345                 350

Phe Asp Glu Leu Arg Asp Pro Asn Ala Arg Leu Pro Asn Gly Arg Phe
        355                 360                 365

Leu Pro Pro Ala Phe His Phe Lys Pro His Glu Leu Lys Gly Val Pro
    370                 375                 380

Leu Glu Met Val Ala Lys Leu Val Pro Glu His Ala Arg Lys Gln Cys
385                 390                 395                 400

Pro Trp Leu Gly Leu
                405


<210> SEQ ID NO 158
<211> LENGTH: 1712
<212> TYPE: DNA
<213> ORGANISM: Arabidopsis thaliana

<400> SEQUENCE: 158

attggggtcc gctctctctc tctctctgcc atcagaagaa aaaaccaaac accgagacaa      60

aacacatcac gaagaagaga gagatttgcc attttcggca aggaagtgtt ttattctagg     120

gcttctctag ttgctgcgta gacaagatgg tggagtgaaa ttgcggcggt gacttttcag     180

attgacaaat tgaattaaag atcttgaata catatggctt ctgtgggaac attaccagct     240

tcttctatgg ctacaaaaca aagcaatgct tctatatgcg ctgaaaaatt acctgaaggg     300

attaatgaga tgaagataaa agatgataag gaaatggaag cagctgtggt tgatgggaat     360

ggaactgaaa caggtcacat tattgttaca actattggtg gtaaaaatgg tcagcctaaa     420

cagaccataa gttatatggc agagcgcatc gttggacaag gttcttttgg aatcgttttt     480

caggccaagt gtttagaaac gggggaaact gttgcaatca agaaagtttt gcaagacaag     540

agatacaaga atcgggagct gcagacaatg cgtcttcttg atcaccctaa tgttgtatcc     600

ctcaagcatt gtttttctc aacgactgaa aaagatgagc tctatctcaa tctggtcctt     660

gaatacgttc ctgagactgt ctatcgcgtc tcaaagcact atagtcgggc aaaccagagg     720

atgcccatta tatatgttaa actctatact tatcagattt gcagagcttt ggcttatatt     780

catggtggag taggagtctg ccacagagac ataaaaccac agaatcttct ggttaatcct     840

catacgcatc aggtcaaact atgcgatttt ggtagcgcaa aagttctggt taaaggcgag     900

ccaaacatct catacatctg ctcccgttac tatcgagcac ctgaacttat atttggagct     960

acagaatata caacaacaat tgacatatgg tctgcaggct gtgttcttgc tgaattgctt    1020

ctgggacagc ctctatttcc aggtgagagt ggagttgacc agctagttga gataataaag    1080

gttcttggaa caccaacacg ggaggaaatc aaatgcatga atccaaacta cacagaattc    1140

aaattcccgc aaataaaggc tcatccttgg cacaaaatat tccataagcg tacacctcca    1200

gaagctgtag accttgtctc aagacttctc cagtattctc caaacctcag atcaaccgct    1260

atggaggcga tagttcaccc gttcttcgat gagctacgtg atcccaatac acgtcttcct    1320

aatggtcgtg ccttgcctcc tctcttcaac tttaaacctc aagagctaaa aggagcaagt    1380
```

-continued

```
ttagagttgt tgtccaagct tatacctgac cacgcccgaa aacaatgttc cttcctcgct   1440

ctctaaatct cttcctctct ctctatatat atgtgtgtgt gtgtgtatgt acacatgcat   1500

ataatatgct tatcgtttct aagtaatgga gatagcttct caggattatc attagctttc   1560

atctttcatg tatctttgtt gtttattgtc ttatcacaac ctttgtactt tattacatac   1620

aatgattagt gtaatgtatg tgacggtctt tgactcgccg gtcgctacag ttatgttgga   1680

tactaaatta taaaataaac ttctcgctcg tc                                 1712


<210> SEQ ID NO 159
<211> LENGTH: 410
<212> TYPE: PRT
<213> ORGANISM: Arabidopsis thaliana

<400> SEQUENCE: 159

Met Ala Ser Val Gly Thr Leu Pro Ala Ser Ser Met Ala Thr Lys Gln
1               5                   10                  15

Ser Asn Ala Ser Ile Cys Ala Glu Lys Leu Pro Glu Gly Ile Asn Glu
            20                  25                  30

Met Lys Ile Lys Asp Asp Lys Glu Met Glu Ala Ala Val Val Asp Gly
        35                  40                  45

Asn Gly Thr Glu Thr Gly His Ile Ile Val Thr Thr Ile Gly Gly Lys
    50                  55                  60

Asn Gly Gln Pro Lys Gln Thr Ile Ser Tyr Met Ala Glu Arg Ile Val
65                  70                  75                  80

Gly Gln Gly Ser Phe Gly Ile Val Phe Gln Ala Lys Cys Leu Glu Thr
                85                  90                  95

Gly Glu Thr Val Ala Ile Lys Lys Val Leu Gln Asp Lys Arg Tyr Lys
            100                 105                 110

Asn Arg Glu Leu Gln Thr Met Arg Leu Leu Asp His Pro Asn Val Val
        115                 120                 125

Ser Leu Lys His Cys Phe Phe Ser Thr Thr Glu Lys Asp Glu Leu Tyr
    130                 135                 140

Leu Asn Leu Val Leu Glu Tyr Val Pro Glu Thr Val Tyr Arg Val Ser
145                 150                 155                 160

Lys His Tyr Ser Arg Ala Asn Gln Arg Met Pro Ile Ile Tyr Val Lys
                165                 170                 175

Leu Tyr Thr Tyr Gln Ile Cys Arg Ala Leu Ala Tyr Ile His Gly Gly
            180                 185                 190

Val Gly Val Cys His Arg Asp Ile Lys Pro Gln Asn Leu Leu Val Asn
        195                 200                 205

Pro His Thr His Gln Val Lys Leu Cys Asp Phe Gly Ser Ala Lys Val
    210                 215                 220

Leu Val Lys Gly Glu Pro Asn Ile Ser Tyr Ile Cys Ser Arg Tyr Tyr
225                 230                 235                 240

Arg Ala Pro Glu Leu Ile Phe Gly Ala Thr Glu Tyr Thr Thr Thr Ile
                245                 250                 255

Asp Ile Trp Ser Ala Gly Cys Val Leu Ala Glu Leu Leu Leu Gly Gln
            260                 265                 270

Pro Leu Phe Pro Gly Glu Ser Gly Val Asp Gln Leu Val Glu Ile Ile
        275                 280                 285

Lys Val Leu Gly Thr Pro Thr Arg Glu Glu Ile Lys Cys Met Asn Pro
    290                 295                 300

Asn Tyr Thr Glu Phe Lys Phe Pro Gln Ile Lys Ala His Pro Trp His
305                 310                 315                 320
```

```
Lys Ile Phe His Lys Arg Thr Pro Pro Glu Ala Val Asp Leu Val Ser
                325                 330                 335

Arg Leu Leu Gln Tyr Ser Pro Asn Leu Arg Ser Thr Ala Met Glu Ala
            340                 345                 350

Ile Val His Pro Phe Phe Asp Glu Leu Arg Asp Pro Asn Thr Arg Leu
        355                 360                 365

Pro Asn Gly Arg Ala Leu Pro Pro Leu Phe Asn Phe Lys Pro Gln Glu
    370                 375                 380

Leu Lys Gly Ala Ser Leu Glu Leu Leu Ser Lys Leu Ile Pro Asp His
385                 390                 395                 400

Ala Arg Lys Gln Cys Ser Phe Leu Ala Leu
                405                 410


<210> SEQ ID NO 160
<211> LENGTH: 1230
<212> TYPE: DNA
<213> ORGANISM: Arabidopsis thaliana

<400> SEQUENCE: 160

atggcctcgg tgggcataga gcctagtgcc gcggttagag aatctactgg aaacgttact      60

gatgctgata gattacccga ggagatgaag gacatgaaaa ttcaagatga taaagaaatg     120

gaagctacga ttgttaatgg caatgtgact gagactggcc atataatagt aactactata     180

ggaggaagaa atggccagcc aaaacagaca atcagttaca tggcggagcg agttgttgga     240

catggctcct ttggtgttgt gtttcaggcc aaatgtttag aaacaggaga aactgttgct     300

ataaagaaag ttctacaaga tcggaggtac aagaatcgtg agcttcaaac aatgaggcta     360

cttgaccatc caaatgttgt gtctttgaaa cattgtttct tctctacaac cgaaaaagat     420

gagctttatc tcaacttggt tctggaatac gttccggaaa ctgtgcaccg cgtcatcaaa     480

cactacaaca aacttaacca acgaatgcct ctcgtttacg tcaaacttta cacttatcag     540

atttttaggt ccttatccta cattcaccga tgtatcggcg tatgtcatcg agacatcaaa     600

cctcaaaact tgttggtaaa tccacacact catcaagtga aactatgcga ttttggaagt     660

gcgaaagtat tggttaaagg agagccaaac atttcataca tttgctcgag gtattacaga     720

gcacctgagc tcatttttgg agccaccgag tatactacag ccattgatgt ctggtctgca     780

ggatgtgttc tcgccgagct tcttctcggg cagccattgt tcccgggtga gagcggtgtt     840

gatcaacttg tagagattat aaaggttttg ggaacaccaa caagggaaga aatcaaatgc     900

atgaacccga attacacaga gttcaaattt cctcagatta aagctcatcc atggcataag     960

attttccaca agagaatgcc tccagaagct gttgatttgg tctcaaggct tcttcaatac    1020

tctcccaatc tccgttgtgc tgctcttgat tcattggtcc acccattctt tgacgagcta    1080

agagatccga atgcgcgatt acccaacgga cgtttccttc caccgctctt taactttaag    1140

cctcatgaac ttaaaggtgt gcctgtggag atggtggcga agttagttcc agaacatgcg    1200

aggaagcaat gtccgtggct cagtttatga                                     1230


<210> SEQ ID NO 161
<211> LENGTH: 409
<212> TYPE: PRT
<213> ORGANISM: Arabidopsis thaliana

<400> SEQUENCE: 161

Met Ala Ser Val Gly Ile Glu Pro Ser Ala Ala Val Arg Glu Ser Thr
1               5                   10                  15
```

```
Gly Asn Val Thr Asp Ala Asp Arg Leu Pro Glu Glu Met Lys Asp Met
            20                  25                  30

Lys Ile Gln Asp Asp Lys Glu Met Glu Ala Thr Ile Val Asn Gly Asn
        35                  40                  45

Val Thr Glu Thr Gly His Ile Ile Val Thr Thr Ile Gly Gly Arg Asn
    50                  55                  60

Gly Gln Pro Lys Gln Thr Ile Ser Tyr Met Ala Glu Arg Val Val Gly
65                  70                  75                  80

His Gly Ser Phe Gly Val Val Phe Gln Ala Lys Cys Leu Glu Thr Gly
                85                  90                  95

Glu Thr Val Ala Ile Lys Lys Val Leu Gln Asp Arg Arg Tyr Lys Asn
            100                 105                 110

Arg Glu Leu Gln Thr Met Arg Leu Leu Asp His Pro Asn Val Val Ser
        115                 120                 125

Leu Lys His Cys Phe Phe Ser Thr Thr Glu Lys Asp Glu Leu Tyr Leu
    130                 135                 140

Asn Leu Val Leu Glu Tyr Val Pro Glu Thr Val His Arg Val Ile Lys
145                 150                 155                 160

His Tyr Asn Lys Leu Asn Gln Arg Met Pro Leu Val Tyr Val Lys Leu
                165                 170                 175

Tyr Thr Tyr Gln Ile Phe Arg Ser Leu Ser Tyr Ile His Arg Cys Ile
            180                 185                 190

Gly Val Cys His Arg Asp Ile Lys Pro Gln Asn Leu Leu Val Asn Pro
        195                 200                 205

His Thr His Gln Val Lys Leu Cys Asp Phe Gly Ser Ala Lys Val Leu
    210                 215                 220

Val Lys Gly Glu Pro Asn Ile Ser Tyr Ile Cys Ser Arg Tyr Tyr Arg
225                 230                 235                 240

Ala Pro Glu Leu Ile Phe Gly Ala Thr Glu Tyr Thr Thr Ala Ile Asp
                245                 250                 255

Val Trp Ser Ala Gly Cys Val Leu Ala Glu Leu Leu Leu Gly Gln Pro
            260                 265                 270

Leu Phe Pro Gly Glu Ser Gly Val Asp Gln Leu Val Glu Ile Ile Lys
        275                 280                 285

Val Leu Gly Thr Pro Thr Arg Glu Glu Ile Lys Cys Met Asn Pro Asn
    290                 295                 300

Tyr Thr Glu Phe Lys Phe Pro Gln Ile Lys Ala His Pro Trp His Lys
305                 310                 315                 320

Ile Phe His Lys Arg Met Pro Pro Glu Ala Val Asp Leu Val Ser Arg
                325                 330                 335

Leu Leu Gln Tyr Ser Pro Asn Leu Arg Cys Ala Ala Leu Asp Ser Leu
            340                 345                 350

Val His Pro Phe Phe Asp Glu Leu Arg Asp Pro Asn Ala Arg Leu Pro
        355                 360                 365

Asn Gly Arg Phe Leu Pro Pro Leu Phe Asn Phe Lys Pro His Glu Leu
    370                 375                 380

Lys Gly Val Pro Val Glu Met Val Ala Lys Leu Val Pro Glu His Ala
385                 390                 395                 400

Arg Lys Gln Cys Pro Trp Leu Ser Leu
                405
```

<210> SEQ ID NO 162
<211> LENGTH: 1967

<212> TYPE: DNA
<213> ORGANISM: Zea mays

<400> SEQUENCE: 162
ttgactgcag gcctcggcac ggtaggcaca aatcattttg gccgctgcgt cgcgttggga 60
gcagtattct actgtgcctg cgtcccgaca agcgaaaaga agagacgggg gagggtggga 120
gaacggatac cgaaaggggt aggagagtga gcagccagag aacagggagg tagagaggag 180
gaggaggtag aaggcgaaag aaggggaacc aaatcttgga cgggaacaca tagatttctt 240
tggtggagga aggaggaggg caacaagagg aggttacagg tagcccaata gatctactgc 300
tgttgaggga gttgatgcaa agctgagttg ctgcgcgttg gctttcttta gagatggctt 360
cagctggtgt tgccccttct gggtacaaga acagcagcag caccagcatt ggtgccgaaa 420
agttgcaaga tcacatgaac gagctaaaga ttagagatga taaggaagtt gaagcaacca 480
taattaatgg gaaagggact gaaactgggc acataattgt caccactact ggtggcaaga 540
atggtcaacc aaaacagaca gtgagctaca tggctgagcg cattgtaggt caaggttctt 600
ttgggatcgt cttccaggcc aagtgtttgg aaacgggtga gactgttgcc ataaagaagg 660
ttcttcaaga caagcgttac aagaaccgcg aactgcagac catgcgcctt cttgaccacc 720
ctaatgttgt tgctttgaag cattgcttct tttcaactac tgagaaggat gagctttatc 780
tgaacttggt ccttgagtat gttccggaga cagttcatcg agttgtgaaa catcacaaca 840
agatgcacca acgcatgcca cttatttatg tgaagcttta tatgtaccag atatgtagag 900
cattggctta cattcatggt actatcggtg tctgccacag agatattaag ccacaaaatc 960
ttctggtgaa cccacacacc caccagctta aaatatgtga ctttggtagt gcaaaagttc 1020
tggtcaaggg ggaaccaaac atatcataca tctgctcgcg atactatagg gctccagagc 1080
tcatatttgg tgccactgag tataccacag cgattgacat ttggtctgct ggatgtgttc 1140
ttgctgagct tatgctaggg cagcctttgt ttccgggtga aagtggtgtg gaccaacttg 1200
ttgaaatcat caaggtcctc ggtacgccaa caagggaaga aattaaatgc atgaacccaa 1260
attacacaga gtttaagttc ccacaaatca aagcacaccc atggcacaag gtattccaca 1320
aaaggatgcc gccagaagct gttgatctgg tctctcggct actccagtac tccccaaatc 1380
tgagatgcac tgctatggag gcacttgttc acccattctt tgatgagctt cgagatccta 1440
atactcgcct tccaaatggt cgctttttgc caccactatt caatttcaag cctcacgaac 1500
ttaaaggagt cccatcagac attgttgcga aattggttcc agaacatgcg aagaagcaat 1560
gctcttatgt tggattgtga aatgaccgcg ccttgggact ggaacctgag gtcgcaatcg 1620
tgcatttccc ctgggatgtt ggatgatctt gaggcatgcg agcctgttgt tgaagatgca 1680
aggttacgta cttgtacgac aatgtgacct gtgtagctga gtagtctatg tcgcagtgac 1740
atgtaacggc accccccttc ctactaactg acgcttactc gagattgcca tagttgatct 1800
tgtaatttgt tatagagcag tatgaatgta tttatggtag cttgaatcta tgtatggatt 1860
cacttcgttt ttccatgttt ccttgtctcc agacccagat tgctaccgta ttgtttcaga 1920
attcctagct acctgttgcc taaaaaaaaa aaaaaaaaac ctcgtgc 1967

<210> SEQ ID NO 163
<211> LENGTH: 408
<212> TYPE: PRT
<213> ORGANISM: Zea mays

<400> SEQUENCE: 163

-continued

```
Met Ala Ser Ala Gly Val Ala Pro Ser Gly Tyr Lys Asn Ser Ser Ser
1               5                   10                  15

Thr Ser Ile Gly Ala Glu Lys Leu Gln Asp His Met Asn Glu Leu Lys
            20                  25                  30

Ile Arg Asp Asp Lys Glu Val Glu Ala Thr Ile Ile Asn Gly Lys Gly
        35                  40                  45

Thr Glu Thr Gly His Ile Ile Val Thr Thr Thr Gly Gly Lys Asn Gly
    50                  55                  60

Gln Pro Lys Gln Thr Val Ser Tyr Met Ala Glu Arg Ile Val Gly Gln
65                  70                  75                  80

Gly Ser Phe Gly Ile Val Phe Gln Ala Lys Cys Leu Glu Thr Gly Glu
                85                  90                  95

Thr Val Ala Ile Lys Lys Val Leu Gln Asp Lys Arg Tyr Lys Asn Arg
            100                 105                 110

Glu Leu Gln Thr Met Arg Leu Leu Asp His Pro Asn Val Val Ala Leu
        115                 120                 125

Lys His Cys Phe Phe Ser Thr Thr Glu Lys Asp Glu Leu Tyr Leu Asn
    130                 135                 140

Leu Val Leu Glu Tyr Val Pro Glu Thr Val His Arg Val Val Lys His
145                 150                 155                 160

His Asn Lys Met His Gln Arg Met Pro Leu Ile Tyr Val Lys Leu Tyr
                165                 170                 175

Met Tyr Gln Ile Cys Arg Ala Leu Ala Tyr Ile His Gly Thr Ile Gly
            180                 185                 190

Val Cys His Arg Asp Ile Lys Pro Gln Asn Leu Leu Val Asn Pro His
        195                 200                 205

Thr His Gln Leu Lys Ile Cys Asp Phe Gly Ser Ala Lys Val Leu Val
    210                 215                 220

Lys Gly Glu Pro Asn Ile Ser Tyr Ile Cys Ser Arg Tyr Tyr Arg Ala
225                 230                 235                 240

Pro Glu Leu Ile Phe Gly Ala Thr Glu Tyr Thr Thr Ala Ile Asp Ile
                245                 250                 255

Trp Ser Ala Gly Cys Val Leu Ala Glu Leu Met Leu Gly Gln Pro Leu
            260                 265                 270

Phe Pro Gly Glu Ser Gly Val Asp Gln Leu Val Glu Ile Ile Lys Val
        275                 280                 285

Leu Gly Thr Pro Thr Arg Glu Glu Ile Lys Cys Met Asn Pro Asn Tyr
    290                 295                 300

Thr Glu Phe Lys Phe Pro Gln Ile Lys Ala His Pro Trp His Lys Val
305                 310                 315                 320

Phe His Lys Arg Met Pro Pro Glu Ala Val Asp Leu Val Ser Arg Leu
                325                 330                 335

Leu Gln Tyr Ser Pro Asn Leu Arg Cys Thr Ala Met Glu Ala Leu Val
            340                 345                 350

His Pro Phe Phe Asp Glu Leu Arg Asp Pro Asn Thr Arg Leu Pro Asn
        355                 360                 365

Gly Arg Phe Leu Pro Pro Leu Phe Asn Phe Lys Pro His Glu Leu Lys
    370                 375                 380

Gly Val Pro Ser Asp Ile Val Ala Lys Leu Val Pro Glu His Ala Lys
385                 390                 395                 400

Lys Gln Cys Ser Tyr Val Gly Leu
                405
```

<210> SEQ ID NO 164
<211> LENGTH: 1752
<212> TYPE: DNA
<213> ORGANISM: Zea mays

<400> SEQUENCE: 164
gcacgagccg cgccggagtt ggaggaggga gaggggacaa gctttccggc gccgacgccg 60
acgcggaccc ggcgccgaca cgatccggtg gatcaagtgc atcacacctt tagggaggcc 120
ccttggacag cagtttgtgc tgcaaattct atatagctct gtcgcagcat ggcctcggtg 180
ggcgtggcac gctcttcttt gggatttcag aatggcacaa gttctagcag tgacccagat 240
cgtcttccca acgagttggg cagtatgagc ataagggacg acaaggacgt tgaagatatt 300
gtagtcaatg gcaatggggc ggagcctggt catatcatag tgaccagcat tgatgggaga 360
aatgggcagg caaagcagac cattagttac atggctgagc gggtggtagg tcatgggtcc 420
ttcggaaccg ttttccaggc caagtgtctt gaaactggtg agaccgtagc tataaaaaag 480
gttcttcaag acaagagata caagaatcgt gagctgcaaa ccatgcgagt gcttgaccac 540
ccaaatgtgg tggctctaaa gcactgtttc ttctcaaaga ctgagaaaga ggagctttac 600
ctcaatttgg tgcttgagta tgtaccggag actgctcatc gtgtcatcaa acattacaac 660
aagatgaacc agcgcatgcc tttgatttat gcaaaactgt atatgtatca gatttgtaga 720
gccttggcat acattcacaa cagcattgga gtgtgccaca gggacattaa gccgcaaaat 780
ctcctggtta atcctcatac ccatcagcta aaattgtgtg actttggcag cgcgaaagtt 840
ctggtaaaag gcgaaccaaa catttcttac atctgttcta ggtactacag agctccagag 900
ctcatatttg gtgctactga atacacaaca gccattgatg tttggtctgc tggctgtgtg 960
ctcgctgagc tgcttctagg acagcctctg ttccctggag aaagcggtgt tgatcagctt 1020
gttgaaatca tcaaggttct gggcacaccc acacgtgaag aaattaagtg catgaatcca 1080
aattataccg agtttaaatt cccgcaaatc aaagctcacc catggcataa gatattccat 1140
aaaaggatgc ctgctgaagc ggtagatctc gtgtccaggc ttctgcagta ctcaccaaaa 1200
cttcggtcga ctgctttgga agcattggtc catccgttct ttgatgaact tcgggatcca 1260
aacacccgct taccgaatgg tcgttttctt ccgcctctct tcaattttaa gccccatgag 1320
ctgaagaacg tgccggcgga tttcatggtg aaattggtcc ctgagcatgc acggaagcaa 1380
tgtgccttcg tagggtggtg atctctggat aagaggatga cgactcgatg attagctgag 1440
gaccaagtta atgtctgtta gaaactgccg gagatcgaca ttgccagatg tggtgtggta 1500
taagataggc aatatgtgtg attatttttt gttcgaggtt atcacccccc ttgccccaga 1560
aaagatgaga agatgtcgat gtaacaagcc ctctgcgctt ctgtaagtag atgagtgttg 1620
ctgcatgccc cctgggtaca tgtatcggtt tgagcagaat tctgtttgcc tgaatcgtgc 1680
catcaccacg cagggatcca tcccttgtgt gacgatgttc agcccaaaaa aaaaaaaaaa 1740
aaaaaaaaaa aa 1752

<210> SEQ ID NO 165
<211> LENGTH: 410
<212> TYPE: PRT
<213> ORGANISM: Zea mays

<400> SEQUENCE: 165

Met Ala Ser Val Gly Val Ala Arg Ser Ser Leu Gly Phe Gln Asn Gly
1               5                   10                  15

Thr Ser Ser Ser Ser Asp Pro Asp Arg Leu Pro Asn Glu Leu Gly Ser

```
            20                  25                  30

Met Ser Ile Arg Asp Asp Lys Asp Val Glu Asp Ile Val Val Asn Gly
        35                  40                  45

Asn Gly Ala Glu Pro Gly His Ile Ile Val Thr Ser Ile Asp Gly Arg
    50                  55                  60

Asn Gly Gln Ala Lys Gln Thr Ile Ser Tyr Met Ala Glu Arg Val Val
65                  70                  75                  80

Gly His Gly Ser Phe Gly Thr Val Phe Gln Ala Lys Cys Leu Glu Thr
                85                  90                  95

Gly Glu Thr Val Ala Ile Lys Lys Val Leu Gln Asp Lys Arg Tyr Lys
            100                 105                 110

Asn Arg Glu Leu Gln Thr Met Arg Val Leu Asp His Pro Asn Val Val
        115                 120                 125

Ala Leu Lys His Cys Phe Phe Ser Lys Thr Glu Lys Glu Glu Leu Tyr
    130                 135                 140

Leu Asn Leu Val Leu Glu Tyr Val Pro Glu Thr Ala His Arg Val Ile
145                 150                 155                 160

Lys His Tyr Asn Lys Met Asn Gln Arg Met Pro Leu Ile Tyr Ala Lys
                165                 170                 175

Leu Tyr Met Tyr Gln Ile Cys Arg Ala Leu Ala Tyr Ile His Asn Ser
            180                 185                 190

Ile Gly Val Cys His Arg Asp Ile Lys Pro Gln Asn Leu Leu Val Asn
        195                 200                 205

Pro His Thr His Gln Leu Lys Leu Cys Asp Phe Gly Ser Ala Lys Val
    210                 215                 220

Leu Val Lys Gly Glu Pro Asn Ile Ser Tyr Ile Cys Ser Arg Tyr Tyr
225                 230                 235                 240

Arg Ala Pro Glu Leu Ile Phe Gly Ala Thr Glu Tyr Thr Thr Ala Ile
                245                 250                 255

Asp Val Trp Ser Ala Gly Cys Val Leu Ala Glu Leu Leu Leu Gly Gln
            260                 265                 270

Pro Leu Phe Pro Gly Glu Ser Gly Val Asp Gln Leu Val Glu Ile Ile
        275                 280                 285

Lys Val Leu Gly Thr Pro Thr Arg Glu Glu Ile Lys Cys Met Asn Pro
    290                 295                 300

Asn Tyr Thr Glu Phe Lys Phe Pro Gln Ile Lys Ala His Pro Trp His
305                 310                 315                 320

Lys Ile Phe His Lys Arg Met Pro Ala Glu Ala Val Asp Leu Val Ser
                325                 330                 335

Arg Leu Leu Gln Tyr Ser Pro Lys Leu Arg Ser Thr Ala Leu Glu Ala
            340                 345                 350

Leu Val His Pro Phe Phe Asp Glu Leu Arg Asp Pro Asn Thr Arg Leu
        355                 360                 365

Pro Asn Gly Arg Phe Leu Pro Pro Leu Phe Asn Phe Lys Pro His Glu
    370                 375                 380

Leu Lys Asn Val Pro Ala Asp Phe Met Val Lys Leu Val Pro Glu His
385                 390                 395                 400

Ala Arg Lys Gln Cys Ala Phe Val Gly Trp
                405                 410
```

<210> SEQ ID NO 166
<211> LENGTH: 1800
<212> TYPE: DNA
<213> ORGANISM: Medicago sativa

<400> SEQUENCE: 166

```
tttttttttt tttttttttt tcaaaatatt ttccatttgt ctcttctttc ttctttccta     60
attccgaatc ccacggattt cacttccatt caaagtcata gctagatcca atccattcca    120
ttcctctgtt tgagttgaag agttgatttg ggggttggat gttcagtttt gaagctgtgt    180
atgatctgaa aggaaataat taagtaaagt gttttgcact tttttaaga agatatgatg    240
gcatcaggtg gtgttgcacc tgcttctgga tttatagata agaatgcaag ttcagttggt    300
gttgaaaagt tgcctgagga gatgaatgac atgaaaatta gggatgataa ggaaatggaa    360
gccgctacca ttgtagatgg aaatgggacc gaaaccggac atataattgt cacaaccatt    420
ggtggtaaaa atggccagcc aaagcagaca ataagttaca tggccgagcg tgttgttgga    480
catggatctt ttggtgtagt ttttcaggca aagtgtttgg agactggaga aactgtggct    540
ataaagaagg ttcttcaaga taagaggtac aagaaccggg aattgcaaac tatgcgcctt    600
ctggaccacc ctaatgttgt atctttgaag cactgcttct tctcaacgac tgaaaaggac    660
gagctttatc ttaacctggt gcttgaatat gttcctgaga ctgtcagccg tgtgattaga    720
cactacaaca aaatgaatca aagaatgcct atgatatatg tcaaacttta ttcttaccag    780
atttgcaggg cacttgctta tattcacaac agtattggag tatgtcacag ggatattaaa    840
cctcaaaatt tactggtcaa tcctcacacc caccaactga agatatgcga ctttggaagt    900
gctaaagtct tggtaaaagg tgaaccaaac atatcttaca tctgttctag gtactataga    960
gctcctgagc ttatattcgg tgcaactgag tacaccacag ccattgacat ctggtcagct   1020
ggttgcgtac ttggtgaact tttgcttggc cagccactgt ttcctggtga gagtggagta   1080
gaccaacttg tggaaattat caaggtttta ggcaccccaa caagggaaga aatcaagtgc   1140
atgaatccta attatacaga gtttaaattt cctcaaatca aagctcatcc atggcataag   1200
atttttcaca agagaatgcc tcctgaagct gtggatcttg tctcaagact attgcaatac   1260
tctccaaatc ttcgaagcac agctttggag gctttggttc atccattcta tgatgacgtg   1320
cgcgatccaa acactcggtt gccaaatggg cgtttccttc caccattatt taacttcaaa   1380
gtcaatgagc tcaagggagt acctgcagag atgctggtga aactggttcc acctcatgca   1440
agaaagcaat gtgccttgtt cgggtcatca tgaagcagcc ttgtgtagtt attaagtact   1500
ttcttctacc tatgtaaagg tgtatctagt caaatttcaa gtggttaaat aggttatttc   1560
tattttcttt ctgtttgatt tgttctcacc caacctacca tccaatttat tattattttt   1620
cttcctcgat gtagaagaaa gctgtgctgt ttaagaagca acttcagctt gattattact   1680
ttgtaggatc tgatgtgttc actcacctta acatgaacca ttgtttattg aagtgataga   1740
cttgatcaca acctcactga actagtagga gatgtttcaa atcttgaaaa aaaaaaaaaa   1800
```

<210> SEQ ID NO 167
<211> LENGTH: 412
<212> TYPE: PRT
<213> ORGANISM: Medicago sativa

<400> SEQUENCE: 167

```
Met Met Ala Ser Gly Gly Val Ala Pro Ala Ser Gly Phe Ile Asp Lys
1               5                   10                  15

Asn Ala Ser Ser Val Gly Val Glu Lys Leu Pro Glu Glu Met Asn Asp
            20                  25                  30

Met Lys Ile Arg Asp Asp Lys Glu Met Glu Ala Ala Thr Ile Val Asp
        35                  40                  45
```

```
Gly Asn Gly Thr Glu Thr Gly His Ile Ile Val Thr Thr Ile Gly Gly
    50                  55                  60

Lys Asn Gly Gln Pro Lys Gln Thr Ile Ser Tyr Met Ala Glu Arg Val
65                  70                  75                  80

Val Gly His Gly Ser Phe Gly Val Val Phe Gln Ala Lys Cys Leu Glu
                85                  90                  95

Thr Gly Glu Thr Val Ala Ile Lys Lys Val Leu Gln Asp Lys Arg Tyr
            100                 105                 110

Lys Asn Arg Glu Leu Gln Thr Met Arg Leu Leu Asp His Pro Asn Val
        115                 120                 125

Val Ser Leu Lys His Cys Phe Phe Ser Thr Thr Glu Lys Asp Glu Leu
    130                 135                 140

Tyr Leu Asn Leu Val Leu Glu Tyr Val Pro Glu Thr Val Ser Arg Val
145                 150                 155                 160

Ile Arg His Tyr Asn Lys Met Asn Gln Arg Met Pro Met Ile Tyr Val
                165                 170                 175

Lys Leu Tyr Ser Tyr Gln Ile Cys Arg Ala Leu Ala Tyr Ile His Asn
            180                 185                 190

Ser Ile Gly Val Cys His Arg Asp Ile Lys Pro Gln Asn Leu Leu Val
        195                 200                 205

Asn Pro His Thr His Gln Leu Lys Ile Cys Asp Phe Gly Ser Ala Lys
    210                 215                 220

Val Leu Val Lys Gly Glu Pro Asn Ile Ser Tyr Ile Cys Ser Arg Tyr
225                 230                 235                 240

Tyr Arg Ala Pro Glu Leu Ile Phe Gly Ala Thr Glu Tyr Thr Thr Ala
                245                 250                 255

Ile Asp Ile Trp Ser Ala Gly Cys Val Leu Gly Glu Leu Leu Leu Gly
            260                 265                 270

Gln Pro Leu Phe Pro Gly Glu Ser Gly Val Asp Gln Leu Val Glu Ile
        275                 280                 285

Ile Lys Val Leu Gly Thr Pro Thr Arg Glu Glu Ile Lys Cys Met Asn
    290                 295                 300

Pro Asn Tyr Thr Glu Phe Lys Phe Pro Gln Ile Lys Ala His Pro Trp
305                 310                 315                 320

His Lys Ile Phe His Lys Arg Met Pro Pro Glu Ala Val Asp Leu Val
                325                 330                 335

Ser Arg Leu Leu Gln Tyr Ser Pro Asn Leu Arg Ser Thr Ala Leu Glu
            340                 345                 350

Ala Leu Val His Pro Phe Tyr Asp Asp Val Arg Asp Pro Asn Thr Arg
        355                 360                 365

Leu Pro Asn Gly Arg Phe Leu Pro Pro Leu Phe Asn Phe Lys Val Asn
    370                 375                 380

Glu Leu Lys Gly Val Pro Ala Glu Met Leu Val Lys Leu Val Pro Pro
385                 390                 395                 400

His Ala Arg Lys Gln Cys Ala Leu Phe Gly Ser Ser
                405                 410
```

<210> SEQ ID NO 168
<211> LENGTH: 1613
<212> TYPE: DNA
<213> ORGANISM: Medicago sativa

<400> SEQUENCE: 168

```
gagcacatgc tttggtttcg tttcgttggt ggatgagtgg ttaaaattga aagggtttca     60
```

-continued

```
gtggcaatgg cgtcggttgg tgttgcacca acttcaggtt ttagagaagt ccttggtgat    120
ggtgaaattg gtgttgatga tatattgcca gaggaaatga gtgatatgaa aattagggat    180
gatagagaaa tggaagccac cgttgttgac ggcaatggaa cggagacagg acatatcatt    240
gtcactacta ttggtggtag aaatggtcag ccaaagcaga ctataagcta tatggcagag    300
cgtgttgtag gacatggatc atttggagtt gtcttccagg ctaagtgctt ggaaactggt    360
gaaaccgtgg ctatcaaaaa ggttcttcaa gacaagaggt acaagaaccg ggaattgcaa    420
acaatgcgac tgcttgatca cccgaatgtc gtctctttaa agcattgttt cttttcaacc    480
accgaaaagg atgaactata cctgaatttg gtacttgagt atgttcctga aacagttcat    540
cgcgtgatta agcattacag caagttgaac caaaggatgc caatgattta tgtgaagctc    600
tatacatacc agatctttag agcattatct tatattcatc gttgcattgg agtctgtcat    660
cgggatatca agccccaaaa tctattggtc aatccacaca cccaccaggt taaattatgc    720
gactttggaa gtgcgaaagt cttggttaaa ggcgaaccaa atatatcgta tatatgttct    780
agatactaca gagcacccga gcttattttt ggagcaactg aatatactac tgctattgat    840
gtatggtctg ttggttgtgt tttggctgag ctgctgcttg gacagccatt gttcccaggt    900
gagagaggag ttgatcagct tgttgagatc atcaaggttc tgggaactcc gacaagagaa    960
gaaattaaat gcatgaatcc taattatacc gaatttaaat tccctcaaat caaagcacat   1020
ccatggcaca agatcttcca taagcgcatg cctgcagaag ctgttgattt ggtatcaaga   1080
ttattacaat actccccaaa cctgcggtgc caagctttag attgcttgac ccatcctttc   1140
ttcgatgagc ttcgtgaccc aaatgctcgc ttgccaactg gccgtttcct cccaccactg   1200
tttaacttca aacctcacga actgaaagga gttccagtcg agaccttgat gaaactggtt   1260
ccagagcatg cgaggaagca atgcccgttt cttggcttgt aatatgtcgt aaaatgtaac   1320
aaaactgcaa gtgttgtttc catatgaacg ttctatttga tgatatgata tttattagta   1380
tctttgttgt attcggttgc ctgtgataga aaatttagag atatatgcta cccaatatta   1440
cccaaaccct tatatgggta ttcagaatac cctttttcctg tatcacagca gattgtaaca   1500
tgcaatagaa gacaagtgtc tacaattatc taaatgttgt atcagtattt gtacttgtat   1560
ttgtatttgt ggagataatg acggattatt gcgtaaaaaa aaaaaaaaaa aaa          1613
```

<210> SEQ ID NO 169
<211> LENGTH: 411
<212> TYPE: PRT
<213> ORGANISM: Medicago sativa

<400> SEQUENCE: 169

```
Met Ala Ser Val Gly Val Ala Pro Thr Ser Gly Phe Arg Glu Val Leu
1               5                   10                  15

Gly Asp Gly Glu Ile Gly Val Asp Asp Ile Leu Pro Glu Glu Met Ser
            20                  25                  30

Asp Met Lys Ile Arg Asp Asp Arg Glu Met Glu Ala Thr Val Val Asp
        35                  40                  45

Gly Asn Gly Thr Glu Thr Gly His Ile Ile Val Thr Thr Ile Gly Gly
    50                  55                  60

Arg Asn Gly Gln Pro Lys Gln Thr Ile Ser Tyr Met Ala Glu Arg Val
65                  70                  75                  80

Val Gly His Gly Ser Phe Gly Val Val Phe Gln Ala Lys Cys Leu Glu
                85                  90                  95
```

-continued

```
Thr Gly Glu Thr Val Ala Ile Lys Lys Val Leu Gln Asp Lys Arg Tyr
            100                 105                 110

Lys Asn Arg Glu Leu Gln Thr Met Arg Leu Leu Asp His Pro Asn Val
        115                 120                 125

Val Ser Leu Lys His Cys Phe Phe Ser Thr Thr Glu Lys Asp Glu Leu
    130                 135                 140

Tyr Leu Asn Leu Val Leu Glu Tyr Val Pro Glu Thr Val His Arg Val
145                 150                 155                 160

Ile Lys His Tyr Ser Lys Leu Asn Gln Arg Met Pro Met Ile Tyr Val
                165                 170                 175

Lys Leu Tyr Thr Tyr Gln Ile Phe Arg Ala Leu Ser Tyr Ile His Arg
            180                 185                 190

Cys Ile Gly Val Cys His Arg Asp Ile Lys Pro Gln Asn Leu Leu Val
        195                 200                 205

Asn Pro His Thr His Gln Val Lys Leu Cys Asp Phe Gly Ser Ala Lys
    210                 215                 220

Val Leu Val Lys Gly Glu Pro Asn Ile Ser Tyr Ile Cys Ser Arg Tyr
225                 230                 235                 240

Tyr Arg Ala Pro Glu Leu Ile Phe Gly Ala Thr Glu Tyr Thr Thr Ala
                245                 250                 255

Ile Asp Val Trp Ser Val Gly Cys Val Leu Ala Glu Leu Leu Leu Gly
            260                 265                 270

Gln Pro Leu Phe Pro Gly Glu Arg Gly Val Asp Gln Leu Val Glu Ile
        275                 280                 285

Ile Lys Val Leu Gly Thr Pro Thr Arg Glu Glu Ile Lys Cys Met Asn
    290                 295                 300

Pro Asn Tyr Thr Glu Phe Lys Phe Pro Gln Ile Lys Ala His Pro Trp
305                 310                 315                 320

His Lys Ile Phe His Lys Arg Met Pro Ala Glu Ala Val Asp Leu Val
                325                 330                 335

Ser Arg Leu Leu Gln Tyr Ser Pro Asn Leu Arg Cys Gln Ala Leu Asp
            340                 345                 350

Cys Leu Thr His Pro Phe Phe Asp Glu Leu Arg Asp Pro Asn Ala Arg
        355                 360                 365

Leu Pro Thr Gly Arg Phe Leu Pro Pro Leu Phe Asn Phe Lys Pro His
    370                 375                 380

Glu Leu Lys Gly Val Pro Val Glu Thr Leu Met Lys Leu Val Pro Glu
385                 390                 395                 400

His Ala Arg Lys Gln Cys Pro Phe Leu Gly Leu
                405                 410


<210> SEQ ID NO 170
<211> LENGTH: 1543
<212> TYPE: DNA
<213> ORGANISM: Medicago sativa

<400> SEQUENCE: 170

gttcaattga agctgcaaaa aaaaaaaaaa tcttgatcta ctttggttgt gataatggca      60

acagcgggtg tagcacctgc ttctggaata gtagatgtaa atgcaagttc agctattgct     120

gttgataagt tacctgatga gattcttggc atgagaatta aggatgataa ggaaatggaa     180

gcacatgtgg tagatggaaa tagtactgaa gcaggacatg taattgtcac taccattggt     240

ggtaaaaatg gccagccaaa gcagacaata agctacatgg ctgagcgtgc tgttggacag     300

ggatcatttg gtgtagtttt ccaggctaag tgcttggaga caggtgaaac tgtggctata     360
```

```
aaaaaggttc ttcaagacaa gaggtataag aaccgggaat tgcaaacaat gcgccttctg    420
gaccacccca atgttgtaac tttgaagcat tgtttctttt caacaactga aaaagacgag    480
ctctatctta acttggtact tgagtttgtt cctgagactg tccatcgtgt gatcagacac    540
tacagcaaaa tgaatcagag gatgccattg atatacgtaa aactttattc ttaccagata    600
tgtagatcac tagcttatat tcataactgt gttggagtgt ctcataggga cataaaacct    660
caaaatttac tggtcaatcc tcacacccat cagctgaagc tgtgtgactt tgggagtgca    720
aaagtcttgg tcaagggtga accaaacata tcttacatct gttcgaggta ttatagagct    780
cctgagctta tatttggtgc aactgaatac acctcagcca ttgacatttg gtcagctggc    840
tgtgtgcttg gcgaactatt gcttggccag cctctctttc ccggtgcgag tggagtagac    900
cagctcgttg aaattatcaa ggttttaggt accccaacaa gggaagaaat aaagtgtatg    960
aatcctaatt acactgagtt caaattccca caaatcaaag ctcatccatg gcacaagatc   1020
tttcgcaagc gtatgccacc ggaagctgtg gatctcgtct caagactact tcaatactct   1080
ccaaatcttc gaagcacagc tttggaggct ctggttcatc ccttctttga tgaattgcgt   1140
gatccaaata cccgcttacc aaatgggcga catcttcctc ctttatttaa cttcaaagcc   1200
aacgagctta agggagtgcc tgctgaaatg ctggtgaagt tggttccgtc tcacgcaaga   1260
aagcagtgtt ctttgtttgc gtcgtcatag acttagaatg ctgtcttgtg taaatattat   1320
ggactccctg tttgtagaat tgtatgtagc ctgtttcatg ttgttaatag tctctctttt   1380
gttatttgtt ccattaattt gtttctacca aagaaaacca cctcagttta ttataagttt   1440
caagttgatc tctcttcacg atttaattgt tctcctgatc ttcaattatt aacagattgt   1500
attaactatt aactattaac tagaacaatt gtttattcta gcg                      1543
```

<210> SEQ ID NO 171
<211> LENGTH: 411
<212> TYPE: PRT
<213> ORGANISM: Medicago sativa

<400> SEQUENCE: 171

```
Met Ala Thr Ala Gly Val Ala Pro Ala Ser Gly Ile Val Asp Val Asn
1               5                   10                  15

Ala Ser Ser Ala Ile Ala Val Asp Lys Leu Pro Asp Glu Ile Leu Gly
            20                  25                  30

Met Arg Ile Lys Asp Asp Lys Glu Met Glu Ala His Val Val Asp Gly
        35                  40                  45

Asn Ser Thr Glu Ala Gly His Val Ile Val Thr Thr Ile Gly Gly Lys
    50                  55                  60

Asn Gly Gln Pro Lys Gln Thr Ile Ser Tyr Met Ala Glu Arg Ala Val
65                  70                  75                  80

Gly Gln Gly Ser Phe Gly Val Val Phe Gln Ala Lys Cys Leu Glu Thr
                85                  90                  95

Gly Glu Thr Val Ala Ile Lys Lys Val Leu Gln Asp Lys Arg Tyr Lys
            100                 105                 110

Asn Arg Glu Leu Gln Thr Met Arg Leu Leu Asp His Pro Asn Val Val
        115                 120                 125

Thr Leu Lys His Cys Phe Phe Ser Thr Thr Glu Lys Asp Glu Leu Tyr
    130                 135                 140

Leu Asn Leu Val Leu Glu Phe Val Pro Glu Thr Val His Arg Val Ile
145                 150                 155                 160
```

```
Arg His Tyr Ser Lys Met Asn Gln Arg Met Pro Leu Ile Tyr Val Lys
                165                 170                 175

Leu Tyr Ser Tyr Gln Ile Cys Arg Ser Leu Ala Tyr Ile His Asn Cys
            180                 185                 190

Val Gly Val Ser His Arg Asp Ile Lys Pro Gln Asn Leu Leu Val Asn
        195                 200                 205

Pro His Thr His Gln Leu Lys Leu Cys Asp Phe Gly Ser Ala Lys Val
    210                 215                 220

Leu Val Lys Gly Glu Pro Asn Ile Ser Tyr Ile Cys Ser Arg Tyr Tyr
225                 230                 235                 240

Arg Ala Pro Glu Leu Ile Phe Gly Ala Thr Glu Tyr Thr Ser Ala Ile
                245                 250                 255

Asp Ile Trp Ser Ala Gly Cys Val Leu Gly Glu Leu Leu Leu Gly Gln
            260                 265                 270

Pro Leu Phe Pro Gly Ala Ser Gly Val Asp Gln Leu Val Glu Ile Ile
        275                 280                 285

Lys Val Leu Gly Thr Pro Thr Arg Glu Glu Ile Lys Cys Met Asn Pro
    290                 295                 300

Asn Tyr Thr Glu Phe Lys Phe Pro Gln Ile Lys Ala His Pro Trp His
305                 310                 315                 320

Lys Ile Phe Arg Lys Arg Met Pro Pro Glu Ala Val Asp Leu Val Ser
                325                 330                 335

Arg Leu Leu Gln Tyr Ser Pro Asn Leu Arg Ser Thr Ala Leu Glu Ala
            340                 345                 350

Leu Val His Pro Phe Phe Asp Glu Leu Arg Asp Pro Asn Thr Arg Leu
        355                 360                 365

Pro Asn Gly Arg His Leu Pro Pro Leu Phe Asn Phe Lys Ala Asn Glu
    370                 375                 380

Leu Lys Gly Val Pro Ala Glu Met Leu Val Lys Leu Val Pro Ser His
385                 390                 395                 400

Ala Arg Lys Gln Cys Ser Leu Phe Ala Ser Ser
                405                 410
```

<210> SEQ ID NO 172
<211> LENGTH: 1724
<212> TYPE: DNA
<213> ORGANISM: Nicotiana tabacum

<400> SEQUENCE: 172

```
tctctctcat cttccctgcg attctctctc tcaatttcag gttttctctg tttctgtgcg     60

agcctctaat gatcggtgta ttctcaatat cctgaagatt ttctgatttc atcggtgaat    120

gactttttga ggtgataata gttcgcaaaa tttcaggaaa tgacttcagt aggcttagca    180

cctgtatccg gtttgagaga atccagtagc catagtgttg gtgtagatag gctgcctgag    240

gagatgaatg acatgagaat cagggatgat aaggaaatcg aagcagctat tgtggatggt    300

aatgggactg agacaggcca tataatagtg acaactattg gtggtagaca tggtcagcca    360

aaacagacta tcagttatat ggctgaacgt attgttggac aaggatcatt tggagtggtt    420

ttccaggcaa aatgcttaga gactggtgaa actgttgcta ttaaaaaggt tcttcaagac    480

aagagatata agaacaggga gctgcagacc atgcgtcttc ttgatcaccc aaatgttgtg    540

tgcctgaagc actgcttctt ttcaacaact gagaaggatg aagtatatct taatttggtt    600

cttgaatacg tccctgaaac tgtccatcgt gttattaaac actacaataa gttgaatcaa    660

aggatgccat tgatactagt gaagctttat acatatcaga ttttcagggc attgtcttac    720
```

```
atccatcaca caattggagt gtgccacagg gacataaagc ctcagaatct tttggtgaat    780
ccacatactc accaggttaa attgtgtgac tttggaagtg ctaaagttct ggttaaagga    840
gaaccaaata tttcttacat ctgctctagg tattatagag cgcctgaact tatatttgga    900
gcaacagagt acactaccgc tattgacatc tggtctgctg gctgtgttct agccgagcta    960
cttcttgggc agcctttgtt tccgggtgaa agtggagttg atcagcttgt tgagattatt   1020
aaggtcttgg gtactcctac cagggaagaa attaaatgca tgaatccaaa ttataacgag   1080
ttcaaattcc cccaaattaa agctcatccg tggcacaaga tatttcacaa gcgcatgcct   1140
ccagaagctg ttgatctggt ttcaagacta ctgcagtact cacctaactt gcgttgcact   1200
gctttagagg cagtgaccca tgccttcttc gatgagcttc gtgatcctaa tacacgcctc   1260
ccaaatggcc gcgtccttcc cccttgttt aactttaagg cccatgagtt aaagggtgtg    1320
tctgcagaga atctattgaa gttggttccg gagcatgcca ggaaacagtg cccgtccctt   1380
ggtttatgag ttcccactgt acggtagata taatttaagt gtaagctatg ttatttctct   1440
gtatccattt ttccccttt gctccccaca tgtaccagtt gtctctttgt attattatcc    1500
tagtttgtaa aagcagaggt aggatgtggt ctttaacatt ccttacctcc aacactttcc   1560
tttcaccctg ttccttttat gtcctactgt tgtaactttt atgtggttaa gggtggactg   1620
ctttctatat gaactattat tttatgatga aatttcaaag tgatttttag tgaaaaaaaa   1680
aaaaaaaaaa aaaaaaaaaa aaaaaaaaaa aaaaaaaaaa aaaa                    1724
```

```
<210> SEQ ID NO 173
<211> LENGTH: 409
<212> TYPE: PRT
<213> ORGANISM: Nicotiana tabacum

<400> SEQUENCE: 173

Met Thr Ser Val Gly Leu Ala Pro Val Ser Gly Leu Arg Glu Ser Ser
1               5                   10                  15

Ser His Ser Val Gly Val Asp Arg Leu Pro Glu Glu Met Asn Asp Met
            20                  25                  30

Arg Ile Arg Asp Asp Lys Glu Ile Glu Ala Ala Ile Val Asp Gly Asn
        35                  40                  45

Gly Thr Glu Thr Gly His Ile Ile Val Thr Thr Ile Gly Gly Arg His
    50                  55                  60

Gly Gln Pro Lys Gln Thr Ile Ser Tyr Met Ala Glu Arg Ile Val Gly
65                  70                  75                  80

Gln Gly Ser Phe Gly Val Val Phe Gln Ala Lys Cys Leu Glu Thr Gly
                85                  90                  95

Glu Thr Val Ala Ile Lys Lys Val Leu Gln Asp Lys Arg Tyr Lys Asn
            100                 105                 110

Arg Glu Leu Gln Thr Met Arg Leu Leu Asp His Pro Asn Val Val Cys
        115                 120                 125

Leu Lys His Cys Phe Phe Ser Thr Thr Glu Lys Asp Glu Val Tyr Leu
    130                 135                 140

Asn Leu Val Leu Glu Tyr Val Pro Glu Thr Val His Arg Val Ile Lys
145                 150                 155                 160

His Tyr Asn Lys Leu Asn Gln Arg Met Pro Leu Ile Leu Val Lys Leu
                165                 170                 175

Tyr Thr Tyr Gln Ile Phe Arg Ala Leu Ser Tyr Ile His His Thr Ile
            180                 185                 190
```

```
Gly Val Cys His Arg Asp Ile Lys Pro Gln Asn Leu Leu Val Asn Pro
        195                 200                 205

His Thr His Gln Val Lys Leu Cys Asp Phe Gly Ser Ala Lys Val Leu
    210                 215                 220

Val Lys Gly Glu Pro Asn Ile Ser Tyr Ile Cys Ser Arg Tyr Tyr Arg
225                 230                 235                 240

Ala Pro Glu Leu Ile Phe Gly Ala Thr Glu Tyr Thr Thr Ala Ile Asp
                245                 250                 255

Ile Trp Ser Ala Gly Cys Val Leu Ala Glu Leu Leu Leu Gly Gln Pro
            260                 265                 270

Leu Phe Pro Gly Glu Ser Gly Val Asp Gln Leu Val Glu Ile Ile Lys
        275                 280                 285

Val Leu Gly Thr Pro Thr Arg Glu Glu Ile Lys Cys Met Asn Pro Asn
    290                 295                 300

Tyr Asn Glu Phe Lys Phe Pro Gln Ile Lys Ala His Pro Trp His Lys
305                 310                 315                 320

Ile Phe His Lys Arg Met Pro Pro Glu Ala Val Asp Leu Val Ser Arg
                325                 330                 335

Leu Leu Gln Tyr Ser Pro Asn Leu Arg Cys Thr Ala Leu Glu Ala Val
            340                 345                 350

Thr His Ala Phe Phe Asp Glu Leu Arg Asp Pro Asn Thr Arg Leu Pro
        355                 360                 365

Asn Gly Arg Val Leu Pro Pro Leu Phe Asn Phe Lys Ala His Glu Leu
    370                 375                 380

Lys Gly Val Ser Ala Glu Asn Leu Leu Lys Leu Val Pro Glu His Ala
385                 390                 395                 400

Arg Lys Gln Cys Pro Ser Leu Gly Leu
                405
```

<210> SEQ ID NO 174
<211> LENGTH: 1573
<212> TYPE: DNA
<213> ORGANISM: Triticum aestivum

<400> SEQUENCE: 174

```
gttggtgtgg tgcgtccttc ctcgcgcttt cagaacgaca cgagtactag tggtgatgcc      60

gaccgacttc cgaacgagat gggcaatatg agcataaggg atgacaggga ccctgaggat     120

atagtagtca acggcaatgg gacggaacca ggccatatta tagtcacaag cattgaggga     180

agaaatgggc aagcaaaaca gaccattagc tacatggctg agcgtgtggt tggtaatggg     240

tcatttggaa ctgttttcca ggctaagtgt cttgaaactg gcgagacggt ggctataaag     300

aaggttcttc aagacaagag atataagaac cgtgagctgc aaacgatgcg agttcttgac     360

cacccaaatg ttgtggcttt aaagcattgt tttttctcaa agactgagaa agaggagctt     420

tacctcaacc tggtgcttga gtatgtgccg gagactgctc atcgtgtcat taagcattat     480

aacaagatga accaacgcat gccattgata tatgcaaaac tgtacatgta tcagatatgt     540

agatctttgg catacattca caacagcatt ggagtatgcc acagagacat caagcctcaa     600

aatcttctgg tgaatccaca tacgcaccaa ttgaaattat gtgacttcgg aagtgcgaaa     660

gtgttggtaa aaggagaacc aaatatttcc tatatctgtt caaggtacta tagagcccca     720

gagctcatat ttggtgctac tgaatacaca acggcaattg acgtttggtc tgctggctgt     780

gttcttgctg aactccttct aggacagcct atattccctg gcgacagtgg tgttgatcag     840

cttgttgaaa tcatcaaggt tttaggtacc cctacaagag aagaaattaa gtgcatgaat     900
```

```
ccaaattata cggagtttaa attcccacaa atcaaagctc acccatggca caagatcttc    960

cataaaagaa tgcctgctga agcagtagat cttgtctcca gactcttgca atattcacca   1020

agcctgcgtt caactgcttt ggaagcatta attcatccat tcttcgatga actccgggac   1080

ccaaacaccc gtttgccgaa cggccgtttt cttcctcccc tctttaactt taagccccat   1140

gagttgaagg gtgtgccgat ggacatcctg gtgaagctca tccctgaaca tgctcggaag   1200

aactgtgcct ttgtaggatg gtgatccgcc agacggctgc ttgaagttta gttcagaaca   1260

aatccagttg ttgtctacta gaaaccccag gagtttgaga ttgtctgcag ccacacggga   1320

tataggcgat gacacatgtg attattattc cttttctcgt ccgagacctc gatgccatgt   1380

attctttccc cctactgccg atgtaacaaa ccacccatga tactgtaagt agatgagaag   1440

tgtttcgacc gttttcccct gagctcatgt gctatgcaat gaaggatgca ccctatgtac   1500

cgccaatatt tggtccagta tttgttcatg gatcgaggcc cccaaaaaaa aaaaaaaaaa   1560

aaaaaaaaaa aaa                                                      1573
```

<210> SEQ ID NO 175
<211> LENGTH: 381
<212> TYPE: PRT
<213> ORGANISM: Triticum aestivum

<400> SEQUENCE: 175

```
Met Gly Asn Met Ser Ile Arg Asp Asp Arg Asp Pro Glu Asp Ile Val
1               5                   10                  15

Val Asn Gly Asn Gly Thr Glu Pro Gly His Ile Ile Val Thr Ser Ile
            20                  25                  30

Glu Gly Arg Asn Gly Gln Ala Lys Gln Thr Ile Ser Tyr Met Ala Glu
        35                  40                  45

Arg Val Val Gly Asn Gly Ser Phe Gly Thr Val Phe Gln Ala Lys Cys
    50                  55                  60

Leu Glu Thr Gly Glu Thr Val Ala Ile Lys Lys Val Leu Gln Asp Lys
65                  70                  75                  80

Arg Tyr Lys Asn Arg Glu Leu Gln Thr Met Arg Val Leu Asp His Pro
                85                  90                  95

Asn Val Val Ala Leu Lys His Cys Phe Phe Ser Lys Thr Glu Lys Glu
            100                 105                 110

Glu Leu Tyr Leu Asn Leu Val Leu Glu Tyr Val Pro Glu Thr Ala His
        115                 120                 125

Arg Val Ile Lys His Tyr Asn Lys Met Asn Gln Arg Met Pro Leu Ile
    130                 135                 140

Tyr Ala Lys Leu Tyr Met Tyr Gln Ile Cys Arg Ser Leu Ala Tyr Ile
145                 150                 155                 160

His Asn Ser Ile Gly Val Cys His Arg Asp Ile Lys Pro Gln Asn Leu
                165                 170                 175

Leu Val Asn Pro His Thr His Gln Leu Lys Leu Cys Asp Phe Gly Ser
            180                 185                 190

Ala Lys Val Leu Val Lys Gly Glu Pro Asn Ile Ser Tyr Ile Cys Ser
        195                 200                 205

Arg Tyr Tyr Arg Ala Pro Glu Leu Ile Phe Gly Ala Thr Glu Tyr Thr
    210                 215                 220

Thr Ala Ile Asp Val Trp Ser Ala Gly Cys Val Leu Ala Glu Leu Leu
225                 230                 235                 240

Leu Gly Gln Pro Ile Phe Pro Gly Asp Ser Gly Val Asp Gln Leu Val
```

```
                245                 250                 255

Glu Ile Ile Lys Val Leu Gly Thr Pro Thr Arg Glu Glu Ile Lys Cys
            260                 265                 270

Met Asn Pro Asn Tyr Thr Glu Phe Lys Phe Pro Gln Ile Lys Ala His
        275                 280                 285

Pro Trp His Lys Ile Phe His Lys Arg Met Pro Ala Glu Ala Val Asp
    290                 295                 300

Leu Val Ser Arg Leu Leu Gln Tyr Ser Pro Ser Leu Arg Ser Thr Ala
305                 310                 315                 320

Leu Glu Ala Leu Ile His Pro Phe Phe Asp Glu Leu Arg Asp Pro Asn
                325                 330                 335

Thr Arg Leu Pro Asn Gly Arg Phe Leu Pro Pro Leu Phe Asn Phe Lys
            340                 345                 350

Pro His Glu Leu Lys Gly Val Pro Met Asp Ile Leu Val Lys Leu Ile
        355                 360                 365

Pro Glu His Ala Arg Lys Asn Cys Ala Phe Val Gly Trp
    370                 375                 380


<210> SEQ ID NO 176
<211> LENGTH: 1581
<212> TYPE: DNA
<213> ORGANISM: Petunia hybrida

<400> SEQUENCE: 176

tctctcaggt ttagggtttc gtattgtccg atcgctatac tttgaagctc tttccgatca      60

ctgttttgtg tttttgtaaa atgtgagctg ttctttagct acaggtttga agctgttaat     120

ctgtcatttg agttgtgccc attactcagt agtataagta agtttatttt tgttgctgat     180

atggcgtctg gtataatgcc ttcggctggt ggaaaacatc gaactgatgc catgcttgtt     240

gacaaacttc ccgaagaaat aaatgaaatg aagatcagag atgataaagc agaaaaggaa     300

atggaagcag ctgtagtgga tggaaatgga actgaaaaag gccacatcat cgtgacaact     360

attgggggca aaaatggtga gcctaagcag accattagtt acatggccga gcgtgttgtt     420

ggacagggtt cgtttggaat agtgttccag gccaaatgcc ttgaaactgg agaaactgtt     480

gcaataaaaa aggttttaca ggataagaga tacaagaatc gggaattgca aacaatacgc     540

cttctagatc atcctaatgt tgttgcactg aggcactgct tcttttcaac cacagaaaag     600

gatgagcttt atctgaattt ggtccttgaa tatgtaccag agactgtcta ccgtgtcttg     660

agacattaca gcaaagcaaa ccaacagatg cctatgattt atgtcaagct ctacacatat     720

cagattttca gagctttggc ctacatacac ggcataggag tctgccacag ggacatcaag     780

cctcagaatc tactggtcaa cccccacacc caccagctta agctctgcga ctttgggagt     840

gcaaaagttc tggtcaaagg cgaaccaaat atttcatata tttgttctcg ttactatcgt     900

gcacccgaac ttatattcgg agcaactgaa tacacttttg caattgacat ttggtctgtg     960

ggttgcgtcc ttgccgaact gcttctgggg cagcccctct ttcctggtga gagtggagtt    1020

gatcagcttg ttgaaataat caaggttctt ggaacaccaa ctcgggagga aatcaagagt    1080

atgaatccaa attacactga gttcaaattc ccacaaatca aagctcaccc ttggcacaaa    1140

atttttcata agcggatgcc tccagaagct gtggaccttg tgtcaaggct tctccaatat    1200

tctccaaatt tgaggtccac tgcgttggag gcttgcactc acactttctt tgatgaactc    1260

cgtgatccta agactcgcct ccctaatggt cggccattgc cacctctttt caacttcagg    1320

cctcaagagc tgaaaggagc gtcggcagac ctcttaaaca agctgatacc agaacatgct    1380
```

```
aagaagcagt gtacctttct tggtgtctag gtttatgaat gttgtgtatc tattgtatac   1440

ttgaaatatt ttgcaaccac tggttaattc tctactttgg ctaaacctgt ttgacatgtc   1500

ttcctttcca tgaaaactta taactgaaac cacattgtgt aagttgttcc tagtagtgca   1560

aatgctattt acttgaactt g                                             1581


<210> SEQ ID NO 177
<211> LENGTH: 409
<212> TYPE: PRT
<213> ORGANISM: Petunia hybrida

<400> SEQUENCE: 177

Met Ala Ser Gly Ile Met Pro Ser Ala Gly Gly Lys His Arg Thr Asp
1               5                   10                  15

Ala Met Leu Val Asp Lys Leu Pro Glu Glu Ile Asn Glu Met Lys Ile
            20                  25                  30

Arg Asp Asp Lys Ala Glu Lys Glu Met Glu Ala Ala Val Val Asp Gly
        35                  40                  45

Asn Gly Thr Glu Lys Gly His Ile Ile Val Thr Thr Ile Gly Gly Lys
    50                  55                  60

Asn Gly Glu Pro Lys Gln Thr Ile Ser Tyr Met Ala Glu Arg Val Val
65                  70                  75                  80

Gly Gln Gly Ser Phe Gly Ile Val Phe Gln Ala Lys Cys Leu Glu Thr
                85                  90                  95

Gly Glu Thr Val Ala Ile Lys Lys Val Leu Gln Asp Lys Arg Tyr Lys
            100                 105                 110

Asn Arg Glu Leu Gln Thr Ile Arg Leu Leu Asp His Pro Asn Val Val
        115                 120                 125

Ala Leu Arg His Cys Phe Phe Ser Thr Thr Glu Lys Asp Glu Leu Tyr
    130                 135                 140

Leu Asn Leu Val Leu Glu Tyr Val Pro Glu Thr Val Tyr Arg Val Leu
145                 150                 155                 160

Arg His Tyr Ser Lys Ala Asn Gln Gln Met Pro Met Ile Tyr Val Lys
                165                 170                 175

Leu Tyr Thr Tyr Gln Ile Phe Arg Ala Leu Ala Tyr Ile His Gly Ile
            180                 185                 190

Gly Val Cys His Arg Asp Ile Lys Pro Gln Asn Leu Leu Val Asn Pro
        195                 200                 205

His Thr His Gln Leu Lys Leu Cys Asp Phe Gly Ser Ala Lys Val Leu
    210                 215                 220

Val Lys Gly Glu Pro Asn Ile Ser Tyr Ile Cys Ser Arg Tyr Tyr Arg
225                 230                 235                 240

Ala Pro Glu Leu Ile Phe Gly Ala Thr Glu Tyr Thr Phe Ala Ile Asp
                245                 250                 255

Ile Trp Ser Val Gly Cys Val Leu Ala Glu Leu Leu Leu Gly Gln Pro
            260                 265                 270

Leu Phe Pro Gly Glu Ser Gly Val Asp Gln Leu Val Glu Ile Ile Lys
        275                 280                 285

Val Leu Gly Thr Pro Thr Arg Glu Glu Ile Lys Ser Met Asn Pro Asn
    290                 295                 300

Tyr Thr Glu Phe Lys Phe Pro Gln Ile Lys Ala His Pro Trp His Lys
305                 310                 315                 320

Ile Phe His Lys Arg Met Pro Pro Glu Ala Val Asp Leu Val Ser Arg
                325                 330                 335
```

```
Leu Leu Gln Tyr Ser Pro Asn Leu Arg Ser Thr Ala Leu Glu Ala Cys
            340                 345                 350

Thr His Thr Phe Phe Asp Glu Leu Arg Asp Pro Lys Thr Arg Leu Pro
        355                 360                 365

Asn Gly Arg Pro Leu Pro Pro Leu Phe Asn Phe Arg Pro Gln Glu Leu
    370                 375                 380

Lys Gly Ala Ser Ala Asp Leu Leu Asn Lys Leu Ile Pro Glu His Ala
385                 390                 395                 400

Lys Lys Gln Cys Thr Phe Leu Gly Val
                405


<210> SEQ ID NO 178
<211> LENGTH: 2193
<212> TYPE: DNA
<213> ORGANISM: Oryza sativa

<400> SEQUENCE: 178

aatccgaaaa gtttctgcac cgttttcacc ccctaactaa caatataggg aacgtgtgct     60

aaatataaaa tgagacctta tatatgtagc gctgataact agaactatgc aagaaaaact    120

catccaccta ctttagtggc aatcgggcta aataaaaaag agtcgctaca ctagtttcgt    180

tttccttagt aattaagtgg gaaaatgaaa tcattattgc ttagaatata cgttcacatc    240

tctgtcatga agttaaatta ttcgaggtag ccataattgt catcaaactc ttcttgaata    300

aaaaaatctt tctagctgaa ctcaatgggt aaagagagag attttttttta aaaaaataga    360

atgaagatat tctgaacgta ttggcaaaga tttaaacata taattatata attttatagt    420

ttgtgcattc gtcatatcgc acatcattaa ggacatgtct tactccatcc caatttttat    480

ttagtaatta aagacaattg acttattttt attatttatc ttttttcgat tagatgcaag    540

gtacttacgc acacactttg tgctcatgtg catgtgtgag tgcacctcct caatacacgt    600

tcaactagca acacatctct aatatcactc gcctatttaa tacatttagg tagcaatatc    660

tgaattcaag cactccacca tcaccagacc acttttaata atatctaaaa tacaaaaaat    720

aattttacag aatagcatga aaagtatgaa acgaactatt taggtttttc acatacaaaa    780

aaaaaaagaa ttttgctcgt gcgcgagcgc caatctccca tattgggcac acaggcaaca    840

acagagtggc tgcccacaga acaacccaca aaaaacgatg atctaacgga ggacagcaag    900

tccgcaacaa ccttttaaca gcaggctttg cggccaggag agaggaggag aggcaaagaa    960

aaccaagcat cctcctcctc ccatctataa attcctcccc ccttttcccc tctctatata   1020

ggaggcatcc aagccaagaa gagggagagc accaaggaca cgcgactagc agaagccgag   1080

cgaccgcctt cttcgatcca tatcttccgg tcgagttctt ggtcgatctc ttccctcctc   1140

cacctcctcc tcacagggta tgtgcccttc ggttgttctt ggatttattg ttctaggttg   1200

tgtagtacgg gcgttgatgt taggaaaggg gatctgtatc tgtgatgatt cctgttcttg   1260

gatttgggat agaggggttc ttgatgttgc atgttatcgg ttcggtttga ttagtagtat   1320

ggttttcaat cgtctggaga gctctatgga aatgaaatgg tttagggtac ggaatcttgc   1380

gattttgtga gtacctttg tttgaggtaa aatcagagca ccggtgattt tgcttggtgt   1440

aataaaagta cggttgtttg gtcctcgatt ctggtagtga tgcttctcga tttgacgaag   1500

ctatcctttg tttattccct attgaacaaa aataatccaa ctttgaagac ggtcccgttg   1560

atgagattga atgattgatt cttaagcctg tccaaaattt cgcagctggc ttgtttagat   1620

acagtagtcc ccatcacgaa attcatggaa acagttataa tcctcaggaa caggggattc   1680
```

cctgttcttc cgatttgctt tagtcccaga attttttttc ccaaatatct taaaaagtca 1740
ctttctggtt cagttcaatg aattgattgc tacaaataat gcttttatag cgttatccta 1800
gctgtagttc agttaatagg taatacccct atagtttagt caggagaaga acttatccga 1860
tttctgatct ccatttttaa ttatatgaaa tgaactgtag cataagcagt attcatttgg 1920
attatttttt ttattagctc tcacccccttc attattctga gctgaaagtc tggcatgaac 1980
tgtcctcaat tttgttttca aattcacatc gattatctat gcattatcct cttgtatcta 2040
cctgtagaag tttctttttg gttattcctt gactgcttga ttacagaaag aaatttatga 2100
agctgtaatc gggatagtta tactgcttgt tcttatgatt catttccttt gtgcagttct 2160
tggtgtagct tgccactttc accagcaaag ttc 2193

<210> SEQ ID NO 179
<211> LENGTH: 54
<212> TYPE: DNA
<213> ORGANISM: Artificial sequence
<220> FEATURE:
<223> OTHER INFORMATION: primer: prm5797

<400> SEQUENCE: 179
ggggacaagt ttgtacaaaa aagcaggctt aaacaatggg ttcagtaggg gttg 54

<210> SEQ ID NO 180
<211> LENGTH: 50
<212> TYPE: DNA
<213> ORGANISM: Artificial sequence
<220> FEATURE:
<223> OTHER INFORMATION: primer: prm5798

<400> SEQUENCE: 180
ggggaccact ttgtacaaga aagctgggtg aagctgtctc atactcctgc 50

<210> SEQ ID NO 181
<211> LENGTH: 1243
<212> TYPE: DNA
<213> ORGANISM: Oryza sativa

<400> SEQUENCE: 181
aaaaccaccg agggacctga tctgcaccgg ttttgatagt tgagggaccc gttgtgtctg 60
gttttccgat cgagggacga aaatcggatt cggtgtaaag ttaagggacc tcagatgaac 120
ttattccgga gcatgattgg gaagggagga cataaggccc atgtcgcatg tgtttggacg 180
gtccagatct ccagatcact cagcaggatc ggccgcgttc gcgtagcacc cgcggtttga 240
ttcggcttcc cgcaaggcgg cggccggtgg ccgtgccgcc gtagcttccg ccggaagcga 300
gcacgccgcc gccgccgacc cggctctgcg tttgcaccgc cttgcacgcg atacatcggg 360
atagatagct actactctct ccgtttcaca atgtaaatca ttctactatt ttccacattc 420
atattgatgt taatgaatat agacatatat atctatttag attcattaac atcaatatga 480
atgtaggaaa tgctagaatg acttacattg tgaattgtga aatggacgaa gtacctacga 540
tggatggatg caggatcatg aaagaattaa tgcaagatcg tatctgccgc atgcaaaatc 600
ttactaattg cgctgcatat atgcatgaca gcctgcatgc gggcgtgtaa gcgtgttcat 660
ccattaggaa gtaaccttgt cattacttat accagtacta catactatat agtattgatt 720
tcatgagcaa atctacaaaa ctggaaagca ataaggaata cgggactgga aaagactcaa 780
cattaatcac caaatatttc gccttctcca gcagaatata tatctctcca tcttgatcac 840

```
tgtacacact gacagtgtac gcataaacgc agcagccagc ttaactgtcg tctcaccgtc    900

gcacactggc cttccatctc aggctagctt tctcagccac ccatcgtaca tgtcaactcg    960

gcgcgcgcac aggcacaaat tacgtacaaa acgcatgacc aaatcaaaac caccggagaa   1020

gaatcgctcc cgcgcgcggc ggcggcgcgc acgtacgaat gcacgcacgc acgcccaacc   1080

ccacgacacg atcgcgcgcg acgccggcga caccggccat ccacccgcgc cctcacctcg   1140

ccgactataa atacgtaggc atctgcttga tcttgtcatc catctcacca ccaaaaaaaa   1200

aggaaaaaaa aacaaaacac accaagccaa ataaaagcga caa                     1243


<210> SEQ ID NO 182
<211> LENGTH: 5
<212> TYPE: PRT
<213> ORGANISM: Artificial Sequence
<220> FEATURE:
<223> OTHER INFORMATION: Group I shaggy-like kinase  motif I
<220> FEATURE:
<221> NAME/KEY: misc_feature
<222> LOCATION: (1)..(1)
<223> OTHER INFORMATION: Xaa can be Arg, His, Val, Asn, or Gln
<220> FEATURE:
<221> NAME/KEY: VARIANT
<222> LOCATION: (2)..(2)
<223> OTHER INFORMATION: /replace="Gly"
<220> FEATURE:
<221> NAME/KEY: VARIANT
<222> LOCATION: (5)..(5)
<223> OTHER INFORMATION: /replace="Asn"

<400> SEQUENCE: 182

Xaa Glu Leu Lys Gly
1               5


<210> SEQ ID NO 183
<211> LENGTH: 7
<212> TYPE: PRT
<213> ORGANISM: Artificial Sequence
<220> FEATURE:
<223> OTHER INFORMATION: Group I shaggy-like kinase motif II
<220> FEATURE:
<221> NAME/KEY: VARIANT
<222> LOCATION: (2)..(2)
<223> OTHER INFORMATION: /replace="Asn"
<220> FEATURE:
<221> NAME/KEY: misc_feature
<222> LOCATION: (4)..(6)
<223> OTHER INFORMATION: Xaa can be any amino acid
<220> FEATURE:
<221> NAME/KEY: VARIANT
<222> LOCATION: (7)..(7)
<223> OTHER INFORMATION: /replace="Ala" /replace="Ser"

<400> SEQUENCE: 183

Lys Gln Cys Xaa Xaa Xaa Gly
1               5


<210> SEQ ID NO 184
<211> LENGTH: 283
<212> TYPE: PRT
<213> ORGANISM: Medicago truncatula

<400> SEQUENCE: 184

Met His Glu Met Ala Phe Phe Gln Ala Asn Phe Met Leu Gln Thr Pro
1               5                   10                  15

His His His Asp Asp His His Gln Pro Ser Ser Leu Asn Ser Ile Leu
            20                  25                  30

Pro Gln Asp Tyr His Gly Gly Pro Ser Phe Leu Gly Lys Arg Cys Met
```

```
        35                  40                  45

Ser Phe Ser Ser Gly Ile Glu Leu Gly Glu Glu Ala Asn Ile Pro Glu
    50                  55                  60

Glu Asp Leu Ser Asp Asp Gly Ser Gln Ala Gly Glu Lys Lys Arg Arg
65                  70                  75                  80

Leu Asn Met Glu Gln Val Lys Thr Leu Glu Lys Ser Phe Glu Leu Gly
                85                  90                  95

Asn Lys Leu Glu Pro Glu Arg Lys Met Gln Leu Ala Arg Ala Leu Asn
            100                 105                 110

Leu Gln Pro Arg Gln Val Ala Ile Trp Phe Gln Asn Arg Arg Ala Arg
        115                 120                 125

Trp Lys Thr Lys Gln Leu Glu Lys Asp Tyr Asp Val Leu Lys Arg Gln
    130                 135                 140

Tyr Asp Ala Ile Lys Leu Asp Asn Asp Ala Leu Gln Ala Gln Asn Gln
145                 150                 155                 160

Lys Leu Gln Ala Glu Ile Leu Ala Leu Lys Asn Arg Glu Pro Thr Glu
                165                 170                 175

Ser Ile Asn Leu Asn Lys Glu Thr Glu Gly Ser Ser Ser Asn Arg Ser
            180                 185                 190

Glu Asn Ser Ser Glu Ile Lys Leu Asp Met Ser Arg Thr Pro Ala Ser
        195                 200                 205

Asp Ser Pro Leu Ser Thr His Gln His Thr Thr Ser Arg Thr Phe Phe
    210                 215                 220

Pro Pro Ser Ala Arg Pro Ser Ser Gly Ile Ala Gln Leu Phe Gln Thr
225                 230                 235                 240

Ser Ser Arg Pro Glu Ile Gln Cys Gln Lys Ile Asp Gln Met Val Lys
                245                 250                 255

Glu Glu Ser Leu Ser Asn Met Phe Cys Gly Met Asp Asp Gln Ala Gly
            260                 265                 270

Phe Trp Pro Trp Leu Glu Gln Gln His Phe Asn
        275                 280


<210> SEQ ID NO 185
<211> LENGTH: 302
<212> TYPE: PRT
<213> ORGANISM: Medicago truncatula

<400> SEQUENCE: 185

Met Lys Arg Leu Asn Asn Thr Ser Asp Ser Phe Ser Thr Pro Leu Ile
1               5                   10                  15

Thr Ile Ser Pro Ser Thr Glu Glu His Ser Pro Arg Asn Lys His Val
            20                  25                  30

Tyr Gly Met Glu Phe Gln Ser Met Met Leu Asp Gly Phe Glu Glu Glu
        35                  40                  45

Gly Cys Val Glu Glu Thr Gly His His Ser Glu Lys Lys Arg Arg Leu
    50                  55                  60

Arg Val Asp Gln Val Lys Ala Leu Glu Lys Asn Phe Glu Val Glu Asn
65                  70                  75                  80

Lys Leu Glu Pro Glu Arg Lys Glu Lys Leu Ala Ile Glu Leu Gly Leu
                85                  90                  95

Gln Pro Arg Gln Val Ala Val Trp Phe Gln Asn Arg Arg Ala Arg Trp
            100                 105                 110

Lys Thr Lys Gln Leu Glu Arg Asp Tyr Gly Val Leu Lys Ala Asn Tyr
        115                 120                 125
```

```
Asp Ala Leu Lys Leu Lys Phe Asp Ala Ile Ala Gln Asp Asn Lys Ala
    130                 135                 140

Phe His Lys Glu Ile Lys Glu Leu Lys Ser Lys Leu Gly Glu Glu Glu
145                 150                 155                 160

Lys Ser Thr Ile Asn Val Leu Val Lys Glu Glu Leu Thr Met Leu Glu
                165                 170                 175

Ser Cys Asp Glu Asp Lys His Asn Pro Ser Ser Glu Thr Ser Asn Pro
            180                 185                 190

Ser Ser Glu Ser Lys Asp His Leu Asp Tyr Asp Cys Ile Ile Asn Asn
        195                 200                 205

Asn Asp Val Gly Ile Gly Glu Thr Ser Ser Leu Phe Pro Val Asp Leu
    210                 215                 220

Lys Asp Gly Ser Ser Asp Ser Asp Ser Ser Ala Ile Ser Ser Ser Gly
225                 230                 235                 240

Val Leu Gln Ser Gln Gln His Leu Leu Leu Ser Pro Glu Ser Ser Ser
                245                 250                 255

Met Asn Cys Phe Gln Tyr Gln Lys Ser Tyr His Val Lys Met Glu Glu
            260                 265                 270

His Asn Phe Leu Ser Ala Asp Glu Ala Cys Asn Phe Phe Ser Asp Glu
        275                 280                 285

Gln Ala Pro Thr Leu Gln Trp Tyr Cys Pro Asp Gln Trp Ser
    290                 295                 300
```

<210> SEQ ID NO 186
<211> LENGTH: 309
<212> TYPE: PRT
<213> ORGANISM: Picea glauca

<400> SEQUENCE: 186

```
Met Ala Cys Asp Arg Ser Ala Leu Tyr Thr Ser Ser Val Ile Met Asn
1               5                   10                  15

Thr Glu Asp Asn Ser Ser Ala His Ala Ile Ala Ala Met Ile Ala Ser
            20                  25                  30

Ser Cys Thr Pro Pro Ala Thr Phe Gln Gly Thr Arg Ser Ile Ser Val
        35                  40                  45

Phe Glu Thr Gly Asn Glu Arg Lys Arg Pro Ala Gly Asn Ser Tyr Ser
    50                  55                  60

Ala Leu Glu Leu Ser Asp Asp Ile Gly Asp Glu Asp Gly Ser Asp Asp
65                  70                  75                  80

Cys Ile His Leu Gly Glu Lys Lys Arg Arg Leu Thr Leu Glu Gln Val
                85                  90                  95

Arg Ala Leu Glu Lys Asn Phe Glu Met Ala Asn Lys Leu Glu Pro Glu
            100                 105                 110

Lys Lys Met Gln Leu Ala Lys Ala Leu Gly Leu Gln Pro Arg Gln Ile
        115                 120                 125

Ala Val Trp Phe Gln Asn Arg Arg Ala Arg Trp Lys Thr Lys Gln Leu
    130                 135                 140

Glu Lys Asp Phe Asn Val Leu Lys Gln Asp Tyr Asp Ala Leu Lys Gln
145                 150                 155                 160

Asp Tyr Asp Asn Leu Met Glu Glu Asn Asn Asn Leu Gln Ala Met Ile
                165                 170                 175

Glu Arg Met Ser Ser Lys Ser Gln Ser Cys Asn Asp Gln Lys Phe Gln
            180                 185                 190

Ala Asn Ser Ser Lys Leu Gln Lys Asp Asp Gln Asp Leu Gln Leu Leu
        195                 200                 205
```

-continued

```
Met Met Ser Ala Thr Lys Val Asp Cys Ala Asp Lys Glu Asn Asn Asn
    210                 215                 220

Glu Gly Pro Ser Ser Ile Gly Ser Glu Gly Ser Ser Val Leu Asp Met
225                 230                 235                 240

Asp Ser Pro Gly Thr Ile Asp Ser Gln Gln Asn Ile Asp Ser Ile Gly
                245                 250                 255

Phe Ser Asn Val Lys Ala Arg Asp Leu Arg Leu Glu Cys Asn Phe Arg
            260                 265                 270

Pro Lys Val Glu Glu Asn Val Ser Gln Ala Asp Glu Pro Cys Asn Tyr
        275                 280                 285

Leu Phe Tyr Asn Asn Leu Glu Thr Gly Pro Leu Leu Trp Asp Tyr Asn
    290                 295                 300

Trp Ser Ser Gly Leu
305
```